(12) United States Patent
Prendergast et al.

(10) Patent No.: US 8,436,151 B2
(45) Date of Patent: May 7, 2013

(54) INDOLEAMINE 2,3-DIOXYGENASE-2 ANTIBODIES

(75) Inventors: George C. Prendergast, Penn Valley, PA (US); Richard Metz, Pennington, NJ (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 0 days.

(21) Appl. No.: 13/289,597

(22) Filed: Nov. 4, 2011

(65) Prior Publication Data

US 2012/0090044 A1    Apr. 12, 2012

Related U.S. Application Data

(60) Division of application No. 12/273,296, filed on Nov. 18, 2008, now Pat. No. 8,058,416, which is a continuation-in-part of application No. PCT/US2007/069271, filed on May 18, 2007.

(60) Provisional application No. 60/801,255, filed on May 18, 2006, provisional application No. 60/886,815, filed on Jan. 26, 2007, provisional application No. 60/914,472, filed on Apr. 27, 2007.

(51) Int. Cl.
*C07K 16/40*    (2006.01)

(52) U.S. Cl.
USPC .................................................. 530/388.26

(58) Field of Classification Search .................. None
See application file for complete search history.

(56) References Cited

U.S. PATENT DOCUMENTS

2005/0118625 A1 *   6/2005   Mounts .............................. 435/6
2006/0110371 A1 *   5/2006   Albert et al. ................... 424/93.7

FOREIGN PATENT DOCUMENTS

EP         1 447 413 A      8/2004
WO         02/057303        7/2002

OTHER PUBLICATIONS

Ota (Nature Genetics, Jan. 2004, vol. 36, No. 1, p. 40-45).*
Sequence Search results 2010, reference 2, which is Ota.*
Lederman et al., Molecular Immunology 28: 1171-1181, 1991.*
Li et al., PNAS 77: 3211-3214, 1980.*
Bozza et al., J. Immunol. 174: 2910-2918, 2005.*
Bost et al., Immunol. Invest. 17:577-586, 1988.*
Bendayan, Histochem. Cytochem. 43: 881-886, 1995.*
Gajewski, T.F., et al. "Immune suppression in the tumor microenvironment." J Immunother. May-Jun. 2006;29 (3):233-40.
Database EMBL. "Homo sapiens cDNA FLJ35183 fis, clone PLACE6015460, weakly similar to Indoleamine 2,3-Dioxygenase (EC 1.13.11.42)." retrieved from EBI accession No. EMBL:AK092502 (Feb. 27, 2006)[Online].
Cady, S.G., et al. "1-Methyl-DL-tryptophan, β-(3-Benzofuranyl)-DL-alanine (the Oxygen analog of Tryptophan), and β-[3-Benzo(b)theinyl]-DL-alanine (the Sulfur Analog of Tryptophan) Are Competitive Inhibitors for Indoleamine 2,3-Dioxygenase." Archives of Biochemistry and Biophysics, 291(2):326-333 (Dec. 1, 1991).
Ball, H. J., et al. "Characterization of an indoleamine 2,3-dioxygenase-like protein found in humans and mice." Gene, 396:203-217 (May 31, 2007).
Metz, R., et al. "Novel Tryptophan Catabolic Enzyme IDO2 Is the Preferred Biochemical Target of the Antitumor Indoleamine 2,3-Dioxygenase Inhibitory Compound D-1-Methyl-Tryptophan." Cancer Research, 67(15):7082-7087 (Aug. 1, 2007).
Databse Geneseq. "Full length human cDNA useful for treating neurological disease Seq 1917." retrieved from EBI accession No. GSN:ADR08411 (Nov. 4, 2004)[Online].
Ota, C., et al. "Complete sequencing and characterization of 21,243 full-length human cDNAs." Nat Genet. Jan. 2004;36(1):40-5. Epub Dec. 21, 2003.

* cited by examiner

*Primary Examiner* — Phillip Gambel
(74) *Attorney, Agent, or Firm* — Dann Dorfman Herrell & Skillman; Robert C. Netter, Jr.

(57) ABSTRACT

The nucleotide and amino acid sequences of indoleamine 2,3-dioxygenase-2 (IDO2) and methods of use thereof are provided.

3 Claims, 123 Drawing Sheets

| | |
|---|---|
| MLHFHYYDTSNKIMEPHRPNVKTAVPLSLESYHISEEYGFLLPDSLKELP | 50 |
| DHYRPWMEIANKLPQLIDAHQLQAHVDKMPLLSCQFLKGHREQRLAHLVL | 100 |
| SFLTMGYVWQEGEAQPAEVLPRNLALPFVEVSRNLGLPPILVHSDLVLTN | 150 |
| WTKKDPDGNLEIGNLETIISFPGGESLHGFILVTALVEKEAVPGIKALVQ | 200 |
| ATNAILQPNQEALLQALQRLRLSIQDITKTLGQMHDYVDPDIFYAGIRIF | 250 |
| LSGWKDNPAMPAGLMYEGVSQEPLKYSGGSAAQSTVLHAFDEFLGIRHSK | 300 |
| ESGDFLYRMRDYMPPSHKAFIEDIHSAPSLRDYILSSGQDHLLTAYNQCV | 350 |
| QALAELRSYHITMVTKYLITAAAKAKHGKPNHLPGPPQALKDRGTGGTAV | 400 |
| MSFLKSVRDKTLESILHPRG | 420 |

Figure 1A

| | |
|---|---|
| MEPHRPNVKTAVPLSLESYHISEEYGFLLPDSLKELPDHYRPWMEIANKL | 50 |
| PQLIDAHQLQAHVDKMPLLSCQFLKGHREQRLAHLVLSFLTMGYVWQEGE | 100 |
| AQPAEVLPRNLALPFVEVSRNLGLPPILVHSDLVLTNWTKKDPDGFLEIG | 150 |
| NLETIISFPGGESLHGFILVTALVEKEAVPGIKALVQATNAILQPNQEAL | 200 |
| LQALQRLRLSIQDITKTLGQMHDYVDPDIFYAGIRIFLSGWKDNPAMPAG | 250 |
| LMYEGVSQEPLKYSGGSAAQSTVLHAFDEFLGIRHSKESGDFLYRMRDYM | 300 |
| PPSHKAFIEDIHSAPSLRDYILSSGQDHLLTAYNQCVQALAELRSYHITM | 350 |
| VTKYLITAAAKAKHGKPNHLPGPPQALKDRGTGGTAVMSFLKSVRDKTLE | 400 |
| SILHP | 405 |

Figure 1B

```
MTLEVPLSLGRYHISEEYGFLLPNPLEALPDHYKPWMEIALRLPHLIENR      50
QLRAHVYRMPLLDCRFLKSYREQRLAHMALAAITMGFVWQEGEGQPQKVL     100
PRSLAIPFVEVSRNLGLPPILVHSDLVLTNWTKRNPEGPLEISNLETIIS     150
FPGGESLRGFILVTVLVEKAAVPGLKALVQGMEAIRQHSQDTLLEALQQL     200
RLSIQDITRALAQMHDYVDPDIFYSVIRIFLSGWKDNPAMPVGLVYEGAA     250
TEPLKYSGGSAAQSSVLHAFDEFLGIEHCKESVGFLHRMRDYMPPSHKAF     300
LEDLHVAPSLRDYILASGPGDCLMAYNQCVEALGELRSYHINVVARYIIS     350
AATRARSRGLTNPSPHALEDRGTGGTAMLSFLKSVREKTMEALLCPGA       398
```

Figure 2A

```
MEPQSQSMTLEVPLSLGRYHISEEYGFLLPNPLEALPDHYKPWMEIALRL      50
PHLIENRQLRAHVYRMPLLDCRFLKSYREQRLAHMALAAITMGFVWQEGE     100
GQPQKVLPRSLAIPFVEVSRNLGLPPILVHSDLVLTNWTKRNPEGPLEIS     150
NLETIISFPGGESLRGFILVTVLVEKAAVPGLKALVQGMEAIRQHSQDTL     200
LEALQQLRLSIQDITRALAQMHDYVDPDIFYSVIRIFLSGWKDNPAMPVG     250
LVYEGAATEPLKYSGGSAAQSSVLHAFDEFLGIEHCKESVGFLHRMRDYM     300
PPSHKAFLEDLHVAPSLRDYILASGPGDCLMAYNQCVEALGELRSYHINV     350
VARYIISAATRARSRGLTNPSPHALEDRGTGGTAMLSFLKSVREKTMEAL     400
LCP                                                    403
```

Figure 2B

```
ESYHISEEYGFLLPDSLKELPDHYRPWMEIANKLPQLIDAHQLQAHVDKMPLLSCQFLKG     89
+ ### ## ## ##+   + ### #   ## ##   ## ##++ ##+   #+#+ +##    #
KEYHIDEEVGFALPNPQENLPDFYNDWMFIAKHLPDLIESGQLRERVEKLNMLSIDHLTD     72

HREQRLAHLVLSFLTMGYVWQEGEAQPAEVLPRNLALPFVEVSRNLGLPPILVHSDLVLT    149
#+ #### ###  +## ### +#      +#####+#+#+ ++#+ # ######++# ##
HKSQRLARLVLGCITMAYVWGKGHGDVRKVLPRNIAVPYCQLSKKLELPPILVYADCVLA    132

NWTKKDPDGFLEIGNLETIISFPGGESLHGFILVTALVEKEAVPGIKALVQATNAILQPN    209
####+  #    #++ + ##  #+    ## ##+ ###  #   ## +      #+
NWKKKDPNKPLTYENMDVLFSFRDGDCSKGFFLVSLLVEIAAASAIKVIPTVFKAMQMQE    192

QEALLQALQRLRLSIQDITKTLGQMHDYVDPDIFYAGIRIFLSGWKDNPAMPAGLMYEGV    269
++ ##+##   +    ++    +   #+##+#+# #++ +##+##### ## +  ##+###
RDTLLKALLEIASCLEKALQVFHQIHDHVNPKAFFSVLRIYLSGWKGNPQLSDGLVYEGF    252

SQEPLKYSGGSAAQSTVLHAFDEFLGIRHSKESG---DFLYRMRDYMPPSHKAFIEDIHS    326
 ++# +++##### ##+#   ##   ###+ +    #    ## ## ####+#+ #+   + #
WEDPKEFAGGSAGQSSVFQCFDVLLGIQQTAGGGHAAQFLQDMRRYMPPAHRNFLCSLES    312

APSLRDYILSSGQDHLLTAYNQCVQALAELRSYHITMVTKYLITAAAKAKHGKPNHLPGP    386
 ##+#++++## #     #   ##+ ##+## #####+ +#####++ #  ++ # #
NPSVREFVLSKGDAGLREAYDACVKALVSLRSYHLQIVTKYILIPA--SQQPKENKTSED    370

PQALKDRGTGGTAVMSFLKSVRDKTLESIL    416
#   #+ +##### +#+###+## # +#+#
PSKLEAKGTGGTDLMNFLKTVRSTTEKSLL    400
```

Figure 3A

```
MAHAMENSWTISKEYHIDEEVGFALPNPQENLPDFYNDWMFIAKHLPDLI    50
ESGQLRERVEKLNMLSIDHLTDHKSQRLARLVLGCITMAYVWGKGHGDVR   100
KVLPRNIAVPYCQLSKKLELPPILVYADCVLANWKKKDPNKPLTYENMDV   150
LFSFRDGDCSKGFFLVSLLVEIAAASAIKVIPTVFKAMQMQERDTLLKAL   200
LEIASCLEKALQVFHQIHDHVNPKAFFSVLRIYLSGWKGNPQLSDGLVYE   250
GFWEDPKEFAGGSAGQSSVFQCFDVLLGIQQTAGGGHAAQFLQDMRRYMP   300
PAHRNFLCSLESNPSVREFVLSKGDAGLREAYDACVKALVSLRSYHLQIV   350
TKYILIPASQQPKENKTSEDPSKLEAKGTGGTDLMNFLKTVRSTTEKSLL   400
KEG                                                 403
```

Figure 3B

```
Mouse    1    MEPQSQSMTLEVPLSLGRYHISEEYGFLLPNPLEALPDHYKPWMEIALRLPHLIENRQLR    60
              MEP    ++    VPLSL  YHISEEYGFLLP+ L+ LPDHY+PWMEIA +LP LI+   QL+
Human    1    MEPHRPNVKTAVPLSLESYHISEEYGFLLPDSLKELPDHYRPWMEIANKLPQLIDAHQLQ    60

Mouse   61    AHVYRMPLLDCRFLKSYREQRLAHMALAAITMGFVWQEGEGQPQKVLPRSLAIPFVEVSR   120
              AHV +MPLL C+FLK +REQRLAH+ L+ +TMG+VWQEGE QP +VLPR+LA+PFVEVSR
Human   61    AHVDKMPLLSCQFLKGHREQRLAHLVLSFLTMGYVWQEGEAQPAEVLPRNLALPFVEVSR   120

Mouse  121    NLGLPPILVHSDLVLTNWTKRNPEGPLEISNLETIISFPGGESLRGFILVTVLVEKAAVP   180
              NLGLPPILVHSDLVLTNWTK++P+G LEI NLETIISFPGGESL GFILVT LVEK AVP
Human  121    NLGLPPILVHSDLVLTNWTKKDPDGFLEIGNLETIISFPGGESLHGFILVTALVEKEAVP   180

Mouse  181    GLKALVQGMEAIRQHSQDTLLEALQQLRLSIQDITRALAQMHDYVDPDIFYSVIRIFLSG   240
              G+KALVQ    AI Q +Q+ LL+ALQ+LRLSIQDIT+  L QMHDYVDPDIFY+ IRIFLSG
Human  181    GIKALVQATNAILQPNQEALLQALQRLRLSIQDITKTLGQMHDYVDPDIFYAGIRIFLSG   240

Mouse  241    WKDNPAMPVGLVYEGAATEPLKYSGGSAAQSSVLHAFDEFLGIEHCKESVGFLHRMRDYM   300
              WKDNPAMP GL+YEG + EPLKYSGGSAAQS+VLHAFDEFLGI H KES  FL+RMRDYM
Human  241    WKDNPAMPAGLMYEGVSQEPLKYSGGSAAQSTVLHAFDEFLGIRHSKESGDFLYRMRDYM   300

Mouse  301    PPSHKAFLEDLHVAPSLRDYILASGPGDCLMAYNQCVEALGELRSYHINVVARYIISAAT   360
              PPSHKAF+ED+H APSLRDYIL+SG      L AYNQCV+AL ELRSYHI +V +Y+I+AA
Human  301    PPSHKAFIEDIHSAPSLRDYILSSGQDHLLTAYNQCVQALAELRSYHITMVTKYLITAAA   360

Mouse  361    RA---RSRGLTNPSPHALEDRGTGGTAMLSFLKSVREKTMEALLCP    403
              +A   +    L  P P AL+DRGTGGTA++SFLKSVR+KT E++L P
Human  361    KAKHGKPNHLPGP-PQALKDRGTGGTAVMSFLKSVRDKTLESILHP    405
```

Figure 3C

```
  1 ATG GAG CCT CAA AGT CAG AGC ATG ACG CTG GAG GTG CCG   IDO2
    M   E   P   Q   S   Q   S   M   T   L   E   V   P
    M   A   L   S   K   I   S   P   T   E   G   S   R
  1 ATG GCA CTC AGT AAA ATA TCT CCT ACA GAA GGT TCT AGA   MU IDO

40 TTG TCC TTG GGG AGA TAC CAC ATT TCT GAG GAA TAT GGC
    L   S   L   G   R   Y   H   I   S   E   E   Y   G
    +           H   I           E   +           G
    R   I   L   E   D   H   H   I   D   E   D   V   G
 40 AGG ATC CTT GAA GAC CAC CAC ATA GAT GAA GAT GTG GGC

79 TTT CTC CTT CCA AAT CCT CTG GAA GCA CTT CCA GAT CAT
    F   L   L   P   N   P   L   E   A   L   P   D   H
    F       L   P   +   P   L           L   P   D
    F   A   L   P   H   P   L   V   E   L   P   D   A
 79 TTT GCT CTA CCA CAT CCA CTG GTG GAG CTG CCC GAC GCA

118 TAC AAG CCT TGG ATG GAA ATT GCC CTC AGA CTT CCT CAC
    Y   K   P   W   M   E   I   A   L   R   L   P   H
    Y       P   W   +           +   A           L   P
    Y   S   P   W   V   L   V   A   R   N   L   P   V
118 TAC AGC CCC TGG GTC CTT GTG GCT AGA AAT CTG CCT GTG

157 TTA ATC GAG AAC CGC CAG CTC CGA GCT CAC GTG TAC AGG
    L   I   E   N   R   Q   L   R   A   H   V   Y   R
    L   I   E   N       Q   L   R           V           +
    L   I   E   N   G   Q   L   R   E   E   V   E   K
157 CTG ATT GAG AAC GGG CAG CTT CGA GAA GAA GTT GAA AAG

196 ATG CCT CTC CTG GAC TGC AGA TTC CTA AAG AGT TAC CGT
    M   P   L   L   D   C   R   F   L   K   S   Y   R
    +   P   L                       L   +       +   R
    L   P   T   L   S   T   D   G   L   R   G   H   R
196 CTG CCC ACA CTG AGC ACG GAC GGA CTG AGA GGA CAC AGG

235 GAG CAG CGC CTG GCA CAC ATG GCG CTG GCC GCT ATC ACC
    E   Q   R   L   A   H   M   A   L   A   A   I   T
        Q   R   L   A   H   +   A   L               I   T
    L   Q   R   L   A   H   L   A   L   G   Y   I   T
235 TTA CAG CGC CTG GCA CAC CTG GCC CTG GGG TAC ATC ACC

274 ATG GGA TTC GTC TGG CAG GAG GGG GAA GGC CAA CCC CAA
    M   G   F   V   W   Q   E   G   E   G   Q   P   Q
    M       +   V   W           G   +                   +
    M   A   Y   V   W   N   R   G   D   D   D   V   R
274 ATG GCG TAT GTG TGG AAC CGA GGG GAT GAC GAT GTT CGA

313 AAG GTG CTG CCA AGA TCT CTT GCC ATT CCT TTT GTT GAG
    K   V   L   P   R   S   L   A   I   P   F   V   E
    K   V   L   P   R   +   +   A   +   P   +       E
    K   V   L   P   R   N   I   A   V   P   Y   C   E
313 AAG GTG CTG CCC CGC AAT ATT GCT GTT CCC TAC TGC GAG
```

Figure 3D

```
352  GTA TCC AGG AAC TTG GGA CTC CCG CCT ATC CTG GTC CAC
      V   S   R   N   L   G   L   P   P   I   L   V   H
      +   S   -   -   L   G   L   P   P   I   L   -   +
      L   S   E   K   L   G   L   P   P   I   L   S   Y
352  CTC TCA GAG AAG TTG GGC CTG CCT CCT ATT CTG TCT TAT

391  TCT GAC CTG GTG CTG ACA AAC TGG ACC AAA AGG AAC CCA
      S   D   L   V   L   T   N   W   T   K   R   N   P
      +   D   -   V   L   -   N   W   -   K   +   +   P
      A   D   C   V   L   A   N   W   K   K   K   D   P
391  GCA GAC TGT GTC CTG GCA AAC TGG AAG AAA AAG GAC CCC

430  GAA GGA CCG TTG GAA ATC AGT AAC CTG GAA ACC ATC ATC
      E   G   P   L   E   I   S   N   L   E   T   I   I
      -   G   P   +   -   -   -   N   +   +   -   +   -
      N   G   P   M   T   Y   E   N   M   D   I   L   F
430  AAT GGG CCC ATG ACA TAC GAG AAC ATG GAC ATT CTG TTC

469  TCA TTT CCG GGG GGA GAG AGC CTG CGG GGC TTC ATC CTA
      S   F   P   G   G   E   S   L   R   G   F   I   L
      S   F   P   G   G   +   -   -   +   G   F   -   L
      S   F   P   G   G   D   C   D   K   G   F   F   L
469  TCA TTT CCT GGT GGG GAC TGC GAC AAG GGC TTC TTC CTC

508  GTG ACA GTC TTG GTG GAG AAG GCA GCA GTG CCC GGC CTT
      V   T   V   L   V   E   K   A   A   V   P   G   L
      V   +   +   L   V   E   -   A   A   -   P   -   +
      V   S   L   L   V   E   I   A   A   S   P   A   I
508  GTC TCT CTA TTG GTG GAA ATC GCA GCT TCT CCT GCA ATC

547  AAG GCC CTG GTT CAG GGA ATG GAG GCC ATT CGG CAA CAC
      K   A   L   V   Q   G   M   E   A   I   R   Q   H
      K   A   +   -   -   -   -   -   A   +   -   +   -
      K   A   I   P   T   V   S   S   A   V   E   R   Q
547  AAA GCA ATC CCC ACT GTA TCC AGT GCA GTA GAG CGT CAA

586  AGT CAG GAC ACC CTG CTA GAA GCC CTG CAG CAG CTG AGA
      S   Q   D   T   L   L   E   A   L   Q   Q   L   R
      -   -   -   -   L   -   +   A   L   -   -   +   -
      D   L   K   A   L   E   K   A   L   H   D   I   A
586  GAC CTG AAA GCA TTG GAA AAG GCA CTG CAC GAC ATA GCT

625  CTC TCC ATC CAG GAT ATC ACC AGA GCC TTG GCC CAA ATG
      L   S   I   Q   D   I   T   R   A   L   A   Q   M
      -   S   +   +   -   -   -   -   -   -   -   +   M
      T   S   L   E   K   A   K   E   I   F   K   R   M
625  ACC AGT CTG GAG AAA GCC AAG GAA ATT TTT AAG AGG ATG

664  CAT GAT TAT GTG GAC CCA GAC ATA TTT TAC TCG GTC ATC
      H   D   Y   V   D   P   D   I   F   Y   S   V   I
      -   D   +   V   D   P   D   -   F   +   -   V   +
      R   D   F   V   D   P   D   T   F   F   H   V   L
664  CGT GAC TTT GTG GAC CCA GAC ACG TTT TTC CAC GTT CTC

703  CGG ATC TTC CTC TCT GGG TGG AAG GAC AAT CCA GCC ATG
      R   I   F   L   S   G   W   K   D   N   P   A   M
      R   I   +   L   S   G   W   K   -   +   -   -   +
      R   I   Y   L   S   G   W   K   C   S   S   K   L
703  CGC ATA TAT CTG TCT GGC TGG AAA TGC AGC TCC AAG CTG
```

Figure 3E

```
742  CCT GTG GGG CTG GTC TAT GAA GGT GTT GCC ACA GAG CCT
      P   V   G   L   V   Y   E   G   VA  A   T   E   P
      P   -   G   L   +   Y   E   G   V   -   -   -   P
      P   E   G   L   L   Y   E   G   V   W   D   T   P
742  CCA GAA GGT CTG CTG TAT GAG GGG GTC TGG GAC ACC CCA

781  CTG AAG TAC TCT GGA GGA AGT GCA GCC CAG AGC TCC GTG
      L   K   Y   S   G   G   S   A   A   Q   S   S   V
      -   -   +   S   G   G   S   A   -   Q   S   S   +
      K   M   F   S   G   G   S   A   G   Q   S   S   I
781  AAA ATG TTT TCA GGG GGC AGT GCA GGC CAG AGC AGC ATC

820  CTT CAT GCC TTC GAT GAG TTC CTG GGC ATT GAG CAT ---
      L   H   A   F   D   E   F   L   G   I   E   H
      -   -   +   -   D   -   -   L   G   I   +   H   -
      F   Q   S   L   D   V   L   L   G   I   K   H   E
820  TTC CAG AGT CTT GAT GTC CTT CTG GGA ATA AAA CAC GAG

859  --- TGC AAG GAA AGT --- GTT GGC TTT CTA CAC AGA ATG AGG GAC TAC
      -   C   K   E   S       V   G   F   L   H   R   M   R   D   Y
      -   -   K   E   S   -   -   F   L   -   -   M   R   +   Y
      A   G   K   E   S   P   A   E   F   L   Q   E   M   R   E   Y
859  GCT GGC AAA GAA TCT CCT GCA GAA TTC CTC CAG GAA ATG AGA GAG TAC

898  ATG CCG CCT TCC CAT AAG GCT TTC CTG GAA GAT CTC CAC
      M   P   P   S   H   K   A   F   L   E   D   L   H
      M   P   P   +   H   +   -   F   L   -   -   L   -
      M   P   P   A   H   R   N   F   L   F   F   L   E
898  ATG CCT CCA GCC CAC CGG AAC TTC CTT TTC TTC TTA GAG

937  GTA GCT CCT TCT CTG AGA GAC TAC ATA CTG GCC TCT GGT
      V   A   P   S   L   R   D   Y   I   L   A   S   G
      -   A   P   -   +   R   +   +   +   +   -   -   -
      S   A   P   P   V   R   E   F   V   I   S   R   H
937  TCA GCT CCC CCA GTC CGT GAG TTT GTC ATT TCA AGA CAC

976  CCT GGG GAC TGC CTG ATG GCC TAT AAC CAG TGT GTG GAG
      P   G   D   C   L   M   A   Y   N   Q   C   V   E
      -   -   D   -   -   -   A   Y   N   +   C   V   -
      N   E   D   L   T   K   A   Y   N   E   C   V   N
976  AAT GAA GAC TTG ACG AAA GCT TAT AAC GAG TGT GTG AAT

1015 GCC CTG GGA GAG CTG CGC AGT TAC CAC ATC AAT GTC GTG
      A   L   G   E   L   R   S   Y   H   I   N   V   V
      -   L   -   -   +   R   -   +   H   +   -   +   V
      G   L   V   S   V   R   K   F   H   L   A   I   V
1015 GGT CTG GTC TCT GTG AGA AAG TTC CAC CTC GCA ATA GTA

1054 GCC AGA TAC ATT ATC TCC GCT GCC ACC AGG GCC AGG AGC
      A   R   Y   I   I   S   A   A   T   R   A   R   S
      -   -   Y   I   +   -   -   +   -   +   -   -   +
      D   T   Y   I   M   K   P   S   K   K   K   P   T
1054 GAT ACT TAC ATT ATG AAA CCT TCG AAG AAG AAG CCC ACT
```

Figure 3F

```
1093  AGG GGG CTA ACT AAT CCC TCA CCC CAT GCC TTG GAA GAC
       R   G   L   T   N   P   S   P   H   A   L   E   D
       -   G   -   -   +   -   -   P   -   -   +   E   -
       D   G   D   K   S   E   E   P   S   N   V   E   S
1093  GAT GGC GAC AAG TCG GAA GAG CCC TCA AAT GTG GAA AGC

1132  AGG GGC ACT GGG GGT ACT GCC ATG CTG AGC TTC TTG AAG
       R   G   T   G   G   T   A   M   L   S   F   L   K
       R   G   T   G   G   T   -   -   +   +   F   L   +
       R   G   T   G   G   T   N   P   M   T   F   L   R
1132  AGA GGG ACT GGG GGT ACG AAT CCC ATG ACT TTC CTA AGG

1171  AGT GTC AGG GAG AAG ACC ATG GAG GCC CTC CTG TGT CCT
       S   V   R   E   K   T   M   E   A   L   L   C   P
       S   V   +   +   -   T   -   +   A   L   L
       S   V   K   D   T   T   E   K   A   L   L   S   W
1171  AGT GTG AAA GAT ACA ACC GAG AAA GCT CTT CTG AGT TGG

1210  GGT GCT TAG
       G   A   -
       P   -
1210  CCT TAG
```

Figure 3G

```
agtccagatgatagttaagaaagcagtaagaatacagagagtccacaatg      50
agatgaaaatgcactgccagttgaaacatcctcctacactggagctttat     100
aaatattttaaagacaaggattggattagatttgacattagaaatgtacc     150
ataatacagaaggcaatggacacctaaagaacagaatgaaaaccttctta     200
ggaaatgaagcttgacacttcacccaccaggccaccacaagaATGTTGCA     250
TTTTCATTATTATGATACTTCAAACAAAATAATGGAGCCCCACAGACCGA     300
ATGTGAAGACAGCAGTGCCATTGTCTTTGGAAAGCTATCACATATCTGAA     350
GAGTATGGCTTTCTTCTTCCAGATTCTCTGAAAGAACTTCCAGATCATTA     400
TAGGCCTTGGATGGAAATTGCCAACAAACTTCCTCAATTGATTGATGCTC     450
ACCAGCTTCAAGCTCATGTGGACAAGATGCCCCTGCTGAGCTGCCAGTTC     500
CTGAAGGGTCACCGGGAGCAGCGCCTGGCCCACCTGGTCCTGAGCTTCCT     550
CACCATGGGTTATGTCTGGCAGGAAGGAGAGGCGCAGCCTGCAGAGGTCC     600
TGCCAAGGAATCTTGCCCTTCCATTTGTCGAAGTCTCCAGGAACTTGGGG     650
CTCCCTCCTATCCTGGTCCACTCAGACTTGGTGCTGACAACTGGACCAA     700
AAAGATCCAGACGGGAACCTGGAGACCATCATCTCATTTCCTGGGGGAG     750
AGAGCCTGCATGGTTTTATACTGGTGACTGCTTTGGTAGAGAAAGAAGCA     800
GTGCCTGGGATAAAGGCTCTTGTTCAGGCCACGAATGCTATCTTGCAGCC     850
CAACCAGGAGGCCCTGCTCCAAGCCCTGCAGCGACTGAGACTGTCTATTC     900
AGGACATCACCAAAACCTTAGGACAGATGCATGATTATGTAGATCCAGAC     950
ATATTTTATGCAGGCATCCGGATCTTTCTCTCTGGATGGAAAGACAACCC    1000
AGCAATGCCTGCAGGGCTGATGTATGAAGGAGTTTCCCAAGAGCCCCTGA    1050
AATACTCCGGCGGGAGTGCAGCTCAGAGCACAGTGCTTCATGCCTTTGAT    1100
GAGTTCTTAGGCATTCGTCATAGCAAGGAAAGTGGTGACTTTCTGTACAG    1150
AATGAGGGATTACATGCCTCCTTCCCATAAGGCCTTCATAGAAGACATCC    1200
ACTCAGCACCTTCCCTGAGGGACTACATCCTGTCATCTGGACAGGACCAC    1250
TTGCTGACAGCTTATAACCAGTGTGTGCAGGCCCTGGCAGAGCTGCGGAG    1300
CTATCACATCACCATGGTCACCAAATACCTCATCACAGCTGCAGCCAAGG    1350
CAAAGCATGGGAAGCCAAACCATCTCCCAGGGCCTCCTCAGGCTTTAAAA    1400
GACAGGGGCACAGGTGGAACCGCAGTTATGAGCTTTCTTAAGAGTGTCAG    1450
GGATAAGACCTTGGAGTCAATCCTTCACCCACGTGGTgagaggctgccc    1500
tctccccagcaatgcagagccccatggagggcaggtgggcctggagaat    1550
gagggtcagggttctgcctgggatcatccaggaaggatctcagccctatt    1600
catgtttctgctctacagagcactatattctccttgttgagagctgttgg    1650
cttcacaaaggagagttgatgtggccaagcctttccctccctacctgatc    1700
actgcttaacggcatgtataatggatacttcctcatgcagaaccccaga    1750
ggagtgactgtatgccattctctttgccaagtaatagaaaaccaatctaa    1800
atgtcaaaaatcagataaaattgccggggatacattacttgttgatttt    1850
cttaaaaaacaaattcacttaacaattcattaagttcatactgagcactg    1900
cctccaagattaaaaccaggatttctgtggtcccagaccagccctcttct    1950
ccctgaatgtgttgagttggtggcaggaggttggaaatgctccagtggag    2000
atgggaagatagaggatgctgacaataaggacttggaagtcactagtgtg    2050
aaaatgagcagttaatgatatgggaacggatgagacttccacgtggtac    2100
ctagatttgcaaattctattgtaatgcctttattttagaagaattattc    2150
tctcttcttactctgaaaatctgtatttgtaaaatgaatgaatggatcct    2200
atataagtaaataagaaactgggaataagtagtaaatcaatgtgtttag    2250
tgtgcaaataaatgtaaatgcttttattg                        2279
```

Figure 4A

```
cgcacaagtacaaccacacagaagacacagctggaaagctccctggcctg     50
ggcattcctctggggcagagacctcacgcgaaaatatggagcctcaaagt    100
cagagcATGACGCTGGAGGTGCCGTTGTCCTTGGGGAGATACCACATTTC    150
TGAGGAATATGGCTTTCTCCTTCCAAATCCTCTGGAAGCACTTCCAGATC    200
ATTACAAGCCTTGGATGGAAATTGCCCTCAGACTTCCTCACTTAATCGAG    250
AACCGCCAGCTCCGAGCTCACGTGTACAGGATGCCTCTCCTGGACTGCAG    300
ATTCCTAAAGAGTTACCGTGAGCAGCGCCTGGCACACATGGCGCTGGCCG    350
CTATCACCATGGGATTCGTCTGGCAGGAGGGGGAAGGCCAACCCCAAAAG    400
GTGCTGCCAAGATCTCTTGCCATTCCTTTTGTTGAGGTATCCAGGAACTT    450
GGGACTCCCGCCTATCCTGGTCCACTCTGACCTGGTGCTGACAAACTGGA    500
CCAAAAGGAACCCAGAAGGACCGTTGGAAATCAGTAACCTGGAAACCATC    550
ATCTCATTTCCGGGGGGAGAGAGCCTGCGGGGCTTCATCCTAGTGACAGT    600
CTTGGTGGAGAAGGCAGCAGTGCCCGGCCTTAAGGCCCTGGTTCAGGGAA    650
TGGAGGCCATTCGGCAACACAGTCAGGACACCCTGCTAGAAGCCCTGCAG    700
CAGCTGAGACTCTCCATCCAGGATATCACCAGAGCCTTGGCCCAAATGCA    750
TGATTATGTGGACCCAGACATATTTTACTCGGTCATCCGGATCTTCCTCT    800
CTGGGTGGAAGGACAATCCAGCCATGCCTGTGGGGCTGGTCTATGAAGGT    850
GCTGCCACAGAGCCTCTGAAGTACTCTGGAGGAAGTGCAGCCCAGAGCTC    900
CGTGCTTCATGCCTTCGATGAGTTCCTGGGCATTGAGCATTGCAAGGAAA    950
GTGTTGGCTTTCTACACAGAATGAGGGACTACATGCCGCCTTCCCATAAG   1000
GCTTTCCTGGAAGATCTCCACGTAGCTCCTTCTCTGAGAGACTACATACT   1050
GGCCTCTGGTCCTGGGGACTGCCTGATGGCCTATAACCAGTGTGTGGAGG   1100
CCCTGGGAGAGCTGCGCAGTTACCACATCAATGTCGTGGCCAGATACATT   1150
ATCTCCGCTGCCACCAGGGCCAGGAGCAGGGGGCTAACTAATCCCTCACC   1200
CCATGCCTTGGAAGACAGGGGCACTGGGGGTACTGCCATGCTGAGCTTCT   1250
TGAAGAGTGTCAGGGAGAAGACCATGGAGGCCCTCCTGTGTCCTGGTGCT   1300
tagcagtcatgtcctgcaccctaacacttagatgttctcatcctgcatcc   1350
cagcgttagaggttcacatcctgcatcctagtgcttagctgttcttgtgc   1400
tatatcccagcgcttagcagtcatgtcctgcatcctagtgcttagcattt   1450
tatatccagcatttagtgcttagagattcacatcctgcatcctagagct   1500
tagcattttatatccagcatccttgtgcgtatcagctatgttttgtatcc   1550
tgcttagcagttaacatcctgcatcctagtacttatctgttctcatcctg   1600
catcctagagcttagcagtcaggtcccgtgggagcaagaaccagggtctg   1650
agctctgtctgagcccaagcatggctttactgctttgttaattgtggctc   1700
ccacctccaccccaccccagccagtttgcttgctagaagcctttctgcac   1750
tgcctaatcccctgcctcacagcagagagctgcagccatgacctcctca   1800
ttcagtattaggtggacaagtcggagatacccaaactcaattttaaaaga   1850
atcaagttgcttttggggcatgttacttcatcttttcttaccctgggcct   1900
cttcccttcttccctacctccctcgtcccttagtcttcacccctctctc   1950
tttctccttttgtcaccctcccctccctgcttactctcttttcccttc   2000
cccctctcctcatccctccttcctttcttccttcccttttgtctgtga   2050
agcaccaggtctgatgggcctcaaactgtgatcttcctgtctcacccttc   2100
aaaggttatgtgtatgtgacgtgtgtgtgtgtgtgtgtgtgtgtgtgtgt   2150
gtgtgtgttcgtttcttttgttttccctagtggagatgacacccaaga    2200
tttgcacataccaggcaattgctccaccacctgactacagtcccagctct   2250
ctgtattcctgaaggaaagtcttgatgagttgcctaggctggtattgagc   2300
tctttagcccaggcaggccttagtctgagtagctgggatgtacagggatg   2350
agccactgagccatgctgctgctgctaacgatgatgacgatgatgatgat   2400
gaagattatgataactacagtcactgcaataatgacggcaaagataatga   2450
aaaaaaaaaaaaa                                        2464
```

Figure 4B

```
ATGGAGCCCCACAGACCGAATGTGAAGACAGCAGTGCCATTGTCTTTGGA          50
AAGCTATCACATATCTGAAGAGTATGGCTTTCTTCTTCCAGATTCTCTGA         100
AAGAACTTCCAGATCATTATAGGCCTTGGATGGAAATTGCCAACAAACTT         150
CCTCAATTGATTGATGCTCACCAGCTTCAAGCTCATGTGGACAAGATGCC         200
CCTGCTGAGCTGCCAGTTCCTGAAGGGTCACCGGGAGCAGCGCCTGGCCC         250
ACCTGGTCCTGAGCTTCCTCACCATGGGTTATGTCTGGCAGGAAGGAGAG         300
GCGCAGCCTGCAGAGGTCCTGCCAAGGAATCTTGCCCTTCCATTTGTCGA         350
AGTCTCCAGGAACTTGGGGCTCCCTCCTATCCTGGTCCACTCAGACTTGG         400
TGCTGACGAACTGGACCAAAAAGATCCAGACGGGTTCCTGGAAATTGGG          450
AACCTGGAGACCATCATCTCATTTCCTGGGGGAGAGAGCCTGCATGGTTT         500
TATACTGGTGACTGCTTTGGTAGAGAAAGAAGCAGTGCCTGGGATAAAGG         550
CTCTTGTTCAGGCCACGAATGCTATCTTGCAGCCCAACCAGGAGGCCCTG         600
CTCCAAGCCCTGCAGCGACTGAGACTGTCTATTCAGGACATCACCAAAAC         650
CTTAGGACAGATGCATGATTATGTAGATCCAGACATATTTATGCAGGCA         700
TCCGGATCTTTCTCTCTGGGTGGAAAGACAACCCAGCAATGCCTGCAGGG         750
CTGATGTATGAAGGAGTTTCCCAAGAGCCCCTGAAATACTCCGGCGGGAG         800
TGCAGCTCAGAGCACAGTGCTTCATGCCTTTGATGAGTTCTTAGGCATTC         850
GTCATAGCAAGGAAAGTGGTGACTTTCTGTACAGAATGAGGGATTACATG         900
CCTCCTTCCCATAAGGCCTTCATAGAAGACATCCACTCAGCACCTTCCCT         950
GAGGGACTACATCCTGTCATCTGGACAGGACCACTTGCTGACAGCTTATA        1000
ACCAGTGTGTGCAGGCCCTGGCAGAGCTGCGGAGCTATCACATCACCATG        1050
GTCACCAAATACCTCATCACAGCTGCAGCCAAGGCAAAGCATGGGAAGCC        1100
AAACCATCTCCCAGGGCCTCCTCAGGCTTTAAAAGACAGGGGCACAGGTG        1150
GAACCGCAGTTATGAGCTTTCTTAAGAGTGTCAGGGATAAGACCTTGGAG        1200
TCAATCCTTCACCCACGTGGTTAGGAT                               1227
```

Figure 4C

```
ATGGAGCCTCAAAGTCAGAGCATGACGCTGGAGGTGCCGTTGTCCTTGGG      50
GAGATACCACATTTCTGAGGAATATGGCTTTCTCCTTCCAAATCCTCTGG     100
AAGCACTTCCAGATCATTACAAGCCTTGGATGGAAATTGCCCTCAGACTT     150
CCTCACTTAATCGAGAACCGCCAGCTCCGAGCTCACGTGTACAGGATGCC     200
TCTCCTGGACTGCAGATTCCTAAAGAGTTACCGTGAGCAGCGCCTGGCAC     250
ACATGGCGCTGGCCGCTATCACCATGGGATTCGTCTGGCAGGAGGGGGAA     300
GGCCAACCCCAAAAGGTGCTGCCAAGATCTCTTGCCATTCCTTTTGTTGA     350
GGTATCCAGGAACTTGGGACTCCCGCCTATCCTGGTCCACTCTGACCTGG     400
TGCTGACAAACTGGACCAAAAGGAACCCAGAAGGACCGTTGGAAATCAGT     450
AACCTGGAAACCATCATCTCATTTCCGGGGGGAGAGAGCCTGCGGGGCTT     500
CATCCTAGTGACAGTCTTGGTGGAGAAGGCAGCAGTGCCCGGCCTTAAGG     550
CCCTGGTTCAGGGAATGGAGGCCATTCGGCAACACAGTCAGGACACCCTG     600
CTAGAAGCCCTGCAGCAGCTGAGACTCTCCATCCAGGATATCACCAGAGC     650
CTTGGCCCAAATGCATGATTATGTGGACCCAGACATATTTTACTCGGTCA     700
TCCGGATCTTCCTCTCTGGGTGGAAGGACAATCCAGCCATGCCTGTGGGG     750
CTGGTCTATGAAGGTGTTGCCACAGAGCCTCTGAAGTACTCTGGAGGAAG     800
TGCAGCCCAGAGCTCCGTGCTTCATGCCTTCGATGAGTTCCTGGGCATTG     850
AGCATTGCAAGGAAAGTGTTGGCTTTCTACACAGAATGAGGGACTACATG     900
CCGCCTTCCCATAAGGCTTTCCTGGAAGATCTCCACGTAGCTCCTTCTCT     950
GAGAGACTACATACTGGCCTCTGGTCCTGGGGACTGCCTGATGGCCTATA    1000
ACCAGTGTGTGGAGGCCCTGGGAGAGCTGCGCAGTTACCACATCAATGTC    1050
GTGGCCAGATACATTATCTCCGCTGCCACCAGGGCCAGGAGCAGGGGCT    1100
AACTAATCCCTCACCCCATGCCTTGGAAGACAGGGGCACTGGGGGTACTG    1150
CCATGCTGAGCTTCTTGAAGAGTGTCAGGGAGAAGACCATGGAGGCCCTC    1200
CTGTGTCCTGGTGCTTAG                                   1218
```

Figure 4D

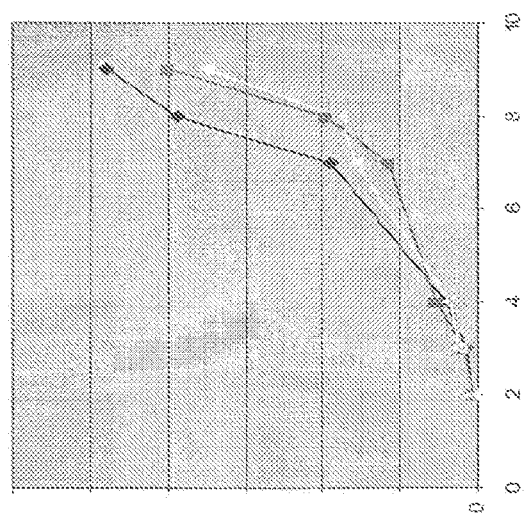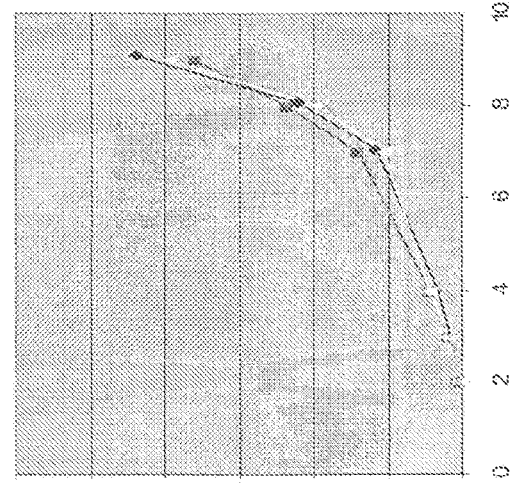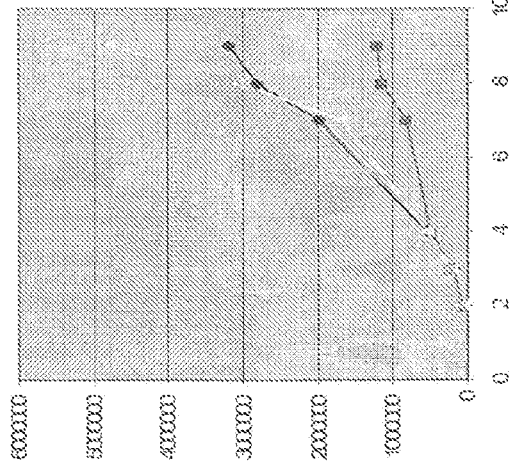
Figure 6

```
TAGTTAGAAG GCAGCTCGTT TCCAGACAGA TCATGCCGGG CCAGCACAGT TCCACGAGGA
GCGATTTTTT TGGATGGGGG AAGAAAGTGA AGAAGAGGAG AAAGAGGAAA AGGGGGTGAA
GGGTCGCGGT CTCAGTCTTT TATTTGTGCC ATGACATAGA TGCCAGGTAA TGAATGATGA
ATGATGCGCA CAGGTGAAGC ATAGGCCTGC CTGGAGTGTA TGGTGGTTGC CATGGCAACA
GACCCAAGAG GGTCCTTGTC GCTTAGGGAT GATGTCATAG CTGGATTCCG AGGCTGGTTG
TAAAGCAGTT TCTGATGCTA ACAATACATA TATATGTAAT GATAACAAAG AAAAAGAGGC
CATGAATTTG AAAGGAAGGA AAGAAGTTAG GAAGGAAGGA AGGAAGGAAG GAAGGAAGGA
AGGAAGGAAG GAAGGAAGGA AGGAAGGAAG GAAGGAAAGA AGATGGGAAT TTGGAGAGAT
GAAAGGGAAG AATGATATAA ATACATTTTA ATTTCAGCAA ATAAATACAT TTTCAAAGAT
AAAAAGCCAA TAAAGAGAAA CCCTGTCTCG AAAAAACAAC AACAAACCAA AAACAAACAA
ACAAACAAGC CAATAAAACT GACTCCTAGT TTAGTCATTT TGATACACTG TCAGAATCCC
TCAGGAACCA AACTCATGTT GAGTATGGAT CTGCACAGCC ATAGCTGAGA GTTAAGTTCG
TGTCTCCCAC TTTGTCCCTG GATTAACAG CCCCTTTCTC ATACTTTATG AATGAGAAGG
GAAAGGGGGT GGGGGCTTCT CTTGGAGTCA GCATTTTAAT TCCTAATCTT CATTGTTGAC
TTACTACTTG GCTTTCTTTC AGAATAAATT TGCGGCCATC CTGGAGTTCA ACCTCAGGGC
AAGGTTCTCC CCTACCGCTG AAGCACCGCA CAAGTACAAC CACACAGAAG ACACAGCTGG
AAAGCTCCCT GGCCTGGGCA TTCCTCTGGG GCAGAGACCT CACGCGAAAA TATGGAGCCT
                                                          >>......>
CAAAGTCAGA GCATGACGCT GGAGGTGCCG TTGTCCTTGG GGAGATACCA CATTTCTGAG
>..........................exon 1 ...........................>
GAATATGGCT TTCTCCTTCC AAATCCTCTG GTAAGGATTG GCTTGTCCTG GTCAGCACAT
>...........exon1 ............>>
GTGTCTGGAT TGTTAGTCTT TACCTTATGT GGTTATTGGA AGGTTCGGTA TAAGTCACCA
GCTGGAGGAA GAGTGGGAAT ACAGTCCTGT GAGTCCCGGA AGAGCAGAGG CAACTGCTAC
TGGGACAGC ACAAAGCCAG TGGTCCCCTC CCCCCAGCCC CCAAAGTTTC CTTAAATCTA
TGGTAGTTAG CACTGACTAA TCAGAAGCAA AGGTGCTATC AGAGAGGAGA GACTGGATGG
AGACATGCCC TAAGGACAAT TAGAACCCTA TAACTACAGC AAAGAGTGGA CATGCACACA
ACCACATGGT GTGACACAGA ATAATGGAGT GGCCCCACTG TATATCCACT CTGCTTTGGA
GACAGGTTCG CCATGCATCC CAGACCTAAG CAGCCAAAGG GCTTAGCCTT CTGTGTTGAT
GCAAACCAGT TTATCTTACT TGCTGGTGAC AGCAGAGATA ATGGGAGACC TGCAATGTTT
TTAGAGCCAG TAAGAAGATT AGATGTTATC GGGAATTTCC GATACTCGTG AGGAATGTTG
GAAAACAAGC AGGCCTGACT TCAGTCCAA CTGCACAGCA GTCTCTAGTA TACCTGCTCT NgoMIV
                         ------
                          NaeI
                         ------
TGTTAAGTGT AGTCTGGGCT TGGGAGACAT ATGCCGGCAA AGTGCTAGTG GCAAAGCCCA
TGCTTTTGGC ATCTTTTAAA AACTGACCGT ACCTAAGGGA GGGTGAAGGC CACTGAGTTA
AAAGTCCAGG GACCCGATGT TGCAGTCGCG GTAACTGCTG ATCAGCACCA ACTCACCTAG
TTCCTCTCTT ACTTGTGATT AAAAATATCA GGGTCTCAAA CACCTATCAC AGTGAGACTC
TTGTTGTTTT GAAACAGAGA ATATTGATTT ATGTAGCCCA GGCTGGCCAC TTGCCTCCAC
TTCCTTACTG CTGGGACCAT AGCTGAACTC CCACAGCAGA TCCTTTTGTG TTGAACGGTA
CTGGAGGGAT CTAATTGAAG AGAACTAAGT TCTCCACAGA AAGATGTCAG CTACGACATC
GGTCATAGAC ATCTGCAAGC TGTCCAGGTT AGGGGTTAGT CATTAGAACC AGGGCCAGAT
CTCACAGCTT GAATCAAGCC AGGCCTTCCT GCTGCTCTCT CACGGACAGT TAGGAAGCAG
ACTGTACTCT GACATGATAG CTTGCAGCCG ACGGCTCCCG GCTCCTCTGT GCTCCTTGTC
ACGCAGGCCC TGCTATAAAC TAAAGTGTCT GACATGACTT CCTGGTGCCT CGTAAAGTTA
TTAAAAGTCA GATTTCTCCT TTGTTCTCGG AATTGGTTCG AGAGCCCTCA GGGGATTTGC
TGAGGGTGTG TGTGTGTGTG TGTGTGTGTG TGTGTGTGTG TGTATTCTAA GAGTGCTTCC
CTAAAAGGGT CCTCTGTACT GTCAACGGAT CTTTCATAGT CTCTCTCTCC CTGTCTCCCT
GTCTCTCTGT CTTTCTGTCT CTCTGTCTCT CTCTGTTTCT GTCTTTCTGT CTCTGTCTGT
CTGTCTGTCT GTCTATCTCT GTGTGTGTGT GTGTATTTTG AAGGTAGGAG GATCTGAGCC
TGAACTACAC ACAGCTAGAT CCTGTGACTC TGTCTCAAAA CAGAGACACA ATCAAACTCT
CAACTAATCG AAACACCACA AGGCACACTC CATTCTGGGT GTGTGGTCTC AGTCCAGCGT
ATTCCCATCC TTCCAAGTTT ACAGGAGAGG AAGGGCTGAT GGCAGATACA CCCTTGTCAT
TACTGGGCAT GTGTCCTGAG TTTGGAAAGA GAACACTGCC AAGCAGGGGA ACGAATATCA
GGGCAGGCCA TAGCTCTGGG GCTTTCTGGG CTGCTTTCCT CTTTGTAAAT ACTGGGACCA
```

Figure 10A

```
GGCAGACATA CAGATAAGAC ACAATAGCAA CATCAAGTTT CCCCCCTATT TGTTAGAAAG
GTTCTATGGT ATGGTGTGAT GGATGGGTAC CCCTTAAAAG AGGTCCCTAG TGCTGTTCAC
ACAGAAAGGA AATATTCCCT GTCCCACCCA GCTACTCATT TATAGCCCAG TAATTTCAAT
ATGATTCTTT CTGTTTCAAT TTTCTTTCAT TCAAGTGATG GTTTCAATG TCTTTTTTGT
TAAAGGAAGA GGAAGAAACC TTGACTAGGA TCAGGTCCTG GCTGCTCCAA AGGTCAAGAC
AGACTCAGTT CGACTTCACT GGACAAACAG TCCTGCAACT TTACACTGGT TGGGAAAGAA
CAGTGGGTTT GGCCCAGTCC AGTGCCCTAG GGCATAGCCA AGACCTGTTC TTCTTGGGCC
AAGGGCAAGT GGTAGGTGGC AGACCTTCCC CATCTCTTTC AGAAAGTCTC ACTTAAGAAA
ACCTAGCTGG CTAGCAAGTT CAAGGGTATA AATTACCCTA TCCAGCTGTT TCTATCAATT
CAAAGACTTC CAATTTTTAG TGTCTCTATG GAACTTTGCT CCTCGAATCT GTAAAAATAC
CACAAGAATT CTTTGCTAAG ACATCTGTCC TCTGTGTATA TTTGGGAGGA CAAGACATCT
TTTTCAGATG AAGAATGTGA GGAAATCAGT TTGCAGGAGA GGAGGCAGTT AAGAGGAGGC
AGCAAGAGGC TGGCCTGCAG CAGAGCTATG ACCCCAAGTG CCAGGCCCAC TCTGAAAATT
GATTTAACAC CCTTCCTAAA CACAATGTGA CTGCTACTTG AGTCATTTCC TCTCACAGCA
CTAAGGGCAG GGCAGGTTAG AGCAGTGGGT CCTGGGCTGT GGGGTGAGAC CTTTAGGGGA
GTTTCAACAA ACAATCCAGA TGCCAGAGCC CCACCCTGTT TATTCAGACT CTAGACCCAA
GAGCTGTACG CTGGGAAGGC CAGATAGGGA GAACAAGCCA GAGAATGCCA GACAGGGAGC
ACAAGCCAGC AAAGTCAGCC GTGAAGGTGC CACGGCCAAT AGAGACTCCT AAGTGCGAAA
ATAAATAAAC TGATGACATG CCCACTCCAT GCTTAAGGGG AAAGTAGATC AGAGAGGGAG
AGAGAGAGAG AGAGAGAGAG GCACCCAGAG GCAGAGGCCT CTGGACGATT CCGTAGTAGA
TAGAGAAAGC AGACTGAAGA TGGCCACCAG ACTGGACATG GCCAAGGCTA CCTGGGAGGA
AAGGAAGAAC AACAGAAGTC AGAGAATAGA GAAAACCTAG TGAGAGAAGC AGGAAGGGGT
TGGGGGGGTG GATGGAGAGA AGTTAGCAAT GACAGCAGGG TTCTAAGAAG AAAGAGTTGG
GGAGGGGAGA TCCTGTGAGC TGGAGGGAGT GGAGTGAGTG GAGGGGAAGA GCTGAGAAGG
GACAGATGCT AGCAGGGGCT TTGAGATGTA CAGCAGGTAC TTGTGATAGG TGACTGGAGG
CCACTGGTGA CCACATGTCC CTTCTGCAAG AGGTAAGGGA AAACATTCCT TTAGGTAGAG
GGAAACCAGT GTCACAAGTC CCTGAGGAAA GCTGGCTTTT TATCTAACCC CCAGAAATCC
TCCTGTAGTC CAGGTGAAGC TCATTTCTGG ACATACAGAC TGCCTTTTGG AGTTTGGGGA
ACTGGAGTTT CCTTTGGACC TGACAGTCAG GAGACGTTGC ACATGTAACG TAGGGGTAGA
CACAAGACTG ACAGGAATGG CAATGAGAGA GGACAACCTC CAGGGAAAAA CCAACATGTC
CCTTCTCATT CAGAAATTCT AAGCACTTGG TTGAAGCATT GGGCCACAGC TGGAGAGAAG
ACCGGATAGG AAATTAATTG CCACGGACAT CTGTATTTTT CAGATAAGAC AAAAAGGAAG
AGGTCTAACA TTGTCCTGAA ATATGAGGTT GCCACTGATG ATCTCTGGAC ACATCAGACT
AGTCAGATAG GGGACTTGAA ACACAATGAA TCCAGAGTCT GTAGTAGAGA CAAAGAGGCC
AGATTGCAAA ATGGTTAATC TTGATCAAGG CTGGAAAATG TGTATGGAAA TAAGAGAGAC
TGTAATATCT TAAGAATGGG GTTTGTCCTT GTGCCAGTAT TAAAGAACAA CAACAAAAAA
AAAAAAAAAA GAAAAGAAA AGAAAGAAA GAAAGAAAGA GAGAAAGAAA GAAAGAGAAA
AAGAAAAATG GAGGAAAGTC ATGGGGAAAC AGGTAATCAG GCTTGAATTA AAAAAATAAA
AAAATAAAAT AAAAAGTTAA AGGACTTGAC TAGTCCCAGG TTTCTGCACA GATGAATTAA
AAAATGAAAA GAAAAGAAAA GAAAAGAAAA GAAAAGAAAG GAAAAAAAG AAAAAAAGAA
AGGAAAAAAA AAGGAAAGAG AAAAACAAAA GACAGGAAAA GAAGGGAGGA AGGAAGAAGA
GAAAGAAAGA AAGACAGACA GAAAGAGAGA GAGAAAGGAA GGAAGAAAGG AAGAGAGAAA
GAAAGAAAGA AAGAAAGAAA GAAAGAAAGA AAGAAAGGAA GGAAGGAGGA AGGAAGGAAG
GAAAGAAAGA AAAGAAAAGA AAAGAAAAGA AAAGAAAAGA AAAGAAATGA AAAGAAAAGA
AAAGAAAAGA AAAGAAAAGA AAAGAAAAGA AAAGAAAAGA AAAGAGAGGA AGGAAGACAG
AGGAAAGGGC CTGGCTGCTT GTAGGTACTG TAGCCCGGGA GATCATAGCC AGAGGCAAGG
ACAGCTAGGG AAATCCAGAG TGGTCATGAC CGTGAACCAC TTGAGGAGAG GGAAGAGAAA
AGGGCAGCCC AGCCCCCAGG CTAGAGAAGT TTAGGGTTGG GGCAGGGTTT GTCAGCCAGT
GGGTCTTTGT AACTCCCGAG AACTTGTAGG CGGCTTTGAT ATGCTAAGTA GGCACCTCAG
CCTTTCCTCT TGGGTTTGAA ACCCAGAAGG CCTCAGCAAG TGGGACAAGC CAAGCCCAAC
TTGGAAAGCA GAGTTTTAAA GGGTGAAACA ACCAACCAAA AAGGTTCACT CTCTTCTAGC
AAGACGCTTA TGCTGCAAAG AGACTTAAGA CAATCCGGGA GCAAGGACAG GACACACGCT
GAGGATGGGA TGCTAAATCA GCCCTGGAAA ATACGTGTCT AATACAGGAG GCTCTCGCCC
AAGATCTATT GGTTTCCTAG CACAGCCGTA AAATGGCTAG CTATTTTAGA ACAGTAACCA
GTTCTCTGAA CTCCATGCCA GCCTGTCCCC AAGTTTCCAG CCCTCTGCTT CAAACACTTC
TTCCAACCCT TCCACCCTCA ATTTCCCAAC AGTCTTCTTA AACAATTCCT TCTCCCCATT
CTCCCAAGAC TAGCCACTCC AAACGGTAAC AACCATATCT TCCATACCAA CTGCCTTCTC
TTCTCCCTCT GCTAGCCCAA TCCCCCCTCC TTCCCTGACT CAGCTGGCTC TTTTATACTC
TATCCAGTTC CTAGTCATCC AAGAAGCAAC CAATGCTTAG GGTCATAGGG TCAAGCCTTT
```

Figure 10B

```
GTAACAGCTA AAAGTTCTTA AAGAGGCCAG TTGACTCGCA ACTGGAGACC CTTTATTACT
TATTTATTTT TATGTCTATG AGTACACTGT AGCTGTCTTC AGACACACAC CAGAAAAGGG
CATCAGATCC CATTACAGGG TTGTGAGCCA CCATGTGGTT GCTGGGAATT GAACTCAGGA
CCTATGGAAG AGCAATCAGG GCTCTTAACC CCGCCGAGCT CATCTGGAGA CCCTTTAAAG
GGCCAGGAGC CCAAGATAAA TCACATTACA GTTACATATG ACCCAAACTC AGGTGAGCTA
GACCAGTGAA GACTTAGACT GATTTCTGGA ATTAAGGCAC TGGGCCTGCA GCACTTCCCT
CCAAAGCCTG CAGTGCAGAA TCTGCCCAGG CCTTTCCCAG GCTCCGGTAG CTTCAACAGC
TTCCTGGCTA CTAGCTCCTG GCATCTTTCC ACCCCTTCCT TATATGGCCT TCTGCTGCTC
AGTGTCTTCT CCCCTGATGC CTTTTCTTCT TCTTTTCTTA CAAGGATGCT GCTCATTGGT
TTTTAAGACC CAAGCTAATC CCAGATAATC TCATCAGTAA AGAGCCCTCT CCAAATAGTA
TCACATACTT AGTTCCTAAG GGGACAACTT ATTTGTGTTC TAAGACTTGG GGCAAAGTAT
GAGCAGATGG TGCAATCTTA GGAATGCTGA CTGAAGAAC TGTCTTGTCC CTAGATTCCC
AAACCTGATC TGTCAGGAAT GAATGGGGGA AAAAAGCCCA GGACAATGAC AGGCAAGAGT
GTAAAATATC AGTGGTCGCC AAGGGGCTTC GGGACATAAA TTCAGTGAGT GAGTGCATTC
TTACCACGTA TGAAGACCAT GCCAAACACA GACATAAATA ACGAAAATTA AAGATTAAAA
GTAAATAAAT TGGCCAGATG TCATGGCAAA TGCCTGCATT CCTAGCAACT AGCAGAAGCA
GGAAGGTATC AAGTTCTAGG CCTGCCTGTA ACACTGAACA CATATGAGAC CAGCCTGAGA
TATGTAGACA AACAAAACAA AACAAAACGA AAGACCATTG ATCAATCAAT AACATAAACG
TTCAGGAAAC ACAGGCCACA CAATCAGGGA GGCTTTGCCT TTGTTTAGGG GCTGGGTTTT
TTTTTATATT TTCCTTTCCT TGTTCTTCTT CTTGTTTGTT TGCTTTTTGT TTGTTTGTTT
GCTTGCTTGC TTGCTTTTGT TTTTTCAAGA CAGGGTTTCT CCGTGTAGGC ATCTCTGGCT
ATCCTGGAAC TCATTCTGTA GATAAGGCTG TCTTTGAACT CAGAGATCTG CTTGCCTCTG
CCTTCTTAAG GCCGGGACTA AAGGTGTGCA CAGTCACTGC CACCTACCTG CTGTTTCTTT
ATCCCCTGCA TTAGTCACCC TCCCACACCC GCCAGAGCTC TGGGATAGAG ACTCTGTGTT
AGGGAATGGA GCCTACAGCT TCCATCAGGT GCTATGTTTT AATTCACATT TTCTATTCCT
CTTTTCTCAT TTGTCTGGGG TGATTCTTTT GGACAAAAAA AAATGTTATC TTTTATAATT
ACTAATTAGG ATACAAACGT TAAAATATAT CTATAATGTA CTCTTGTATA TCATTCATAA
TACCTATTTC GTATTATACT TCCTTATAGT ATATAGCATA TTTTGATAAC AAGGTCACGA
GGTCCCAGGC CTGGAACCAA CTTTTTCCTA TGTAATTGGT TGAAGTTACT GACACCGTAG
TAGACTTAGC CCTCTGGAAA CAGCCTTTGG CAATGAATTT GACTCTGTTT CAGACAACCA
TCACTTTCCT GGAAACGGCC TCTGGCCCAT TCATTACATA TTTCTTGCCC ATCTGTGACA
CGCTCTGGGT ACAATCAGCA TGACTCACTA AGAGGGTGTT CCCGTTTGCT TCTGGTTTCT
GTGAGAAAAC AAACAAAAGC AACTCTGGGA GGCAAGGGTT TATTCAGATT ATAAGTCCCT
GTCACAGTCA ATCGCTGAGG GATGCCAGGT CAAGAGCTCA AGCAGGGCCC TGGATGCAGG
AAGCAGAAAT CAGAGAAATG ATGCTCTGTG GCTTCCTCTC AATTCACACC TCCCGGGACC
ACCTGCCTAG GGATGGCCCC ACCCATAGTG GGCTGGACCT CCCTCCATCA ATCACTAATC
AAGAAAACAC CCCACAGATT TGTCTACAGG CCGATCTGGT AGAGACAATT TCTCAGTGAA
GGCTCCTTCT GACTTAATGT CAAGTTGGCA AAAACTAACA GGCACAGATG GAACCAGTC
ATAACAGTGC TCTGTACAGT TCTCCCATTG CTCTTTAGAA TGGTCTCACA TGGCCTCTCA
CAATGCTCAC ACAGCTTCTC CTGGGAATTT AATGCCCCTT GCTTCAACTT CTCTTTGCTG
TGCCATGATG CTAGCCTTTC CTATGTCCAA TCCCCCACCC ACATCCACTG AGGTTCTTGT
AGACTAGAAC CTTCCACATG AGACAGACTA CCTTAACCCT TGTCTTAGGG GTAGGCTGGC
AGGGTTACTA TTTCTATAAA ACATACTTTC AATTCCATTT TAACGTTTCA TATGTATTAT
ATATATTTAT ATTATCAATG TAGTGATGCT AAATAGACAA ACAGATGACT TAAGTCTTAA
TGATGATCCT ATAAGAATTC CTAAAATATA TCTGTGGTTA TTAAGCTCTT TTATAGTGGG
ACAGCCATTA AGTCCTTTTC TAATTGTCAA AACTGCAATG AGAACTCTGC CAGTCTCCCA
AGTGTCTCTA GTTAATTGCT ATTAGATCGT AACCAGACTT TCTCCTACTC AGAGCACATT
CCAAGCGGTT GTAAGACAAT CAGTCAAAGT TTATAAAAAG GGACAATTTA TATATATCCT
GCTAGGACAG AAGATAAAAT ATTGGCTGGT TTTGTCGATA CTAAGCTTCA CTAATAACTT
AGTTATGGTT TGAACCCTTC AGTGAACAGG GTGATGGATG TTGAGCAGGA TTTTTACTCC
TCATGGATAT GCATGTAAAC TTTCTCTGTT GTAAACTTAT ATATCAATTT ATGATTTGAT
TTTTGTGTGT GAACTTGTGA TGAACTTTGT AACATGTGAT CATTCTGAAA GATGTATAAG
TACTAAGGAC AAAAGATGA GAGGCAGATA GAGTTGAATC CCCCCCCCCC CCCCCCAAGA
ATCAATCATT TCCCTTCCTA GAATTTTTGC TCCTGTAGAG AATTTTTCAC TTTCCCCACT
TAGGATCTTT CTGCCTTTCC CCTTAGTTAG CTTTCGTAGG AAACTTTTTA CAACTTAGTA
                                        BstBI
                                        -------
ATAAATGCTA TAATCATTTT TCGAAGTGTC CCCTTTTCTT CCTGTGACTT CCGACTAGCA
```

Figure 10C

```
GGCCGAAAGT TAGAGTGGAA CAGCTTCTGC TGAGATAGTG CGAAGGCTAT CTACTTTATC
CTTTGCTGTT TGAGGAAGAT GTGCTAAGTG CCAGAGACTG CAGTTTCTGG CCTCCGAGGA
ACACAGAAGG CAGGTCAGCT ACAGTAGCAT CGAGAAGAAC CCAACAAGAA AGAAGAGCTC
CATGCCAGGG CTGGCAGCAT TCCTATGTTT TATGTAATAT TTACTGCTGA GCAGGGGATA
ATATCTGACA TCATATGTTA CTTATACATT TTTGTTGATT AAAAACTATA ATAATCATCC
CTTCTCAGCA CCCACAGAAA ACCAAGGCAT GTGGATCTCT GTGAGCTTGG GGCCAGCCTG
GTTCACATGG TGAGTTCCAG GTCAGCTGGT GTTACATAAC ATGACCTTGT CTCAAAAATA
TAATAATAAT AACAATAATA ATACAATATT ATATATTTTA TAATAAATAA TAACAATCAC
TAGTATTAAA ATAAAAATAA AAGAAAATAT AAAATCATGC TTGTTAAATA TTGCTTTATA
GGACATTATT TGACTGTCTT TTAACCTGGC AAATACCCAT CAGCATTCTT TCTCAAAACT
CAGTACCACT CGAGGCCTCC TTGACCCACT GTCTCGGTTA TTCAGCACTA ATGATCTAAG
TGTATTTTTG GCACACAGTT CATATTGTAG ACAGCACTTT GTAATTTTTT TCTTTTATGT
TTACTTTTTT TTTTTAACTT GGATAAATAA GTATAGGCCA GGACATTTAT CTGTAAAAAG
AAAGGATGTG TATTGGAAAG TTTCTATGAG CTTTGTGTCA GAAGGGGTTT GGCCTGGCCA
CTGACCACAT GTGCTAGGGA GGGAGAGTTA ACCTCCCCTC TCCCCATGGG GAGCCTTAGC
TGTTTATTCT GTTGCTGTGG TAAGATGTCC TGGTAAGCAA CAGAGGCAGG GAGGGAGGGG
TTTGTTTGGG TTCACAGTTC AGCAGAAGCC ACAGGTGGCC TGACCTTAAG GCATCTGGCC
TTGTCGCACC CACACCCAGA GCCACGGGGA TCTTAGCTGC CGTTCTCATC GTTCCATAGT
CTAGGGTCTA GGCCCATGTA ATGATGCCAC CCACAGCCAT CCTAACTAGA CAAACAACCA
CTCAGAGCTG TGCCCAGAGG CTCACCTCTC AGTCATTCCA GACCCCGTTA ACAGACGGC
CAGTACTAAC TGTTACACTT TCTGTATTTC AGTGTGGGAA GAACAAAAGA GAAGCCTCAT
GGCACAAACA CCCACCGATT AAGACAAGCA TCAGCATGAA GACTAGAAAC AATATTAAAC
AATATTAAAA GTGACTTTGG GAAGAGGGGA AATTTTTAAG TATGATTTAA GACCAGAAAA
CGAGTGAGAT GTGGTTTGTT TCATTATTCC ATTAGGAACA GCTATTTAAA ATACACATAA
AGGACACCAT ACCTGGGATA TATACTGGGT TTTAGTCTGG ACTAAAGGAT GACACTTGGT
TTTTAAACAA AGGAAAAATT GAGTGACTAA AGCTTATGAA AATTGAACTT GCAGAAATCT
AAAAATTTAA ATCTAGAATA GTAACAAATT GATATCATCA ATTCGGGAGT TACATAGATC
ACCTAACAAA CCACATTGGG ACCTCCTAAG TGTTATCATT TTAGACAAGA GGGTAAGAAT
CGGGGTACTC TTTCGTCTAC TTTAGAGAGT TCATGCTTTT TTGAATGCCC TGTTAGCAAT
GTTGATCCAG AAGACTACAT CATCTTCTTC TTTATGAATT GGGAAGCCAG CAACAAAGCA
ACTGAGTAGC AAAGGCTTAT TCTTGGCTAA GAATAGGAGA CATGAGAAAC AAACTCACAA
GTTCACTCCG CGATCTGTTG TGGTTATAGG CATAGGATCA AGGAGTTGAG TGGGAAGGAG
AGGCTAGTAA TCAGGGACA TATTGTTACT GGGAGACATG TTCAAGTATT TCCTAAGACT
AGGTGGAGAT TTCCCAGGAA ATCCATCAAT ATATCTTTTT CAACTATTTT AAAAACTTCA
CTCATTTATT TTAGTATGTG TGTGAAAAAG AGACAGAGAT ATATAGAGAG AGAAAGGGGG
AGGGAGGGAG AAGGAGACGG GGAAAGAAAG ACAGGGAGAT AGAGAGACAG AGAAAAAAGA
CAGAGGGAGG AATGGGTAGA GGGAAAGGGA GAGAGAGAAG AGGGTCAGAG AGAGGGGGGG
AGAGAGAGAA AGAAAAGGGG GGGAGGGGAA AAGGGAGAGA GAAATAGAGA CAGAGAGGGA
GGGAGGGAAA GAAGAAGGAA AGGGGGAGGG GGAGGGGGAG AGAGAGAAAG ACACACACAC
ACACACACAC ACACACACAC ACACACACAC ACACACGGGG GTGGGGGGAG AGAGAATGCT
GATGTCATAG TGTGCCACTG GAGATCAGTG GACAACTGTC TCAGGAACTA GTTCTCTCCT
GCCACCTTGT GGGATGCAGG ATGACCTTAG ATCCTACCTG CTGGCTAGCC TACCTTTCCC
ATCTTTTATG GATCTTTCTT GTCAGAAACG AATGACTGTG ATGTTACTGA GGTTGGTTGG
CATGGAGCAT GCAATGTAGG TGTTATATTG TGAAGGTAGA GGTGTTTAGC AGTCACTCCG
GCACTTATCT GAGACCCAAA TAATTCTGGC CAACCTACCT GAAGAGCAAC CTCTGGCCTA
TACTATCTTG TTATAAAGG AAATCAGATT AAAGCCAGGA AGACATTCTC TAGGCTAACT
AGGAAGACTT CTCTCTCCTG CCCTCTACAC TGAAACATTC CTCTTTAAAA AAATTATGTG
TCTTTGGAAT TATTATTATT AGTATTAGTA GTAGTATTTT GGTTGCTATT GTTGCACATG
TTAAGCAATG AGCTAACATT TCCCATCATG CCTACCATCA TATAAATGTT AGGTTTGAGT
TCGGGCTAA GCAGACCACA TTTCCATGTC ATCTTACAGG TACTTGCAGG CCCACCATAG
AACAGTTGTA GAACTCTGAC AAACTTCCAG AGCTCCGCTG AACTTCAGAA AATACTGAAT
CCCAGAGGTC CCACAAGTCT CTATCCTCCT CTCTGCAGAA CCCTCAGAGC TGATTCTGGG
CTTCCTGGTG CTACACGGAA ATATAAAACA ACCCGTCTGA ATGTATCAGA CAAATTCCCT
AGATAACCAG ACGGTAGAGA GCAATGGCTA AGTCACATCC CCCAGGGATG GGGGAACCTC

PacI
        ---------
ACTAATTAAT TAAATGGTAA ATGTGGTAGG TACATGTACG AACTGACATC AAAGAAGATG
CATGCTGTCT AACCAGAAAC TTGCCTGGTG CTACTGTCTC TAGTATGATA AATTTAAATC
```

Figure 10D

```
TGACAGTTAG GAGTAACCAA TATAATTCTG TACTTTCTTC AGTCTCTAGA GCAGAGACTC
TCAACCTGTG GTTTGAGACC CCCTTTGGAG CTTGCATATC AGAGATTTTG CATAGCCAAT
ATTTACACTA TTATTTGTAA CTTGTAACAA CTTTACAGTT ATGAAGTAGC AACAAAATAA
CTTTATGGTT GCGGGGGGGG GGGGGTCACC ACAACATGAG GAACTGTATT AAAGAGTTGC
ACACGGTATT AGGAAGGGTG AGACCCCGTG CTATAGAGGA AAGGCTGGAA AGTCAAATGG
TTTTTACATG AGTTGTAGTG CTGCCTAAGA GGAGTGTTTA GCAATCTTCT GGGTAAGACT
CAAAGAGACC CAGAAGCCTA GCAATACCCG TGGTAGAGGT GTCACCTCCT ACTCAAATGG
GTTGTAAAAC ACCTTTCAAA CTGCTCTCCT CTCTTCTGGA TTACTGGCAA GCCTTGGTCC
CTGTCTGTGG TTGTCAGACT CAGGCTGTGT CAATCACTTA GCGGATGGAT AACTGGCTAC
AGAGCTCCAC CAGAAGGTCA GCTTCCGTAT GTCTGGGGTG AGGACCAGGA GCCTGTGGGT
TGAATCGTTC CCAAGGGATA AAAGTACTGT GGACGCTGAG TGCACTCGGA TGCTTTGTGG
TTGCGTTTGT CTGTTGAGCT TACAGCAGTC CATGCATGAG ACATTGGAAA CAAAGAGCTG
CAGCCTTCCT CTGGGATCTA AGGGGAAAGA ATAGACTGCA GCCTAGAGTC TTGGTTCTCA
GAAATGAACT GTTTAAGGTT TCTCACGTAA GCTAGGAAGG CAGAGCCCAG CTAGGTTTCA
TTTAATTATG ATGGGATTCC TTATTTAGGT ACCAAAGAAG GAAAAGGCTC CTCTGGTGAT
GGTTAGTGAC AGCTTCTTTT CTGGGTCCCA GCCAATCAAG GGGCATCTG AGTTCTACAG
ACTTTAAGTG CGTGATTTTT CTATTTCAAA GTAAACACGA GATATTCTAG CCCAGCATTT
GAGTCACTAT GTTCAAATAT ATTCTAAAAT GCCCAGATCA CACCAGCGAG ATTAAGTAAG
TTGGCAGTTC ACAGATACAT CAACATGAAT CTATCTTTCT TTCTTTCTTT CTTTCTTTCT
TTCTTTCTTT CTTTCTTTCT TTCTTTCTTT CATTCATTAT CTATTTATCT GCCTACCTAT
CATCTATCTA CCTACCTAGC TATCTAGCTA TGTCTATCTT CCAGTCCGTA AATCTATCTC
TGTGCATCTA TCTATCTATC TATCTATCTA TCTATCTATC TATCTATCTA TCTATCTATC
TATCTATCTT TCATTATCTA TTTATCTGTC TACCTATCAT CTATCTACCT ACCTAGCTAT
CTAGCTATGT CTATCTTCCA GTCTGTAAAT CTATCTCTGT GCATCTATCT ATCTATCTAT
CTATCTATCT CTATCATTTA TCAACCATCT TTCTATCCAT CATCCATCTC TCTCTCTCTC
ATATCTCTCT CATATATATA CATATGCATA TGTATACGAG ATCCTTTCTC CTGAGGAAGG
AGTCAAGATT CACAGTCCTA GGCAAGTGCT GTACTCCTGG GCAATAGGGC AGCCTTTGCT
TTTATTCTTA GTCTTTCTCT TGATGCCAAC CAAATGCGTA TCAGCTTCAA TTCTGCTCTC
TTCAGCTGTG TACCTGCAGC TGTTTCCTGG AGAAAATGAC ACCATCAACC ATTTCTCTCC
AGGACAAAGG CTGGGTGGGC TGGGAGGGGT GCGGGTGGAG TGAGTGCAGG ACAGGAGACC
AAAGGCTGAA CCAGATGACG GTCTTGCCCA GAACGCCTCC ACCCGTCCAG AACTACAGCC
GCTGCTCCCC ATGCAGTTTG ACTCTGAAAG TATAACAACG TAAAAACAGA ATTCTAGGCC
TTTAGGCCCA GGCTTGAGAA TGTGGCCTTT GTAAAGGTAT GCTAATCATA AAAGAGATAG
CGACATTCCT CTACCCACCC GCTTCCTGGG TTCAAAGAGT GCTCATTCAA AGAAAGTCAC
CCTGAGGATT ACCAGAACCT GCAATGCAAA TGTGCTATTG TTAGAGGCTC TTAGAAGCTG
TCTTGAGAGT TAACACTTAC CAGGTATTCC TTGTGACTCT TGTAACTTTA CACTTCCTTG
TGACTCTTAA CTGGTATCTT TGGTATCTTC CAACAATGCC CTCCCCACTT CCTTGAGTTT
CGGTTTCTTC CTTTAAATAC CCCCTTACCC AGCTACTCGG GGTGCCACGG TCCTCTACCC
```

Eco III
-------

```
CTGCGTGGTG TATGACCATG GGCCCGAGAG CGCTTTTGAA TAAAAATCCT CTTGCAATTT
GCAGCAAGAC CCGTTTCTTG TGGGTGATTT TGGGGTGTCG CCTCTCCTGA GTCAGAACGT
GGGGGAGCCC TCACATTGTG GGTCTTTCAA CTCGAGGCTT CCAGTTCGTC CTGAGTTACT
TTAGAGTCAA AGAAAGAAAA GGGAAGATTA AATGAAGTTC AAAACCTCCA CAGCGTATGG
CAAGATGTTG GAAATACTAG GGATGCAAGT CAACCAGGAG TTTTAGCCCA GAATCACAGG
AGATCTAGAT GTTCATGACC CCGACCCCCA CCCCTAAAC CCAACTTCCA CCCCCACCCC
CGCCACCCCA ACAGCAACAA GAAGTGACAC GTGGGTCTCC TGTTGATCTC TGCCTCTCCA
GAGCTGGACT TTCAAGTGTC CTGGCTTATT ACTGTCCCTC TGTGTTGTCA CATTTGCTCA
GGGTCAGCTC TCCTCTCCTC TTCCCGGTTC TTAGCATAAC GCTTATTCCT CTCTGTAGTC
TCACAGCCTG ATCTTTACCC CCAGTGAGCT GAGAAACTGG ATCCATGGGA AGCTAAGCCC
```

BsrBI
-------

```
CTCACTTCTG CATCTGCCAG GATGCATCTC CTTCTCCGCT CCTCTTCTTC CTCATGCCTT
GCTGCCTCTG TGTCCCCCGC CCCCCTCTTC TTCCCAGTGT TCCTCTTCCA GCAGCAGACC
ATGAACTCCA TACTGCTCTT ATCCCTAGAA GACCTCTGTA AAGCAGGTT CCCTTTCATT
GATGTCTCTC CTAAAAAGTC CATCACATCG CCCCACACTT CCCCAGCACA GGACCATTTG
```

Figure 10E

```
GACTTAGCTT CCAAGATCCT GTTCTCAGTT TCAATAGCAA AGGTGTAGAG AAACTGGCAT
GAACCTCTTT GTGTTGCTTT GTCTCTAAGG GATGGCCTTC TTTTAACTCT TGCCTTGGAC
                                                          BbeI
                                                          -------
                                                          KasI
                                                          -------
                                                          EheI
                                                          -------
                                                          NarI
                                                          -------
TGGGCTCAGT GGGCCCTCCT CAATCCGTGC GAATCAGAGG ACAGATGGGC GCCGTAGAGT
CGGCGAGTGA CAAACAGAAA CGGCGGCGAG TGTGTAGAAT CTGAGTGTAT TTTTACAAAG
TGAACACCAG TCTTATATAG TACAGAAAAT AAAGGGATAG GATGTCACAG CAGGCAAAGT
ACATTGAAGT TACCTGACAC AAAACAAAGT AATGACTTCA AAAGGACTTT CAGGAACCAG
GTAATAGTTA CAGTAAAGAT AAAACAGCTC TGCTTAGGGT CAGCTAAGGA CAGGTAAGGA
TTTCACACCC TACTCACAAT TTGTGCTACT CCTTTGAACC TTGTGAAAGC TAGCACCAGG
GAGTTCTGCT CTAGCAGACC TTCTCATGAA TAATGCAATA CCACAAACCC CCTATTTCCT
AGGACTTGAT AAATTCTTTC ATGAGTATAA CTTGGCTGTT CTTTTAAGTA TCTGTGGGGA
AGCTCCATTT GTCAGAAGAA TTCACCAACT TGCTTCTAAT ATGCAATGTA GCCTGCTATA
CCTGGCTGTA CAAGATTCCT GTCTCAGTGG GATTCTCTAA CTCTTTCATG GTAAACCCAC
CTATTAGCTA GGCCATGGTG TATTCCCTTG TTTGGGTTAG ACTTGGCTAC TGTCCTAAGT
CCTAAGTAAT CACCCTGCAG ACCAGCCCTG AGCTATTCTA GCTCTGTTCT TTGTAATGCC
TAATTAGTTT CACCATTTCT ACTAGAAGTA AATTTGAATG TTACTGAATA GGTAACATTC
TCACTGAATT TCTACTGAAT TCCAAGCTCG TCGGCTTCAA GAATTTTCTA GGACGTTGGA
ACACTGGTGG AGGCTTACCT ATGTTAAAAT TCAACCTTTA AAGGCACTTA TAATAAAACA
ATACTAAAAG AGAGCATGTG CATCCATATA CCAGACTAAC ACGGGGATAG GGTATGAGTA
TACAGGTTAT GAGAATGCCA AGGTTCTAGG AGGTTGAGTT TCCTTGAAAC TCTTTGCCTC
CATGAGTGCT TCCAGGCCTC TCGGCCTGTC AAGCAGACTT CACTGGAGTG GGTATAGCAA
            ClaI
            -------
ACTCTGTATC GATGCCCTTG ATCTTCTGAT TATTGCCTTT CATAAAATTA TCTTACATTT
TGACTGCCAT ATGGTCTTTC TCTATGGCTC ATTGAACCCC GAGAGTGTTC TTTTTATCTG
TGCCAGTGGA GTCAGTTCCT GTGCCTACCT TGTAAATATC CCCAGTGTGC TAATCTAGGC
TTTCCTTGGT GTTTCGGTTT GCATAACCTT AAGAAGCACT GGCCACACTC TGTGCTTTCT
CTTTTAGTGA CTTCTGAGTC ACACTTCTTG GCACATCATT TGAATTTCTA CAGAAGTGGA
AGCTGAATTG ATTGAGAACT AGCTTTTTGC CTACTCTGAT CTCTACTTGC ATTTCCTGTA
TGTGCTCTGA CCCATTGCAT GGCTGCTCTG TTCATAAACA CGGTCATGGT TTTCACCCCA
TTTCTTCATA ACTCAGAGGC CTATGGGCT CCATCCATGT TTTGTGTACA ATTTTTTATT
TTTTTATTTT ATTTTATTTT GGTTTTTCGA GACAGGGTTT CTCTGTGTAG TCCTGGCTGT
CCTGGAACTC ACTCTGTAGA CCAGGCTGGC CTCCAACTCA GAAATCTGCC TGCCTCTGCC
                BssHII
                ------
TCCCAAGTGC TGGGATTAAA GGCGCGCTTG ACCACCGCCC TGCTTCCTGT ACATTTCTG
AAAGGCCAAA TCACCTTCTT TTGCAACGCA TACAGCTTTC CGCTGAGATC GCCCAGGTCT
GTTGCTTGTT TTCAGAAGCT GACACAGACA ATGGGAGTGG AGGAGTTTCA GTACAAGTCG
                                                          MunI
                                                          ------
ATTCATAGAG ATAGATGCAG CCTAACTGGG CAGCCCAAGC CTTCAATTGC AGCTATGCTG
GAGGCTGAAG CAGGGGGACC TCAAGGTCAA CGGCAGCCTG AGAAACTCAC AGAGACTGTC
TCAAAATAAA AAATATATAT ATAAAATAAA ACTATACACT TGACTCTTAT CTACAATGTA
GTACGTGGGA GGAGGCTGAG GTCGAAGACT GTGAGTTTGA TCAGCCTGGG CTACATAGCA
AACATCTGCC TCAAAAGACT GGAAATACAA AACTAAAAGT GAAGAAAAGA GAAGCCACGT
TCAGACTTCA AAACCAGGCT CCATTGTCAT GTTTCTGGGA CTATTCCCTA TCCATTCCCA
GAGTAGACTG ACAGAATTAG CCCCCACCCC TTCTCGAGCG TCTCAAGCCC ACACCTGAGC
ATAGAGCATG TGATTTACAT GGGGATCCAT TTTTCCTCCA CTTCTCCCCT CCCGTGTTAT
```

Figure 10F

```
ATGATCGGAG CCTAAGGTCT GTAACCTTGT CAGCTGCGTG TCCGTGTGGC TAGTCTAGCC
TAAGGCCAGG CTTGCCGGAA GTTCTCTTGG CACACCTGGG TTGACTTGAC TTCTCCTGAA
GAGCATTCCA AAGCTGCTCT CTGTAAAATT CTCAGCTGTT TCTATTTGAA ATGCAGGAAG
                                                          >>.>
CACTTCCAGA TCATTACAAG CCTTGGATGG AAATTGCCCT CAGACTTCCT CACTTAATCG
>.........................Exon 2 ..........................>
AGAACCGCCA GCTCCGAGCT CACGTGTACA GGGTACGTCG ATTTGTTCTT TGCTTCATGC
>...........Exon 2 .............>>
TCCTCCTCTC CCCACCCGTT CCGTCTCCAT ATCCCTTTCC TTCTCAGCTC TCTGGGAGTG
AAACGGTTGA CCTGGCAGTG GGAACCGACT GTCACCACTG AGGCTTTCAG CAAACCTGTC
TTCCTTAGTG CGCACAAACA GCACCTGAGA TGTGTCAAGT CCTCATCGTG TTTGTGCAAA
AGACGATGAT AGATGAGACT TGAAAATAAA TTCTGGGGAA ACGAGGAAGA CACACATTGG
AGATTGGTGG GAGCCGCTTG GCCTGCTTCT GTAAAAGCCT GCCTGTCAGG CAGAGTCAAG
CCAGGGGCTG AATGTTCTGT TAATCTCGGA GGAAGGAACA CGGAGGAATA GAGGCCTCTG BsaBI
          ------------
GATGAGTACA GATATCAGAT ATACATCAGC CGCTGTCTCT GCTGGCTTGT GACTTTGCTT
CCCGTGATAC TACAGAGTAT ATAAAGCCTT AGAGAATTAA ACTCAAGGCT GCTGCAGCAC
TGACTGGATA GCCTTCCCGG TTTTTAAGCT TTGTTTCTGA GTCTTCTTTT CCATCTCTCC
TACAATCCTC ACTCACCCCT CAGAAGACCT GTTCAACTTT GTACTGGCAG GACCGGCAGG
GGAGATGCTC AGTGGACTTG TCCCAAGTCA CGTGGTCACT GCTCTGCTTC CTCTGGGCAG
GTACCTTGAC CTTAGTGTGT TACATACTAG TCAGATCAAA TGTCTTTCTG ATTTTTAAAC
TCAGAGTCAG TCTTGGCTAT GTAGAAGAAG TGAAATCCAT AGACACCACA TTAGAATCTG BtrI
              ------
CATGCACCTA AGTATATGAC GCACGTCTGT GACAGAGCGA GCAATTTCCC TCCAAAAGGA
ATAAGAAAAA TATGACCCCC ACAGAAGACA TTCTTCCATT CAGGAATTTT ATAGTAAGTG
TGAAACGGAG AGTTGGCCTC AGAATCTTGC TTCCTTCTTT GAGAAATGGA TGAAGTTCTC
ATTTAATGGT TGTGAGCATC AATGGCTTTT GTAAGGACCC TCCCCCTCCT CATCTTCATC
TGTCACAAGC ACACCACAAG ATGTCAGATG TTCAAGCAAG GCGCTCCACC CTCCAGGACC
TTCTTTGCTG ATGCTTAATG TCCAATTATG AGTTGATTTT TAAAAATATT CATTGAATGA
TCCTTATAGC ATATTCAGAA ATCAGGACAG GCAGCTGGCC TTGGTAATAC TCTAGATAAC
CCCCCCTCTG AACCCCCAC TGAGGCTGAA GACCATGTAA GAAAGTGCAA CTAAAGGAGT
TAATTGTTGC ACAAAACTCA CACAAAGCCT CACAAAGGTA GTTTGTACAC GCTGTTGACA
CATTACACTA ACAAAAACAT CGAGGGGAAA AAAGTAGAGA AACAGTAGAA GATAATAATT
AATGGTGACC TATGGCCTAC ACACACACAC ACACACACAC ACACACACAC ACACACACAC
ACACACACAT GCACACATCA CCACACACGT GTGTATGCAT ATGCTCACAC ATGTACAAAC
ATATATCACC ACATATGTGA CACACACATA CACACTCATA TCACCACACA CATGTGTACA
CACATGCACA CACACACATC ACCACACACA TATGCATACA TAGGAACATA TAGTACACAC
ATATCACCAC ATAGATGGCA CACACACACT CACATACCAT CACATATATG CATGCATATA
GACATGCACA CACATGCCCC CCCACACAAA CACACATATA TGTACAAAAC CTATAGTGAA
CACACTACCC TGAGTCAAGC TATGAGTTTT AAGAACATAC ATACTGTCCC CCAAAACTCG
TCACAAGGTG TTTTGTCCTC AAAGGGAAAG CTCCTCTCTA TCTAACTGAT GTCTAGAACC
CACAAATATG TTAGTTGTGT ACCAGAGGGG ACGGCGGGTG GTTAGTTAGT AGAGGGTCTC
CCACAAACCC ATGTGTCTGT CTTCATCCAC CATCTTTTAC ACTGATGAAT GAGTTACTAG
CCAGTAACTC ATGCAGTGAG GCAAAGCAGT TATGATGGTT CTGGGTGACA AGCAAGTGAA
GAGTATTGGT GAGGATACTA AGCACGCGCA TGCACTTTGC TACAACTAGT CTGTCATGTG
AACTGCCATC TCACAGAAAC ATTCATACAA AAAAAAGTGC AGATGAATAT GCAAAGCTGT
TTGCTGTAGC CACTTTCATA GCAACGGTAA ATACAATGTA ACAGAAATAC AATGTAACAG
AAGACAGGAG AGCAGAAGGA GAAGCCCATG AATCTCCATT CACAAATATA TCTGTTACAT
AAATGAAAAG GGACAGATAT TAAGTGGTCA CGTAGGCACC TGCCTGTATC CTTCCGCCAC NruI
                                                 ------
GCTACACATC TTTGCTCTGT AGTTTACTGA GCATTAGGAA GTTCGCGACA GTATCTATAT
GCAGAATTAT TGAACCTCTA CTTCAACAAC ATGTGCATGT GAGCTTAATA TTTATAGATG
ATAGAGGTAG AAATAGACAT ATTTACTATC TGACAGAGTC CTAACATGTA GCCCAGGATG
```

Figure 10G

```
GCTTTGAATT AGACATCTTC CTATCTCCGC CTCCAGAGTG CTGGTATCAG TCTTCATAAA
GACTTCTATA TGAAAACAAA TGTCCTGTTT TCTATGTATT CGCCTTCGTG TCAAACTATA
CTTTTCAAGA AGTTCAAGAA GTGATGTCCA CAAGAACCTG ATGTGTGTCA GAAACACTCA
GCTCCCCAGT GAAGTTGGCA GGAGGGCTCG CCTGGTTCAG AGAAGCCTTG CGTGCTCCCT
GAGTTCTGAG AGGAGAGTAT CGAGGTTAAT TCTCCCAGGT TAAATACGCA ATCAAATAAT
GTCAGGGAGA TGACGGGTGT GTGTCGTCCT CCCAGACCAT CTGTGACTGT TTGAGTAAGC
AAAAGGATTG ACTAAAAAGC TATCATTTCC TTTTCAGTCC CTACAGTCAC TTTTGAATCA
CAGGTATGTT TAGGAGGTGA GGCCAACAAT CCTGAAATGT GCAGGGACTC TCCAGAAAGC
AGTCATCATC CCCTGGACCT CGTTCCTTTA CACCGAGGCG TCCTGGCTTG TAGGTGGCCT
TCTTCAACAA CTGAGGGGTG ACAAGGACAA AGCCTGAGAA GACACAGCCT AGATTGTGAA
GACTTTGAAA GATTTTTATA CTGACTGCAT GCTAAAATAT CTTTTATACG TTGACTCAAC
AAAGTACATT ATCAGAACTA ATTTTACTTC TTGTTTGCCT TAAAAAAAAA AAAGTGGCTG
CTGAAA

GTATACGAGA TCCTTTCTCC TGAGGAAGGA GTCAAGATTC ACAGTCCTAG GCAAGTGCTG
TACTCCTGGG CAATAGGGCA GCCTTTGCTT TTATTCTTAG TCTTTCTCTT GATGCCAACC
AAATGCGTAT CAGCTTCAAT TCTGCTCTCT TCAGCTGTGT ACCTGCAGCT GTTTCCTGGA
GAAAATGACA CCATCAACCA TTTCTCTCCA GGACAAAGGC TGGGTGGGCT GGGAGGGGTG
CGGGTGGAGT GAGTGCAGGA CAGGAGACCA AAGGCTGAAC CAGATGACGG TCTTGCCCAG
AACGCCTCCA CCCGTCCAGA ACTACAGCCG CTGCTCCCCA TGCAGTTTGA CTCTGAAAGT
ATAACAACGT AAAAACAGAA TTCTAGGCCT TTAGGCCCAG GCTTGAGAAT GTGGCCTTTG
TAAAGGTATG CTAATCATAA AAGAGATAGC GACATTCCTC TACCCACCCG CTTCCTGGGT
TCAAAGAGTG CTCATTCAAA GAAAGTCACC CTGAGGATTA CCAGAACCTG CAATGCAAAT
GTGCTATTGT TAGAGGCTCT TAGAAGCTGT CTTGAGAGTT AACACTTACC AGGTATTCCT
TGTGACTCTT GTAACTTTAC ACTTCCTTGT GACTCTTAAC TGGTATCTTT GGTATCTTCC
AACAATGCCC TCCCCACTTC CTTGAGTTTC GGTTTCTTCC TTTAAATACC CCCTTACCCA
GCTACTCGGG GTGCCACGGT CCTCTACCCC TGCGTGGTGT ATGACCATGG GCCCGAGAGC
GCTTTTGAAT AAAAATCCTC TTGCAATTTG CAGCAAGACC CGTTTCTTGT GGGTGATTTT
GGGGTGTCGC CTCTCCTGAG TCAGAACGTG GGGGAGCCCT CACATTGTGG GTCTTTCAAC
TCGAGGCTTC CAGTTCGTCC TGAGTTACTT TAGAGTCAAA GAAAGAAAAG GGAAGATTAA
ATGAAGTTCA AAACCTCCAC AGCGTATGGC AAGATGTTGG AAATACTAGG GATGCAAGTC
AACCAGGAGT TTTAGCCCAG AATCACAGGA GATCTAGATG TTCATGACCC CGACCCCCAC
CCCCTAAACC CAACTTCCAC CCCCACCCCC GCCACCCCAA CAGCAACAAG AAGTGACACG
TGGGTCTCCT GTTGATCTCT GCCTCTCCAG AGCTGGACTT TCAAGTGTCC TGGCTTATTA
CTGTCCCTCT GTGTTGTCAC ATTTGCTCAG GGTCAGCTCT CCTCTCCTCT TCCCGGTTCT
TAGCATAACG CTTATTCCTC TCTGTAGTCT CACAGCCTGA TCTTTACCCC CAGTGAGCTG
AGAAACTGGA TCCATGGGAA GCTAAGCCCC TCACTTCTGC ATCTGCCAGG ATGCATCTCC
TTCTCCGCTC CTCTTCTTCC TCATGCCTTG CTGCCTCTGT GTCCCCCGCC CCCTCTTCT
TCCCAGTGTT CCTCTTCCAG CAGCAGACCA TGAACTCCAT ACTGCTCTTA TCCCTAGAAG
ACCTCTGTAA AAGCAGGTTC CCTTTCATTG ATGTCTCTCC TAAAAAGTCC ATCACATCGC
CCCACACTTC CCCAGCACAG GACCATTTGG ACTTAGCTTC CAAGATCCTG TTCTCAGTTT
CAATAGCAAA GGTGTAGAGA AACTGGCATG AACCTCTTTG TGTTGCTTTG TCTCTAAGGG
ATGGCCTTCT TTTAACTCTT GCCTTGGACT GGGCTCAGTG GGCCCTCCTC AATCCGTGCG
AATCAGAGGA CAGATGGGCG CCGTAGAGTC GGCGAGTGAC AAACAGAAAC GGCGGCGAGT
GTGTAGAATC TGAGTGTATT TTTACAAAGT GAACACCAGT CTTATATAGT ACAGAAAATA
AAGGGATAGG ATGTCACAGC AGGCAAAGTA CATTGAAGTT ACCTGACACA AAACAAAGTA
ATGACTTCAA AAGGACTTTC AGGAACCAGG TAATAGTTAC AGTAAAGATA AAACAGCTCT
GCTTAGGGTC AGCTAAGGAC AGGTAAGGAT TTCACACCCT ACTCACAATT TGTGCTACTC
CTTTGAACCT TGTGAAAGCT AGCACCAGGG AGTTCTGCTC TAGCAGACCT TCTCATGAAT
AATGCAATAC CACAAACCCC CTATTTCCTA GGACTTGATA AATTCTTTCA TGAGTATAAC
TTGGCTGTTC TTTTAAGTAT CTGTGGGGAA GCTCCATTTG TCAGAAGAAT TCACCAACTT
GCTTCTAATA TGCAATGTAG CCTGCTATAC CTGGCTGTAC AAGATTCCTG TCTCAGTGGG
ATTCTCTAAC TCTTTCATGG TAAACCCACC TATTAGCTAG GCCATGGTGT ATTCCCTTGT
TTGGGTTAGA CTTGGCTACT GTCCTAAGTC CTAAGTAATC ACCCTGCAGA CCAGCCCTGA
GCTATTCTAG CTCTGTTCTT TGTAATGCCT AATTAGTTTC ACCATTTCTA CTAGAAGTAA
ATTTGAATGT TACTGAATAG GTAACATTCT CACTGAATTT CTACTGAATT CCAAGCTCGT
CGGCTTCAAG AATTTTCTAG GACGTTGGAA CACTGGTGGA GGCTTACCTA TGTTAAAATT
CAACCTTTAA AGGCACTTAT AATAAACAA TACTAAAAGA GAGCATGTGC ATCCATATAC
```

Figure 10H

```
CAGACTAACA CGGGGATAGG GTATGAGTAT ACAGGTTATG AGAATGCCAA GGTTCTAGGA
GGTTGAGTTT CCTTGAAACT CTTTGCCTCC ATGAGTGCTT CCAGGCCTCT CGGCCTGTCA
                                    ClaI
                                    -------
AGCAGACTTC ACTGGAGTGG GTATAGCAAA CTCTGTATCG ATGCCCTTGA TCTTCTGATT
ATTGCCTTTC ATAAAATTAT CTTACATTTT GACTGCCATA TGGTCTTTCT CTATGGCTCA
TTGAACCCCG AGAGTGTTCT TTTTATCTGT GCCAGTGGAG TCAGTTCCTG TGCCTACCTT
GTAAATATCC CCAGTGTGCT AATCTAGGCT TTCCTTGGTG TTTCGGTTTG CATAACCTTA
AGAAGCACTG GCCACACTCT GTGCTTTCTC TTTTAGTGAC TTCTGAGTCA CACTTCTTGG
CACATCATTT GAATTTCTAC AGAAGTGGAA GCTGAATTGA TTGAGAACTA GCTTTTTGCC
TACTCTGATC TCTACTTGCA TTTCCTGTAT GTGCTCTGAC CCATTGCATG GCTGCTCTGT
TCATAAACAC GGTCATGGTT TTCACCCCAT TTCTTCATAA CTCAGAGGCC CTATGGGCTC
CATCCATGTT TTGTGTACAA TTTTTTATTT TTTTATTTTA TTTTATTTTG GTTTTTCGAG
ACAGGGTTTC TCTGTGTAGT CCTGGCTGTC CTGGAACTCA CTCTGTAGAC CAGGCTGGCC
TCCAACTCAG AAATCTGCCT GCCTCTGCCT CCCAAGTGCT GGGATTAAAG GCGCGCTTGA
CCACCGCCCT GCTTCCTGTA CATTTTCTGA AAGGCCAAAT CACCTTCTTT TGCAACGCAT
ACAGCTTTCC GCTGAGATCG CCCAGGTCTG TTGCTTGTTT TCAGAAGCTG ACACAGACAA
TGGGAGTGGA GGAGTTTCAG TACAAGTCGA TTCATAGAGA TAGATGCAGC CTAACTGGGC
AGCCCAAGCC TTCAATTGCA GCTATGCTGG AGGCTGAAGC AGGGGGACCT CAAGGTCAAC
GGCAGCCTGA GAAACTCACA GAGACTGTCT CAAAATAAAA AATATATATA TAAAATAAAA
CTATACACTT GACTCTTATC TACAATGTAG TACGTGGGAG GAGGCTGAGG TCGAAGACTG
TGAGTTTGAT CAGCCTGGGC TACATAGCAA ACATCTGCCT CAAAAGACTG GAAATACAAA
ACTAAAAGTG AAGAAAAGAG AAGCCACGTT CAGACTTCAA AACCAGGCTC CATTGTCATG
TTTCTGGGAC TATTCCCTAT CCATTCCCAG AGTAGACTGA CAGAATTAGC CCCCACCCCT
TCTCGAGCGT CTCAAGCCCA CACCTGAGCA TAGAGCATGT GATTTACATG GGGATCCATT
TTTCCTCCAC TTCTCCCCTC CCGTGTTATA TGATCGGAGC CTAAGGTCTG TAACCTTGTC
AGCTGCGTGT CCGTGTGGCT AGTCTAGCCT AAGGCCAGGC TTGCCGGAAG TTCTCTTGGC
ACACCTGGGT TGACTTGACT TCTCCTGAAG AGCATTCCAA AGCTGCTCTC TGTAAAATTC
TCAGCTGTTT CTATTTGAAA TGCAGGAAGC ACTTCCAGAT CATTACAAGC CTTGGATGGA
AATTGCCCTC AGACTTCCTC ACTTAATCGA GAACCGCCAG CTCCGAGCTC ACGTGTACAG
GGTACGTCGA TTTGTTCTTT GCTTCATGCT CCTCCTCTCC CCACCCGTTC CGTCTCCATA
TCCCTTTCCT TCTCAGCTCT CTGGGAGTGA AACGGTTGAC CTGGCAGTGG GAACCGACTG
TCACCACTGA GGCTTTCAGC AAACCTGTCT TCCTTAGTGC GCACAAACAG CACCTGAGAT
GTGTCAAGTC CTCATCGTGT TTGTGCAAAA GACGATGATA GATGAGACTT GAAAATAAAT
TCTGGGGAAA CGAGGAAGAC ACACATTGGA GATTGGTGGG AGCCGCTTGG CCTGCTTCTG
TAAAAGCCTG CCTGTCAGGC AGAGTCAAGC CAGGGGCTGA ATGTTCTGTT AATCTCGGAG
GAAGGAACAC GGAGGAATAG AGGCCTCTGG ATGAGTACAG ATATCAGATA TACATCAGCC
GCTGTCTCTG CTGGCTTGTG ACTTTGCTTC CCGTGATACT ACAGAGTATA TAAAGCCTTA
GAGAATTAAA CTCAAGGCTG CTGCAGCACT GACTGGATAG CCTTCCCGGT TTTTAAGCTT
TGTTTCTGAG TCTTCTTTTC CATCTCTCCT ACAATCCTCA CTCACCCCTC AGAAGACCTG
TTCAACTTTG TACTGGCAGG ACCGGCAGGG GAGATGCTCA GTGGACTTGT CCCAAGTCAC
GTGGTCACTG CTCTGCTTCC TCTGGGCAGG TACCTTGACC TTAGTGTGTT ACATACTAGT
CAGATCAAAT GTCTTTCTGA TTTTTAAACT CAGAGTCAGT CTTGGCTATG TAGAAGAAGT
GAAATCCATA GACACCACAT TAGAATCTGC ATGCACCTAA GTATATGACG CACGTCTGTG
ACAGAGCGAG CAATTTCCCT CCAAAAGGAA TAAGAAAAAT ATGACCCCCA CAGAAGACAT
TCTTCCATTC AGGAATTTTA TAGTAAGTGT GAAACGGAGA GTTGGCCTCA GAATCTTGCT
TCCTTCTTTG AGAAATGGAT GAAGTTCTCA TTTAATGGTT GTGAGCATCA ATGGCTTTTG
TAAGGACCCT CCCCCTCCTC ATCTTCATCT GTCACAAGCA CACCACAAGA TGTCAGATGT
TCAAGCAAGG CGCTCCACCC TCCAGGACCT TCTTTGCTGA TGCTTAATGT CCAATTATGA
GTTGATTTTT AAAAATATTC ATTGAATGAT CCTTATAGCA TATTCAGAAA TCAGGACAGG
CAGCTGGCCT TGGTAATACT CTAGATAACC CCCCTCTGA ACCCCCACT GAGGCTGAAG
ACCATGTAAG AAAGTGCAAC TAAAGGAGTT AATTGTTGCA CAAAACTCAC ACAAAGCCTC
ACAAAGGTAG TTTGTACACG CTGTTGACAC ATTACACTAA CAAAAACATC GAGGGGAAAA
AAGATGGGAA ACAGTAGAAG ATAATAATTA ATGGTGACCT ATGGCCTACA CACACACACA
CACACACACA CACACACACA CACACACACA CACACACATG CACACATCAC CACACACGTG
TGTATGCATA TGCTCACACA TGTACAAACA TATATCACCA CATATGTGAC ACACACATAC
ACACTCATAT CACCACACAC ATGTGTACAC ACATGCACAC ACACACATCA CCACACACAT
ATGCATACAT AGGAACATAT AGTACACACA TATCACCACA TAGATGGCAC ACACACACTC
```

Figure 10I

```
ACATACCATC ACATATATGC ATGCATATAG ACATGCACAC ACATGCCCCC CCACACAAAC
ACACATATAT GTACAAAACC TATAGTGAAC ACACTACCCT GAGTCAAGCT ATGAGTTTTA
AGAACATACA TACTGTCCCC CAAAACTCGT CACAAGGTGT TTTGTCCTCA AAGGGAAAGC
TCCTCTCTAT CTAACTGATG TCTAGAACCC ACAAATATGT TAGTTGTGTA CCAGAGGGGA
CGGCGGGTGG TTAGTTAGTA GAGGGTCTCC CACAAACCCA TGTGTCTGTC TTCATCCACC
ATCTTTTACA CTGATGAATG AGTTACTAGC CAGTAACTCA TGCAGTGAGG CAAAGCAGTT
ATGATGGTTC TGGGTGACAA GCAAGTGAAG AGTATTGGTG AGGATACTAA GCACGCGCAT
GCACTTTGCT ACAACTAGTC TGTCATGTGA ACTGCCATCT CACAGAAACA TTCATACAAA
AAAAAGTGCA GATGAATATG CAAAGCTGTT TGCTGTAGCC ACTTTCATAG CAACGGTAAA
TACAATGTAA CAGAAATACA ATGTAACAGA AGACAGGAGA GCAGAAGGAG AAGCCCATGA
ATCTCCATTC ACAAATATAT CTGTTACATA AATGAAAAGG GACAGATATT AAGTGGTCAC
GTAGGCACCT GCCTGTATCC TTCCGCCACG CTACACATCT TTGCTCTGTA GTTTACTGAG
                    NruI
                    ------
CATTAGGAAG TTCGCGACAG TATCTATATG CAGAATTATT GAACCTCTAC TTCAACAACA
TGTGCATGTG AGCTTAATAT TTATAGATGA TAGAGGTAGA AATAGACATA TTTACTATCT
GACAGAGTCC TAACATGTAG CCCAGGATGG CTTTGAATTA GACATCTTCC TATCTCCGCC
TCCAGAGTGC TGGTATCAGT CTTCATAAAG ACTTCTATAT GAAAACAAAT GTCCTGTTTT
CTATGTATTC GCCTTCGTGT CAAACTATAC TTTTCAAGAA GTTCAAGAAG TGATGTCCAC
AAGAACCTGA TGTGTGTCAG AAACACTCAG CTCCCCAGTG AAGTTGGCAG GAGGGCTCGC
CTGGTTCAGA GAAGCCTTGC GTGCTCCCTG AGTTCTGAGA GGAGAGTATC GAGGTTAATT
CTCCCAGGTT AAATACGCAA TCAAATAATG TCAGGGAGAT GACGGGTGTG TGTCGTCCTC
CCAGACCATC TGTGACTGTT TGAGTAAGCA AAAGGATTGA CTAAAAAGCT ATCATTTCCT
TTTCAGTCCC TACAGTCACT TTTGAATCAC AGGTATGTTT AGGAGGTGAG GCCAACAATC
CTGAAATGTG CAGGGACTCT CCAGAAAGCA GTCATCATCC CCTGGACCTC GTTCCTTTAC
ACCGAGGCGT CCTGGCTTGT AGGTGGCCTT CTTCAACAAC TGAGGGGTGA CAAGGACAAA
GCCTGAGAAG ACACAGCCTA GATTGTGAAG ACTTTGAAAG ATTTTTATAC TGACTGCATG
CTAAAATATC TTTTATACGT TGACTCAACA AAGTACATTA TCAGAACTAA TTTTACTTCT
TGTTTGCCTT AAAAAAAAAA AAGTGGCTGC TGAAAATTTT CAAAGAAAAC CCGTGACTCA
TTGCATGATT CTCGTGATCG GGGCTGTGGT CAATCCGCAC GCAGAACTGC TTCAATCCTT
CTTGATTCTG TGACCTCCGA GACGAAAATT CCTCTTTGGT TCCCGCAGGG GTGTTTAGCC
TCAAATTTCA AGTCATCCTC TTCCCCCTAG CGGCCGGAGG AGGAAGGGCT CTGCATACCC
CAGCCCGCCC CTAGGAAGCC AATGTCCCCA GCGTTTTACA AGTGGCGCAT GCCCTCTGAG
GCAAGCCTGC GGAGCAAAGG GAGTGAAGTG GTGGCGAGAG CTGAAGAGAT GAGCAATGAG
CCGGTGGCAG CCAGGCAGGA CAGGGAAGCT GGCGTGGTCG GATTGTGTAC TGATGCTGTT
TTTCAGGGTG GCCCTTTCCG TGTCACCAGG AGCTGTGGTT TCCAATGGGG ATGAAGTGGG
GACAGAGCTG GGTGGAAAGC CCCGCCACCT CATCTGGCTG GCTGTGGTT GTTTGAGCAT
CAGAGCAAGC TTTATATCCA GCCGATCCAT GGTTTTGTG GGGGACTTTA CATCCCTAAC
CTCACTGGGT CTCGCTGCGT TCAAAATTTT AATACAGTTA CAGGGTTCGA GAAGCTGAGG
GCTTCCAGGT ATTACATATC TATTAATGCT GCTGTGCGGG CTTGGAGGGA AGAACTTATC
TCGCCCTCAA TGCTTACTCT GTGATCCTCA AAGCAATAGA TGGAGACCAG TGTATGGCAC
AAACTGGGCA CATCCTAGGC CATGGACCCC AGGACCTGGC ACCTCCTCTA CTGCATTCCT
CTAAGAGCTG GTTTAAGTGG GTGTGCATGA AGCTAATAGC TGCAATAGCT GTGGGACCCT
CAAGTCACGG GTCCTGGTCC TGGTCCTCCA CCGTTGTTTT TTGTTTTTTG GTTTTGTTT
TTGTTTTTTG TTTTTTGTTT TTTTTTTTTG GCTTTGTTTT GTTTTGTTTT GTTTTGTTTT
GTTTTGTTTT GTTTTTTCAG CTGCTAATCC TTTTAATCTC TTGACTAGAT GCCTCTCCTG
                                                  >>...EX 3 ...>
GACTGCAGAT TCCTAAAGAG TTACCGTGAG CAGCGCCTGG CACACATGGC GCTGGCCGCT
>...............................EX 3 ......................>
ATCACCATGG GATTCGTCTG GCAGGAGGGG GAAGGCCAAC CCCAAAAGGT GAGGAGCAAG
>......................EX3   ......................>>
GAGAAATCAG GCTCTGCTGA GGTCCCTGCA CCTGGAATTA CGACACCAGC TCCAGGTTCC
GTTGCCTAGT TTCCAAAAAT CAGCGGAAGG CAAGAAAAGA GGGTTAGATT TTTTTTTTCC
ATTTTTCTTT TCTTTTCTTT TTCTTTTTTT TTTTCTTTTG CTACGGAGCT GATTTCTTT
TAGACTAATG TCCACTTTCA AAGACTCCAG CCATTCCAAT AATATGTGAG GAGCTTCCTT
AGGCCCAAG GACTCAGAAA ACACCCTGCA GAATTTTATA CTTCTAAATA CATTGGTTAT
TATGACTTTC ATAATTACCC CATTGTACAG ACATCTGGGG ATCTGTCCCA AGCTCAAGGC
CTTTGTCCCA GAGCAGCCTG GGACAGTTG GGAAAGCCAG TTTCTGAGTC CACTGAAGTA
```

Figure 10J

```
GCCATCCTTC TCCAGTACAA CTTGGACACT TCCTTATTTC CTTATTCTGC CCAGCTGATT
GCTGCTTTAG TTTATTAACC CTTTGTCTAA CTCCCTCCAA TAACTTTCTA GTTTCAGTCT
GTCCCTCAGA GCACAAACCC TTTCTTCTCT ACCCCTGGAG GAAACTAATA TTTCTTTTGA
GTCATGGTCT TACAAAGCAG CCCCAAACCA GTCTAGAACC TGCTCTCTTG TCCAAGTTGT
TCTCCAACCT GTGATCTTCT TGCCCCGGCC TTCCAAATGC TGGCATTGCA GTCACTCCAG
GCACGTGACA CCCTGTGCAG TTATGCTCCC AGTCAGTGTT GGGATGGAAT CCAGGACCTG
TGTGTGCCGA GTGAATACTT TATCACTCAA CAGGACCTCC GTTTTCTCTT CCTTTCCCCT
AAGTTTCTCT TTCCCAGAAA TCAAGGTGTT GACATCATTC CAGAATGCGT GAGAAGCCCG
AGGTGTGCTT CAAGGGCTCA TCTTACCCAC AGAGAAACAC TTGAGACCAA GAAGCAAGGA
CAGCACAGAG CTCCTGTTCC TTCAGACTCT AACACGATAC CATATTGTAT CTCATCTAAA
GGACTCGAGT GTCTAGGGTC TGCTGTTGGA AAGTTTAAAA CCCAGGCCAG TGTGACAGAA
CCTCCTGATG AGTTCTGCTG CATAGGCCCC CTAAACCAAT CTCCTGAATT ATGAGTTAGA
GAGGAGGAAG CAATGTCCAG CCCCCAAGGC CATCCCAGGC TCATCACCCC TCATTTTGGA
AGTCTTCCCT GACCTTCCCA GTGGAAGTGT CTGACTCACA TCTTCCCATT CTCCCCAGCC
CTGACTTCTG TGGATGCTTG GCAGAGCTCT ACGCCCTGTA AGCTGTAACT GTTCTCTACC
TAAAGCACAC CTCTTCCCTA ACTCGGAGGA AGAAAGAATG GCAGACACAG ATCTTTAGAC
TCTTCAGTCC TGGGCTGGGG AGACGACTCA GTGGGTAAAT TGGGAGCAAG CAGGCCGAGA
CACTGAAGCT AAGATTCCCA CAACCAGTGA GAAAACTGGC ACAGGCAGCA GGGAGCAAGA
GAGACCCTGT CTCAAACATG GTGGAAGGTG TCAACTGGAG TCCACACATT CCCCTTGGCA
TGAATGTGCC TACATTTACG TCTGTCTGTC TGTCTGTCTG TCTGTCTCTC TGTGTCTCTC
TCACACACAC ACACAAACAG ACAGAGAGAG ACAGAGACAG GGAGAAATTT CTATTTTAGA
AGGAAAATGA TTGGGGGGAG GGGAACATAA AAATGTTCTT TTGTTGTTGT TGTTTGTTTG
TTTGTTGTTT TGTTTTTACA CCTCTACCAG TTTGGCCTTT CCATGGCCGG GACCTCATGG
ACCTGAGCAT CTGCTCTGGA CTGTGGACAG ATAGAGATCT GTACTCAAGG GACACCCCAA
ACGTTAGTGG GTGAAAGGGT AGGGCTATGG ACAGGGCTT TGCAACCTGA AGGGTCCTTG
GGGCGTGAGC GAGAAGCTTG TGTTTCAGTG GAGTCCTGAA CGGGTGTTAG GAGGTTGATG
TCATACCCCA GGTCGGAACC CTAGCAAATC ATGTTAAGAG TCAGAAGAGA CAAAGGACGG
TCAAGGGGGG GGGGGTCTGT CATTGAGTGA CTACCTGACG TTATGGGCT TGACTCATGA
GGTGACACAA ACATCAGTTC TGCAAGCTGA AATTCTCTGT CCTCTTTATC CTTTCTGGGG
TGCGCTCTCT ATCTCTCTGT CTCTGTCTCT GTCTGTCTGT CTGTCTGTCT GTCTGTCTGT
CTTTCTCCTA TCCCCCCCTC TCTCACACAC ACATATACAC ACCTCTGTTT TTTTTTATCT
ATGTACATCT TTACTTCTAT TTGCATCAT GTGCATCTAG CCTTGTATCT ATATATAGAT
CATATATATT ATTTATAATC TATCATCCAT CTAGAAAGCA CTTTACCTTG ATAGTTCTTA
GTCTTTGATT TACATTAAAC ATTTTGGTGA AATAATTCTC TTTCTCCTTT TCTCCTCCTT
CTCCTCCTCC TTCTTTCTCC TCCTCTTCCT TCTCCTCCTT TTTCTCCTGT CTCCTCTTCT
TCCTCCTCTT CCTCCTCCTC CTCTTTCTCC TGTCTCCTCT TCTTCCTCCT CTTCCTGGTA
CAGTTTCCAG AGGTTCTGTT TATCATGTGC ACAGTGTATT CCATCTCTGG GTTTTGCATC
TCTTGAAATG TGTTCTCATA ACCAGCATTC TCACCGGGTC TCTCCCATGA AGCATGTGTA
GGGTATAGGT GTGGAACATT CAGAGAATTC GTGCTTGGTC TCCAGGTCGC TTATCACAGG
CAACCGTGAT GATTTTCTCT GCCAGTAGAA TATACTAATT GTCTGGATTC CTGTCCTAAA
GGTGCTGCCA AGATCTCTTG CCATTCCTTT TGTTGAGGTA TCCAGGAACT TGGGACTCCC
>>............................eX4 .........................>
GCCTATCCTG GTCCACTCTG ACCTGGTGCT GACAAACTGG ACCAAAAGGA ACCCAGAAGG
>..........................eX 4 ...........................>>
GTAAGGAGGG AAAGGATTCC TTCAGTTAGC AGCAGATTGA GAAAAGACTC AGGACTTGAA
CTGTCTTCGC AGAAAAGACT CAGGGTCTTA GGGCTGTTTT ATAGTGAGCT GTGTGCTCCC
ATTCATTTAA TTTAGGGTTC CAATAAAAGG GAATGCACAC ATTTAAACCT GAGACATTTC
TTCTTCCTGG GCTCTCAGGC ACACTGGCTT GCTGCTTCCA GTGCCCATCT GGATCTCTTA
ATCAGACTGT CAGCCTCCAG CTGTAATAAT GACACTGGGC TGTTTTTTCT CAGCATGTTC
TGTGTTCCAT TCAAGTCAGG TTAGGATGGG GTGTCTGGAG GTGATCTCTA TGGTTCTGAA
TAAATGATTT CACGTGGGTG GAATTCTGAT TCACACCATC TATTCTGTCT AGTTTACACC
ATTCCACACT TGTCCCGGGC ACAAAGCAT CTGTTTATTG ACTTTCAAC AAACAACCAA
                                                      SalI
                                                      ------
TCCATGGAAA CTTCATTTTC ACAGTTGAAT CTGTCTCAGG CGGTCGACGC AAGGCAGCAT
TTACTTTTGT TATAAATTAA AACAGCAAAC AAGAAGTCCA GGCTGGACAT AAAGGGACCT
TTCTTGGCAT GCTGGTTGTA GGTAGCCATG CAGTGCTGAA AGAGATGGTT GAGATCTGCT
GTGGACCCTT TCAAGAGACC CTTCCTTTTA AGAACTGGGG AGGGCTCCTC TTATCTACAG
```

Figure 10K

```
TCTGCTGAGC CTTAGAACTT CATGCTTTCT GGGATGATGA TGTCATATGA CGATGATGTC
ATATGATAAT GTTACATGAT GTCATACGAT GTTGATGTTG TATGGTGATG CTATATGATG
AATGGTATCA TGATGGCATC ATATGTTGAT GATAAGCTTG TTTGTGACTG GGGACTGAAT
GAACCTTCAC CTGTGAGGCA GGAGCTCCAC CCCTGTTTTC TATCCCCAGC CCTCTCTTCA
GCGTTTATTT AGATACAGTT TCTCTCACAA TGCCAAAGCT GACCTGAAAT TCACACTGTA
GCATAAGCAG TCCCTGACTT GGTGATCCTT AGACCTCCTC AGCCCCTTGA CTATCTGCCA
CTAACAGCAT GCACAACCAG GCCTGACTTG GTCTTTGACC AATTATACAG CAACGAAAAA
CTGATCTGCA TTGAAAGCTA CTAAATCTAA CTTAGAATTG GAGTAGGTGA GATGATAAAT
ATGTGCGCCT GGACTATTGT GAAGCTGGGT TTGTGATTCA AGGGAAATTG GGAGATGAAG
TCTTAAGGGA GGTGACAGGG TTGAAAACAA CCCCAGGAAA TGAATGTCCC ATCAAGTGAG
GTACAGCACC CAGAGATGCA AATGCAAGCC TGGAGCTCCC CCACCGTATT TCTTCTGAGC
CATCATCTTC CTGAGTCTTT TAAGATGTCT ACCCAGGGCT TATTAAGTGC TTTGAAGAAA
TGAAAGAAAT AGAAGCAACA CCCCCCCCCA CCTCCACCCC CACCACCCAA ACAGTTCAGT
ATTGAGACAA AGTAGCTCTT AACACAAGTC AAAGAACAAC ATAAACAGTA TCTTCAGAAC
TCCAGGGGGA ACAGCAGGGA AAGCATGGTG CCTGACCAGA CGCTGATGTA AGGCCACTCC
TAACAGGTGG GTAGGATTAG AGTAACTGAA GTGGGGTCTG CACCGAGAGG CAGCTAGAGA
GAGGCAAGCA AGAATGTGTA CATACACAGA CACACGACAC GGGCTGTCAA GTGAGATCTG
GTTTCTGCTG TCACCCAGTG GCTCACTGTC CATCCTAGGT GGGTCCTGAT CCGTACATGT
GCCAGGGCAT TGCAGATGAG TGTGGGAGCC TGGGTACCCG GGACCTCAAG AATTATATCT
GGTTACTAAC TAAGTTGTTT TCTTTTTTTT TTTCTTTTTC TCTTTGTTAT CACCAATAAC
TATTATGCGA CCAGACCGTT GGAAATCAGG TAAGATGTGC CTTTAGAACC ACCCACTGTT
           >>......Ex5 .....>>
ACCTTTAAAG GCTTGTGATA AAGCAAGAGG GTGGCATGGT CAGCTGTATG GATGGAATAG

BstBI
                        --------
CATCAGCTGT CTATGAACTC CTGAAAATTC GAAGTGCATT AAAAAGTCAA TAGTCCAAGC
AGTAGCTCTG ATGGAGGTTA GCTTCTAGGG GTGCAGGGAT TAATTTTTCT TAACCACATT
TTCCTGTATG TCCATGATTT AAAAAAAAAG TGTAGTGTAA GAAAAGAAAC CGTGGCTCTG
TGAAAACTGG CAGAGATTTC TTATTTCTGA AGAACATCAG CAAAAGGCCA GAAACAGGCA
GGTCACAGTG ACAGAAGGGT CCCTTTGTAA TCCCTTCTTA CCTGATGGGC TGGAGCCCTT
GTGAGTAGGT GTGGTCTATA GTCATAGGCT CCACCTTCCC CGGGGAGCAG AGCTAGCAGA
GGAGCCAGAG TCACATCCTG CGCTCTCTCT CTCTCTCTCT CTCACACACA CACACACACA
CACACACACA CACACACACA CACACACCCT CCTCAGCTCT GTGGAGCATA CAGGTGGATG
GCAAATATTC CCCAGGCTAA CACCTCTGCT GGACCGAGGA GATGTGTGAC TCACCTCCGC
TTTGCTGTTT TGAGGTTTGA GGCTGGGCTT TGCTTATGTT TGAGATGCTG GGGACAACGC
AGATGTGTGC AGATACTCAT CTGGGTTCTG TATCAGGTCA GATTTGGCTC TGATGGGAAG
ACAGGACAGC AGCAGGTTGA TTAGAAATGA CCTCCCTCCT CCTCCTCCTC CTCTTCTTCT
TCTTCTTCTT CTTCTTCTTC TTCTTCTTCT TCTTCTTCTT CTTCTTCTTC TTCTTCTTCT
TCTTCTTCTT CTTCTTCTTC TTCTTCTTCT TCTTCTTCTT CTTCTTCCAC ACATTATATT
CTATCCACAG TTTCTCCTCC CCTACTCCTC CCAGTCCTCC TCTCACTTCT CCTTTCCCTA
GATCTACTCC TACTTTTCCA AAAAAAAAAA AAAAAAAAAG CAAGCCTCCT GGAGCTATCC
TCCAAACCTG CCCTGACATA GTTACAAACA GCAGCCCCTC ATTTCAAGGC TTGATGAGGC
AACCCACTAG GAGGACAAGG ATCCAAAGAG CAGGCAAGAG TCAGAGACAC TCTTCCACTC
CCACTATTCG GAGTTCCACA GGAACACGAA ACTACACACA ACCACAACAT ATGAGCAGAC
GGCGTAGGTC ACGCCGATGC AGGTTCTGTG ATTGTCACTT CAGTCTCTGT GAGCCCCCAT
GAGGTCGGCT TGTTTTTGAT TCCGTGGGCT GTGTTCTCCT GGCGTTCTCA ACCCCTCTGA
CTACTGTAGT CTGTCCTGCC CCTCTTCTGT AGCGTTCCTG GAGCTCCACC TACTGTTTGG
ATGTGGTAAT GACAGGCTTC CGGCCGCGGT TCTGTGGCAG CAATTCATCC TTGGGTTAGA
ACTCTAGTCA GGCACGCAGG CACACACCCA TAATGGTCAT AGTTCTCAGG TCATAGGAAT
TTGGCTCTAA CTGATCTGAT TTTCTTCTTT TCTTGGTCTC TTCCTCCAGT AACCTGGAAA
                                                     >>..Ex 6 ...>
CCATCATCTC ATTTCCGGGG GGAGAGAGCC TGCGGGGCTT CATCCTAGTG ACAGTCTTGG
>..............................Ex6    ............................>
TGGAGAAGGC AGCAGTGCCC GGCCTTAAGG TATCTTCTTA CTCACCCGGC CCTCTCCCTA
>.............Ex 6 .............>>
TGGTGGTTTT CCCCACGTGG ACAGACAGAG GCCTCCTCCT CCTAGGGTTG ACGATGAAGA
GACATATCTG AGTTCTAGCC TGTGGTGTCA GTGCCCTTTT AGCCTGGAGT GAACCGACTT
CTCCGTCTAC ACCCAGGTAC CACACGCTGA GTGCAACAGA CACCCACTGC GCTAGCTGTT
```

Figure 10L

```
CCACTTCATG GACCTGCAGA AGCTAGAGAC TCAGAGGTCA AAAAGAAAAA GACTGTTTTA
TGGAAAGGCA GATAAAGGCA TATCCATGCA TATCTGTAGG GATGCCAGAG TAGAAACGAC
TGTGATATGG GAAACCCAGA AGGAATGAGA AAGCACTTGT GTTGAGGCTC TTGATGTCAC
AATTTACGCT CCAGAGATAT TCCAGTAGTG TGGGCTACTC CGTGGCGATC TGCATCCCGC
GGGGGTTTTA ATAAAAAAAG TTACTTCGTA GCACCTCAAC TGAGAACGTG GATCTTATTC
CTAGGCCCTG GTTCAGGGAA TGGAGGCCAT TCGGCAACAC AGTCAGGACA CCCTGCTAGA
     >>........................Ex 7 ............................>
AGCCCTGCAG CAGCTGAGAC TCTCCATCCA GGATATCACC AGAGCCTTGG CCCAAATGCA
>...................Ex7     ............................>
TGGTAAGATA CTGGAGCAGC GTCTCCAGTG GCCTGGACTT GGGCAGGTCC TACGTGGATG
>
ATGGTGGTCC ATCTCTCCAC AAGATGGCGC TAGTGTTCTA TATTTAGCGT AAAGCGTCCC
AGTCAGAGAA TTGTTTTTTT TTTTTTTTTT CCAGTCGGCA GAAATATTTT TTTTAGAATC
GTTCTTTATA GTTTCGTGTG GTTGGGGTAG CTTCCCTTCT CCAGGGTCCA GATACGACTT
TGGCATGCTG ATCTCTTAAC GAAGCCTGGG AGATTGGATG GGCCACAAGG GGGAATGTTG
GTTATACAGG TTAGGCTTGC TGGCGGGCAG GGCTGTCCCG TGGGGGCGTC TGTAAGGCCC
TCAAGAGTCA TTTGCTTTTC CTCTCTGACC ATGTTACAAA TCCAGAAAGA CCCTCATGAT
CCGCTGAAGG AGGTCCAAGG ACCCGGAGAG CTCCCCAATT AGACTCCTTC CAAGCCATCT
GATCCTGAGA CAAATTTCTC TATGTGATGA CTTTTTTTCA AGGTTTTAGA ACTAGCTGTA
TTCACACACG TGGCGAAGGA GAAGGACACG TGTCCACACT TTTCAAAGAT GGCAACAGTA
TCCTCCACAC CATCCCATGA AGCCCTTAGT GTGGGCACGC CCTCCTCGCG TCTCCGGATG
GAGGATATGT CCTAGCCTCT GAAATACTTG CAGTCAAAAT AGGGCACTAG TGAGGACAGT
TTAGTCCAGT GTTCAGTGAG TTTTCATCCC CAGTGCTGAG ACGCCATGGG AAGGGCAGTG
TTCCTGGCAC ACAAGCAGGC TGACAACAGC CTATCAGACA AGGACACACA GCTAAGGGGC
TAAGGGCTGT CCGATGATCC TTACTCAGTG TGGCACTGAG GAGCGGAAAC AGGTCGCCAC
CACCTTGCCT CTATGCAGGC ACCTTGCCAG CAGTACAGAG TCAGCAAGGG GAGGCGCTTG
CCATACTATA ACAGTTACCA TAAAAGAGAG ATCATGTTTA AAAACAAAAT CAAACGCTGG
AAGGCATAGG CAGGGGGTCG TGCGTGTCCT TGGCACGGAG TCTGGTCTGC ATGGGCTGCT
TTTGTGTGTG ATTCGGAGAG CGTGGCTGGG TGGATTCCCT CCACTCCCAA ACCCCCAACT
AGATTTTACC AATAACCAAT CACTGTGTTT AGAGCCCAGC TTCAGCAAGC ATCCTGGGTT
TCCCTCAGGA CATCCTTCCT TCCTTCCCAG GCATGTAGGG TCCATAAAAA TGCCTTTTGT
GGACATCGGA GGCCCACTGC GCTGCAAGCC AAGTCCCCAG GCCTTTGCCC AGCCTAACAT
AGTTGTACAA ATAAGGTTTG TTTAATGCCA TTTGCAAGCA AAAATTCTCC ACTGAAATAT
GGTCCCAGGA CTGTTCGTTA GCTCTTACGT AAGAAATGAT TCAGGAAGAA CAGGTTGGAA
ATATAATCCC CCATACTTTC TTCTGAAGTT TTCATCTTTT ATACTTAAGT TCTTAACTCA
TCTATTATCA TCTGCATGTG CTATGAGATA GCAAATGAAT TCAATCTCCC TCCTGCAGGT
AACGTCCACA TGGTCTCTCC TTAGATTTGG TTAAAGGAGC AGGTTTTCTG CAGTGGCCTC
TGCTCTTTCC CTTTGGGTGT GTCTCTCTGC TCTGGGTGCC CTTAGTCTCT TCTTCCTTTT
CTCTGGAAAG TTCCCTCCCT GGTTTTCTTC TTCAGGGGCC TGGCTGTCTC TCGGGAGCCT
TAGCAGGAAC CACAAAAAGA AACACAGAAA CCAAACCCTC AAATGGGGAC TTAGTTCAAG
CTGCATTAAG TATGGATTCT GATATTATAC GTGCAATTTC TATCACGGAA GGAAAACAGG
CCAAGGGACT AGAAGCAGCA TAAAATATTA GTCTGCATTT CCTGATGACT TCTTCTAACT
CATTTGTCAC GGTTGCTGGG TGGTCTTTAT CTGTCACATG CTGTCTTGAC ACAAGGACCC
CTCTCTGGTA TACACCTTCA TTGGCTACCC AGTTTCCCTG TGTGAGAATT CAGCATCTGC
ATTTTCATGC GCAGGGTTCC TTGAGTTTCT TCCAAAGGAA GGCAGATGCC TAAATTCTGT
TTTATCAACA GTTATTTGCA TTCTTGTGTG TGGCAAACAT ATCTTTTTAT TTAGTTACTT
CTGCGCTGTT TGTTTCTACC TTATAGAATG AAGCAGGTAT TTAAACGTTA ACTTGGAATC
CAGCCCTTTG GTAAACTACA TTCTTATTGA TTACAGCAGT AATTTACAGG GTTAGCTGGG
TTTCTATGCA GAGATCTTGT TGCTGAGACG TATGCTTAGG TTCATCATTA ATTATCTTTT
TCTTAAAAAT AATTTTCCCT CACATAATAT ATCCTTCCCC TTTTCTCCCC TCAGTTTCTG
CCCACCTTCC CTCCCACCCA GATCCACCAC CTTCTGTGTT ACACTGGAAA ACCAACAGGC
TTCTAAGGGG TAATAATAAA ATAAAGTAAG AGAAAACAAA AACTATCATG TTAAGTTGGA
CAAGACAAAC AAACAGATGG AAAGGAGCCT GGGAAAGGGC ACATGCACAC ACACACACAC
ACACACACAC ACACACACAC ACACCAAGAG ACAAAAAGTC AGCTGTAAGT GCACATGCAT
CCACACACTC AGGATACCAC AAAACACTAA ACCAGAAATC ATAGCATATA TACAAAGGAC
CTGTAGGGTA AAAAAAAAA AAAAAAAAAA AAAAAAAGT GTGTGTGTGT GTGTGTGTGT
GTGTGTGTGT GTGTGATAGA GAGAGAGAGA GAGAGATGGG GGGAGGGAGA GGGAGAGGGA
GAGGGGAGG GAGGAGAAGG AGAGGGAGAG GAAGAGAGGG AGGAGAGGGA GAGAGAGGGA
GAGGGGAGA GGGGGAGGGA GGAGAGGGAG AGAGGGAGAG AGGGAGAGGG AGGAGAGAGA
```

Figure 10M

```
GGGAGAGAGG GAGAGGGGGA GGGAGGAGAA GGAGAGAGAG AGGGAGGAGA GGAGGGAGGG
GGAGGGGAGG GGGAGGGGAG GGGGAGGGGA GGGGGAGGGG GAGGGGAGGA GAAACAGACA
GAGAGAGACA GACACAGAGA TATGAGACAG AGAGACAGAT CCTGTCTAGA GCGCTGGCGA
GTTTTATGTG AACTCAGCAC ATATAGATCA TCTAAGAGGA GAGCTCCTCA GTGCAGAAGA
GGCCCTCATA GGGCAGGGCT GTGCTCAAGC CTGTGGGCA TTTTCTCAAT TAGTGATTGA
TGGGGAGGAC CCAGCCCATC GTGAGTGGAG CCACCCCTGG GCTGGTGGTC CAGGTTTCTA
TAAGAGAGCA GGCTGAGCAA CCTATGAGGA TCAAGCCAGT AAGCAGCGTC CCTCCACGGT
CTCTGCATCA GCTCCTGCCT CCAGGTGCCA TCCCTGTTGG CGTTCCTGTC CTGAGTTCCC
TTGATTAGGA AGCACGGTGT GGAAGCATAC GATGGATAAA TGCTTTGTTC CTCAAGTTGC
TTGGGTCAGG TTGGTTTTTC ACAGTGATAG CAACCGTAAC CAAGACAACA TGTGAAGTAA
AATAAAAGAT AAAAATAAGA TACACTCTTG AAAATGGAGG GGGTAGGAGT CCCTGTTGTG
ACATTATGAG AGACTGAACC TCCAAAGACG CCATTTTGTT TGACTTCTGC TGCAGTCTAG
TACTGGACAT GCAGCCTGCC CTAAGAGGTG GGGACCAGGA GGGGAAGCAG TGATCGGGAT
GTAAAATGAA TGAATGAATG AGTGAATGAA TGAATGAATG AATGAGGAAA AGAGTATTTT
GTTTTCCCAG TGAGACTTCC TTAGAGAAAA CTAAATTTTT GTTTCAAGT AGCTGTCACT
TGGAGGCAGC ATCGGGTGA GGGGTGAGTG CTGTGTCCAC TTCTCCTCTC AGCTGTGACC
CTGTGTGGTG CAGACCAGTG AAGGCCCTGT GCATGCTGTG ACTTCGTTGA CCTTGGTGAT
TGAAAAGGCC TTGTTTTCTT GGTGTCCTTC ACCCCCCCCC CTCCGCCCAA CTCTTAATTT
CTGTTTTCTC TACCATATGG TTCTCTGAGC ACTGAGGGGT GGGGGTTGAT GGAAACATCA
AAGACCATTT ATAACTGAGT GTTCCGAGGT CTCTCACTCT CTGCACACTG TCTGGCTGTG
GGTCTCTGCG TTTGTTTCCT ATCTGCTGCA GGAGGAAGCC TGTCCGATGG TGACGGAGCA
AGGCGCTGAT CTCTGAGAAC AGCAGAACAT CATCAAGAGT CATTGTGTTG CGTTTTGTTT
TTTGTTTTTG TTTTTGTTTT TGTTTTAAAG TCAATATTAT TTAGTTTCCC CCCTAGGTCC
CTGGGCTATC TAGTTTCAGC ATGTTGGTCA CCCAATCAAT TTCGGGCATG AATTCCATTG
TGTGGAGTGG GACTTAAGTC AAATCAGACG TAGCTTAGAT GCTTCTATAA ACTTTGTACA
ACTGCACTAG CATATCTTGC AAACAGGATA CCATTGTAGA ACAAAGGGTC TGTAACTGGC
TATACACACA CACACACACA CACACACACA CACACACACA CACACATATA TATTATATTA
TATATTATAT ATTAATTATA TATTTATGAA TCACTTTTGA AATATCTACC GAATATATTT
TATATTTCA TGTAAATTCT ATTGTATCTA TCAACATGAT CACTTGGCTT TACCTTTAAT
TCATTAAGTT GTGTAAAATA GTAATGCATA CACATCCCAC TTCCTATGCA AAGGGCTGGA
TACTGTACTT AACAATCTGG AGAAGAAGCA AACATCAAAG TCTAGGGGAG GTCCCAGAAA
ACAGGCTAGC TCAGGGGACA CAGTCGCACT GGTGAAGACC ACCCTGGGGA GTCACACCCT
AGAAGGGAGA GTGTAACCAT ACTAAGGAAT CACACTTGAG GAGAGGTGAG ACTACCCTGG
GGAGTCACAC CTGAGAAGAG AGGGTGTGAC CACCCTAGGG AGTCAGGAAG TCACACTGGT
GAAGAGTGGG GGTGTGGGAT GACCACACTG AGGAGTCACA CTTGAGGAAG GGGGGTGGCC
ACACTGAGGA GTGTCTGAAA GCATTGAGAC TGTACATCTC AGGTTATCAG GGCTTCAGAG
AAAACAGACA GGGAGAAGAG ACAAGAACTG GATTCTGTGC GCAAAGGGGG AAAAGCAAGC
AGATGTGAAG GGTGTGCTGT TAGAGTTTAT CTAAAGATGT TTCTTTCAGA AATAAAGAGA
TATAAGCTTT AATTTGGATG AAATAAATGT GGTCTAATTT CCCAGAATGT AGAGGAACTC
ACTAATGTAG CAAGATTGGC CTTTCAAAGC AGACCAAAGA CATTGAGAAT TAAGATAGCT
ATGATGGCGT GCTTCCTTAG GTGGAAGTCC TATATGGAAT CCCATACTCC CCAAATGTGA
CTGGTCGGTG CAGCTTGGGG CTAACAGCTC TGTTGACCTG TGGTGACCCC TGGAAAGCCC
TGTGGGATAG AGGAACTCCT GGATGTCAGT CATTTGCTCT GCCTCTCTTG TGAAAGCAGT
GGTCTCTGTT TTTCTTCCTT CTCTCGGCTT TTCATATTCT CTTGCATATC CTGTTTATTT
GAAATGTTTC TTAAAGGATG CTCATAGTCT CTCACTGGTG GTGGTGAAGT ACAAAACCCT
GCTGCACAGC AAACAGAGGG GGCCAGCATA CGGAACGGAT TAACAGCCCT ATGAGAGCCC
ACACGCTCTT CAAGAGAACA TTCCATCTGT ATTTGCTGCT GCCATTCTGG GATCTGCATA
CATCAGATAG GAGTGGGAAG CCCTGGGAAA ACAGCAGGGT CCAAGGCACA TGTGGCCAAT
TGCTTTTTGC CCATGGTAAA GTTCACATTT GATTGCTTTC CAGATTATGT GGACCCAGAC
                                                >>......Ex 8 ......>
ATATTTACT CGGTCATCCG GATCTTCCTC TCTGGGTAAG TACAGCTTAA TTGGTTTCCT
>>>
GCTTGAGACC TGTAGAGTTC CCCAGATTTG TGCGAGGATA GACAGACAGA AGCTTCCTAA
AGTAAGAAGT ATAGCAAGTG ACTCAAGCTG GCAAAGTCAC CACCTGGGTC CACTCTAGGA
GGCTGGACCC CAAAATGATC AGAAGGAAAA AGGTTCCAAC AAAGCTGGGA ACTTAAATCC
AAAAGGGGCA AAAGGGGCTG TCTTCAGCCA CCAGAGGGAG ACCATGGACC CTCTGAGAAC
CCCAACGTGA TGACAGGGGC AAAAATTAAA GATGGGAGAG AGAGTGGGCA GGGAGAATGT
GGGGAGGAGA TGGAAGGGAG GGTAGAGGAG AGAAAGGCTG GAAAATGATA GCTACTTCTT
TGTCCCTTGA CCTTTGAGGA CATAGCATTC AGGGGACCCA TCAGGAGACA AGAGTCCAGG
```

Figure 10N

```
CTGTCACCTG ACAGAACCAT CAATGCCTTG ATCTTAGACT CCCTCTCCTT CGGAGTTGTG
AGAAATACAG TATGATTGAT CATATTCAGC TTGAAGTATT TTGCTATGGT GGTAGCAGGT
ACCCTTGATT TGTCTCACGG CTATACACTT CTCTGTCTGT CTGCCTACCT CGCATGCCCC
CTGCTCCATC AAGCACATGT CTTCACCCAG TTATTTCTAC CTTGACAAGC TTTAACCAGG
TTGCCATCCA ATTCACCAAC CAACAGAGCC GATTCACTTT TGAACGTTTG TGTCTTGTTG
ACTTGGAGGT GCCGGTGATG TTATCAGAAG CATCCAAGCT GTGCCTGGAG ACAGCAAGAG
ACAGACCAGA TGCCGAATCT ATTACCATTA CTGCCAAGTC CCATTGGGAG AAAAACTAAA
GTGTGCATTC GTGCATGTGT GCGTGTACGT GTGTGTCTAG AACTGAAAAT TTTATTTCCT
TGCAAGTATC AGACTAGAGT TTTCCTGGCC TGCTAGGTCC TCTGTTGCCT CTCCCCACCA
TGTCCCCAAT TTGACTCCTG ACACAGCACT GGCACTTGGC ATTTTTCTAG AATTACACAT
TTTCCTGACT TTTCTCTTGA CTACCGCCAG AGGAAATTTC TCTTAAAGGG GCTCCTGTGG
CTGTGCTCAA TCTAGTCGGA TGAGTCAGGG AAATTCCCAC ATTAAAGCTA AACTGATCAG
TGGCCTTAAT CCCATCTGAA AAGTCCTCCT GCCCTGTCCT GTAATAAATA TATCATGGTG
ACCGGAACAG CTCATAGTAT TAAGAGTCCT AGGAATTCGG TTGGGAACCT TGGGGAGCTA
TTTTTAGAAT CCTACCCTCC AGTGTCTTTC AAAGGAATCA TTTCTACTTC CTCTTGGCAG
AGACTTGATA AGAACCAGAA GGGGACTTTG TTTGCATCGA CATAAGTTCC GGGCAATGAC
ACTTTTTATC TGGTATTTGG CATAAAGGCC ATCCCTCCAC TTCAAATGCT GAGACTGTTT
ACTGTGCCGC TAAGTGGCTG TACAAGATCC TAAATGTAGC TGTAGTTTCA ACAAACATCT
GGATTGTTGG GAGTTTCCAG TAGACTTCTC TTTAAAATGT CAGCCTCGCT ATTCTGCATC
TATCCCGAGT TTCTCATTTG CTTCTTTAAA ACACAGTTTT ATTTAAGAGT GGATGTCCTG
TGGAAATGAG ATGTATTCCC TCCAGTTCCC AGCCTGCCAC AGGTCTCAGA GAGGCCAGGA
ACGGGGGGCC CAGGTTGCTC TGCAGGGAAA CATCGCCTCA TTTTGTTGTC TGCCTTAACT
TCCTCTTTCC TTGGGATTGC TAGAAATACA CCAGGAGCAG GTCTAAAAAT AACCTTACCG
TAGAGGCCAG AATTTAAAAT GGCCCCATCC CTTTACAAAT GGCAGCTCAG CCCTACGTGG
AGAAAGAGGC AGTTGTGTCT CCCAGTGCTG CTGGGGATGG GGTGTAAAAA CAGACCCAAG
TTCATCATCT GACCTCAGAG CTGGTGTTTT CTGCATCACC TTCAGCATGG CTGGCTTTGG

AatII
                                          ------
CGAAGGCACT CCAGCGAGTG CTGAAAGGAC ATTGCCTGAT GACGTCCTTG GCATTTGTCA
TATCTGATAG ATCCCTTAAG CACTGGTTGT GCCGTACTGA CTGAAAAGCT CTTTTCTCCT
TCCTTCCTTC CTTCCTTCCT TCCTTCCTTC CTTCCTTCCT TCCTTCCAAT AAATCCATAG
TGAGGGCCTA CCACATCCTA GACACCACTG TATGTGCTGG AAACAGCAGT AAAGAAAAGC
AGTCACGTGG TCCTTGTGGA GCCTGTGACT TCAGGATGGG GAGAAGGTAT TGACAAAGCA
AACCGAATCA AAGCAAACAT CCAACAGTAT GTGTTACAAC TAGAGGCTGC ATGAAGCAAT
GCCGGGTAGG ATGCGGGCTG CTAGGGAGGG ACCACTGGGT GTGGTGGCTC AGGTATCTTG
TTTACTGATA TCTAGAAATA CCACATCCCC AGTGATATGG GAACAGATGT CACAGGCAAT
GGAGTGCTCT CAGAAGAAGA TTCCTGTTGT AAGAGGAGGG AACAGTTCCT GTGACAGGAG
GAGGGAGCAG ACATGAAGAA TAGACTTAGA TGTATGTGAG AAGGAGGATG CCTGCCATTG
TGGAGGACTC TCAGTGTGGG CAGTGCTGCC TTCCTTTCTG AGTGGCACAG TCCTGTTTGG
GGCTGCAGGT TGTCAGTACC CCTCCTGAGT GGGGTAGGGT GGCAGAGAAC AAGATTACAA
AGAAAGCATC AGAGGTGGAC CCAAGGGAA GATGCCGAGA TGGAGATGAA TGTCAACCAT
CTTGAAGATG AGGGGAGAGG TGGAGAGTAT ACAGCCTGTG GGTCCTGACG CCTGTCACAG
AGAAACAGAA ACATGTGCGT GCCCTTGGCC GCTCTGGACA CAGATTGCAG CCCATGTGCT
GGTGTGGACC AGGTCCATTA TCCACACCGT CGTCATGTCT GCAACATCAC TTGCTCATAA
AATACCATTC TACAGTTTCT CTAGCCCCGA ACTCTTATAT TTGTTTTTGG GTTGTTCACA
GGCCTCTTTG GATTCCATTC AAATCCTCGA ACAGGTGCAA GAAGCAGATT CCCCTACAGA
CTAGGGAAC TGAGGGTCAG AAAGGCTGTG CACTGTAGCT GAGAGATGAG AGTGGCAGCA
GGCATTCTTA GCCTCCAGGG TTGCTAGAAC AATAAATAGC TGGTGCTTAC CGAATGTCTA
ATGTGCTCCA GACACCTGGC AAATAGTATT TGAGTCGGAT CTTACAATGA CCCATAAGCT
AAGTATGAAT GTCAATGCCA ACATAGCTC TTATCTCAAA GGAATAAGAG TTAGTTTATT
CTTTGGCCAA ATATTAATGC CCAGAAACAC AGATTCCAGT TGTCCCAAAT TAACATGTTC
CACTGGGGAA ATGAAGGAGT TTTCATAGCT CAAGGGCAAA GCAAGTTACC AATCAAGGGG
TTTTTTGAGA ACACTGGTGG GGGCCCCAGG CAGGCAAGTT ACAGCAAACA AGAACTCTGT
ACATAGTCAC ATGCAGACGG GTAGTGGAAG CCTGTTGTCT ACTAGGTCAA TACATTCCAA
ACCATCAAAG ATACTGGGTC AGGCAGGACG GAGTTAAAGA TAGCCCATTG TCGTTTGACT
CTGGATCTTC AAACTTTCCA ACTCTCCACG ATCAATCAGT TTTGTAGAAT CTTTAACATA
GGCATGGCTT CCCCCTCCCT CCTCCCACAC ACCCCAGCGC CACCTGGAAC TTCAGTTTAT
ACTAACACTA CTCAGACAAG GGAGCCAAGG CTCTGAGAGG TCCCATGTGC TAACCCAGGG
```

Figure 100

```
CTAGCAACCA ATGCACAGTA GAGCTTAGAT TCTGTATCTG CCCAGAATAG AGACCTTGTC
CCACAGTTTG TGTGACGCTC CCTTCTACCT GTGTATCCTT TCTTCTTCTT TCTTATGCTG
TATCTCTTTT CTGAACATGA CTTCCTCAGT TGGTTACCAT TGAAATTCAC TAATCGGTTG
ACTTTAAACA GCCACCAAAT CTGGCAACCT GGCCACTTGC TGTGTTGGCA GCCTCAGAGC
AGAGTCTGGG GAAAGGTCTA GGATGCAGGT GGGGGGAGCT AGCCTGAACA CAAGGCTTGG
ATTGACAGGG AGCAGAAACA GCCATGTAAA CCTGCTACTT GCCCTGTCAA CCAGGGGCTG
GTTTGCTTGC TGGCAAAAGA GGTCAATGTG CTTCTTGGCG AAGGTAGACA TCTATGGGAT
AAAGAAAAGT AGACTGCAAC TTAGAGATGC ATGTGTGTGT GTGTGTGTGT GTGTGTGTGT
GTGTGTGTGT TCCTGGAATG CTGGGGGTCT GGGAACTTAG CTCAAGTCTT TGATTCTTTA
GGAAAGAAGG TAAAAATTGC CTGGTCCTAT CTACTGTCAA GTGGTCGGGG TGAGAGAGTG
AGTGTATGCT CGTGTATGTA TGTGAGCACT GCAGGTGTCT GCATGGTGTG CCATGGTGCT
CCACTGGGCT TCATGCTGTG CTCCCCTAGG CTTCAGTCAA GTCAAGACTA GGTCAAGTCA
TGGAGGGTAA ACAGAAGAGA GAGAGAGCAG AAAATGAGGG ACACAGGAAG GGTAGAGGGG
GAAAGAGAGG GTTGTGAAGC TCACGCGTGA TCAGGAGCCC CAGGCTTTCT TCTTCCAGCC
GCCCATAGGC TCTGGTGCCC ACAACATTGG TTACAACCCC GCTCTCCATC ATCATGCTTG
TCATCACTGC TGTGACAAAC CGCTTAATAA TGGTTCTCAC GGAACATTAA AAGCCAAGCC
AAGTTTAACA CCTCGAACAT TTCCAAGTGT TATGGGGAAT AACAGTTAAG TGTCTGGGTG
TGCTTGTGTG TAATTGGGAA TCTGTAGTGG TGGGGTTACC AGTGTCAGGC CACAGTGTTT
GTGATGAGCA GAGGGGTCGG GGTCTTTCTC AGATCCCTTA TCTTGTCCTG TCAATGGTGG
TGATGTAATA GGTGCACGCC TGTGACAGAG CTGTTTAAAG CATTGTAAGA CCAATGAGTA
AAGTTCCTAC CCTTGCTTCT CCTTTAAGTG AGGCAGAAAA AGGCTCCACC ATGACGTGGT
GTAAAGATGA AGTCAATCTA ATACTTCCTT GGATACTCTA GCAAGCTTCA TTCACACTTT
TTATTTCTTC CTCTTCCTCT TCCTCTTCCT CTTCCTCTTC CTCTTCCTCT TCCCCTCCTC
CTCTTCCTCC TCCTCTTCCT CCTCCTCTTC CTCCTCCTCC TCTTCCTCCT TCTCCTCTTC
CTCCTCCCCC TCCCCTTCCC CTGTGCTCCT CATTATTATT ATTATTGCTC CTGTCTAGGT
                                                                >>>
GGAAGGACAA TCCAGCCATG CCTGTGGGGC TGGTCTATGA AGGTGTTGCC ACAGAGCCTC
>..............................Ex 9 ................................>
TGAAGTACTC TGGAGGAAGT GCAGCCCAGA GCTCCGTGCT TCATGCCTTC GATGAGTTCC
>..............................Ex 9 ................................>
TGGGCATTGA GCATTGCAAG GAAAGTGGTG AGCAGCAGTC TGATCTCACC TATGCTTTGA
>............Ex 9 .............>>
TGGGACAGCG AGGTAGACTA GGGAGACATC TCTAGCAACT GATAAAGACG GGTGTAAATG
AAAATGTCCT GAAGTTTATC CTTGCCTAAG CCAGCAGGCA GCTGTGTGCA TGTGCCCTCT
CTTACACTGA GTTAGTCAGT ATTGGGCAT CGGATCTTAT TAGGGTCTTC CAACAGTCCT
GTGACCTGGG TTGTTCACTG TCCTGTTGGC TGGGGTCTTT TATCCGCAGA TTCCCCTTTC
TACAATGAGG TGATAATGTC ACATTGAAAG GCCAGTCTGG AGCAGCAAGT GATAGTGCTG
AACTTCTCTG CTAAAGCCTT TCCCATGAAA TGGCCCAGCC TCCCACTGAA TCTATGTGGA
CCAGGCGAGG GAGCCCATCG CTTTGAAGCC TTTAAAATAG TTGTTATTGA TTTTTCTGGC
AGCATAGAGC TATCCTTTAA TGACTACCAA AAAAAAAAAT ATTGCTACCA AACTTTAATT
TGGATCAGAA CCAAAAAGAA TTAAAACTCT CTGGCACGAA CCTGTTCTCT GGAACAGTCA
GGGTTGTTTC TGGGTTTCAG CATTTGATTT TAGTCACTGA CTCTCAACAA CCAACCAACC
AAACAAACAA ACAAACAACC AAACAACCAA ACAACAACAA CAAAACCTAA CCCAAACAAC
AACAGTTAAA GGTGTAATGG TTTTCAAGAA AACACTGAGT TTTCAGTGTT TCGGCTTCTC
TGGGTTTTTA CTAAAATACC TGCTTACCAA TGTCGTCTCT ACGTGCACAG TAACTTCCAT
TTCCTGCCCC CCTGCCCGCC CCCCATTTAT AAGTATCTAG CAAACAGAAT TCACCAGAGT
GTTCTGTGTT TGTGTGTGTG CGTGTAGACT CGTCTCTTAG TCCTCAGCAG GGAATACCAC
ATCAGTCATA CACACGGAGC AGTAGATTTC TGTCCAACTT TATTATCTGA GAGATGTTTG
CTTCTTTTTC TCCCCTGTGT CTCCTGTCAA CAACCAGAAA TGAACATTTG AGCATTTGGC
AGCTATAACA AAAGCCCGAC AAGGCTGAGG GAGAGCCCTA TCAAGCATTT CTGGTACCTG
AGTGTTTGGA ACAGTGGGCA AACCCTCCCA AATGTCTGCC TCGAGCTAAC GTATTTCTCC
CGGCTGTTTC TTTCAGTTGG CTTTCTACAC AGAATGAGGG ACTACATGCC GCCTTCCCAT
                 >>...................Ex 10   .....................>
AAGGCTTTCC TGGAAGATCT CCACGTAGCT CCTTCTCTGA GAGACTACAT ACTGGCCTCT
>............................Ex 10   ...............................>
GGTCCTGGGG ACTGCCTGAT GGCCTATAAC CAGTGTGTGG AGGCCCTGGG AGAGCTGCGC
>............................Ex 10   ...............................>
AGTTACCACA TCAATGTCGT GGCCAGATAC ATTATCTCCG CTGCCACCAG GGCCAGGAGC
>............................Ex 10   ...............................>
```

Figure 10P

```
AGGGGGCTAA CTAATCCCTC ACCCCATGCC TTGGAAGACA GGGGCACTGG GGGTACTGCC
>..........................Ex 10    ............................>
ATGCTGAGCT TCTTGAAGAG TGTCAGGGAG AAGACCATGG AGGCCCTCCT GTGTCCTGGT
>..........................Ex 10    ............................>
GCTTAGCAGT CATGTCCTGC ACCCTAACAC TTAGATGTTC TCATCCTGCA TCCCAGCGTT
>...>>
AGAGGTTCAC ATCCTGCATC CTAGTGCTTA GCTGTTCTTG TGCTATATCC CAGCGCTTAG
CAGTCATGTC CTGCATCCTA GTGCTTAGCA TTTTATATCC AGCATCTTAG TGCTTAGAGA
TTCACATCCT GCATCCTAGA GCTTAGCATT TTATATCCAG CATCCTTGTG CGTATCAGCT
ATGTTTTGTA TCCTGCTTAG CAGTTAACAT CCTGCATCCT AGTACTTATC TGTTCTCATC
CTGCATCCTA GAGCTTAGCA GTCAGGTCCC GTGGGAGCAA GAACCAGGGT CTGAGCTCTG
TCTGAGCCCA AGCATGGCTT TACTGCTTTG TTAATTGTGG CTCCCACCTC CACCCCACCC
CAGCCAGTTT GCTTGCTAGA AGCCTTTCTG CACTGCCTAA TCCCCCTGCC TCACAGCAGA
GAGCTGCAGC CATGACCTCC TCATTCAGTA TTAGGTGGAC AAGTCGGAGA TACCCAAACT
CAATTTTAAA AGAATCAAGT TGCTTTTGGG GCATGTTACT TCATCTTTTC TTACCCTGGG
CCTCTTCCCT TCTTCCCTAC CTCCCTCGTC CCTTAGTCTT TCACCCCTCT CTCTTTCTCC
TTTTGTCACC CTCCCCCTCC CCTGCTTACT CTCTTTTCCC TTCCCCCCTC TCCTCATCCC
TCCTTCCTTT CTTCCTTCCC TTTTTGTCTG TGAAGCACCA GGTCTGATGG GCCTCAAACT
GTGATCTTCC TGTCTCACCC TTCAAAGGTT ATGTGTATGT GACGTGTGTG TGTGTGTGTG
TGTGTGTGTG TGTGTGTGTG TGTTCGTTTC TTTTGTTTTT CCCTAGTGGA GATGACACCC
AAAGATTTGC ACATACCAGG CAATTGCTCC ACCACCTGAC TACAGTCCCA GCTCTCTGTA
TTCCTGAAGG AAAGTCTTGA TGAGTTGCCT AGGCTGGTAT TGAGCTCTTT AGCCCAGGCA
GGCCTTAGTC TGAGTAGCTG GGATGTACAG GGATGAGCCA CTGAGCCATG CTGCTGCTGC
TAACGATGAT GACGATGATG ATGATGAAGA TTATGATAAC TACAGTCACT GCAATAATGA
```

Figure 10Q

```
CCAAAAGTTG TTTGGTAGGA GAGGGTTGAG GCTGGGAGAG GTGGCTCATG CCTGTAATCC
CAGCACTTTG GGAGGCCAAG GTGGGTGGAT CTCCTGAGGT CAGGAGTTCC AGACCAGCCT
GGTCAACATG GTGAAACCCC ATCTCTACTA AAAATACAAA AAATTGGCGT GGTGGTGGGT
GCCTACAATC CCAATTACTT GGGAGACTGA GGCAGGATAA TCGCTCGAAC CTGGGAGGCA
GAGGTTGCAG TGAGCAGAGA TCGCGCCACT GCACTCAAGC CTAACCAACA GGGGCAAAAC
TCTAGGACTA GAGCTAAGGT ATCAAAAAAA AAAAAAAAAA AAAAAAGAAG TAGAGTGTTT
AATTAAATAA TTTGTTCTTG CTGTAAAATG TAAAGTAGAT ATTCCTCTTC AAAGACTTTC
CTCCCCGTCT AATTAGGAAT AAATAGTAAC TTCTCTTAGA AGCAAAATTT ATTCAAAGAC
CTGTGCTAAC ATTCTTAAAT ATCTGCTAGC CACAATAAGG AAATCAATGT ACTTTATGTT
CTTAGCTCCC ACAATTTAGC CTAAATATTT TCCCTGGCAT GTTTATACTG GTCTAAGCAA
GCATTAGGTC ATAGCCTGTT CCTCTTCCTT ATTTAAAAGT GTTTTTACCT TTCTCAGCGT
TCCACAAGTT ACTTCCTCCT TCCTTTGTTC TCCTCTACCT GTGCCTCTTT TAAAAAGTTC
TAAGTTGCTA GCCAATTGGG ACAAATACAG AATGTAAGGT CCCATTCCAG CCAACGGAAA
CTGGACACAG CAGTAGGGTG GATGTGTCAG GTTATAAATG ACCCTGTCTC CTTTGTTTGG
TGTACTCTAG TGGCAAAACT GCTGGCAAGT GTACCTTTTC TGCAGGAAGT AAAAATGGCC
TTACTAAATA AATTAAATTT ATGTTCAAGT GCTATTTCTT TTTTTTTTTT TTTCGAGATG
GAATTTCACT TTTGTTGCCC AGCCTGGAGT GCAATGGCGC GATCTCGGCT CACTGCAACC
TCCACCTCCC AGGTTCAAGC AATTCTCCTG CCTCAGCCTC CCGAGTAGCT GGGATTACAG
GCATGCGCCA CCACGCTCGG CTAATTTTGT ATTTTTAGTA GAGATGGGGT TTCTCCATGA
TGAGGCTGGT CTCAAACTCC TGACCTCAGG TGATCCGCCT GCCTTGGCCT TCCAAAGTGC
CTTGGCCTTC CAAAGTGGCG TGAGCCACTG CGCCCAGCCT CGAGTGCTAT TTCTTTACGG
CACGGAAGAA CAAACATTTC AAACAATGCT ATTACCAAGT TTGTTAGTAT TTATTATCTC
ATTTGCTAAA CCTAAAAAAT ATATATCCTT CTTTAACGTG ATCGAATATT TCAAAAAGTT
ATTGTGTTGT TTCTTAAAAT AAATCAATCA TAATCCTAGA CTATGTTACT CAAACTACAT
ACAACACCTT CTGAGCTTCT GGCAGGCCCT TCCTCCCCTC CCTGCTCACC ACAGATCACT
GGAATAATTG TCTGCATGTA ACTTCTAATT TTGAAGTGGT TGTGGTTTAT CAAACCTGGA
ACATGGCACT TCCAAGTACA TGAGCTAAGG TCACAGTAAG ACTCAAGCCC CTTCAACAGA
ATACCTGGAA TTTCTCTGTT AAAGATTTTC TCCTTTACCT GACTACATGT TTGTAATGCA
GATCCCTCCA GGAGCGCTTA CTTATAAACT GTCCTGGATC ACTAACGCGA CATTTTGATG
TAAATTAGTT TATCTTGACG TGCTAATGGT AGAAAAAAAG AGAACATGAG GAAACTTGGG
TGCTTTCAGG GCTGGTAGGA AGGATTAAAT CTTTGCGGCA ATTTCTGAGA AGGGGAAGGA
AACCTTGCTA ACAATTTTGA TAGTTTACTC CATTTGGCTG GAGTAACTCT GATCCATTTG
                                    KpnI
                                    --------
TCAAATTCAC GATGGAGCAG GTACCTGTTA GGGTACAGGT TTGATAAACC ACAACCACAG
GTCTATTTCA TTTCTCCTTT TCCAAAGTGG AACAAATTTG TCTCTGGGGT TAAAACTGCT
TTTCTCATAT TGGTGTGTAA GAGAAAATGA GGGAATTTCT TTGAGTTTGT TTGGTTTGTC
TGTTTGTTTA AGCAGCATTT TTTAAATAAT TTACTCAGCC CTGTCTCAGA GAAAGTCCAT
GATGATCTGG AATTCAACCT CAGGGAAAAG TTCTCTCCTG TGCCTGAGAC ACTGCGCAAC
TAACTGGAAC CGAAGGATGG AACCTGGGTG TTTAATTTAT TAGGAACAAT TGATTCTTCA
GTGACACTTT CCATGCAGAT ACTTCAAACA AAATAATGGA GCCCACAGA CCGAATGTGA
                                                   >>.........Exon1 .........>
AGACAGCAGT GCCATTGTCT TTGGAAAGCT ATCACATATC TGAAGAGTAT GGCTTTCTTC
>............................Exon 1 .............................>
TTCCAGATTC TCTGGTAAGG ATAGAGCCTT GGTAAGGATA GGTCAGAATA TGTTTCTTGA
>....Exon 1 ....>>
GATGTTGGTT GGTTTGTTTT TTAAAAATGT ATGTGATTAT TAAGAGACCA ATATAAATAT
CAAGTTGTTT ACCTGAGAAA GATGCTACAA AGAGCATAGA TTATCATTAC TATCAAAAGA
GAAGTGACAG ATACCACAGA GAACAGGTCA ATGGAACAT TTTTGTTTC AGTTCTTTT
GACTAGATTG TCAGGCCAGA GAAATTATAA GCAAACCTGT AGTTATCAAG AAAAGCATG
AACTTAAATA TAAATAAAGA ACAAATACAG AGCCTCAGCA CCTGGAACAT GGCACTTCCA
AGTACATGAG CTAAGGTCAC AGTAAGACTC AAGCCCCTTC AACAGAGTAC CTGGAATTTC
TCTGTTAAAG ATTTTCTCCT TTGCATGACT ACATGTTTGT AATGCAGATC CCCCAGGAG
CGCTTACTTA TAAACTGTCC TGGATCACTA TCGCGACATT TGATGTAAA TTAGTTTATC
TTGACTTGCT AATGGTAGAA AAAAGAGAA CATGAGGAAA CTTGGGTGCT TCAGGGCTG
GTAGGAAGGA TTAAATCTTT GTGGCAATTT CTGAGAAGGG GAAGGAAACC TTGCTAACAA
ACAATACCTC TTTCTTAATT CTACTTAGGG CTCAAATTGT AATGCAAATC TTTTTCATCA
```

Figure 11A

TTTAGCCCTT ATAAACACTG TTTTTCTCAT CTGGTGTGGT CCAAGGCCTA GAACATTAAA
ACTATCAAAG CTTTTACAGA CCATCAGGTG TCATCCCCCT CTTTCTACAT CTGAGCTAGC

```
                                                             SpeI
                                                             ------
TGAAATCCAG AGGAAATGAC TTGCTGAAAG TCATGAGTGG CAAAAGCAGA ACTAGTTCTG
CTTATAACTC TTGACTTTTA GTTATTATTA TTATTAATTA TTATTATTAC ATCCTAAATG
AGGGCCAAGG CCACTCAGTT AAAAATCGTG GGGTCCAGGC CAGGTGCAGT GGCTCACGCC
TATAATCCCA GCACTTTTGG GAGGCCAAGG CAGGTGGATC ACTTGAGGTT CAGGAGTTCA
AGACCAGGTT GATCAACATG GTGAAACCCC GTCTCTACTA AAAATACAAA AATTGGCCAG
 GCGTGGTGGC ACATGCCTGT AGTTCCAGCT ATTGGGGAGG CTGAGGCAGG AGAATCCTTG
 AACCCAGGAG GGGGAGGTTG CAATGAGTGG AGATCATGCT GTTGGGAATG AAGTTTTTGG
 TGTCACAGAA AAAGAATGAA CATGGGAACA AATGATCTCT CAGCAAAAGG ACCTTTACTT
 TCTGCAGAAA GGGTGCTACT CAATAGCTGT CCAGCCACGA GAGCACACCA AACAAAGGAG
 ACAGAGTTAT TTATAACCTG ACGCATCTAC CCTACTGCTG TGTCCAGCTT CCATTGGCTG
 GAATAGGACC TCACATTTTA CACTTTACCC AATCGGCTAT TAGTTTAAAA CTTTTTTAAT
 TGGATAAGGG AACAGAACAA AGAAAGAAAA GCAAGTTGCC CAGGGATAGT TAAGGAAACA
 TCTCCATATA AGGAATGGCA TGCACTATGG GCTGGGCTT TTCTAGTTCT GTACAGACAT
 GCCGGAGCAA GCTACGACAG CTGATTTGGA CAGCCACTAA TAGTGGCTAG CAATCTTATA
 GTAAGAAATT GTGACTTTTT ATAATCTTTG AAGAACTTTC CCATTTCTGA CAGTGCCACT
 GCACTCCAGC CTGGGCAACA AGAGCGAAAC TCGTCTCAAA ACAAAACAAA ACAAAACAAA
 ACAAAACAAA ACAGCTCTCT ACTCTTGGAA GCAGCAGAGT TTTTATCTTC ATTTATATCA
 CTCCGGTAAC ACTCAGAAGT AGACAAGCCT CAGGGTAGGT ATTCAGTAAA AGCCCACTGA
 ATTCCACACT ATTCTTTAAT CATAGTTAAA TGGCAAATTA GGCTGGAGGG TGGGGGTGGA
 ACCTCTCCAA AATTACTGCA ATGACTGCAA CATCGGACCC AAGATTTTT TTTTTTTTT
 CTGAGATAGA ATCTCTTTCT ATCGCCCAGG CTGGAGTGCA GTGGCACTGT GAGAAATGGG
                                           AhdI
                                           -------------
AATGGACCGG ACTGTTTCCT CTGACACTGC CACTAGGTTG ACCAAGTGTC CCTATTTGTT
AGGTACTGGA TGGACGCCTG ACATGCAAGA CTCTCAGTGC TAAATCAGGA AAGTGCTGGG
ACAATTCGGA TGAGTCGGTC ACGCTAAGTT GCACTTAATA GCTCTTGTGA CTTTGACTGA
ATTACAAACA TCCCCTGACC CTCAATTTTC ACATTTACTG GATGGAGATC TGGTGCCACC
TCCACTAGAT TGCTATGGAG AATGAATGTG AAAGCATTTT CATAAATCCA GTGTAAGGAC
CAGAAGCCAG TCTTCTGACC TTGAGCCAGT GCTTGTTAAA AACTCCACTC TATACATCTA
ACCCAATTCA GGAATATCCT GCCTAGTTCC AAAGGAAGAA AAGACCAAAT TGCTCTTATT
GGGATTAAAT GCGTACACTG AGCTGAGGAA AAACAGTATT ACAAATGAGC TAAACATGAC
GTAGATCCAC AGTTGTAGAA TTCCCCTCTT TGTTCTTTCC TCTTTCATAA CTACGGAAAC
AGATGAGAAA CATTTACGGC ATCAGGTTCT TGTGATGCTC CCTGCCTGAT ATGCTATGGT
TTTGTTAATG GAATGTCCAT TCCTGAGCTT ATGCAGAAAA AAGTCCCTTG GGAAAGTGGT
TTTACTGTGT TATGTTCATT TTCCCCATAG TTCTCAAAAT GTACTTCCTT GTTTCAGTTT
TAATTTTCTT TCATTGGTGT GACCATTTTC AACTGCTCCC TTTCTGGGAA GAGGTAGCAG
ACGGACATTT TCATCAAAAT CTGCCCCAGG TTGCTTCACA GATAAGGAGG GACCCAGCCA
CTAAAATCAC CAGGCAGAGT GTTGCAAGAG TAGATAGAGA ATCACAATTG CTGCCCTGC
TCAAGGGGAC ACCAGATCTT ACTTTCGTTT AGTTGAAAGG CAAGCGTCAG AGTCGGGAGG
CTGTACCTTC ATGTCCAGTG GCCTCACAGA AGTTCCTTCA GTATCTCTTT TAGATGAAAC
TCTTTTAGAA GTTCCTTCAG TATCTCTTTT GGTTTCTCAC TATAGATAGT TACTTGAACA
TGTCTGAAGA AAACGTGGTC AAGACAGTGA ATAAAAAAAA TTCTGGTTTT GGGAAGCAGT
CTGACTTAGT TTCAAATATT CTATCCCACT GTTTCTGTCA ATGTTCAAAC CTTTCCAAGC
TCCAACATTT ATTGTGGAAA ATGTGTGCCT CACCAACTCA TGCAAATAAA TGTTTCATGT
GCCCTACGTG TGTAGAGGGG GCATGGATGT GTGTTTTGG AGGGAGGGCT AATTTTTCTT
TAGACATGGA GAATACGAGG AAATTAGCTT GGCATCAAGA AGGTTACAGC AGGAGACAAG
AGTGAAGAGA ACTGAGAGAG CCCGGAAATG AGGCTCTGGA GTTCAGATTT TTTTTTTTT
GAGATGGCGT CTTGTACCCC AGGTTGGAGT GCAATGGCAA AATCTCAGCT CACTGCAACC
TCCGCCTCCC GGGTTCAAGC GATTCTCCTG CCTCAGCCTC CTGAGTAGCT GGGATTACAG
GCATGAGCCA CCATGCCTGG CTAATTCTGT AGTTTTAGTA CAGATGGGGT TTCTCCATGT
TGGTCAGGCT GGTCTCAAAC TCCCAACCTC AGGTGATCCA CCCTCCTTGG CCTCCCAAAG
TTCAAGGATT ACAGCCATGA ACCACTGCGC CTGGCCTAAT TTTTGTATTT TTAGTAGAGA
CAGGGTTTCA CCATGTTGGT CAGGCTGGTC TTGAACTCCT GACCTCGTGA TCTGCCCACC
```

Figure 11B

```
TCAGCCTCAT GAAGTGCTGG GATTACAGGC ATGAGCCACA GGGCCAGGCC TGGAGTTCAG
ATTTAACACA TCCTGTAAAT GACATGATGC ATCTGATATT TGAAGAGTTT TCCTCAAAGA
ATGTTACATG CAAGGTGGTT TAGAGTTGTT GTTTCCGGCT ATATAGCAAA AGTACTTGGG
GAGTTTTAAA AAATACTGAT GCCGAAGCTC CACCTAGAAT AGTTCATTCA GAATCTCTAG
CATAATTGAC CTCAGTACTT GAAATATGAT TATTATAAAT GTTAGTCAAC TGCTTTTTTA
GGCTCTATGA CTGATAGAAA TCTTTCACTT TTATATCATC TCCAGTTAAT GAGTCCCATA
AATTGAAATC TAGTGTTTAA ATTTTTACTT CATATTTATT TTTACTGATT GTTTTATTAT
TATTATTTTT GAGACAGAGT CCGCTTTGTC GCCCAGGCTA GAGTGCAGTG ACGCCATCTC
GGCTCCCTGC AACCTCCGCC TCCTGGGTTC AAACGATTCT CCTGCCTCAG CCTCCTGAGT
AGCTGGGATT ACAGGAGCCC ACCACCAACC ACACCCAGCT AATTTTTGTA TTTTTAGTAG
ACGGGGTTTC GCCATGTTGG CCAGGCTGGT CTCGACCCCC TGACCTCAAG TGATCCACCC
GCCTCGGCCC TCTGTCTCAA AACAAAAACA AAAACAATAA CAAAACTTTT CTCTTCTACC
CGAGATGTTT AAGTTTAAAT CACACCATTT GTACAAAAAT TCCCTGTCTT GTCCTTAAAA
ATAATTTGTA ATCACTAGCT AGTTTTGAGA TCGATTGCCA TCTAACCGAA TGCCATTTGT
TCTCTCTCTC TAGTTTCAAC TTAATAACCC TTTCTGCATT TTCTATTCTT TCAAAATTTT
TCCGGCCATT TTATTGTTTC TATTTAGTGA AAATTTATTC ACTGGTTTCT ATGCCTAAGG
GCATTTAGGA AGTTGCTTAG GATACAGACG TGATAAAAAG ACCAGTGTAA AAACTCTCCA
CTCCTAGACA TTATATTCTA GTCCTCATCT CCTGTCATTT AAGTCCTCAG TGATTCTATG
CACTTTTGCT TTTGGTTTGG GCAGATGCTC TGAGTTTAAT GTTTCTCTGA GATGAGGACC
CCCTATTCAA CTCACAAATC CCATAAGGAG GCCTCTGTGC CTTTGCTGGT GCCCAGACA
GGGTGCTGAT GCTTACTTAT CTTCAAGATT GTGAAGTCAG ATTTAATAGT ATAGTCGTTT
GCCAGAGCTG CTGTAACAGT AGCCACAAAC AGTTGGGCTT AAAATACCAC AAACAGGAGG
GCTTAAATCA CAGAAGTTGA TTTTCTCACA GTTCTTGAGG CAGGAAGTCC AAGATCAAGG
TGTCGTGGAG TTGGTTTCTT CTGATGTCTT GCTCCTTGGC TTGTAGATGG CCTCCTTATT
ATTGTGTCCT CACATGGTCT TTTCTCCACT ATGCACAAAT TCCCTATGTC TCTCTCTCTT
TTTTTTTTTT TTTTTTTTTT TTGAGACAGA GTTGCACTCT GTCACCCAGG CTGGAGTGCA
GTGGTGCAAT CTCGGCTCAC TGCAACCTTT GCCTCCCGGG TTCAAGCAAT TCTCCTGCCT
CAGTCTCCTG AATAGCTGGT ATTACAGGTG CGCACCACAA AGCCCAGCTA ATTTTTGTA
TTTTTAGTAG AGATAGGGTT TCGCTATTTT GGTCAGGTTG GTTTTGAACT CCTGGCCTCA
AGTGATCCGC GCACCTCGGC CTCTCAAAGT GCTAGGATTA CAGGCATAAG CTACTGTGCC
CAGTCTCCCC CTGTCTCTTT GTGTCCAAAT TTCCTCTTCT TTAGGGACAC CAATCAGATT
AAATTGGACC CACCCTAAAG GCCTCATTTC AATGTACCTC CTTCAAGGGC CTATCTCCAA
ATACAGTTAT ATTTTTAGGT ACTAGGGCTA GGGCTTCAGC ATAGGAATTT GGGGGAGACA
CAATTTAGCA CATAGCAGAA AATATAAGGC CAGGAAAAAA TATTCTGGCA TGCTAGATGG
ACTCATTAAC AAATATTAAC CAATATAAAC CAATTAACAA ATATTTCTTT AATATTTGCC
TTTTTTTTTT TTTTTTTTTG AAACAGAGTT TCACTCTTGT TGCCTAGGCT GGAGTGCAGT
GGCACGTTCT TGGCTCACTG AAACCTCTGC CTCCTGGGTT CAAGTGATTC TCCTGCCTCA
TCCTCCCAAG TAGCTGGGAT TACAGGTGCG GCCATCACA CCCGGCTTAT TTTTTGTATT
TTTAGTAGAG ATGGGGTTTC ACTATGTTGG CCAGGCTGGT CTCGAACTTC TGACCTCAGG
TGATCCACCT GCCTTGGCAT CTGAAAATGC TGGGGTTACA GGTTGCCTGG TGATTTTTAA
GAGGAATGAC TGAGCTCTCA TGCCAGGTGG GGGGAGGGGA CAGAGAAAGT TGAATACTCT
GACGATAGCC ATGATCCATA GCTCTGAAGC TTAGACTCGA ATCTACCCAT CCCGCAAGGA
AGAAAACAAA GAAATAAAAA AGAAGAAAAG AAATCTCCCA ATGTCAGGTC CCACCCTCTT
TAGAAGTAAT TTCAGCAAAA CTTTGTTGCT ATTTTGGCAT GTCCTCTACT GTAGTAGCTT
GTCAAAATAC TGTCCCCAAA CGTTTTCTAT ATTTCTAGAT TTTACTGTTT AATGTATAAT
AATAATGTTC TAACATTAAA ACGTAACCAT AGCAATGCTC CGACTCACTT GATCTTTAAA
TATATTGTTG AACTCAATTT TGTGACATCT TCAGAATTGT CTTTTTGTAT TCATAAATAG
CAACAGTGGA TAGTTGCCTT GGTTAGTGTT ATTATTTCAA GGATTAATCT TTAGGTTACG
TTTTCTTCAT AAGATGCATT AGATGACTTT TTTTTTTTTT TTTTTGAGAC AGAGTCTTGC
TCTGTTGCTC AGACTGGAGT GCAGTGGTGC AGTCTCAGCT CACTGCAATC TCCACCTCCT
GGCTCAAGAG AGTCTCTCGA CTCAGCCTCC TGAGTAGCTG GGATTACAGG CACGCACCAC
CATGCCTGGC TAATTTTTGT ATCCTTTTTA GTAAAGACGG GATTTCCCCA TGTTGGCCAG
GCTGATCTCC AACTCCTGAC CTCAAGTGAT CCATCTGGCT TGGCCTCCCA AAGTGCTGGG
ATTACAGGCA TGAGCCACCA CACGCAGCCA ATTAGATGCC TTCTCATGCT TTTCTGTGTT
GTGAAACAGA TCATCTATCC GTTGATATAG CATAGCTCTT CAGACTACAG ACATTTTAGG
CTATAAGTTT TGAATTACAT TTTCTATTCC CTTTATGCTT CTTGTTCTAG TTAGGTTTTT
TATTTCTAAA TAAAAATATG AATTTTTGCA ATTTCCCAAA TGCGAACTCA ACTGAAATTT
TCAAGTGTAT TAGCAAAATT TATTCATAGC AGCCTCTTAC ATTTCATTAA GAATTGATTT
TTTCTTATTC CCTGTTGAAG TTTGTTTATA AAATATAGTA ATAGTAATAA CTATATAGAA
```

Figure 11C

```
AGTGTTCACT TTGTAGTAGG CCCTATGTTA ACTTTAACTA CACTTTTTAA ATCTAAGCCT
CATAGTAGTC TTGGATGGAT GCGGTGGCTC ACGCCTGTAA CCCCAGCACT TTGGGAGGCT
GAGGCGGGTG GATCACGATG TCAGGAGTTC AAGACCAGCC TGGCCAACAT GGTGACACTG
TCTCTACTAA AAAGACAAAA ATCAGCCGGA CGTGGTGGTA TACACCTGTA GTCCCAGCTA
TTTGGGATGC TGAGTCAGGA GAATTGCTTG AACCCAGGTG GTGGAGGTTG CAGTGAACCG
AGATCACACA AGTGCACTCT AGCCTGGATG ACAGAGTGAG ACTCCATCTC AAAAAAAAAA
AAAAAAAAAA AAAGAGATCA ATAAATAAAA TAAATAAATA ATCCTCACAA TAGTCTTCAC
CATTTGCAAA TGATCCATTT GACAATAAAT GAATTCAGCA CTATCATGGA AATATATTTC
CAAGCTGACC AGTTTTCTCC ATTTCCACCC CACTTCAATC CACCTTCATG TAGCCCTAGG
ACTATTGTCT CCTCCCCTTG TTTCCTTATT TCCATTCCTG TTCAGCTGTA ACACATTCTG
TTCATAGCAG TCAAGTGATG CTTACAAATG GAAATCAGGC TAGAGGTGGT AGTTCACACC
TATAATTCCA GCATTTGGG AGGCTGAGGC AGGAGGATCA CATGAGGCCA GGAGTTTGAG
ACCAGCCTGG GCAACATAGC GAGACCCCAT CTCTACAAAA ATAAAAAAGA ATTAGCTGTG
CATGATCCTA TGTGCCTGTG TTCCAGCTAC TTGGGAGGCT GAGGTGGGAA GATTGCTTGA
CCCAGGGAGT TTGAGGCTGC AATAAGCTAT ATTTGTACCA CTACACTCCA GTGTGGGTGA
CAGAGTGAGA TCCTGTCTCT AAAAAACGTA AAATGAAAAT AAAACCTTGA TAGTTTGCTC
TTTAAAACTC TTCCTACAGG GCCCTGTGA TGCTCACCTG TCTCTAGAAG GGCATGTAAT
AGCTCTTTCT CCTTCACTTT ACTTTGATGC AATGTCAGAA CAGCTTCTTT CCATCAAAAC
TTAAACCTTT GATTTCATTT AAAATCATCT GCTTCAAATT CTAATCTTTC TGATAGTTTA
GGTTCTAATT TTTCTGATGT TAATATTGTC ACCCAAGTTT CCTGTTCATA TTTACCTGGT
TTATTTTATT TTTATTTTTA TTTATGTATT TGAGATGGAG TCTAGCTCTG TCACCCAGGC
TGGAGTGCAG TGGTGCGATC TCAGCTCACT GCAACCTTCG CCTCCTGGGT TCACGCCATT
CTCCTGCCTC AGCCTCCCGA GTAGCTGGGA TTACAGGGAC CCGCCACCAT GCCCGGCTCA
TTTTTTGTAT TTCTACTAGA GACGTGGTTT CACCGTGTTA GCCAGGATGG TCTTGATCTC
CTGACCTCGT GATCTGCCCG CATCGGCCTC CTAGAGTGCT GGGATTACAG GCGTGAGCCA
CCGCGCCCAG ACTTTATTTT ATTTTTTGAG ACGAAGTCTT GCTCTCTTCC CCAGGCTGGA
GTGCAGTGGC TTGATCTCAG CTCACTGCAA CCTCTGCCTC CCAGGTTCAG GCGATTCTCC
CGCCTCTGCC TCCCAGGTTC AGGCGATTCT CCCGCCTCAG CCTCCCGAAC AGCTGGGGTT
ACAGATGCCT GCTACCACAC CCAGCTAATT TTTTTCTTTT TTTGGAGACA GTCTCACTCT
GTCGCCCAGG CTGGAGTGCA CTGGCGTGAT CTCAGCTCAC TGCAACCTCC GCCTCCTGGG
TTCAAGCGAT TCTCCTGCAT CAACCTCCTA AGTAGCTGGG ATTACAGACG TCTGCCACCA
CATCAAACTA ATTTTTGTAT TTTTAGTAGC TGAGATTATA GGCTCGTGTC ACCACGCCTG
GCTAATTTTT GTATTTTTAG TAGAGACGGG GTTTCACCAT GATGGCCAGG CTCGTCTTGA
ACCTCTGACC TCAAGTGATC TGCCCATCTC AGCCTCCCAA AGTGCTGGGA TTACAGGTGT
GAGCCACTGG GCCTGGCACC TGGTTTATTT TTGTGCATGC TTTTATTTTT AATTTTCCTA
TGCTACTTTC TTAGCCAAAA TTTATACTTA ATCTAATCAA GCATTAATCT AACAAAGAGT
TTAGTGTTCA TATAAAATAC AGTTTTACAA ATCTGTTTTT CTTTAAATTA TAAATTTGTT
AAGAAAATTA TCCAAAGAAT GATCCAGAAA CAAAAGAATG GCTGTGTGTC TTTTCAATAT
CATCCTGGAG CATTGTCTCA ACCATCTCAC TTTACGGTGA CTAAAACATC TAGAGGTTTT
CCCTTTGTTT TCTGTACTTC TTAGTATTGA TTAATACTGT TGTGCTACTT CAGTCTGAAG
TTCCATGTTA ATCTGTAGAT TTTTTTTTTT TTTTTGAGA CAGTGTCTCG CTCTGTCGCC
CAGGCTGGAG TGCAGTGGTG CGATTGGCTC ACTGCAAGCT CTGCCTCCCA GGTTCAGGCC
ATTCTCCTGC CTTAGCCTCC CGAGTAGCTG GGACTACAGG TGCCCGCCAC CACGCTGGGC
TAATTTTTTC TATTTTTTTT TTTAGGAGAG ACGGGGTTTC ACCGTGTTAG CCAGGATGGT
CTTGATCTCC TGACTTCGTG ATCTGCCTAC CTTGGCCTCC CAAAGTGCTG GGATTACAGG
CGTGAGCCAC TGTGCCCGGC TGTTAATTTG TAGATTTTTA TACAGAAAAG CAGCAAAATA
TTTCTGTTGA GTAGAAAATA TAACTCCAAT GCTTATGACT GTATTCCTTA TAGGACACTA
ACTCATTATG TGTCTAACCT AGCAATTTTA TGTCAACACT ATTTTCTCAA ACCTCTATAA
ACTTTGGCTG GGCACAGTGG GTCACACCTG TAATCTTAGC ACTTTGAGAG GCTGAGGCAG
GTGGATCACC TTAGGTCAGG AGTTCAAGAC AAGGCTGGCC AACATGGCAA ACCCCATCT
CTACTAAAGA TACAAAAAAT TAGCCAGGCA TGGTGACATG CCCCTGTAAT CCCAGCTACT
CAGGAGGCTG AGGCAGGAGA ATCTCTTGAA CTCAGGAGGT GGAGCAAGA TCATGCCACT
GCATTCCAGC CTGAGCAATA GGGTGAAACT GTGCCTCAAA ATGAATAAAT AAAATAAATA
AATAAGTCAG AGATTGTGAA TAGGATGTTG GATATACCCA AGTTATGAAT TAATTAGGAG
CTTGAACCCA GGAGGCAGAG GTTGCAGTGA GCTGAGATCG CACCACTGCA CTTTAGCCTG
AGCGATAGAG TGAAACTGTG TCTCAATCAA TCAATCAATC AGAGATTGTG AGTAGGATGT
TGGATGTACC CAAGTTATGA ATTAATTAGG AGCTTGAACC CAGGTTTGTC TCAGATCCTC
AGGGACTGAA GACTTCCAAG TGAATTATGG GTAATGTATA GGTCTATACT ACTCCAAATT
TACAGTTTTC AGACTTCCCT GGGTTCTCAT GGACCTTCCA TGTCATTTCT ATGTTTAGGT
```

Figure 11D

```
TGAGGTCCCT GGTCTTTTCT CCTCTGTAAT TAATTTCACA CCCACCCCTA TCTCAACTCA
CACAACTTGA TCTTCACTCC CATCTGCTAA GAAATTGAGT CCATAAAAAG TGAACTCCTT
TAAACTCTAG ATCTTCTACT GCTGCAAGGA CAGACATTCC ATTCTGGCTC TCTCTCTCCT
CCTTTGCTTC TTCCAGTCCT TTGCTCCTTC TGCATTCTGT TACTCTCCTC TCTCCTTTGT
CTTCAATCTC TCCCTCTTGC AATAGCCAAC TATAAACTGC TCAAGCTTCT CATTCTTAAA
AGATCTCTCT GAAATGCAAA TTCCCTACTG CCTTATGGCT CTCCTTCAAA AGTAATCTAC
ATTTTCTCTA TTTTCTAATT CCTCAACACA CTAACGTTTG AACCCTGCTT CTATGACCCT
GACCTAAATT TCTATTAAAT GTACATAGAT AAACTAATAT ATATTTGTGA CTTCCTAATA
TTGTTTTGTT TTTTAAAGAG GTCAATCTTA CTTTAACTCT GTAATGATGC GGTTGACCTT
CTGATGATTC TCTACTTCTG TGAAATCCTC TACTGTCTTG ACTTTTTAAT TAATTTATTT
TTTTTTGAGA CGGAGTCTCG CTCTGTTGCC CAGGATGGAG TGCAGTGGCA CAATCTCGGC
TCACTGCAAG CTCCACCTCC CGGGTTCATG CCATTCTCCT GCCTCAGCCT CCCGAGTAGC
TGGGACTACA GGTGCCCGCC AACACGCCCA GCTAATTTTT TTGTATTTTT AGTAGAGACG
GGGTTTCACC GTGTTAGCCA GGATGGTCTT GATCTCCTGA CCTCGTGATC TGCCTGCATT
GGCCTCCCAA AGAGTTGGGA TTATAGGCGT GAGCCACCGC ACCTGGCCCT ACTGTCTTGA
CTTTTATAGG GTCATTCTAT TCAAGCTCAT TGAGCGTCTG TCACTATGTT TTTGATCTGT
ATTGCTGGAA TCAGTTCCTC TATCTGCCTT GTGAATATTC TCCATTGTGC TAATCTAGGC
    >>........................Exon?...........................>
TTCTCCTTTC ATTTTTCATA TTCCCTCACA TGGCTTTATA CACTCTTGTG GTTTTAACCA
>>
CAATATAGGG TTTTTACTGT AGTTATGCTT TCAAATTGTA TACTTCTTTT TTTTTTTTTT
TTTGAAATG GAGTGTTACT CTGTTACTCC AGTCTGGAGT GCAGTGGTAC GATCTTGGCT
CACTGCAACT TTCGCCTCCC AGGTTCAAGC GATTCTCCTA CATCAGCCTC CCGAGTAGCT
GGGATTACAG GCATGTGCCA ACACGCCTGC CTAATTTTTT ATTTTAGTA GAGACAGGAT
TTCACCATGT TGGTCAAGCC CGTCACAAAC TCCTGACCTT AGGTGATCCG CCCTCCTCGG
CCTCCCCAAG TGCTGAAATT ACAGGTATGA GCCATCGTGC CCAGCCCCAA TTGTATGTTT
CTAATATGAC TTTTCTCCTG AACTTTAAAC TGTGTATCCA ACTTCTCAGC ACAGTCATAT
CTTTTGATTC CACAGGTAAT TTAATGTCAA TATATTTAAA AATGAATTTA CCACCTTTAT
CCCCACTCTT TGACTTTCAC CTGCATTTCT GTTTCAATTC TTGTTTCCAT CCATTCATTT
GCTCACCTAA TTCATAAACA TGGAAATCAT CCTCAATTCC TCTTCTTCTT AGCCCAAAAA
TTCAATTGTG CAGGTTATGC ACTGAGAAAA AGAGCCTCAG GTTAGGGGA TAAATCAGAG
ATTGGTGAAC TTTTTCTGAA GGGCCAAATA CTAACTGCTT TAAGCTTGCT TACCATATGG
TTTATGTTGC AACTACCAAC TCTCCTGCTG TAATGTAAAA GCAACCATAG ATAGCATGTA
AACAAATGAG ACAGGCTGGG TGCCAATGAA AATTCACGAA AATTAATGTA GTTTACTGTC
CCTTGGGTGA GAGTTGGGGG TCACTGAAAT TCGGACTATG TCTTACTTGG CTAAACCACA
GGCCTAGAGT GGGCCATAAA TGGAGCTATT GGGCTAGTGA TTTTCTTGCC TTAAGCCCCC
AGCCCCAAAT TTAATAATCA CATCATTTTA ATTTCATTTT CCAAGTGTAT CTTTAATATA
TGGCTTCTCC TTTCCAAATT CACTGTCATT ACCTAAGTTT AGTCCTTGAA CAATATTTTA
AAGGCTTCCT TATCTGACTT TATATCTTAA AGTCCTACAA ATTTATCTTC CTAAAATTCA
AATCAAACCA TGTCACCAAC TTACAGAAAG GGAAAATTCA TATATTCTAC ACACAGCACA
TTTCATGTAA CTTTCTAGGC TCATCTTTCA TCATCCTTTT GATGCAGGAT TTTCTGCTCC
TCAGCTCAGC GAAATCCAGG ATCTTGTCTC ATGACCAGGA AGAATTAGGC AGGTGGACAT
AGTGAAGGGT GAGGATGACG GAATTTATTA AGCAAAGGG GAGTTCTCTG CAAAGAGAGG
GGTTTCACCA GCAGTCTCCC ACCTCACAAT GGAGCACCAG GACTTTCACA CACAAACTGA
AAAGGCTAGG CTCCTCCCCA GCATAAGGCA TGAATTCCTG GTGGTTCCAC CAGTTTTCCT
ACTATGCATG TGGGTGTGCC CAAGCAAACC ATAGGTAGTA TCAGAAAAGG CAACATTTGA
TTGGTTAAAA GGCATTATTC ACCCAAGCAA ACCATAGGTA GTATCAGAAA AGGCAACATT
TGATTGGTTA AAAGGCATTA TTCAGAAAGA ATCAATCGGG AAAGGGTGAG CCAATAGGGG
AAGTTCTCCC TCTGGGTCAC GGGTTTCATC TGGGACCAGG AGTCTGGCCT TTCAGCCTTT
AGACTGTTTT AGGCTTGAAG GTGGGTTTCA CAGGGACCCT TCCCTATCTG CCTAGGCATC
TGTCTGCCTC CTGCCTCTAT CACTTTCTCT TGAGTTTTAT ATTTTAGCAA CACTGAGTCA
TCTTTGTCCC AGGAAGCACC TACATCTGTT TATCTGCTGT CCCCTCTACC TTTACTACCT
TCCCTTCTTC ACATTTATAC CCAGAAAAGT CACTTCCCCT CCAAAAATTG GGATCAACTG
TCATATTTTT ATGAATATTT CACTTTAATT CCTCACAACA GCTGACAGAA TTAACTACTT
CCTCTTCTTT GCAAGTTATT TGGCTCACAC AGATATCAGT AATTAAACAT ATTTTACTGC
ATTGGCATAT ATCTGACTAA TGTGTTTTTC TCCCGTACTA GGCAATATGC TCCTTAGTCA
TCTGTGTATC TGAGGTGAGC ACAGGGCCTA ACTAGCATAT GGTGCATTCT CAATGTTCGT
TCAACTGCAT TGACTTGAAT TCCCCTGAAG ACTGAAATGT GAAAATAGCT ACTCTCGGAA
GCCCCTTTCC AGAGAGGTCT AAAATATTTA CATGTTTCTA TTTTAAATGC AGAAAGAACT
```

Figure 11E

```
                                                                 >>..>
TCCAGATCAT TATAGGCCTT GGATGGAAAT TGCCAACAAA CTTCCTCAAT TGATTGATGC
>..............exon 2 ............................>
TCACCAGCTT CAAGCTCATG TGGACAAGGT ATTCTTCTCT TCACCCCCTC ATCACATTCT
>..............exon 2..............>>
GTTTTCATCA TCATACCACT TTTCTTTCTT AGCCTTGTGG AAGTGTGTCA ATTGTCCTGG
GAAACTGTTC ATTACCATTG AACTTATCAG CAAAGCTATA TCTTCCTTCC TGAAAAACAG
AATGACCCCT TCGTAATCTG ATACATGTGT TTTCCTAAGG TTTTCAGAGC CAGCACAAAA
CAATGCCTGA CACATGCCAA TAACTCACCA AATGTTTGTT TAAAGAAGAA TCTGGGTGGG
AATGATAAAC TAACTAATGG ACAAGGTATC GCCTAAGAAG GTCAGCTTGG AAATTCTCAG
GTTCCTCATT CCATGTACGT ACTCAAGGCT CTGTTGTTAC TGAGGGGGTC TAACTTGATT
TTGTCCTAGG TGTTATAGAA TAGTTAAATG GAGGGAATTT CTGAATTATA AAATTGGCCA
TGGGTTCTAC AAAACATCCA ATAAGCCTGT AAATTCCACA AAAGTGTTGA TTAGGCTGAT
ACAAAGGTAA TTGCAGTTTT TGCCATTACT TTTAATGACA AAAACCACAA ACACTTTTGT
ACCAACCTAA TAGCTATGTA ACCCTGAAAA AGTTACTCAA CTCTGTAATC CCATTTCCTT
ATTTATAAAA TGAGAGAAAC TCTGGTCTCA CAGTATTGTT ATGGGAAGTA AATCACTTTC
AAAGTGGCCC TTTTGTAGTT CTTGTCCTAT AATAGCATTC AGTATACATT CATTACTTCT
CTGTAGTCTC TTCTCCATCT GTCCTAATCT ATCAGTTTGG AGTACCACAT AATTGCGGAA
GTCCATGAAA AGTTTTCCGC CTCCAAAAT TTCCCTTTGC TGATGGATAA TATTTAATGT
CTAGAATTAC AAATTCTTTT TAAAATACTC ATTGAATGTT TGCTTTGTGC AAAGCACTAG
AACCTTGTAA AAGATGAGTA AGGGACTGGC TTCAATGTCT GTGAAGATAG CAAACTAAAC
AGAGTAATTT CTTTGCCTGA TAGATAAAAT GTTGTGTTGA CATGACCAAA GAAATCCAAA
AATAAGAAAA AAACTATCTG TAAACACAGA AAAATAGAGA AAAGTTCCAA TGATGGAATA
AAAATTTAAA GGATTTTTTT GAACGTATTA AGCAAATCAT GTATAAAATC CAGAAATAAG
TTTACAGGAC CCATGTCAAG GATTTAACCA AAGCAGAGGG AGATCCCCAT GAGTCCCCTT
TTCCCATCTC AGAATAGCAG AGAAGAGAAG CAAGGGAAGC CTGGAACAGT TGGCAAGAGG
GCAGGTTAGA ATTCAGTTTG TGAATTATGA GGTCGTCTGC CGTAGGCATT TACCAGGCTT
TATTTGATTT AACTGCCATA AAGGAAGAGA AGGACTTGTT AAATTGGGGC TCCTCTTAGC
ACAGCATTGA AACCAGTCCC TATTCCTTCT TGGCCTTTTG GCTAAAATTG AGTGTGAAAT
CTATCACCTA ACATTTGTAC TGGGTTTAGG CTGGGTGTGG TGGCTCACGC CTGTAATCCT
AGCACTTTGG GAGGCCAAGG CTGGCGGATT GCCTGAGCTC AGGAGTTCGA GACCAGCCTG
AGAAACATGG TGAAACCATG TCTCTACTAA AAATAGAAAA AATTAGCAGG GTATGGTGGC
ACATGCCTGT AGTCCCAGCT ATTTGGGAGG CTGGGGCAGA AGAATCACTT GAACCCAGGA
GACAGAGGTT GCAGTTAGCT GAGATCACAC CACTGAACTC TAGCCTGGGC ACAGAGTGA
GACTCTGTCT CAAAAAACAA AACAAAACAA ACAAACAAAT ATATATATAT TAAAATACAA
ATTTTTACTG GGTTTAATAG TGTCTTCCTA GAAGTCATGT TCATGCATAA TCTGTGAAAG
TGGTCTTATT TGGAAATAGG GTGTGTACAG TTGTATTCGA GTTAAGCTGA GGTGATACTG
GATTAAATTG TATATGATGA GTGTCCTTAT AAGAAGAGGA AAAATTAAAC ACAGGAACAT
AGACTCAAGG GAAAACATCA CGTGAAGATG GAGGTAGAAT TGGAATGATG CATTGACAAG
CCAAGATGTG CCAAGGATTG CTGGCAGTCA CCAGGAGTTA GGAGACAGGC ATGGAACAGA
ATGGAACAAA TTCTCCCTCA GAGGCTCCAG AAGAAATCAA CCCTATTGAT ACCTTAATTT
GGGACTTCTA TCTTCCATAA CTGTGGCAGA GTACATTTCT GCTATTTTAA GTCATGATGT
TTGTGGTCAT TAGTTATGGC AGCGCATAAA ACTAACACAA CACTCTTGGT CTCTATCGCT
TCTTTTTTTT TTTTTTTTT TTGAGACAGA GTCTCACTCT GTCTCCCAGG CTGGAATGCA
GTGGTGCAAT CTTGGCTCAC TGCAACCTCC AGCTCCCAGG TTCAAGCAAT TCTCCTGCCT
CAGCCTCCTG AGTAGCTGGG ACTACAGGCA CCCGCCACCA TGCCCATGTA ATTTTTGTAT
TTGTAGTAGA GACGGGGTTT CACCATATTG GCCAGGCTGG TCTCGAACTC CTAACCTTGT
GATCCACCAG CCTCAGCCTC CCAAAGCCCT GGGATTACAG GCCTGAGCCA CCATGCACGG
CCTCTATCCC TACTCTTAAT TGCCTGGAAA ATACCTAACA AATGAAGGCC AGTTTTAGA
CTTTACCACC AAAGGCTGAA ATTGAAACAG GAATTGTTTG TGAGAAGCAA ACACAATAGT
TTCGAGAGAC TGAATCAGTT AGCAATTTCC TGTGAGAGGC AAATGTAATA GTTTCTAGAA
CCACAGATGG AGCTATAACA AAAACATGTG TTCTCTGGAT CCTTTACTTG CTACAGACAA
CACAATAAGT GAATTTACAG CTTTGATCTT ACAGTGCACC TAAGCCAACC ACCTTGTCTT
AGAATGTCTC AACATACCTA TCTGTATCTT GAAACAAAT ATATTAATTG CCTTAGACCC
ATTCACTCAC ATTTCCTAGG AAGACATGAT CAGAGGGAGC TATGCAAGAA GAAATCCAGC
AGAACTCTGG AAATACAATA AGAAATCCA TATTGACAC TAATCTTAAT AAAACTAACC
TTCGTTCATG AATTTGAATA GACAAATTA CCAAATAATA TGGAAAAAT GGGCAACTCA
AAAAGAAGAG GGTAGCCCAC TTGGCATTCA GGACCAATGG CCTCCAATAA ATAAGATGAT
ATTAGTGCTT TAAATATTTT ATTTAGTGTA TCCAGTATAT TGCCTTCCTA AATTAAGTGA
```

Figure 11F

```
AAGCTGATAT ATAAAAAGAA CTATTAGAAA TAAAAAACCA CACACATCCC AGAACTCCTC
AATATAAACC TAACAAATTC AGTAAAACAT TGATTGCAAA AAATATATAT AGTGACTTAG
GGACTTCCTT GATAAATTTC ATAAAGCATA AAGAAAAATC AAAGAGTGCA AACCATCAGA
AAAATACAAA TATATAAAAA AGAGAAATAC AGGTGATCCA AATTCCTTTT AATGGAATCC
CATAAGCAGA TGGGTGGAGG AAAAGTAAAA CTTCCAACAT ATAAGCACAA AATTTTTAGA
CCTTAAGAAA TATTTGAGTT TTTTATATCA GAAAGACAGT GTTGGGGTGA GGGTTGGGGG
GCACATGTAA ATACTCAGAT AAAATTGTGA ATTTTCTAGG GTAAAGAAAT CTGCATATTC
ATAGAAAACA AAAATGAAAA ATAGTTTATT TACAGAGTAA ATACATACGA CTGTTTACCT
GTAATGCTAA ATATTAAAAG ACAGTTTCTT TTCTTTTTTT TGAGACAGAG TTTCACTCTT
GTCGCCCAGG CTGGAGTGCA GTGGTGCTAT ATCGACTCAC TGCAACCTCT GCCTCTGGGT
TCAAGCAATT GTCCTGCCTC AGCTTCCCGA GTAGCTGGGA TTACAGGCAC CCGCCACCAC
ACCCAGCTCA TTTTTGTATT TTTATTAGAG ACGGGGTTTC ACCATGTTGG CCAGGCTGGT
CTCAAACTCC TGACCTCAGG TGATCCACCC GCCTTGGCCT CCCAAAGTGC TGGGATTACA
GGCGTGAGCC ACCGTGCTGG CCTAAAAGAC AATTTCATAC CTATTTGTAT GGCTAATTTT
TTAAAAATCT GGCCATATCA AAATACTGAA GAGGACGTAT AGCAATAGAG ACTTTCATTC
ATTGCTGGTT GAAATGCAAA ATGGTACAGC CAGTTTGAAA ACTAGCTTGG CAGATTCTTA
TAAAATGAAA CATAGATTTA CCATGCAACT CAGCAATGGC ATTCCTAAGC ATTTATCCAA
GTAAATGGAA AATGTATGTT CCCAGAAAAA AAATCCATAT ATGAATGTTT ATAACAGCTT
TATTCATAAT CACCAAAAAA AAAAAAAAAT CTGGAAGAAA ACAGGATATC CTTCAACCGG
GGAATGAATA AACCAAATTA TAATAATTGT AAATTGTGGG ATGGATAGTG AATAGTATT
CAGCGATACA AATGATTGAG CAATTAATTT GTGCAATGAC AGGGATGAAC CTTAAATACA
TTTACCTAAA TGAAAGATGT CAGGCCTATA TTGTATGATT CTTTTCAAAT GACTTTTTAG
AAAGGGCAAA ACTAGAAGGA TTAAATATAG CTTTATGGTT ACTAGAGACA GGTAAGGAGT
GGGTAGTTGA CTGCAAAGGT AATATATAGG GGAATGTTTA GCATGATGAA ACTGTTTTAT
ATGGCACTCA GGTGATGGAT ATATGGCTCT AGGCACTGAA AAACCCATGG AATTGTATGT
CACAAAGAAT GGACTTTCAT GTATGCAAAT TTTAAAAAAT AAACCAGAAA ATTGGGAGAA
TACTAGGATG GAATGCAGAC TGTGATAAAT AAAACTAACT GGACTCTCAG CAAACTAACA
CAGGAACAGA ACACCAAACA CCGCATGTTC TTACTTATAA GTGGGAGTTG AACAATGAGA
ACACAAGGAC ACAGAGAGGG GAACATCACA CACCGGGGCC TGTTGTGGGG TGGGGGGCTA
GGGGAGGGAG AGCATTAGGA CAAATACCTA AAGCATGAGG GGCTTAAAAC CTAGATGATG
GGTTGACAGG CGCAGCAAAC CACCATGGCA CATGTATACA TATGTAACAA ACCAGCACAT
TCTGCACATG TATCCCAGAA CTTAAAGCAA ATTTTTAAAA AAGTAAAAAA AAAAAAAACA
AACAACAACA CCTAACTGGA CTACAAATGC ACTATATAAC TTCGATGAAG AGAGTGGGGA
GTAGGGAAAG GAACGGACTT AAATTACTCC AGAAAATAGT GTTGTGTTGT GACTAGAATC
TATAAGGCTT ACGGTAAATG AAACTTTACA GGATCACTAT ACTCTAATTG GTAAATCAGT
TTTTCATGGG GTGCGGGTGA ACAGTTGTGA AACTGCTTTA CATGTAGTCA TACCTTTGCA
TTTTGCAGAT ATTTCAATTT TTACAAATTG AAGATTCGTA GCAACCTTGC ATCAAGCAAG
TCTGTCAACC CCATTTTTCC AATAGTGTGT ACGCATTTGG TGTCTGTGTG TCATATTTTG
ATAATTATAA CAATAGTTAA AACTTTTTCT TTACTATTAC ATCTGTTACA GTGATCTGTG
ATCAGTGATC TTTAATGTTA CTATCATAAT CGTTTTGAAG GTGCCATAAA CTGTGCCCCT
ATAAGTCCTG AAACTTAATT GATAAATGTA TGTGTTCTGA CTGCTCCACT GACCAGCCAT
TGCCCCATCT CTCTCCCCCT CCTCAGGCCT CCTGATTTCC TGAGACATAA TAATATTGAA
ATTAGGCCAA TTAATAATCC TACAATGGCC TCTAAGTGTT CAAGTGAAAG GAGTTGCATG
TCTCTCACTT TAAAAATCTA AAACTAGAGG CTGGTCATGG TGGCTCAGGC CTCTAATCCC
AGCACTTTGG GAAGCCAAGG CGGGGAGATC ACCTGAGTTC AGGACTTCGA GACCAGCCTG
GCCAACATGG CGAAACTCTG TCTTGACTAA AAATGCAAAA ATTAGCCAGG CATGGTGGTG
CACACCTGTA ATCCTAGCTA CTCAGGAGAC TGAGGCAGAA CAATCGTTTG AACCCTGGAA
ATGGAGGTTG CAGTGAGCCT AGATTGTGCG ATTGCACTCC AGCCAGGGCA ACAAGAGTAA
AACTCCTTCT CAAAAAAAAA AAAAAAAATA TCTAAAGCTA GAAATGATTA AGCTTGGTGA
GAAAGTCATG TCAAAACCAG ATAGGCTTAA AGCTGGGCCT CTTTTGCCAA ACAGCCAAGC
TGGGAGTGCA AAGGAAAAGC TTTTGAAGAA AATTAAAAGT GCTACTCCAG TGAACATACG
AATGATAAGA AAGCAAAAGA GCCTTATTGC TGGTATAGAG GAAGTTTGAG TATTTTGGAT
AGAAGATCAA ACCAGCCACA ACTTCCCTTA AACCAAAGCC TAATTCAAAG AAAGGCCCTA
ATTCTCTTCA ATTCTACAAA GTCTGAGAGG GCTGAAGAAG CTGTAGTAAA AAAGTTTTAA
ACCAGCAGAA TCTGGTTCAT GAAGTATGAG CTAGAAGCC ATCTCCACAA CATAAAAGTG
CAAGGTGAAG CAGCAAGTGC TGATGGAGAA GCTGCAGCTA ATTATCCAGA AGATCCAGCT
AAAATCATCA ATGAAGGTGG CTACATTTAT TTTTTATTTT TGTTATTTAT TAATTTATTT
ATTTTGAGAC AAAGTCTTGC TCTGTCCCCC AGGCTGGAGT GTGGTGGCAT GATGTTGGCT
CACTGCAACC TCCACCTCCT AGGTTCAAGC AATTCTCCTG CCTCAGCCTT CCCAGTACCT
```

Figure 11G

```
GGGATTACAG GCATCTGCCA CAACGCCTGA CTAATTTTTG TATCTTTGGT AGAGACGGGG
TTTCACCACA TTGGCCAGGC TGGTCTTGAA CTCCTGACCT CAGGTGATCC ACCCGCCTTG
GCCTCCCAAA GAGCTGGATT ACAGGCATGA GCCACCACGC CTGGCCAGTG GCTACATTTA
AAAATAGGTG TTCAATGCAG ACAAAACCAT CTTTTATTGG AAGAAGATTC CAACCAGGAC
TTTTTTTTTT TTTTTTTTTT TGAGACAGAG TCTCACTCTG TCGCCAGGCT GGAGTGCAGT
GATGCGATCT CAGCTCACTG CAATCTCTGC CTCCCGGGTT CAAGTGTTTC CCTGCCTCA
GCCTCCTGAG TAGCTGGGAC TACAGGCACG TGCCACCATG CCCAGCTAAT TTTTGCAGTT
TTAGTAGAGA CGGGGTTTCA CCATGTTGGC CAAGATGGTC TCTATCTCTG ACCTCGTGAT
CCACCCCCCT TGGCCTCCCA AAGTGCTGGG ATTACAGGTG TGAGCCACTG CGCCCGGCCC
AGGACTTTCA TAGTTAGAAA AAAGTCAATG CCTAGCTTGA AAGGACAGGC TGACTCTCTT
GTTAGGGGCT AGTGCAGCTG GTGACTTTAA GTTGAAGCCA GTGCTCATTT ACCATTCCTG
AAATCTTAGG GCCCTTACCA GCTATGCTAA ATCTACTCTG CCTGTGCTCT GTAAACGGAC
AATAAGGCCT GGATGATGGC ATATCTATTT ACAGCATGCT TTACTGAATA CTTTAAGCTC
ACTGTTGCGA CCTACTGCTC AGAAAAAAAT ATTCCTTTCA AAATATTACT GCTTATTAAC
AATGCCTCTG GTCACCCAAG AGCTCTACTG GAGATATACA GGAAATAAAT GTTGTTTTCA
TGTCTGCTAA CACATTTGTT CTGCAACCTA TGGATCAAGG GGTCATTTTG GCTTTCAAGT
CTTATTATTT AAGAACTATA CTTTGTAAGG CTATTCCTGA CACAGATAAT GATCCCTCTG
AAGAATCTGG GCAAAGTCAA ATGGAAACCT GGAAAGGATT CACTATTCTA GATACTATTA
AAAGCATTCA TGATTCATGG AGGACGTCAA AATAAAAACA TTAATAGGAG TTTGCAAGAA
GTCAACCCTC ATGGATGACT TTGAGGGGTT CAAGACTTGA GCAGAGGAAG TCACTGGAGA
TGTCGCAGAA ATAGTATGAG AACTAAAATT AGAAGTGGAA TCTGATTTTA TAACTGAGTT
GCTGCAATCT TACGATTGAA CTTTTCTTTT CTTTTTTTTT TGAG

ATGCCCCTGC TGAGCTGCCA GTTCCTGAAG GGTCACCGGG AGCAGCGCCT GGCCCACCTG
>>..........................EXON3 ...........................>
GTCCTGAGCT TCCTCACCAT GGGTTATGTC TGGCAGGAAG GAGAGGCGCA GCCTGCAGAG
>...........................EXON 3 ............................>>
GTGAGGGCCA GAGAGCAGCT TCTCCTGTTA CCCGGCAGGT TACCTGCGCC TGGAGTAACG
TGCTCCCTGC TTGGTGCTAC CCTGTTTTCC TGGAAAATGG GTACTTTCTT CTTCTCGATG
GGCATCAGTT TAAGCAACGA TGAAGGGCTC ATTTATTATT TATTATTATT ATTTTTTTAT
TTTATTTTGA GCCAGTCTCA CTCTGTCACT CAGGCTGGAG GGCAGTGGGG TGATCTTGGC
TCACTGCAAC CTCCCCTTCC AGGTTCAAGC AATTCTCCTG CCTCAGCCTT TCTTGTAGCT
GAGACTACAG GCACCCACCA CCACACCTGG CTAATTTTTG TATTTTTAGT AGAGATGGGT
TTCACCATGT TGCCCAGGCT GGTCTCGAAC TCTTGACCTC AGGTAATCTG CCTGCCTGGG
CTTCCCACAG TGCTGGGATT ATAGGCGTGA GCCACTGCGT TCAGCCTGAA GGGCCATTTA
AATGAAGGAT TTTTTATTT TAATTTTTCT GACTAAGAGC TAATTTGTTT TTTAAACTGG
TAGCTATTTC TTCCTTTTAT AAGCTTTTGA ATGTTTGTTT GTTTGTTTTT GGCACTCTCT
TCCAAGAATG TTTGAAGACC TGCATTTGAA GGCAGATTGC CTTTTTGCTT TAAAACAGGG
TTGCACCATG TTGCCCAGGC TGGAGTGCAG TGGTGCAATC ATAGCTCACT GCAGCCTCAA
CTCCTCCCAG GCTCAAGCAA CCCTCCCACC TCAGCCTCCT GAGAAGCTGG GGCTACCAGC
ATGTACCGCC ACACCCAGCT AATGTTAAAA ATTTTTTGTA GAGATGAGGG TCTTGCTGTT
TTGCCCAGGC TGATCTTAAA CTCCTGGCCT CAAGTGATCC TCCTGCCTTT GCCTCCTGTG
CTGGGATTAC AGGCGTGAGC CACCATGCCG GCCTGAAGA CAGACTCTGA GAATTCATAA
                                                             SapI
                                                          --------
AAACCTCACA GCATTTTGTA CTCTTATGTA TATAAATTAT CTAGGTTGCT CTTCATAATC

Cfr I
               ------
CTGTAAAGTA ACAAGAGCCA TACCGGCCCA TTTTACAACT GAAAAGCACA GACACTTATT
TCCTTAATCA AGGTCAGACA GCAAATTAGT GGAAAAGCCA AGGCCAGAAC CCAGGTCTTC

SpeI
       -------
TGATTTTACT AGTGCAGCCT TCTTTCCCCA GGGGACACAT TGACATTTAC AACACTCATC
TTTATTTTTT TTTAATACT GCTTTCTATC CAGCCAATTA TTAGTCTGTC TTTTAATAAT
TCATCCAAAT CTCTTCTGAA TCATTGCATA ACTTTGTACA GTTCCACCC ACAGTGTCTT
```

Figure 11H

```
TTACTTTTAT TTTTGGAAGT AACTGTTTTT AAAAGTTACT GTTATTTTTA AAAGTGTGCC
TTCCCCAGAA ATCAGGGAGT TACCCATGTC CTAGAACTCC ACGGTGAAGA GAACAGCCTG
TGCCCATCGT GTTTGCCTGA TTGATCCTAC CTCTTGTCTC TCGGGGAAAC ACAGGAGACT
CAGGGAAGAG GAAAAGTGTA GAGTCATTGC AGCCTTGTTA TTTGTCAATG CATCTCTTTT
CTTTTTCTTT TTCTTTTTTT GATACAGAGT TTCACTCTTG TCGCCCAGGC TAGAGTGCAG
TGGCGTGATC TCGGCTCACT GCAACCTCGG CTTCCTGGGT CCAAGGGATT CTCCTGACTC
AGTCTCCTGA GTAGCTGGGA TTACAGGCAC CTGCCGCCAC GGCCAGCTAA TTTTTTTTGT
ATTTTTAGTA GAGACGGGTT TCACCACGTT GGCCAGGCTG ATCTCGAACT CCTGACCTCA
GGTGATCCAC CCACCTGAGC CTCCCAAAGT GCTGTGATTA CAGGCATGGG CCCCAGCACC
CGGCCAGTGC ATTGCATTTT TTTTTTTTTT TTCGAGACGG AGTCTCACTC TGTCACCCAG
                                            EciI
                                            -------
GCTGGAGTGC AGTGGCACGA TCTTGGCTCA CTGCAAGCTC CGCCTCCCAG GTTCACGCCA
                                  NarI
                                  -------
                                  KasI
                                  -------
                                  EheI
                                  -------
                                  BsaHI
                                  -------
                                  BbeI
                                  -------
GTCTCCTATC TCAGCCTCCC AAGTAACTGG GACTACAGGC GCCCACCACA ACGCCTGGCT
AATTTTTATA TTTTTAGTAA AGACGGCGTT TCACCATGTT AGCCAGGATG GTCTCGATCT
CTTGACCTCG TGATCTGCCC GCCTTCGCCT CCCAAAGTGC TGGGATTACA GGCGTGAGCC
ACCGTGCCCG GCGTGCATTT TTAAAAGTGT GTCTGATGCT GAAAAGTTTG AAGTCTAGGC
ACGTCCCAGT GGGTCCTCTT TATACCATCC CCTCTGCAAA CCATTATCCT AAATTGGGGT
TTGGGGGAGA GAAGAGTGAC AGTGGAAAGA AGTCTCCACC TCCCAGCTGT GCCCTGGTAG
        SanDI
        ---------
TTCCAGGGGA CCCGGAGGCT CCCCACACCC ACCACCCCGC CTCAGATCAC CTTTCACTTT
CTTTGTTTCT CCTCCCTTGA CTTTTCAGCT CAGAAAGTAC CTGGCTCTCC AATGCCTTCT
GAGGAAAGTT TACCCGAGGT TCACATTGCA AGACTCATTA AAGCTCTTTA GTGTTTTCCA
CCCGAGAAAA AATTCAAGGG AAAAATGAAG ACAAAAGCAG GGCATTCTTA ATGGATATTT
      AflII
      -------
TATCTTAAGG AGAAATGAAA ATGGAGATGG AAGAGGGGGC ACAAGGATGG GGTTTGAATC
TAGACTCGTT CAGCCTTTAC CTCCGATAGA GAACCTCATA CAGCTTTTCT GGACTTCTGG
CTGATAAAGA GCCGTGGAGG GTTCCTTGGA TAAAAAAGGT TGAAGGGGGT CTGTCCTGTG
GTGGCTTACT TGAAGGTATT ACTGGGTTTG ACTTATGGAG TAAGAGACGG AGTCAGTTTC
CCCACAGGCT GAGGCAGTCT GTCCTCATGC TTTTCTAGGG CACTGTGGTC TCCCAGGCTC
ATACCTAGGT GCACACACAG GTTTCTGCAT CTAGCTTTGT ATCTCTATGA GTCGGTCAAT
                                                          NheI
                                                          -------
CAATAAATCT ATCTATCATC TGTCTACTGA TCTATCATCT ATCTATCTAG CTAGCTATCA
TCTCTCTATC ATCTATCTAT GTATCTATCA TCTCTCTCTA TATATGTGTG TATATATATA
TATATATGTA TATATATATT TCTATCCTTC CATCTACTTA CCTATCTATC AAAATTTTTT
TCCGTTGATA ATATTCTCGG GCCCCAGTTT ATGTTTAATT GTTTTGGTAA TGCCTTTCTT
TGCACAGTCA GTTTACAGAG GTTATTTTAT ATTCTATATG TATGTGTGGT CCAGCGTTGT
AATTTTCACA TATATTGCAC CGTGTACTCA TAAGCAGTAT TTCCACTGGG TCATTAACAG
AAAGATATGT GTGCGGCATA TGAATGTGCA TCACTCAGGT AATTCAAGCT TGGTTCCCAG
ATCATTTCTG TACCACAGGA TTGCCGAAAT AAAAGACAAC CATGGTTATT TCCTCTGCTG
CAAGCTTTCT AGAATATGCT ATTTGTCTGG ATTTATATCT GAAAGGTCCT GCCAAGGAAT
```

Figure 11I

```
                                                  >>...EXON4   ...>
CTTGCCCTTC CATTTGTCGA AGTCTCCAGG AACTTGGGGC TCCCTCCTAT CCTGGTCCAC
>........................EXON4    .........................>
TCAGACTTGG TGCTGACGAA CTGGACCAAA AAAGATCCAG ACGGGTAAGG AAGGAAGAGA
>...................EXON 4    ...................>>
ATGCTTTGAA TTTCCATAAC TTTCCCCCAG GAAACACCCA GGCTTTTTTT TATAATTAGG
GAAGTTCATA TTTATGGTCT GCCGTATGGT TCCAAAGAAG GGGTGAGCTT GACCAAAAAT
TCAAATATCA CAGGCCCCAG AAGTTTCCTC TTAATCCATT CTGAACACAT TGGCTCAGAC

DrdI
  ------------
CATTTTGTCT TGTTTGTTTC CACATGACGT GTGAATTTCT CAACCTGACC TTCAAGCTCC
TGCAAAATCA GCTTTTATTT GTTCTTTCTC TTCAAACTGT TTATTCCCTA AGATGCCCTC
CATTCATATC AGGTTAAAAC CAGTTGGCTT TGATAAGTAA TCATTATATA ATGATCAGAA
GAGAATGATT ATGGATGAAT TCAGAGCAGA TGCTCCAGGT GGGTTGGATT GAGAATTTGA
TTAATAATTC CATCTATTCC ACCAAAGTCA CATCATTCCT TGACAGTTG GGCTGGGAAT
AGGGGCATTT GTCTACAGAA GGAATAGCAT GAGATTTTAA CAAACAAGAA ATTCAACAAA
CAGAATTAGA CAGATGATCT GAGATGTTAA ATTTTCCTTT CACCTTAATT TTTGCAGCCA
AATTTATTTC AGCTCTAGAT GAAAGAGACA GCACTTTCTT TTGTGGCTGA CTACAACAGC
TGAAGATTCA CTGAGGTTTG ATATGAGGAA GAACTTCCTC AGCCATGGGA TTGCCAGAGG
CGATGATGGG AATCTACTTA AAAGGGTTAC ATATTTAGTA GACAGCCTAG ATTTTAAGAC

Eco  I
        ------
        BsiEI
        ------
TAATTTATGT GCCCCGGCCG GGCCCGGTGG CTCACCCCTG TAATCCCGGC ACTTTGGGAG
GCTGAGGCAG GTGGATCATC TGAGGTCAGG AGTTGAAGAC CAGCCTGGCC AACATGGTGA
AACCCCGTCT CTACTAAAAA TACAAAAAAA TTAGCCGGGC ATGGTGGCAC ATACCTGTAA
TGCCAGCTGC TCGGGAGGCT GAGGCAGGAG AATTGCTTGA ACGAAGGAAG TAGAGGTTGC
AGTGAGCGAA ATCATGCCAT TGCACTCCAG CCTAGGTGAC AAACTCTGTC TCAAAAGAAA
AAAAAATTAT GTGCCCCATT GGAAGAAGTG AGATTCGGCC ATCTCATCTC TCTCGGGAGC
TCTGAGCCCT GGAGTTTTAT GTTTTCTGCA ATTATGAATT GTGATCCTTG ATTAATTATG
CTTTAATAAT AAAATGGGTG ACTACTGAAA GCTGCTGAAT CTGGGTAAGA ATTTGGATGA
AAAAAATAAT ATATGTGCGT AATTTATTCT GTTCAAGGTA CTGAATATTG AATAAGCTGG
ATTTATTACT CAAAGAGAAA GACAGAATAA GAGAAGGTTG AAGGGAAAAA TGACTGTACT
AGAATGGTAG TCAAAAATGC AACAACAGGC AGGTGCAGCG GCTCATGCCT ATAATCCCAG
CACATTGGGA GGCCCAGGTG GGCAGGTCAC CTGAGATCAG GAGTTTGAGA CCAGCGTGGC

SfiI
      ------------
CAACATGGCC AAACCCCCTC TCTACTAAAA ATACAAAAAT TAGCCAGGTG TGGCAGTGGG
TGCCTGCAAT CCCAGCTACT CAGGAGGCTG AGGCAGGAGA ATCACTTGAA CCTGGGAGGC
AGAGGTTGCA GTAAGCTGAG ACTGCACCAC TGCACTCCAG CCTGGGTGAC AGAGTGAGAT
CCTATCTCAA AAACAAACAA AACAAAACAA AACAATAACA AAAAGCTAT TAATAGCTTC
CTAGGGAGTA AGAGTGAAGG GCTAGTTTAA TTCCAGAGAT GCGGACACAG TCCTGGGTCT
CACCAATTAT TCTGCTTGGT AATTACCTTT TGAAGCCTTT TAATATGCCT AACACAGAGC
TAAGTGCTAT GAAGAAATGA AAGAAATAGA AGCAAAGTAC TCCCCATGTG GTTAAATAAC

PshAI
                ------------
AAGACACTAC ATGACAAATG TCAAAGAGTG ACTCAAACAA TATGTCCTTT AGAATTTCAG
AGAAATGACA TCAATGCAGG CTTTACAAGT CAGTAAAAAT CTTGGTGATG AGGCAGAACT
TGATGTAAGG CAAATCCTAA AAGTTGAGTA GGAATCAACT AGCTAGAATA AAATGTGGGG
TTGTGGTAAA TACAAAAATG TAAGATGAGT GAAATAACTT ATTTATTTAT TTATTTATTT
TCAGAGACGG AGTCTCCCTC TGTCTCCCAG GCTGGAGTGC AGTGGCATGA TCTCGGCTCA
CTGCAACCTC TGCCTCCTGG GTTTGAGCAA TTCTCCTGCC TCAGCCTCCT GAGTAGCTGG
GATTGCAGGC ACCTACCACC ACACCCGACT AATTTTTGTA TTTTTAGAGA GATGGGGTTT
TACCACGTTG GCCAGTCTGG TATCGAATCC TCGACCTCAT AATCCACCTG CCTCAGCCTT
```

Figure 11J

```
CCAAAGTGCT AGGATTACAG GCATGAGCCA CTGTGCCCAG CCTAATAATA TATTAAGATG
GCCACAGGCC AAATATTCTG GGGCTGGAAT GTGAGTGGAA ATGTCGCTCA CCCTTTATCA
CATAGCACCC CATAGTCCAG CCACAACTTG CAGAATTCAA AGTAAGTGTG GATGTGTGTG
TGCCTGCAGT GCCTTGCACA CAAGTGTGCA TGCCTGTGGA CATGTGACCC TAGAAGTTAT
TAATATATCT GGTTTACAAA CTGAATTGTT CTTTTATTTT TTTTCTCTCT TGGTGGTCAT
CAATAACTGA AATTGGGCTA GATTCCTGGA AATTGGGTAA GTTCTCAGAA ATCATTTACG
                    >>...Exon 5 ...>>
CACTTTAGAA TCCAGGCCAA ATTTAAAATC TTACAATAAA ACAAAGAACA AAGCATGCTA
AATTATATGT ATAATATAAT ATCAACCATA TAAAATGCAT AAAAAATATA CTAGAAGGAA
ATGTGCCTAA AATTCACAGT CTAAAATTTA ACAGTGATTG CCTCTTCCTT GTATAGATAA
GGGATTTTTT TTTACTGTAT TTTCCAGTCT GTACATAATA AACAAGTAA TGTGCAATGC
AAACAAAACA AAATGAAACT TTATCAAATT TCAGTAACTC CTTGAAGTTT AATTTTTTTT
TTGAGACTGA GTCTTAGTCT GTTGCCCAGG TTGGAGTGCA GTGGTGTGAT CTCGGCTCAC
TGCAACCTCT GCCTCTGGGT TCAAGGGATT CTCCTGCCTC AGCCTCCCGA GTACCTGAGA
TTACAGGCAC CCACCACCAC ACCTGGCTAA TTTTTGTATT TTTAGTTGAG ACAGCGTTTC
ACTATATTGG CCAGGCAGGT CTTGAACTCC TGACCTCAGG TGATCCACCC GCCTTGGCCT
CCCAAAGTGC TGGGATTGCA GGCGTGAGCC ACTGCACCCA GTTGAAGTTT AATAGTGTGA
AAAAAATATT TCTCATCTCA CTATATCTTC TATGGGAGGC CAGATTGCAG ATTGTCTACA
GAAAAATCCC TTCAAAGAC CTTGTTATTA CATAGACTGG AGCTCATGGG GCAGGTCTGG
TCCACACATC CTTAGGCTCC GCTTCTCCTG GAAAACAAAA ATAGCCTCTG ATCCAGTGTT
GCCTCTCCCA TCACCAAACC TCAGCTTCTA TCGCCAAACT CATCAAATAA GAGTGTCCAG
TAGAAAAACT GGGCAGATGG GGGCACAGAA GGTGAAGACA TCATTTCCCA AGCTAATGTT
GCTGCTGGAA CAATGTAAGT CTTGACTTTG TCTTGGTTTG GTTTGGTTTG ACATTGGTTT
GTTTTTCATC TTTGTCTCAT GCTTAAAATG TGAAGGGCAA ATATGATCCT TAGAGTTAAG
GTTTAGGTT TTGTAGATGT TTTACTCCAT TTAAATGACA GCAGATCATT TAGAAATGAT
TCCTCTGTAA CAGCCTTCCA GATCCCATTC GATTGTACAG CATTGAGATA GATAGATAGA
TAGATAGATA GATAGATAGA TAGATAGATA GACGGAATTT GGCCCTGTGT TCCCACCCAT BamHI
                                -------
ATCTCATGTC AAATTGTAAC CCCCACATGT CAGGAGAGGG ATCCAGTGGG AGGTGACAGG
ATCATGGGGT TGGATTTCCC CAATGCTATT CTCATGATAG TGAGTTCTCA CAATATCTCA
TTATTATTAT TATTATTATT ATTATTGCAA CAGAGTCTCA CTCTATCTCC CAGGCTGGAG
TGCAGTGGTG TCATCTCGGC TCTCTGCAAC CTCTTGCCTC AGTCTCTTGC GTAGCTGGGA
TTACAGGCAT GCCCCGCCAT GCCCAGCTAA TTTTTGTATT TTTAGTAGAG ACGGAGTTTC
ACCATGTTGG CCAGGCTGAT CTCGAACTCC TGACCTCAGG TAATCTGCCT ACCTCGCTCT
CCCAAAGTGC TGGAATTACA GGCGTGAGCC ACTGTGCCTG GCCAGTTCTC ACAAGATCTG
ATGGTTTAAA AGTGTGGCAC TTCCCCCACC TCCTGCCGCC ATGTAAGATG CTTGCTTACC StuI
                                -------
CTTCCACCAT GATTGAAAAG TTTCATGAGG CCTCCTAGCC ATGCTTCCTG GTAAGCCTAA
GGATCTCTGA GTCAATTACA CCTCGTTTCT TTATAAATTA CCCAGTCTCA GGTATTTCTT
TATAGCAGTG TAAGAATGAA CTAATACACA CATAAACAGA TTAGAGGCAG CACTGGCCTG
AGTTGTGAAA CTCTTCCCAG CCTGGTCCTG CGATTAGCTG GCTATATGAC CTTGGACAAG
CTGCTTTGCT TCTCTGGGCC ATGGTTTCAT ACCTGCAAAA AAAAGAGCAT GGACTTGGCT
GTTGCCTGGG TCTCTCTAGC CCTGTGGAGA ATCAGCTACA TCTCTTACTA GGAACTTCTC
ATTCAGCCAG TTATTCCACT GCGGAGATGG TCCAGGACCA TTAGGGCCAT GCTAGACATT
GGGAGGCTGC CTGTCAGGTG AACATGAAAT TGAACTTATC TGTTCTCTTT CCTCCCTGAA
TGTTGCTGAA GGTAGATGCC CATCCTCAGG GCTGTCTTAC GGAGAGGAGA AAGTTGTGCA
GTGATTCCAC CCTGCAGTTA TCTAACTCGG CAGGGAACTC TGGGCAGTGA GTACTCACGG EcoNI
                                ------------
TACAGTCTCC ACACCTCTAA TCATGTGCTC CTCTCCTTCC CAAGGAACCT GGAGACCATC
                                        >>....EXON 6 .....>
ATCTCATTTC CTGGGGGAGA GAGCCTGCAT GGTTTTATAC TGGTGACTGC TTTGGTAGAG
>...........................EXON 6 ...........................>
```

Figure 11K

```
AAAGAAGCAG TGCCTGGGAT AAAGGTATCT TCTCACTTGA TAGCACCTTT TCTTTTTAAA
>........EXON6   .........>>

DraIII
                          ---------
TGAGCTTGAG CTTTACTTCC CACTCAGTGC CTTTCCTGCA GTGGATTTCT CAACACAAAT
GAACATAGAC CTTGTCCTGC TTAGTTCAAG TCTGAGAGAA GAGATCTAAG CTCTAGGCCA

AhdI
                                                ------------
CCATATTTGC TCCCTTTTCT CAATTCCTAT AAAACTCGGA ATGGACCTTT TGTCCATTCA
ACAAACAGGC ATTGGTTTGG CAATGGGAA  ATTGGATCGA ACAAGACAGA CATTTTCCCA

BciVI
                 ------
GCCCTGACAG AAGCTTATGA TGGATACAGT GGATGAAGAT GGATTAACGT GGATTACAGG
TGTGAGCCAC TGCACCGGGC CTCAAACTGG AAATTCTTCA GGAGTCAGAC AGGTATCAGG
AAGGCTGGAT AGAAGACAAA AGACAGTGAT GCAGCTTGTG ATCAACTACA GCGTTAATGC
CTTGCCTAAA AATATTTCAG TTAGATTTCT GCCTTCGCTC TGTCGCTCAG GCCAGAGTGC
AATGGCGTGG TTTTAGCTCA CTGCAATCTC CACCTCCCAG GTTCAAGCAA TTCTCCTCCC
TCAGCCTCCT AAGTAGTGCA CGCCACCACG CCTGGCTAAT TTTTGTATTT TTAGTAGAGA
CAGGGTTTCA CCATGTTGGT CAGGCTGGCC TCGAACTCCT GACCTCGTGA TCTGCTTGCC
TCAGCCTCCC AAAGTGCTGG GATTACAGGT GTGAGCCACC CTGCCCAGCC AACACTACCT
CCCTTGATAA GCATATGTTG AGCACCTACT GGTCCTCAAT AGGGTGACCC ATTTCTGCTA

Eco III
      -------
TATTATAGCG CTTTCTTTCT CTCTCAGTAG TTAAACTCCA TGGTTACTTT AGTTCTCATC
CATGTGTTTA GTCCATTAGA AGATACAGAG TCAAATATCG GCCTTCCAAG TGTAGTTCAG
ATGAAGTAGA GACTCAAGGA AGACAAGGA

AGTCTTCCCA GCAGAGGGGA TTCTAGAGCT GGGGGCTCTG TAGAATCTGT CTGTGTATTA
GTCCATTTTC ACACTGTTAT AAACATACTA CCTGAGACTG GGTAATTTAT AAAGGAAAGA
AGTTTAATTG ACTCATAGTT CTGCATGGAT GGGGAGGCCT CAGGAAACTT ACAGCCATGG
AGGAAAGTGA AGGGGAAGCA AGAACCTCTT CACGAGGCAG CAGGAGAGAG AGCAAAGGGG
GGAGCTGCCA AACACTTTTA TACAATCAGA TTTTGTGAAA ACTCTCCCTC GTATCATGAG
AACAGTATGG GAGAGCCCAC CCCCATAATT CAATCACCTC CACCAGGTC  CCTCCATCAG
CCTGTGGGGA TTACCATCCA AGATGAGATT TGGGTGGGGA CACAGATTTC AACACAGATT
TAAATCTGAC TTTATATGAG AGCTTCGGAG CAAGGATGCC CCAGTTGGAG ATGCAGTAGA
ACTGATCATA ACGTGACAAA TCCGAGAGAA GAAGAGTAAA ATAATAGTAC TCAGGCCCTT
GGGAGGTGCA AGAAGTAACA GCCAGATGAA ATTCCAGAAA CACTTACCTA GGGGTCTGTC
TGGGAGGTCC CCAGGGAGCT TCTGGCTGTC AGGCCAACCC CACAGTGGAT CTAGCTTAGG
ACGTTCCCAG GAAGCTCTGA CAAACTGTCC GGTCCTCCCC TGGGTTCCAA CAGTATGAGG
CTTACTCTGC CTGCATGGAC TTTAAGGGAG TGCTAATAAG TTGTGTACAT GCATCTCATC
CCTAGGCTCT TGTTCAGGCC ACGAATGCTA TCTTGCAGCC CAACCAGGAG GCCCTGCTCC
  >>.......................EXON 7 ............................>
AAGCCCTGCA GCGACTGAGA CTGTCTATTC AGGACATCAC CAAAACCTTA GGACAGATGC
  >..........................EXON7  ...........................>
ATGGTAAGAT GCTTCCGAAG CTCCTGAAGG ATCCCCCAGG GGTCCTGGGC TCTGCTTAGG
>>>
GGAAGAGGGC CTGGGGACCA GGCATGTCCT GAAGGGGGTG ATAATACATT CATCCACCAG
ATGACGCTGG TGGACTATCT TTGTTTTAGG TTAAACACAT ATTATCTTGG AGAGCTATTG
TCACAGCTTT GTATTCTCCC TCTCCTTTAT ATTCTCCCGT GATTAAGATG GTTTCCCTTC
TGCAGTGGCC AGATATTTCT TAGGCATGTT GAGGTCTTGC CTGAAGCTTG AGAGGAGGGG
ATGGGATGCA CAGTAATGTT GGTCGCGCGT GCCCCATCCT GCAGTGTTAG GTACTGCAGA
GCAGGTTGTC TACACTCTGT AATGCCCCTT TTATTCTAAC CCCTGTGTT  GGTTCCTGAG
ATGTCTGACC TTGGTTTTAA GCCTTGTCTA ATGGATGGCC TGTATTCCCT TTCTGTAGCT
AGGGCAGGCT GATTTGTCAA AGGTAGGAAA GTTGTCAGAA TCAAAATGGA GTCACTTGTG
TTGAATAAAA ATTTTTAAAC CTTGACAAAT AGAGCTGGGG AAGGCTACAA AGAGAGAGCT
```

Figure 11L

```
CCCGTGTATA AATGCCTGAT AACAAAATCT TTTCCAAAGG ACTGAAAAAA TCACCACCTT
GCACAAAGGC CATCACAACC TTACATACAC AAAAAAATAC TTACACAACG ACATCTGCCC
AGCAACTGCC TTTCCAACAT TGGCCTTGTG CCACCCTTTT TATTGATGCT CATAGCCAAG
GTTAATGATC TCAAAACAGT TACATAATTG TCCTCATTTT TCCTTTAAAA ACCTTTGTCT
TCCTTTATCT TTCTGAATAC CCACATGGTT TATTATGGCA CATGTATTCC CATTGCAATG
CCCTATTCCA GAATAAATAT CAGTTTCCAT TAGGGAGCCT CTCCCTGTTA ATCTGCTTAA
```

AgeI
                    -------

```
CACAGGCATG GTCAGTTACG GGGCCCAACC TTCCTGGACC GGTTACATCT TATTCTGGTT
ACTGCATTCA GTTTCCAACA TCTGGGAGGC TCTTCAAATT CTTCTCTCAG AGGAATCTGA
AGAATGTATG TGTTTAGGAG GATGTGAGAG AGGGGTGTGG TTTCTTAACA AGAGAATATC
AGAGTCTAAG TATCATTTTC CCTGAATCTT GCTTCCCTGC AGGAAAGAAA GATTCTGGGA
AAAGAGAGTG TTTACAAGAA GCAGGACTGG AGGGAGGGAG AAAGACGCTA GGTACTGCCA
AGCTTTATTA TCTTGTATTA AAAAAGTAAA TATAATTTGT CATCCCAGCC TCTCAGCACT
AGTAGAAATC TATCTGAAGT CACAGGATTA GGTATTATCC ACTTCCTGGT TTTATAGTTT
ATATTTGTAT TTTCTCTATT TCCTTGAATT TTAATTTTAA AGCCCTCATG ATCACATCAG
TAGGTCTTCT GCCAAACAGC TCCCTTAAGT TGTATGGTGG CTTTGCCAAG CTGAAATGAG
ATGAGATGTG TTTTAGCTTT GCCAAGAAAG CCTGAGTCCA TCACTTAGGA TAGCAAGGCT
ATTAGGGAGA TAGTGCAGGT GTCTTCAGAT CACATGGATG AGCAAAAGGA AGCAATTTTG
GAAGATTATG AGAAACCTTC CAACAGGTCC CAGTGTACAT AGCAGTAAGA TGGTGCATGC
AGTGTCTAAC TGTCACAGGC TTTCCTAGGG CTCACTTTCA GACTCACTTC TTTTTTTTTT
TTTTTTTTTT TGTGAGATGG AGTCTCACTC TGTCACTCAG GCTGGAGTGC AGTGGCACGA
TCTTGGCTCA CTGCAAGCTC TGCCTCCCGG GTTCAAGCGA TTCTCTTGCC TCAGTCTCCC
TAGTAGCTGG GATTATAGGC ATGCACCACC ATGCCAGCT AATTTTTGTA TTTTTAGTAG
AGATGGGGTT TCGCCATGTT GGCCAGGCTG GTCTCGAACT CCTGACCTCA GGTGATCTGC
CTACCTTGGC CTCCCAAAGT GCTGGGATTA CAGCCGTGAG CCACTGCGCC CAGCTCAGAC
TCACTTTTA GGCCCAGGCC AACCTGCTGT GTTCTCCTGC TCAGCTTCTG CAGGAGGTCT
CATCGTCTAA GGAGGTCCCA GGGCTACCGC CCTTGTTTTC TCAAAAGGCA CATTTTCCCA
CACAGACATA ATTTCGTTTC AGTGTTTTAC TCCTAGTCAC ATTCATCTAT ATGGACAAAT
```

BssHII
                             -------

```
AGCTGAATGG ATTGGACTGT GTTTTCTAAA GATGGCCCCA TGCCATCCTG CGCGCTCCTC
CACAGCGTGG CCTGGGCATT CCTTTCGACC AGGGGTGGAC TCTGTGCCCC TACTTGTGAT
GTACGTGTTG CCAATAGAAT GTAGTATAGG GGATAGCACA GACTTCTGAG GCAAGACTAG
AAGAGGTGAT GCAGGTTTAA CCTTGTGTCC TGAGCCACTA GGTAAAAAGT CCACCTACCC
TGAGATCACT CTGCTGTGCA AACGACACAG GCAAACCACA TCAAAGAGCC ATGTGGGTTC
TCCAGTTGGC TTCTGCCCAG GAGTGAAGGT GCCCTCAGAT GGTTCTAGGC TCCCATCCCA
ACTTATGTCC TGTCTTGAAG TCTTCCCAAC TGAGGCACCA GCCACTGTGG AGCAGAGTCA
AGCCATTGCC ATCTTGTTCT GCCCAGATTC CCCATCAACA GAATATAGTG GTTTTTTCAC
ACCTCTATGT TTGGAGTGGT TTCTATGCAG CAATAGTAAC CACAAGAAAT AAAGTTATAA
AAATAGTAAC AAACACTAGA AACTGCAAGA TTTAAGGAAT CACCTGAATG CTCCAGTCAT
TGTCTCTGGT TTGTAATGAT AAACTTTCTT CTGCGTGATA AATAGAGCTT GGCTGGACTT
TTTCCCTCTG CTTCCATTCC CCAAAATGGA GCGTACCAAA CAATTGCTTC TTTCAGAGCC
CAGCTTTAGC AAGAGTCATG AGCTCTAATC CCTTCATCCA TAAATACTTC CTTTCCAGGC
ACGTAGAGCC CTTCACACTC AGGGCTGAGT AGAAAATGCC TGTTGCAGAC TGCAGTGGCG
```

KpnI
       ------
       Acc I
       ------

```
TTTTGGAGAG CCACCCTCCT GGTACCTGAG TCACTAGTCC TTTGCCCAGC TTTTCTCAGT
```

Eco III
  -------

```
TTTGTAAAGC GCTCACTTCT GAGTGGAAGA CAGAACCAGC CCGGTCTATT TTCATAATCT
GCCCCCATAA GGCAGAAGTC CACACGGTAC TGGAAACATA ACCATATCTA TGTCAGTCTG
CCACTGCCTG CCGCCTGTCA ACCGTGCGTG TCTGCATCCA GTCCTTCTTT GGAGCTGCTT
```

Figure 11M

```
TCCAGCGACT CAGCCAGATC TGAGCTTTCT GACTCATTGG AAGGTTAAAC TATTTTCAGA
CTTTCAAGTG TTGAGATTAT TAAGACATGT GTTTTTTTTT TTCTTCTTTT TTTGGCATGC
TTACTGATCG CCCCTGTTCT CTAGGAAGTA ATGTTCTTCT TGGAAAAGGT GAAGGATATT
TTTCTCCCCA AAAAGCCATG GAAATGTTTG CCTTTATTTA CTTCCAAATT AACAGAATTT
CCAGCTTTTG CTTGACCCAT CGGCGCATTG GCAGCGTTAA GAATTTTTTC TTTTAGCAGT
AATGAGGAGT CGAAGGGTTT CTTCCTAACC ATTTAGTGTA TGCATTTAAA TCAGGTTTCT
TTTTGAGTAA ATTGGGGCTA AGCTGTAGTG TGAACTTCTG CTACTGTTCC TTTCTCATTA
GTTCACTTGA TTTCATGGAA GGAATTTTCC ATCTCAGCCT GTGAACTTAT TTTGTCTAAA
CTCAATTGGA AAGTAATTAA CACTGAGATT CTTCTTTAAT AAATTCTATA TGATAATAAA
ATCATACAAA CATCTCTTTA TTTTTCTTTT TGACCTAGAA AAGATGTTCA CAGGCCAGAC
CTGGTGGCTG AAGCCTGTAA TCCCAGCACA CTGAGAGGAA GAGGCGGGTG GATCACATGA
GGTCAGTCCG AGGGCAGGGT AGCCAACGTG GTGAAACCCC ATCTCTAGTA AAACACAAA
AATTAGCTGG GCATGGTGGC ACATGCCTGC AATCCCAGCT ACTCAGGAGG CTGAGGCAGG
AGAATCACTT GAACCTGGGA GATGGAAGTT GCAGTGAGCC TAGATCCTGC CACTGCACTC
CAGCCTGGGC GACAGAGTGA GACTCTGTCC CCAAAAAAAT AAATAAATAA AAGATGTTCA
CAATATATTG TTAAGTGAAA AAAGCAGGCT ACATAACTTG CATAATATGA GTGCATTTTA
ATAAAAATAT ACATATTTAG CAAAATAAAA GGACAAATGG TATTTATTAA AATATTTACG
TTGATTATTT CAACACAGAG GATGATAGTT GATTTTGCTT AATTTCTTCC CTCCTTCTTT
TCAATTTGAA TTTTCTATAA TGAAGATTGT TTCTTTTTCT TTCTTTCTTT TTTTTTTTG
```

```
                                              NarI
                                              ------
                                              KasI
                                              ------
                                              EheI
                                              ------
                                              BsaHI
                                              ------
                                              BbeI
                                              ------
AGATGGAGTT TCGCTCTTGT TGCCCAGGCT GGGGTGCGAT GGCGCCATCT CGGTTCACCA
CAACCTCTGC GTCCCAGGTT TAAGTGATTC TTCTGCCTCA GCCTCCCTAG TAGCTGGGAT
TATAGGCGTG TGCCACCACA CCCGGCTGAT TTTGTATTTT TAGTAGAGAC GGGCTTTCTC
CATGTTGGTC AGGCTGGTCT CGAACTCCTG ACCTTAGGTG ATCTGCCCAC CTCAGCCTCC
CAAAGTGCTG GGATTACAGG CATGAGCCAC CGCGCCTGGA CTGATTATTT TTTAAATAGG
GTTAGAAAGT GAGGAAGTTA CTAAACTCCG ATTAGCCCAA ATATGCCCCA GTGGGTCCTT
CTGGCAGAGT AAATGTCTCG GTTCAGCCTG AATCTGGGAA ATTGTTCCTA CGGTTCAGCC
TGAATCTGGG AAATTGTTCC TACCTTATAA ACTGGAGTAT CCTTCAGAAA TGACATTTAC
TCAAACTTCC TTTTAGGCAG ACTGCATAAT AGCAATTTTT AATATTAACC ATTTAAAAAA
```

```
           PacI
           --------
AACCTTCAGA TTAATTAACA CCAAAAGAAT AATTGGGAAA ATACAACTCC TCACTTTAAA
AAAGAAACAA CCAAAGTAAA TACTAAAAAA CTATATGATG TTATATTATC TAAGCTTAGT
TTACTGCAAA GATCAAGAGC ACACTACTAG TTGACGGCCT CTATTCACAC TGTTCATAGC
CCTCGCTCGC TTCTCCAGCC ATTCACTCAC TCATGCAAAA GGTCTGTACA CACAATGATG
CCTGATGGTA TAATAGGAAC CTTAACATTT CAATTAAAAG GCAAAATGAG GACACTTACC
ATCAGCCTAT AAAATTATTC TTATTATTCT TCTTCTTCTT CTCCTCCTCC TCCTCCTCTT
CTTCCTTCTT CTTCTTCTTC TTCTTCTCCT TCTCCTTCTC CTTCTCCTTC TCCTTCTCCT
TCTCCTTCTC CTTCTCCTTC TTCTTCTTCC TCTTCTTCTT CTTCTTCTTC TTCTTTTTTT
TTTGAGATGG AGTCTTGCTC TGTTGCCCAG GCTGGAGTGC AGTGGTGTGA TCTCGGCTCA
CTGCAACCTC TGCCTCCCAG GTTCAAGCTA TTCTCCTGCC TCAGCCTCCC AAGTAACTGG
GATTACAGGT GCATGCCACC ACGCCCGGAT AATTTTTTGT ATTTTTACTA GGGATGGGGT
TTCACCATGT TGGCCAGGCT AGTCTCTAAC TCCTGACCTC AAGTGATCCA CCTGCCTCGG
CCTCCCAAAG TGCTGGGTGT GGGCGGCAAG CCACCCAGGT GCCAAGGCAA GAGACAGAGG
GCACGAGCTG TTCCAGTATA ATGAGGAAAA TATATAGAAT AAGAATAGTT ATACTAGAAA
TAGATTATAG ATATGATTAC ATATGAATAT CATTCTTCAT TAGTTTGTAG CACTACTCTT
TATTCCAGTA TTATAATAAT CTTTGTTCTA CAATTATAAC CTAGGAAAAA CCAGGCCATA
```

Figure 11N

```
CAGAGATAGG AGCTAAAGGG ACAGGGTGAG AAGTGACCAG AAGAGTGTGA GCCTTCTGTT
ATGCCCGGAC AGGGCCACTA GAGGGCTCCT TGGTCTAGCG GTAACGCCCG CGTCTGGGAA

RsrII
           --------
GATGCCTGTC ACCTAACGGA CCGTGGTCTA GCGGTAGCGT CAGTGCCTAG AAAAGGCACT
CTTTTTAAAT ATACTTTTTA TTTTTGTTTA ATCTTCCCTG ATTTCCTATA GATCTGAGAT
ATGTCATGCT TATTTTCATT GCTATCTAAA AATCTCAATA AACTTTATAC CTAAGAGTAA

BsiEI
                                              ------
AAAAAAAAAA AAAGAAAAGA AAAGGCGCTC GTTACTTAGC CGACCGGGAA AGGGAGTCTC
CCTTTCCCCG GGGGAGTTAG AGAAGACTCT GCTCCACCAC CTCTTGTGGA GGGCCTGACA
TGAGTCAGGC CTGCCTGCAG TCATCTGGAG GCCTAACCGT CTCCCTGTGA TGCTGTGCTT
CAGCGGTCAC GCTCCTAGTC CTGAACACCT GGCTCCGCCT TTTAGATAGC AGTAGCAGAA
TTAGTGAAAG TACTAAAAGT CTTTGAAATG CAGAAGTAAT GGCGTAAGCT GTCACGTCTC
TCTCTCCGCC TCAGCTGCCA AACAGAGAAG GGTCCCCTGT CCAGTGGACA CGTGACTTGG
GTGACCTTAC CTGTCATTGG AGACGACTCA TACTCCTTAC CCTGCCCCTT GCCTTGTATC
TAATAAATAA CAGCTCAATC TGGCATTTGG GGCCACTACT GGTCTCCGCA TCTTGGTGGT
AGTGGTCCCC CGGGCCCAGC CGTCTTTTAT TCTATCTCTT TGTCTTGTGT CTTTATTTCT
ACCATCTCTT GTCTCCGCAC ACGAGGAGAA AAACCCACAG ACCCTGTAGG CTGGCCCCT
ACAGCTGGGA ATTACAGGCA TGAGCCACCG CATCCAGCCA GCCTAAAATT CTTCTGAAGG
ATAATAATAT AGTACTTGAA GACACGGTTT GAAAAAATC ATACTAAATG AAAGGGCACC
ATTTTACAAG CACTAGAACT ACATTAAACT TAAATGAATT CCAACACTCT TAATAATGTA
ACTCAAAAAC AAGTCTAGTG TTAACAAAAG CTCCAATAAC TAAAACTACA TTAACAGGCA
CAATGAACAT TGTAAACGCC GCTAATTGGC ACCAAGTTTA ATAGGGCAGA CAATATTTTC
TTCTGCATTC ACACTTACTC AGTTACACTG TTGAAAAATG CTGCTGCTCA AGCTATGAAT
GCTTTACAAA AGAAATCATT TTAATAAATA CAGTAAATGC TAAAACTCTA GCTAAACTAT
TATGCAAGAT ATACAACCAA GACAAATACA AATTCATAAT ACAAGCAACT TGCATTCAAA
ATGAACTCTA CCACTATATT TTATTAAAAG GGCAGACTTT ATGAATTAAC CCAGCTGCTT
CCTGAATTAC AAAAGTGGCA TGACTCAATA TGAAATAAG AAACTGTCTA CAAATTTCTG
ACAGTAATAA ATTGTAATAT ACAATACATG CAGGAGTCTT ACGGAAGAAT AAACTCTCCT
AGGAAACAAA AATATTTAT ACTTTTAAAA TCCAAAGTAA AAAAAAAGA AATCATTGCC
AGATGCGGTG GCTCATGCCT GTAATCCAAG CACTTTGGGA GGCCAAGGCA GGATCGCTTG
AGCCCAGGAG TTTGAGACCA GCCTGGGCAA CATAGCAAAA CCCCATCTCT ACAAAAAAT
ACAAAAATTA GATGGTAATG GTGGTGAGCG CCTGTGGTTC CAGCTACCCA GGAGGCTGAG
GTGGGAGGAT GCACCTCAAG GCTGCAATGA GCCAAGGTCA CACCATTGTA CTGAAGCCTG
GGACAGAGT GAGACCCTGT CTCAATAAGT AAATAAATAA ATATCTTTTA TGAAAAAGAT
TCTCTAGTCA GAATTAACAC CTCAACTAGC CAAACATCAG GAAGTTACAT TACAGCTACT
TAATACACAA AGGGACACAT TTTCACCAGT CGTTGTCTTC TGATATTTCT ATTCCAGAAA
CACACACTCT CACTTCCCTA CACTCCCCAT CCCATCATTT CTTCAGAGCA TGGAAACAGA
ATTTGTTGAA CACCAGAAAT CTCTTGCTAT GGTGGTACAT AAGTCATAAC ATTTGTTGCT
GCCCAGCAGC AGGTATGAAG CCGGCTGGTG ACTGGCTAGC AAATGCCTAT TCTGTAAGCT
CCTCACTTAG CCCATCTGTA GCTCTGACTT CTCCACCAAT TCCCTTCTCT CCTTTCACAG
CCTTTCTGAG TTTCTGAGGG ATAATTTCAG AGGTTCCATA TAACTGTCAA AGCCTATGGT
AGACATGGCA AAGTGAAAAT CCTCTCCACT GGCCATTTCT GTTTCTCTTG GGGGCATCTT
TCACTTGCCT CAGGTGTTAT AAAGCTGATG AACACACGTA CACGTTGTTT AACACTTTCT
TGGGCATTTC CCATTTGAGA TATGGCATGT TTCATTATCC TAGTGACATG TGCAATCAGA
AAATGTATAT TTTGTTCTCT GCAACTTTCT TTTGAAAAAT GTATATTTGA ACAAAATATA
CATTTTTTGT ATCTTCATGA CCATTCATGC TGTCCTCACT GTCATCATGA GGCTCTATAT
AACATAATGA CTCCTCCAGG GCAGTCTTCG GAAATTCCCA GTGCAGAAGC ACGTGTCATA
CAGCAGTCCC CATTCATCTC CAGTGCAGCT CTGGCTGGCT CCCATGTCTG ATCAGCTGTT
TGGTTGGACA GAAAATGACT GCAAGGGAAT CAGTTCCAGT GTGAGCTCTG TTTGCAGAAC
TCAGACTCCC CTCCCTCCCA TGTTAATGCT TTTTTCTTC TTCTTTTTTT TTTTTTTTT
TTTTTGACAG AGTCTCATTC TGTCACCCAG GCTGGAGTGC AATGCTATGA TCTCGGCTCA
CTACAACCTG TGCCTCCCCG GTTCAAGCAA TTCTCGTGCC TCAACTTCCC GAGTAGCTGA
GATTACAGGT GCACACCACC ACACCCCACT AATTTTTTTG TATTTTTAGT AGAGACGGGG
TTTTGCCATG TTGCCAAGGC TGGTGTCAAA CTCCTGAGCT CAGGAAATCC ACCTTCCTCA
GCCTCCCAAA GTGCTAGGAT TACAGGCGTG AGCCACCATG CCCAGCCCCA TGTTAATGCT
```

Figure 110

```
TCTAAAGTTT GCCCTCACTT CTTTAGAAAT TCCTTCAGTA CATCCTTTAA GACTTCCTCT
AGTGAGTGTC TGCTGGTGGT AAACTCTCCC CTCTAAAAGT TGCTTTATTT CTCCTCAATT
CCTGAAGGAT ATTTTTGCTA GCAGCTATAT TCTTTTAGAT GTTGAACATA TCGGTACAAA
AGCTTCTGGT TTCCATGGTT GCTATTGAGA TGTTAGCTGT CGGTTTATCT TTCTCCCCTG
ACTATGTGTA CCTGTTTCTC TGTATCTGTC TACTTTTTGG GTTGCTCAAT TTATTGGCCT
TGGGCTTCAT TCTGCTGCTG CTTTTTTTTT TTTTTTTTTT TTGAGATGGA GTCTTCCTCT
GTTGCCCAGG CTGGAGTGCA GTGGTGCAAT CTTGGCTCAA TGCAACCTCT GCCTCTCGGT
TCAAGCGATT CTCCTGCCTC AGCCTACCGA GTAGCTGGGA TTACAGGCAC CTGCCAACAC
GCCAGGCTAA TTTTTGTATT TTTAGTAGAA ATAGGATTTC ACTATGTTGG CCAGGCTGGT
CTCAAACTCT TGACTTCAGG TGATCCACCC ACCTCAGTCT CCCAAAGTGC TAAGATTACA
GGCCTGAGCC ACCACGCCTG GCCACAATTT TTAAACTTTT TATTTTTACA GGCACCTGCC
AACATGCACA ACTAATTTTT GTATTTTTAG TAGAAACAGG ATTTCACTGT GTTGGCCAGG
CTGGTCTCAA ACTCTTGACC TCAGGTCATC CACCACCTTG GTCTCCCAAA GTGCTAGGAT
TACAGGCGGG AGCCACCATG CCTGGCCAAA ATTGTTAAAC TTTTTATTTT CTTCCTCAAG
AGGATGAGAA GAAAGGTCAA TTGTAAGCTT TAGAAGTCTT GCCCAATAGC CAATCTGAGA
ATATTCTCCG TAAACATTCA CCAGAGGCAG CCAGTGACCA TGGGATACTT TTGGTGAGAG
GAATTGATTG CTGGGGTCAG GAATGGGAGG AAAGCATACT TCTCATTAGA TACCTTGTTG
AACTTCGTAA ATTGTGTGCC AAATGCATGT CTTACCTAGA CTTCATAAAT TAATTTCTTT
AAAAATAATC AAAGACAATT TTTTAAAGAC TTATTTAATT TAAGGTGATT ATAAAACATC
CAGTATACTT TCACTATTAA AAAAGTAAGT ATTCCTGTCT GGGCTTGGTG GATCACACCT
GTAATCCCAG CACTCTGGGA GGCTGAGGTG GTCGGATCAT GAGGTCAAGA GATTGAGACC
ATCCTGGCCA ATATGATGAA ACCATGTCTC TCCTAAAAAT ACAAAAACTA GCTGGGCGTA
GTGGCGTGCC TGTAGTCCTA GTTACTCAGG AAGCTGAGGC AGGAGAATCG CTTGAACCCA
GGAGGCGGAG GTTGCAGTGA ACTGAGATCG TGCCACTGCA CTCCAGTGTG GCAACAGAGT
GAGACTCCAT CTTCAAAAAA AAAAAAAAGT ATTCCTAAAC AGCATATTAT CATGATATAT
TATTTTGTTT TGTAGGGTTT TGAACCTTGT CTAAAAGAA TTAAAATGTA TAAATTTCTT
CCTGCAATTT CCCTATTTCA CTAAGGGTCA TTCACATTGG TCATATAGAC ATAGCACATT
TTCACCACTA TATAGCAGCA TTTTGTACAA ATAGACTACA ATTTACTTAT TCTGCACTTA
TTTCTGTTTG TTTGTTTTGC TATGAAAAGC AATGTCATTA CATATATTCA TGCCCATAGC
TACAAGTTTA CATATTTCAG GTTTTCTGTA GGGTGGACAC CAGGGAGTTG AATTGTTCAA
CAGGACTTTA CATTCATCTT TAGTTTTATT GGCCAACACC AAATTGTTCT TCACAATGTT
TGAACTAAGT TGAAATTCCA CCTCCCCATC ACATTTAGTT TTGTCAACTT CATTTCTTCA
TTCATTAATT CATTCATTCA GTCTTTTGTT TATTTGTTTA TTGCCAGTCT GATAGGCGTA
TAGTGGTGCT TCATCATGGT TTTACTTTGC ATTTCTCTGA TTTTCTTTTT AAATTTTTAA
AAAATTATTT TTATGTAGAA ACAAGGTCTC GCTACATGGC CCAGGCTGGT CTTGAACTCC
TGGCTTCAAA TGATCCTCCC ACATTGGCCT TTCAAAGTAC CGAGATTGAT TATAGGCGTG
TGCCACTGTG GCCAGCTGAT TTCCCTGATT TCTGATGAGT TAACAATCTC TTCTTTCTCT
CTCTCTCTCT CTGTGTATAC AGGTACTCAC CATTCGTGCC TATTTCTGT AAAAATATGTG
GCTTTCCTCA TTTTTTTTTT TTTTTTTTT TTTGAGGCA GAGTCTCGCT CTGTTGCAGG
CTAGAGTGCA GTGGTGCGAT CTTGGCTCAC CACAACCTCC ACTTCCTGGG TTCGAGCAAT
TCTCCTGCCT CAGCCTTCAG AGTAGCTGGG ACTACAGGCG TGCACCACCA TGCCCAGCTA
ATTTTTGTAT TTTTAGTAGA GATTGGGTTT CACTATGTTG GCCAGACTGG TCTCAAACTC
CTGACTTTGT GATCTGCCCA CCTCAGCCTC CCAAAGTGCT GGGATTACAG GAGTGAGCCA
CTGCGCCCAG CCATCTTTCC TCATTTTTAT ACTAATTAGG CTTTTATCTT ACTTGTTTTT
TTTAATGTTT TTTGTACACT CTGAAGGCTG ATTTTTGTTA ATTGTATGTG TTGCATTTTT
TATGGTTTGT CTTATGCCTT TTGAAAGTAA AAGTTCTTAA TTTAAATATA GCCAACCTGT
AAATCATTTG TGAAAGTCTG TGGTTTAAGA GGTCTTGAAT AAGAAATTAT CCCATCATCA
TAAGTCATAA ATACTTTTTT GTTGTTGTTG AGACAGAATC TCATTTTGTT GTCCAGGCTG
GAGTGCAGTG GGTTGATCTC AGCTCACTGC AACCTCTGCC TCCTGGGTTC AGCAATTCTC
CTGCCTCAGC CTCCCAAGTA GCTGTGATAA TAAGCATGTG CCACCACACC AGTCTAATTT
TTGTATTTTT AGTGGAGACA GGATTTCATC ATGTTGGCCA GGCTGGTCTC AAACTCCTGA
CTTCAAGTGA TCCACCTGTC TCAGCCTCCC AAAGTGCTGG GATTATAGGT GTGAACCACC
ATGCCTGGCC CATAAATACA TTTTTATGTA TTTTCTTCTA AGTTGTTTT GTCTTTCACT
TTTTAGTTTT TAATTCACAT ATAATTACTA CTTGCTACTT ATAATTATCT GTAAGTAGTA
TGAGATGAGA AATAAATTCT ATTTCCCTCC TATGGATAAG CACAAACCTG CAGTATTAGC
ACAGTCTTAT GTCAGATTTT CTAAAATGAA TGGGTGTGTT TTCTAGGCTC TCTGTTCTGT
TTCATTATCT GTCTTTTCCT GCAACGATAT CATCTGCCTT AAAAACTCTA GCCTTGTGGT
ATTCCTCATT TTCAAGCAGA GCAAACCCCG TCACCTTGCT TTTCTCCTCC AGCATCGCTT
GTGCTATCCT GGACTAAGAC CTTCATATAG ACTGTTAGAA TCATCTAGCC AAGTTCCATT
```

Figure 11P

```
TTAAAAATCT ATGTTGGAGC TGGGCGCGGT GGCTCACGCC TGTAATCCCA GCACTTTGGG
AGGCTGAGGA GGGCAGATCA CTTGAGGTCA GGAGTTGGAG ACCAGCCTGA TGAAACCCCG
TCTCTACTAA AAATACAAAA ATTAGCTGGA CGTTGGGCAC TTGAATTCTA GCTACTCAGG
AGGCTGAGGC AGGAGAATCG CTTGAACCTG GCAGGCGGGG GGTGCAGTGA GCCGCGATCA
TGCCACTGTA CTCCAGCCTG GGTGACAGAG TGAGGCTCCA TCTCCAAAAA TAAATAAATA
AATAAAATAA AATATCTATG TTGGAAATTT TGTACAAATT TTATTAAATG TCTACATTAA
TTTGGAGAAA AATGACTTGA TTTTGATTAT CTATTCAATA TTTCTGTATT ATGAATAAGG
CAAAAAGAGA GGCAGAGAAT AGCATAAAAT AATAACTAAA ATTCCTGGGT AAACCACCTC
AAATCATTTC TTCATATGGC TCAATATTCT TTTGTGACAT GGCCTGAAAT ATATCCAGAC
AGAGAACTCT TCTCTTCAAT ACATTTCTTC TTTTAGGTAT TCATATTGAG TTTTCCTGTC
CATGAACATG GTATAAGAGA GTATATCCCT TCGGGAGGCC AAGGTGGGTG GATCACCTGA
GGTCAGGAGT TTGAGACGAG CCTGGCCAAC ATGGTAAAGT CCCATCTCTA CTAAAAACCC
AAGAATTATC CAGGTGTGGT GACACATGCC TGTAGTCCCA GCTACTCAGG ATGCTGAAGC
AGGAGAATTG CTTGAACCAA GGAGGCGGAG GTTGCAATGA GCCAAGGTCA TGCCATTGCA
CTCCAGCCTG GGTGAAGAGC GAGACTCCAT CTCAAAAAAA AAAAAAAAAA AAAAAAGAAA
ACGAGAATAT ATCCTTTCAT TTACTAGTTT TTCTTCAATT TCTTTCAAGA TAAAGGGCTT
ACCTATCTTC TGCTTTATTC ATAGTTACTT GATATTTTG TTTCTAATAA ATATGGTGTC
TGTCTATTTA CCTGCCTCTT ACCTGTTCAT TTCCAGTTTC AAAAATGATG TTGATATTTG
AATATTAACC TTAAATCTAG CACCTTGGTA AACACTATTA TTCATTCTAA TAATTATCAG
TAGATTATAT GTGTTTTTTA TTTATAAATC ATATTGTTTG AGTAGCATGC TTTGCTTCTT
CATTTATAAA ATTTACAACT TTTATTTCTT TTTAATAATT TTTTTCTTAT TCTCCTGGCT
AGGACTTCTA ACACAGTATT GAGTGGAAGT GCTGATCCTT GTTTAGTTTC ACATTTGAAA
AAAGATTGCT TTTACTATTT CACTGTTAAG TATAATATGC ACCATAGGCT TTCTGTGGAT
TCCTTTTATC CATTTAAGAA CATCTCTTAT TCCTAATTAG CTGAAGTTTT CTGCATGTTT
GTTTTCATCA TGAGTGGATT TTTTTACATC TATTGAAATC ATTTTACATA GAAGATATTT
CACACCTATT GAAATGGTCA TTTCACTTTT CCTTCTTTAA TATGTTAAGT TGGGCAAAAT
ATTAAAGTAT CACCTGTCAT TCTGCTTCAG CAAAAAGTAG TAGTGTCTTA GCAGTATTGG
TGAAAAGACA GCATCAAATA AAAAAGATGT AGAAGTAGGA CCCAGTAAAA ATCTAGCGCA
TGGGGCATTG TCACATGTAA GCAGACAGAA TGTGACACCA CCAAGGAGCA TCTGAAGGGC
TGGAGGCTGA AGGAAGACAT GAGTCACCCA GGCTCATGGA CACTTCAGAG AAATTAGGGA
GCAGGAAGAA GAAATAGGAT CAAAGACTAC GTATGTTGGT TGGAAAAGGA AGCTGATGGT
ATGGAGATGT TATTATTTAG GTCTCACATA AAAGATGTAG ATAAATAGGT AGATAGGTAG
ATAGATGATA GATAGAGAGA TAGATAGATA AATACATAGA TAGATAGATG ATAAATAGAT
GTTGTTATTT AGGCCTCACA TAAAGATGTA GACAGATTAG ACAGACAGAT GATAGATAGA
TAGATAGATA GATAGATAGA TAGATAGATA GACGATAGAT AGATAGATAG ATAATCTCAG
AAACAGAGAC ACAGTGATCT CAGTAAGATA GGCATATGCC AGGTGACAGA ATTCAGAGGG
GTCCCACTAC GTGAAAACAA TAGAACAACC TTCGAAAAGA AATTTAGTAC AAATAAGAGG
GCAGGCTTCC TTACATACAA GTTAGTAAAC TGGAAGAATC AGTTATCCTC AAACATTGGA
ATAGATCAAA AATAGTTGTT TATATTAATG AAGGTAGCTA AACATGAAGC TAAGTGAACC
TGTCTCTGAC CTAGTGTGGC AATCCCTGGG CAAGGGACAC TTGCTCCGCT CTTGTATCCT
TCACTGAATA TTCAGACTTT CAGTTAAGCA TCGGTGAATT TAGTTTTCAT CTCTTGTGAA
AACCTTGAGA GAGGTAATTC TCTCTGCTTT TCTTCTTTTC CCTTCCTTCA TTTTCTCAAA
CATTGCCTGT TTAAAATACG AAATTTTAAA AGATGGCCTT GTTCTCTTTT TTGTTGTTAT
TATTAAGTAC AGAGAAAGGA AGAACCACAA ATAGCAAAGG GCAACATATG GAATAGTTTA
GAAGTTCCGG GAGCACCCAT GAGGGCAACT GCAGAAGAGA ACATTCTATC CCCCGTTGCT
GCAGCTTTCA TTCCAGGTCT CCATGCATAT CAGATAGGGA AGGAACTCCG GGACAGCAGC
AGGGCCCATG CACATGTAAC CAATTGCTTT CTTTGCCTGT AGTAAAGTTC ACATTTTGAT
                                                 AccIII
                                                 ------
TGCTTCTCCA GATTATGTAG ATCCAGACAT ATTTTATGCA GGCATCCGGA TCTTTCTCTC
         >>.................EXON 8 .......................>
TGGGTAAGTA TAGTTCAGTT GTTTTCCTGT GTGAAGTCTC TGTAGCATTG ACTGAATGTA
>>>
TAAGGGGACG AAGAGACAGA AGCTTCCTAG CGTAAGAAAC ATACCAAGTG ACTCTTGCTA
GGGATCCACT CTCAGGTAAA AGAAGTGGGA TACCATCTGC ACAACAAATA ACACTGAGGG
CTAAGTATTT CAGTTAAGAG TGTTTGTTCC TAGGCAGTTC AGATCCATTT ATATTCACTT
TTCTTAGAAT CCTAGCTCAA TGACAGAAGA AGAAAAACAC AGTATGTCAC TCACACAGTT
CTATCACTTA CATCTACTTT TTCTTCTTGT TATTAAGGCA TGTAGAAGGC TGGGGAGTGT
```

Figure 11Q

```
AGTATAGAGT TGGATAGCAT CGAAGCTTTC TTCTAAAGTT CCTGGAAGAG CTACACTGTG
GTTTGAACGA ATGTGTCCCT CCAAAATTCA TATGTTAAAA CCTAATTGTG ATGGTGAGGT
ATTCGAAGGT GGGTTCTCTG GGAGGTGATT ATGTCTCCTC TGAGAGGAGA AGACAATCCC
CTGAGTGGAA CTAATGCCCT TATAAAGGGG CTGGAGGGAG TTCACTTGGC CCTTTTTGCT
CCTTTTTTCT TCCATTCCTT GTCCCTTCCA CTATGTGAGG ACACGGGAGT TGAGGCATTA
CCTTGGACGT GGAGACCAGG CCCTCACCAG ACACTGAACT TGCCAGCACC TTGATCTTGG
ACTTCCCAGC CTCCAGAACT GTGAGAAATA CATTTCTGTT ATGGGTAGTC CCCAACTCAA
TACAGTTTGA CTTACCATTT TTTGACTTTA TGTTGGTGCA AAAGCATACA TATTCAGTAG
AAACTACTTT GAGTACCCAT ACAACCATTC TGTTTTCAC ATTTGGTACA GTATTTAATA
AATTCCATAA CATATTCAAC ATGTTGACAT AAATAAGCTT TGCGTTAGGT GATTTTGCCC
AACTGTGGGC TAATGTAAGT GTTCTGAGCA CATTTAAGGG CAGCTAGGCT AAGCTAAGGT
GTTTGGTAGG TCAGATGTAT TAAATGCATT TTTTGTCTTA TGATATTTC AACTTACATT
GGGTTTATCA GGATGTAACC CACTGTGAAT TAAGGAATAT CTGTATTTAC AAATTACCCA
GTCTAATGTA TTTTGTTGTA GCAACAGGAA CAAACTAAAA CACTACCCCA AACCATTTT
TTCATATTTT CTGAGTACTC TTCTTTTGTC ACATGGCTTG AAATTTCTTC ACATAGAGAA
CTCTACTATT ATTTTATTTT ATTTTATTTT ATTTTATTTT TTGAGACAGA GTCTTGCTCT
TTTCACCCAG GCTGGAGTGC AGTGGTGCCA TCTTGGCTCA CGGCAACCTC TGCCTCCTGG
ATTCAAACTA CTCTCCTGCC TCAGCCTCCC GAGTAGCTGC GATTACAGGT GGCTGCCACC
AAGCCTGGCT AATTCTTGTA TTTTTAGTAG AGACGGAGTA TTGCCATGTT AGTCAGGCTG
GTCTCGAACT CCTGACCTCA GGTGATCTGC CCACCTTGGC CTCCCAAAAT GTTGGGATTA
CAGGCTTGAG CCACCACGTC TGGCTGATAA CTCTACTTTT AGATACTCTC TTTGCTTAAA
CAAATTAGCC ATTCCTTCCT TGACATGTTT TAATCAGATT GCCTTCCTAT TAACTTCGGA
AATTAAGAGT TTCTGCTATG TTTTTGTTTA ATTTTAAAC AGTGAAAAAT GAAAGGTGGA
GGCAATGGCT GGATGAGGTA AATATGTCAA ATAGATATCA TCTAGTGGGC CATCTTATTA
ACTAGGAGAC ACCTGAAGTG CTATCAATAG AAATAATCTG AAGCTGTGTC TGGATACAGC
AAGAGACATG CAAATGCTAA AAATCTACTA TATTACATTG GTGCAAGGAC AGAGTAGCAA
CACATACTAA GTATTTTCTC CAGATTGGGT GTGTTTGACG TGTGAAGCAC TTCAAACAGA
GTCCAGCCTG GGAGGGAGTG GGGATGGAAT CCTCCTTGTA GAGGGTACAG AGTGGAAGCA
AGAAGGTTTC CAAGATTGAG AGTAATGGGT GTATGGTTTA TGGGGGAAAG GGAAAACAAA
AAGAAGGGTG CAGAAATGGA GCTGGGAGTG TGTTTTAGTA TTTAGGCTTT CTCTGTATAC
CTTTGATAGG ATTAGAAAAA GAAAAATGGA CCATTTTTAA AAATTTCATG CTACCACATA
GCAGGCTTAT ACTATAGATG CAGAAACAGA CTGGGATTTA GGAAGCACCC CAATTCTGGA
AAATCCCTTT TTGCTTCACA TTGCTCTCTA AATCTGTATG TTTTCCCTTG TTACGTAACA
ATTTACCACA AATTTAGCAG CTTAAAACAA TATGCATTCA TTGTTTCACA ATTCTGTAAG
TCGGAATCAT AGGCAAGCTC AACTGACTTT TCCATTTAGG GTCGCAAAAG GCCGAAGTCA
ATTTATCTAT TGGGCTGGGC TCTTAACTGA AGATCTGGGG AAGAATTCCC TTCAAAACTC
ATTTAGGTTG TTGTCAGAAT TCAGTGTTTT GTGGTTCTAG AACTGAGATC TGTTTCCTTG
TTGGCTGTCA GACAGGAGCT GCTCTCAGCT TCTTGAGGCA TCCAGTATTC CTTATCATGT
GTTTTTTTTT TTCCATCTCA GCACTGGCAC TTTTTTTTTT TTTTTTTTTG AGACAGAGTC
TTGCTTTGTC ACCCAGGCTG GGGTGCAGTG GCACGATCTC GGCTCACCAC AACCTCCATC
TCCCGGGTTC AAGTGATTCT CCTGCCTCAG CCTCCCGAGT AGCTGGGATT ACAGGCACCC
GCCACCAGCC CGGCTGATTT TTGTATTTTT CATAGAGATG TGGTCTCACC ATGTTGGCCA
GGCTGGTCTT GAACTCCTGA CCTCAAGTGA TCCTCCCACT TCAGCCTCCC AAAGTGCTGA
GATTACAGGC ATGAGCCATC ATGCCCAGCC AGCACTGACA ATTCTAATCC TTCTAGCACT
TTGATTCCTT CTCACCTCTC CTTCTGCCTC TAGCCAGAGA AAACTCTCTG ATTTTAAAGG
TCTTATGTGA TTAGATTCAG CTTACCTAGG TAATTCAGGA TAACTCCCTA TGTCAAGGTC
AACTGATTAA TAACCTTAAT TACACCTGCA AAGTCCCCTT TGCCATAATA TATCATACTG
ACAGACATGC TATAGCATAA TACTAATAGT TCTAAGAATT ATGATAAGAA TCTTGGAAAA
CCATTTTTAG AATTATACCT ACCACAGTAT CCTTCAAGGG ATAAATTGAT TCTACTTCTT
CTCTATGTCA GAAGCATCTG ATGAGGATGA ACTATATATT CTGAAATCCC CATGATTAGA
TGTGTACTAG AAGGTGATTT TACTTTCATT AAAATAAATT CGGAGTCATT GACACATTTT
ATCTTTGATT TACATAAATG CCTCCGCTCT GTTTCTTACC CTCAAAATAT TTCCCATGTA
GCTAAGTGGC CAGTACCGAA TCCTACATGC ATTAATAAGT GTAGATGGAC AAAAATATCT
GGATTACTGA GAATTCCCAT TAGCATTGTC TAGAAAAATG TAAATTTGCT TTTTTGTTCT
TGATTTATCC TATTTTTGAT TTATTATTTA TATTTATTTA TTTATTTATT TATTTTTAGA
TGGAGGTCTC GCTTTGTCGC CCAGGCTGGA GCGCAATGGC GCAATCTTGG CTCACTGCAA
CCTCTGCCTC CCAGGTTCAA GCTTTCCTCC TGCCTCAGCC TCCCAAGTAG CTGGGACTAC
AGGCACCTGC CACAGTGCCC GGCTAATTTT TGTATTTTCA GTAGAGACAG GGTTTTGCCC
TGTGGGCCAG GCTGTTCTTG AACTCCTGAC CTCAGGTGAT CTGCCCACCT TGGTCCCCCA
```

Figure 11R

```
AAGTGCTGGG ATTACAGGCA TGAGCCACCA CACCTGGCCT TTTTGCTTAC TTTTTAAAAA
CATTTTTATT TAGGAGAATG GAGATATTTC ATATGTAGAT GACACATATT CATTCCCTTT
AGTTCCCACA CACATTCAAT TTCTTGAGGA AGTTAGCCTT TGCAAAAAAA AAAAAATGAT
CTCATTTTTT TTTCCCCACT AAAACTTCTC ATTTTCTTGG GGTTGCTAGA AAGTTGCTAC
AAGAAAGGCT AAAAATAATT GTGCCTACAG ATATTTGAAA GGAAAATAGT TCCTCTTTTT
TCACAGTAGC AGCTTGGACC TGAGAATGTA TGGGAGCAAT AATTGGGCTG CTCAAAGAAA
CACAATTTCC CTTCCTCAGA CTAGAATTAC CAACCTAGAG AACATGAGTT TTTAAAGTAG
ATGTGCTTCT TTTATCTTTT TGGACTTGTA TGCTGGTGTT TTCTCTGTCA CCTTCACTGT
GGAAATCCTC TTGAGGGTGA GGCACTGAAA GCAGATTGAT TAATGTCTCT TGGCCATTTG
AGACATTGGA TGGCTCTTTT AAGTTGGCCA CGTTCTTTCA AGAACTATGC TTGGGCTACA
TATTCTGGAT ATATAATACA TACTTGTAGG ATGTTATTTT TAAATCATTC ATTTATCACA
TATTTAGTGA GTGCCTACCC CATGTCAGTT CTAGGTGCTG AAATAGAGC AGTAAAACCA
ACCCTCAACT TGGCCCCTCT GGAGCTTACA TTTCAATGCG GTGGGTGGGG GGATGGACAA
TTAATACACA AGTAAATCTA ATAAAAGCGT CATACAATAT ACATTACAAT GGTAAGCACA
ATGAAGAAAT GGAAAGCTGG ATAGAGAGTA TTAGAGACTG TCGAATGTAG TGGCCAAATT
TTCCTGTTTA TTGTGGTCCA AGAGTGCCAC AGCCCTCTAT GACATTTGAG CAGACACCTG
GAGGAAGTGA GGGAGTGAGC CGCCAAGAAG GAATGGCAAG TGCAATAACC CTGAGGTGGG
AGCGTGTTGG TCGTGGTGGA AGAGCTGCAG GAAGCCAGCA GGGCCGCAAC ACTCAGGGA
GAATAAGAAA GAGTGAGGTG ACAGTAGAGA CCGGATCATG TAGAGCTTTG TCAGCTTCTT
TTCTGAGTGA GATGGACAAC ACGGACACGT TTTGAAAAGA ATAACAATGT GATCTGCCTT
CAGTTGCAAA TCATCTCTGT ATTGACTGAG TAGGAAATAA ACTCCAAGAA TAAAGACGGA
AACAGGGAAA ATATTTAAGA AGCGATCATT ACAATCCAGG GTGGTGGCTT GTACTAGGGT
ACAAGGGCTA AAGGTGTTGA GAAATGGTCA GATTCTGGAT ATATACTGAA ATCAAAGTTG
ATGGAAAGAT ATGAGTCAAA GATAATTTGC AGGTTTTGGG GTCCTGGTTC ACTGAAAGAA
CAGAGACATC ATTTACTCCA ATGAGGAAGA CTATAGGAGG AACAGGTTTA GCAAAGAAGA
AAGGAAATCA GGAGATCAGT TTGGGACAC GGTCATATCA AGTAGGCAGT TGGATGTATG
GGTCTGGAAT ATAGGGGAGT GGTCTAGCTA TCAGTGTAAA TAGCTTTTTA CATTTGTAAA
TAGTCAGGAT ATAGGCTTTT CTTTTTCTTT TTGTGAGACA CAGTCTTGCT CTTTCGCCCA
AACTGGAGTG CAATGGCACA ATCTCAGCTC ACTGCAACCT CTGCCTCTGG GTTCAAGCGA
TACTCCTGCC TCAGCCTCCC GAGTAGCTGG GACTACAGGT GTGCACCACC ATACCAGGCT
AATTTTTGTG TTTTTAATGG AAATGGGGTT TCACCATGTT GACCAGGCTG GTGTCAAACT

ClaI
           ------
CCTGACCTCA ATCGATCTCC CCGCCTGGGC CTCCCAAAGT GCTGGGATTA CAGGCATGAG
CCACCCCATC CAGCTGGGAT ATAGTTGTTT TCTAAATCTA TGAGGCTAGA GAAGACCATT
TGGGAATTGA GAGCAGTGAG CAGTCCACGG ACTGACCCTT TGAGAGTGCA ACATTTAGCA
GTACTCAAGA TGGGAAGGAG CTAGTGAAAA AGCCCAAAT GACTACATAA GACCATCAAC
CAGATTACAA AGAAAGACCC GAACATGTGT GCCCATATAT CACCCAACAG CAGTTATGTC
TTTCATGTTT CTTCCCCATA AAATGTTGTT CATCAACTTT ATTAGACTAG GGTCTTAACA
TTGGACAAAT CACAAAACCT CTCTGGAGCC TATTTTATTT TTCAACAGCT GTAGGAAGCA
AATACAAATT GGAAATCTAA GGCTCAGAAA GATTTGTACA AAGTTACACA GTAATGAAAG
GGGAGCCGGG ATTCCCACTC ACTCTAAAGA ATATGATAAA ATGGCTAGTA TTCACTGAAT
GCTTAACATG TTCCAGGCCC TGGGCAGGTA TTATTTTAAT TAGTTCTCAC AATAATCCAA
TAAGGGAGAT ACTAATTTAC TCAGATGAGA AAGCTGAGGC TCAGAGAGGT TAATGAACTA
AGCCAAGGCT CACTGTTAAT AAATAGCAAA GGTAAAATTA AATTCCATAT CTGCTTGAGA
TAGAGGCCTT GCTCCTAATA GCTGCAGCCT GTCAGGGCCT GGCAGCAGTA ACCTCTCCTT
TCCTCTTCCC ACCATTCCCC TGCACTGCTT TCTGTACCGC ATCTCTTTTC AGAGTGATGT
TGCCCCAATT GCGGAGGCCA CTGTGCTGTT TATCCAGTGA AAGCTGTAGC ACAGCCAACC
CAAAGCGTCC CCAGTGAAAA CAACCTGGCT CCTTACAGCA CTTCCAGCCT CAGAGCAGTA
TTTGAAAAAT ATCATGAACA GCAAACACAG CAGTCTGTCT GTGGCTTTTA TATGTGTATA
TGGTGTGTGT GTATGTCCCT TCTCTTGAGC AAAATAACTT TTAGAATTAT AGAAAAAAAA

PmeI
                         ---------
TGTGCAACAT CAATGTGGAT CTGCTGTTTA AACTCATAAC AGAGAAAGTA GCTTGTTTCT
GGCTATAGGA GGAAAAGACG ATATTCCTTA GTAAAAATGG AAATCCACAT ATGGGGTTCT
TGTAAAAATG AAGATAGAAA ATTGCAAGTT TGGGGATCAA GTTCTGGTTC TATCATCCTT
TAACAGTATG ACCCTGGAAC CTTAATTGCT TTGAGTCTTT GTTACTTTAT CTATGAAATG
```

Figure 11S

```
AAGTATTTAA AAAAACTCCA AAAATCTGTC CTGATGTACA CACAAGAGGT CAAATGAGAA
AATGAATGTG AAGATGCTTT ATAAACTATA CAGCATGGTA GGTGCAAATG TGACATGAAC
TTGTTTTGGA CACATTATAA AGTCACCCCC ACAAACTGTG ATTGTTCAAG ACTATGCAAA
GTCAGACACA GGAAAATAAG TAAAACAGAT GGAGGCATAA AGAGGGGGAA CTCAGAGAAA
ACAGTGAAGA ACAGGAATCA GGAAGACAAA GGAGAGGAAA GGTGGGGAGG AGAGGAGAAG
GAAAGGGGGA AGGGAATGGA GGAGAGGAGA ACAGCTGCTT CACAGAGCAT GGCCGGCAGC
CCAGTCCCAG CCTTTCTGCA TGTCCCTGAC TTCAGCCTCT GGCGAGGCAC AGGCTTACTC
TGTGCTTCCT GCTGTTACTC TTCTTATCCA TCCTTATTAT CAATACCTGT GGTCAACAAA
GTATTTGATA AAGGCATCCT CAAAGTCAGG TAACATCTGT ACGTTATAGA TTACAAAGTT
GAGTAATATC CAGAATTGGT AGTTTAACGT GATGACTTCT TAACAATTAT CACTGTTTCA
GGGAAGGGCA AAGGTGTGTG TGTGTGTGTG TTCATCTGTG TGTATCTGTG TATGTAATTG
TGGGTGTTTG TGTATATTTG TGAGGCTCTT TACTTGGCGG AGTTAAAAAG TATCTGCTCA
TCAAGGTTGA GATTAGCAAA GGAAGTGAAG ATTTTTCCAG AGCCCCTAAA ATGTGCCTTT
TGACCAACAC TGAGGACATC TTTATAACTG AGTATGTGCA ATAAATATGT CTTGGGACCT
GTGCCACAAA TTCCTCTCTA AATAGCCTTT ACCTCTCTGG AATAACCCTT TAGATGAGGA
AGAAAAGGGC TGTGATTTTA TAGCTTGTTA TGAAGCTGGA GTGAAGATGA TGCTTCAGTA
CTTACCCTAC AAAGATACCC CCAATCCCTC ACCCTAAAAT TACCATTGAA ATCATGTTCC
CTTTCTCATT CACTCTCAGT TTCCATGTCA GAAAATATAC CATTACCTCC CTGCACCCCT
TTCATCTCTC TCACTTTTCT CTTGCTTAGA TGGAAAGACA ACCCAGCAAT GCCTGCAGGG
                        >>...........EXON 9 ...............>
CTGATGTATG AAGGAGTTTC CAAGAGCCC CTGAAATACT CCGGCGGGAG TGCAGCTCAG
>.................EXON 9 ...............>
AGCACAGTGC TTCATGCCTT TGATGAGTTC TTAGGCATTC GTCATAGCAA GGAAAGTGGT
>................EXON 9 ..............>>
AAGTCAGACA TTTTGTTTTC CCTTGAGAGT AGAGGGAGGA AGAGGAGAGG TGTTTTTTTT
TTTTCCAATT GATAAAACCA AATATAAATT AAAATGTCAT GAAGTTTATA CTTCTCTAAG
TCAGCCAAGA AACTGCATGA CTGCCAATGT TTTTGTGTCA AGCCAATTAA TATTGGAATA
TCAGATGTCA GCTTGATCTT GGGTTTTACT TCCAAATCTT AAAATGTTGC TCTGTTTCCA
ACTGTTCACT ATCACTTTGG TTTGGATCTT TAGACACTAG CTTCCTTTTT CTGAAATGGG
GGAGAGATGT GGAGTTTGAA GGCTATGAGT CTGGGCCAGC TGGAAACAGG TCTGGGATCT
TCCAAGAAAG TCCTTCCCCA CAAAATGGTG CAACTTCTAG CCAAATCTAT TTATACCAGC
AGAGGGATCT ATCACCCTGG AAGCTTGAAA TTGTTCATTT TCTTACCTGC CAGGATCAAG
TTAAGTTTTT AACAGTTGCA AAAAGACACT TCATACTATG GAGTTTTCAA GTTGGATTAG
AAGAAAAAGA ATCACCAGAA CTTAGTGTCG TAGATTCAAG TCACTTCTCT AAAACTGTCA
TAATTTTTCA CGGATTTTGG CATTTGGTGA CATTAATGGT TGATTTACTT ACCATGCATA
ATATTAAACC CATAACGAAT TTCCTATAAA TATCTATTGA TTTGATTTTT AAATCACTTG
GCTTCAAGAG GCTATTACTA AAACAGTGAC TCATTCTTTA TCTTTTTTGC CTTCACGGGC
TTTATATAAC TTTCTCCTTT TCTTGTGCTC CCTCCAAAAC AAAGCACTGA GAAAACAAAA
TTCACCAGAG TATTCAGCTA GTCAGTTCAA GGGTTTGTGT TCTACATTTG AAGATATTCC
TTATAGCAGC TACCAACGGG ATACTTTGTT TACATTTGTT GTGTAGTAAA TATTTATATA
TTGGCAAACA AATCTAGTTC CAACTCTGTC ATCTGAGATG TTCTTACTTT GTTTCCTCTT
CTCCATCTCC TGTCAACTGT TAGAAATATA CATTTGAGTA CGTGAAGTCT GCAAACAAAA
GGGCCAAGGT AGATTTGAGT TAGAACACCA GCAACAGTTT CTGGTGCATT CTTGTCTGAA
AAAGCAGAGA AGATTGGGCA CCGTGGGTCA TGCCTGTAAT CCCAAAATTT GGAAGTCTG
AGGCAGGTGG ATCGCTTGAG CCCAGGAGTT CAAGACAAGC CTGGGCAACA TAGCAAGAAC
CCGTCTCTAC TAAAAGGAAT ACAAAAAAAT ATTAGCTGGG TGTGGTGGCG CACACCTGTA
GTTTCAGCTA CTCAGAAGAC TGAGGTGGGA GGATCACTTG AACTCAGGGG CAGAGGTGGC
AGTAAGCTGA GATCACACCA CTGCACTCCA GCCTGGGCAA CAGAGCAAGA TCTCATCTAG
AGAAAAAAAA AATAAAAAAG AAGAAGAAGC AGACGAGCTC TGCTATATTT CCATGTGGAG
CTATGACGTT ATGCTGTATT GTTTCTTTCA GGTGACTTTC TGTACAGAAT GAGGGATTAC
                        >>..........EXON10 ..........>
ATGCCTCCTT CCCATAAGGC CTTCATAGAA GACATCCACT CAGCACCTTC CCTGAGGGAC
>.................EXON 10 ..............>
TACATCCTGT CATCTGGACA GGACCACTTG CTGACAGCTT ATAACCAGTG TGTGCAGGCC
>.................EXON 10 ..............>
CTGGCAGAGC TGCGGAGCTA TCACATCACC ATGGTCACCA AATACCTCAT CACAGCTGCA
>.................EXON 10 ..............>
GCCAAGGCAA AGCATGGGAA GCCAAACCAT CTCCCAGGGC CTCCTCAGGC TTTAAAAGAC
>.................EXON 10 ..............>
```

Figure 11T

```
                                                                    DrdI
                                                                 ---------
---
AGGGGCACAG GTGGAACCGC AGTTATGAGC TTTCTTAAGA GTGTCAGGGA TAAGACCTTG
>.............................EXON    ............................>
GAGTCAATCC TTCACCCACG TGGTTAG
>..........EXON   ..........>>
```

Figure 11U

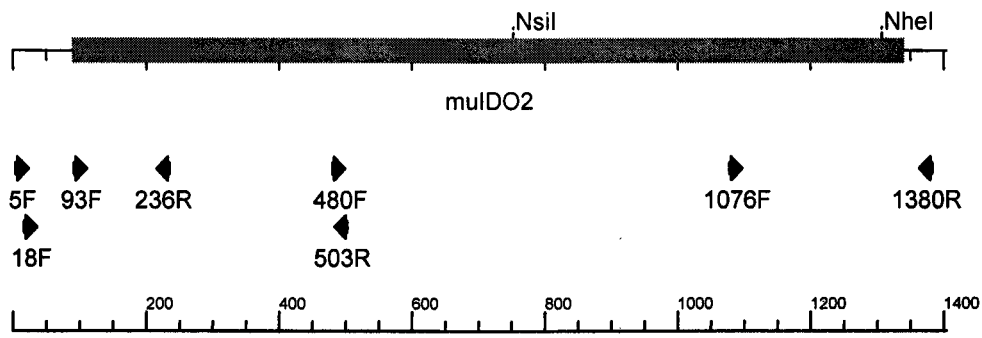

muIDO2 mRNA  (1402 bps)

Primers

| | |
|---|---|
| mF480A | 5' ACTCTGACCTGGTGCTGACAAACT |
| mR1380A | 5' TGCAGGATGTGAACCTCTAACGCT |
| mF93B | 5' TGGAGCCTCAAAGTCAGAGCATGA |
| mR503B | 5' AGTTTGTCAGCACCAGGTCAGAGT |
| mF1076C | 5' TGCCTGATGGCCTATAACCAGTGT |
| mR1380C | 5' TGCAGGATGTGAACCTCTAACGCT |
| mF18D | 5' AACCACACAGAAGACACAGCTGGA |
| mR236DE | 5' TGAGGGCAATTTCCATCCAAGGCT |
| mF5E | 5' ACCGCACAAGTACAACCACACAGA |
| MUIDO-2-L898 | 5' AGCCTTATGGGAAGGCGGCATG |
| MUIDO-2-L430 | 5' ACTGATTTCCAACGGTCCTTC |
| MUIDO-2-L160 | 5' TCGGAGCTGGCGGTTCTCGAT |
| MUIDO-2-U313 | 5' AAGGTGCTGCCAAGATCTC |
| MUIDO-2-U820 | 5' CTTCATGCCTTCGATGAG |

Figure 12A

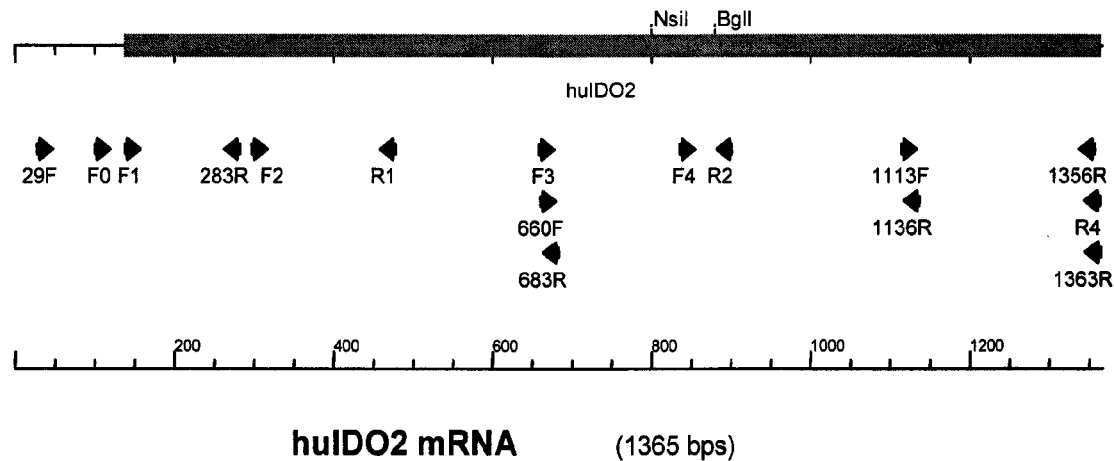

Human IDO2 Primers

| | |
|---|---|
| hF660B | 5'AGAGAAAGAAGCAGTGCCTGGGAT |
| hR1136B | 5'TAAGCTGTCAGCAAGTGGTCCTGT |
| hF29C | 5'TGAGACACTGCGCAACTAACTGGA |
| hR683C | 5'ATCCCAGGCACTGCTTCTTTCTCT |
| hF1113D | 5'ACAGGACCACTTGCTGACAGCTTA |
| hR1356D | 5'ACGTGGGTGAAGGATTGACTCCAA |
| hR283E | 5'TGTTGGCAATTTCCATCCAAGGC |
| hR1363F | 5'AACCACGTGGGTGAAGGATTGACT |
| HUIDO2F0 | TTCAGTGACACTTTCCATGCAG |
| HuIDO2F1 | ATGGAGCCCCACAGACCGAATG |
| HuIDO2R1 | GAAGGGCAAGATTCCTTGGCAG |
| HUIDO2F2 | ATTGATGCTCACCAGCTTCAAG |
| HuIDO2R2 | CTTCATACATCAGCCCTGCAGG |
| HuIDO2F3 | GTAGAGAAAGAAGCAGTGCCTG |
| HuIDO2F4 | GGCATCCGGATCTTTCTCTCTG |
| HuIDO2R4 | CTAACCACGTGGGTGAAGGATTG |

Figure 12B

Mouse IDO1 primers

| | | |
|---|---|---|
| MUIDO-12-U1140 | GGTACTGCCATGCTGAGC | 62 |
| MUIDO-1-L157 | AAGCTGCCCGTTCTCAATCAG | 67 |
| MUIDO-1-L433 | CTCGTATGTCATGGGCCCATTG | 70 |
| MUIDO-1-L900 | GAAGTTCCGGTGGGCTGGAGGC | 75 |
| MUIDO-1-u315 | GGTGCTGCCCCGCAATAATGC | 74 |
| MUIDO-1-U822 | CCAGAGTCTTGATGTCCTTC | 59 |
| MUIDO-1-U1120 | CCTCAAATGTGGAAAGCAGAG | 63 |

Additional cloning primers

| | |
|---|---|
| Ido2 5'KpnATG | ATCCGGTACCATGGAGCCTCAAAGTCAG |
| Ido2 5' SacI | GTTGAGCTCTCCAGGAACTTGGGA |
| Ido2 5'EcorI | AGTGTTGAATTCCTACAGGAAATGAGG |
| Ido2 5'HinDIII | CTGAAAGCTTATAACCAGTGTGTGGAG |
| Ido2 3'BsrGI | CATCCTGTACACGTGAGCTCG |
| Ido2 3' SacI | TGGAGAGCTCAACAAAAGGAATGG |
| Ido2 3'EcorI | CTGTAGGAATTCAACACTTTCCTTGCAATG |
| Ido2 3'HinDIII | TATAAGCTTTCAGGCAGTCCCCAG |
| 5'UTR mu 1 | GAAGACACAGCTGGAAAGCTC |
| 5'UTR mu 2 | CCATGCTGACCTCCAGGCTC |

IDO

| | |
|---|---|
| Ido 5'KpnATG | ATCCGGTACCATGGCACTCAGTAAAATA |
| Ido 5'BsrGI | GAAGTGTACAAGCTGCCCACACTG |
| Ido 5' NsiI | GAGGATGCATGACTTTGTGGAC |
| Ido 3'BsrGI | AGCTTGTACACTTCTTCTCGAAG |
| Ido 3' NsiI | GTCATGCATCCTCTTAAAAATAAC |

The Universal 3' Primer for pcDNA3,1/-V5his-TOPO

| | |
|---|---|
| TOPO 3' NheI | GTCGCGCTAGCAAACTCAATGGTGATGGTGATG |

Figure 12C

ATGTTGCATTTTCATTATTATG*ATACTTCAAACAAAATAATGGAGCCCCACAG
ACCGAATGTGAAGACAGCAGTGCCATTGTCTTTGGAAAGCTATCACATATCT
GAAGAGTATGGCTTTCTTCTTCCAGATTCTCTG*AAAGAACTTCCAGATCATTA
TAGGCCTTGGATGGAAATTGCCAACAAACTTCCTCAATTGATTGATGCTCACC
AGCTTCAAGCTCATGTGGACAAG*ATGCCCTGCTGAGCTGCCAGTTCCTGAA
GGGTCACCGGGAGCAGCGCCTGGCCCACCTGGTCCTGAGCTTCCTCACCATG
GGTTATGTCTGGCAGGAAGGAGAGGCGC*AGCCTGCAGAG*GTCCTGCCAAGG
AATCTTGCCCTTCCATTTGTCGAAGTCTCCAGGAACTTGGGGCTCCCTCCTAT
CCTGGTCCACTCAGACTTGGTGCTGACGAACTGGACCAAAAAAGATCCAGAC
GGGTTCCTGGAAATTGGG*AACCTGGAGACCATCATCTCATTTCCTGGGGGAG
AGAGCCTGCATGGTTTTATACTGGTGACTGCTTTGGTAGAGAAAGAAGCAGT
GCCTGGGATAAAG*GCTCTTGTTCAGGCCACGAATGCTATCTTGCAGCCCAAC
CAGGAGGCCCTGCTCCAAGCCCTGCAGCGACTGAGACTGTCTATTCAGGACA
TCACCAAAACCTTAGGACAGATGCAT*GATTATGTAGATCCAGACATATTTTAT
GCAGGCATCCGGATCTTTCTCTCTGGG*TGGAAAGACAACCCAGCAATGCCTG
CAGGGCTGATGTATGAAGGAGTTTCCCAAGAGCCCCTGAAATACTCCGGCGG
GAGTGCAGCTCAGAGCACAGTGCTTCATGCCTTTGATGAGTTCTTAGGCATTC
GTCATAGCAAGGAAAGTGGT*GACTTTCTGTACAGAATGAGGGATTACATGCC
TCCTTCCCATAAGGCCTTCATAGAAGACATCCACTCAGCACCTTCCCTGAGGG
ACTACATCCTGTCATCTGGACAGGACCACTTGCTGACAGCTTATAACCAGTGT
GTGCAGGCCCTGGCAGAGCTGCGGAGCTATCACATCACCATGGTCACCAAAT
ACCTCATCACAGCTGCAGCCAAGGCAAAGCATGGGAAGCCAAACCATCTCCC
AGGGCCTCCTCAGGCTTTAAAAGACAGGGGCACAGGTGGAACCGCAGTTATG
AGCTTTCTTAAGAGTGTCAGGGATAAGACCTTGGAGTCAATCCTTCACCCACG
TGGTTAGGAT

Figure 14

←------6665 bases to the end of ID01 coding region--------------
CCCTGGCCTT GGAAGATGCC CTAGAGACGC TGAGGTGGTT GTACTTTTGC CATAGGAGTG
GCAGCCAGAG AACTGAGCCC AATGAATGCA AAGGCTGGTG CCTGGAAATA TTGTGACTTT
GCCACAGAAA GAAGATGGAG AATTTTAAAG TTGGAAATCT GCCTGGTAAG GGATCATTTG
CTGGTGTCTG CAAAGTTGAG TCCATACACA CTGGTTTGGA AATTTCAGTC CAGATGATAG
                                                                                     >>..Exon a...>
TTAAGAAAGC AGTAAGAATA CAGAGAGTCC ACAATGAGAT GAAAATGCAC TGCCAGTTGA
>.........................Exon 1a..............................>
AACATCCTCC TACACTGGAG CTTTATAAAT ATTTTAAAGA CAAGGATTGG ATTAGATTTG
>.........................Exon 1a..............................>
ACATTAGAAA TGTACCATAA TACAGAAGGC AATGGACACC TAAAGAACAG AATGAAAACC
>.........................Exon 1a..............................>
TTCTTAGGAA ATGAAGCTTG ACACTTCACC CACCAGGCCA CCACAAGAAT GTTGCATTTT
                                                                                     >>.ATG-ORF..>
>.........................Exon 1a..............................>
CATTATTATG GTAAGTACAC TGGTAACTTC TTTTCTAACC TCGTATGCAT AATGTAAACA
>........>>
>........>>
TCAAGACTGA CAATTTGGGG CTAGCAACTC AATTGGAAAA TCACTGTTCT CTATTGTAAA
ATTCCTAATT ATGTTTCCCT AGAAATTGCA AAGTGCACAT GTACTTGCAT TTAATGTTTG NcoI
  ------
GTCCATGGGC TGAATGCTTT GTGCATTACT TTTCTGGTTG TTGTTGTTGT TGTTGTTGTT
GTTGTTGTTG TTGTTGTTTT GAGACAGAGT CTCACTCTGT TGCCAGGCTG GAGTGCAGTG
GCATGATCTC GGCTCACTGC AACCTCTGCC TCCCAGGTTC AAGCAATTCT TCTGCCACAG
CCTTCCAAGT AACTGGGATT ACAGGCGCTC ACCACCACAC CCTGCTAATT TTTGTACTTT
TAGTAGAGAC GGGGTTTCAC CATGTTGGCC AGGCTGGCCT CAAACTCCTG ACCTCAAGTG
ATCCACCTGC TTTGACCTCC CAAAATGCTG GGATTACAGG CATGAGCCAC CTTGCCCAGC
CTGTGCATTA CTTTTGAGGA CACATTTGAC AATGGCACAG TCAAGAACAC CACATAAAGT
AGTATTGGCA GATTATGAAA TAGCAATTGT TTTGGAAGAC AGCAAAACCT GAAGTATTTT
CAGACATGTA CATTATGAAG TATTATACCT TCTTTAACTA TGTGCAAGTT AAAATCAGTC
ATAACTGAAA ATCAAAAGGG CAATAATGAA CATACTTCAT CCAGAAGAGG TATCCACAAA
ACTTCTGAAA GAGGTCTTAG TATATCCAGG GATGGAGATA TTATTACAAT GTATTATCCA
AATGATGGAA GTTTTCTCTT GCTGATAGAA TGCATCCACC TACTAACATC AGTAAGTACA
GGTTTAACAA TTTACCAGAA ATGTACTGGA GGAAATATGA ATATGCTTCC AGATTTATTC
TACCTAAAGG ATCTGGCTCT ATTTTACAAG GTCATCTATT TTACAAGGTA CTGTAGATGC
ATTTTGATGA AAAAAATTAC CCTGCTATTG ATTTTGAGGT CTGGTATTAT GATAGAGCAA
AAACTATCCA AAAGAGATTT AATTCAAGTC ATTGCAAAAT CTTGGAAAAT GTGTGAGAAA
TCTTACACAT GGAAAGGAGG AAGTAAAGAT GGTAGCTTAA ACATGTGTTC CACTGTGAAC
AATTCTCTGC AAACCCACCC CCAAAAGTCA AGGAGGCTGA CAGGCTGAAG AAAGAGGCTG
TCAAATCTAG TTTCTCAGAA AAAGAAAAAT TAATAGGGAC TTAAGAACAG AAGCCATATA
TCTGCCCTGA GATGAGCTGG TGGATCCTCA CACTGTTACC CCCAGACCCA GGGCTTATAT
ACCACAGGGA AAGACAATTG CAGTAATTTG CTTAACGGCA GGATTTACGG CAAGTACATG
CTCTTAAGAG TAGATTAAGT AGTAACCTTA GAGGCATTCC TAGAACTGGA GTTAATCAGA
AGTCAACACA GTGGATTAGC ATCCAAGATG GAGTTGCTTT AGCCTCCACA AAGAGAAAAT
GAAGATAAAT TTGGTCCATG CTAATTAGGG GGTGTTCCAT TTGTTTGAAA CTGAAATCTA
TAATTTCCAA AGAAGAAAAT AAACGTGGAA GTCGTCCTTC CTTTTTGGTA TGCATAGACA
ATCTGGCAGT GTTAGGCCCC TAAGGCCTTA TCACCTCCTC CTTCTGTGGG TCAAACTTTA
CAGTGAGAGG AAAGACATCT TTTAAAAGAA GAATAATCAT GACTAGTTTA ATCATGACTA
GTTCATCTTC CCTGCAATAG ATACCCATAT TTAACATACC TATTGTACAA AGAATATGAT
TGCACAGCTA CAACTTTGGG ACAAACTCCT TTTCTGCCGC TTTCAATGAT CGTCTTCCAA
AATCAGAACA GCTTTTGAAT TTTATTTTGT GAAAAATGTC GTTTGAGTGA CACAGTAAAC
TCTGTGGAGC TCTGTGGATA CAGTTGAATG ATGGCTCCCA GTTTATCATG CAGGTGGGAT
TATATTCCAA CAGTTATGTT TCACAGAAAG GCAAAATAAC CAGGTACGGA AAAAATGAAA
AATTTGCAGC TTACATCAAA CAGAAATTGC AGTGTCTTTC ATCTCTTTAA AGTTTTCTAA
TCAAAATTCT AGTTTTCATC AATTAAAACT TTATTTAGGT AGATACATTT AATAAGTAAC
TTTTTGTTGG CTTAAAGGGA ATGAACTTTA TGTAATGTAA CTGTCTATTT CAGGAAGCTT

Figure 15A

```
                                                                AhdI
                                                              -----------
TTCTATGAGA ATTTAAAACT ACACCAAAAT ATCTTCTTTT TTTTTTTTTT GAGACAAGGT
GTCACATTGT CTCTCAGGCT GGAGTGCAGT GGTGTGATCC TAGCTCACTG TAGCCTTGAA
TTCCTGGGCT CAACTGATCC TGCTACCTCA ACCCCCACG  TAGCTAGGAC TACAGGCCTG
CACCACCACA TCTGGCTAAT TTTTTATATT TTTGTAGAGA AATGGTCTGG CTACGTTGCC
CAGGCTGGTC CCAAACTCCT GGCCTCAGGT GATCCTCCTG CGTCAACCTC CCAAAGTGTT
GGGATTACAG GTGTGAGCAA ACCTGCCATC TCAAACATG  TGTATTTTAA TGAGACAACA
AAGATCAAGG GAACTTTAGT CCTTACAATG TAATGATCAA AAAAGTGAAA TAGATAATCA

AccI
           ------
ACATAACATT GCTTGTAGAC CATGCAAACA ATCTTATTGC ATTTGTATAT TTGTAATGAA
CTGTTTTATA ATAACAAAAT GTAAAATGTG TATTTTATTT GTCCTTTTAT TGTTTTCCTA

SwaI
                                                     --------
CTTCTTAGAC ATGTTAAGAA CTATGGAAAA AGATATGGGA GTTTGTGAAA ATTTAAATAA
TTCATATTTA TATTACAAGA AACAGATATT AGAATATGTT TGTTTATAT  TTCTTTTGTA
GCAGAATTTT CTAGCCAGGC ATTGTGGCTT ACACCTGTAA TTCCAGCACT TTGGGAGGCT
GAGGTGGGAC AATCACTTAA GCCCAAGAGT TTGAAATCAG TGAGGGCAAC ATAGTGAGAC
TCTATCTCTA CAAAAAATTC TCTATCTATA TCTATATAAA GGAATTTTGT GAGGAAAACT
ATATATTTTG TATATAAATG AATTTATCA  GGAAATATAT CTGTAAATGA ATTTTATAAA
ATATAGCATC ACTTTATCCT TGATTTATTT CATTTAATAA TTATTTTAAA GTAATATACT
AATAAACTCA TTTTAAAAAC TGCTATGACC ATAAAACTAT TAGAGATAAC ATAAGAGAAA
ATCTAGGTGA CCTTGGGTTT GGAGATAACT TTTTATATAT AACACCAAAG GCGCAATCAA
TGAAAAAAAA TGACAAGCTC TATATCACAT ATCAATATTA AAATGTGATC TGTGAAAGGC
ATCGTCAAGA GAACAAAAAG ACAAGCCACA GACTGGGAGA AAATATTTGC AAAAGACATA
TGTGATAAAA GACAATTATC AAAATATACA AATAATTCTT AAAACTCAAA AATAAGAAAA
TGAACAACTC AGTTAAATAA TGGGCAAAAG ATCTCAACAG AAACCCCATC AAAGAAGAAA
CACAGTGGCA AGCATATGAA AATATGATCT ACATCATATG CCATTAGGAA ATTGCAAATT
AAAACAATGA GATACCACTA CATTTCTACA TTGGTGAAAA TTCCAAGTAC TGACAGCACT
CTCAGTGCTG GTGAGGATAT GGTGCAGTAG AAATCCACAC TCATGCCGGG CACAGTGGCT
CATGCCTGTA ATCCCAGCAC TTTGGGAGGC TGAGGCGGGT GGATCACCAG GTCAGGAGTT
TGAGATCAGC CTGACCAACA TGGTGAAACC CCGGCTCTAC TAAAAATACA AAAATTAGCC
CGGTGTGGTG GCGGGCGCCT GCTACTCGGG AGTCTGAGGC AGGAGAATCG CTTGAACCCA
GGAGGTGGAG GTTGCAGTGA GCCGAGATGG CGCCACTGCA CTCTAGCCTG GGCGACAGAG
CAAGACTCCA TCTCAAAAAA AAAAAAAAAA AAAAGAGGCC AGGAGTGGTG GCTCACACCT
GTAATCCCAG CACTTTGGGA GACTGAGGTA GGCGGATCAC TTGAGGTCAG GAGTTGGAGA
CCAGCCTTGC CAACATGACA AAACCCTGTC TCTACTAAAA CCACAAAAAT TAGCCAGGAG
TATTGGCACA TGCCTGTAGT CCCAGTTACT CGGGAGGCTG AGACAGGAGA ATTTCTTGAA
CCCGGGAGGC GGAGGCTGCA GTGAGCCGAT ATCGCACCAC TGTACTCCAG CCTGAACGAC
AGGGCGAGAC TCTGTCTCAA AAAAAAAAA  AAAAAAAAAA AAAAGGAAAG AAAGAAAGAA

SnaBI
                                   -------
AGAAAAAAGA AAATTCCGTG ATTGCAGTCT TTACGTATTT ATTTGTTATT AAGTACAGTA
AATAAAGAA  GGATAGATGT CATGGAAAAT GTCACGAAAA TAAAAGAGTT AAAAAAAAAA

DrdI
                                                    -------------
AAAAGTAGGC TGCAATGCCA GATGCCTGAA AAGTTAATCA ACGAAAGGAC TTAAATGTCC
CCATTGAATT TAGGAACAAA GAAGTAATTA ATGAACTGGG CAAAAACACT CAATGTACCA
GCGTTATCGA TTTAGAAACT GAAACTAAGT ATATCTGATG TTGCTTTTAG GAAACAAGTA
AATGAGGTCC TAAAAAGTTA AACTGTGACC ATATTTTCTT TCCTTTTTCT AATTTCTCCT
TGGGCCATTT CCAAAAAGCC CTAATACCCC GACTGATAGA AATGGATACC TTGCTGTGCA
CTGGTACTAC TGTGATTCAT GGAAGCTGA  TCATGCAACC CAAGACGCCA AAATTCCCAG
CCTTACTGTT ACGAAGAAA  GTTTCTAAGC ACAATTGTCT CTAGCCAACT TCCTCTTAGT
AAGAAAGAGG CCAGGCAGGG CTTCATGCAG GGTACAGCCC TGAGTTTCTT ACTGCGTGGT
```

Figure 15B

```
                                                      BsaWI
                                                      ------
AAGTTTCTGG GGCTGGGAGT AAAGCAGCGT GACCGAAAGC AGTACAAAGT TCTACCGGAC
ACGCAGATCC CGGTCCTACA AATATGAGGT CCATAATGAG ACTGAGATAT CATTCATCCA
ACAAATATTT ATTGAATACC AAACATTGGG CTTACGGCTA AAGGAAAATA CAAAGTTGTG
TTGGATATGG GTTCTGTTTT CAAGGAGCTT ATAATCTAAT AGGAAAGATG AGGTTACTAC
ATTAGTAGCA ATCAGACCAG ATAGAACTGG AAGTGTGATG TAAATGAGGT ACAGATTGAT
TGTAGAATTT TGCAGAAAGA AACAATTCT GAAGAAATGT TCATGGAAGT ATTAGCAGTT
GAGATGTATC TTAAAAGATA AGTGGGGTTC CTGTTGGAAA CATTCAAAAC TCTCTCTTCT
AGCTATTTTA AAATACGCAA TATATTATTA ACTATGGTCA CCTTACTGTG CTATAGAACA
CTAGAACTTA TTCCTACTAT CTAACTATAA TTTTGTACCC ACTAACCAAC CTCTCCCTGT
CCCTCCTCCC CCTATTCATC CCACCCTCTG GTAACCACTG TTCTACTCTC TGCTTCCCAA
AACAAAGAAA TGATCACTGT TTCGGTGATG GAGATGTCAA TTACCCTGAT TTGATCATTA
CACATTGCAT ACATGTATAG AAATATCACA TGCAACTCTT AAGTATATAC CATTCTTATG
TACCAAATAC AAATAAAATT GAAAAAAAAA AAAAACTTTG GCTGGGCGCG GTAGGTCATG
CCAGCACTTT GGGAGGCTGA GGCAGGCGGA TCACCTGAGG TCAGGAGTTC CAGACCAGCC
TGGCCAACAT GGTGAAACCC AATCTCTTCT AAAAATACA AAAATTAGCT TGGTGTGGTG

PspOMI
------
ApaI
------
GCAGGGGCCC GTAATCCCAG CTACTCAGGA GGCTGAGGCA GGAGAAATGC TTGAACCTGG
AAGGCAGAGG CTACAGTGAG CCGAGATCAT GCCACTGCAC TTCAGCCTGG GTGACAAAGC
AAGACTCCAT CTCAAAAAA AAAAAAAAA AGCCTCCTGA GTAACTGGGA CTACAGGCAT
GCGACAATAC TCCCGGCTCT CTTTTTAAAA ATGAGAAGTA GAAGTAGTGG TGACTGTCAA
GAAAGTATTT TGGAAAAATA CTATGAATAA CCAGACCAAA GAAACCAAAT ACCAGTTGTT
TCAGGAGCAG TAAATCATTT TTGAGGGCTT GAGCAAAGGT CTTGCTAGAA AGGTGCTTAG
GGGTCAGATT TTGGACATAA TGCCAGGCCA AGAAAATTTG CACTTTATTT CATTAACAAT
GAGGAGCTCT TGAAAGTTTT ATTGGCAGGA CCTAAGATAG TTACAGACCC ACAAGTAACA
TGGGTCTAGA CCTTGGGAAC AAGAAAAGTC AAGATCGAGT ATGCAGACTT GGGAACCGAG
TATAACTAAT GGTTAAGATT AAATAAAAAT ACATAAGAAC ACTGAGATAG AGAAATGGCT
CATTAATGCT GCAAATGTCT GCATGTTTAG GGATGAAATA GAAAAGAAG TCAGAAAAAT
ACAGTTCAAA CAATAGGAAA GAAACCAGA AATGCATGAT TCTAAGAAAT GAATGGGTGG
ACATGGTGGC TCACATCTGT AATCCCAGCA CTTTGGGAGG CCGAGGCAGA AGGATAGCTA
CAGCCCAGGA GTTCAAGACC ACCCAGAGCA ACACAGCAAA ACCCCATCTC TACAAAAAAC
AAAAATAAAA ATTAGCCAAG CATGGTGGTA CACACCTGTA GTCCCAGCTA CTCACTCAAC
AGGCTGAGGC AGAAGGATCA CTTGAGCCCA GGAGGTGAAG GATACAGTAA GCTATGATTG
CACCATTGCA CTCCAGCCTG GCTGAGAGAA TGAGAGCTTG TTTCCAAAAA TAAAAAATAA
GAAAGAATTT TTAGAATGAG AGGAAAACAA CATGAAACAT GAGAAAATA ACATTCCCTG
TTATATGGTA GGTGCTTCGC TTATAGTTTC TCATTAATTC ATCATGTAAT GTCTCTGGGA
TAAACATTAT GGATTTCCTG CAGAAACAGA AGCTCAGAAT TTTATGCCAG GTGTTGAAAG
GCCATGTAGC TAATAGATGA TAGAACACAG ACTCACACTC TGGTAGTCCT GAGTTAACAG
TAGAAAAGTC CTGGGCTGGG CGTGGTGGTT CACGCCTGTA ATCCCAGCAT TTTGGGAGGT
TGAGGCAGGC AGATCACCAG AGGTCAGGAG TTTGAGACCA GCCTGGCCAA CATGACTAAA
GCCTGTCTCT ACCAAAACCA CAATTACCCA GCGTGGTGGC GGGCACTTAT AGTACCAACT
ACTCAGGAGG CTGAGGCAGA AGAATTGCTT GAACCTGGGA GGTAGAGGTT TCAGTGAGGC
AAGATCAAGC CACGGCACTC CAGCCTGGGT GACAGAATGA GACTCTGTAT AACAAACAAA
CAAACAAAAT CAGTAAGAAA GTCCCAGACT AAGAGGCATC AAATCAGGAT TCTACTCCAA
CTCTGATGCC AGCTTCCAGG AATACACTTG ATAAGTTGTT TCATTCCCAT AAATCTTGGG
TGATTCGTGT TTAATGAGAG CATTGAACTG AATCATTTAT TCTATGACTC AGTTCTAATA
TTTCACAATT CTATGGTTGT ATAATATTAC AGGAAATTCT TGAGAAGGTG CAGAGGGAAT
GGATGAAAAA AACCACATGA CTAACATAAA AAATAATGGG GCCATCTTTT CATTTGAGAT
TGAAGGAAAG AACGAGAGGA CAATTAAACA TGCAGAGTCT GAGAACTTGC ATTTAGGAGG
CATAAGATGC TGAACTGCAA AATTGGTTAG ATATTGGGCT GAAGAGAATT GAGAATTTTT
TAATAATAAA AACTCTTGGC AGGGCGCAGT GGCTCACGCC TGTAATCCCA GCAGTTTGGG
AGGCTGAGGT GGGTGGATCA CTTGAGGTCA GGAGTTTGAG ACCAGCGTGA CTAACGTGGG
GAAACCCCGT CTTTAAGAAA AATGCAAAAA ATATTAGCTG GGTGTGGTGG TACAAGCCTG
```

Figure 15C

PmlI
---

```
TAATCCCAGC TACTTGAGAG GCTTAGGCAG GAGGATCACG TGAGCCCAGG AGGTGGAGGT
TGCAGTAAGC CGAGATTGTG CCACTGTACT CCAGTCTGGA TGACAGAGGG ACACTATCTC
AAAAAACAAA CAAACACTCT TAAGAAATTA GGTGTAGAAA GAATGTTCCT CAATACCATA
AAGGCCATAT GTAAGAAACC TATAGCTGGC CGGGCGCGGT GGCTCAAGCC TGTAATCCCA
```

NruI
---

```
GCACTCTAGG AGGCCGAGGC GGGCAGATCG CGAGGTCAGG AGATCGAGAC CATCCTGGCT
AACACAGTGA AACCCCGTCT CTACTAAAAA TACAAAAAAT TAGCCGGGCG AGGTGGCTGG
TGCCTGTAGT CCCAGCTACT CGGGAGGCTG AGGCAGGAGA ATGGCGTGAA CCCCGGGGGG
CGGAGCCTGC AGTGAGCTGA GATCGCGCCA CTGCACTCCA GCCTGGGCGA CAGCGAGACT
CCATCTCAAA AAAAAAAAA AAAAAAAAA GGAAACCTAT AGCTAACATC ATACTGAATG
GTGAACAGTT GAATGCTTTC GTCTAAGAAC TGGAACAAGA CAAGCACGCC AACTCTCACC
ACTCTTACTC AACATAGTAC TTTAAGTCCT AGCCAGAGCA ATCAAACAGG GGAAGTGGAT
AATTGAGAAT GGCTCGAGAG GTGCTGTGGC TCAGTCCTGT TGTCCTGGCA CAGAAGGAGC
TGAGGCCAGG CGTTCAAGAA TGGCTCCTAG ATGTCTCATA AGGAACCATA AATCAAACAA
CTTTCAAAAC TGAAACCTGC GTGAGAACGG TTGCATTAGT TAATCTGGGA GCTTCCTGCT
TTTTTTTAGC TTTCATATTT ATCTTAGAGA AAGGGAGGAA GGAGAGATGT GTATGGATAC
ATAAGCATTC AAATACATTT GTGTATAATC TTATGACCAG AATTCAGGTC CAATGAACAA
AAAGGTAGGG TCTTCGGAAT TTCCCCAGTG AGATCTATGA CCTGAATATT ATTACGCAAG
GATCCACTTT GGGATTACAG GCGTGAACCA CTACACCCAG CCCAGGACTT TCCTGCTGTT
AACTCAGGAC TACCACAATG TGAGTCTCTG TTCTGTAATG CCCAACCTTG TTTTTACTAA
CCCCGCTTTT AGACTCCCCG TTTTCCTTTA ATCACCTAGC CTTGTTTCCA CCTGAATTGA
CTCTCCCTTA GCTAAGAGAG CCAGACAGAC TCCATCTTGG CTCTTTCACT GGCAGCCCCT
TCCTCAAGGA CTTAGCTTGT GCAAGCTGAC TCCCAGCACA TCCAGGAATG CAATTAACTG
GTAAGATACT GTGGCAAGCT ATATCCGCAA TTCACAGGAA TTCGTCTGAT TGATAACGCC
CAAAGCCCCG AGTCTATCAC CTTGTAATAG TCTTAAAGCC CCTGCACCTG GAACTGTTTA
CTTTCCTGTA ACCATTTATC CTTTTAACTT TTTGCCTAAT TTATTTCTGT AAAATTGTTT
TAACTGGACC CCCCTCCCCT TTCTAAACCA AAGTATAAAA GAAAATCTAG TCCCTTCTTT
```

BsiEI
---

```
GGGGCTGAGA GAATTTTGAG CGATAGCCGT CTCTCGGTCG CTGGCTAATA AAGGATTCTT
AATTTGTCTG AAAGTGTGGC GTTTTTCCAA CTCGTTCAGG TACAACAGTT CTAGCATCTA
TTAGCTATGT GGCCTTTCAA CACCTGGCAT AAAATTCTGA ACAATGGCTT GGAAATTAAG
ATACCTTAGC TCTAGTCCTT GCTCTGCTAA TAATTAATAG AGTGAAACTG GACAGGGTTA
TTCACATGTG TGTGCCTCAG TTTACTGTTA ACTGAAGAAT GACAAAGTTC ATAAATTTGA
```

SbfI
---

```
AAAGGAGAGG TTTCTTATAT GGGGTTGCAA CCTGCAGGGT GGCCATGCTA CAGTCTGGGA
AGCATTGCCT CTGGCTGGAA GCCAGAAACA GGCACTTTCA GGGTCAGAAG AATAAGACAG
AGATTTATGC TGAATGGGGT GACCAAATAT ACATATTCAA TAGGCTATAG GAGGAGTTAT
GAATATTTAT GAAAGGAGAA ATGTGTACAT GTGCAATTTG GCTTCATGCC CCTTCATGGG
ACCTACATTC AAAAAATGGC AGCCTTAGCA TGATCTGAGG GAGGATCTTT CAGCCCTCTG
AGGTCAAAAG TGAAGGAGAG GACAGGAAAC CCTCACTGTG TGTTCTCCGT AGGGGCCAGA
ACCACTGCAT GTTTGGTGAA CCTGCTGGT TGTTATGTTG AAACTGCAAA AGGGAGGGAT
AACAGTCAGG TGCTTGTTTG ATACCAGGGG TAGAGGAGAC TTTCAAAAGG GCTGGTTTCT
GTTTAGCCCT TAGGGAAGAA TGTCTAAAGA GAATTACCTA CAAGGGTATA ACGAGGAGTG
TCTGACATTC CATCTAGTAA TGAACTAGAA CTCAGTTTTC AAGTTAACTC TGGGACCCTC
TTAGCCAAGA AGAGGTCCAT TCAGTTGGTT GAAGAGCTTA GGATTTCATT TATATCTCTC
ATCACTAATC TGCAAAAGCT GGTAGTGAAA CCGCCTTTGC AAAATTATGA CTGAGACAGC
GAAAGAGATC TAACTTAATC GATTCCGTCT TGCTTCTAAC CTCCAAGCTG TCCTTATTCA
TTCCCGGGCA TAGGCTGAAC TAACTCCGGG AGAAGCTTAG TTTATAGTTT TTAGTTTAAA
ACAAAGATAG TAACAGCCCT TTCCCAAAGC AGACCTCCTT CTTGCCTTGG AACTAGACTG
```

Figure 15D

```
                                                                    PvuII
                                                                   ------
                                                          MspA I
                                                          ------
            CCTTTAGTGG GACTAACATT AGCCACAAGA TTAGAAACTG TGGCTTAGGA GTCATACAGC
            TGGAGGCTAC AAGATTCTGA CTCTCCCTAA ACTGCTCCTA AGATCAGTCC TTGAGATATT
            TTGCAGACCC TGTACTTGAT GGATCAGGTG GCACCACCCA GATTGATAAA GTGGCTCATC
            TGATCTTGTG GCCCCCACCC AGGAACTGAC TCAGCACAAG AAGAGAGCTT TGACTCTCTA

EcoNI
                                                         -------------
            TGATTTCATC TCTGACCCGT CAGCACTCCT GGCTCGCTGG CCTCCCTCAG GCCACCAAGT
            TGTCCTTAAA AACTCTGCTC CCACTGGGCG GTGGCTCATG CCTGTAATCC CAGCACTTTG
            GGAGGCCAAG GCAGGCGGAT CACAAGGTCA GGAGATTGAG ACCATCTGGC TAACATGGTA
            AACCCTGTCT CTACTAAAAG TACAAAAAAT TAGCTGGGCA TGGTGGCACG CACCTGTAGT
            CCCAGCTACT CGGGAGGCTG AGGCAGGAGA ATCACTTGAA CCTGGGAGGC AGAGGTTACA
            GTGAGCCGAG ATCATGCCAC TGCACTCCAG CCTGGGCAAC AGAGTGAGAG ACTTCATCTC

BsrBI
                                  -------
            AAAAAAATAA ATAGATAAAT AACCTCCGCT CCCTGAATGA ATGCTCCCGG AGACTGATTT
            GAATCATAAT AAAACTCCAG TCTCCCGCAC AGCCTGCTCT TCATGAATTA CTCTTTCTCT
            ATTGCAAATC CCCTGTCTTG ATAAATTGGC TCTGTCTAGA CAGTGGGCAA GGTGACCTCA
            CTGGGCAGTT ACAGTAGTAC CCACTTCATA AGTGAAATCA CTTATCTTAG TGGTAGGGTC
            CCAAAAGTTG TTTGGTAGGA GAGGGTTGAG GCTGGGAGAG GTGGCTCATG CCTGTAATCC
            CAGCACTTTG GGAGGCCAAG GTGGGTGGAT CTCCTGAGGT CAGGAGTTCC AGACCAGCCT
            GGTCAACATG GTGAAACCCC ATCTCTACTA AAATACAAA AAATTGGCGT GGTGGTGGGT
            GCCTACAATC CCAATTACTT GGGAGACTGA GGCAGGATAA TCGCTCGAAC CTGGGAGGCA
            GAGGTTGCAG TGAGCAGAGA TCGCGCCACT GCACTCAAGC CTAACCAACA GGGGCAAAAC
            TCTAGGACTA GAGCTAAGGT ATCAAAAAAA AAAAAAAAA AAAAAGAAG TAGAGTGTTT
            AATTAAATAA TTTGTTCTTG CTGTAAAATG TAAAGTAGAT ATTCCTCTTC AAAGACTTTC
            CTCCCCGTCT AATTAGGAAT AAATAGTAAC TTCTCTTAGA AGCAAAATTT ATTCAAAGAC
            CTGTGCTAAC ATTCTTAAAT ATCTGCTAGC CACAATAAGG AAATCAATGT ACTTTATGTT
            CTTAGCTCCC ACAATTTAGC CTAAATATTT TCCCTGGCAT GTTTATACTG GTCAAGCAA
            GCATTAGGTC ATAGCCTGTT CCTCTTCCTT ATTTAAAAGT GTTTTTACCT TTCTCAGCGT
            TCCACAAGTT ACTTCCTCCT TCCTTTGTTC TCCTCTACCT GTGCCTCTTT TAAAAAGTTC
            TAAGTTGCTA GCCAATTGGG ACAAATACAG AATGTAAGGT CCCATTCCAG CCAACGGAAA
            CTGGACACAG CAGTAGGGTG GATGTGTCAG GTTATAAATG ACCCTGTCTC CTTTGTTTGG
            TGTACTCTAG TGGCAAAACT GCTGGCAAGT GTACCTTTTC TGCAGGAAGT AAAAATGGCC
            TTACTAAATA AATTAAATTT ATGTTCAAGT GCTATTTCTT TTTTTTTTTT TTTCGAGATG
            GAATTTCACT TTTGTTGCCC AGCCTGGAGT GCAATGGCGC GATCTCGGCT CACTGCAACC
            TCCACCTCCC AGGTTCAAGC AATTCTCCTG CCTCAGCCTC CCGAGTAGCT GGGATTACAG
            GCATGCGCCA CCACGCTCGG CTAATTTTGT ATTTTTAGTA GAGATGGGGT TTCTCCATGA
            TGAGGCTGGT CTCAAACTCC TGACCTCAGG TGATCCGCCT GCCTTGGCCT TCCAAAGTGC
            CTTGGCCTTC AAAGTGGCG TGAGCCACTG CGCCCAGCCT CGAGTGCTAT TTCTTTACGG
            CACGGAAGAA CAAACATTTC AAACAATGCT ATTACCAAGT TTGTTAGTAT TTATTATCTC
            ATTTGCTAAA CCTAAAAAAT ATATATCCTT CTTTAACGTG ATCGAATATT TCAAAAAGTT
            ATTGTGTTGT TTCTTAAAAT AAATCAATCA TAATCCTAGA CTATGTTACT CAAACTACAT
            ACAACACCTT CTGAGCTTCT GGCAGGCCCT TCCTCCCCTC CCTGCTCACC ACAGATCACT
            GGAATAATTG TCTGCATGTA ACTTCTAATT TTGAAGTGGT TGTGGTTTAT CAAACCTGGA
            ACATGGCACT TCCAAGTACA TGAGCTAAGG TCACAGTAAG ACTCAAGCCC CTTCAACAGA
            ATACCTGGAA TTTCTCTGTT AAAGATTTTC TCCTTTACCT GACTACATGT TTGTAATGCA
            GATCCCTCCA GGAGCGCTTA CTTATAAACT GTCCTGGATC ACTAACGCGA CATTTTGATG
            TAAATTAGTT TATCTTGACG TGCTAATGGT AGAAAAAAAG AGAACATGAG GAAACTTGGG
            TGCTTTCAGG GCTGGTAGGA AGGATTAAAT CTTTGCGGCA ATTTCTGAGA AGGGGAAGGA
            AACCTTGCTA ACAATTTTGA TAGTTTACTC CATTTGGCTG GAGTAACTCT GATCCATTTG
```

Figure 15E

```
                            KpnI
                            ------
TCAAATTCAC GATGGAGCAG GTACCTGTTA GGGTACAGGT TTGATAAACC ACAACCACAG
GTCTATTTCA TTTCTCCTTT TCCAAAGTGG AACAAATTTG TCTCTGGGGT TAAAACTGCT
TTTCTCATAT TGGTGTGTAA GAGAAAATGA GGGAATTTCT TTGAGTTTGT TTGGTTTGTC
TGTTTGTTTA AGCAGCATTT TTTAAATAAT TTACTCAGCC CTGTCTCAGA GAAAGTCCAT
GATGATCTGG AATTCAACCT CAGGGAAAAG TTCTCTCCTG TGCCTGAGAC ACTGCGCAAC
TAACTGGAAC CGAAGGATGG AACCTGGGTG TTTAATTTAT TAGGAACAAT TGATTCTTCA
GTGACACTTT CCATGCAGAT ACTTCAAACA AAATAATGGA GCCCCACAGA CCGAATGTGA
                                           >>.........Exon1  .........>
AGACAGCAGT GCCATTGTCT TTGGAAAGCT ATCACATATC TGAAGAGTAT GGCTTTCTTC
>.............................Exon 1 ............................>
TTCCAGATTC TCTGGTAAGG ATAGAGCCTT GGTAAGGATA GGTCAGAATA TGTTTCTTGA
>....Exon 1 ....>>
GATGTTGGTT GGTTTGTTTT TTAAAAATGT ATGTGATTAT TAAGAGACCA ATATAAATAT
CAAGTTGTTT ACCTGAGAAA GATGCTACAA AGAGCATAGA TTATCATTAC TATCAAAAGA
GAAGTGACAG ATACCACAGA GAACAGGTCA AATGGAACAT TTTTTGTTTC AGTTTCTTTT
GACTAGATTG TCAGGCCAGA GAAATTATAA GCAAACCTGT AGTTATCAAG AAAAAGCATG
AACTTAAATA TAAATAAAGA ACAAATACAG AGCCTCAGCA CCTGGAACAT GGCACTTCCA
AGTACATGAG CTAAGGTCAC AGTAAGACTC AAGCCCCTTC AACAGAGTAC CTGGAATTTC
TCTGTTAAAG ATTTTCTCCT TTGCATGACT ACATGTTTGT AATGCAGATC CCCCCAGGAG
CGCTTACTTA TAAACTGTCC TGGATCACTA TCGCGACATT TGATGTAAA TTAGTTTATC
TTGACTTGCT AATGGTAGAA AAAAAGAGAA CATGAGGAAA CTTGGGTGCT TTCAGGGCTG
GTAGGAAGGA TTAAATCTTT GTGGCAATTT CTGAGAAGGG GAAGGAAACC TTGCTAACAA
ACAATACCTC TTTCTTAATT CTACTTAGGG CTCAAATTGT AATGCAAATC TTTTTCATCA
TTTAGCCCTT ATAAACACTG TTTTTCTCAT CTGGTGTGGT CCAAGGCCTA GAACATTAAA
ACTATCAAAG CTTTTACAGA CCATCAGGTG TCATCCCCCT CTTTCTACAT CTGAGCTAGC SpeI
                                                   ------
TGAAATCCAG AGGAAATGAC TTGCTGAAAG TCATGAGTGG CAAAAGCAGA ACTAGTTCTG
CTTATAACTC TTGACTTTTA GTTATTATTA TTATTAATTA TTATTATTAC ATCCTAAATG
AGGGCCAAGG CCACTCAGTT AAAAATCGTG GGGTCCAGGC CAGGTGCAGT GGCTCACGCC
TATAATCCCA GCACTTTTGG GAGGCCAAGG CAGGTGGATC ACTTGAGGTT CAGGAGTTCA
AGACCAGGTT GATCAACATG GTGAAACCCC GTCTCTACTA AAAATACAAA AATTGGCCAG
GCGTGGTGGC ACATGCCTGT AGTTCCAGCT ATTGGGGAGG CTGAGGCAGG AGAATCCTTG
AACCCAGGAG GGGGAGGTTG CAATGAGTGG AGATCATGCT GTTGGGAATG AAGTTTTTGG
TGTCACAGAA AAAGAATGAA CATGGGAACA AATGATCTCT CAGCAAAAGG ACCTTTACTT
TCTGCAGAAA GGGTGCTACT CAATAGCTGT CCAGCCACGA GAGCACACCA AACAAAGGAG
ACAGAGTTAT TTATAACCTG ACGCATCTAC CCTACTGCTG TGTCCAGCTT CCATTGGCTG
GAATAGGACC TCACATTTTA CACTTTACCC AATCGGCTAT TAGTTTAAAA CTTTTTTAAT
TGGATAAGGG AACAGAACAA AGAAAGAAAA GCAAGTTGCC CAGGGATAGT TAAGGAAACA
TCTCCATATA AGGAATGGCA TGCACTATGG GCTGGGGCTT TTCTAGTTCT GTACAGACAT
GCCGGAGCAA GCTACGACAG CTGATTTGGA CAGCCACTAA TAGTGGCTAG CAATCTTATA
GTAAGAAATT GTGACTTTTT ATAATCTTTG AAGAACTTTC CCATTTCTGA CAGTGCCACT
GCACTCCAGC CTGGGCAACA AGAGCGAAAC TCGTCTCAAA ACAAAACAAA ACAAAACAAA
ACAAAACAAA ACAGCTCTCT ACTCTTGGAA GCAGCAGAGT TTTTATCTTC ATTTATATCA
CTCCGGTAAC ACTCAGAAGT AGACAAGCCT CAGGGTAGGT ATTCAGTAAA AGCCCACTGA
ATTCCACACT ATTCTTTAAT CATAGTTAAA TGGCAAATTA GGCTGGAGGG TGGGGGTGGA
ACCTCTCCAA AATTACTGCA ATGACTGCAA CATCGGACCC CAAGATTTTT TTTTTTTTT
CTGAGATAGA ATCTCTTTCT ATCGCCCAGG CTGGAGTGCA GTGGCACTGT GAGAAATGGG AhdI
                                                   ------------
AATGGACCGG ACTGTTTCCT CTGACACTGC CACTAGGTTG ACCAAGTGTC CCTATTTGTT
AGGTACTGGA TGGACGCCTG ACATGCAAGA CTCTCAGTGC TAAATCAGGA AAGTGCTGGG
ACAATTCGGA TGAGTCGGTC ACGCTAAGTT GCACTTAATA GCTCTTGTGA CTTTGACTGA
ATTACAAACA TCCCCTGACC CTCAATTTTC ACATTTACTG GATGGAGATC TGGTGCCACC
TCCACTAGAT TGCTATGGAG AATGAATGTG AAAGCATTTT CATAAATCCA GTGTAAGGAC
```

Figure 15F

```
CAGAAGCCAG TCTTCTGACC TTGAGCCAGT GCTTGTTAAA AACTCCACTC TATACATCTA
ACCCAATTCA GGAATATCCT GCCTAGTTCC AAAGGAAGAA AAGACCAAAT TGCTCTTATT
GGGATTAAAT GCGTACACTG AGCTGAGGAA AAACAGTATT ACAAATGAGC TAAACATGAC
GTAGATCCAC AGTTGTAGAA TTCCCCTCTT TGTTCTTTCC TCTTTCATAA CTACGGAAAC
AGATGAGAAA CATTTACGGC ATCAGGTTCT TGTGATGCTC CCTGCCTGAT ATGCTATGGT
TTTGTTAATG GAATGTCCAT TCCTGAGCTT ATGCAGAAAA AAGTCCCTTG GGAAAGTGGT
TTTACTGTGT TATGTTCATT TTCCCCATAG TTCTCAAAAT GTACTTCCTT GTTTCAGTTT
TAATTTTCTT TCATTGGTGT GACCATTTTC AACTGCTCCC TTTCTGGGAA GAGGTAGCAG
ACGGACATTT TCATCAAAAT CTGCCCCAGG TTGCTTCACA GATAAGGAGG GACCCAGCCA
CTAAAATCAC CAGGCAGAGT GTTGCAAGAG TAGATAGAGA ATCACAATTG GCTGCCCTGC
TCAAGGGGAC ACCAGATCTT ACTTTCGTTT AGTTGAAAGG CAAGCGTCAG AGTCGGGAGG
CTGTACCTTC ATGTCCAGTG GCCTCACAGA AGTTCCTTCA GTATCTCTTT TAGATGAAAC
TCTTTTAGAA GTTCCTTCAG TATCTCTTTT GGTTTCTCAC TATAGATAGT TACTTGAACA
TGTCTGAAGA AAACGTGGTC AAGACAGTGA ATAAAAAAAA TTCTGGTTTT GGGAAGCAGT
CTGACTTAGT TTCAAATATT CTATCCCACT GTTTCTGTCA ATGTTCAAAC CTTTCCAAGC
TCCAACATTT ATTGTGGAAA ATGTGTGCCT CACCAACTCA TGCAAATAAA TGTTTCATGT
GCCCTACGTG TGTAGAGGGG GCATGGATGT GTGTTTTTGG AGGGAGGGCT AATTTTTCTT
TAGACATGGA GAATACGAGG AAATTAGCTT GGCATCAAGA AGGTTACAGC AGGAGACAAG
AGTGAAGAGA ACTGAGAGAG CCCGGAAATG AGGCTCTGGA GTTCAGATTT TTTTTTTTTT
GAGATGGCGT CTTGTACCCC AGGTTGGAGT GCAATGGCAA AATCTCAGCT CACTGCAACC
TCCGCCTCCC GGGTTCAAGC GATTCTCCTG CCTCAGCCTC CTGAGTAGCT GGGATTACAG
GCATGAGCCA CCATGCCTGG CTAATTCTGT AGTTTTAGTA CAGATGGGGT TTCTCCATGT
TGGTCAGGCT GGTCTCAAAC TCCCAACCTC AGGTGATCCA CCCTCCTTGG CCTCCCAAAG
TTCAAGGATT ACAGCCATGA ACCACTGCGC CTGGCCTAAT TTTTGTATTT TTAGTAGAGA
CAGGGTTTCA CCATGTTGGT CAGGCTGGTC TTGAACTCCT GACCTCGTGA TCTGCCCACC
TCAGCCTCAT GAAGTGCTGG GATTACAGGC ATGAGCCACA GGGCCAGGCC TGGAGTTCAG
ATTTAACACA TCCTGTAAAT GACATGATGC ATCTGATATT TGAAGAGTTT TCCTCAAAGA
ATGTTACATG CAAGGTGGTT TAGAGTTGTT GTTTCCGGCT ATATAGCAAA AGTACTTGGG
GAGTTTTAAA AAATACTGAT GCCGAAGCTC CACCTAGAAT AGTTCATTCA GAATCTCTAG
CATAATTGAC CTCAGTACTT GAAATATGAT TATTATAAAT GTTAGTCAAC TGCTTTTTTA
GGCTCTATGA CTGATAGAAA TCTTTCACTT TTATATCATC TCCAGTTAAT GAGTCCCATA
AATTGAAATC TAGTGTTTAA ATTTTTACTT CATATTTATT TTTACTGATT GTTTTATTAT
TATTATTTTT GAGACAGAGT CCGCTTTGTC GCCCAGGCTA GAGTGCAGTG ACGCCATCTC
GGCTCCCTGC AACCTCCGCC TCCTGGGTTC AAACGATTCT CCTGCCTCAG CCTCCTGAGT
AGCTGGGATT ACAGGAGCCC ACCACCAACC ACACCCAGCT AATTTTTGTA TTTTTAGTAG
ACGGGGTTTC GCCATGTTGG CCAGGCTGGT CTCGAACCCC TGACCTCAAG TGATCCACCC
GCCTCGGCCC TCTGTCTCAA AACAAAAACA AAAACAATAA CAAAACTTTT CTCTTCTACC
CGAGATGTTT AAGTTTAAAT CACACCATTT GTACAAAAAT TCCCTGTCTT GTCCTTAAAA
ATAATTTGTA ATCACTAGCT AGTTTTGAGA TCGATTGCCA TCTAACCGAA TGCCATTTGT
TCTCTCTCTC TAGTTTCAAC TTAATAACCC TTTCTGCATT TTCTATTCTT TCAAAATTTT
TCCGGCCATT TTATTGTTTC TATTTAGTGA AAATTTATTC ACTGGTTTCT ATGCCTAAGG
GCATTTAGGA AGTTGCTTAG GATACAGACG TGATAAAAAG ACCAGTGTAA AAACTCTCCA
CTCCTAGACA TTATATTCTA GTCCTCATCT CCTGTCATTT AAGTCCTCAG TGATTCTATG
CACTTTTGCT TTTGGTTTGG GCAGATGCTC TGAGTTTAAT GTTTCTCTGA GATGAGGACC
CCCTATTCAA CTCACAAATC CCATAAGGAG GCCTCTGTGC CTTTGCTGGT GCCCCAGACA
GGGTGCTGAT GCTTACTTAT CTTCAAGATT GTGAAGTCAG ATTTAATAGT ATAGTCGTTT
GCCAGAGCTG CTGTAACAGT AGCCACAAAC AGTTGGGCTT AAAATACCAC AAACAGGAGG
GCTTAAATCA CAGAAGTTGA TTTTCTCACA GTTCTTGAGG CAGGAAGTCC AAGATCAAGG
TGTCGTGGAG TTGGTTTCTT CTGATGTCTT GCTCCTTGGC TTGTAGATGG CCTCCTTATT
ATTGTGTCCT CACATGGTCT TTTCTCCACT ATGCACAAAT TCCCTATGTC TCTCTCTCTT
TTTTTTTTTT TTTTTTTTTT TTGAGACAGA GTTGCACTCT GTCACCCAGG CTGGAGTGCA
GTGGTGCAAT CTCGGCTCAC TGCAACCTTT GCCTCCCGGG TTCAAGCAAT TCTCCTGCCT
CAGTCTCCTG AATAGCTGGT ATTACAGGTG CGCACCACAA AGCCCAGCTA ATTTTTTGTA
TTTTTAGTAG AGATAGGGTT TCGCTATTTT GGTCAGGTTG GTTTTGAACT CCTGGCCTCA
AGTGATCCGC GCACCTCGGC CTCTCAAAGT GCTAGGATTA CAGGCATAAG CTACTGTGCC
CAGTCTCCCC CTGTCTCTTT GTGTCAAAAT TTCCTCTTCT TTAGGGACAC CAATCAGATT
AAATTGGACC CACCCTAAAG GCCTCATTTC AATGTACCTC CTTCAAGGGC CTATCTCCAA
ATACAGTTAT ATTTTTAGGT ACTAGGGCTA GGGCTTCAGC ATAGGAATTT GGGGGAGACA
CAATTTAGCA CATAGCAGAA AATATAAGGC CAGGAAAAAA TATTCTGGCA TGCTAGATGG
```

Figure 15G

```
ACTCATTAAC AAATATTAAC CAATATAAAC CAATTAACAA ATATTTCTTT AATATTTGCC
TTTTTTTTTT TTTTTTTTTG AAACAGAGTT TCACTCTTGT TGCCTAGGCT GGAGTGCAGT
GGCACGTTCT TGGCTCACTG AAACCTCTGC CTCCTGGGTT CAAGTGATTC TCCTGCCTCA
TCCTCCCAAG TAGCTGGGAT TACAGGTGCG GGCCATCACA CCCGGCTTAT TTTTTGTATT
TTTAGTAGAG ATGGGGTTTC ACTATGTTGG CCAGGCTGGT CTCGAACTTC TGACCTCAGG
TGATCCACCT GCCTTGGCAT CTGAAAATGC TGGGGTTACA GGTTGCCTGG TGATTTTTAA
GAGGAATGAC TGAGCTCTCA TGCCAGGTGG GGGGAGGGGA CAGAGAAAGT TGAATACTCT
GACGATAGCC ATGATCCATA GCTCTGAAGC TTAGACTCGA ATCTACCCAT CCCGCAAGGA
AGAAAACAAA GAAATAAAAA AGAAGAAAAG AAATCTCCCA ATGTCAGGTC CCACCCTCTT
TAGAAGTAAT TTCAGCAAAA CTTTGTTGCT ATTTTGGCAT GTCCTCTACT GTAGTAGCTT
GTCAAAATAC TGTCCCCAAA CGTTTTCTAT ATTTCTAGAT TTTACTGTTT AATGTATAAT
AATAATGTTC TAACATTAAA ACGTAACCAT AGCAATGCTC CGACTCACTT GATCTTTAAA
TATATTGTTG AACTCAATTT TGTGACATCT TCAGAATTGT CTTTTTGTAT TCATAAATAG
CAACAGTGGA TAGTTGCCTT GGTTAGTGTT ATTATTTCAA GGATTAATCT TTAGGTTACG
TTTTCTTCAT AAGATGCATT AGATGACTTT TTTTTTTTTT TTTTGAGAC AGAGTCTTGC
TCTGTTGCTC AGACTGGAGT GCAGTGGTGC AGTCTCAGCT CACTGCAATC TCCACCTCCT
GGCTCAAGAG AGTCTCTCGA CTCAGCCTCC TGAGTAGCTG GGATTACAGG CACGCACCAC
CATGCCTGGC TAATTTTTGT ATCCTTTTTA GTAAAGACGG GATTTCCCCA TGTTGGCCAG
GCTGATCTCC AACTCCTGAC CTCAAGTGAT CCATCTGGCT TGGCCTCCCA AAGTGCTGGG
ATTACAGGCA TGAGCCACCA CACGCAGCCA ATTAGATGCC TTCTCATGCT TTTCTGTGTT
GTGAAACAGA TCATCTATCC GTTGATATAG CATAGCTCTT CAGACTACAG ACATTTAGG
CTATAAGTTT TGAATTACAT TTTCTATTCC CTTTATGCTT CTTGTTCTAG TTAGGTTTTT
TATTTCTAAA TAAAAATATG AATTTTTGCA ATTTCCCAAA TGCGAACTCA ACTGAAATTT
TCAAGTGTAT TAGCAAAATT TATTCATAGC AGCCTCTTAC ATTTCATTAA GAATTGATTT
TTTCTTATTC CCTGTTGAAG TTTGTTTATA AAATATAGTA ATAGTAATAA CTATATAGAA
AGTGTTCACT TTGTAGTAGG CCCTATGTTA ACTTTAACTA CACTTTTTAA ATCTAAGCCT
CATAGTAGTC TTGGATGGAT GCGGTGGCTC ACGCCTGTAA CCCCAGCACT TTGGGAGGCT
GAGGCGGGTG GATCACGATG TCAGGAGTTC AAGACCAGCC TGGCCAACAT GGTGACACTG
TCTCTACTAA AAAGACAAAA ATCAGCCGGA CGTGGTGGTA TACACCTGTA GTCCCAGCTA
TTTGGGATGC TGAGTCAGGA GAATTGCTTG AACCCAGGTG GTGGAGGTTG CAGTGAACCG
AGATCACACA AGTGCACTCT AGCCTGGATG ACAGAGTGAG ACTCCATCTC AAAAAAAAAA
AAAAAAAAAA AAAGAGATCA ATAAATAAAA TAAATAAATA ATCCTCACAA TAGTCTTCAC
CATTTGCAAA TGATCCATTT GACAATAAAT GAATTCAGCA CTATCATGGA AATATATTTC
CAAGCTGACC AGTTTTCTCC ATTTCCACCC CACTTCAATC CACCTTCATG TAGCCCTAGG
ACTATTGTCT CCTCCCCTTG TTTCCTTATT TCCATTCCTG TTCAGCTGTA ACACATTCTG
TTCATAGCAG TCAAGTGATG CTTACAAATG GAAATCAGGC TAGAGGTGGT AGTTCACACC
TATAATTCCA GCATTTTGGG AGGCTGAGGC AGGAGGATCA CATGAGGCCA GGAGTTTGAG
ACCAGCCTGG GCAACATAGC GAGACCCCAT CTCTACAAAA ATAAAAAAGA ATTAGCTGTG
CATGATCCTA TGTGCCTGTG TTCCAGCTAC TTGGGAGGCT GAGGTGGGAA GATTGCTTGA
CCCAGGGAGT TTGAGGCTGC AATAAGCTAT ATTTGTACCA CTACACTCCA GTGTGGGTGA
CAGAGTGAGA TCCTGTCTCT AAAAAACGTA AAATGAAAAT AAAACCTTGA TAGTTTGCTC
TTTAAAACTC TTCCTACAGG GCCCCTGTGA TGCTCACCTG TCTCTAGAAG GGCATGTAAT
AGCTCTTTCT CCTTCACTTT ACTTTGATGC AATGTCAGAA CAGCTTCTTT CCATCAAAAC
TTAAACCTTT GATTTCATTT AAAATCATCT GCTTCAAATT CTAATCTTTC TGATAGTTTA
GGTTCTAATT TTTCTGATGT TAATATTGTC ACCCAAGTTT CCTGTTCATA TTTACCTGGT
TTATTTTATT TTTATTTTTA TTTATGTATT TGAGATGGAG TCTAGCTCTG TCACCCAGGC
TGGAGTGCAG TGGTGCGATC TCAGCTCACT GCAACCTTCG CCTCCTGGGT TCACGCCATT
CTCCTGCCTC AGCCTCCCGA GTAGCTGGGA TTACAGGGAC CCGCCACCAT GCCCGGCTCA
TTTTTTGTAT TTCTACTAGA GACGTGGTTT CACCGTGTTA GCCAGGATGG TCTTGATCTC
CTGACCTCGT GATCTGCCCG CATCGGCCTC CTAGAGTGCT GGGATTACAG GCGTGAGCCA
CCGCGCCCAG ACTTTATTTT ATTTTTTGAG ACGAAGTCTT GCTCTCTTCC CCAGGCTGGA
GTGCAGTGGC TTGATCTCAG CTCACTGCAA CCTCTGCCTC CCAGGTTCAG GCGATTCTCC
CGCCTCTGCC TCCCAGGTTC AGGCGATTCT CCCGCCTCAG CCTCCCGAAC AGCTGGGGTT
ACAGATGCCT GCTACCACAC CCAGCTAATT TTTTCTTTT TTTGGAGACA GTCTCACTCT
GTCGCCCAGG CTGGAGTGCA CTGGCGTGAT CTCAGCTCAC TGCAACCTCC GCCTCCTGGG
TTCAAGCGAT TCTCCTGCAT CAACCTCCTA AGTAGCTGGG ATTACAGACG TCTGCCACCA
CATCAAACTA ATTTTGTAT TTTTAGTAGC TGAGATTATA GGCTCGTGTC ACCACGCCTG
GCTAATTTTT GTATTTTTAG TAGAGACGGG GTTTCACCAT GATGGCCAGG CTCGTCTTGA
ACCTCTGACC TCAAGTGATC TGCCCATCTC AGCCTCCCAA AGTGCTGGGA TTACAGGTGT
```

Figure 15H

```
GAGCCACTGG GCCTGGCACC TGGTTTATTT TTGTGCATGC TTTTATTTTT AATTTTCCTA
TGCTACTTTC TTAGCCAAAA TTTATACTTA ATCTAATCAA GCATTAATCT AACAAAGAGT
TTAGTGTTCA TATAAAATAC AGTTTTACAA ATCTGTTTTT CTTTAAATTA TAAATTTGTT
AAGAAAATTA TCCAAAGAAT GATCCAGAAA CAAAAGAATG GCTGTGTGTC TTTTCAATAT
CATCCTGGAG CATTGTCTCA ACCATCTCAC TTTACGGTGA CTAAAACATC TAGAGGTTTT
CCCTTTGTTT TCTGTACTTC TTAGTATTGA TTAATACTGT TGTGCTACTT CAGTCTGAAG
TTCCATGTTA ATCTGTAGAT TTTTTTTTTT TTTTTTGAGA CAGTGTCTCG CTCTGTCGCC
CAGGCTGGAG TGCAGTGGTG CGATTGGCTC ACTGCAAGCT CTGCCTCCCA GGTTCAGGCC
ATTCTCCTGC CTTAGCCTCC CGAGTAGCTG GGACTACAGG TGCCCGCCAC CACGCTGGGC
TAATTTTTTC TATTTTTTTT TTTAGGAGAG ACGGGGTTTC ACCGTGTTAG CCAGGATGGT
CTTGATCTCC TGACTTCGTG ATCTGCCTAC CTTGGCCTCC CAAAGTGCTG GGATTACAGG
CGTGAGCCAC TGTGCCCGGC TGTTAATTTG TAGATTTTTA TACAGAAAAG CAGCAAAATA
TTTCTGTTGA GTAGAAAATA TAACTCCAAT GCTTATGACT GTATTCCTTA TAGGACACTA
ACTCATTATG TGTCTAACCT AGCAATTTTA TGTCAACACT ATTTTCTCAA ACCTCTATAA
ACTTTGGCTG GGCACAGTGG GTCACACCTG TAATCTTAGC ACTTTGAGAG GCTGAGGCAG
GTGGATCACC TTAGGTCAGG AGTTCAAGAC AAGGCTGGCC AACATGGCAA ACCCCATCT
CTACTAAAGA TACAAAAAAT TAGCCAGGCA TGGTGACATG CCCCTGTAAT CCCAGCTACT
CAGGAGGCTG AGGCAGGAGA ATCTCTTGAA CTCAGGAGGT GGAGCCAAGA TCATGCCACT
GCATTCCAGC CTGAGCAATA GGGTGAAACT GTGCCTCAAA ATGAATAAAT AAAATAAATA
AATAAGTCAG AGATTGTGAA TAGGATGTTG GATATACCCA AGTTATGAAT TAATTAGGAG
CTTGAACCCA GGAGGCAGAG GTTGCAGTGA GCTGAGATCG CACCACTGCA CTTTAGCCTG
AGCGATAGAG TGAAACTGTG TCTCAATCAA TCAATCAATC AGAGATTGTG AGTAGGATGT
TGGATGTACC CAAGTTATGA ATTAATTAGG AGCTTGAACC CAGGTTTGTC TCAGATCCTC
AGGGACTGAA GACTTCCAAG TGAATTATGG GTAATGTATA GGTCTATACT ACTCCAAATT
TACAGTTTTC AGACTTCCCT GGGTTCTCAT GGACCTTCCA TGTCATTTCT ATGTTAGGT
TGAGGTCCCT GGTCTTTTCT CCTCTGTAAT TAATTTCACA CCCACCCCTA TCTCAACTCA
CACAACTTGA TCTTCACTCC CATCTGCTAA GAAATTGAGT CCATAAAAG TGAACTCCTT
TAAACTCTAG ATCTTCTACT GCTGCAAGGA CAGACATTCC ATTCTGGCTC TCTCTCTCCT
CCTTTGCTTC TTCCAGTCCT TTGCTCCTTC TGCATTCTGT TACTCTCCTC TCTCCTTTGT
CTTCAATCTC TCCCTCTTGC AATAGCCAAC TATAAACTGC TCAAGCTTCT CATTCTTAAA
AGATCTCTCT GAAATGCAAA TTCCCTACTG CCTTATGGCT CTCCTTCAAA AGTAATCTAC
ATTTTCTCTA TTTTCTAATT CCTCAACACA CTAACGTTTG AACCCTGCTT CTATGACCCT
GACCTAAATT TCTATTAAAT GTACATAGAT AAACTAATAT ATATTTGTGA CTTCCTAATA
TTGTTTTGTT TTTTAAAGAG GTCAATCTTA CTTTAACTCT GTAATGATGC GGTTGACCTT
CTGATGATTC TCTACTTCTG TGAAATCCTC TACTGTCTTG ACTTTTTAAT TAATTTATTT
TTTTTTGAGA CGGAGTCTCG CTCTGTTGCC CAGGATGGAG TGCAGTGGCA CAATCTCGGC
TCACTGCAAG CTCCACCTCC CGGGTTCATG CCATTCTCCT GCCTCAGCCT CCCGAGTAGC
TGGGACTACA GGTGCCCGCC AACACGCCCA GCTAATTTTT TTGTATTTTT AGTAGAGACG
GGGTTTCACC GTGTTAGCCA GGATGGTCTT GATCTCCTGA CCTCGTGATC TGCCTGCATT
GGCCTCCCAA AGAGTTGGGA TTATAGGCGT GAGCCACCGC ACCTGGCCCT ACTGTCTTGA
CTTTTATAGG GTCATTCTAT TCAAGCTCAT TGAGCGTCTG TCACTATGTT TTTGATCTGT
ATTGCTGGAA TCAGTTCCTC TATCTGCCTT GTGAATATTC TCCATTGTGC TAATCTAGGC
       >>.......................Exon?......................>
TTCTCCTTTC ATTTTTCATA TTCCCTCACA TGGCTTTATA CACTCTTGTG GTTTTAACCA
>>
CAATATAGGG TTTTTACTGT AGTTATGCTT TCAAATTGTA TACTTCTTTT TTTTTTTTTT
TTTTGAAATG GAGTGTTACT CTGTTACTCC AGTCTGGAGT GCAGTGGTAC GATCTTGGCT
CACTGCAACT TTCGCCTCCC AGGTTCAAGC GATTCTCCTA CATCAGCCTC CCGAGTAGCT
GGGATTACAG GCATGTGCCA ACACGCCTGC CTAATTTTTT ATTTTAGTA GAGACAGGAT
TTCACCATGT TGGTCAAGCC CGTCACAAAC TCCTGACCTT AGGTGATCCG CCCTCCTCGG
CCTCCCCAAG TGCTGAAATT ACAGGTATGA GCCATCGTGC CCAGCCCCAA TTGTATGTTT
CTAATATGAC TTTTCTCCTG AACTTTAAAC TGTGTATCCA ACTTCTCAGC ACAGTCATAT
CTTTTGATTC CACAGGTAAT TTAATGTCAA TATATTTAAA AATGAATTTA CCACCTTTAT
CCCCACTCTT TGACTTTCAC CTGCATTTCT GTTTCAATTC TTGTTTCCAT CCATTCATTT
GCTCACCTAA TTCATAAACA TGGAAATCAT CCTCAATTCC TCTTCTTCTT AGCCCAAAAA
TTCAATTGTG CAGGTTATGC ACTGAGAAAA AGAGCCTCAG GTTAGGGGA TAAATCAGAG
ATTGGTGAAC TTTTTCTGAA GGGCCAAATA CTAACTGCTT TAAGCTTGCT TACCATATGG
TTTATGTTGC AACTACCAAC TCTCCTGCTG TAATGTAAAA GCAACCATAG ATAGCATGTA
AACAAATGAG ACAGGCTGGG TGCCAATGAA AATTCACGAA AATTAATGTA GTTTACTGTC
```

Figure 15I

```
CCTTGGGTGA GAGTTGGGGG TCACTGAAAT TCGGACTATG TCTTACTTGG CTAAACCACA
GGCCTAGAGT GGGCCATAAA TGGAGCTATT GGGCTAGTGA TTTTCTTGCC TTAAGCCCCC
AGCCCCAAAT TTAATAATCA CATCATTTTA ATTTCATTTT CCAAGTGTAT CTTTAATATA
TGGCTTCTCC TTTCCAAATT CACTGTCATT ACCTAAGTTT AGTCCTTGAA CAATATTTTA
AAGGCTTCCT TATCTGACTT TATATCTTAA AGTCCTACAA ATTTATCTTC CTAAAATTCA
AATCAAACCA TGTCACCAAC TTACAGAAAG GGAAAATTCA TATATTCTAC ACACAGCACA
TTTCATGTAA CTTTCTAGGC TCATCTTTCA TCATCCTTTT GATGCAGGAT TTTCTGCTCC
TCAGCTCAGC GAAATCCAGG ATCTTGTCTC ATGACCAGGA AGAATTAGGC AGGTGGACAT
AGTGAAGGGT GAGGATGACG GAATTTATTA AGCAAAGGG GAGTTCTCTG CAAAGAGAGG
GGTTTCACCA GCAGTCTCCC ACCTCACAAT GGAGCACCAG GACTTTCACA CACAAACTGA
AAAGGCTAGG CTCCTCCCCA GCATAAGGCA TGAATTCCTG GTGGTTCCAC CAGTTTTCCT
ACTATGCATG TGGGTGTGCC CAAGCAAACC ATAGGTAGTA TCAGAAAAGG CAACATTTGA
TTGGTTAAAA GGCATTATTC ACCCAAGCAA ACCATAGGTA GTATCAGAAA AGGCAACATT
TGATTGGTTA AAAGGCATTA TTCAGAAAGA ATCAATCGGG AAAGGGTGAG CCAATAGGGG
AAGTTCTCCC TCTGGGTCAC GGGTTTCATC TGGGACCAGG AGTCTGGCCT TTCAGCCTTT
AGACTGTTTT AGGCTTGAAG GTGGGTTCA CAGGGACCCT TCCCTATCTG CCTAGGCATC
TGTCTGCCTC CTGCCTCTAT CACTTTCTCT TGAGTTTTAT ATTTTAGCAA CACTGAGTCA
TCTTTGTCCC AGGAAGCACC TACATCTGTT TATCTGCTGT CCCCTCTACC TTTACTACCT
TCCCTTCTTC ACATTTATAC CCAGAAAAGT CACTTCCCCT CCAAAAATTG GGATCAACTG
TCATATTTTT ATGAATATTT CACTTTAATT CCTCACAACA GCTGACAGAA TTAACTACTT
CCTCTTCTTT GCAAGTTATT TGGCTCACAC AGATATCAGT AATTAAACAT ATTTTACTGC
ATTGGCATAT ATCTGACTAA TGTGTTTTC TCCCGTACTA GGCAATATGC TCCTTAGTCA
TCTGTGTATC TGAGGTGAGC ACAGGGCCTA ACTAGCATAT GGTGCATTCT CAATGTTCGT
TCAACTGCAT TGACTTGAAT TCCCCTGAAG ACTGAAATGT GAAAATAGCT ACTCTCGGAA
GCCCCTTTCC AGAGAGGTCT AAAATATTTA CATGTTCTA TTTTAAATGC AGAAAGAACT
                                                                    >>..>
TCCAGATCAT TATAGGCCTT GGATGGAAAT TGCCAACAAA CTTCCTCAAT TGATTGATGC
>................exon 2 ...........................>
TCACCAGCTT CAAGCTCATG TGGACAAGGT ATTCTTCTCT TCACCCCTC ATCACATTCT
>...............exon 2...............>>
GTTTTCATCA TCATACCACT TTTCTTTCTT AGCCTTGTGG AAGTGTGTCA ATTGTCCTGG
GAAACTGTTC ATTACCATTG AACTTATCAG CAAAGCTATA TCTTCCTTCC TGAAAAACAG
AATGACCCCT TCGTAATCTG ATACATGTGT TTTCCTAAGG TTTTCAGAGC CAGCACAAAA
CAATGCCTGA CACATGCCAA TAACTCACCA AATGTTTGTT TAAAGAAGAA TCTGGGTGGG
AATGATAAAC TAACTAATGG ACAAGGTATC GCCTAAGAAG GTCAGCTTGG AAATTCTCAG
GTTCCTCATT CCATGTACGT ACTCAAGGCT CTGTTGTTAC TGAGGGGGTC TAACTTGATT
TTGTCCTAGG TGTTATAGAA TAGTTAAATG GAGGGAATTT CTGAATTATA AAATTGGCCA
TGGGTTCTAC AAAACATCCA ATAAGCCTGT AAATTCCACA AAAGTGTTGA TTAGGCTGAT
ACAAAGGTAA TTGCAGTTTT TGCCATTACT TTTAATGACA AAAACCACAA ACACTTTTGT
ACCAACCTAA TAGCTATGTA ACCCTGAAAA AGTTACTCAA CTCTGTAATC CCATTTCCTT
ATTTATAAAA TGAGAGAAAC TCTGGTCTCA CAGTATTGTT ATGGGAAGTA AATCACTTTC
AAAGTGGCCC TTTTGTAGTT CTTGTCCTAT AATAGCATTC AGTATACATT CATTACTTCT
CTGTAGTCTC TTCTCCATCT GTCCTAATCT ATCAGTTTGG AGTACCACAT AATTGCGGAA
GTCCATGAAA AGTTTTCCGC TCTCCAAAAT TTCCCTTTGC TGATGGATAA TATTTAATGT
CTAGAATTAC AAATTCTTTT TAAAATACTC ATTGAATGTT TGCTTTGTGC AAAGCACTAG
AACCTTGTAA AAGATGAGTA AGGGACTGGC TTCAATGTCT GTGAAGATAG CAAACTAAAC
AGAGTAATTT CTTTGCCTGA TAGATAAAAT GTTGTGTTGA CATGACCAAA GAAATCCAAA
AATAAGAAAA AAACTATCTG TAAACACAGA AAAATAGAGA AAAGTTCCAA TGATGGAATA
AAAATTTAAA GGATTTTTTT GAACGTATTA AGCAAATCAT GTATAAAATC CAGAAATAAG
TTTACAGGAC CCATGTCAAG GATTTAACCA AAGCAGAGGG AGATCCCCAT GAGTCCCCTT
TTCCCATCTC AGAATAGCAG AGAAGAGAAG CAAGGGAAGC CTGGAACAGT TGGCAAGAGG
GCAGGTTAGA ATTCAGTTTG TGAATTATGA GGTCGTCTGC CGTAGGCATT TACCAGGCTT
TATTTGATTT AACTGCCATA AAGGAAGAGA AGGACTTGTT AAATTGGGGC TCCTCTTAGC
ACAGCATTGA AACCAGTCCC TATTCCTTCT TGGCCTTTTG GCTAAAATTG AGTGTGAAAT
CTATCACCTA ACATTTGTAC TGGGTTTAGG CTGGGTGTGG TGGCTCACGC CTGTAATCCT
AGCACTTTGG GAGGCCAAGG CTGGCGGATT GCCTGAGCTC AGGAGTTCGA GACCAGCCTG
AGAAACATGG TGAAACCATG TCTCTACTAA AAATAGAAAA AATTAGCAGG GTATGGTGGC
ACATGCCTGT AGTCCCAGCT ATTTGGGAGG CTGGGGCAGA AGAATCACTT GAACCCAGGA
GACAGAGGTT GCAGTTAGCT GAGATCACAC CACTGAACTC TAGCCTGGGC CACAGAGTGA
```

Figure 15J

```
GACTCTGTCT CAAAAAACAA AACAAAACAA ACAAACAAAT ATATATATAT TAAAATACAA
ATTTTTACTG GGTTTAATAG TGTCTTCCTA GAAGTCATGT TCATGCATAA TCTGTGAAAG
TGGTCTTATT TGGAAATAGG GTGTGTACAG TTGTATTCGA GTTAAGCTGA GGTGATACTG
GATTAAATTG TATATGATGA GTGTCCTTAT AAGAAGAGGA AAAATTAAAC ACAGGAACAT
AGACTCAAGG GAAAACATCA CGTGAAGATG GAGGTAGAAT TGGAATGATG CATTGACAAG
CCAAGATGTG CCAAGGATTG CTGGCAGTCA CCAGGAGTTA GGAGACAGGC ATGGAACAGA
ATGGAACAAA TTCTCCCTCA GAGGCTCCAG AAGAAATCAA CCCTATTGAT ACCTTAATTT
GGGACTTCTA TCTTCCATAA CTGTGGCAGA GTACATTTCT GCTATTTTAA GTCATGATGT
TTGTGGTCAT TAGTTATGGC AGCGCATAAA ACTAACACAA CACTCTTGGT CTCTATCGCT
TCTTTTTTTT TTTTTTTTTT TTGAGACAGA GTCTCACTCT GTCTCCCAGG CTGGAATGCA
GTGGTGCAAT CTTGGCTCAC TGCAACCTCC AGCTCCCAGG TTCAAGCAAT TCTCCTGCCT
CAGCCTCCTG AGTAGCTGGG ACTACAGGCA CCCGCCACCA TGCCCATGTA ATTTTTGTAT
TTGTAGTAGA GACGGGGTTT CACCATATTG GCCAGGCTGG TCTCGAACTC CTAACCTTGT
GATCCACCAG CCTCAGCCTC CCAAAGCCCT GGGATTACAG GCCTGAGCCA CCATGCACGG
CCTCTATCCC TACTCTTAAT TGCCTGGAAA ATACCTAACA AATGAAGGCC AGTTTTAGA
CTTTACCACC AAAGGCTGAA ATTGAAACAG GAATTGTTTG TGAGAAGCAA ACACAATAGT
TTCGAGAGAC TGAATCAGTT AGCAATTTCC TGTGAGAGGC AAATGTAATA GTTTCTAGAA
CCACAGATGG AGCTATAACA AAACATGTG TTCTCTGGAT CCTTTACTTG CTACAGACAA
CACAATAAGT GAATTTACAG CTTTGATCTT ACAGTGCACC TAAGCCAACC ACCTTGTCTT
AGAATGTCTC AACATACCTA TCTGTATCTT GAAACAAAAT ATATTAATTG CCTTAGACCC
ATTCACTCAC ATTTCCTAGG AAGACATGAT CAGAGGGAGC TATGCAAGAA GAAATCCAGC
AGAACTCTGG AAATACAATA AGAAAATCCA TATTAGACAC TAATCTTAAT AAAACTAACC
TTCGTTCATG AATTTGAATA GACAAAATTA CCAAATAATA TGGAAAAAAT GGGCAACTCA
AAAAGAAGAG GGTAGCCCAC TTGGCATTCA GGACCAATGG CCTCCAATAA ATAAGATGAT
ATTAGTGCTT TAAATATTTT ATTTAGTGTA TCCAGTATAT TGCCTTCCTA AATTAAGTGA
AAGCTGATAT ATAAAAAGAA CTATTAGAAA TAAAAAACCA CACACATCCC AGAACTCCTC
AATATAAACC TAACAAATTC AGTAAAACAT TGATTGCAAA AATATATAT AGTGACTTAG
GGACTTCCTT GATAAATTTC ATAAAGCATA AAGAAAATC AAAGAGTGCA AACCATCAGA
AAAATACAAA TATATAAAAA AGAGAAATAC AGGTGATCCA AATTCCTTTT AATGGAATCC
CATAAGCAGA TGGGTGGAGG AAAAGTAAAA CTTCCAACAT ATAAGCACAA AATTTTTAGA
CCTTAAGAAA TATTTGAGTT TTTTATATCA GAAAGACAGT GTTGGGGTGA GGGTTGGGGG
GCACATGTAA ATACTCAGAT AAAATTGTGA ATTTTCTAGG GTAAAGAAAT CTGCATATTC
ATAGAAAACA AAAATGAAAA ATAGTTTATT TACAGAGTAA ATACATACGA CTGTTTACCT
GTAATGCTAA ATATTAAAAG ACAGTTTCTT TTCTTTTTTT TGAGACAGAG TTTCACTCTT
GTCGCCCAGG CTGGAGTGCA GTGGTGCTAT ATCGACTCAC TGCAACCTCT GCCTCTGGGT
TCAAGCAATT GTCCTGCCTC AGCTTCCCGA GTAGCTGGGA TTACAGGCAC CCGCCACCAC
ACCCAGCTCA TTTTTGTATT TTTATTAGAG ACGGGGTTTC ACCATGTTGG CCAGGCTGGT
CTCAAACTCC TGACCTCAGG TGATCCACCC GCCTTGGCCT CCCAAAGTGC TGGGATTACA
GGCGTGAGCC ACCGTGCTGG CCTAAAAGAC AATTTCATAC CTATTTGTAT GGCTAATTTT
TTAAAAATCT GGCCATATCA AAATACTGAA GAGGACGTAT AGCAATAGAG ACTTTCATTC
ATTGCTGGTT GAAATGCAAA ATGGTACAGC CAGTTTGAAA ACTAGCTTGG CAGATTCTTA
TAAAATGAAA CATAGATTTA CCATGCAACT CAGCAATGGC ATTCCTAAGC ATTTATCCAA
GTAAATGGAA AATGTATGTT CCCAGAAAAA AAATCCATAT ATGAATGTTT ATAACAGCTT
TATTCATAAT CACCAAAAAA AAAAAAAAAT CTGGAAGAAA ACAGGATATC CTTCAACCGG
GGAATGAATA AACCAAATTA TAATAATTGT AAATTGTGGG ATGGATAGTG AATAGTATT
CAGCGATACA AATGATTGAG CAATTAATTT GTGCAATGAC AGGGATGAAC CTTAAATACA
TTTACCTAAA TGAAAGATGT CAGGCCTATA TTGTATGATT CTTTTCAAAT GACTTTTTAG
AAAGGGCAAA ACTAGAAGGA TTAAATATAG CTTTATGGTT ACTAGAGACA GGTAAGGAGT
GGGTAGTTGA CTGCAAAGGT AATATATAGG GGAATGTTTA GCATGATGAA ACTGTTTTAT
ATGGCACTCA GGTGATGGAT ATATGGCTCT AGGCACTGAA AAACCCATGG AATTGTATGT
CACAAAGAAT GGACTTTCAT GTATGCAAAT TTTAAAAAAT AAACCAGAAA ATTGGGAGAA
TACTAGGATG GAATGCAGAC TGTGATAAAT AAAACTAACT GGACTCTCAG CAAACTAACA
CAGGAACAGA ACACCAAACA CCGCATGTTC TTACTTATAA GTGGGAGTTG AACAATGAGA
ACACAAGGAC ACAGAGAGGG GAACATCACA CACCGGGGCC TGTTGTGGGG TGGGGGCTA
GGGGAGGGAG AGCATTAGGA CAAATACCTA AAGCATGAGG GGCTTAAAAC CTAGATGATG
GGTTGACAGG CGCAGCAAAC CACCATGGCA CATGTATACA TATGTAACAA ACCAGCACAT
TCTGCACATG TATCCCAGAA CTTAAAGCAA ATTTTTAAAA AAGTAAAAAA AAAAAAAACA
AACAACAACA CCTAACTGGA CTACAAATGC ACTATATAAC TTCGATGAAG AGAGTGGGGA
GTAGGGAAAG GAACGGACTT AAATTACTCC AGAAAATAGT GTTGTGTTGT GACTAGAATC
```

Figure 15K

```
TATAAGGCTT ACGGTAAATG AAACTTTACA GGATCACTAT ACTCTAATTG GTAAATCAGT
TTTTCATGGG GTGCGGGTGA ACAGTTGTGA AACTGCTTTA CATGTAGTCA TACCTTTGCA
TTTTGCAGAT ATTTCAATTT TTACAAATTG AAGATTCGTA GCAACCTTGC ATCAAGCAAG
TCTGTCAACC CCATTTTTCC AATAGTGTGT ACGCATTTGG TGTCTGTGTG TCATATTTTG
ATAATTATAA CAATAGTTAA AACTTTTTCT TTACTATTAC ATCTGTTACA GTGATCTGTG
ATCAGTGATC TTTAATGTTA CTATCATAAT CGTTTTGAAG GTGCCATAAA CTGTGCCCCT
ATAAGTCCTG AAACTTAATT GATAAATGTA TGTGTTCTGA CTGCTCCACT GACCAGCCAT
TGCCCCATCT CTCTCCCCCT CCTCAGGCCT CCTGATTTCC TGAGACATAA TAATATTGAA
ATTAGGCCAA TTAATAATCC TACAATGGCC TCTAAGTGTT CAAGTGAAAG GAGTTGCATG
TCTCTCACTT TAAAAATCTA AAACTAGAGG CTGGTCATGG TGGCTCAGGC CTCTAATCCC
AGCACTTTGG GAAGCCAAGG CGGGGAGATC ACCTGAGTTC AGGACCAGCC GACCAGCCTG
GCCAACATGG CGAAACTCTG TCTTGACTAA AAATGCAAAA ATTAGCCAGG CATGGTGGTG
CACACCTGTA ATCCTAGCTA CTCAGGAGAC TGAGGCAGAA CAATCGTTTG AACCCTGGAA
ATGGAGGTTG CAGTGAGCCT AGATTGTGCG ATTGCACTCC AGCCAGGGCA ACAAGAGTAA
AACTCCTTCT CAAAAAAAAA AAAAAAAATA TCTAAAGCTA GAAATGATTA AGCTTGGTGA
GAAAGTCATG TCAAAACCAG ATAGGCTTAA AGCTGGGCCT CTTTTGCCAA ACAGCCAAGC
TGGGAGTGCA AAGGAAAAGC TTTTGAAGAA AATTAAAAGT GCTACTCCAG TGAACATACG
AATGATAAGA AAGCAAAAGA GCCTTATTGC TGGTATAGAG GAAGTTTGAG TATTTTGGAT
AGAAGATCAA ACCAGCCACA ACTTCCCTTA AACCAAAGCC TAATTCAAAG AAAGGCCCTA
ATTCTCTTCA ATTCTACAAA GTCTGAGAGG GCTGAAGAAG CTGTAGTAAA AAAGTTTTAA
ACCAGCAGAA TCTGGTTCAT GAAGTATGAG GCTAGAAGCC ATCTCCACAA CATAAAAGTG
CAAGGTGAAG CAGCAAGTGC TGATGGAGAA GCTGCAGCTA ATTATCCAGA AGATCCAGCT
AAAATCATCA ATGAAGGTGG CTACATTTAT TTTTTATTTT TGTTATTTAT TAATTTATTT
ATTTGAGAC AAAGTCTTGC TCTGTCCCCC AGGCTGGAGT GTGGTGGCAT GATGTTGGCT
CACTGCAACC TCCACCTCCT AGGTTCAAGC AATTCTCCTG CCTCAGCCTT CCCAGTACCT
GGGATTACAG GCATCTGCCA CAACGCCTGA CTAATTTTTG TATCTTTGGT AGAGACGGGG
TTTCACCACA TTGGCCAGGC TGGTCTTGAA CTCCTGACCT CAGGTGATCC ACCCGCCTTG
GCCTCCCAAA GAGCTGGATT ACAGGCATGA GCCACCACGC CTGGCCAGTG GCTACATTTA
AAAATAGGTG TTCAATGCAG ACAAAACCAT CTTTTATTGG AAGAAGATTC CAACCAGGAC
TTTTTTTTTT TTTTTTTTTT TGACACAGAG TCTCACTCTG TCGCCAGGCT GGAGTGCAGT
GATGCGATCT CAGCTCACTG CAATCTCTGC CTCCCGGGTT CAAGTGTTTC CCCTGCCTCA
GCCTCCTGAG TAGCTGGGAC TACAGGCACG TGCCACCATG CCCAGCTAAT TTTTGCAGTT
TTAGTAGAGA CGGGGTTTCA CCATGTTGGC CAAGATGGTC TCTATCTCTG ACCTCGTGAT
CCACCCCCCT TGGCCTCCCA AAGTGCTGGG ATTACAGGTG TGAGCCACTG CGCCCGGCCC
AGGACTTTCA TAGTTAGAAA AAAGTCAATG CCTAGCTTGA AAGGACAGGC TGACTCTCTT
GTTAGGGGCT AGTGCAGCTG GTGACTTTAA GTTGAAGCCA GTGCTCATTT ACCATTCCTG
AAATCTTAGG GCCCTTACCA GCTATGCTAA ATCTACTCTG CCTGTGCTCT GTAAACGGAC
AATAAGGCCT GGATGATGGC ATATCTATTT ACAGCATGCT TTACTGAATA CTTTAAGCTC
ACTGTTGCGA CCTACTGCTC AGAAAAAAAT ATTCCTTTCA AAATATTACT GCTTATTAAC
AATGCCTCTG GTCACCCAAG AGCTCTACTG GAGATATACA GGAAATAAAT GTTGTTTTCA
TGTCTGCTAA CACATTTGTT CTGCAACCTA TGGATCAAGG GGTCATTTTG GCTTTCAAGT
CTTATTATTT AAGAACTATA CTTTGTAAGG CTATTCCTGA CACAGATAAT GATCCCTCTG
AAGAATCTGG GCAAAGTCAA ATGGAAACCT GGAAAGGATT CACTATTCTA GATACTATTA
AAAGCATTCA TGATTCATGG AGGACGTCAA AATAAAAACA TTAATAGGAG TTTGCAAGAA
GTCAACCCTC ATGGATGACT TTGAGGGGTT CAAGACTTGA GCAGAGGAAG TCACTGGAGA
TGTCGCAGAA ATAGTATGAG AACTAAAATT AGAAGTGGAA TCTGATTTTA TAACTGAGTT
GCTGCAATCT TACGATTGAA CTTTTCTTTT CTTTTTTTTT TGAG
ATGCCCCTGC TGAGCTGCCA GTTCCTGAAG GGTCACCGGG AGCAGCGCCT GGCCCACCTG
>>........................EXON3     .........................>
GTCCTGAGCT TCCTCACCAT GGGTTATGTC TGGCAGGAAG GAGAGGCGCA GCCTGCAGAG
>.........................EXON 3    ..........................>>
GTGAGGGCCA GAGAGCAGCT TCTCCTGTTA CCCGGCAGGT TACCTGCGCC TGGAGTAACG
TGCTCCCTGC TTGGTGCTAC CCTGTTTTCC TGGAAAATGG GTACTTTCTT CTTCTCGATG
GGCATCAGTT TAAGCAACGA TGAAGGGCTC ATTTATTATT TATTATTATT ATTTTTTTAT
TTTATTTTGA GCCAGTCTCA CTCTGTCACT CAGGCTGGAG GGCAGTGGGG TGATCTTGGC
TCACTGCAAC CTCCCCTTCC AGGTTCAAGC AATTCTCCTG CCTCAGCCTT TCTTGTAGCT
GAGACTACAG GCACCCACCA CCACACCTGG CTAATTTTTG TATTTTTAGT AGAGATGGGT
TTCACCATGT TGCCCAGGCT GGTCTCGAAC TCTTGACCTC AGGTAATCTG CCTGCCTGGG
CTTCCCACAG TGCTGGGATT ATAGGCGTGA GCCACTGCGT TCAGCCTGAA GGGCCATTTA
```

Figure 15L

```
AATGAAGGAT TTTTTTATTT TAATTTTTCT GACTAAGAGC TAATTTGTTT TTTAAACTGG
TAGCTATTTC TTCCTTTTAT AAGCTTTTGA ATGTTTGTTT GTTTGTTTTT GGCACTCTCT
TCCAAGAATG TTTGAAGACC TGCATTTGAA GGCAGATTGC CTTTTTGCTT TAAAACAGGG
TTGCACCATG TTGCCCAGGC TGGAGTGCAG TGGTGCAATC ATAGCTCACT GCAGCCTCAA
CTCCTCCCAG GCTCAAGCAA CCCTCCCACC TCAGCCTCCT GAGAAGCTGG GGCTACCAGC
ATGTACCGCC ACACCCAGCT AATGTTAAAA ATTTTTTGTA GAGATGAGGG TCTTGCTGTT
TTGCCCAGGC TGATCTTAAA CTCCTGGCCT CAAGTGATCC TCCTGCCTTT GCCTCCTGTG
CTGGGATTAC AGGCGTGAGC CACCATGCCG GGCCTGAAGA CAGACTCTGA GAATTCATAA

SapI
                                                     --------
AAACCTCACA GCATTTGTA CTCTTATGTA TATAAATTAT CTAGGTTGCT CTTCATAATC

Cfr I
                        ------
CTGTAAAGTA ACAAGAGCCA TACCGGCCCA TTTTACAACT GAAAAGCACA GACACTTATT
TCCTTAATCA AGGTCAGACA GCAAATTAGT GGAAAAGCCA AGGCCAGAAC CCAGGTCTTC

SpeI
         -------
TGATTTTACT AGTGCAGCCT TCTTTCCCCA GGGACACAT TGACATTTAC AACACTCATC
TTTATTTTTT TTTTAATACT GCTTTCTATC CAGCCAATTA TTAGTCTGTC TTTTAATAAT
TCATCCAAAT CTCTTCTGAA TCATTGCATA ACTTTGTACA GTTTCCACCC ACAGTGTCTT
TTACTTTTAT TTTTGGAAGT AACTGTTTTT AAAAGTTACT GTTATTTTTA AAAGTGTGCC
TTCCCCAGAA ATCAGGGAGT TACCCATGTC CTAGAACTCC ACGGTGAAGA GAACAGCCTG
TGCCCATCGT GTTTGCCTGA TTGATCCTAC CTCTTGTCTC TCGGGGAAAC ACAGGAGACT
CAGGGAAGAG GAAAAGTGTA GAGTCATTGC AGCCTTGTTA TTTGTCAATG CATCTCTTTT
CTTTTTCTTT TTCTTTTTTT GATACAGAGT TTCACTCTTG TCGCCCAGGC TAGAGTGCAG
TGGCGTGATC TCGGCTCACT GCAACCTCGG CTTCCTGGGT CCAAGGGATT CTCCTGACTC
AGTCTCCTGA GTAGCTGGGA TTACAGGCAC CTGCCGCCAC GGCCAGCTAA TTTTTTTTGT
ATTTTTAGTA GAGACGGGTT TCACCACGTT GGCCAGGCTG ATCTGAACT CCTGACCTCA
GGTGATCCAC CCACCTGAGC CTCCCAAAGT GCTGTGATTA CAGGCATGGG CCCCAGCACC
CGGCCAGTGC ATTGCATTTT TTTTTTTTT TTCGAGACGG AGTCTCACTC TGTCACCCAG

EciI
                                    -------
GCTGGAGTGC AGTGGCACGA TCTTGGCTCA CTGCAAGCTC CGCCTCCCAG GTTCACGCCA

NarI
                                    -------
                                    KasI
                                    -------
                                    EheI
                                    -------
                                    BsaHI
                                    -------
                                    BbeI
                                    -------
GTCTCCTATC TCAGCCTCCC AAGTAACTGG GACTACAGGC GCCCACCACA ACGCCTGGCT
AATTTTTATA TTTTTAGTAA AGACGGCGTT TCACCATGTT AGCCAGGATG GTCTCGATCT
CTTGACCTCG TGATCTGCCC GCCTTCGCCT CCCAAAGTGC TGGGATTACA GGCGTGAGCC
ACCGTGCCCG GCGTGCATTT TTAAAAGTGT GTCTGATGCT GAAAAGTTTG AAGTCTAGGC
ACGTCCCAGT GGGTCCTCTT TATACCATCC CCTCTGCAAA CCATTATCCT AAATTGGGGT
TTGGGGGAGA GAAGAGTGAC AGTGGAAAGA AGTCTCCACC TCCCAGCTGT GCCCTGGTAG

SanDI
         ---------
TTCCAGGGGA CCCGGAGGCT CCCCACACCC ACCACCCCGC CTCAGATCAC CTTTCACTTT
CTTTGTTTCT CCTCCCTTGA CTTTTCAGCT CAGAAAGTAC CTGGCTCTCC AATGCCTTCT
```

Figure 15M

```
GAGGAAAGTT TACCCGAGGT TCACATTGCA AGACTCATTA AAGCTCTTTA GTGTTTTCCA
CCCGAGAAAA AATTCAAGGG AAAAATGAAG ACAAAAGCAG GGCATTCTTA ATGGATATTT

AflII
    ------
TATCTTAAGG AGAAATGAAA ATGGAGATGG AAGAGGGGGC ACAAGGATGG GGTTTGAATC
TAGACTCGTT CAGCCTTTAC CTCCGATAGA GAACCTCATA CAGCTTTTCT GGACTTCTGG
CTGATAAAGA GCCGTGGAGG GTTCCTTGGA TAAAAAAGGT TGAAGGGGGT CTGTCCTGTG
GTGGCTTACT TGAAGGTATT ACTGGGTTTG ACTTATGGAG TAAGAGACGG AGTCAGTTTC
CCCACAGGCT GAGGCAGTCT GTCCTCATGC TTTTCTAGGG CACTGTGGTC TCCCAGGCTC
ATACCTAGGT GCACACACAG GTTTCTGCAT CTAGCTTTGT ATCTCTATGA GTCGGTCAAT
                                                              NheI
                                                              -------
CAATAAATCT ATCTATCATC TGTCTACTGA TCTATCATCT ATCTATCTAG CTAGCTATCA
TCTCTCTATC ATCTATCTAT GTATCTATCA TCTCTCTCTA TATATGTGTG TATATATATA
TATATATGTA TATATATATT TCTATCCTTC CATCTACTTA CCTATCTATC AAAATTTTTT
TCCGTTGATA ATATTCTCGG GCCCCAGTTT ATGTTTAATT GTTTTGGTAA TGCCTTTCTT
TGCACAGTCA GTTACAGAG GTTATTTTAT ATTCTATATG TATGTGTGGT CCAGCGTTGT
AATTTTCACA TATATTGCAC CGTGTACTCA TAAGCAGTAT TTCCACTGGG TCATTAACAG
AAAGATATGT GTGCGGCATA TGAATGTGCA TCACTCAGGT AATTCAAGCT TGGTTCCCAG
ATCATTTCTG TACCACAGGA TTGCCGAAAT AAAAGACAAC CATGGTTATT TCCTCTGCTG
CAAGCTTTCT AGAATATGCT ATTTGTCTGG ATTTATATCT GAAAGGTCCT GCCAAGGAAT
                                                          >>...EXON4 ...>
CTTGCCCTTC CATTTGTCGA AGTCTCCAGG AACTTGGGGC TCCCTCCTAT CCTGGTCCAC
>............................EXON4 .....................................>
TCAGACTTGG TGCTGACGAA CTGGACCAAA AAAGATCCAG ACGGGTAAGG AAGGAAGAGA
>...................EXON 4 ...................>>
ATGCTTTGAA TTTCCATAAC TTTCCCCCAG GAAACACCCA GGCTTTTTTT TATAATTAGG
GAAGTTCATA TTTATGGTCT GCCGTATGGT TCCAAAGAAG GGGTGAGCTT GACCAAAAAT
TCAAATATCA CAGGCCCCAG AAGTTTCCTC TTAATCCATT CTGAACACAT GGCTCAGAC

DrdI
    ------------
CATTTTGTCT TGTTTGTTTC CACATGACGT GTGAATTTCT CAACCTGACC TTCAAGCTCC
TGCAAAATCA GCTTTTATTT GTTCTTTCTC TTCAAACTGT TTATTCCCTA AGATGCCCTC
CATTCATATC AGGTTAAAAC CAGTTGGCTT TGATAAGTAA TCATTATATA ATGATCAGAA
GAGAATGATT ATGGATGAAT TCAGAGCAGA TGCTCCAGGT GGGTTGGATT GAGAATTTGA
TTAATAATTC CATCTATTCC ACCAAAGTCA CATCATTCCT TGACAGTTG GCTGGGAAT
AGGGCATTT GTCTACAGAA GGAATAGCAT GAGATTTTAA CAAACAAGAA ATTCAACAAA
CAGAATTAGA CAGATGATCT GAGATGTTAA ATTTTCCTTT CACCTTAATT TTTGCAGCCA
AATTTATTTC AGCTCTAGAT GAAAGAGACA GCACTTTCTT TTGTGGCTGA CTACAACAGC
TGAAGATTCA CTGAGGTTTG ATATGAGGAA GAACTTCCTC AGCCATGGGA TTGCCAGAGG
CGATGATGGG AATCTACTTA AAAGGGTTAC ATATTTAGTA GACAGCCTAG ATTTTAAGAC

Eco I
            ------
            BsiEI
            ------
TAATTTATGT GCCCCGGCCG GGCCCGGTGG CTCACCCCTG TAATCCCGGC ACTTTGGGAG
GCTGAGGCAG GTGGATCATC TGAGGTCAGG AGTTGAAGAC CAGCCTGGCC AACATGGTGA
AACCCCGTCT CTACTAAAAA TACAAAAAAA TTAGCCGGGC ATGGTGGCAC ATACCTGTAA
TGCCAGCTGC TCGGGAGGCT GAGGCAGGAG AATTGCTTGA ACGAAGGAAG TAGAGGTTGC
AGTGAGCGAA ATCATGCCAT TGCACTCCAG CCTAGGTGAC AAACTCTGTC TCAAAAGAAA
AAAAAATTAT GTGCCCCATT GGAAGAAGTG AGATTCGGCC ATCTCATCTC TCTCGGGAGC
TCTGAGCCCT GGAGTTTTAT GTTTTCTGCA ATTATGAATT GTGATCCTTG ATTAATTATG
CTTTAATAAT AAAATGGGTG ACTACTGAAA GCTGCTGAAT CTGGGTAAGA ATTTGGATGA
AAAAAATAAT ATATGTGCGT AATTTATTCT GTTCAAGGTA CTGAATATTG AATAAGCTGG
ATTTATTACT CAAAGAGAAA GACAGAATAA GAGAAGGTTG AAGGGAAAAA TGACTGTACT
```

Figure 15N

```
AGAATGGTAG TCAAAAATGC AACAACAGGC AGGTGCAGCG GCTCATGCCT ATAATCCCAG
CACATTGGGA GGCCCAGGTG GGCAGGTCAC CTGAGATCAG GAGTTTGAGA CCAGCGTGGC

SfiI
   -------------
CAACATGGCC AAACCCCCTC TCTACTAAAA ATACAAAAAT TAGCCAGGTG TGGCAGTGGG
TGCCTGCAAT CCCAGCTACT CAGGAGGCTG AGGCAGGAGA ATCACTTGAA CCTGGGAGGC
AGAGGTTGCA GTAAGCTGAG ACTGCACCAC TGCACTCCAG CCTGGGTGAC AGAGTGAGAT
CCTATCTCAA AAACAAACAA AACAAACAA AACAATAACA AAAAGCTAT TAATAGCTTC
CTAGGGAGTA AGAGTGAAGG GCTAGTTTAA TTCCAGAGAT GCGGACACAG TCCTGGGTCT
CACCAATTAT TCTGCTTGGT AATTACCTTT TGAAGCCTTT TAATATGCCT AACACAGAGC
TAAGTGCTAT GAAGAAATGA AAGAAATAGA AGCAAAGTAC TCCCCATGTG GTTAAATAAC

PshAI
              -----------
AAGACACTAC ATGACAAATG TCAAAGAGTG ACTCAAACAA TATGTCCTTT AGAATTTCAG
AGAAATGACA TCAATGCAGG CTTTACAAGT CAGTAAAAAT CTTGGTGATG AGGCAGAACT
TGATGTAAGG CAAATCCTAA AAGTTGAGTA GGAATCAACT AGCTAGAATA AAATGTGGGG
TTGTGGTAAA TACAAAAATG TAAGATGAGT GAAATAACTT ATTTATTTAT TTATTTATTT
TCAGAGACGG AGTCTCCCTC TGTCTCCCAG GCTGGAGTGC AGTGGCATGA TCTCGGCTCA
CTGCAACCTC TGCCTCCTGG GTTTGAGCAA TTCTCCTGCC TCAGCCTCCT GAGTAGCTGG
GATTGCAGGC ACCTACCACC ACACCCGACT AATTTTTGTA TTTTTAGAGA GATGGGGTTT
TACCACGTTG GCCAGTCTGG TATCGAATCC TCGACCTCAT AATCCACCTG CCTCAGCCTT
CCAAAGTGCT AGGATTACAG GCATGAGCCA CTGTGCCCAG CCTAATAATA TATTAAGATG
GCCACAGGCC AAATATTCTG GGCTGGAAT GTGAGTGGAA ATGTCGCTCA CCCTTTATCA
CATAGCACCC CATAGTCCAG CCACAACTTG CAGAATTCAA AGTAAGTGTG GATGTGTGTG
TGCCTGCAGT GCCTTGCACA CAAGTGTGCA TGCCTGTGGA CATGTGACCC TAGAAGTTAT
TAATATATCT GGTTTACAAA CTGAATTGTT CTTTTATTTT TTTTCTCTCT TGGTGGTCAT
CAATAACTGA AATTGGGCTA GATTCCTGGA AATTGGGTAA GTTCTCAGAA ATCATTTACG
                     >>...Exon 5 ...>>
CACTTTAGAA TCCAGGCCAA ATTTAAAATC TTACAATAAA ACAAAGAACA AAGCATGCTA
AATTATATGT ATAATATAAT ATCAACCATA TAAAATGCAT AAAAAATATA CTAGAAGGAA
ATGTGCCTAA AATTCACAGT CTAAAATTTA ACAGTGATTG CCTCTTCCTT GTATAGATAA
GGGATTTTTT TTTACTGTAT TTTCCAGTCT GTACATAATA AACAAGTAA TGTGCAATGC
AAACAAAACA AAATGAAACT TTATCAAATT TCAGTAACTC CTTGAAGTTT AATTTTTTTT
TTGAGACTGA GTCTTAGTCT GTTGCCCAGG TTGGAGTGCA GTGGTGTGAT CTCGGCTCAC
TGCAACCTCT GCCTCTGGGT TCAAGGGATT CTCCTGCCTC AGCCTCCCGA GTACCTGAGA
TTACAGGCAC CCACCACCAC ACCTGGCTAA TTTTTGTATT TTTAGTTGAG ACAGCGTTTC
ACTATATTGG CCAGGCAGGT CTTGAACTCC TGACCTCAGG TGATCCACCC GCCTTGGCCT
CCCAAAGTGC TGGGATTGCA GGCGTGAGCC ACTGCACCCA GTTGAAGTTT AATAGTGTGA
AAAAAATATT TCTCATCTCA CTATATCTTC TATGGGAGGC CAGATTGCAG ATTGTCTACA
GAAAAATCCC TTCAAAGAC CTTGTTATTA CATAGACTGG AGCTCATGGG GCAGGTCTGG
TCCACACATC CTTAGGCTCC GCTTCTCCTG GAAAACAAAA ATAGCCTCTG ATCCAGTGTT
GCCTCTCCCA TCACCAAACC TCAGCTTCTA TCGCCAAACT CATCAAATAA GAGTGTCCAG
TAGAAAAACT GGGCAGATGG GGGCACAGAA GGTGAAGACA TCATTTCCCA AGCTAATGTT
GCTGCTGGAA CAATGTAAGT CTTGACTTTG TCTTGGTTTG GTTTGGTTTG ACATTGGTTT
GTTTTTCATC TTTGTCTCAT GCTTAAAATG TGAAGGGCAA ATATGATCCT TAGAGTTAAG
GTTTTAGGTT TTGTAGATGT TTTACTCCAT TTAAATGACA GCAGATCATT TAGAAATGAT
TCCTCTGTAA CAGCCTTCCA GATCCCATTC GATTGTACAG CATTGAGATA GATAGATAGA
TAGATAGATA GATAGATAGA TAGATAGATA GACGGAATTT GGCCCTGTGT TCCCACCCAT BamHI
                                                        --------
ATCTCATGTC AAATTGTAAC CCCCACATGT CAGGAGAGGG ATCCAGTGGG AGGTGACAGG
ATCATGGGGT TGGATTTCCC CAATGCTATT CTCATGATAG TGAGTTCTCA CAATATCTCA
TTATTATTAT TATTATTATT ATTATTGCAA CAGAGTCTCA CTCTATCTCC CAGGCTGGAG
TGCAGTGGTG TCATCTCGGC TCTCTGCAAC CTCTTGCCTC AGTCTCTTGC GTAGCTGGGA
TTACAGGCAT GCCCCGCCAT GCCCAGCTAA TTTTTGTATT TTTAGTAGAG ACGGAGTTTC
ACCATGTTGG CCAGGCTGAT CTCGAACTCC TGACCTCAGG TAATCTGCCT ACCTCGCTCT
```

Figure 150

```
CCCAAAGTGC TGGAATTACA GGCGTGAGCC ACTGTGCCTG GCCAGTTCTC ACAAGATCTG
ATGGTTTAAA AGTGTGGCAC TTCCCCCACC TCCTGCCGCC ATGTAAGATG CTTGCTTACC
                            StuI
                            -------
CTTCCACCAT GATTGAAAAG TTTCATGAGG CCTCCTAGCC ATGCTTCCTG GTAAGCCTAA
GGATCTCTGA GTCAATTACA CCTCGTTTCT TTATAAATTA CCCAGTCTCA GGTATTTCTT
TATAGCAGTG TAAGAATGAA CTAATACACA CATAAACAGA TTAGAGGCAG CACTGGCCTG
AGTTGTGAAA CTCTTCCCAG CCTGGTCCTG CGATTAGCTG GCTATATGAC CTTGGACAAG
CTGCTTTGCT TCTCTGGGCC ATGGTTTCAT ACCTGCAAAA AAAAGAGCAT GGACTTGGCT
GTTGCCTGGG TCTCTCTAGC CCTGTGGAGA ATCAGCTACA TCTCTTACTA GAACTTCTC
ATTCAGCCAG TTATTCCACT GCGGAGATGG TCCAGGACCA TTAGGGCCAT GCTAGACATT
GGGAGGCTGC CTGTCAGGTG AACATGAAAT TGAACTTATC TGTTCTCTTT CCTCCCTGAA
TGTTGCTGAA GGTAGATGCC CATCCTCAGG GCTGTCTTAC GGAGAGGAGA AAGTTGTGCA
GTGATTCCAC CCTGCAGTTA TCTAACTCGG CAGGGAACTC TGGGCAGTGA GTACTCACGG
                                    EcoNI
                                    ------------
TACAGTCTCC ACACCTCTAA TCATGTGCTC CTCTCCTTCC CAAGGAACCT GGAGACCATC
                                                >>....EXON 6 .....>
ATCTCATTTC CTGGGGAGA GAGCCTGCAT GGTTTTATAC TGGTGACTGC TTTGGTAGAG
>.........................EXON 6 ............................>
AAAGAAGCAG TGCCTGGGAT AAAGGTATCT TCTCACTTGA TAGCACCTTT TCTTTTAAA
>........EXON6 ..........>>
                    DraIII
                    ----------
TGAGCTTGAG CTTTACTTCC CACTCAGTGC CTTTCCTGCA GTGGATTTCT CAACACAAAT
GAACATAGAC CTTGTCCTGC TTAGTTCAAG TCTGAGAGAA GAGATCTAAG CTCTAGGCCA
                                            AhdI
                                            -------------
CCATATTTGC TCCCTTTTCT CAATTCCTAT AAAACTCGGA ATGGACCTTT TGTCCATTCA
ACAAACAGGC ATTGGTTTGG GCAATGGGAA ATTGGATCGA ACAAGACAGA CATTTTCCCA
                    BciVI
                    ------
GCCCTGACAG AAGCTTATGA TGGATACAGT GGATGAAGAT GGATTAACGT GGATTACAGG
TGTGAGCCAC TGCACCGGGC CTCAAACTGG AAATTCTTCA GGAGTCAGAC AGGTATCAGG
AAGGCTGGAT AGAAGACAAA AGACAGTGAT GCAGCTTGTG ATCAACTACA GCGTTAATGC
CTTGCCTAAA AATATTTCAG TTAGATTTCT GCCTTCGCTC TGTCGCTCAG GCCAGAGTGC
AATGGCGTGG TTTTAGCTCA CTGCAATCTC CACCTCCCAG GTTCAAGCAA TTCTCCTCCC
TCAGCCTCCT AAGTAGTGCA CGCCACCACG CCTGGCTAAT TTTTGTATTT TTAGTAGAGA
CAGGGTTTCA CCATGTTGGT CAGGCTGGCC TCGAACTCCT GACCTCGTGA TCTGCTTGCC
TCAGCCTCCC AAAGTGCTGG GATTACAGGT GTGAGCCACC CTGCCCAGCC AACACTACCT
CCCTTGATAA GCATATGTTG AGCACCTACT GGTCCTCAAT AGGGTGACCC ATTTCTGCTA
        Eco III
        -------
TATTATAGCG CTTTCTTTCT CTCTCAGTAG TTAAACTCCA TGGTTACTTT AGTTCTCATC
CATGTGTTTA GTCCATTAGA AGATACAGAG TCAAATATCG GCCTTCCAAG TGTAGTTCAG
ATGAAGTAGA GACTCAAGGA AGACAAGGA
```

Figure 15P

```
AGTCTTCCCA GCAGAGGGGA TTCTAGAGCT GGGGGCTCTG TAGAATCTGT CTGTGTATTA
GTCCATTTTC ACACTGTTAT AAACATACTA CCTGAGACTG GGTAATTTAT AAAGGAAAGA
AGTTTAATTG ACTCATAGTT CTGCATGGAT GGGGAGGCCT CAGGAAACTT ACAGCCATGG
AGGAAAGTGA AGGGGAAGCA AGAACCTCTT CACGAGGCAG CAGGAGAGAG AGCAAAGGGG
GGAGCTGCCA AACACTTTTA TACAATCAGA TTTTGTGAAA ACTCTCCCTC GTATCATGAG
AACAGTATGG GAGAGCCCAC CCCCATAATT CAATCACCTC CCACCAGGTC CCTCCATCAG
CCTGTGGGGA TTACCATCCA AGATGAGATT TGGGTGGGGA CACAGATTTC AACACAGATT
TAAATCTGAC TTTATATGAG AGCTTCGGAG CAAGGATGCC CCAGTTGGAG ATGCAGTAGA
ACTGATCATA ACGTGACAAA TCCGAGAGAA GAAGAGTAAA ATAATAGTAC TCAGGCCCTT
GGGAGGTGCA AGAAGTAACA GCCAGATGAA ATTCCAGAAA CACTTACCTA GGGGTCTGTC
TGGGAGGTCC CCAGGGAGCT TCTGGCTGTC AGGCCAACCC CACAGTGGAT CTAGCTTAGG
ACGTTCCCAG GAAGCTCTGA CAAACTGTCC GGTCCTCCCC TGGGTTCCAA CAGTATGAGG
CTTACTCTGC CTGCATGGAC TTTAAGGGAG TGCTAATAAG TTGTGTACAT GCATCTCATC
CCTAGGCTCT TGTTCAGGCC ACGAATGCTA TCTTGCAGCC CAACCAGGAG GCCCTGCTCC
  >>............................EXON 7 .........................>
AAGCCCTGCA GCGACTGAGA CTGTCTATTC AGGACATCAC CAAAACCTTA GGACAGATGC
  >............................EXON7 .............................>
ATGGTAAGAT GCTTCCGAAG CTCCTGAAGG ATCCCCCAGG GGTCCTGGGC TCTGCTTAGG
>>>
GGAAGAGGGC CTGGGGACCA GGCATGTCCT GAAGGGGGTG ATAATACATT CATCCACCAG
ATGACGCTGG TGGACTATCT TTGTTTTAGG TTAAACACAT ATTATCTTGG AGAGCTATTG
TCACAGCTTT GTATTCTCCC TCTCCTTTAT ATTCTCCCGT GATTAAGATG GTTTCCCTTC
TGCAGTGGCC AGATATTTCT TAGGCATGTT GAGGTCTTGC CTGAAGCTTG AGAGGAGGGG
ATGGGATGCA CAGTAATGTT GGTCGCGCGT GCCCCATCCT GCAGTGTTAG GTACTGCAGA
GCAGGTTGTC TACACTCTGT AATGCCCCTT TTATTCTAAC CCCCTGTGTT GGTTCCTGAG
ATGTCTGACC TTGGTTTTAA GCCTTGTCTA ATGGATGGCC TGTATTCCCT TTCTGTAGCT
AGGGCAGGCT GATTTGTCAA AGGTAGGAAA GTTGTCAGAA TCAAAATGGA GTCACTTGTG
TTGAATAAAA ATTTTTAAAC CTTGACAAAT AGAGCTGGGG AAGGCTACAA AGAGAGAGCT
CCCGTGTATA AATGCCTGAT AACAAAATCT TTTCCAAAGG ACTGAAAAAA TCACCACCTT
GCACAAAGGC CATCACAACC TTACATACAC AAAAAAATAC TTACACAACG ACATCTGCCC
AGCAACTGCC TTTCCAACAT GGCCTTGTG CCACCCTTTT TATTGATGCT CATAGCCAAG
GTTAATGATC TCAAAACAGT TACATAATTG TCCTCATTTT TCCTTTAAAA ACCTTTGTCT
TCCTTTATCT TTCTGAATAC CCACATGGTT TATTATGGCA CATGTATTCC CATTGCAATG
CCCTATTCCA GAATAAATAT CAGTTTCCAT TAGGGAGCCT CTCCCTGTTA ATCTGCTTAA
                                                  AgeI
                                                 -------
CACAGGCATG GTCAGTTACG GGCCCAACC TTCCTGGACC GGTTACATCT TATTCTGGTT
ACTGCATTCA GTTTCCAACA TCTGGGAGGC TCTTCAAATT CTTCTCTCAG AGGAATCTGA
AGAATGTATG TGTTTAGGAG GATGTGAGAG AGGGGTGTGG TTTCTTAACA AGAGAATATC
AGAGTCTAAG TATCATTTTC CCTGAATCTT GCTTCCCTGC AGGAAAGAAA GATTCTGGGA
AAAGAGAGTG TTTACAAGAA GCAGGACTGG AGGGAGGGAG AAAGACGCTA GGTACTGCCA
AGCTTTATTA TCTTGTATTA AAAAAGTAAA TATAATTTGT CATCCCAGCC TCTCAGCACT
AGTAGAAATC TATCTGAAGT CACAGGATTA GGTATTATCC ACTTCCTGGT TTTATAGTTT
ATATTTGTAT TTTCTCTATT TCCTTGAATT TTAATTTTAA AGCCCTCATG ATCACATCAG
TAGGTCTTCT GCCAAACAGC TCCCTTAAGT TGTATGGTGG CTTTGCCAAG CTGAAATGAG
ATGAGATGTG TTTTAGCTTT GCCAAGAAAG CCTGAGTCCA TCACTTAGGA TAGCAAGGCT
ATTAGGGAGA TAGTGCAGGT GTCTTCAGAT CACATGGATG AGCAAAAGGA AGCAATTTTG
GAAGATTATG AGAAACCTTC CAACAGGTCC CAGTGTACAT AGCAGTAAGA TGGTGCATGC
AGTGTCTAAC TGTCACAGGC TTTCCTAGGG CTCACTTTCA GACTCACTTC TTTTTTTTTT
TTTTTTTTTT TGTGAGATGG AGTCTCACTC TGTCACTCAG GCTGGAGTGC AGTGGCACGA
TCTTGGCTCA CTGCAAGCTC TGCCTCCCGG GTTCAAGCGA TTCTCTTGCC TCAGTCTCCC
TAGTAGCTGG GATTATAGGC ATGCACCACC ATGCCCAGCT AATTTTTGTA TTTTTAGTAG
AGATGGGGTT TCGCCATGTT GGCCAGGCTG GTCTCGAACT CCTGACCTCA GGTGATCTGC
CTACCTTGGC CTCCCAAAGT GCTGGGATTA CAGCCGTGAG CCACTGCGCC CAGCTCAGAC
TCACTTTTTA GGCCCAGGCC AACCTGCTGT GTTCTCCTGC TCAGCTTCTG CAGGAGGTCT
CATCGTCTAA GGAGGTCCCA GGGCTACCGC CCTTGTTTTC TCAAAAGGCA CATTTTCCCA
CACAGACATA ATTTCGTTTC AGTGTTTTAC TCCTAGTCAC ATTCATCTAT ATGGACAAAT
```

Figure 15Q

```
                                                BssHII
                                                -------
AGCTGAATGG ATTGGACTGT GTTTTCTAAA GATGGCCCCA TGCCATCCTG CGCGCTCCTC
CACAGCGTGG CCTGGGCATT CCTTTCGACC AGGGGTGGAC TCTGTGCCCC TACTTGTGAT
GTACGTGTTG CCAATAGAAT GTAGTATAGG GGATAGCACA GACTTCTGAG GCAAGACTAG
AAGAGGTGAT GCAGGTTTAA CCTTGTGTCC TGAGCCACTA GGTAAAAAGT CCACCTACCC
TGAGATCACT CTGCTGTGCA AACGACACAG GCAAACCACA TCAAAGAGCC ATGTGGGTTC
TCCAGTTGGC TTCTGCCCAG GAGTGAAGGT GCCCTCAGAT GGTTCTAGGC TCCCATCCCA
ACTTATGTCC TGTCTTGAAG TCTTCCCAAC TGAGGCACCA GCCACTGTGG AGCAGAGTCA
AGCCATTGCC ATCTTGTTCT GCCCAGATTC CCCATCAACA GAATATAGTG GTTTTTTCAC
ACCTCTATGT TTGGAGTGGT TTCTATGCAG CAATAGTAAC CACAAGAAAT AAAGTTATAA
AAATAGTAAC AAACACTAGA AACTGCAAGA TTTAAGGAAT CACCTGAATG CTCCAGTCAT
TGTCTCTGGT TTGTAATGAT AAACTTTCTT CTGCGTGATA AATAGAGCTT GGCTGGACTT
TTTCCCTCTG CTTCCATTCC CCAAAATGGA GCGTACCAAA CAATTGCTTC TTTCAGAGCC
CAGCTTTAGC AAGAGTCATG AGCTCTAATC CCTTCATCCA TAAATACTTC CTTTCCAGGC
ACGTAGAGCC CTTCACACTC AGGGCTGAGT AGAAAATGCC TGTTGCAGAC TGCAGTGGCG

KpnI
                      ------
                      Acc I
                      ------
TTTTGGAGAG CCACCCTCCT GGTACCTGAG TCACTAGTCC TTTGCCCAGC TTTTCTCAGT

Eco III
   -------
TTTGTAAAGC GCTCACTTCT GAGTGGAAGA CAGAACCAGC CCGGTCTATT TTCATAATCT
GCCCCCATAA GGCAGAAGTC CACACGGTAC TGGAAACATA ACCATATCTA TGTCAGTCTG
CCACTGCCTG CCGCCTGTCA ACCGTGCGTG TCTGCATCCA GTCCTTCTTT GGAGCTGCTT
TCCAGCGACT CAGCCAGATC TGAGCTTTCT GACTCATTGG AAGGTTAAAC TATTTTCAGA
CTTTCAAGTG TTGAGATTAT TAAGACATGT GTTTTTTTT TTCTTCTTTT TTTGGCATGC
TTACTGATCG CCCCTGTTCT CTAGGAAGTA ATGTTCTTCT TGGAAAAGGT GAAGGATATT
TTTCTCCCCA AAAAGCCATG GAAATGTTTG CCTTTATTTA CTTCCAAATT AACAGAATTT
CCAGCTTTTG CTTGACCCAT CGGCGCATTG GCAGCGTTAA GAATTTTTTC TTTTAGCAGT
AATGAGGAGT CGAAGGGTTT CTTCCTAACC ATTTAGTGTA TGCATTTAAA TCAGGTTTCT
TTTTGAGTAA ATTGGGGCTA AGCTGTAGTG TGAACTTCTG CTACTGTTCC TTTCTCATTA
GTTCACTTGA TTTCATGGAA GGAATTTTCC ATCTCAGCCT GTGAACTTAT TTTGTCTAAA
CTCAATTGGA AAGTAATTAA CACTGAGATT CTTCTTTAAT AAATTCTATA TGATAATAAA
ATCATACAAA CATCTCTTTA TTTTTCTTTT TGACCTAGAA AAGATGTTCA CAGGCCAGAC
CTGGTGGCTG AAGCCTGTAA TCCCAGCACA CTGAGAGGAA GAGGCGGGTG GATCACATGA
GGTCAGTCCG AGGGCAGGGT AGCCAACGTG GTGAAACCCC ATCTCTAGTA AAAACACAAA
AATTAGCTGG GCATGGTGGC ACATGCCTGC AATCCCAGCT ACTCAGGAGG CTGAGGCAGG
AGAATCACTT GAACCTGGGA GATGGAAGTT GCAGTGAGCC TAGATCCTGC CACTGCACTC
CAGCCTGGGC GACAGAGTGA GACTCTGTCC CCAAAAAAAT AAATAAATAA AAGATGTTCA
CAATATATTG TTAAGTGAAA AAAGCAGGCT ACATAACTTG CATAATATGA GTGCATTTTA
ATAAAAATAT ACATATTTAG CAAAATAAAA GGACAAATGG TATTTATTAA AATATTTACG
TTGATTATTT CAACACAGAG GATGATAGTT GATTTGCTT AATTTCTTCC CTCCTTCTTT
TCAATTTGAA TTTTCTATAA TGAAGATTGT TTCTTTTTCT TTCTTTCTTT TTTTTTTG

NarI
                                         ------
                                         KasI
                                         ------
                                         EheI
                                         ------
                                         BsaHI
                                         ------
                                         BbeI
                                         ------
AGATGGAGTT TCGCTCTTGT TGCCCAGGCT GGGGTGCGAT GGCGCCATCT CGGTTCACCA
```

Figure 15R

```
CAACCTCTGC GTCCCAGGTT TAAGTGATTC TTCTGCCTCA GCCTCCCTAG TAGCTGGGAT
TATAGGCGTG TGCCACCACA CCCGGCTGAT TTTGTATTTT TAGTAGAGAC GGGCTTTCTC
CATGTTGGTC AGGCTGGTCT CGAACTCCTG ACCTTAGGTG ATCTGCCCAC CTCAGCCTCC
CAAAGTGCTG GGATTACAGG CATGAGCCAC CGCGCCTGGA CTGATTATTT TTTAAATAGG
GTTAGAAAGT GAGGAAGTTA CTAAACTCCG ATTAGCCCAA ATATGCCCCA GTGGGTCCTT
CTGGCAGAGT AAATGTCTCG GTTCAGCCTG AATCTGGGAA ATTGTTCCTA CGGTTCAGCC
TGAATCTGGG AAATTGTTCC TACCTTATAA ACTGGAGTAT CCTTCAGAAA TGACATTTAC
TCAAACTTCC TTTTAGGCAG ACTGCATAAT AGCAATTTTT AATATTAACC ATTTAAAAAA

PacI
           --------
AACCTTCAGA TTAATTAACA CCAAAAGAAT AATTGGGAAA ATACAACTCC TCACTTTAAA
AAAGAAACAA CCAAAGTAAA TACTAAAAAA CTATATGATG TTATATTATC TAAGCTTAGT
TTACTGCAAA GATCAAGAGC ACACTACTAG TTGACGGCCT CTATTCACAC TGTTCATAGC
CCTCGCTCGC TTCTCCAGCC ATTCACTCAC TCATGCAAAA GGTCTGTACA CACAATGATG
CCTGATGGTA TAATAGGAAC CTTAACATTT CAATTAAAAG GCAAATGAG GACACTTACC
ATCAGCCTAT AAAATTATTC TTATTATTCT TCTTCTTCTT CTCCTCCTCC TCCTCCTCTT
CTTCCTTCTT CTTCTTCTTC TTCTTCTCCT TCTCCTTCTC CTTCTCCTTC TCCTTCTCCT
TCTCCTTCTC CTTCTCCTTC TTCTTCTTCC TCTTCTTCTT CTTCTTCTTC TTCTTTTTTT
TTTGAGATGG AGTCTTGCTC TGTTGCCCAG GCTGGAGTGC AGTGGTGTGA TCTCGGCTCA
CTGCAACCTC TGCCTCCCAG GTTCAAGCTA TTCTCCTGCC TCAGCCTCCC AAGTAACTGG
GATTACAGGT GCATGCCACC ACGCCCGGAT AATTTTTTGT ATTTTTACTA GGGATGGGGT
TTCACCATGT TGGCCAGGCT AGTCTCTAAC TCCTGACCTC AAGTGATCCA CCTGCCTCGG
CCTCCCAAAG TGCTGGGTGT GGGCGGCAAG CCACCCAGGT GCCAAGGCAA GAGACAGAGG
GCACGAGCTG TTCCAGTATA ATGAGGAAAA TATATAGAAT AAGAATAGTT ATACTAGAAA
TAGATTATAG ATATGATTAC ATATGAATAT CATTCTTCAT TAGTTTGTAG CACTACTCTT
TATTCCAGTA TTATAATAAT CTTTGTTCTA CAATTATAAC CTAGGAAAAA CCAGGCCATA
CAGAGATAGG AGCTAAAGGG ACAGGGTGAG AAGTGACCAG AAGAGTGTGA GCCTTCTGTT
ATGCCCGGAC AGGGCCACTA GAGGGCTCCT TGGTCTAGCG GTAACGCCCG CGTCTGGGAA

RsrII
           --------
GATGCCTGTC ACCTAACGGA CCGTGGTCTA GCGGTAGCGT CAGTGCCTAG AAAAGGCACT
CTTTTTAAAT ATACTTTTTA TTTTTGTTTA ATCTTCCCTG ATTTCCTATA GATCTGAGAT
ATGTCATGCT TATTTTCATT GCTATCTAAA AATCTCAATA AACTTTATAC CTAAGAGTAA

BsiEI
                              ------
AAAAAAAAAA AAAGAAAAGA AAAGGCGCTC GTTACTTAGC CGACCGGGAA AGGGAGTCTC
CCTTTCCCCG GGGGAGTTAG AGAAGACTCT GCTCCACCAC CTCTTGTGGA GGGCCTGACA
TGAGTCAGGC CTGCCTGCAG TCATCTGGAG GCCTAACCGT CTCCCTGTGA TGCTGTGCTT
CAGCGGTCAC GCTCCTAGTC CTGAACACCT GGCTCCGCCT TTAGATAGC AGTAGCAGAA
TTAGTGAAAG TACTAAAAGT CTTTGAAATG CAGAAGTAAT GGCGTAAGCT GTCACGTCTC
TCTCTCCGCC TCAGCTGCCA AACAGAGAAG GTCCCCTGT CCAGTGGACA CGTGACTTGG
GTGACCTTAC CTGTCATTGG AGACGACTCA TACTCCTTAC CCTGCCCCTT GCCTTGTATC
TAATAAATAA CAGCTCAATC TGGCATTTGG GCCACTACT GGTCTCCGCA TCTTGGTGGT
AGTGGTCCCC CGGGCCCAGC CGTCTTTTAT TCTATCTCTT TGTCTTGTGT CTTTATTTCT
ACCATCTCTT GTCTCCGCAC ACGAGGAGAA AAACCCACAG ACCCTGTAGG CTGGCCCCT
ACAGCTGGGA ATTACAGGCA TGAGCCACCG CATCCAGCCA GCCTAAAATT CTTCTGAAGG
ATAATAATAT AGTACTTGAA GACACGGTTT GAAAAAAATC ATACTAAATG AAAGGGCACC
ATTTTACAAG CACTAGAACT ACATTAAACT TAAATGAATT CCAACACTCT TAATAATGTA
ACTCAAAAAC AAGTCTAGTG TTAACAAAAG CTCCAATAAC TAAAACTACA TTAACAGGCA
CAATGAACAT TGTAAACGCC GCTAATTGGC ACCAAGTTTA ATAGGGCAGA CAATATTTTC
TTCTGCATTC ACACTTACTC AGTTACACTG TTGAAAAATG CTGCTGCTCA AGCTATGAAT
GCTTTACAAA AGAAATCATT TTAATAAATA CAGTAAATGC TAAAACTCTA GCTAAACTAT
TATGCAAGAT ATACAACCAA GACAAATACA AATTCATAAT ACAAGCAACT TGCATTCAAA
ATGAACTCTA CCACTATATT TTATTAAAAG GGCAGACTTT ATGAATTAAC CCAGCTGCTT
CCTGAATTAC AAAAGTGGCA TGACTCAATA TGAAAATAAG AAACTGTCTA CAAATTTCTG
ACAGTAATAA ATTGTAATAT ACAATACATG CAGGAGTCTT ACGGAAGAAT AAACTCTCCT
```

Figure 15S

```
AGGAAACAAA AATATTTTAT ACTTTTAAAA TCCAAAGTAA AAAAAAAAGA AATCATTGCC
AGATGCGGTG GCTCATGCCT GTAATCCAAG CACTTTGGGA GGCCAAGGCA GGATCGCTTG
AGCCCAGGAG TTTGAGACCA GCCTGGGCAA CATAGCAAAA CCCCATCTCT ACAAAAAAAT
ACAAAAATTA GATGGTAATG GTGGTGAGCG CCTGTGGTTC CAGCTACCCA GGAGGCTGAG
GTGGGAGGAT GCACCTCAAG GCTGCAATGA GCCAAGGTCA CACCATTGTA CTGAAGCCTG
GGGACAGAGT GAGACCCTGT CTCAATAAGT AAATAAATAA ATATCTTTTA TGAAAAGAT
TCTCTAGTCA GAATTAACAC CTCAACTAGC CAAACATCAG GAAGTTACAT TACAGCTACT
TAATACACAA AGGGACACAT TTTCACCAGT CGTTGTCTTC TGATATTTCT ATTCCAGAAA
CACACACTCT CACTTCCCTA CACTCCCCAT CCCATCATTT CTTCAGAGCA TGGAAACAGA
ATTTGTTGAA CACCAGAAAT CTCTTGCTAT GGTGGTACAT AAGTCATAAC ATTTGTTGCT
GCCCAGCAGC AGGTATGAAG CCGGCTGGTG ACTGGCTAGC AAATGCCTAT TCTGTAAGCT
CCTCACTTAG CCCATCTGTA GCTCTGACTT CTCCACCAAT TCCCTTCTCT CCTTTCACAG
CCTTTCTGAG TTTCTGAGGG ATAATTTCAG AGGTTCCATA TAACTGTCAA AGCCTATGGT
AGACATGGCA AAGTGAAAAT CCTCTCCACT GGCCATTTCT GTTTCTCTTG GGGCATCTT
TCACTTGCCT CAGGTGTTAT AAAGCTGATG AACACACGTA CACGTTGTTT AACACTTTCT
TGGGCATTTC CCATTTGAGA TATGGCATGT TCATTATCC TAGTGACATG TGCAATCAGA
AAATGTATAT TTTGTTCTCT GCAACTTTCT TTTGAAAAAT GTATATTTGA ACAAAATATA
CATTTTTGT ATCTTCATGA CCATTCATGC TGTCCTCACT GTCATCATGA GGCTCTATAT
AACATAATGA CTCCTCCAGG GCAGTCTTCG GAAATTCCCA GTGCAGAAGC ACGTGTCATA
CAGCAGTCCC CATTCATCTC CAGTGCAGCT CTGGCTGGCT CCCATGTCTG ATCAGCTGTT
TGGTTGGACA GAAAATGACT GCAAGGGAAT CAGTTCCAGT GTGAGCTCTG TTTGCAGAAC
TCAGACTCCC CTCCCTCCCA TGTTAATGCT TTTTTTCTTC TTCTTTTTTT TTTTTTTTTT
TTTTTGACAG AGTCTCATTC TGTCACCCAG GCTGGAGTGC AATGCTATGA TCTCGGCTCA
CTACAACCTG TGCCTCCCCG GTTCAAGCAA TTCTCGTGCC TCAACTTCCC GAGTAGCTGA
GATTACAGGT GCACACCACC ACACCCCACT AATTTTTTTG TATTTTTAGT AGAGACGGGG
TTTTGCCATG TTGCCAAGGC TGGTGTCAAA CTCCTGAGCT CAGGAAATCC ACCTTCCTCA
GCCTCCCAAA GTGCTAGGAT TACAGGCGTG AGCCACCATG CCCAGCCCCA TGTTAATGCT
TCTAAAGTTT GCCCTCACTT CTTTAGAAAT TCCTTCAGTA CATCCTTTAA GACTTCCTCT
AGTGAGTGTC TGCTGGTGGT AAACTCTCCC CTCTAAAAGT TGCTTTATTT CTCCTCAATT
CCTGAAGGAT ATTTTGCTA GCAGCTATAT TCTTTTAGAT GTTGAACATA TCGGTACAAA
AGCTTCTGGT TTCCATGGTT GCTATTGAGA TGTTAGCTGT CGGTTTATCT TTCTCCCCTG
ACTATGTGTA CCTGTTTCTC TGTATCTGTC TACTTTTTGG GTTGCTCAAT TTATTGGCCT
TGGGCTTCAT TCTGCTGCTG CTTTTTTTTT TTTTTTTTTT TTGAGATGGA GTCTTCCTCT
GTTGCCCAGG CTGGAGTGCA GTGGTGCAAT CTTGGCTCAA TGCAACCTCT GCCTCTCGGT
TCAAGCGATT CTCCTGCCTC AGCCTACCGA GTAGCTGGGA TTACAGGCAC CTGCCAACAC
GCCAGGCTAA TTTTTGTATT TTTAGTAGAA ATAGGATTTC ACTATGTTGG CCAGGCTGGT
CTCAAACTCT TGACTTCAGG TGATCCACCC ACCTCAGTCT CCCAAAGTGC TAAGATTACA
GGCCTGAGCC ACCACGCCTG GCCACAATTT TTAAACTTTT TATTTTTACA GGCACCTGCC
AACATGCACA ACTAATTTTT GTATTTTTAG TAGAAACAGG ATTTCACTGT GTTGGCCAGG
CTGGTCTCAA ACTCTTGACC TCAGGTCATC CACCACCTTG GTCTCCCAAA GTGCTAGGAT
TACAGGCGGG AGCCACCATG CCTGGCCAAA ATTGTTAAAC TTTTTATTTT CTTCCTCAAG
AGGATGAGAA GAAAGGTCAA TTGTAAGCTT TAGAAGTCTT GCCCAATAGC CAATCTGAGA
ATATTCTCCG TAAACATTCA CCAGAGGCAG CCAGTGACCA TGGGATACTT TTGGTGAGAG
GAATTGATTG CTGGGGTCAG GAATGGGAGG AAAGCATACT TCTCATTAGA TACCTTGTTG
AACTTCGTAA ATTGTGTGCC AAATGCATGT CTTACCTAGA CTTCATAAAT TAATTTCTTT
AAAAATAATC AAAGACAATT TTTTAAAGAC TTATTTAATT TAAGGTGATT ATAAAACATC
CAGTATACTT TCACTATTAA AAAAGTAAGT ATTCCTGTCT GGGCTTGGTG GATCACACCT
GTAATCCCAG CACTCTGGGA GGCTGAGGTG GTCGGATCAT GAGGTCAAGA GATTGAGACC
ATCCTGGCCA ATATGATGAA ACCATGTCTC TCCTAAAAAT ACAAAAACTA GCTGGGCGTA
GTGGCGTGCC TGTAGTCCTA GTTACTCAGG AAGCTGAGGC AGGAGAATCG CTTGAACCCA
GGAGGCGGAG GTTGCAGTGA ACTGAGATCG TGCCACTGCA CTCCAGTGTG CAACAGAGT
GAGACTCCAT CTTCAAAAAA AAAAAAAAGT ATTCCTAAAC AGCATATTAT CATGATATAT
TATTTTGTTT TGTAGGGTTT TGAACCTTGT CTAAAAGAA TTAAAATGTA TAAATTTCTT
CCTGCAATTT CCCTATTTCA CTAAGGGTCA TTCACATTGG TCATATAGAC ATAGCACATT
TTCACCACTA TATAGCAGCA TTTTGTACAA ATAGACTACA ATTTACTTAT TCTGCACTTA
TTTCTGTTTG TTTGTTTTGC TATGAAAAGC AATGTCATTA CATATATTCA TGCCCATAGC
TACAAGTTTA CATATTTCAG GTTTTCTGTA GGGTGGACAC CAGGGAGTTG AATTGTTCAA
CAGGACTTTA CATTCATCTT TAGTTTTATT GGCCAACACC AAATTGTTCT TCACAATGTT
TGAACTAAGT TGAAATTCCA CCTCCCCATC ACATTTAGTT TTGTCAACTT CATTTCTTCA
```

Figure 15T

```
TTCATTAATT CATTCATTCA GTCTTTTGTT TATTTGTTTA TTGCCAGTCT GATAGGCGTA
TAGTGGTGCT TCATCATGGT TTTACTTTGC ATTTCTCTGA TTTTCTTTTT AAATTTTTAA
AAAATTATTT TTATGTAGAA ACAAGGTCTC GCTACATGGC CCAGGCTGGT CTTGAACTCC
TGGCTTCAAA TGATCCTCCC ACATTGGCCT TTCAAAGTAC CGAGATTGAT TATAGGCGTG
TGCCACTGTG GCCAGCTGAT TTCCCTGATT TCTGATGAGT TAACAATCTC TTCTTTCTCT
CTCTCTCTCT CTGTGTATAC AGGTACTCAC CATTCGTGCC TATTTTCTGT AAAATATGTG
GCTTTCCTCA TTTTTTTTTT TTTTTTTTTT TTTTGAGGCA GAGTCTCGCT CTGTTGCAGG
CTAGAGTGCA GTGGTGCGAT CTTGGCTCAC CACAACCTCC ACTTCCTGGG TTCGAGCAAT
TCTCCTGCCT CAGCCTTCAG AGTAGCTGGG ACTACAGGCG TGCACCACCA TGCCCAGCTA
ATTTTTGTAT TTTTAGTAGA GATTGGGTTT CACTATGTTG GCCAGACTGG TCTCAAACTC
CTGACTTTGT GATCTGCCCA CCTCAGCCTC CCAAAGTGCT GGGATTACAG GAGTGAGCCA
CTGCGCCCAG CCATCTTTCC TCATTTTAT ACTAATTAGG CTTTTATCTT ACTTGTTTTT
TTTAATGTTT TTTGTACACT CTGAAGGCTG ATTTTTGTTA ATTGTATGTG TTGCATTTTT
TATGGTTTGT CTTATGCCTT TTGAAAGTAA AAGTTCTTAA TTTAAATATA GCCAACCTGT
AAATCATTTG TGAAAGTCTG TGGTTTAAGA GGTCTTGAAT AAGAAATTAT CCCATCATCA
TAAGTCATAA ATACTTTTTT GTTGTTGTTG AGACAGAATC TCATTTGTT GTCCAGGCTG
GAGTGCAGTG GGTTGATCTC AGCTCACTGC AACCTCTGCC TCCTGGGTTC AGCAATTCTC
CTGCCTCAGC CTCCCAAGTA GCTGTGATAA TAAGCATGTG CCACCACACC AGTCTAATTT
TTGTATTTTT AGTGGAGACA GGATTTCATC ATGTTGGCCA GGCTGGTCTC AAACTCCTGA
CTTCAAGTGA TCCACCTGTC TCAGCCTCCC AAAGTGCTGG GATTATAGGT GTGAACCACC
ATGCCTGGCC CATAAATACA TTTTTATGTA TTTTCTTCTA AAGTTGTTTT GTCTTTCACT
TTTTAGTTTT TAATTCACAT ATAATTACTA CTTGCTACTT ATAATTATCT GTAAGTAGTA
TGAGATGAGA AATAAATTCT ATTTCCCTCC TATGGATAAG CACAAACCTG CAGTATTAGC
ACAGTCTTAT GTCAGATTTT CTAAAATGAA TGGGTGTGTT TTCTAGGCTC TCTGTTCTGT
TTCATTATCT GTCTTTTCCT GCAACGATAT CATCTGCCTT AAAAACTCTA GCCTTGTGGT
ATTCCTCATT TTCAAGCAGA GCAAACCCCG TCACCTTGCT TTTCTCCTCC AGCATCGCTT
GTGCTATCCT GGACTAAGAC CTTCATATAG ACTGTTAGAA TCATCTAGCC AAGTTCCATT
TTAAAAATCT ATGTTGGAGC TGGGCGCGGT GGCTCACGCC TGTAATCCCA GCACTTTGGG
AGGCTGAGGA GGGCAGATCA CTTGAGGTCA GGAGTTGGAG ACCAGCCTGA TGAAACCCCG
TCTCTACTAA AAATACAAAA ATTAGCTGGA CGTTGGGCAC TTGAATTCTA GCTACTCAGG
AGGCTGAGGC AGGAGAATCG CTTGAACCTG GCAGGCGGGG GGTGCAGTGA GCCGCGATCA
TGCCACTGTA CTCCAGCCTG GGTGACAGAG TGAGGCTCCA TCTCCAAAAA TAAATAAATA
AATAAAATAA AATATCTATG TTGGAAATTT TGTACAAATT TTATTAAATG TCTACATTAA
TTTGGAGAAA AATGACTTGA TTTTGATTAT CTATTCAATA TTTCTGTATT ATGAATAAGG
CAAAAAGAGA GGCAGAGAAT AGCATAAAAT AATAACTAAA ATTCCTGGGT AAACCACCTC
AAATCATTTC TTCATATGGC TCAATATTCT TTTGTGACAT GGCCTGAAAT ATATCCAGAC
AGAGAACTCT TCTCTTCAAT ACATTTCTTC TTTTAGGTAT TCATATTGAG TTTTCCTGTC
CATGAACATG GTATAAGAGA GTATATCCCT TCGGGAGGCC AAGGTGGGTG GATCACCTGA
GGTCAGGAGT TTGAGACGAG CCTGGCCAAC ATGGTAAAGT CCCATCTCTA CTAAAAACCC
AAGAATTATC CAGGTGTGGT GACACATGCC TGTAGTCCCA GCTACTCAGG ATGCTGAAGC
AGGAGAATTG CTTGAACCAA GGAGGCGGAG GTTGCAATGA GCCAAGGTCA TGCCATTGCA
CTCCAGCCTG GGTGAAGAGC GAGACTCCAT CTCAAAAAAA AAAAAAAAAA AAAAAAGAAA
ACGAGAATAT ATCCTTTCAT TTACTAGTTT TTCTTCAATT TCTTTCAAGA TAAAGGGCTT
ACCTATCTTC TGCTTTATTC ATAGTTACTT GATATTTTTG TTTCTAATAA ATATGGTGTC
TGTCTATTTA CCTGCCTCTT ACCTGTTCAT TTCCAGTTTC AAAAATGATG TTGATATTTG
AATATTAACC TTAAATCTAG CACCTTGGTA AACACTATTA TTCATTCTAA TAATTATCAG
TAGATTATAT GTGTTTTTTA TTTATAAATC ATATTGTTTG AGTAGCATGC TTTGCTTCTT
CATTTATAAA ATTTACAACT TTTATTTCTT TTTAATAATT TTTTTCTTAT TCTCCTGGCT
AGGACTTCTA ACACAGTATT GAGTGGAAGT GCTGATCCTT GTTTAGTTTC ACATTTGAAA
AAAGATTGCT TTTACTATTT CACTGTTAAG TATAATATGC ACCATAGGCT TTCTGTGGAT
TCCTTTTATC CATTTAAGAA CATCTCTTAT TCCTAATTAG CTGAAGTTTT CTGCATGTTT
GTTTTCATCA TGAGTGGATT TTTTTACATC TATTGAAATC ATTTTACATA GAAGATATTT
CACACCTATT GAAATGGTCA TTTCACTTTT CCTTCTTTAA TATGTTAAGT TGGGCAAAAT
ATTAAAGTAT CACCTGTCAT TCTGCTTCAG CAAAAAGTAG TAGTGTCTTA GCAGTATTGG
TGAAAAGACA GCATCAAATA AAAAAGATGT AGAAGTAGGA CCCAGTAAAA ATCTAGCGCA
TGGGGCATTG TCACATGTAA GCAGACAGAA TGTGACACCA CCAAGGAGCA TCTGAAGGGC
TGGAGGCTGA AGGAAGACAT GAGTCACCCA GGCTCATGGA CACTTCAGAG AAATTAGGGA
GCAGGAAGAA GAAATAGGAT CAAAGACTAC GTATGTTGGT TGGAAAAGGA AGCTGATGGT
ATGGAGATGT TATTATTTAG GTCTCACATA AAAGATGTAG ATAAATAGGT AGATAGGTAG
```

Figure 15U

```
ATAGATGATA GATAGAGAGA TAGATAGATA AATACATAGA TAGATAGATG ATAAATAGAT
GTTGTTATTT AGGCCTCACA TAAAGATGTA GACAGATTAG ACAGACAGAT GATAGATAGA
TAGATAGATA GATAGATAGA TAGATAGATA GACGATAGAT AGATAGATAG ATAATCTCAG
AAACAGAGAC ACAGTGATCT CAGTAAGATA GGCATATGCC AGGTGACAGA ATTCAGAGGG
GTCCCACTAC GTGAAAACAA TAGAACAACC TTCGAAAAGA AATTTAGTAC AAATAAGAGG
GCAGGCTTCC TTACATACAA GTTAGTAAAC TGGAAGAATC AGTTATCCTC AAACATTGGA
ATAGATCAAA AATAGTTGTT TATATTAATG AAGGTAGCTA AACATGAAGC TAAGTGAACC
TGTCTCTGAC CTAGTGTGGC AATCCCTGGG CAAGGGACAC TTGCTCCGCT CTTGTATCCT
TCACTGAATA TTCAGACTTT CAGTTAAGCA TCGGTGAATT TAGTTTTCAT CTCTTGTGAA
AACCTTGAGA GAGGTAATTC TCTCTGCTTT TCTTCTTTTC CCTTCCTTCA TTTTCTCAAA
CATTGCCTGT TTAAAATACG AAATTTTAAA AGATGGCCTT GTTCTCTTTT TTGTTGTTAT
TATTAAGTAC AGAGAAAGGA AGAACCACAA ATAGCAAAGG GCAACATATG GAATAGTTTA
GAAGTTCCGG GAGCACCCAT GAGGGCAACT GCAGAAGAGA ACATTCTATC CCCCGTTGCT
GCAGCTTTCA TTCCAGGTCT CCATGCATAT CAGATAGGGA AGGAACTCCG GGACAGCAGC
AGGGCCCATG CACATGTAAC CAATTGCTTT CTTTGCCTGT AGTAAAGTTC ACATTTTGAT

AccIII
                                                         ------
TGCTTCTCCA GATTATGTAG ATCCAGACAT ATTTTATGCA GGCATCCGGA TCTTTCTCTC
           >>...................EXON 8........................>
TGGGTAAGTA TAGTTCAGTT GTTTTCCTGT GTGAAGTCTC TGTAGCATTG ACTGAATGTA
>>>
TAAGGGGACG AAGAGACAGA AGCTTCCTAG CGTAAGAAAC ATACCAAGTG ACTCTTGCTA
GGGATCCACT CTCAGGTAAA AGAAGTGGGA TACCATCTGC ACAACAAATA ACACTGAGGG
CTAAGTATTT CAGTTAAGAG TGTTTGTTCC TAGGCAGTTC AGATCCATTT ATATTCACTT
TTCTTAGAAT CCTAGCTCAA TGACAGAAGA AGAAAAACAC AGTATGTCAC TCACACAGTT
CTATCACTTA CATCTACTTT TTCTTCTTGT TATTAAGGCA TGTAGAAGGC TGGGGAGTGT
AGTATAGAGT TGGATAGCAT CGAAGCTTTC TTCTAAAGTT CCTGGAAGAG CTACACTGTG
GTTTGAACGA ATGTGTCCCT CCAAAATTCA TATGTTAAAA CCTAATTGTG ATGGTGAGGT
ATTCGAAGGT GGGTTCTCTG GGAGGTGATT ATGTCTCCTC TGAGAGGAGA AGACAATCCC
CTGAGTGGAA CTAATGCCCT TATAAAGGGG CTGGAGGGAG TTCACTTGGC CCTTTTTGCT
CCTTTTTTCT TCCATTCCTT GTCCCTTCCA CTATGTGAGG ACACGGGAGT TGAGGCATTA
                         Clone 152 alternative exon 8
                                              A not in mRNA seq
CCTTGGACGT GGAGACCAGG CCCTCACCAG ACACTGAACT TGCCAGCACC TTGATCTTGG ACTTCCCAGC CTCCAGAACT GTGAGAAATA CATTTCTGTT ATGGGTAGTC CCCAACTCAA
TACAGTTTGA CTTACCATTT TTTGACTTTA TGTTGGTGCA AAAGCATACA TATTCAGTAG
AAACTACTTT GAGTACCCAT ACAACCATTC TGTTTTTCAC ATTTGGTACA GTATTTAATA
AATTCCATAA CATATTCAAC ATGTTGACAT AAATAAGCTT TGCGTTAGGT GATTTTGCCC
AACTGTGGGC TAATGTAAGT GTTCTGAGCA CATTTAAGGG CAGCTAGGCT AAGCTAAGGT
GTTTGGTAGG TCAGATGTAT TAAATGCATT TTTTGTCTTA TGATATTTTC AACTTACATT
GGGTTTATCA GGATGTAACC CACTGTGAAT TAAGGAATAT CTGTATTTAC AAATTACCCA
GTCTAATGTA TTTTGTTGTA GCAACAGGAA CAAACTAAAA CACTACCCCA AACCATTTTT
TTCATATTTT CTGAGTACTC TTCTTTTGTC ACATGGCTTG AAATTTCTTC ACATAGAGAA
CTCTACTATT ATTTTATTTT ATTTTATTTT ATTTTATTTT TTGAGACAGA GTCTTGCTCT
TTTCACCCAG GCTGGAGTGC AGTGGTGCCA TCTTGGCTCA CGGCAACCTC TGCCTCCTGG
ATTCAAACTA CTCTCCTGCC TCAGCCTCCC GAGTAGCTGC GATTACAGGT GGCTGCCACC
AAGCCTGGCT AATTCTTGTA TTTTTAGTAG AGACGGAGTA TTGCCATGTT AGTCAGGCTG
GTCTCGAACT CCTGACCTCA GGTGATCTGC CCACCTTGGC CTCCCAAAAT GTTGGGATTA
CAGGCTTGAG CCACCACGTC TGGCTGATAA CTCTACTTTT AGATACTCTC TTTGCTTAAA
CAAATTAGCC ATTCCTTCCT TGACATGTTT TAATCAGATT GCCTTCCTAT TAACTTCGGA
AATTAAGAGT TTCTGCTATG TTTTTGTTTA ATTTTTAAAC AGTGAAAAAT GAAAGGTGGA
GGCAATGGCT GGATGAGGTG AATATGTCAA ATAGATATCA TCTAGTGGGC CATCTTATTA
ACTAGGAGAC ACCTGAAGTG CTATCAATAG AAATAATCTG AAGCTGTGTC TGGATACAGC
AAGAGACATG CAAATGCTAA AAATCTACTA TATTACATTG GTGCAAGGAC AGAGTAGCAA
CACATACTAA GTATTTTCTC CAGATTGGGT GTGTTTGACG TGTGAAGCAC TTCAAACAGA
GTCCAGCCTG GGAGGGAGTG GGGATGGAAT CCTCCTTGTA GAGGGTACAG AGTGGAAGCA
AGAAGGTTTC CAAGATTGAG AGTAATGGGT GTATGGTTTA TGGGGGAAAG GGAAAACAAA
```

Figure 15V

```
AAGAAGGGTG CAGAAATGGA GCTGGGAGTG TGTTTTAGTA TTTAGGCTTT CTCTGTATAC
CTTTGATAGG ATTAGAAAAA GAAAAATGGA CCATTTTTAA AAATTTCATG CTACCACATA
GCAGGCTTAT ACTATAGATG CAGAAACAGA CTGGGATTTA GGAAGCACCC CAATTCTGGA
AAATCCCTTT TTGCTTCACA TTGCTCTCTA AATCTGTATG TTTTCCCTTG TTACGTAACA
ATTTACCACA AATTTAGCAG CTTAAAACAA TATGCATTCA TTGTTTCACA ATTCTGTAAG
TCGGAATCAT AGGCAAGCTC AACTGACTTT TCCATTTAGG GTCGCAAAAG GCCGAAGTCA
ATTTATCTAT TGGGCTGGGC TCTTAACTGA AGATCTGGGG AAGAATTCCC TTCAAAACTC
ATTTAGGTTG TTGTCAGAAT TCAGTGTTTT GTGGTTCTAG AACTGAGATC TGTTTCCTTG
TTGGCTGTCA GACAGGAGCT GCTCTCAGCT TCTTGAGGCA TCCAGTATTC CTTATCATGT
GTTTTTTTTT TTCCATCTCA GCACTGGCAC TTTTTTTTTT TTTTTTTTTG AGACAGAGTC
TTGCTTTGTC ACCCAGGCTG GGGTGCAGTG GCACGATCTC GGCTCACCAC AACCTCCATC
TCCCGGGTTC AAGTGATTCT CCTGCCTCAG CCTCCCGAGT AGCTGGGATT ACAGGCACCC
GCCACCAGCC CGGCTGATTT TTGTATTTTT CATAGAGATG TGGTCTCACC ATGTTGGCCA
GGCTGGTCTT GAACTCCTGA CCTCAAGTGA TCCTCCCACT TCAGCCTCCC AAAGTGCTGA
GATTACAGGC ATGAGCCATC ATGCCCAGCC AGCACTGACA ATTCTAATCC TTCTAGCACT
TTGATTCCTT CTCACCTCTC CTTCTGCCTC TAGCCAGAGA AAACTCTCTG ATTTTAAAGG
TCTTATGTGA TTAGATTCAG CTTACCTAGG TAATTCAGGA TAACTCCCTA TGTCAAGGTC
AACTGATTAA TAACCTTAAT TACACCTGCA AAGTCCCCTT TGCCATAATA TATCATACTG
ACAGACATGC TATAGCATAA TACTAATAGT TCTAAGAATT ATGATAAGAA TCTTGGAAAA
CCATTTTTAG AATTATACCT ACCACAGTAT CCTTCAAGGG ATAAATTGAT TCTACTTCTT
CTCTATGTCA GAAGCATCTG ATGAGGATGA ACTATATATT CTGAAATCCC CATGATTAGA
TGTGTACTAG AAGGTGATTT TACTTTCATT AAAATAAATT CGGAGTCATT GACACATTTT
ATCTTTGATT TACATAAATG CCTCCGCTCT GTTTCTTACC CTCAAAATAT TTCCCATGTA
GCTAAGTGGC CAGTACCGAA TCCTACATGC ATTAATAAGT GTAGATGGAC AAAAATATCT
GGATTACTGA GAATTCCCAT TAGCATTGTC TAGAAAAATG TAAATTTGCT TTTTTGTTCT
TGATTTATCC TATTTTTGAT TTATTATTTA TATTTATTTA TTTATTTATT TATTTTTAGA
TGGAGGTCTC GCTTTGTCGC CCAGGCTGGA GCGCAATGGC GCAATCTTGG CTCACTGCAA
CCTCTGCCTC CCAGGTTCAA GCTTTCCTCC TGCCTCAGCC TCCCAAGTAG CTGGGACTAC
AGGCACCTGC CACAGTGCCC GGCTAATTTT TGTATTTTCA GTAGAGACAG GGTTTTGCCC
TGTGGGCCAG GCTGTTCTTG AACTCCTGAC CTCAGGTGAT CTGCCCACCT TGGTCCCCCA
AAGTGCTGGG ATTACAGGCA TGAGCCACCA CACCTGGCCT TTTTGCTTAC TTTTTAAAAA
CATTTTTATT TAGGAGAATG GAGATATTTC ATATGTAGAT GACACATATT CATTCCCTTT
AGTTCCCACA CACATTCAAT TTCTTGAGGA AGTTAGCCTT TGCAAAAAAA AAAAAATGAT
CTCATTTTTT TTTCCCCACT AAAACTTCTC ATTTTCTTGG GGTTGCTAGA AAGTTGCTAC
AAGAAAGGCT AAAAATAATT GTGCCTACAG ATATTTGAAA GGAAAATAGT TCCTCTTTTT
TCACAGTAGC AGCTTGGACC TGAGAATGTA TGGGAGCAAT AATTGGGCTG CTCAAAGAAA
CACAATTTCC CTTCCTCAGA CTAGAATTAC CAACCTAGAG AACATGAGTT TTTAAAGTAG
ATGTGCTTCT TTTATCTTTT TGGACTTGTA TGCTGGTGTT TTCTCTGTCA CCTTCACTGT
GGAAATCCTC TTGAGGGTGA GGCACTGAAA GCAGATTGAT TAATGTCTCT TGGCCATTTG
AGACATTGGA TGGCTCTTTT AAGTTGGCCA CGTTCTTTCA AGAACTATGC TTGGGCTACA
TATTCTGGAT ATATAATACA TACTTGTAGG ATGTTATTTT TAAATCATTC ATTTATCACA
TATTTAGTGA GTGCCTACCC CATGTCAGTT CTAGGTGCTG GAAATAGAGC AGTAAAACCA
ACCCTCAACT TGGCCCCTCT GGAGCTTACA TTTCAATGCG GTGGGTGGGG GGATGGACAA
TTAATACACA AGTAAATCTA ATAAAAGCGT CATACAATAT ACATTACAAT GGTAAGCACA
ATGAAGAAAT GGAAAGCTGG ATAGAGAGTA TTAGAGACTG TCGAATGTAG TGGCCAAATT
TTCCTGTTTA TTGTGGTCCA AGAGTGCCAC AGCCCTCTAT GACATTTGAG CAGACACCTG
GAGGAAGTGA GGGAGTGAGC CGCCAAGAAG GAATGGCAAG TGCAATAACC CTGAGGTGGG
AGCGTGTTGG TCGTGGTGGA AGAGCTGCAG GAAGCCAGCA GGGCCGCAAC ACTCAGGGGA
GAATAAGAAA GAGTGAGGTG ACAGTAGAGA CCGGATCATG TAGAGCTTTG TCAGCTTCTT
TTCTGAGTGA GATGGACAAC ACGGACACGT TTTGAAAAGA ATAACAATGT GATCTGCCTT
CAGTTGCAAA TCATCTCTGT ATTGACTGAG TAGGAAATAA ACTCCAAGAA TAAAGACGGA
AACAGGGAAA ATATTTAAGA AGCGATCATT ACAATCCAGG GTGGTGGCTT GTACTAGGGT
ACAAGGGCTA AAGGTGTTGA GAAATGGTCA GATTCTGGAT ATATACTGAA ATCAAAGTTG
ATGGAAAGAT ATGAGTCAAA GATAATTTGC AGGTTTGGG GTCCTGGTTC ACTGAAAGAA
CAGAGACATC ATTTACTCCA ATGAGGAAGA CTATAGGAGG AACAGGTTTA GCAAAGAAGA
AAGGAAATCA GGAGATCAGT TTGGGACACG GTCATATCA AGTAGGCAGT GGATGTATG
GGTCTGGAAT ATAGGGGAGT GGTCTAGCTA TCAGTGTAAA TAGCTTTTTA CATTTGTAAA
TAGTCAGGAT ATAGGCTTTT CTTTTTCTTT TTGTGAGACA CAGTCTTGCT CTTTCGCCCA
AACTGGAGTG CAATGGCACA ATCTCAGCTC ACTGCAACCT CTGCCTCTGG GTTCAAGCGA
```

Figure 15W

```
TACTCCTGCC TCAGCCTCCC GAGTAGCTGG GACTACAGGT GTGCACCACC ATACCAGGCT
AATTTTTGTG TTTTTAATGG AAATGGGGTT TCACCATGTT GACCAGGCTG GTGTCAAACT

ClaI
           ------
CCTGACCTCA ATCGATCTCC CCGCCTGGGC CTCCCAAAGT GCTGGGATTA CAGGCATGAG
CCACCCCATC CAGCTGGGAT ATAGTTGTTT TCTAAATCTA TGAGGCTAGA GAAGACCATT
TGGGAATTGA GAGCAGTGAG CAGTCCACGG ACTGACCCTT TGAGAGTGCA ACATTTAGCA
GTACTCAAGA TGGGAAGGAG CTAGTGAAAA AGCCCCAAAT GACTACATAA GACCATCAAC
CAGATTACAA AGAAAGACCC GAACATGTGT GCCCATATAT CACCCAACAG CAGTTATGTC
TTTCATGTTT CTTCCCCATA AAATGTTGTT CATCAACTTT ATTAGACTAG GGTCTTAACA
TTGGACAAAT CACAAAACCT CTCTGGAGCC TATTTTATTT TTCAACAGCT GTAGGAAGCA
AATACAAATT GGAAATCTAA GGCTCAGAAA GATTTGTACA AAGTTACACA GTAATGAAAG
GGGAGCCGGG ATTCCCACTC ACTCTAAAGA ATATGATAAA ATGGCTAGTA TTCACTGAAT
GCTTAACATG TTCCAGGCCC TGGGCAGGTA TTATTTTAAT TAGTTCTCAC AATAATCCAA
TAAGGGAGAT ACTAATTTAC TCAGATGAGA AAGCTGAGGC TCAGAGAGGT TAATGAACTA
AGCCAAGGCT CACTGTTAAT AAATAGCAAA GGTAAAATTA AATTCCATAT CTGCTTGAGA
TAGAGGCCTT GCTCCTAATA GCTGCAGCCT GTCAGGGCCT GGCAGCAGTA ACCTCTCCTT
TCCTCTTCCC ACCATTCCCC TGCACTGCTT TCTGTACCGC ATCTCTTTTC AGAGTGATGT
TGCCCCAATT GCGGAGGCCA CTGTGCTGTT TATCCAGTGA AAGCTGTAGC ACAGCCAACC
CAAAGCGTCC CCAGTGAAAA CAACCTGGCT CCTTACAGCA CTTCCAGCCT CAGAGCAGTA
TTTGAAAAAT ATCATGAACA GCAAACACAG CAGTCTGTCT GTGGCTTTTA TATGTGTATA
TGGTGTGTGT GTATGTCCCT TCTCTTGAGC AAAATAACTT TTAGAATTAT AGAAAAAAAA

PmeI
                              ---------
TGTGCAACAT CAATGTGGAT CTGCTGTTTA AACTCATAAC AGAGAAAGTA GCTTGTTTCT
GGCTATAGGA GGAAAAGACG ATATTCCTTA GTAAAATGG AAATCCACAT ATGGGGTTCT
TGTAAAAATG AAGATAGAAA ATTGCAAGTT TGGGGATCAA GTTCTGGTTC TATCATCCTT
TAACAGTATG ACCCTGGAAC CTTAATTGCT TTGAGTCTTT GTTACTTTAT CTATGAAATG
AAGTATTTAA AAAAACTCCA AAAATCTGTC CTGATGTACA CACAAGAGGT CAAATGAGAA
AATGAATGTG AAGATGCTTT ATAAACTATA CAGCATGGTA GGTGCAAATG TGACATGAAC
TTGTTTTGGA CACATTATAA AGTCACCCCC ACAAACTGTG ATTGTTCAAG ACTATGCAAA
GTCAGACACA GGAAAATAAG TAAAACAGAT GGAGGCATAA AGAGGGGGAA CTCAGAGAAA
ACAGTGAAGA ACAGGAATCA GGAAGACAAA GGAGAGGAAA GGTGGGGAGG AGAGGAGAAG
GAAAGGGGGA AGGGAATGGA GGAGAGGAGA ACAGCTGCTT CACAGAGCAT GGCCGGCAGC
CCAGTCCCAG CCTTTCTGCA TGTCCCTGAC TTCAGCCTCT GGCGAGGCAC AGGCTTACTC
TGTGCTTCCT GCTGTTACTC TTCTTATCCA TCCTTATTAT CAATACCTGT GGTCAACAAA
GTATTTGATA AAGGCATCCT CAAAGTCAGG TAACATCTGT ACGTTATAGA TTACAAAGTT
GAGTAATATC CAGAATTGGT AGTTTAACGT GATGACTTCT TAACAATTAT CACTGTTTCA
GGGAAGGGCA AAGGTGTGTG TGTGTGTGTG TTCATCTGTG TGTATCTGTG TATGTAATTG
TGGGTGTTTG TGTATATTTG TGAGGCTCTT TACTTGGCGG AGTTAAAAAG TATCTGCTCA
TCAAGGTTGA GATTAGCAAA GGAAGTGAAG ATTTTCCAG AGCCCCTAAA ATGTGCCTTT
TGACCAACAC TGAGGACATC TTTATAACTG AGTATGTGCA ATAAATATGT CTTGGGACCT
GTGCCACAAA TTCCTCTCTA AATAGCCTTT ACCTCTCTGG AATAACCCTT TAGATGAGGA
AGAAAAGGGC TGTGATTTTA TAGCTTGTTA TGAAGCTGGA GTGAAGATGA TGCTTCAGTA
CTTACCCTAC AAAGATACCC CCAATCCCTC ACCCTAAAAT TACCATTGAA ATCATGTTCC
CTTTCTCATT CACTCTCAGT TTCCATGTCA GAAATATAC CATTACCTCC CTGCACCCCT
TTCATCTCTC TCACTTTTCT CTTGCTTAGA TGGAAAGACA ACCCAGCAAT GCCTGCAGGG
                                      >>............EXON 9 ..............>
CTGATGTATG AAGGAGTTTC CCAAGAGCCC CTGAAATACT CCGGCGGGAG TGCAGCTCAG
>................EXON 9 ............................>
AGCACAGTGC TTCATGCCTT TGATGAGTTC TTAGGCATTC GTCATAGCAA GGAAAGTGGT
>................EXON 9 ............................>>
AAGTCAGACA TTTTGTTTTC CCTTGAGAGT AGAGGGAGGA AGAGGAGAGG TGTTTTTTTT
TTTTCCAATT GATAAAACCA AATATAAATT AAAATGTCAT GAAGTTTATA CTTCTCTAAG
TCAGCCAAGA AACTGCATGA CTGCCAATGT TTTTGTGTCA AGCCAATTAA TATTGGAATA
TCAGATGTCA GCTTGATCTT GGGTTTTACT TCCAAATCTT AAAATGTTGC TCTGTTTCCA
ACTGTTCACT ATCACTTTGG TTTGGATCTT TAGACACTAG CTTCCTTTTT CTGAAATGGG
```

Figure 15X

```
GGAGAGATGT GGAGTTTGAA GGCTATGAGT CTGGGCCAGC TGGAAACAGG TCTGGGATCT
TCCAAGAAAG TCCTTCCCCA CAAAATGGTG CAACTTCTAG CCAAATCTAT TTATACCAGC
AGAGGGATCT ATCACCCTGG AAGCTTGAAA TTGTTCATTT TCTTACCTGC CAGGATCAAG
TTAAGTTTTT AACAGTTGCA AAAAGACACT TCATACTATG GAGTTTTCAA GTTGGATTAG
AAGAAAAAGA ATCACCAGAA CTTAGTGTCG TAGATTCAAG TCACTTCTCT AAAACTGTCA
TAATTTTTCA CGGATTTTGG CATTTGGTGA CATTAATGGT TGATTTACTT ACCATGCATA
ATATTAAACC CATAACGAAT TTCCTATAAA TATCTATTGA TTTGATTTTT AAATCACTTG
GCTTCAAGAG GCTATTACTA AAACAGTGAC TCATTCTTTA TCTTTTTTGC CTTCACGGGC
TTTATATAAC TTTCTCCTTT TCTTGTGCTC CCTCCAAAAC AAAGCACTGA GAAAACAAAA
TTCACCAGAG TATTCAGCTA GTCAGTTCAA GGGTTTGTGT TCTACATTTG AAGATATTCC
TTATAGCAGC TACCAACGGG ATACTTTGTT TACATTTGTT GTGTAGTAAA TATTTATATA
TTGGCAAACA AATCTAGTTC CAACTCTGTC ATCTGAGATG TTCTTACTTT GTTTCCTCTT
CTCCATCTCC TGTCAACTGT TAGAAATATA CATTTGAGTA CGTGAAGTCT GCAAACAAAA
GGGCCAAGGT AGATTTGAGT TAGAACACCA GCAACAGTTT CTGGTGCATT CTTGTCTGAA
AAAGCAGAGA AGATTGGGCA CCGTGGGTCA TGCCTGTAAT CCCAAAATTT TGGAAGTCTG
AGGCAGGTGG ATCGCTTGAG CCCAGGAGTT CAAGACAAGC TGGGCAACA TAGCAAGAAC
CCGTCTCTAC TAAAAGGAAT ACAAAAAAAT ATTAGCTGGG TGTGGTGGCG CACACCTGTA
GTTTCAGCTA CTCAGAAGAC TGAGGTGGGA GGATCACTTG AACTCAGGGG CAGAGGTGGC
AGTAAGCTGA GATCACACCA CTGCACTCCA GCCTGGGCAA CAGAGCAAGA TCTCATCTAG
AGAAAAAAAA AATAAAAAAG AAGAAGAAGC AGACGAGCTC TGCTATATTT CCATGTGGAG
CTATGACGTT ATGCTGTATT GTTTCTTTCA GGTGACTTTC TGTACAGAAT GAGGGATTAC
                                           >>..........EXON10..........>
ATGCCTCCTT CCCATAAGGC CTTCATAGAA GACATCCACT CAGCACCTTC CCTGAGGGAC
>............................EXON 10.............................>
TACATCCTGT CATCTGGACA GGACCACTTG CTGACAGCTT ATAACCAGTG TGTGCAGGCC
>............................EXON 10.............................>
CTGGCAGAGC TGCGGAGCTA TCACATCACC ATGGTCACCA AATACCTCAT CACAGCTGCA
>............................EXON 10.............................>
GCCAAGGCAA AGCATGGGAA GCCAAACCAT CTCCCAGGGC CTCCTCAGGC TTTAAAAGAC
>............................EXON 10.............................>
                                                              DrdI
                                                        ------------
AGGGGCACAG GTGGAACCGC AGTTATGAGC TTTCTTAAGA GTGTCAGGGA TAAGACCTTG
>..............EXON    .............................>
GAGTCAATCC TTCACCCACG TGGTTAG
>..........EXON    ..........>>
```

Figure 15Y

```
wt hu ido2                            ATGGAGCCCCACAG ACCGAATGTGAAGACAGCAG TGCCATTGTCTCTTTGGAAAGC
hu ido2 Δ 3/4/6      >#1> GGCTTATGGAGCCCCACAG ACCGAATGTGAAGACAGCAG TGCCATTGTCTTTGGAAAGC
hu ido2 Δ 8          >#1> GGCTTATGGAGCCCCACAG ACCGAATGTGAAGACAGCAG TGCCATTGTCTTTGGAAAGC
hu ido2 Δ 6/8        >#1> GGCTTATGGAGCCCCACAG ACCGAATGTGAAGACAGCAG TGCCATTGTCTTTGGAAAGC
hu ido2 Δ 4/5        >#1> GGCTTATGGAGCCCCACAG ACCGAATGTGAAGACAGCAG TGCCATTGTCTTTGGAAAGC
hu ido2 R235W        >#1> GGCTTATGGAGCCCCACAG ACCGAATGTGAAGACAGCAG TGCCATTGTCTTTGGAAAGC
hu ido2 Stop         >#1> TATGGAGCCCCACAG ACCGAATGTGAAGACAGCAG TGCCATTGTCTTTGGAAAGC
                          .............CGGCTTATGGAGCCCCACAG ACCGAATGTGAAGACAGCAG TGCCATTGTCTTTGGAAAGC
                      # 1  M  E  P  H  R  P  N  V  K  T  A  V  P  L  S  L  E  S
                                                              Exon 1 wt hu ido2           #55  TATCACATATCTGAAGAGTA TGGCTTTCTCTTCTTCCAGATT CTCTGAAAGAACTTCCAGAT
hu ido2 Δ 3/4/6      #60  TATCACATATCTGAAGAGTA TGGCTTTCTCTTCTTCCAGATT CTCTGAAAGAACTTCCAGAT
hu ido2 Δ 8          #60  TATCACATATCTGAAGAGTA TGGCTTTCTCTTCTTCCAGATT CTCTGAAAGAACTTCCAGAT
hu ido2 Δ 6/8        #60  TATCACATATCTGAAGAGTA TGGCTTTCTCTTCTTCCAGATT CTCTGAAAGAACTTCCAGAT
hu ido2 Δ 4/5        #60  TATCACATATCTGAAGAGTA TGGCTTTCTCTTCTTCCAGATT CTCTGAAAGAACTTCCAGAT
hu ido2 R235W        #60  TATCACATATCTGAAGAGTA TGGCTTTCTCTTCTTCCAGATT CTCTGAAAGAACTTCCAGAT
hu ido2 Stop         #12  TATCACATATCTGAAGAGTA TGGCTTTCTCTTCTTCCAGATT CTCTGAAAGAACTTCCAGAT
                          Y  H  I  S  E  E  Y  G  F  L  L  P  D  S  L  K  E  L  P  D
                                                              EXON1       >|< Exon 2 wt hu ido2           #115 CATTATAGGCCTTGGATGGA AATTGCCAACAAACTTCCTC AATTGATTGATGCTCACCAG
hu ido2 Δ 3/4/6      #120 CATTATAGGCCTTGGATGGA AATTGCCAACAAACTTCCTC AATTGATTGATGCTCACCAG
hu ido2 Δ 8          #120 CATTATAGGCCTTGGATGGA AATTGCCAACAAACTTCCTC AATTGATTGATGCTCACCAG
hu ido2 Δ 6/8        #120 CATTATAGGCCTTGGATGGA AATTGCCAACAAACTTCCTC AATTGATTGATGCTCACCAG
hu ido2 Δ 4/5        #120 CATTATAGGCCTTGGATGGA AATTGCCAACAAACTTCCTC AATTGATTGATGCTCACCAG
hu ido2 R235W        #120 CATTATAGGCCTTGGATGGA AATTGCCAACAAACTTCCTC AATTGATTGATGCTCACCAG
hu ido2 Stop         #72  CATTATAGGCCTTGGATGGA AATTGCCAACAAACTTCCTC AATTGATTGATGCTCACCAG
                          H  Y  R  P  W  M  E  I  A  N  K  L  P  Q  L  I  D  A  H  Q
                                                              Exon 2
```

Figure 16A

| | | | | |
|---|---|---|---|---|
| wt hu ido2 | CTTCAAGCTCATGTGGACAA | GATGCCCCTGCTGAGCTGCC | AGTTCCTGAAGGGTCACCGG | #175 |
| hu ido2 Δ 3/4/6 | CTTCAAGCTCATGTGGACAA | G:::::::::::::::::: | :::::::::::::::::::: | #180 |
| hu ido2 Δ 6/8 | CTTCAAGCTCATGTGGACAA | GATGCCCCTGCTGAGCTGCC | AGTTCCTGAAGGGTCACCGG | #180 |
| hu ido2 Δ 8 | CTTCAAGCTCATGTGGACAA | GATGCCCCTGCTGAGCTGCC | AGTTCCTGAAGGGTCACCGG | #180 |
| hu ido2 Δ 4/5 | CTTCAAGCTCATGTGGACAA | GATGCCCCTGCTGAGCTGCC | AGTTCCTGAAGGGTCACCGG | #180 |
| 234-M13R-pUC.ab1 | CTTCAAGCTCATGTGGACAA | GATGCCCCTGCTGAGCTGCC | AGTTCCTGAAGGGTCACCGG | #180 |
| hu ido2 R235 Stop | CTTCAAGCTCATGTGGACAA | GATGCCCCTGCTGAGCTGCC | AGTTCCTGAAGGGTCACCGG | #176 |
| | CTTCAAGCTCATGTGGACAA | GATGCCCCTGCTGAGCTGCC | AGTTCCTGAAGGTCACCGG | #132 |
| | L Q A H V D K | M P L L S C | Q F L K G H R | |
| | Exon 2 >\|< | Exon 3 | BstEII | |

| | | | | |
|---|---|---|---|---|
| wt hu ido2 | GAGCAGCGCCTGGCCCACCT | GGTCCTGAGCTTCCTCACCA | TGGGTTATGTCTGGCAGGAA | #235 |
| hu ido2 Δ 3/4/6 | :::::::::::::::::::: | :::::::::::::::::::: | :::::::::::::::::::: | #240 |
| hu ido2 Δ 6/8 | GAGCAGCGCCTGGCCCACCT | GGTCCTGAGCTTCCTCACCA | TGGGTTATGTCTGGCAGGAA | #240 |
| hu ido2 Δ 8 | GAGCAGCGCCTGGCCCACCT | GGTCCTGAGCTTCCTCACCA | TGGGTTATGTCTGGCAGGAA | #240 |
| hu ido2 Δ 4/5 | GAGCAGCGCCTGGCCCACCT | GGTCCTGAGCTTCCTCACCA | TGGGTTATGTCTGGCAGGAA | #240 |
| 234-M13R-pUC.ab1 | GAGCAGCGCCTGGCCCACCT | GGTCCTGAGCTTCCTCACCA | TGGGTTATGTCTGGCAGGAA | #240 |
| hu ido2 R235 Stop | GAGCAGCGCCTGGCCCACCT | GGTCCTGAGCTTCCTCACCA | TGGGTTATGTCTGGCAGGAA | #236 |
| | GAGCAGCGCCTGGCCCACCT | GGTCCTGAGCTTCCTCACCA | TGGGTTATGTCTGGCAGGAA | #192 |
| | E Q R L A H | L V L S F L T | M G Y V W Q E | |
| | | SexAI | Exon 3 | |

| | | | | |
|---|---|---|---|---|
| wt hu ido2 | GGAGAGGCGCAGCCTGCAGA | GGTCCTGCCAAGGAATCTTG | CCCTTCCATTTGTCGAAGTC | #295 |
| hu ido2 Δ 3/4/6 | :::::::::::::::::::: | :::::::::::::::::::: | :::::::::::::::::::: | #300 |
| hu ido2 Δ 6/8 | GGAGAGGCGCAGCCTGCAGA | GGTCCTGCCAAGGAATCTTG | CCCTTCCATTTGTCGAAGTC | #300 |
| hu ido2 Δ 8 | GGAGAGGCGCAGCCTGCAGA | GGTCCTGCCAAGGAATCTTG | CCCTTCCATTTGTCGAAGTC | #300 |
| hu ido2 Δ 4/5 | GGAGAGGCGCAGCCTGCAGA | G::::::::::::::::::: | :::::::::::::::::::: | #300 |
| hu ido2 R235 | GGAGAGGCGCAGCCTGCAGA | GGTCCTGCCAAGGAATCTTG | CCCTTCCATTTGTCGAAGTC | #296 |
| hu ido2 Stop | GGAGAGGCGCAGCCTGCAGA | GGTCCTGCCAAGGAATCTTG | CCCTTCCATTTGTCGAAGTC | #296 |
| | GGAGAGGCGCAGCCTGCAGA | GGTCCTGCCAAGGAATCTTG | CCCTTCCATTTGTCGAAGTC | #252 |
| | G E A Q P A E | V L P R N L | A L P F F V E V | |
| | Exon 3 | >\|< Exon 4 | | |

```
wt hu ido2           #715                              TCTGGATGGAAAGACAACCC AGCAATGCCTGCAGGGCTGA TGTATGAAGGAGTTTCCCAA
hu ido2 Δ 3/4/6      #715                              TCTGGATGGAAAGACAACCC AGCAATGCCTGCAGGGCTGA TGTATGAAGGAGTTTCCCAA
hu ido2 Δ 6/8        #715                              ::::ATGGAAAGACAACCC AGCAATGCCTGCAGGGCTGA TGTATGAAGGAGTTTCCCAA
hu ido2 Δ 8          #715                              ::::ATGGAAAGACAACCC AGCAATGCCTGCAGGGCTGA TGTATGAAGGAGTTTCCCAA
hu ido2 Δ 4/5        #715                              TCTGGATGGAAAGACAACCC AGCAATGCCTGCAGGGCTGA TGTATGAAGGAGTTTCCCAA
hu ido2 R235         #715                              TCTGGATGGAAAGACAACCC AGCAATGCCTGCAGGGCTGA TGTATGAAGGAGTTTCCCAA
hu ido2 Stop         #715                              ::::ATGGAAAGACAACCC AGCAATGCCTGCAGGGCTGA TGTATGAAGGAGTTTCCCAA
Alternative Exon 8
AACTTGCCAGCACCTTGATCTTGACTTCCCAGC CTCCAGAACTATGAAAGACAACCC  #672     TCTGGATGGAAAGACAACCC AGCAATGCCTGCAGGGCTGA TGTATGAAGGAGTTTCCCAA
                                                                    S  G  W  K  D  N  P  A  M  P  A  G  L  M  Y  E  G  V  S  Q
                                                                    Exon8>|<_____Exon 9_____ wt hu ido2           #775   GAGCCCCTGAAATACTCCGG CGGGAGTGCAGCTCAGAGCA CAGTGCTTCATGCCTTTGAT
hu ido2 Δ 3/4/6      #775   GAGCCCCTGAAATACTCCGG CGGGAGTGCAGCTCAGAGCA CAGTGCTTCATGCCTTTGAT
hu ido2 Δ 6/8        #775   GAGCCCCTGAAATACTCCGG CGGGAGTGCAGCTCAGAGCA CAGTGCTTCATGCCTTTGAT
hu ido2 Δ 8          #775   GAGCCCCTGAAATACTCCGG CGGGAGTGCAGCTCAGAGCA CAGTGCTTCATGCCTTTGAT
hu ido2 Δ4/5         #775   GAGCCCCTGAAATACTCCGG CGGGAGTGCAGCTCAGAGCA CAGTGCTTCATGCCTTTGAT
hu ido2 R235         #775   GAGCCCCTGAAATACTCCGG CGGGAGTGCAGCTCAGAGCA CAGTGCTTCATGCCTTTGAT
hu ido2 Stop         #732   GAGCCCCTGAAATACTCCGG CGGGAGTGCAGCTCAGAGCA CAGTGCTTCATGCCTTTGAT
                            E  P  L  K  Y  S  G  G  S  A  A  Q  S  T  V  L  H  A  F  D
                            _____Exon 9_____ wt hu ido2           #835   GAGTTCTTAGGCATTCGTCA TAGCAAGGAAAGTGGTGACT TTCTGTACAGAATGAGGGAT
hu ido2 Δ 3/4/6      #835   GAGTTCTTAGGCATTCGTCA TAGCAAGGAAAGTGGTGACT TTCTGTACAGAATGAGGGAT
hu ido2 Δ 6/8        #835   GAGTTCTTAGGCATTCGTCA TAGCAAGGAAAGTGGTGACT TTCTGTACAGAATGAGGGAT
hu ido2 Δ 8          #835   GAGTTCTTAGGCATTCGTCA TAGCAAGGAAAGTGGTGACT TTCTGTACAGAATGAGGGAT
hu ido2 Δ 4/5        #835   GAGTTCTTAGGCATTCGTCA TAGCAAGGAAAGTGGTGACT TTCTGTACAGAATGAGGGAT
hu ido2 R235         #835   GAGTTCTTAGGCATTCGTCA TAGCAAGGAAAGTGGTGACT TTCTGTACAGAATGAGGGAT
hu ido2 Stop         #835   GAGTTCTTAGGCATTCGTCA TAGCAAGGAAAGTGGTGACT TTCTGTACAGAATGAGGGAT
hu ido2 R235 Stop    #835   GAGTTCTTAGGCATTCGTCA TAGCAAGGAAAGTGGTGACT TTCTGTACAGAATGAGGGAT
hu ido2 Stop         #792   GAGTTCTTAGGCATTCGTCA TAGCAAGGAAAGTGGTGACT TTCTGTACAGAATGAGGGAT
                            E  F  L  G  I  R  H  S  K  E  S  G  D  F  L  Y  R  M  R  D
                            __Bsm I__ Exon 9       >|<_Bsr GI    Exon 10_
```

Figure 16E

| | | |
|---|---|---|
| wt hu ido2 | #895 | TACATGCCTCCTCCTTCCCATAA GGCCTTCATAGAAGACATCC ACTCAGCACCTTCCCTGAGG |
| hu ido2 Δ 3/4/6 | #895 | TACATGCCTCCTCCTTCCCATAA GGCCTTCATAGAAGACATCC ACTCAGCACCTTCCCTGAGG |
| hu ido2 Δ 6/8 | #895 | TACATGCCTCCTCCTTCCCATAA GGCCTTCATAGAAGACATCC ACTCAGCACCTTCCCTGAGG |
| hu ido2 Δ 8 | #895 | TACATGCCTCCTCCTTCCCATAA GGCCTTCATAGAAGACATCC ACTCAGCACCTTCCCTGAGG |
| hu ido2 Δ 4/5 | #895 | TACATGCCTCCTCCTTCCCATAA GGCCTTCATAGAAGACATCC ACTCAGCACCTTCCCTGAGG |
| hu ido2 R235W | #895 | TACATGCCTCCTCCTTCCCATAA GGCCTTCATAGAAGACATCC ACTCAGCACCTTCCCTGAGG |
| hu ido2 Stop | #852 | TACATGCCTCCTCCTTCCCATAA GGCCTTCATAGAAGACATCC ACTCAGCACCTTCCCTGAGG |
| | | Y M P P S H K A F I E D I H S A P S L R |
| | | Exon 10 |
| wt hu ido2 | #955 | GACTACATCCTGTCATCTGG ACAGGACCACTTGCTGACAG CTTATAACCAGTGTGTGCAG |
| hu ido2 Δ 3/4/6 | #955 | GACTACATCCTGTCATCTGG ACAGGACCACTTGCTGACAG CTTATAACCAGTGTGTGCAG |
| hu ido2 Δ 6/8 | #955 | GACTACATCCTGTCATCTGG ACAGGACCACTTGCTGACAG CTTATAACCAGTGTGTGCAG |
| hu ido2 Δ 8 | #955 | GACTACATCCTGTCATCTGG ACAGGACCACTTGCTGACAG CTTATAACCAGTGTGTGCAG |
| hu ido2 Δ 4/5 | #955 | GACTACATCCTGTCATCTGG ACAGGACCACTTGCTGACAG CTTATAACCAGTGTGTGCAG |
| hu ido2 Δ 4/6 | #955 | GACTACATCCTGTCATCTGG ACAGGACCACTTGCTGACAG CTTATAACCAGTGTGTGCAG |
| hu ido2 R235W | #955 | GACTACATCCTGTCATCTGG ACAGGACCACTTGCTGACAG CTTATAACCAGTGTGTGCAG |
| hu ido2 stop | #912 | GACTACATCCTGTCATCCTGG ACAGGACCACTTGCTGACAG CTTATAACCAGTGTGTGCAG |
| | | D Y I L S S G Q D H L L T A Y N Q C V Q |
| | | Exon 10 |
| wt hu ido2 | #1015 | GCCCTGGCAGAGCTGCGGAG CTATCACATCACCATGGTCA CCAAATACCTCATCACAGCT |
| hu ido2 Δ 3/4/6 | #1015 | GCCCTGGCAGAGCTGCGGAG CTATCACATCACCATGGTCA CCAAATACCTCATCACAGCT |
| hu ido2 Δ 6/8 | #1015 | GCCCTGGCAGAGCTGCGGAG CTATCACATCACCATGGTCA CCAAATACCTCATCACAGCT |
| hu ido2 Δ 8 | #1015 | GCCCTGGCAGAGCTGCGGAG CTATCACATCACCATGGTCA CCAAATACCTCATCACAGCT |
| hu ido2 Δ 4/5 | #1015 | GCCCTGGCAGAGCTGCGGAG CTATCACATCACCATGGTCA CCAAATACCTCATCACAGCT |
| hu ido2 Δ 4/6 | #1015 | GCCCTGGCAGAGCTGCGGAG CTATCACATCACCATGGTCA CCAAATACCTCATCACAGCT |
| hu ido2 R235W | #1015 | GCCCTGGCAGAGCTGCGGAG CTAACACATCACCATGGTCA CCAAATACCTCATCACAGCT |
| hu ido2 stop | #972 | GCCCTGGCAGAGCTGCGGAG CTATCACATCACCATGGTCA CCAAATACCTCATCACAGCT |
| | | A L A E L R S YXH I T M V T K Y L I T A |
| | | Exon 10    BstEII |

Figure 16F

```
wt hu ido2            #1075  GCAGCCAAGGCAAAGCATGG GAAGCCAAACCATCTCCCAG GGCCTCCTCCTCAGGCTTTAAAA
hu ido2 Δ 3/4/6       #1075  GCAGCCAAGGCAAAGCATGG GAAGCCAAACCATCTCCCAG GGCCTCCTCCTCAGGCTTTAAAA
hu ido2 Δ 6/8         #1075  GCAGCCAAGGCAAAGCATGG GAAGCCAAACCATCTCCCAG GGCCTCCTCCTCAGGCTTTAAAA
hu ido2 Δ 8           #1075  GCAGCCAAGGCAAAGCATGG GAAGCCAAACCATCTCCCAG GGCCTCCTCCTCAGGCTTTAAAA
hu ido2 Δ 4/5         #1075  GCAGCCAAGGCAAAGCATGG GAAGCCAAACCATCTCCCAG GGCCTCCTCCTCAGGCTTTAAAA
hu ido2 R235W         #1075  GCAGCCAAGGCAAAGCATGG GAAGCCAAACCATCTCCCAG GGCCTCCTCCTCAGGCTTTAAAA
hu ido2 Stop          #1075  GCAGCCAAGGCAAAGCATGG GAAGCCAAACCATCTCCCAG GGCCTCCTCCTCAGGCTTTAAAA
                      #1032  GCAGCCAAGGCAAAGCATGG GAAGCCAAACCATCTCCCAG GGCCTCCTCCTCAGGCTTTAAAA
                              A  A  K  A  K  H  G   K  P  N  H  L  P  G   P  P  Q  A  L  K
                                                         Exon 10                 BSE R I wt hu ido2            #1135  GACAGGGGCACAGGTGGAAC CGCAGTTATGAGCTTTCTTA AGAGTGTCAGGGATAAGACC
hu ido2 Δ 3/4/6       #1135  GACAGGGGCACAGGTGGAAC CGCAGTTATGAGCTTTCTTA AGAGTGTCAGGGATAAGACC
hu ido2 Δ 6/8         #1135  GACAGGGGCACAGGTGGAAC CGCAGTTATGAGCTTTCTTA AGAGTGTCAGGGATAAGACC
hu ido2 Δ 8           #1135  GACAGGGGCACAGGTGGAAC CGCAGTTATGAGCTTTCTTA AGAGTGTCAGGGATAAGACC
hu ido2 Δ 4/5         #1135  GACAGGGGCACAGGTGGAAC CGCAGTTATGAGCTTTCTTA AGAGTGTCAGGGATAAGACC
hu ido2 R235W         #1135  GACAGGGGCACAGGTGGAAC CGCAGTTATGAGCTTTCTTA AGAGTGTCAGGGATAAGACC
hu ido2 Stop          #1135  GACAGGGGCACAGGTGGAAC CGCAGTTATGAGCTTTCTTA AGAGTGTCAGGGATAAGACC
                      #1092  ........................ GACAGGGGCACAGGTGGAAC CGCAGTTATGAGCTTTCTTA AGAGTGTCAGGGATAAGACC
                              D  R  G  T  G  G  T   A  V  M  S  F  L  K   S  V  R  D  K  T
                                                          Exon 10 wt hu ido2            #1195  TTGGAGTCAATCCTTCACCC ACGTGGTTAGGAT
hu ido2 Δ 3/4/6       #1195  TTGGAGTCAATCCTTCACCC ACGTGGTTAG
hu ido2 Δ 6/8 (C155)  #1195  TTGGAGTCAATCCTTCACCC ACGTGGTTAG
hu ido2 Δ 8           #1195  TTGGAGTCAATCCTTCACCC ACGTGGTTAG
hu ido2 Δ 4/5         #1195  TTGGAGTCAATCCTTCACCC ACGTGGTTAG
hu ido2 R235W         #1195  TTGGAGTCAATCCTTCACCC ACGTGGTTAG
hu ido2 Stop          #1195  TTGGAGTCAATCCTTCACCC ACGTGGTTAG
                      #1152  ........................ TTGGAGTCAATCCTTCACCC ACGTGGTTAGGAT
                              L  E  S  I  L  H  P   R  G
                                      Exon 10
```

Figure 16G

| Position | Target sequences |
|---|---|
| 58 | AATGTGAAGACAGCAGTGCCATT |
| 64 | AAGACAGCAGTGCCATTGTCTTT |
| 194 | AATTGATTGATGCTCACCAGCTT |
| 490 | AACCTGGAGACCATCATCTCATT |
| 687 | AACCTTAGGACAGATGCATGATT |
| 800 | AAGGAGTTTCCCAAGAGCCCCTT |
| 924 | AATGAGGGATTACATGCCTCCTT |
| 1213 | AAGAGTGTCAGGGATAAGACCTT |

| Position | Sequence |
|---|---|
| 58 | 5'UGUGAAGACAGCAGUGCCAUU<br>UUACACUUCUGUCGUCACGGA 5' |
| 64 | 5'GACAGCAGUGCCAUUGUCUUU<br>UUCUGUCGUCACGGUAACAGA 5' |
| 194 | 5'UUGAUUGAUGCUCACCAGCUU<br>UUAACUAACUACGAGUGGUCG 5' |
| 490 | 5'CCUGGAGACCAUCAUCUCAUU<br>UUGGACCUCUGGUAGUACAGU 5' |
| 687 | 5'CCUUAGGACAGAUGCAUGAUU<br>UUGGAAGCCUGUCUACGUACU 5' |
| 800 | 5'GGAGUUUCCCAAGAGCCCCUU<br>UUCCUCAAAGGGUUCUCGGGG 5' |
| 924 | 5'UGAGGGAUUACAUGCCUCCUU<br>UUACUCCCUAAUGUACGGAGG 5' |
| 1213 | 5'GAGUGUCAGGGAUAAGACCUU<br>UUCUCACAGUCCCUAUUCUGG 5' |
| 183 | 5'CAAACUUCCUCAAUUGAUUGAUGCT<br>UUGUUUGAAGGAGUUAACUAACUACGA 5' |
| 73 | 5'GUGCCAUUGUCUUUGGAAAGCUATC<br>GUCACGGUAACAGAAACCUUUCGAUAG 5' |
| 1215 | 5'GAGUGUCAGGGAUAAGACCUUGGAG<br>UUCUCACAGUCCCUAUUCUGGAACCUC 5' |
| 897 | 5'CAAGGAAAGUGGUGACUUUCUGUAC<br>UCGUUCCUUUCACCACUGAAAGACAUG 5' |
| 841 | 5'GCAGCUCAGAGCACAGUGCUUCATG<br>CACGUCGAGUCUCGUGUCACGAAGUAC 5' |
| 1128 | 5'GCAUGGGAAGCCAAACCAUCUCCCA<br>UUCGUACCCUUCGGUUUGGUAGAGGGU 5' |
| 561 | 5'AGAGAAAGAAGCAGUGCCUGGGATA<br>CAUCUCUUUCUUCGUCACGGACCCUAU 5' |
| 698 | 5'CCUUAGGACAGAUGCAUGAUUAUGT<br>UUGGAAUCCUGUCUACGUACUAAUACA 5' |

Figure 20A

| Position | Sequence |
|---|---|
| 311 | 5'AAGGAACCCAGAAGGACCGUU<br>UUUUCCUUGGGUCUUCCUGGC 5' |
| 418 | 5'CCUGGAAACCAUCAUCUCAUU<br>UUGGACCUUUGGUAGUAGUGU 5' |
| 451 | 5'UGAGGGACUACAUGCCGCCUU<br>UUACUCCCUGAUGUACGGCGG 5' |
| 885 | 5'AAGGUGCUGCCAAGAUCUCUU<br>UUUUCCACGACGGUUCUAGAG 5' |
| 427 | 5'CCAGAAGGACCGUUGGAAAUCAGTA<br>UGGGUCUUCCUGGCAACCUUUAGUCAU 5' |
| 783 | 5'GAAGUACUCUGGAGGAAGUGCAGCC<br>GACUUCAUGAGACCUCCUUCACGUCGG 5' |
| 858 | 5'CAAGGAAAGUGUUGGCUUUCUACAC<br>ACGUUCCUUUCACAACCGAAAGAUGUG 5' |
| 272 | 5'CCAUGGGAUUCGUCUGGCAGGAGGG<br>GUGGUACCCUAAGCAGACCGUCCUCCC 5' |
| 1145 | 5'GUACUGCCAUGCUGAGCUUCUUGAA<br>CCCAUGACGGUACGACUCGAAGAACUU 5' |
| 756 | 5'CUAUGAAGGUGCUGCCACAGAGCCT<br>CAGAUACUUCCACGACGGUGUCUCGGA 5' |
| 1172 | 5'GUGUCAGGGAGAAGACCAUGGAGGC<br>CUCACAGUCCCUCUUCUGGUACCUCCG 5' |
| 14 | 5'GUCAGAGCAUGACGCUGGAGGUGCC<br>UUCAGUCUCGUACUGCGACCUCCACGG 5' |

Figure 20B

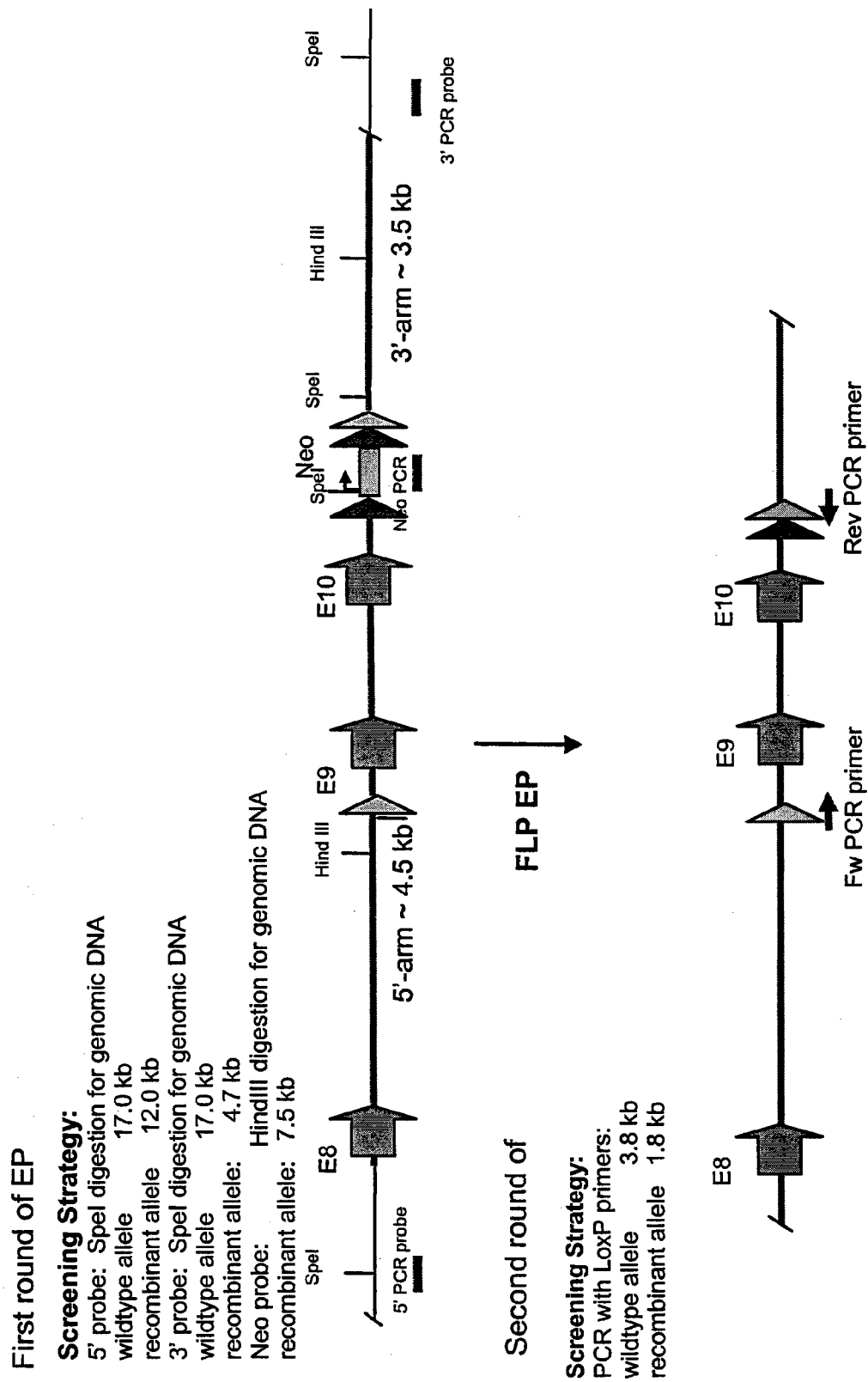

```
   1  AAGCTTTACT CGTAAAGCGA GTTGAAGGAT CATATTTAGT TGCGTTTATG
  51  AGATAAGATT GAAAGCACGT GTAAAATGTT TCCCGCGCGT TGGCACAACT
 101  ATTTACAATG CGGCCAAGTT ATAAAGATT  CTAATCTGAT ATGTTTTAAA
 151  ACACCTTTGC GGCCCGAGTT GTTTGCGTAC GTGACTAGCG AAGAAGATGT
 201  GTGGACCGCA GAACAGATAG TAAAACAAAA CCCTAGTATT GGAGCAATAA
 251  TCGATTTAAC CAACACGTCT AAATATTATG ATGGTGTGCA TTTTTTGCGG
 301  GCGGGCCTGT TATACAAAAA AATTCAAGTA CCTGGCCAGA CTTTGCCGCC
 351  TGAAAGCATA GTTCAAGAAT TTATTGACAC GGTAAAAGAA TTTACAGAAA
 401  AGTGTCCCGG CATGTTGGTG GGCGTGCACT GCACACACGG TATTAATCGC
 451  ACCGGTTACA TGGTGTGCAG ATATTTAATG CACACCCTGG GTATTGCGCC
 501  GCAGGAAGCC ATAGATAGAT TCGAAAAAGC CAGAGGTCAC AAAATTGAAA
 551  GACAAAATTA CGTTCAAGAT TTATTAATTT AATTAATATT ATTTGCATTC
 601  TTTAACAAAT ACTTTATCCT ATTTTCAAAT TGTTGCGCTT CTTCCAGCGA
 651  ACCAAAACTA TGCTTCGCTT GCTCCGTTTA GCTTGTAGCC GATCAGTGGC
 701  GTTGTTCCAA TCGACGGTAG GATTAGGCCG GATATTCTCC ACCACAATGT
 751  TGGCAACGTT GATGTTACGT TTATGCTTTT GGTTTTCCAC GTACGTCTTT
 801  TGGCCGGTAA TAGCCGTAAA CGTAGTGCCG TCGCGCGTCA CGCACAACAC
 851  CGGATGTTTG CGCTTGTCCG CGGGGTATTG AACCGCGCGA TCCGACAAAT
 901  CCACCACTTT GGCAACTAAA TCGGTGACCT GCGCGTCTTT TTTCTGCATT
 951  ATTTCGTCTT TCTTTTGCAT GGTTTCCTGG AAGCCGGTGT ACATGCGGTT
1001  TAGATCAGTC ATGACGCGCG TGACCTGCAA ATCTTTGGCC TCGATCTGCT
1051  TGTCCTTGAT GGCAACGATG CGTTCAATAA ACTCTTGTTT TTTAACAAGT
1101  TCCTCGGTTT TTTGCGCCAC CACCGCTTGC AGCGCGTTTG TGTGCTCGGT
1151  GAATGTCGCA ATCAGCTTAG TCACCAACTG TTTGCTCTCC TCCTCCCGTT
1201  GTTTGATCGC GGGATCGTAC TTGCCGGTGC AGAGCACTTG AGGAATTACT
1251  TCTTCTAAAA GCCATTCTTG TAATTCTATG GCGTAAGGCA ATTTGGACTT
1301  CATAATCAGC TGAATCACGC CGGATTTAGT AATGAGCACT GTATGCGGCT
1351  GCAAATACAG CGGGTCGCCC CTTTTCACGA CGCTGTTAGA GGTAGGGCCC
1401  CCATTTTGGA TGGTCTGCTC AAATAACGAT TTGTATTTAT TGTCTACATG
1451  AACACGTATA GCTTTATCAC AAACTGTATA TTTTAAACTG TTAGCGACGT
1501  CCTTGGCCAC GAACCGGACC TGTTGGTCGC GCTCTAGCAC GTACCGCAGG
1551  TTGAACGTAT CTTCTCCAAA TTTAAATTCT CCAATTTTAA CGCGAGCCAT
1601  TTTGATACAC GTGTGTCGAT TTTGCAACAA CTATTGTTTT TTAACGCAAA
1651  CTAAACTTAT TGTGGTAAGC AATAATTAAA TATGGGGGAA CATGCGCCGC
1701  TACAACACTC GTCGTTATGA ACGCAGACGG CGCCGGTCTC GGCGCAAGCG
1751  GCTAAAACGT GTTGCGCGTT CAACGCGGCA AACATCGCAA AAGCCAATAG
1801  TACAGTTTTG ATTTGCATAT TAACGGCGAT TTTTTAAATT ATCTTATTTA
1851  ATAAATAGTT ATGACGCCTA CAACTCCCCG CCCGCGTTGA CTCGCTGCAC
1901  CTCGAGCAGT TCGTTGACGC CTTCCTCCGT GTGGCCGAAC ACGTCGAGCG
```

Figure 23B

```
1951  GGTGGTCGAT GACCAGCGGC GTGCCGCACG CGACGCACAA GTATCTGTAC
2001  ACCGAATGAT CGTCGGGCGA AGGCACGTCG GCCTCCAAGT GGCAATATTG
2051  GCAAATTCGA AAATATATAC AGTTGGGTTG TTTGCGCATA TCTATCGTGG
2101  CGTTGGGCAT GTACGTCCGA ACGTTGATTT GCATGCAAGC CGAAATTAAA
2151  TCATTGCGAT TAGTGCGATT AAAACGTTGT ACATCCTCGC TTTTAATCAT
2201  GCCGTCGATT AAATCGCGCA ATCGAGTCAA GTGATCAAAG TGTGGAATAA
2251  TGTTTTCTTT GTATTCCCGA GTCAAGCGCA GCGCGTATTT TAACAAACTA
2301  GCCATCTTGT AAGTTAGTTT CATTTAATGC AACTTTATCC AATAATATAT
2351  TATGTATCGC ACGTCAAGAA TTAACAATGC GCCCGTTGTC GCATCTCAAC
2401  ACGACTATGA TAGAGATCAA ATAAAGCGCG AATTAAATAG CTTGCGACGC
2451  AACGTGCACG ATCTGTGCAC GCGTTCCGGC ACGAGCTTTG ATTGTAATAA
2501  GTTTTTACGA AGCGATGACA TGACCCCGT AGTGACAACG ATCACGCCCA
2551  AAAGAACTGC CGACTACAAA ATTACCGAGT ATGTCGGTGA CGTTAAAACT
2601  ATTAAGCCAT CCAATCGACC GTTAGTCGAA TCAGGACCGC TGGTGCGAGA
2651  AGCCGCGAAG TATGGCGAAT GCATCGTATA ACGTGTGGAG TCCGCTCATT
2701  AGAGCGTCAT GTTTAGACAA GAAAGCTACA TATTTAATTG ATCCCGATGA
2751  TTTTATTGAT AAATTGACCC TAACTCCATA CACGGTATTC TACAATGGCG
2801  GGGTTTTGGT CAAAATTTCC GGACTGCGAT TGTACATGCT GTTAACGGCT
2851  CCGCCCACTA TTAATGAAAT TAAAAATTCC AATTTTAAAA AACGCAGCAA
2901  GAGAAACATT TGTATGAAAG AATGCGTAGA AGGAAAGAAA AATGTCGTCG
2951  ACATGCTGAA CAACAAGATT AATATGCCTC CGTGTATAAA AAAAATATTG
3001  AACGATTTGA AAGAAAACAA TGTACCGCGC GGCGGTATGT ACAGGAAGAG
3051  GTTTATACTA AACTGTTACA TTGCAAACGT GGTTTCGTGT GCCAAGTGTG
3101  AAAACCGATG TTTAATCAAG GCTCTGACGC ATTTCTACAA CCACGACTCC
3151  AAGTGTGTGG GTGAAGTCAT GCATCTTTTA ATCAAATCCC AAGATGTGTA
3201  TAAACCACCA AACTGCCAAA AAATGAAAAC TGTCGACAAG CTCTGTCCGT
3251  TTGCTGGCAA CTGCAAGGGT CTCAATCCTA TTTGTAATTA TTGAATAATA
3301  AAACAATTAT AAATGCTAAA TTTGTTTTTT ATTAACGATA CAAACCAAAC
3351  GCAACAAGAA CATTTGTAGT ATTATCTATA ATTGAAAACG CGTAGTTATA
3401  ATCGCTGAGG TAATATTTAA AATCATTTTC AAATGATTCA CAGTTAATTT
3451  GCGACAATAT AATTTTATTT TCACATAAAC TAGACGCCTT GTCGTCTTCT
3501  TCTTCGTATT CCTTCTCTTT TTCATTTTTC TCCTCATAAA AATTAACATA
3551  GTTATTATCG TATCCATATA TGTATCTATC GTATAGAGTA AATTTTTTGT
3601  TGTCATAAAT ATATATGTCT TTTTTAATGG GGTGTATAGT ACCGCTGCGC
3651  ATAGTTTTTC TGTAATTTAC AACAGTGCTA TTTTCTGGTA GTTCTTCGGA
3701  GTGTGTTGCT TTAATTATTA AATTTATATA ATCAATGAAT TTGGGATCGT
3751  CGGTTTTGTA CAATATGTTG CCGGCATAGT ACGCAGCTTC TTCTAGTTCA
3801  ATTACACCAT TTTTTAGCAG CACCGGATTA ACATAACTTT CCAAAATGTT
3851  GTACGAACCG TTAAACAAAA ACAGTTCACC TCCCTTTTCT ATACTATTGT
```

Figure 23C

```
3901 CTGCGAGCAG TTGTTTGTTG TTAAAAATAA CAGCCATTGT AATGAGACGC
3951 ACAAACTAAT ATCACAAACT GGAAATGTCT ATCAATATAT AGTTGCTGAT
                                                        >>>
4001 ATCATGGAGA TAATTAAAAT GATAACCATC TCGCAAATAA ATAAGTATTT
     >................pr........................>
4051 TACTGTTTTC GTAACAGTTT TGTAATAAAA AAACCTATAA ATATTCCGGA
     >................pr.....................>>
4101 TTATTCATAC CGTCCCACCA TCGGGCGCGG ATCAGATCTG CAGCGGCCGC

KpnI
              -------
4151 TCCAGAATTC TAGAAGGTAC CATGGAGCCT CAAAGTCAGA GCATGACGCT
                                  >>............muIDO2............>
4201 GGAGGTGCCG TTGTCCTTGG GGAGATACCA CATTTCTGAG GAATATGGCT
     >....................muIDO2......................>
4251 TTCTCCTTCC AAATCCTCTG GAAGCACTTC CAGATCATTA CAAGCCTTGG
     >....................muIDO2......................>
4301 ATGGAAATTG CCCTCAGACT TCCTCACTTA ATCGAGAACC GCCAGCTCCG
     >....................muIDO2......................>
4351 AGCTCACGTG TACAGGATGC CTCTCCTGGA CTGCAGATTC CTAAAGAGTT
     >....................muIDO2......................>
4401 ACCGTGAGCA GCGCCTGGCA CACATGGCGC TGGCCGCTAT CACCATGGGA
     >....................muIDO2......................>
4451 TTCGTCTGGC AGGAGGGGGA AGGCCAACCC CAAAAGGTGC TGCCAAGATC
     >....................muIDO2......................>
4501 TCTTGCCATT CCTTTTGTTG AGGTATCCAG GAACTTGGGA CTCCCGCCTA
     >....................muIDO2......................>
4551 TCCTGGTCCA CTCTGACCTG GTGCTGACAA ACTGGACCAA AAGGAACCCA
     >....................muIDO2......................>
4601 GAAGGACCGT TGGAAATCAG TAACCTGGAA ACCATCATCT CATTTCCGGG
     >....................muIDO2......................>
4651 GGGAGAGAGC CTGCGGGGCT TCATCCTAGT GACAGTCTTG GTGGAGAAGG
     >....................muIDO2......................>
4701 CAGCAGTGCC CGGCCTTAAG GCCCTGGTTC AGGGAATGGA GGCCATTCGG
     >....................muIDO2......................>
4751 CAACACAGTC AGGACACCCT GCTAGAAGCC CTGCAGCAGC TGAGACTCTC
     >....................muIDO2......................>
4801 CATCCAGGAT ATCACCAGAG CCTTGGCCCA AATGCATGAT TATGTGGACC
```

Figure 23D

```
                  >......................muIDO2......................>
         4851     CAGACATATT TTACTCGGTC ATCCGGATCT TCCTCTCTGG GTGGAAGGAC
                  >......................muIDO2......................>
         4901     AATCCAGCCA TGCCTGTGGG GCTGGTCTAT GAAGGTGCTG CCACAGAGCC
                  >......................muIDO2......................>
         4951     TCTGAAGTAC TCTGGAGGAA GTGCAGCCCA GAGCTCCGTG CTTCATGCCT
                  >......................muIDO2......................>
         5001     TCGATGAGTT CCTGGGCATT GAGCATTGCA AGGAAAGTGT TGGCTTTCTA
                  >......................muIDO2......................>
         5051     CACAGAATGA GGGACTACAT GCCGCCTTCC CATAAGGCTT TCCTGGAAGA
                  >......................muIDO2......................>
         5101     TCTCCACGTA GCTCCTTCTC TGAGAGACTA CATACTGGCC TCTGGTCCTG
                  >......................muIDO2......................>
         5151     GGGACTGCCT GATGGCCTAT AACCAGTGTG TGGAGGCCCT GGGAGAGCTG
                  >......................muIDO2......................>
         5201     CGCAGTTACC ACATCAATGT CGTGGCCAGA TACATTATCT CCGCTGCCAC
                  >......................muIDO2......................>
         5251     CAGGGCCAGG AGCAGGGGGC TAACTAATCC CTCACCCCAT GCCTTGGAAG
                  >......................muIDO2......................>
         5301     ACAGGGGCAC TGGGGGTACT GCCATGCTGA GCTTCTTGAA GAGTGTCAGG
                  >......................muIDO2......................>
         5351     GAGAAGACCA TGGAGGCCCT CCTGTGTCCT GGTGCTTAGG GTCAAGACAA
                  >...............muIDO2...............>>
         5401     TTCTGCAGAT ATCCAGCACA GTGGCGGCCG CTCGAGTCTA GAGGGCCCGC
         5451     GGTTCGAAGG TAAGCCTATC CCTAACCCTC TCCTCGGTCT CGATTCTACG

NheI
                                                                ------
         5501     CGTACCGGTC ATCATCACCA TCACCATTGA GTTTGCTAGC CACTAGTACC
         5551     GACTCTGCTG AAGAGGAGGA AATTCTCCTT GAAGTTTCCC TGGTGTTCAA
         5601     AGTAAAGGAG TTTGCACCAG ACGCACCTCT GTTCACTGGT CCGGCGTATT
         5651     AAAACACGAT ACATTGTTAT TAGTACATTT ATTAAGCGCT AGATTCTGTG
         5701     CGTTGTTGAT TTACAGACAA TTGTTGTACG TATTTTAATA ATTCATTAAA
         5751     TTTATAATCT TTAGGGTGGT ATGTTAGAGC GAAAATCAAA TGATTTTCAG
         5801     CGTCTTTATA TCTGAATTTA AATATTAAAT CCTCAATAGA TTTGTAAAAT
         5851     AGGTTTCGAT TAGTTTCAAA CAAGGGTTGT TTTCCGAAC CGATGGCTGG
         5901     ACTATCTAAT GGATTTTCGC TCAACGCCAC AAAACTTGCC AAATCTTGTA
         5951     GCAGCAATCT AGCTTTGTCG ATATTCGTTT GTGTTTTGTT TTGTAATAAA
         6001     GGTTCGACGT CGTTCAAAAT ATTATGCGCT TTTGTATTTC TTTCATCACT
```

Figure 23E

```
6051  GTCGTTAGTG TACAATTGAC TCGACGTAAA CACGTTAAAT AAAGCTTGGA
6101  CATATTTAAC ATCGGGCGTG TTAGCTTTAT TAGGCCGATT ATCGTCGTCG
6151  TCCCAACCCT CGTCGTTAGA AGTTGCTTCC GAAGACGATT TTGCCATAGC
6201  CACACGACGC CTATTAATTG TGTCGGCTAA CACGTCCGCG ATCAAATTTG
6251  TAGTTGAGCT TTTTGGAATT ATTTCTGATT GCGGGCGTTT TTGGGCGGGT
6301  TTCAATCTAA CTGTGCCCGA TTTTAATTCA GACAACACGT TAGAAAGCGA
6351  TGGTGCAGGC GGTGGTAACA TTTCAGACGG CAAATCTACT AATGGCGGCG
6401  GTGGTGGAGC TGATGATAAA TCTACCATCG GTGGAGGCGC AGGCGGGGCT
6451  GGCGGCGGAG GCGGAGGCGG AGGTGGTGGC GGTGATGCAG ACGGCGGTTT
6501  AGGCTCAAAT GTCTCTTTAG GCAACACAGT CGGCACCTCA ACTATTGTAC
6551  TGGTTTCGGG CGCCGTTTTT GGTTTGACCG GTCTGAGACG AGTGCGATTT
6601  TTTTCGTTTC TAATAGCTTC CAACAATTGT TGTCTGTCGT CTAAAGGTGC
6651  AGCGGGTTGA GGTTCCGTCG GCATTGGTGG AGCGGGCGGC AATTCAGACA
6701  TCGATGGTGG TGGTGGTGGT GGAGGCGCTG GAATGTTAGG CACGGGAGAA
6751  GGTGGTGGCG GCGGTGCCGC CGGTATAATT TGTTCTGGTT TAGTTTGTTC
6801  GCGCACGATT GTGGGCACCG GCGCAGGCGC CGCTGGCTGC ACAACGGAAG
6851  GTCGTCTGCT TCGAGGCAGC GCTTGGGGTG GTGGCAATTC AATATTATAA
6901  TTGGAATACA AATCGTAAAA ATCTGCTATA AGCATTGTAA TTTCGCTATC
6951  GTTTACCGTG CCGATATTTA ACAACCGCTC AATGTAAGCA ATTGTATTGT
7001  AAAGAGATTG TCTCAAGCTC GCCGCACGCC GATAACAAGC CTTTTCATTT
7051  TTACTACAGC ATTGTAGTGG CGAGACACTT CGCTGTCGTC GACGTACATG
7101  TATGCTTTGT TGTCAAAAAC GTCGTTGGCA AGCTTTAAAA TATTTAAAAG
7151  AACATCTCTG TTCAGCACCA CTGTGTTGTC GTAAATGTTG TTTTTGATAA
7201  TTTGCGCTTC CGCAGTATCG ACACGTTCAA AAAATTGATG CGCATCAATT
7251  TTGTTGTTCC TATTATTGAA TAAATAAGAT TGTACAGATT CATATCTACG
7301  ATTCGTCATG GCCACCACAA ATGCTACGCT GCAAACGCTG GTACAATTTT
7351  ACGAAAACTG CAAAAACGTC AAAACTCGGT ATAAATAAT CAACGGGCGC
7401  TTTGGCAAAA TATCTATTTT ATCGCACAAG CCCACTAGCA AATTGTATTT
7451  GCAGAAAACA ATTTCGGCGC ACAATTTTAA CGCTGACGAA ATAAAAGTTC
7501  ACCAGTTAAT GAGCGACCAC CCAAATTTTA TAAAAATCTA TTTTAATCAC
7551  GGTTCCATCA ACAACCAAGT GATCGTGATG GACTACATTG ACTGTCCCGA
7601  TTTATTTGAA ACACTACAAA TTAAAGGCGA GCTTTCGTAC CAACTTGTTA
7651  GCAATATTAT TAGACAGCTG TGTGAAGCGC TCAACGATTT GCACAAGCAC
7701  AATTTCATAC ACAACGACAT AAAACTCGAA AATGTCTTAT ATTTCGAAGC
7751  ACTTGATCGC GTGTATGTTT GCGATTACGG ATTGTGCAAA CACGAAAACT
7801  CACTTAGCGT GCACGACGGC ACGTTGGAGT ATTTTAGTCC GGAAAAAATT
7851  CGACACACAA CTATGCACGT TTCGTTTGAC TGGTACGCGG CGTGTTAACA
7901  TACAAGTTGC TAACGTAATC ATGGTCATAG CTGTTTCCTG TGTGAAATTG
7951  TTATCCGCTC ACAATTCCAC ACAACATACG AGCCGGAAGC ATAAAGTGTA
```

Figure 23F

```
8001  AAGCCTGGGG TGCCTAATGA GTGAGCTAAC TCACATTAAT TGCGTTGCGC
8051  TCACTGCCCG CTTTCCAGTC GGGAAACCTG TCGTGCCAGC TGCATTAATG
8101  AATCGGCCAA CGCGCGGGGA GAGGCGGTTT GCGTATTGGG CGCTCTTCCG
8151  CTTCCTCGCT CACTGACTCG CTGCGCTCGG TCGTTCGGCT GCGGCGAGCG
8201  GTATCAGCTC ACTCAAAGGC GGTAATACGG TTATCCACAG AATCAGGGGA
8251  TAACGCAGGA AAGAACATGT GAGCAAAAGG CCAGCAAAAG GCCAGGAACC
8301  GTAAAAAGGC CGCGTTGCTG GCGTTTTTCC ATAGGCTCCG CCCCCCTGAC
8351  GAGCATCACA AAAATCGACG CTCAAGTCAG AGGTGGCGAA ACCCGACAGG
8401  ACTATAAAGA TACCAGGCGT TTCCCCCTGG AAGCTCCCTC GTGCGCTCTC
8451  CTGTTCCGAC CCTGCCGCTT ACCGGATACC TGTCCGCCTT TCTCCCTTCG
8501  GGAAGCGTGG CGCTTTCTCA TAGCTCACGC TGTAGGTATC TCAGTTCGGT
8551  GTAGGTCGTT CGCTCCAAGC TGGGCTGTGT GCACGAACCC CCCGTTCAGC
8601  CCGACCGCTG CGCCTTATCC GGTAACTATC GTCTTGAGTC AACCCGGTA
8651  AGACACGACT TATCGCCACT GGCAGCAGCC ACTGGTAACA GGATTAGCAG
8701  AGCGAGGTAT GTAGGCGGTG CTACAGAGTT CTTGAAGTGG TGGCCTAACT
              <<................ColE1..................<
8751  ACGGCTACAC TAGAAGGACA GTATTTGGTA TCTGCGCTCT GCTGAAGCCA
              <....................ColE1........................<
8801  GTTACCTTCG GAAAAGAGT TGGTAGCTCT TGATCCGGCA AACAAACCAC
              <....................ColE1........................<
8851  CGCTGGTAGC GGTGGTTTTT TTGTTTGCAA GCAGCAGATT ACGCGCAGAA
              <....................ColE1........................<
8901  AAAAGGATC TCAAGAAGAT CCTTTGATCT TTTCTACGGG GTCTGACGCT
              <....................ColE1........................<
8951  CAGTGGAACG AAAACTCACG TTAAGGGATT TTGGTCATGA GATTATCAAA
              <....................ColE1........................<
9001  AAGGATCTTC ACCTAGATCC TTTTAAATTA AAAATGAAGT TTTAAATCAA
              <....................ColE1........................<
9051  TCTAAAGTAT ATATGAGTAA ACTTGGTCTG ACAGTTACCA ATGCTTAATC
              <....................ColE1........................<
9101  AGTGAGGCAC CTATCTCAGC GATCTGTCTA TTTCGTTCAT CCATAGTTGC
              <....................ColE1........................<
9151  CTGACTCCCC GTCGTGTAGA TAACTACGAT ACGGGAGGGC TTACCATCTG
              <....................ColE1........................<
9201  GCCCCAGTGC TGCAATGATA CCGCGAGACC CACGCTCACC GGCTCCAGAT
              <....................ColE1........................<
9251  TTATCAGCAA TAAACCAGCC AGCCGGAAGG GCCGAGCGCA GAAGTGGTCC
              <....................ColE1........................<
9301  TGCAACTTTA TCCGCCTCCA TCCAGTCTAT TAATTGTTGC CGGGAAGCTA
```

Figure 23G

```
              <..................ColE1..................<
       9351   GAGTAAGTAG TTCGCCAGTT AATAGTTTGC GCAACGTTGT TGCCATTGCT
              <..........ColE1..........<<
       9401   ACAGGCATCG TGGTGTCACG CTCGTCGTTT GGTATGGCTT CATTCAGCTC
       9451   CGGTTCCCAA CGATCAAGGC GAGTTACATG ATCCCCCATG TTGTGCAAAA
       9501   AAGCGGTTAG CTCCTTCGGT CCTCCGATCG TTGTCAGAAG TAAGTTGGCC
                                               >>.......amp.......>
       9551   GCAGTGTTAT CACTCATGGT TATGGCAGCA CTGCATAATT CTCTTACTGT
              >..................amp..................>
       9601   CATGCCATCC GTAAGATGCT TTTCTGTGAC TGGTGAGTAC TCAACCAAGT
              >..................amp..................>
       9651   CATTCTGAGA ATAGTGTATG CGGCGACCGA GTTGCTCTTG CCCGGCGTCA
              >..................amp..................>
       9701   ATACGGGATA ATACCGCGCC ACATAGCAGA ACTTTAAAAG TGCTCATCAT
              >..................amp..................>
       9751   TGGAAAACGT TCTTCGGGGC GAAAACTCTC AAGGATCTTA CCGCTGTTGA
              >..................amp..................>
       9801   GATCCAGTTC GATGTAACCC ACTCGTGCAC CCAACTGATC TTCAGCATCT
              >..................amp..................>
       9851   TTTACTTTCA CCAGCGTTTC TGGGTGAGCA AAAACAGGAA GGCAAAATGC
              >..................amp..................>
       9901   CGCAAAAAAG GAATAAGGG CGACACGGAA ATGTTGAATA CTCATACTCT
              >..................amp..................>
       9951   TCCTTTTTCA ATATTATTGA AGCATTTATC AGGGTTATTG TCTCATGAGC
              >..................amp..................>
      10001   GGATACATAT TTGAATGTAT TTAGAAAAAT AAACAAATAG GGGTTCCGCG
              >..................amp..................>
      10051   CACATTTCCC CGAAAAGTGC CACCTGACGT CTAAGAAACC ATTATTATCA
              >..................amp..................>
      10101   TGACATTAAC CTATAAAAAT AGGCGTATCA CGAGGCCCTT TCGTCTCGCG
              >..................amp..................>
      10151   CGTTTCGGTG ATGACGGTGA AAACCTCTGA CACATGCAGC TCCCGGAGAC
              >..................amp..................>
      10201   GGTCACAGCT TGTCTGTAAG CGGATGCCGG GAGCAGACAA GCCCGTCAGG
              >..................amp..................>
      10251   GCGCGTCAGC GGGTGTTGGC GGGTGTCGGG GCTGGCTTAA CTATGCGGCA
              >..................amp..................>
      10301   TCAGAGCAGA TTGTACTGAG AGTGCACCAT ATGCGGTGTG AAATACCGCA
```

Figure 23H

```
        >.......amp........>>
10351   CAGATGCGTA AGGAGAAAAT ACCGCATCAG GCGCCATTCG CCATTCAGGC
10401   TGCGCAACTG TTGGGAAGGG CGATCGGTGC GGGCCTCTTC GCTATTACGC
10451   CAGCTGGCGA AAGGGGGATG TGCTGCAAGG CGATTAAGTT GGGTAACGCC
10501   AGGGTTTTCC CAGTCACGAC GTTGTAAAAC GACGGCCAGT GCC
```

Figure 23I

```
   1  AAGCTTTACT CGTAAAGCGA GTTGAAGGAT CATATTTAGT TGCGTTTATG
  51  AGATAAGATT GAAAGCACGT GTAAAATGTT TCCCGCGCGT TGGCACAACT
 101  ATTTACAATG CGGCCAAGTT ATAAAAGATT CTAATCTGAT ATGTTTTAAA
 151  ACACCTTTGC GGCCCGAGTT GTTTGCGTAC GTGACTAGCG AAGAAGATGT
 201  GTGGACCGCA GAACAGATAG TAAAACAAAA CCCTAGTATT GGAGCAATAA
 251  TCGATTTAAC CAACACGTCT AAATATTATG ATGGTGTGCA TTTTTTGCGG
 301  GCGGGCCTGT TATACAAAAA AATTCAAGTA CCTGGCCAGA CTTTGCCGCC
 351  TGAAAGCATA GTTCAAGAAT TTATTGACAC GGTAAAAGAA TTTACAGAAA
 401  AGTGTCCCGG CATGTTGGTG GGCGTGCACT GCACACACGG TATTAATCGC
 451  ACCGGTTACA TGGTGTGCAG ATATTTAATG CACACCCTGG GTATTGCGCC
 501  GCAGGAAGCC ATAGATAGAT TCGAAAAAGC CAGAGGTCAC AAAATTGAAA
 551  GACAAAATTA CGTTCAAGAT TTATTAATTT AATTAATATT ATTTGCATTC
 601  TTTAACAAAT ACTTTATCCT ATTTTCAAAT TGTTGCGCTT CTTCCAGCGA
 651  ACCAAAACTA TGCTTCGCTT GCTCCGTTTA GCTTGTAGCC GATCAGTGGC
 701  GTTGTTCCAA TCGACGGTAG GATTAGGCCG GATATTCTCC ACCACAATGT
 751  TGGCAACGTT GATGTTACGT TTATGCTTTT GGTTTCCAC GTACGTCTTT
 801  TGGCCGGTAA TAGCCGTAAA CGTAGTGCCG TCGCGCGTCA CGCACAACAC
 851  CGGATGTTTG CGCTTGTCCG CGGGGTATTG AACCGCGCGA TCCGACAAAT
 901  CCACCACTTT GGCAACTAAA TCGGTGACCT GCGCGTCTTT TTTCTGCATT
 951  ATTTCGTCTT TCTTTTGCAT GGTTTCCTGG AAGCCGGTGT ACATGCGGTT
1001  TAGATCAGTC ATGACGCGCG TGACCTGCAA ATCTTTGGCC TCGATCTGCT
1051  TGTCCTTGAT GGCAACGATG CGTTCAATAA ACTCTTGTTT TTTAACAAGT
1101  TCCTCGGTTT TTTGCGCCAC CACCGCTTGC AGCGCGTTTG TGTGCTCGGT
1151  GAATGTCGCA ATCAGCTTAG TCACCAACTG TTTGCTCTCC TCCTCCCGTT
1201  GTTTGATCGC GGGATCGTAC TTGCCGGTGC AGAGCACTTG AGGAATTACT
1251  TCTTCTAAAA GCCATTCTTG TAATTCTATG GCGTAAGGCA ATTTGGACTT
1301  CATAATCAGC TGAATCACGC CGGATTTAGT AATGAGCACT GTATGCGGCT
1351  GCAAATACAG CGGGTCGCCC CTTTTCACGA CGCTGTTAGA GGTAGGGCCC
1401  CCATTTTGGA TGGTCTGCTC AAATAACGAT TTGTATTTAT TGTCTACATG
1451  AACACGTATA GCTTTATCAC AAACTGTATA TTTTAAACTG TTAGCGACGT
1501  CCTTGGCCAC GAACCGGACC TGTTGGTCGC GCTCTAGCAC GTACCGCAGG
1551  TTGAACGTAT CTTCTCCAAA TTTAAATTCT CCAATTTTAA CGCGAGCCAT
1601  TTTGATACAC GTGTGTCGAT TTTGCAACAA CTATTGTTTT TTAACGCAAA
1651  CTAAACTTAT TGTGGTAAGC AATAATTAAA TATGGGGAA CATGCGCCGC
1701  TACAACACTC GTCGTTATGA ACGCAGACGG CGCCGGTCTC GGCGCAAGCG
1751  GCTAAAACGT GTTGCGCGTT CAACGCGGCA ACATCGCAA AAGCCAATAG
1801  TACAGTTTTG ATTTGCATAT TAACGGCGAT TTTTTAAATT ATCTTATTTA
1851  ATAAATAGTT ATGACGCCTA CAACTCCCCG CCCGCGTTGA CTCGCTGCAC
1901  CTCGAGCAGT TCGTTGACGC CTTCCTCCGT GTGGCCGAAC ACGTCGAGCG
```

Figure 24B

```
1951  GGTGGTCGAT GACCAGCGGC GTGCCGCACG CGACGCACAA GTATCTGTAC
2001  ACCGAATGAT CGTCGGGCGA AGGCACGTCG GCCTCCAAGT GGCAATATTG
2051  GCAAATTCGA AAATATATAC AGTTGGGTTG TTTGCGCATA TCTATCGTGG
2101  CGTTGGGCAT GTACGTCCGA ACGTTGATTT GCATGCAAGC CGAAATTAAA
2151  TCATTGCGAT TAGTGCGATT AAAACGTTGT ACATCCTCGC TTTTAATCAT
2201  GCCGTCGATT AAATCGCGCA ATCGAGTCAA GTGATCAAAG TGTGGAATAA
2251  TGTTTTCTTT GTATTCCCGA GTCAAGCGCA GCGCGTATTT AACAAACTA
2301  GCCATCTTGT AAGTTAGTTT CATTTAATGC AACTTTATCC AATAATATAT
2351  TATGTATCGC ACGTCAAGAA TTAACAATGC GCCCGTTGTC GCATCTCAAC
2401  ACGACTATGA TAGAGATCAA ATAAAGCGCG AATTAAATAG CTTGCGACGC
2451  AACGTGCACG ATCTGTGCAC GCGTTCCGGC ACGAGCTTTG ATTGTAATAA
2501  GTTTTTACGA AGCGATGACA TGACCCCCGT AGTGACAACG ATCACGCCCA
2551  AAAGAACTGC CGACTACAAA ATTACCGAGT ATGTCGGTGA CGTTAAAACT
2601  ATTAAGCCAT CCAATCGACC GTTAGTCGAA TCAGGACCGC TGGTGCGAGA
2651  AGCCGCGAAG TATGGCGAAT GCATCGTATA ACGTGTGGAG TCCGCTCATT
2701  AGAGCGTCAT GTTAGACAA GAAAGCTACA TATTTAATTG ATCCCGATGA
2751  TTTTATTGAT AAATTGACCC TAACTCCATA CACGGTATTC TACAATGGCG
2801  GGGTTTTGGT CAAAATTTCC GGACTGCGAT TGTACATGCT GTTAACGGCT
2851  CCGCCCACTA TTAATGAAAT TAAAAATTCC AATTTTAAAA AACGCAGCAA
2901  GAGAAACATT TGTATGAAAG AATGCGTAGA AGGAAAGAAA AATGTCGTCG
2951  ACATGCTGAA CAACAAGATT AATATGCCTC CGTGTATAAA AAAAATATTG
3001  AACGATTTGA AGAAAACAA TGTACCGCGC GGCGGTATGT ACAGGAAGAG
3051  GTTTATACTA AACTGTTACA TTGCAAACGT GGTTTCGTGT GCCAAGTGTG
3101  AAAACCGATG TTTAATCAAG GCTCTGACGC ATTTCTACAA CCACGACTCC
3151  AAGTGTGTGG GTGAAGTCAT GCATCTTTTA ATCAAATCCC AAGATGTGTA
3201  TAAACCACCA AACTGCCAAA AAATGAAAAC TGTCGACAAG CTCTGTCCGT
3251  TTGCTGGCAA CTGCAAGGGT CTCAATCCTA TTTGTAATTA TTGAATAATA
3301  AAACAATTAT AAATGCTAAA TTTGTTTTTT ATTAACGATA CAAACCAAAC
3351  GCAACAAGAA CATTTGTAGT ATTATCTATA ATTGAAAACG CGTAGTTATA
3401  ATCGCTGAGG TAATATTTAA AATCATTTTC AAATGATTCA CAGTTAATTT
3451  GCGACAATAT AATTTTATTT TCACATAAAC TAGACGCCTT GTCGTCTTCT
3501  TCTTCGTATT CCTTCTCTTT TTCATTTTTC TCCTCATAAA AATTAACATA
3551  GTTATTATCG TATCCATATA TGTATCTATC GTATAGAGTA AATTTTTTGT
3601  TGTCATAAAT ATATATGTCT TTTTTAATGG GGTGTATAGT ACCGCTGCGC
3651  ATAGTTTTTC TGTAATTTAC AACAGTGCTA TTTTCTGGTA GTTCTTCGGA
3701  GTGTGTTGCT TTAATTATTA AATTTATATA ATCAATGAAT TTGGGATCGT
3751  CGGTTTTGTA CAATATGTTG CCGGCATAGT ACGCAGCTTC TTCTAGTTCA
3801  ATTACACCAT TTTTTAGCAG CACCGGATTA ACATAACTTT CCAAAATGTT
3851  GTACGAACCG TTAAACAAAA ACAGTTCACC TCCCTTTTCT ATACTATTGT
```

Figure 24C

```
3901 CTGCGAGCAG TTGTTTGTTG TTAAAAATAA CAGCCATTGT AATGAGACGC
3951 ACAAACTAAT ATCACAAACT GGAAATGTCT ATCAATATAT AGTTGCTGAT
                                                        >>>
4001 ATCATGGAGA TAATTAAAAT GATAACCATC TCGCAAATAA ATAAGTATTT
     >..................pr........................>
4051 TACTGTTTTC GTAACAGTTT TGTAATAAAA AAACCTATAA ATATTCCGGA
     >..................pr....................>>

NotI
                                                  --------
4101 TTATTCATAC CGTCCCACCA TCGGGCGCGG ATCAGATCTG CAGCGGCCGC

KpnI
               --------
4151 TCCAGAATTC TAGAAGGTAC CATGGAGCC CCACAGACCG AATGTGAAGA
                                >>..........huIDO2...........>
4201 CAGCAGTGCC ATTGTCTTTG GAAAGCTATC ACATATCTGA AGAGTATGGC
     >.....................huIDO2.....................>
4251 TTTCTTCTTC CAGATTCTCT GAAAGAACTT CCAGATCATT ATAGGCCTTG
     >.....................huIDO2.....................>
4301 GATGGAAATT GCCAACAAAC TTCCTCAATT GATTGATGCT CACCAGCTTC
     >.....................huIDO2.....................>
4351 AAGCTCATGT GGACAAGATG CCCCTGCTGA GCTGCCAGTT CCTGAAGGGT
     >.....................huIDO2.....................>
4401 CACCGGGAGC AGCGCCTGGC CCACCTGGTC CTGAGCTTCC TCACCATGGG
     >.....................huIDO2.....................>
4451 TTATGTCTGG CAGGAAGGAG AGGCGCAGCC TGCAGAGGTC CTGCCAAGGA
     >.....................huIDO2.....................>
4501 ATCTTGCCCT TCCATTTGTC GAAGTCTCCA GGAACTTGGG GCTCCCTCCT
     >.....................huIDO2.....................>
4551 ATCCTGGTCC ACTCAGACTT GGTGCTGACG AACTGGACCA AAAAAGATCC
     >.....................huIDO2.....................>
4601 AGACGGGTTC CTGGAAATTG GAACCTGGA GACCATCATC TCATTTCCTG
     >.....................huIDO2.....................>
4651 GGGGAGAGAG CCTGCATGGT TTTATACTGG TGACTGCTTT GGTAGAGAAA
     >.....................huIDO2.....................>
4701 GAAGCAGTGC CTGGGATAAA GGCTCTTGTT CAGGCCACGA ATGCTATCTT
     >.....................huIDO2.....................>
4751 GCAGCCCAAC CAGGAGGCCC TGCTCCAAGC CCTGCAGCGA CTGAGACTGT
```

Figure 24D

```
                >..............huIDO2..................>
4801    CTATTCAGGA CATCACCAAA ACCTTAGGAC AGATGCATGA TTATGTAGAT
                >..............huIDO2..................>
4851    CCAGACATAT TTTATGCAGG CATCCGGATC TTTCTCTCTG GGTGGAAAGA
                >..............huIDO2..................>
4901    CAACCCAGCA ATGCCTGCAG GGCTGATGTA TGAAGGAGTT TCCCAAGAGC
                >..............huIDO2..................>
4951    CCCTGAAATA CTCCGGCGGG AGTGCAGCTC AGAGCACAGT GCTTCATGCC
                >..............huIDO2..................>
5001    TTTGATGAGT TCTTAGGCAT TCGTCATAGC AAGGAAAGTG GTGACTTTCT
                >..............huIDO2..................>
5051    GTACAGAATG AGGGATTACA TGCCTCCTTC CCATAAGGCC TTCATAGAAG
                >..............huIDO2..................>
5101    ACATCCACTC AGCACCTTCC CTGAGGGACT ACATCCTGTC ATCTGGACAG
                >..............huIDO2..................>
5151    GACCACTTGC TGACAGCTTA TAACCAGTGT GTGCAGGCCC TGGCAGAGCT
                >..............huIDO2..................>
5201    GCGGAGCTAT CACATCACCA TGGTCACCAA ATACCTCATC ACAGCTGCAG
                >..............huIDO2..................>
5251    CCAAGGCAAA GCATGGGAAG CCAAACCATC TCCCAGGGCC TCCTCAGGCT
                >..............huIDO2..................>
5301    TTAAAAGACA GGGGCACAGG TGGAACCGCA GTTATGAGCT TTCTTAAGAG
                >..............huIDO2..................>
5351    TGTCAGGGAT AAGACCTTGG AGTCAATCCT TCACCCACGT GGTTAACGCT
                >..............huIDO2..................>>
5401    CGAGTCTAGA GGGCCCGCGG TTCGAAGGTA AGCCTATCCC TAACCCTCTC
5451    CTCGGTCTCG ATTCTACGCG TACCGGTCAT CATCACCATC ACCATTGAGT

NheI
        ------
5501    TTGCTAGCCA CTAGTACCGA CTCTGCTGAA GAGGAGGAAA TTCTCCTTGA
5551    AGTTTCCCTG GTGTTCAAAG TAAAGGAGTT TGCACCAGAC GCACCTCTGT
5601    TCACTGGTCC GGCGTATTAA AACACGATAC ATTGTTATTA GTACATTTAT
5651    TAAGCGCTAG ATTCTGTGCG TTGTTGATTT ACAGACAATT GTTGTACGTA
5701    TTTTAATAAT TCATTAAATT TATAATCTTT AGGGTGGTAT GTTAGAGCGA
5751    AAATCAAATG ATTTTCAGCG TCTTTATATC TGAATTTAAA TATTAAATCC
5801    TCAATAGATT TGTAAAATAG GTTCGATTA GTTTCAAACA AGGGTTGTTT
5851    TTCCGAACCG ATGGCTGGAC TATCTAATGG ATTTCGCTC AACGCCACAA
5901    AACTTGCCAA ATCTTGTAGC AGCAATCTAG CTTTGTCGAT ATTCGTTTGT
```

Figure 24E

```
5951  GTTTTGTTTT GTAATAAAGG TTCGACGTCG TTCAAAATAT TATGCGCTTT
6001  TGTATTTCTT TCATCACTGT CGTTAGTGTA CAATTGACTC GACGTAAACA
6051  CGTTAAATAA AGCTTGGACA TATTTAACAT CGGGCGTGTT AGCTTTATTA
6101  GGCCGATTAT CGTCGTCGTC CCAACCCTCG TCGTTAGAAG TTGCTTCCGA
6151  AGACGATTTT GCCATAGCCA CACGACGCCT ATTAATTGTG TCGGCTAACA
6201  CGTCCGCGAT CAAATTTGTA GTTGAGCTTT TTGGAATTAT TTCTGATTGC
6251  GGGCGTTTTT GGGCGGGTTT CAATCTAACT GTGCCCGATT TTAATTCAGA
6301  CAACACGTTA GAAAGCGATG GTGCAGGCGG TGGTAACATT TCAGACGGCA
6351  AATCTACTAA TGGCGGCGGT GGTGGAGCTG ATGATAAATC TACCATCGGT
6401  GGAGGCGCAG GCGGGCTGG CGGCGGAGGC GGAGGCGGAG GTGGTGGCGG
6451  TGATGCAGAC GGCGGTTTAG GCTCAAATGT CTCTTTAGGC AACACAGTCG
6501  GCACCTCAAC TATTGTACTG GTTTCGGGCG CCGTTTTGG TTTGACCGGT
6551  CTGAGACGAG TGCGATTTTT TTCGTTTCTA ATAGCTTCCA ACAATTGTTG
6601  TCTGTCGTCT AAAGGTGCAG CGGGTTGAGG TTCCGTCGGC ATTGGTGGAG
6651  CGGGCGGCAA TTCAGACATC GATGGTGGTG GTGGTGGTGG AGGCGCTGGA
6701  ATGTTAGGCA CGGGAGAAGG TGGTGGCGGC GGTGCCGCCG GTATAATTTG
6751  TTCTGGTTTA GTTTGTTCGC GCACGATTGT GGGCACCGGC GCAGGCGCCG
6801  CTGGCTGCAC AACGGAAGGT CGTCTGCTTC GAGGCAGCGC TTGGGGTGGT
6851  GGCAATTCAA TATTATAATT GGAATACAAA TCGTAAAAAT CTGCTATAAG
6901  CATTGTAATT TCGCTATCGT TTACCGTGCC GATATTTAAC AACCGCTCAA
6951  TGTAAGCAAT TGTATTGTAA AGAGATTGTC TCAAGCTCGC CGCACGCCGA
7001  TAACAAGCCT TTTCATTTTT ACTACAGCAT TGTAGTGGCG AGACACTTCG
7051  CTGTCGTCGA CGTACATGTA TGCTTTGTTG TCAAAAACGT CGTTGGCAAG
7101  CTTTAAAATA TTTAAAGAA CATCTCTGTT CAGCACCACT GTGTTGTCGT
7151  AAATGTTGTT TTTGATAATT TGCGCTTCCG CAGTATCGAC ACGTTCAAAA
7201  AATTGATGCG CATCAATTTT GTTGTTCCTA TTATTGAATA AATAAGATTG
7251  TACAGATTCA TATCTACGAT TCGTCATGGC CACCACAAAT GCTACGCTGC
7301  AAACGCTGGT ACAATTTTAC GAAAACTGCA AAAACGTCAA AACTCGGTAT
7351  AAAATAATCA ACGGGCGCTT TGGCAAAATA TCTATTTTAT CGCACAAGCC
7401  CACTAGCAAA TTGTATTTGC AGAAAACAAT TCGGCGCAC AATTTTAACG
7451  CTGACGAAAT AAAAGTTCAC CAGTTAATGA GCGACCACCC AAATTTTATA
7501  AAAATCTATT TTAATCACGG TTCCATCAAC AACCAAGTGA TCGTGATGGA
7551  CTACATTGAC TGTCCCGATT TATTTGAAAC ACTACAAATT AAAGGCGAGC
7601  TTTCGTACCA ACTTGTTAGC AATATTATTA GACAGCTGTG TGAAGCGCTC
7651  AACGATTTGC ACAAGCACAA TTTCATACAC AACGACATAA AACTCGAAAA
7701  TGTCTTATAT TTCGAAGCAC TTGATCGCGT GTATGTTTGC GATTACGGAT
7751  TGTGCAAACA CGAAAACTCA CTTAGCGTGC ACGACGGCAC GTTGGAGTAT
7801  TTTAGTCCGG AAAAAATTCG ACACACAACT ATGCACGTTT CGTTTGACTG
7851  GTACGCGGCG TGTTAACATA CAAGTTGCTA ACGTAATCAT GGTCATAGCT
```

Figure 24F

```
7901  GTTTCCTGTG TGAAATTGTT ATCCGCTCAC AATTCCACAC AACATACGAG
7951  CCGGAAGCAT AAAGTGTAAA GCCTGGGGTG CCTAATGAGT GAGCTAACTC
8001  ACATTAATTG CGTTGCGCTC ACTGCCCGCT TTCCAGTCGG GAAACCTGTC
8051  GTGCCAGCTG CATTAATGAA TCGGCCAACG CGCGGGGAGA GGCGGTTTGC
8101  GTATTGGGCG CTCTTCCGCT TCCTCGCTCA CTGACTCGCT GCGCTCGGTC
8151  GTTCGGCTGC GGCGAGCGGT ATCAGCTCAC TCAAAGGCGG TAATACGGTT
8201  ATCCACAGAA TCAGGGGATA ACGCAGGAAA GAACATGTGA GCAAAAGGCC
8251  AGCAAAAGGC CAGGAACCGT AAAAAGGCCG CGTTGCTGGC GTTTTTCCAT
8301  AGGCTCCGCC CCCCTGACGA GCATCACAAA AATCGACGCT CAAGTCAGAG
8351  GTGGCGAAAC CCGACAGGAC TATAAAGATA CCAGGCGTTT CCCCCTGGAA
8401  GCTCCCTCGT GCGCTCTCCT GTTCCGACCC TGCCGCTTAC CGGATACCTG
8451  TCCGCCTTTC TCCCTTCGGG AAGCGTGGCG CTTTCTCATA GCTCACGCTG
8501  TAGGTATCTC AGTTCGGTGT AGGTCGTTCG CTCCAAGCTG GGCTGTGTGC
8551  ACGAACCCCC CGTTCAGCCC GACCGCTGCG CCTTATCCGG TAACTATCGT
8601  CTTGAGTCCA ACCCGGTAAG ACACGACTTA TCGCCACTGG CAGCAGCCAC
8651  TGGTAACAGG ATTAGCAGAG CGAGGTATGT AGGCGGTGCT ACAGAGTTCT
                                         <<........ColE1........<
8701  TGAAGTGGTG GCCTAACTAC GGCTACACTA GAAGGACAGT ATTTGGTATC
      <.................ColE1.......................<
8751  TGCGCTCTGC TGAAGCCAGT TACCTTCGGA AAAAGAGTTG GTAGCTCTTG
      <.................ColE1.......................<
8801  ATCCGGCAAA CAAACCACCG CTGGTAGCGG TGGTTTTTTT GTTTGCAAGC
      <.................ColE1.......................<
8851  AGCAGATTAC GCGCAGAAAA AAAGGATCTC AAGAAGATCC TTTGATCTTT
      <.................ColE1.......................<
8901  TCTACGGGGT CTGACGCTCA GTGGAACGAA AACTCACGTT AAGGGATTTT
      <.................ColE1.......................<
8951  GGTCATGAGA TTATCAAAAA GGATCTTCAC CTAGATCCTT TTAAATTAAA
      <.................ColE1.......................<
9001  AATGAAGTTT TAAATCAATC TAAAGTATAT ATGAGTAAAC TTGGTCTGAC
      <.................ColE1.......................<
9051  AGTTACCAAT GCTTAATCAG TGAGGCACCT ATCTCAGCGA TCTGTCTATT
      <.................ColE1.......................<
9101  TCGTTCATCC ATAGTTGCCT GACTCCCCGT CGTGTAGATA ACTACGATAC
      <.................ColE1.......................<
9151  GGGAGGGCTT ACCATCTGGC CCCAGTGCTG CAATGATACC GCGAGACCCA
      <.................ColE1.......................<
9201  CGCTCACCGG CTCCAGATTT ATCAGCAATA AACCAGCCAG CCGGAAGGGC
```

Figure 24G

```
              <.............ColE1...............<
 9251  CGAGCGCAGA AGTGGTCCTG CAACTTTATC CGCCTCCATC CAGTCTATTA
              <.............ColE1...............<
 9301  ATTGTTGCCG GGAAGCTAGA GTAAGTAGTT CGCCAGTTAA TAGTTTGCGC
              <.............ColE1...............<
 9351  AACGTTGTTG CCATTGCTAC AGGCATCGTG GTGTCACGCT CGTCGTTTGG
       <<
 9401  TATGGCTTCA TTCAGCTCCG GTTCCCAACG ATCAAGGCGA GTTACATGAT
 9451  CCCCCATGTT GTGCAAAAAA GCGGTTAGCT CCTTCGGTCC TCCGATCGTT
                                                           >
 9501  GTCAGAAGTA AGTTGGCCGC AGTGTTATCA CTCATGGTTA TGGCAGCACT
       >.................amp......................>
 9551  GCATAATTCT CTTACTGTCA TGCCATCCGT AAGATGCTTT TCTGTGACTG
       >.................amp......................>
 9601  GTGAGTACTC AACCAAGTCA TTCTGAGAAT AGTGTATGCG GCGACCGAGT
       >.................amp......................>
 9651  TGCTCTTGCC CGGCGTCAAT ACGGGATAAT ACCGCGCCAC ATAGCAGAAC
       >.................amp......................>
 9701  TTTAAAAGTG CTCATCATTG GAAAACGTTC TTCGGGGCGA AAACTCTCAA
       >.................amp......................>
 9751  GGATCTTACC GCTGTTGAGA TCCAGTTCGA TGTAACCCAC TCGTGCACCC
       >.................amp......................>
 9801  AACTGATCTT CAGCATCTTT TACTTTCACC AGCGTTTCTG GGTGAGCAAA
       >.................amp......................>
 9851  AACAGGAAGG CAAAATGCCG CAAAAAAGGG AATAAGGGCG ACACGGAAAT
       >.................amp......................>
 9901  GTTGAATACT CATACTCTTC CTTTTTCAAT ATTATTGAAG CATTTATCAG
       >.................amp......................>
 9951  GGTTATTGTC TCATGAGCGG ATACATATTT GAATGTATTT AGAAAAATAA
       >.................amp......................>
10001  ACAAATAGGG GTTCCGCGCA CATTTCCCCG AAAAGTGCCA CCTGACGTCT
       >.................amp......................>
10051  AAGAAACCAT TATTATCATG ACATTAACCT ATAAAAATAG GCGTATCACG
       >.................amp......................>
10101  AGGCCCTTTC GTCTCGCGCG TTTCGGTGAT GACGGTGAAA ACCTCTGACA
       >.................amp......................>
10151  CATGCAGCTC CCGGAGACGG TCACAGCTTG TCTGTAAGCG GATGCCGGGA
       >.................amp......................>
10201  GCAGACAAGC CCGTCAGGGC GCGTCAGCGG GTGTTGGCGG GTGTCGGGGC
```

Figure 24H

```
           >................amp..................>
10251  TGGCTTAACT ATGCGGCATC AGAGCAGATT GTACTGAGAG TGCACCATAT
           >..............amp................>>
10301  GCGGTGTGAA ATACCGCACA GATGCGTAAG GAGAAAATAC CGCATCAGGC
10351  GCCATTCGCC ATTCAGGCTG CGCAACTGTT GGGAAGGGCG ATCGGTGCGG
10401  GCCTCTTCGC TATTACGCCA GCTGGCGAAA GGGGGATGTG CTGCAAGGCG
10451  ATTAAGTTGG GTAACGCCAG GGTTTTCCCA GTCACGACGT TGTAAAACGA
10501  CGGCCAGTGC C
```

Figure 24I

INDOLEAMINE 2,3-DIOXYGENASE-2 ANTIBODIES

This application is a divisional application of U.S. application Ser. No. 12/273,296, filed Nov. 18, 2008, now U.S. Pat. No. 8,058,416, which is a continuation-in-part of PCT/US2007/069271, filed on May 18, 2007, which claims priority under 35 U.S.C. §119(e) to U.S. Provisional Patent Application No. 60/801,255, filed on May 18, 2006, U.S. Provisional Patent Application No. 60/886,815, filed on Jan. 26, 2007, and U.S. Provisional Patent Application No. 60/914,472, filed on Apr. 27, 2007. The foregoing applications are incorporated by reference herein.

Pursuant to 35 U.S.C. §202(c), it is acknowledged that the U.S. Government has certain rights in the invention described herein, which was made in part with funds from the National Institutes of Health, Grant No. CA109542.

FIELD OF THE INVENTION

This invention relates generally to the fields of cellular metabolism, oncology, and immunology. Specifically, the invention provides the nucleotide and amino acid sequence of indoleamine 2,3-dioxygenase-2 (IDO2) and methods of use thereof.

BACKGROUND OF THE INVENTION

Tumors, virus-infected cells, and diseased cells characteristically express atypical, potentially immunoreactive antigens. Accumulating evidence suggests that the failure of the immune system to mount an effective response against progressively growing tumors or virally infected cells is not due to a lack of recognizable antigens. Immunosuppression is poorly understood and mechanisms by which cells escape immune surveillance have been poorly explored. Recently, it has been shown that cytotoxic T cells become tolerized by a reduction in local concentrations of tryptophan that are elicited by indoleamine 2,3-dioxygenase-1 (IDO1) activity.

IDO1 is an oxidoreductase that catalyzes the rate-limiting step in tryptophan catabolism. This enzyme is structurally distinct from tryptophan dioxygenase (TDO), which is responsible for dietary tryptophan catabolism in the liver. IDO1 is an IFN-γ target gene that has been suggested to play a role in immunomodulation (Mellor and Munn (1999) Immunol. Today, 20:469-473). Elevation of IDO1 activity depletes the levels of tryptophan in local cellular environments. Induction of IDO1 in antigen-presenting cells, where IDO1 is regulated by IFN-γ, blocks the activation of T cells, which are especially sensitive to tryptophan depletion. T cells must undergo 1-2 rounds of cell division to become activated, but in response to tryptophan depletion they arrest in G1 instead. In this way, IDO1 has been proposed to inhibit the $T_H1$ responses that promote cytotoxic T cell development.

IDO1 has been proposed to modulate gene expression. This modulation is proposed to occur through a pathway involving GCN2, whose activation has been shown to lead to altered gene expression. The proposed pathway involves the following steps. First, IDO1 activity results in the metabolism of tryptophan. Second, the deprivation of tryptophan leads to tRNAs being uncharged. The presence of uncharged tRNAs results in the activation of GCN2 kinase and a general response pathway for amino acid starvation. Third, the active GCN2 kinase phosphorylates serine 52 of the alpha subunit of eukaryotic initiation factor 2 (eIF2α), which is known to be an important translation control mechanism. The regulation of eIF2α activity is governed by the phosphorylation of serine 52. Currently, there are at least three known kinases, i.e., IFN-inducible dsRNA-dependent protein kinase, heme-regulated repressor, and general control (GCN2), which can phosphorylate serine 52 in eIF2α. The phosphorylation of serine 52 in eIF2α prevents the GDP-GTP exchange activity of eIF2α resulting in the suppression of protein synthesis.

GCN2 has been shown to be important for IDO1-dependent responses since a GCN2 knock-out animal phenocopies the IDO1 knock-out animal.

The role of IDO1 in immunosuppression has been demonstrated by the ability of 1-methyl-tryptophan (1MT), a specific and bioactive IDO1 inhibitor (Cady and Sono (1991) Arch. Biochem. Biophys. 291:326-333), to elicit MHC-restricted and T cell-mediated rejection of allogeneic mouse concepti (Mellor et al. (2001) Nat. Immunol. 2:64-68; Munn et al. (1998) Science. 281: 1191-93). This effect is consistent with the high levels of IDO1 expression in placental trophoblast cells (Sedlmayr et al. (2002) Mol. Hum. Reprod. 8:385-391).

Significantly, IDO1 activity has been shown to be elevated frequently in human tumors and/or in cancer patients (Yasui et al. (1986) Proc. Natl. Acad. Sci. USA. 83:6622-26; Taylor and Feng (1991) FASEB J. 5:2516-22). Since IDO1 can modulate immune responses, one logical implication is that IDO1 elevation in cancer may promote tumor immunosuppression (Mellor and Munn (1999) Immunol. Today, 20:469-473; Munn et al. (1999) J. Exp. Med. 189:1363-72; Munn et al. (1998) Science. 281:1191-93). This possibility is supported by the observation that many cancers, including breast cancer, are characterized by a loss of beneficial immune functions that can limit malignant development. For example, $T_H1$ responses (of which IFN-γ production is a hallmark) that promote the production of cytotoxic T cells are suppressed during cancer progression. A resultant hypothesis from this data was that if IDO1 drives cancer progression by blunting T cell activation, then IDO1 inhibition in animals should blunt tumor growth by reversing IDO1-mediated immunosuppression.

Notably, there are two stereoisomers of the IDO1 inhibitor 1MT, e.g., D-1MT and L-1MT. L-1MT inhibits IDO1 and exhibits a characteristic pattern of antitumor activities. In contrast, D-1MT shares the same in vivo properties, but does not inhibit IDO1 itself. One explanation for these results is that D-1MT inhibits an enzyme that is related to, but distinct from IDO1. However, no enzymes related to IDO1 have been identified.

SUMMARY OF THE INVENTION

In accordance with the present invention nucleic acid molecules encoding indoleamine 2,3-dioxygenase-2 (IDO2) and isoforms, splice variants, and mutants thereof are provided. In another embodiment of the instant invention, primers, probes, antisense molecules, and siRNAs for detection and regulation of IDO2 are provided.

Another aspect of the invention includes amino acid sequences of IDO2. Additionally, antibodies immunologically specific for IDO2 are encompassed by this invention.

In yet another embodiment of the instant invention, methods are provided for the screening of compounds for their ability to the modulate activities of IDO2. The screening methods can be performed in vitro or in host cells, or in animals transgenic for IDO2 expression.

BRIEF DESCRIPTION OF THE DRAWINGS

FIGS. 1A and 1B provide amino acid sequences of isoforms of IDO2 (SEQ ID NO: 1 and SEQ ID NO: 2, respectively).

FIGS. 2A and 2B provide amino acid sequences of mouse IDO2 isoforms (SEQ ID NO: 3 and SEQ ID NO: 4, respectively).

FIG. 3A provides a sequence alignment of the amino acid sequences of a human IDO2 (top strand; amino acids 30-416 of SEQ ID NO: 1 shown) and a human IDO1 (bottom strand; amino acids 13-400 of SEQ ID NO: 5). The underlined residues indicate the conserved histidine and aspartic acid residues necessary for heme binding. # indicates identical and + indicates similar amino acids. FIG. 3B provides the amino acid sequence of human IDO1 (GenBank Accession No AAH27882.1; SEQ ID NO: 5). FIG. 3C provides a sequence alignment of the amino acid sequence of a human IDO2 (SEQ ID NO: 2) and the amino acid sequence of a mouse IDO2 (SEQ ID NO: 4). + indicates similar amino acids. FIGS. 3D-3G provide an amino acid and nucleotide alignment of a murine IDO2 (amino acid, SEQ ID NO: 4; nucleotide, SEQ ID NO: 13) and a murine IDO1 (amino acid, SEQ ID NO: 6; nucleotide, SEQ ID NO: 7). The underlined region indicate exon boundaries.

FIG. 4A is a nucleotide sequence of human IDO2 (SEQ ID NO: 8) which encodes SEQ ID NO: 1. The nucleotide sequence in capital letters (SEQ ID NO: 9) is the sequence encoding the human IDO2 protein. FIG. 4B is a nucleotide sequence of mouse IDO2 (SEQ ID NO: 10) which encodes SEQ ID NO: 3. The nucleotide sequence in capital letters (SEQ ID NO: 11) is the sequence encoding the mouse IDO2 protein. FIGS. 4C and 4D are nucleotide sequences (SEQ ID NO: 12 and SEQ ID NO: 13, respectively) encoding human and murine IDO2 proteins, respectively. Underlined nucleotides indicate the first nucleotide of a new exon.

FIG. 6 provides graphs of the growth of T-Rex™ cells with no vector (center panel), pcDNA4TO-muIDO1 (left panel) or pcDNA4TO-muIDO2 (right panel). Cells were grown in media alone or in the presence of doxycycline, tryptophan, or both doxycycline and tryptophan.

FIGS. 10A-10Q provide a genomic sequence of murine IDO2 (SEQ ID NO: 14) with select restriction enzyme sites and intron/exon boundaries included.

FIGS. 11A-11U provide a genomic sequence of human IDO2 (SEQ ID NO: 15) with select restriction enzyme sites and intron/exon boundaries included.

FIGS. 12A (SEQ ID NOs: 30-43, top to bottom) and 12B (SEQ ID NOs: 44-59, top to bottom) provide a schematic of IDO2 nucleic acid molecules and IDO2 primers for murine and human IDO2, respectively. FIG. 12C provides IDO1 primers and cloning primers (SEQ ID NOs: 60-82, top to bottom).

FIG. 13 provides a schematic of the locations of the introns and exons of IDO2 including exon 1a.

FIG. 14 provides a nucleotide sequence (SEQ ID NO: 20) of IDO2 which comprises 11 exons and encodes SEQ ID NO: 1. Asterisks depict the exon junctions.

FIGS. 15A-15Y is a genomic sequence of human IDO2 (SEQ ID NO: 21) with select restriction enzyme sites and intron/exon boundaries included.

FIGS. 16A-16G provide a nucleotide sequence alignment of a human IDO2 (SEQ ID NO: 12) with IDO2 splice variants and mutants: IDO2 £3/4/6 (SEQ ID NO: 22), IDO2 Δ8 (SEQ ID NO: 23), IDO2 Δ6/8 (SEQ ID NO: 24), IDO2 Δ4/5 (SEQ ID NO: 25), IDO2 R235W (SEQ ID NO: 26), IDO2 Y332stop (SEQ ID NO: 27), and a splice variant yielding an alternative exon 8 (SEQ ID NO: 29). SEQ ID NO: 28 is the amino acid sequence. Exon boundaries are indicated and the encoded amino acids are also provided.

FIGS. 20A (SEQ ID NOs: 83-122, top to bottom) and 20B (SEQ ID NOs: 124-147, top to bottom) provide target sequences and siRNA sequences for human and mouse IDO2, respectively.

FIG. 22 is a schematic of a screening strategy for IDO-2 knockin mice upon removal of the selection marker NeoR.

FIGS. 23B-23I provide the sequence of vector pVLmuIDO2 (SEQ ID NO: 162).

FIGS. 24B-24I provide the sequence of vector pVLhuIDO2 (SEQ ID NO: 163).

DETAILED DESCRIPTION OF THE INVENTION

Figure 1C:
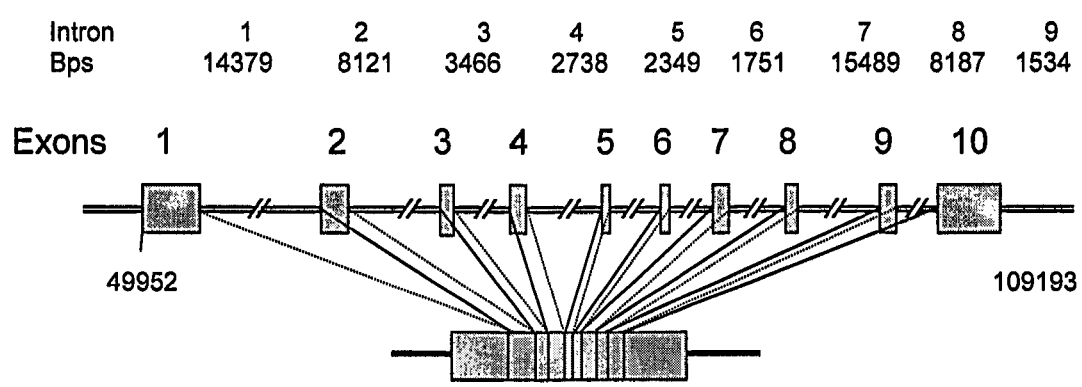
FIG. 1C provides a schematic of the IDO2 genome organization based on GenBank Accession No. NW_923907.1 when the IDO2 isoform comprises 10 coding exons and about 1227 coding bases.

The involvement of IDO1 in immune suppression, particularly the suppression of T cell immunity, has been well documented. As stated hereinabove, there is evidence to suggest that a previously unidentified enzyme related to IDO1 is also involved in immune suppression. Indeed, L-1MT has been shown to be effective at inhibiting IDO1 activity and tumor progression, but the stereoisomer D-1MT does not significantly inhibit IDO1 activity yet retains antitumor properties. Further, at least one IDO1 antisera has been generated which recognizes, in addition to IDO1, a differently regulated protein with a slightly larger apparent molecular weight as determined by Western blot.

In accordance with the instant invention, a novel homolog of IDO has been identified and named indoleamine 2,3-dioxygenase-2 (IDO2, also referred to as indoleamine 2,3-dioxygenase-like-1 (INDOL1) and IDO-NT). Amino acid sequences of human and mouse IDO2 are provided herein (see, e.g., FIGS. 1 and 2, respectively). Nucleotide sequences of human and mouse IDO2 are also provided (see, e.g., FIGS. 4A and 4B, respectively). Notably, IDO2 has approximately 45% sequence identity with human IDO1 (FIG. 3A).

Significantly, IDO2 shares the structural features of IDO1 that are known to be essential for heme binding and tryptophan catabolic activity. Indeed, the histidine and aspartic acid residues required for heme binding are conserved between IDO1 and IDO2 (see FIG. 3A).

Various isoforms, splice variants, and mutant IDO2 nucleic acids and proteins are provided. One isoform of IDO2 is also slightly larger than IDO1 (420 amino acids versus 403 amino acids). This size difference may account for the larger species sometimes seen in Western blots with antisera directed to IDO1. Indeed, portions of the sequence of the IDO1 peptide used to generate the antisera are conserved in IDO2. Based on these facts, it appears that certain IDO1 antisera are capable of cross-reacting with IDO2.

The 5' untranslated region of the IDO2 gene comprising the promoter elements, has a high degree of homology with the consensus sequences for the key immune regulatory transcription factors STAT1 and IRF-7. Significantly, IRF-7 is the master regulator of dendritic cells which present antigen to T cells and control T cell activation versus anergy. This similarity in the 5' regulatory region to the consensus sequence of these immune regulatory transcription factors suggests that IDO2 plays a role in the regulation of the immune response. Indeed, in silico analysis (e.g., an electronic Northern based on serial analysis of gene expression (SAGE)) determined that the highest expression of IDO2 would be in dendritic cells, where IDO1 is also known to be expressed, and pre-dendritic cells (such as JAWS II cells).

IDO2 nucleic acid molecules and proteins may be useful in the diagnosis and prognosis of immune modulation, like IDO1. IDO2 may also be used in the methods described by U.S. Pat. Nos. 6,451,840 and 6,482,416 for IDO1. Furthermore, as described hereinbelow, IDO2 is a candidate therapeutic target for diseases and disorders associated with immune modulation and/or protein misfolding such as cancer, viral infections, and other pathological conditions.

The activation of GCN2 translation control pathway alters the expression of the transcription factor Nuclear Factor IL6 (NFIL6; also known in the literature as C/EBPβ/IL6DBP/TCF5). The CCAAT-enhancer binding protein beta (C/EBPβ) is a basic leucine zipper (bZIP) transcription factor selectively expressed during differentiation of liver, adipose tissue, blood cells, and endocrine pancreas. C/EBPβ encodes four isoforms arising from the differential initiation of translation at four different in-frame AUGs, thereby producing the 40 kDa, 35 kDa, 20 kDa and 8.5 kDa C/EBPβ isoforms. The Lap and LIP isoforms of NF-IL6 have a variety of pleiotropic activities and are involved in regulation cell function, cell growth, and immune response. Lap-1 and Lap-2 have an antiproliferative effect, regulate cell cycle control and cytokine expression, and are pro-inflammatory. LIP is a dominant negative isoform. Therefore, the altered expression of LIP is a relevant biomarker for IDO1 and IDO2 activity in any cell expressing NF-IL6.

IDO1 expression leads to the increase in LIP (also called liver inhibitory protein) which is a dominant negative regulator of Lap1/2 activities, since it lacks certain activation and regulatory domains on LAPs (Liver activation proteins) and can form heterodimers with the LAP proteins, thereby altering their activity. By inference, it may be concluded that the activation of LIP is dependent on the deprivation of tryptophan, the activation of the GCN2 pathway and the increase in LIP production, which in turn results in altered gene expression and cell function. The data described herein support this model since the addition of exogenous tryptophan, even when IDO1 is highly expressed, blocks the production of LIP and activation of the GCN2 pathway.

IDO2 expression also leads to the activation of GCN2 kinase and increased LIP production. However the activation of the GCN2-LIP pathway is not inhibited by the addition of exogenous tryptophan. Therefore, it may be concluded that the mechanism of action for IDO2 is not tryptophan deprivation but rather the direct activation of the GCN2 kinase-LIP pathway. This is may be due to the generation of uncharged tryptophan tRNAs directly, the charging of tRNAs with kynurenine, or some other effect on the GCN2-LIP pathway.

It is also demonstrated herein that IDO2 activity can be inhibited by 1-methyl-D-tryptophan (1M-D-T) which blocks the activation of GCN2 kinase and subsequent altered LIP expression.

The activation of IDO2, like IDO1, has distinct and important properties for the regulation of immune responses. It is known that IDO1 exerts its activity locally by depriving the local cell environment of tryptophan, activating the GCN2 pathway, and suppressing T-cell activation and other immune activities. IDO2 directly activates the GCN2 pathway and exerts its activity globally and systemically in any cell in which it is expressed, including immune T cells and antigen presenting cells. IDO2 may also impact cell activities at distal locations as the altered expression of LIP/LAP is known to affect the expression of soluble growth factors and cytokines that can impact cell responses, like immune activation. One such scenario would be the activation of IDO2 in an antigen presenting cell (APC), such as a dendritic cell, which converts the APC in the presence of antigen to a tolerogenic cell that suppresses the immune response to a particular antigen.

I. DEFINITIONS

The term "IDO inhibitor" refers to an agent capable of inhibiting the activity of indoleamine 2,3-dioxygenase (IDO) (such as IDO1 and IDO2) and thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site (including, without limitation, 1-methyl-tryptophan); "a noncompetitive IDO Inhibitor" is a compound that reversibly inhibits IDO enzyme activity at a non-catalytic site (including, without limitation, norharman); and "an irreversible IDO inhibitor" is a compound that irreversibly destroys IDO enzyme activity by forming a covalent bond with the enzyme (including, without limitation, cyclopropyl/aziridinyl tryptophan derivatives). IDO inhibitors include, without limitation, 1-methyl-DL-tryptophan (1MT; Sigma-Aldrich; St. Louis, Mo.), β-(3-benzofuranyl)-DL-alanine (Sigma-Aldrich), beta-(3-benzo(b)thienyl)-DL-alanine (Sigma-Aldrich), 6-nitro-L-tryptophan (Sigma-Aldrich), indole 3-carbinol (LKT Laboratories; St. Paul, Minn.), 3,3'-diindolylmethane (LKT Laboratories), epigallocatechin gallate (LKT Laboratories), 5-Br-4-Cl-indoxyl 1,3-diacetate (Sigma-Aldrich), 9-vinylcarbazole (Sigma-Aldrich), acemetacin (Sigma-Aldrich), 5-bromo-DL-tryptophan (Sigma-Aldrich), 5-bromoindoxyl diacetate (Sigma-Aldrich), phenyl-TH-DL-trp (3-(N-phenyl-thiohydantoin)-indole) (Sigma-Aldrich), propenyl-TH-DL-trp (3-(N-allyl-thiohydantoin)-indole) (Asinex; Moscow, Russia), methyl-TH-DL-trp (3-(N-methyl-thiohydantoin)-indole) (Sigma-Aldrich), brassinin (LKT Laboratories), 5-methyl-brassinin (Mehta, et al. (1994) Anticancer Res., 14:1209-1213); 3,3'-diindolylmethane (DIM; LKT Laboratories), indole-3-carbinol (I3C; LKT Laboratories), and the IDO inhibitors provided in U.S. patent application Ser. No. 10/550,444 and U.S. Provisional Application 60/730,706. IDO inhibitors may selectively or preferentially inhibit IDO1 (an "IDO1 inhibitor") and/or IDO2 (an "IDO2 inhibitor"). IDO inhibitors include, without limitation, nucleic acid molecules (e.g., siRNA, antisense oligonucleotides), peptides, chemical compounds, and antibodies, or biologically active fragments thereof.

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "replicon" is any genetic element, for example, a plasmid, cosmid, bacmid, plastid, phage or virus, which is capable of replication largely under its own control. A replicon may be either RNA or DNA and may be single or double stranded. Generally, a "viral replicon" is a replicon which contains the complete genome of the virus. A "sub-genomic replicon" refers to a viral replicon that contains something less than the full viral genome, but is still capable of replicating itself. For example, a sub-genomic replicon may contain most of the genes encoding for the non-structural proteins of the virus, but not most of the genes encoding for the structural proteins.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "percent similarity," "percent identity" and "percent homology," when referring to a particular sequence, are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "oligonucleotides" as used herein refers to sequences, primers and probes of the present invention, and is defined as a nucleic acid molecule comprised of two or more ribo- or deoxyribonucleotides, preferably more than three.

The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m = 81.5° C. + 16.6 \text{ Log } [\text{Na}+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1× SSC and 0.5% SDS at 65° C. for 15 minutes.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein, is generally found between exons, and is "spliced out" during processing of the mRNA transcript. As used herein, the term "exon" refers to a nucleic acid sequence found in genomic DNA that is predicted and/or experimentally confirmed to contribute contiguous sequence to a mature (e.g., spliced) mRNA transcript and/or is translated into protein.

As used herein, the phrase "splice variants" refers to RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule, which may encode different amino acid sequences. The term splice variant may also refer to the proteins encoded by the above RNA molecules. As used herein, the phrase "alternative splicing" includes all types of RNA processing that lead to expression of plural protein isoforms from a single gene. As such, the phrase "splice variant" embraces mRNAs transcribed from a given gene that, however processed, collectively encode plural protein isoforms. For example, and by way of illustration only, splice variants can include exon insertions, exon extensions, exon truncations, exon deletions, alternatives in the 5' untranslated region and alternatives in the 3' untranslated region.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668).

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas* exotoxin, and others listed above); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). In a particular embodiment, the chemotherapeutic agent is selected from the group consisting of: placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

II. NUCLEIC ACID MOLECULES

Nucleic acid molecules encoding the IDO2 proteins of the invention may be prepared by two general methods: (1) synthesis from appropriate nucleotide triphosphates and (2) isolation and/or amplification from biological sources. These methods utilize protocols well known in the art. The availability of nucleotide sequence information, such as the sequences provided herein, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides may be synthesized in stages, due to any size limitations inherent in the oligonucleotide synthetic methods.

Nucleic acid sequences encoding the IDO2 proteins of the invention may be isolated from appropriate biological sources using methods known in the art. In one embodiment, a cDNA clone is isolated from a cDNA expression library, preferably of human origin. In an alternative embodiment, utilizing the sequence information provided by the cDNA sequence, genomic clones encoding altered IDO2 proteins may be isolated. Additionally, cDNA or genomic clones having homology with human and mouse IDO2 may be isolated from other species using oligonucleotide probes corresponding to predetermined sequences within the human and mouse IDO2 encoding nucleic acids.

Figure 13:
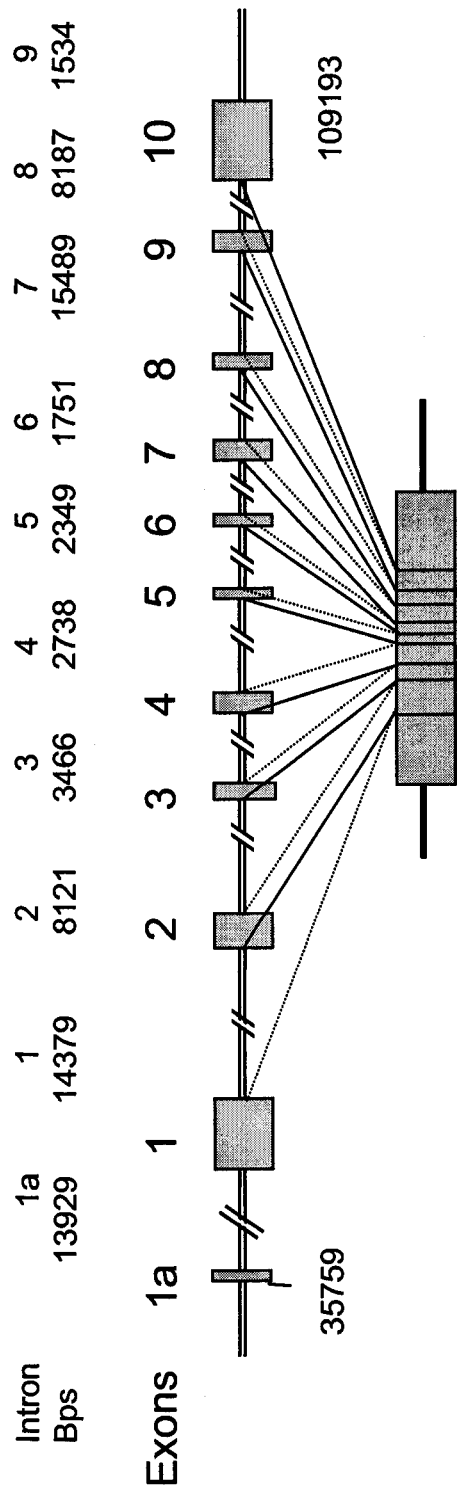

The present invention also encompasses splice variants of IDO2. FIGS. 1C and 13 provide a schematic of the locations of the introns and exons of IDO2. Generally, IDO2 comprises 10 or 11 exons depending on whether exon 1a is included. The genomic region is about 73234 basepairs from the start codon ATG to the stop codon TAG with about 1266 coding bases. FIG. 14 provides a nucleotide sequence of IDO2 comprising all exons.

Exemplary nucleotide sequences encoding human IDO2 are SEQ ID NOs: 8, 9, 12, 15, 20, and 21 and exemplary nucleotide sequences encoding mouse IDO2 are SEQ ID NOs: 10, 11, 13, and 14. The nucleotide sequence of certain splice variants and mutants are also provided in SEQ ID NOs: 22-25. An IDO2 nucleotide sequence may have 75%, 80%, 85%, 90%, 95%, 97%, or 99% homology with any of these nucleic acid molecules.

The instant invention also encompasses IDO2 nucleic acid molecules which lack at least one of the 11 exons depicted in FIGS. 13 and 15A-15Y. For example, the IDO2 nucleic acid molecule may lack any one of the eleven exons (e.g., IDO2 $\Delta$1a, IDO2 $\Delta$1, IDO2 $\Delta$2, IDO2 $\Delta$3, IDO2 $\Delta$4, IDO2 $\Delta$5, IDO2 $\Delta$6, IDO2 $\Delta$7, IDO2 $\Delta$8, IDO2 $\Delta$9, and IDO2 $\Delta$10). The nucleic acid molecule may also lack 2, 3, 4, 5, 6, 7, 8, 9, or 10 exons, wherein the exons are either consecutive or nonconsecutive. In a particular embodiment, the IDO2 splice variants are selected from the group consisting of: IDO2 $\Delta$1a, IDO2 $\Delta$3/4/6, IDO2 $\Delta$8, IDO2 $\Delta$6/8, and IDO2 $\Delta$4/5.

The instant invention also encompasses allelic variants and mutants of IDO2. Natural allelic variants of the instant invention include, without limitation, IDO2 R235W and IDO2 Y332stop.

In accordance with the present invention, nucleic acids having the appropriate level of sequence homology with a nucleic acid molecule encoding IDO2 may be identified by using hybridization and washing conditions of appropriate stringency.

Nucleic acids of the present invention may be maintained as DNA in any convenient vector. IDO2 encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the IDO2 nucleic acid molecules of the invention. Primers capable of specifically amplifying IDO2 encoding nucleic acids described herein are also contemplated herein. As mentioned previously, such oligonucleotides are useful as probes and primers for detecting, isolating or amplifying altered IDO2 genes.

It will be appreciated by persons skilled in the art that variants (e.g., allelic variants) of IDO2 sequences exist, for example, in the human population, and must be taken into account when designing and/or utilizing oligonucleotides of the invention. Accordingly, it is within the scope of the present invention to encompass such variants, with respect to the IDO2 sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Such variants would not demonstrate altered IDO2 activity or protein levels. Additionally, the term "substantially complementary" refers to oligonucleotide sequences that may not be perfectly matched to a target sequence, but such mismatches do not materially affect the ability of the oligonucleotide to hybridize with its target sequence under the conditions described.

The present invention also encompasses antisense nucleic acid molecules which may be targeted to translation initiation sites and/or splice sites to inhibit the expression of IDO2. Such antisense molecules are typically between about 15 and about 30 nucleotides in length and often span the translational start site of mRNA molecules. Antisense constructs may also be generated which contain the entire IDO2 sequence in reverse orientation. Antisense oligonucleotides targeted to any known nucleotide sequence can be prepared by oligonucleotide synthesis according to standard methods.

Small interfering RNA (siRNA) molecules designed to inhibit expression of IDO2 are also encompassed in the instant invention. Typically, siRNA molecules are double-stranded RNA molecules between about 12 and 30 nucleotides in length, more typically about 21 nucleotides in length (see Ausubel et al.). Exemplary siRNAs for human and mouse IDO2 are provided in FIGS. 20A and 20B, respectively.

Several methods of modifying oligodeoxyribonucleotides are known in the art. For example, methylphosphonate oligonucleotide analogs may be synthesized wherein the negative charge on the internucleotide phosphate bridge is eliminated by replacing the negatively charged phosphate oxygen with a methyl group. See Uhlmann et al., Chemical Review, 90:544-584 (1990). Another common modification, which is utilized in a preferred embodiment of the present invention, is the synthesis of oligodeoxyribonucleotide phosphorothioates. In these analogs, one of the phosphate oxygen atoms not involved in the phosphate bridge is replaced by a sulphur atom, resulting in the negative charge being distributed asymmetrically and located mainly on the sulphur atoms. When compared to unmodified oligonucleotides, oligonucleotide phosphorothioates are improved with respect to stability to nucleases, retention of solubility in water and stability to base-catalyzed hydrolysis. See Uhlmann et al., supra at 548-50; Cohen, J. S. (ed.) *Oligodeoxynucleotides: Antisense Inhibitors of Gene Expression*, CRC Press, Inc., Boca Raton, Fla. (1989).

Other modifications of oligodeoxyribonucleotides to produce stable, membrane permeable oligonucleotide analogs are commonly known in the art. For a review of such methods, see generally, Uhlmann et al., supra, and Cohen, supra which also describe methods for synthesis of such molecules. In addition, modified oligoribonucleotides may be utilized in the present invention. However, oligodeoxyribonucleotides are preferred due to their enhanced stability, ease of manufacture and the variety of methods available for analog synthesis.

Still other modifications of the oligonucleotides may include coupling sequences that code for RNase H to the antisense oligonucleotide. This enzyme (RNase H) will then hydrolyze the hybrid formed by the oligonucleotide and the specific targeted mRNA. Alkylating derivatives of oligonucleotides and derivatives containing lipophilic groups can also be used. Alkylating derivatives form covalent bonds with the mRNA, thereby inhibiting their ability to translate proteins. Lipophilic derivatives of oligonucleotides will increase their membrane permeability, thus enhancing penetration into tissue. Besides targeting the mRNAs, other antisense molecules can target the DNA, forming triple DNA helixes (DNA triplexes). Another strategy is to administer sense DNA strands which will bind to specific regulator cis or trans active protein elements on the DNA molecule.

Deoxynucleotide dithioates (phosphorodithioate DNA) may also be utilized in this invention. These compounds which have nucleoside-$OPS_2O$ nucleoside linkages, are phosphorus achiral, anionic and are similar to natural DNA. They form duplexes with unmodified complementary DNA. They also activate RNase H and are resistant to nucleases, making them potentially useful as therapeutic agents. One such compound has been shown to inhibit HIV-1 reverse transcriptase (Caruthers et al., INSERM/NIH Conference on Antisense Oligonucleotides and Ribonuclease H, Arcachon, France 1992).

In accordance with the present invention, antisense oligonucleotides and siRNA may be produced by expression of DNA sequences cloned into plasmid or retroviral vectors. Using standard methodology known to those skilled in the art, it is possible to maintain the antisense RNA-encoding DNA in any convenient cloning vector (see Ausubel et al., eds. *Current Protocols in Molecular Biology*, John Wiley and Sons, Inc., (2005)).

Various genetic regulatory control elements may be incorporated into antisense RNA-encoding expression vectors to facilitate propagation in both eukaryotic and prokaryotic cells. Different promoters may be utilized to drive expression of the antisense sequences, the cytomegalovirus immediate early promoter being preferred as it promotes a high level of expression of downstream sequences. Polyadenylation signal sequences are also utilized to promote mRNA stability. Sequences preferred for use in the invention include, but are not limited to, bovine growth hormone polyadenylation signal sequences or thymidine kinase polyadenylation signal sequences. Antibiotic resistance markers are also included in these vectors to enable selection of transformed cells. These may include, for example, genes that confer hygromycin, neomycin or ampicillin resistance.

Cells and transgenic animals comprising a nucleic acid encoding IDO2 are also encompassed by the instant invention. The term "transgenic animal" is intended to include any non-human animal, preferably vertebrate, in which one or more of the cells of the animal contain heterologous/exogenous nucleic acid encoding IDO2, optionally from a different species. IDO1 encoding nucleic acids may also be inserted. Non-human animals include without limitation, rodents, mice, rats, non-human primates, sheep, dog, cow, amphibians, zebrafish, reptiles, and the like. In a preferred embodiment, the animal is a mouse. In another embodiment, the transgenic animal comprising a heterologous nucleic acid encoding IDO2 has modulated (e.g., increased) susceptibility to cancer and/or infection by microbes (e.g., viruses, bacteria, pathogens) compared to a wild-type mouse. In another embodiment, these transgenic animals exhibit at least one of increased LIP production, decrease in LAPs, decreased activation of GCN2, decreased e1f2-α phosphorylation, and modulation of production of pro-inflammatory cytokines.

IDO2 knockout animals are also encompassed by the instant invention. Modifications and/or deletions may render the naturally occurring gene nonfunctional, thereby producing a "knock out" transgenic animal (e.g., IDO2$^{-/-}$). In other words, the transgenic mice comprise homozygous null mutations in the endogenous IDO2 gene. The transgenic animal of the instant invention may comprise a genome comprising a disruption of an endogenous IDO2 gene, wherein the IDO2 gene disruption leads to the failure to express IDO2 and/or a functional IDO2 (e.g., an IDO2 which lacks tryptophan catabolism activity and/or heme binding). The disruption of the endogenous IDO2 can be obtained through the disruption (e.g., insertion of a nucleic acid sequence (e.g., selectable marker) or deletion (e.g., all or part)) of at least one exon. In a particular embodiment, exon 1 is disrupted. In another embodiment, exon 9 and/or 10 is disrupted. Knock-in animals are also encompassed in the present invention as transgenic IDO2 animals. In one preferred embodiment, the IDO2 gene or exons of IDO2 gene are flanked by site specific recombinase recognition sequences such as Cre/LoxP. These mice are conditional knock-out of IDO2 since the portion of the IDO2 gene flanked by the loxP sequences can be excised in vivo upon exposure to the site-specific recombinase Cre, provided into the genome of the offspring by crossing the knock-in IDO2 mouse with a transgenic mouse carrying the Cre recombinase under the control of a tissue-specific or inducible promoter.

The transgenic mouse may also comprise a knockout of the endogenous IDO1 gene. In a particular embodiment, the transgenic animal is devoid of IDO2 activity. In another embodiment, the transgenic animal has undetectable levels of IDO2. In yet another embodiment, the transgenic animal is fertile and transmits the homozygous null mutations to its offspring. In still another embodiment, the IDO2 knockout animal has modulated (e.g., decreased) susceptibility to cancer and/or infection by microbes (e.g., virus, bacteria, fungus, parasite, pathogen) compared to a wild-type animal. In another embodiment, the IDO2 knockout animals exhibit at least one of decreased LIP production, increase in LAPs, increased activation of GCN2, increased e1f2-α phosphorylation, and modulation of production of pro-inflammatory cytokines.

Transgenic animals of the instant invention may be useful for the establishment of a nonhuman model for diseases involving improper expression and/or regulation of IDO2. The transgenic animals may also be useful as in vivo models for drug screening studies for certain human diseases, and for eventual treatment of disorders or diseases associated with IDO2, such as, without limitation, diseases that have an autoimmune component, diseases associated with improper IDO1 and/or IDO2 expression and/or regulation, and the like. In a particular embodiment, the course of microbial infection in mice devoid of IDO2 activity (i.e., knockout) or comprising a heterologous/exogenous nucleic acid encoding IDO2 may be assessed by a) inoculating the transgenic mouse with a microbe; b) inoculating a wild type mouse with the same microbe; and c) determining whether the course of infection in the transgenic mice is altered to that observed in the wild-type mice, thereby determining whether mice devoid of IDO2 or expressing heterologous/exogenous IDO2 are more/less/equally susceptible to infection by the microbe. In yet another embodiment, the susceptibility to cancer instead of a microbe can be determined by the above method.

III. PROTEINS

IDO2 proteins of the present invention may be prepared in a variety of ways, according to known methods. The proteins may be purified from appropriate sources, e.g., transformed bacterial or animal cultured cells or tissues, by immunoaffinity purification. The availability of nucleic acid molecules encoding IDO2 protein enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.).

Alternatively, larger quantities of IDO2 protein may be produced by expression in a suitable prokaryotic or eukaryotic system. For example, part or all of a DNA molecule encoding for IDO2 may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

IDO2 protein produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

IDO2 protein of the invention, prepared by the aforementioned methods, may be analyzed according to standard procedures. For example, such protein may be subjected to amino acid sequence analysis, according to known methods.

The instant invention encompasses the amino acid sequences encoded by the nucleic acid molecules described herein. Exemplary amino acid sequences of human IDO2 are SEQ ID NO: 1, 2, and 29 and exemplary amino acid sequences of murine IDO2 are SEQ ID NO: 3 and 4. An IDO2 amino acid sequence may have 75%, 80%, 85%, 90%, 95%, 97%, or 99% homology with these sequences.

IV. ANTIBODIES

The present invention also encompasses antibodies capable of immunospecifically binding to proteins of the invention. Specifically, the antibodies may specifically bind to IDO2 to the exclusion of IDO1. Alternatively, antibodies can be generated which recognize both IDO2 and IDO1. The antibodies may also be generated to bind IDO2 splice variants and mutants of the instant invention either in addition to IDO2 and/or IDO1 or to the exclusion of other IDO2 proteins. Polyclonal antibodies directed toward IDO2 protein and variants thereof may be prepared according to standard methods. In a particular embodiment, monoclonal antibodies are prepared, which react immunospecifically with the various epitopes of the IDO2 protein. Monoclonal antibodies may be prepared according to general methods known in the art. For example, polyclonal and monoclonal antibodies may be prepared as described in Current Protocols in Molecular Biology, Ausubel et al. eds. Antibodies may be prepared by chemical cross-linking, hybrid hybridoma techniques and/or by expression of recombinant antibody fragments expressed in host cells, such as bacteria or yeast cells. The antibody molecules may then be isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Polyclonal or monoclonal antibodies that immunospecifically interact with IDO2 proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

Additionally, target-specific antibodies, optionally selected by a functional assay, may be isolated. The crystal structure may then be obtained for the antibody. This structure yields a pharmacore upon which subsequent drug design can be based. Alternatively, the protein crystallography may be bypassed altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

V. THERAPEUTIC USES

The present invention also encompasses methods for tumor suppression. Specifically, a therapeutically effective amount of at least one IDO2 inhibitor (optionally one which does not inhibit IDO1) can be administered to a patient, in need thereof, for the treatment of cancer. Cancers that may be treated using the present protocol include, but are not limited to: prostate cancers, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

The at least one IDO2 inhibitor (optionally one which does not inhibit IDO1) may also be administered in combination with at least one signal transduction inhibitor (STI), as described, in the context of IDO inhibitors, in PCT/US04/05155 and PCT/US04/05154 and U.S. patent application Ser. Nos. 10/550,444 and 10/551,151, with at least one chemotherapeutic agent, and/or at least one immunomodulator, as described in U.S. patent application Ser. Nos. 10/550,444 and 10/551,151.

The present invention also encompasses pharmaceutical compositions comprising at least one of the IDO2 inhibitor(s) (optionally one which does not inhibit IDO1) in a pharmaceutically acceptable carrier. Such a pharmaceutical composition may be administered, in a therapeutically effective amount, to a patient in need thereof for the treatment of cancer. The pharmaceutical compositions may further comprise at least one STI, at least one chemotherapeutic agent, and/or at least one immunomodulator.

The present invention also encompasses methods for the treatment of chronic viral infections (see U.S. patent application Ser. Nos. 10/550,444 and 10/551,151). Specifically, a therapeutically effective amount of at least one IDO2 inhibitor (optionally one which does not inhibit IDO1) can be administered to a patient having a chronic viral infection. Additionally, at least one chemotherapeutic agent and/or at least one antiviral agent may be co-administered with the at least one IDO2 inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, and human immunodeficiency virus (HIV). Notably, parasitic infections (e.g. malaria) may also be treated by the above methods wherein compounds known to treat the parasitic conditions may also be co-administered.

Suitable antiviral agents include, without limitation: acyclovir; gangcyclovir; foscarnet; ribavirin; and antiretrovirals such as, for example, nucleoside analogue reverse transcriptase inhibitors (e.g., azidothymidine (AZT), ddI, ddC, 3TC, d4T), non-nucleoside reverse transcriptase inhibitors (e.g., efavirenz, nevirapine), nucleotide analogue reverse transcriptase inhibitors, and protease inhibitors.

The present invention also encompasses pharmaceutical compositions comprising at least one of the IDO2 inhibitor (optionally one which does not inhibit IDO1) in a pharmaceutically acceptable carrier for the treatment of chronic viral infections. Such a pharmaceutical composition may be administered, in a therapeutically effective amount, to a patient in need thereof for the treatment of a chronic viral infection. The pharmaceutical compositions may further comprise at least one chemotherapeutic agent and/or at least one antiviral agent.

The pharmaceutical compositions of the present invention can be administered by any suitable route, for example, by injection, by oral, pulmonary, nasal or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

IDO2 may also be used to tolerize the immune system for a desired antigen. The IDO2 may be delivered as a nucleic acid molecule and/or a protein, optionally in a pharmaceutically acceptable carrier. The IDO2 may be administered to antigen presenting cells with the desired antigen in vivo or in vitro. For example, the antigen presenting cells, optionally obtained from the patient to be treated, can be treated ex vivo and then administered to the patient. These methods may be used to treat, for example, diabetes, lupus, Myastenia Gravis, Crohn's disease, and other autoimmune disorders.

IDO2 inhibitors as described hereinabove may also be used to alter the immune system to become active against a particular antigen. The antigen may be "foreign", e.g., viral, bacterial, and tumor specific antigens. Alternatively, the antigen may be a "self" antigen, e.g., amyloid, scrappie prions, and other misfolded proteins. The administration of the IDO2 inhibitors to patients would helpful in treating disorders/diseases associated with the particular antigen. The IDO2 inhibitors may be administered to APCs in vivo, in vitro, or ex vivo. The APCs may be loaded with the antigen of interest.

IDO2 and IDO2 inhibitors may also be administered to patients in need thereof to modulate the production of pro-inflammatory cytokines (e.g., IL6, TNFα, CD14, IL-1β, IL-8, IL-12, MCP1, m-CSF, G-CSF, and iNOS). IDO2 inhibitors would decrease LIP production, thereby leading to an apparent increase in LAPs, which regulate pro-inflammatory cytokines. IDO2, administered as a nucleic acid molecule and/or protein, or agents which augment IDO2 expression levels or activity would increase LIP activity, thereby causing a decrease in LAP activities.

IDO2 may also be involved in the production of proteins possessing a modified tryptophan amino acid. Specifically, IDO2 may generate kynurenine tRNAs in place of tryptophan tRNAs. As such, kynurenine may be incorporated into a peptide. The ability to incorporate a modified amino acid into a protein implicates IDO2 as an epigenetic post transcriptional modifier of gene function. The modifications by IDO2 may relate not only to normal biological function but also encompass modifications which affect disease states. For example, modified or misfolded proteins due to the incorporation of IDO2 altered amino acids may be causative factors in several diseases or disorders including, without limitation, cancer, immune disease, Alzheimer's, prion disorders, metabolic disorders, cardiovascular disease, Parkinson's, Huntington's, age-related disorders, and neurological disorders. Indeed, it has been previously demonstrated that the nitrosylation of tryptophan in beta amyloid results in the misfolding of the protein and abnormal amyloid production. Similarly, the incorporation of kynurenine into a protein may provide a "normal" biological role in altering protein function. However, under chronic conditions brought about by over-expression or over-activity of IDO2 (such as a chronic inflammation), the incorporation kynurenine may lead to "abnormal" gene products and/or expression which could alter critical factors controlling cell growth, differentiation, and function. Accordingly, the administration of IDO2 inhibitors to patients having disorders or diseases associated with proteins altered by IDO2 may be therapeutic. In order to determine if IDO2 inhibition would be therapeutic for a particular disease, the proteins associated with the disease may be screened for the presence of kynurenine and/or screened to determine if the protein is misfolded.

In addition to the IDO2 inhibitors described hereinabove, the splice variants and mutants of the instant invention may be employed to inhibit IDO2 and/or IDO1 activity in a subject. As described hereinbelow in Example 2, IDO2 splice variants and mutants (e.g., natural allelic variants R235W and Y332stop) can inhibit the activity of IDO2. Accordingly, IDO2 splice variants and/or nucleic acid molecules encoding the IDO2 splice variants and mutants may be administered to a subject in accordance with the methods described hereinabove as an IDO2 inhibitor.

VI. SCREENING METHODS

The biochemistry of IDO has been well established, the enzyme having first been isolated in 1963 (Higuchi, K., et al. (1963) Federation Proc. 22:243 (abstr.); Shimizu, T., et al. (1978) J. Biol. Chem. 253:4700-6). IDO is a monomeric, heme-containing oxidoreductase with a molecular weight of approximately 41 kDa. To maintain the active ferrous form during in vitro catalysis, the enzyme requires methylene blue in combination with either superoxide or a reductant such as ascorbic acid. In vivo, it is suggested that a flavin or tetrahydrobiopterin may fulfill the role of the methylene blue dye and that there is likely to be a specific site for noncompetitive IDO inhibitors. Active enzyme can be produced by expressing the cloned, His-tagged version of the mammalian gene in bacteria (Littlejohn, T. K., et al. (2000) Prot. Exp. Purif. 19:22-29). This provides a convenient source of enzyme for biochemical analysis. A conventional biochemical assay for IDO activity based on spectaphotometric measurement of the production of kynurenine (the hydrolysis product of N-formyl-kynurenine) from tryptophan (Daubener, W., et al. (1994) J. Immunol. Methods 168:39-47) may be used as the read-out for both the enzymatic and cell-based assays. An enzymatic assay provides a facile, high-throughput screen for identifying compounds with IDO inhibitory activity. This assay may also be used to determine Ki values for specific compounds, which is important for the development of SAR (structure activity relationship) around the different compound series. A cell-based assay can confirm the IDO inhibitory activity of identified compounds and address the initial issue of bioavailability—the ability of compounds to inhibit intracellular IDO. Specificity for IDO inhibition may be examined in the cell-based assay by comparing against the other known tryptophan catabolizing enzyme tryptophan dioxygenase (TDO, also referred to in the literature as TDO2).

Because of the homology between IDO1 and IDO2, methods employed for screening for inhibitors of IDO1 activity may be employed for screening compounds which modulate IDO2 activity of the IDO2 proteins described herein. Indeed, as demonstrated hereinbelow, IDO2 can produce kynurenine from tryptophan, thereby allowing the above enzyme assays to be employed with IDO2. Inhibitors may be specific for IDO2 or may effectively inhibit both IDO1 and IDO2. For example, D-1MT does not inhibit IDO1, but is an inhibitor of IDO2 activity. IDO inhibitors, as described hereinabove, may also be screened for their ability to inhibit IDO2. While the above describes the screening of compounds to identify inhibitors of IDO2, the screening assays can be employed to screen for modulators of IDO2 activity, e.g., for compounds that increase IDO2 expression levels or activity and/or compounds which decrease IDO2 activity.

In accordance with the present invention, the nucleotide sequences of both human and mouse IDO2 have been determined. For biochemical studies, IDO2 protein, optionally tagged with a purification tag which allows the isolation of the protein, may be expressed and isolated from an expression system. For example, C-terminal His-tagged IDO2 protein may be produced in E. coli using the IPTG-inducible pET5a vector system and isolated over a nickel column. The yield of the partially purified protein can be verified by gel electrophoresis and the concentration estimated by comparison to protein standards. To assay IDO2 enzymatic activity, a 96-well plate spectraphotometric assay for kynurenine production may be run following published procedures (Littlejohn, T. K., et al. (2000) Prot. Exp. Purif. 19:22-29; Takikawa, O., et al. (1988) J. Biol. Chem. 263:2041-8; see also U.S. patent application Ser. Nos. 10/550,444 and 10/551,151).

With regard to cell-based assays, cells, e.g., COS-1 cells and 293 cells, may be transfected (e.g., transiently transfected) with a plasmid expressing IDO2 (see Munn et al. (1999) J. Exp. Med. 189:1363-1372 for an exemplary method). Optionally, a companion set of cells is transfected with a TDO or IDO expressing plasmid. After transfection, the cells are contacted with the test compound. Subsequently, the supernatant can be spectraphotometrically assayed for kynurenine as described for the enzyme assay.

The following examples are provided to illustrate various embodiments of the present invention. The examples are illustrative and are not intended to limit the invention in any way.

Example 1

Reagents

Blasticidin (Invitrogen; Carlsbad, Calif.) was prepared as a 1000× solution at 5 mg/mL in sterile water and stored in 500 µL aliquots frozen at −20° C. Zeocin (Zeo; Invitrogen) was prepared as 100 mg/mL aliquots and stored frozen at −20° C.

Doxycycline (Dox; Sigma, St. Louis, Mo.) was prepared as a 20 mg/mL master stock in ethanol and stored frozen at −20° C. The working 100× stock (2 µg/mL) was prepared by diluting the master stock 1:10,000 in growth media. The working stock was stored in 500 µL aliquots and stored frozen and in the dark at −20° C.

1-Methyl-D-Tryptophan (1M-D-T; Sigma-Aldrich Cat #45283) was solubilized in DMSO/0.1 N HCL as a 100 mM stock solution and stored in 100 µL aliquots at −20° C. 1-Methyl-L-Tryptophan (1M-L-T; Sigma-Aldrich Cat #447439) was solubilized in DMSO/0.1 N HCL as a 100 mM stock solution and stored in 100 µL aliquots at −20° C. 1-Methyl-DL-Tryptophan (1M-DL-T; Sigma-Aldrich Cat #860646) was solubilized in DMSO/0.1 N HCL as a 100 mM stock solution and stored in 100 µL aliquots at −20° C. 5-(indol-3-methyl)-3-methyl-2-thio-Hydantoin (MTH; Sigma-Aldrich Cat #M6006) was solubilized in DMSO as a 100 mM stock solution and stored in 100 µL aliquots at −20° C. L-Tryptophan (Tryp; Sigma-Aldrich Cat #T0254) was solubilized in DMSO as a 100 mM stock solution and stored in 100 µL aliquots frozen at −20° C.

Dulbecco's Modified Eagle Medium (DMEM) was obtained from Mediatech, Inc. (Herndon, Va.; Cat#10-013-CV). Alpha minimum essential medium (α-MEM) was obtained from Invitrogen and contains ribonucleosides and deoxynucleosides/4 mM glutamax/1 mM sodium pyruvate and was stored at 4° C. Trypsin EDTA (1×) was obtained from Mediatech (Cat #25-053-CI) 10 mL aliquots were stored frozen at −20° C. until use. Fetal bovine serum (FBS) was obtained from Hyclone (Logan, Utah; Cat #SV30014.03) and 50 mL aliquots were stored frozen at −20° C. until use. Penicillin/streptomycin 100× (Pen/Strep) was obtained from Mediatech (Cat#30-002-C) which contained 10,000 I.U. Penicillin/mL and 10,000 µg/mL Streptomycin. L-Glutamine (L-glut) was obtained from Mediatech (Cat #25-005-CV) as a 200 mM solution (29.23 mg/mL with 8.5 g/L NaCl). Optimem was obtained from Invitrogen (Cat #31985-062) and stored in 10 mL aliquots at 4° C.

Antibodies to the phosphorylated eIF2α (anti-eIF2α-P (ser52)) were affinity purified. Rabbit polyclonal antibodies raised against the short amino acid sequence containing the phosphorylated Ser-52 (Santa Cruz Biotechnology, Santa Cruz, Calif., sc-12412). For Western blotting, anti-eIF2α-P was diluted at 1:200 in blocking buffer (PBS/0.1% tween-20, 3% w/v non-fat dry milk, phosphatase inhibitor cocktail (Calbiochem, La Jolla, Calif., Cat #524625)).

Antibodies to the c-terminal region of C/EBPβ were affinity purified rabbit polyclonal antibodies raised against a peptide corresponding to the C-terminus of C/EBPβ of rat origin (Santa Cruz Biotechnology, sc-150). For Western blotting anti-C/EBPβ was diluted at 1:200 in blocking buffer (PBS/0.1% tween-20, 3% w/v non-fat dry milk).

Anti-V5-Horse radish peroxidase (HRP) conjugated antibody was purchased from Invitrogen and stored at 4° C. For Western blotting anti-V5-HRP was diluted at 1:5000 in blocking buffer (PBS/0.1% tween-20, 3% w/v non-fat dry milk). Affinity purified goat anti-rabbit IgG antibody and affinity purified horse anti-mouse IgG antibody conjugated to HRP (Cell Signaling technologies, Danvers, Mass., cat #7074 and #7076, respectively) were typically diluted 1:1000 in blocking buffer (PBS/0.1% tween-20, 3% w/v non-fat dry milk).

GM-CSF was stored frozen at −20° C. as a 1000× solution (5 mg/mL). Interferon-γ (IFN-γ), IL-10, and lipopolysaccharide (LPS) were stored frozen at −20° C. as a 1000× solution.

Methods

Western Analysis:

Cell lysates were prepared as follows: Cells were removed from the dish by scrapping or pipetting in PBS and collected by centrifugation (2000 rpm/5 minutes). The supernatant was discarded and the cell pellet was lysed in RIPA buffer [50 mM Tris-HCl pH 7.4/150 mM NaCl/1% Triton x-100/1% Sodium deoxycholate/0.1% SDS] plus a protease inhibitor cocktail (Calbiochem Cat #539134). Typically $5 \times 10^5$ cells were resuspended in 200 µL of RIPA buffer. Cells lysates were vortexed and incubated on ice or frozen at −20° C. until use. Prior to use lysates were clarified by centrifugation (10,000 rpm/15 minutes) and heat denatured at 95° C. in SDS/sample buffer (100 mM Tris/25% glycerol/2% SDS/0.01% bromophenol blue/25 mM DTT). Proteins were separated by PAGE using NuPAGE® Gels (Invitrogen) and transferred at 100 Volts on to Immobilon-NC Nitrocellulose membranes (Millipore, Billerica, Mass., Cat #HAHY00010) in transfer buffer (25 mM Tris pH 8.3/192 mM glycine/20% methanol). The protein containing membranes were typically blocked at room temperature for 1 hour in blocking buffer (PBS/0.1% tween-20, 3% w/v non-fat dry milk). Primary antibody was added to the blot in blocking buffer at the suggested dilution, incubated by shaking at room temperature for 1 hour or at 4° C. for 12-18 hours and washed 5-6 times in PBS/0.1% Tween. For secondary antibody applications, the secondary antibody containing HRP was added in blocking buffer at the appropriate dilution, incubated by shaking at room temperature for 1 hour, and washed 5-6 times in PBS/0.1% Tween. The western membranes were developed by Chemiluminescence using SuperSignal® West Pico substrate (Pierce, Rockford, Ill., Cat #34078), exposed to autography film for an appropriate period of time (3 seconds to 18 hours), and developed.

Kynurenine Detection Assay:

This assay measures the product of the indoleamine 2,3-dioxygenase conversion of L-tryptophan to N-formyl-kynurenine by acid hydrolysis to kynurenine, which is measured indirectly though the absorbance (480 nm) of imine produced by the reaction of the aromatic amino group of klynurenine with p-dimethylaminobenzaldehyde (Ehrlich's reagent) as described by Takikawa et al. (J. Biol. Chem. (1988) 263:2041-2048). Typically, 200 µL of media from the test sample is combined with 12.5 µL of 30% TCA and incubated at 50° C. for 30 minutes. Evaporation was avoided by sealing the rim of the plate or tubes with parafilm. Samples are clarified by centrifugation for 10 minutes at 3-10K rpm. 100 µL of the supernatant was removed to a fresh well in an assay plate and mixed with 100 µL of fresh Ehrlich's reagent (2% p-dimethylaminobenzaldehyde w/v with glacial acetic acid). The plates were incubated for 10-30 minutes at room temperature and the absorbance was read at 490 nm. Typically, assays were performed in triplicate and the data analyzed using Excel software program (Microsoft). Background/control samples were typically derived from media from uninduced cells or cells that lack IDO1/2 expression vectors. Typically, control values were averaged and subtracted from the sample values.

Surforhodamine B Colorimeter Assay:

This assay is used to assess cell density and is based on the measurement of cellular protein content and performed as described Vichai and Kirtikara (Nature Protocols (2006) 1:1112). For a 96 well dish, sample wells were maintained in 200 µL of media and fixed by adding 100 µL of cold 10% (wt/v) TCA to each well and the plates were incubated at 4° C. for at least 1 hour. The supernatant may be removed and saved for Kynurenine detection assay. The plates are then washed four times by dipping the plate slowly into a 2 liter beaker of tap water. The wash is removed by gently flicking or blotting the plate. The water in the 2 liter beaker is changed after each wash. Any excess water was blotted and the plates were air dried. Plates can be stored indefinitely at room temperature at this stage. For analysis, 100 µL of 0.057% (wt/v) Surforhodamine B (SRB)/1% acetic acid (v/v) solution was added and the plates incubated at room temperature for 30 minutes. Plates were then rinsed four times in 1% acetic acid by dipping in a 2 L beaker of wash solution, as performed with the first wash. The plates were then allowed to air dry in an exhaust hood. Sample wells were then developed by adding 200 µL of 10 mM Tris base (pH 10.5), incubating at room temperature for 30 minutes with gentle shaking, and measuring the optical density (O.D.) at 510 nm. Typically samples were performed in triplicate and the data analyzed using Excel software program (Microsoft).

Cell Culture:

293-T-REx™ cells (Invitrogen) constitutively express a tet operator repressor protein and were maintained in DMEM/10% FBS/1×Pen/Strep/2 mM L-glut/blasticidin (5 ng/mL) at 37° C. with a 5% $CO_2$ in air atmosphere and typically split prior to confluency. Cells were passaged by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium/10% DMSO), stored in 1.8 mL cyropreservation vials (~2-5×$10^6$ cells per vial) in liquid nitrogen vapor storage tanks.

JawsII (ATCC CRL-11904) is an immortalized mouse dendritic cell line derived from the bone marrow of p53 knockout Blk/6 mouse (U.S. Pat. No. 5,648,219). Cells were maintained in DMEM/10% FBS supplemented with GM-CSF at 5 ng/mL and grown at 37° C. with a 5% $CO_2$ in air atmosphere. For maintenance floating cells are removed by pipetting. Detached cells were removed by rinsing in 0.25% trypsin/EDTA and pooled with the floating cells. Cells were collected by centrifugation (1000 rpm 1 minute) and resuspended in fresh media, and subcultured at a 1:2 ratio. For long term cryopreservation, floating and adherent cells were detached and pooled from the plate as described above, collected by centrifugation, resuspended in freeze medium (growth medium/5% DMSO), stored in 1.8 mL cyropreservation vials (~2-5×$10^6$ cells per vial) in liquid nitrogen vapor storage tanks.

Transfection:

Typically, T-REx™ cells were transfected by lipofection whereby complexes are formed by mixing 1.6 µg of circular plasmid and 4 µL Lipofectamine 2000 (Invitrogen) in a final volume of 400 µL Optimem, as per protocol. These complexes were then added directly to expanding cultures of cells for a total of 6 to 20 hours. After 24-48 hours, cells were either split and placed in media and selection antibiotic (typically 100 ug/mL Zeo) or induced with Dox for transient expression.

RNA Preparation:

Total RNA was prepared from tissue and cultured cells using PureLink™ Micro-to-Midi Total RNA Purification System (Invitrogen, Cat #12183-018). For RNA preparation from tissue, the tissue (~10 mg) was cut into small pieces and mixed with 500 µL of kit lysis buffer and passaged through a 21 G needle in lysis buffer several times until the lysate was well homogenized. Then the lysate was passaged over the spin homogenizer column (Invitrogen). The supernatants were then processed as standard lysates. Briefly 1 volume of 70% Ethanol was added to the lysates, mixed well by vortexing, and loaded on to the RNA spin column, as described. Following the first wash, the samples were treated with RNase-free Dnase-I on the column as described in the protocol. The RNA was eluted in nuclease-free water and immediately stored at −80° C. The concentration of RNA was determined spectrophotometrically (O.D. at 260 nm).

Reverse Transcription:

c-DNA was prepared from total RNA that was reverse transcribed using ThermoScript™ RT-PCR system (Invitrogen) according to the manufacturer's protocol. Briefly, 1-2 µL of RNA ranging from 0.01 to 1 µg of total RNA was mixed with either a specific reverse strand primer (10 pm) or a random hexamer (50 ng), 1 mM dNTP, 1×cDNA synthesis buffer, 20 mM DTT/40 U RNaseOUT™, and 15 units of ThermoScript™ RT in a 20 µL volume. Reaction conditions varied, but typically the reaction was heated to 55° C. for 2 minutes and incubated at 52° C. for the specific primer for 60 minutes and terminated by heating at 85° C. for 5 minutes. For random priming the reactions were incubated at 25° C. for 20 minutes and then 50 minutes at 50° C.

PCR:

Double stranded molecules were generated by PCR amplification under the appropriate cycling conditions (typically, 2 minute denaturation at 95° C.; followed by 30 cycles of 30 seconds at 95° C. (denaturation); 30 seconds at 55° C. (annealing); and 30 seconds at 72° C. (extension); and a final 2 minute extension at 72° C.). Typically, 50 µL reaction mixes contained template DNA (0.2-100 ng), 10 pmoles of each primer flanking the target sequence, 0.2 mM of each dNTPs, appropriate $MgCl_2$ concentrations (1-2.5 mM), and 3-4 units of Taq Polymerase. For cloning, PCR products were typically purified using a commercially available PCR product cleanup procedure (Promega or Qiagen) and eluted in sterile $dH_2O$.

Results

The complete open reading frames (ORF) of the murine and human IDO2 mRNA have been delineated and confirmed by sequence analysis by RT-PCR. The exons corresponding to the ORF have been mapped by comparison to the genomic sequence in the GenBank and Celera Databases.

Both IDO1 and IDO2 are present on chromosome 8. The distance between the coding regions varies between the sequences available for human and mouse. In the mouse, the distance between the last exon of IDO1 and the first exon of IDO2 is about 4500 bases. The distance between the two genes, as determined from the available human genomic region, is about 20,000 bases.

Amino acid sequences of human and murine IDO2 are provided in FIGS. 1 and 2, respectively. Coding regions of human and murine IDO2 are provided in FIGS. 4A and 4B, respectively. FIGS. 3A, 3C, and 3D provide sequence alignments of human IDO1 and IDO2 amino acid sequences, human and murine IDO2 amino acid sequences, and murine IDO1 and IDO2 nucleotide and amino acid sequences, respectively.

The complete coding regions of murine IDO1 and IDO2 were cloned in-frame with the V5/His TAG coding region in pcDNA4/TO (Invitrogen) which contains a regulatory region that is repressed by the tetracyclin regulated repressor (TetR). The complete coding regions of IDO1 and IDO2 were generated using gene specific primers [IDO2 5'KpnATG (TCCGGTACCATGGAGCCTCAAAGTCAG, SEQ ID NO: 16) and IDO1 5'KpnATG (ATCCGGTACCATGGCACTCAGTAAAATA, SEQ ID NO: 17)] and 3' primers that were gene specific and removed the termination codon [IDO2minstop (TGTCCTGGTGCTAAGGGTCAAGACAATTCT, SEQ ID NO: 18) and IDO1 minus stop (TGAGTTGGCCTAAGGGTCAAGACAATTCT, SEQ ID NO: 19)]. The IDO1 and 2 coding regions where then cloned in-frame with the V5/His carboxyl terminal Tag in the pcDNA4 TO vector (Invitrogen).

Figure 5:
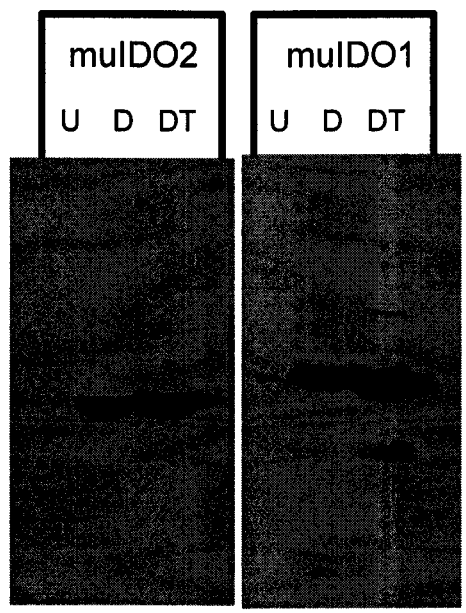
FIG. 5 provides a Western blot of murine IDO1 and IDO2 expression in T-REx™-293 cells. U is untreated cells, D is doxycycline treated cells, and DT refers to doxycycline and tryptophan treated cells.

Murine IDO1 and IDO2 were expressed as fusions with a C-terminal V5 epitope. Both were detected by Western blot analysis in T-REx™-293 cells following the addition of doxycycline (2 µg/mL) or doxycycline combined with tryptophan (100 µM) (FIG. 5). Little or no IDO1 or IDO2 was detected in the absence of doxycycline. IDO2 migrates slightly faster (apparent lower molecule weight) than IDO1. Both proteins were detected using an HRP-conjugated antibody to the V5 C-terminal tag (Invitrogen). Bound antibody was detected by chemiluminescence (SuperSignal® West Pico, Pierce).

The growth characteristics of T-REx™ expressing IDO1 and IDO2 were also examined. FIG. 6 shows that growth curves of the T-REx™ cells with no vector (center panel), pcDNA4TO-muIDO1 (left panel) or pcDNA4TO-muIDO2 (right panel). Cells were grown unsupplemented (media alone), or in the presence of doxycycline (Dox-20 ng/mL), tryptophan (Tryp-100 µM) or both doxycycline and tryptophan (Dox/Tryp). All cells grew normally in the absence of doxycycline (media alone) or in the presence of additional Tryptophan (100 µM). In the presence of doxycycline (20 ng/mL) the IDO1 expressing cells grow less well due to deprivation of tryptophan from the media. IDO1 expressing cells in the presence of doxycycline and tryptophan grew well until day 8-10. IDO2 expressing cells consistently grew better in the presence of doxycycline and tryptophan. For IDO2 containing cells, no significant changes in cell growth was observed following doxycycline or tryptophan additions alone. Similarly the growth characteristic of T-REx™ cells with no vector was unaffected by the doxycycline, tryptophan or dox/tryp treatments.

Figure 7:
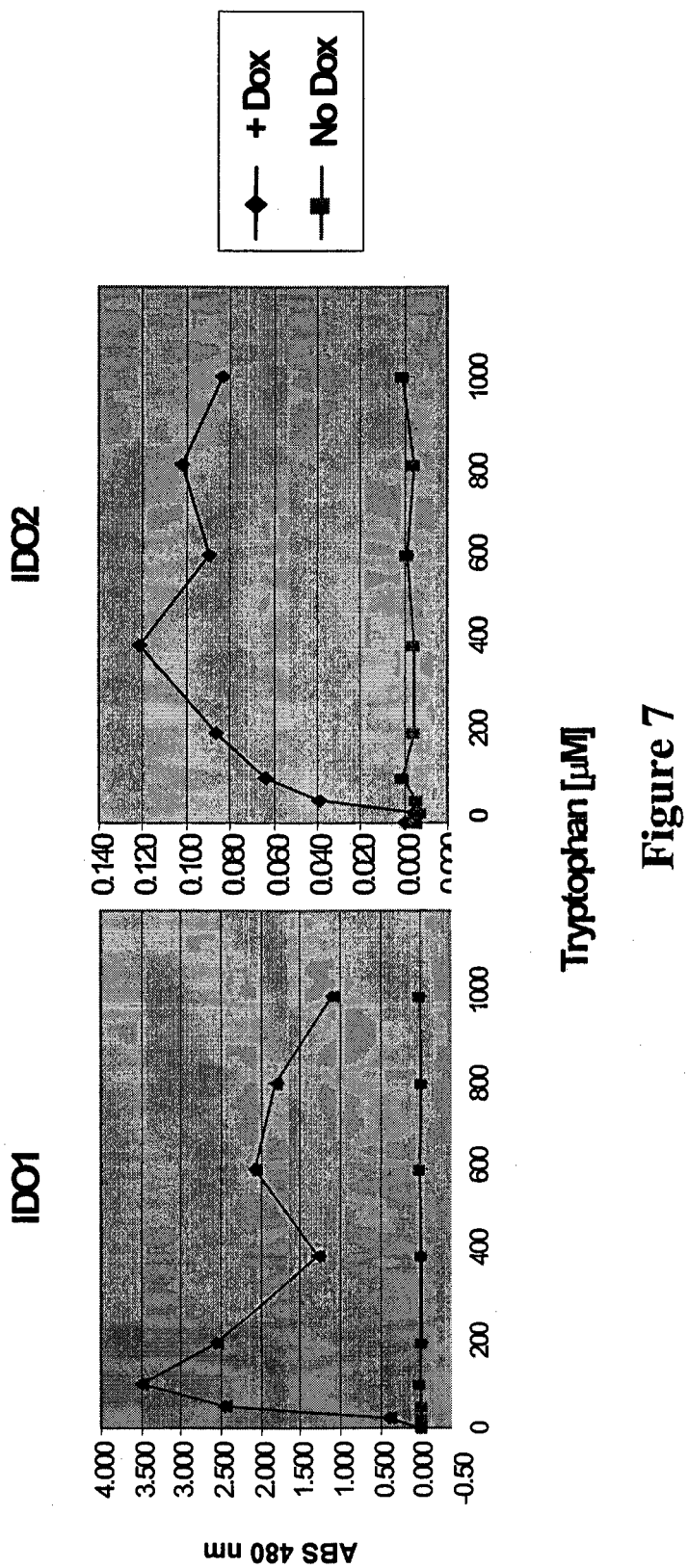
FIG. 7 provides graphs demonstrating the ability of IDO1 and IDO2 expressing 293 cells to metabolize tryptophan. A kynurenine assay was conducted to determine the ability of IDO1 and IDO2 expressing cells to metabolize tryptophan. The expression of IDO1 or IDO2 was induced by the presence of doxycycline. The cells were also exposed to increasing amounts of tryptophan.

The ability of IDO1 and IDO2 expressing 293 cells to metabolize tryptophan was also studied (FIG. 7). The kynurenine assay indicates that tryptophan is metabolized in IDO1 and IDO2 expressing cells. The assay was performed in triplicate on media harvested 72 hours in the absence of induction (no doxycycline) or following induction with doxycycline (20 ng/mL). Cells were also exposed to increasing amounts of supplemental tryptophan to the media (0 to 1000 µM). Significantly higher levels of kynurenine were detected in both IDO1 and IDO2 expressing cells when the tryptophan levels were higher than media alone. No significant kynurenine was detected in IDO2 expressing cells in the absence of supplemental tryptophan. These data suggest that IDO1 and IDO2 possess indoleamine dioxygenase activity. However the activity of IDO2 is far lower than that of IDO1 (note the abs scale is different between IDO1 and IDO2 experiments). Taken together these data suggest the IDO2, although possessing weak indoleamine dioxygenase activity, may have a different and preferred substrate than IDO1. Potential substrates of IDO2 include, without limitation, hydroxyl tryptophan, serotonin, melatonin, indoleacrylate, methyltryptamine, and indole-3-propanoate. Alternatively, IDO2 may require a co-factor for its full activation that is different that that present for IDO1.

Figure 8A:
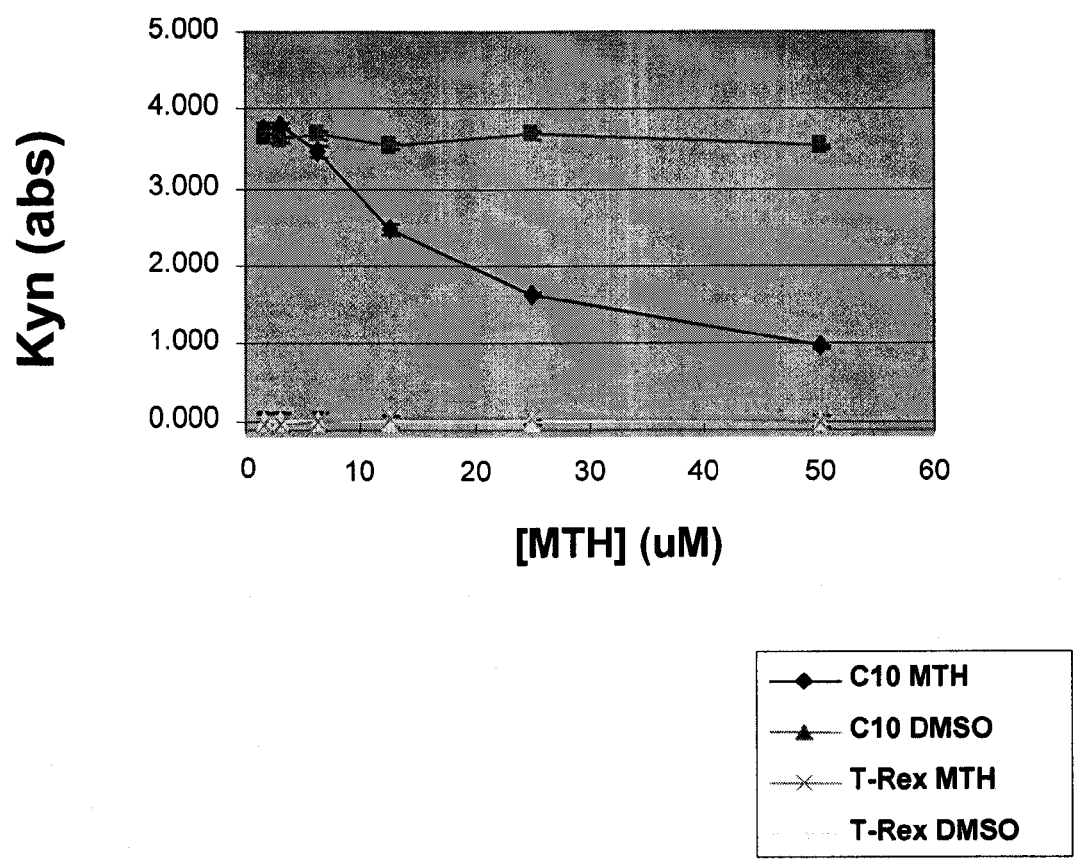
FIG. 8A provides a graph demonstrating the inhibition of IDO1 by methyl thiohydantione (MTH). T-Rex cells or IDO1 expressing T-Rex cells (C10) were treated with doxycycline in the presence of increasing concentrations of DMSO (carrier) or a known IDO1 inhibitor (MTH). The cells were maintained in growth media plus supplements for 5 days, after which the media was harvested and subjected to analysis for the presence of kynurenine.

IDO1 expressing 293 cells metabolize tryptophan and can be inhibited by methyl thiohydantione (MTH). T-REx™ cells or IDO1 expressing T-REx™ cells were treated with doxycycline in the presence of increasing concentrations of DMSO (carrier) or known IDO1 inhibitor (MTH). The cells were maintained in growth media plus supplements for 5 days, after which the media was harvested and subjected to analysis for the presence of kynurenine. The decrease in kynurenine production in the IDO1 expressing cells was observed in a dose dependent manner while no changes in kynurenne were observed in DMSO only treated cells (FIG. 8A). The control T-REx™ cells (no vector) do not produce any detectable kynurenine. The presence of inhibitor was not toxic to the cells. These data demonstrate the ability to use this cell based assay to assess indoleamine dioxygenase activity of IDO1 by using a known IDO1 inhibitor.

Figure 8B:
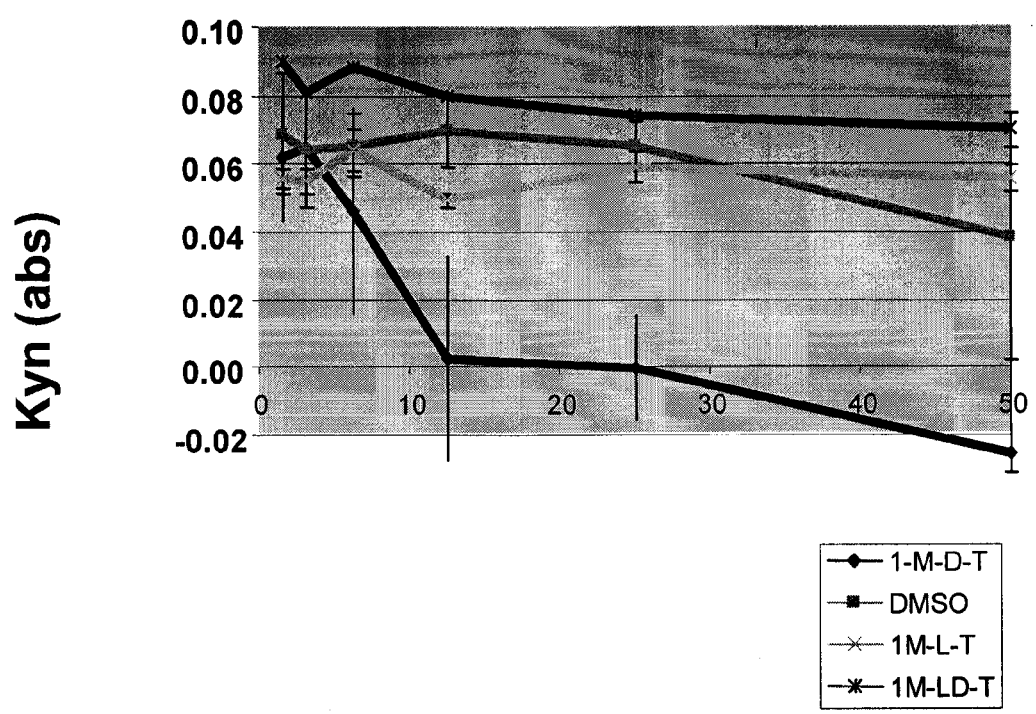
FIG. 8B provides a graph demonstrating that IDO2 metabolizes tryptophan and can be inhibited by 1-methyl-D-tryptophan (1M-D-T). IDO2 expressing T-Rex cells were treated with doxycycline in the presence of increasing concentrations of DMSO (carrier) or the D, L and mixed DL racemic isomers of 1-methyl-tryptophan, (1M-D-T, 1M-L-T and 1M-LD-T, respectively). The cells were maintained in growth media plus supplements for 5 days after which the media was harvested and subjected to analysis for the presence of kynurenine.

IDO2 expressing 293 cells metabolize tryptophan and can be inhibited by 1-methyl-D-tryptophan (1M-D-T). IDO2 expressing T-REx™ cells were treated with doxycycline in the presence of increasing concentrations of DMSO (carrier) or a variety of potential inhibitors, including the D, L and mixed DL racemic isomers of 1 methyl-tryptophan, (1M-D-T, 1M-L-T and 1M-LD-T, respectively) (FIG. 8B). The cells were maintained in growth media plus supplements for 5 days, after which the media was harvested and subjected to analysis for the presence of kynurenine. The decrease in kynurenine production in the IDO2 expressing cells was observed only with 1M-D-T in a dose dependent manner while no changes in kynurenine levels was observed in DMSO only treated cells or the other inhibitors. The control T-REx™ cells (no vector) do not produce any detectable kynurenine and were used as background absorbance values which were subtracted from the experimentally obtained values. The presence of inhibitor was not toxic to the cells.

Figure 9A:
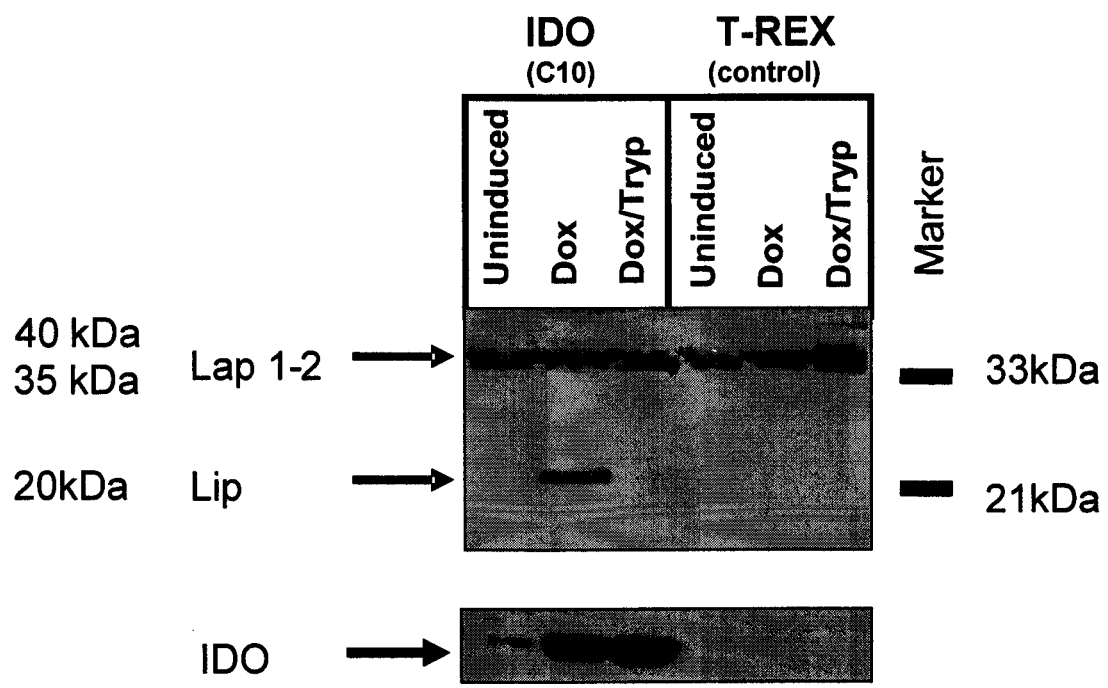
FIG. 9A is a Western blot demonstrating that IDO1 and tryptophan deprivation stimulates the expression of the LIP isoforms of NFIL-6. T-REx™ cells (control) and T-REx™ cells expressing IDO1 were either uninduced or induced with doxycycline in the presence or absence of added tryptophan (100 μM).

FIG. 9A demonstrates that IDO1 induces LIP expression. IDO1 is expressed in these cells when stimulated by doxycycline. When doxycycline is added to these cells, LIP is expressed (72 hours after stimulation). However, in the presence of exogenously added tryptophan (100 µM) the expression of LIP is eliminated; even when IDO1 is expressed. These data demonstrate that the LIP activation occurs via tryptophan deprivation, GCN2 activation, and differential LIP synthesis.

Figure 9B:
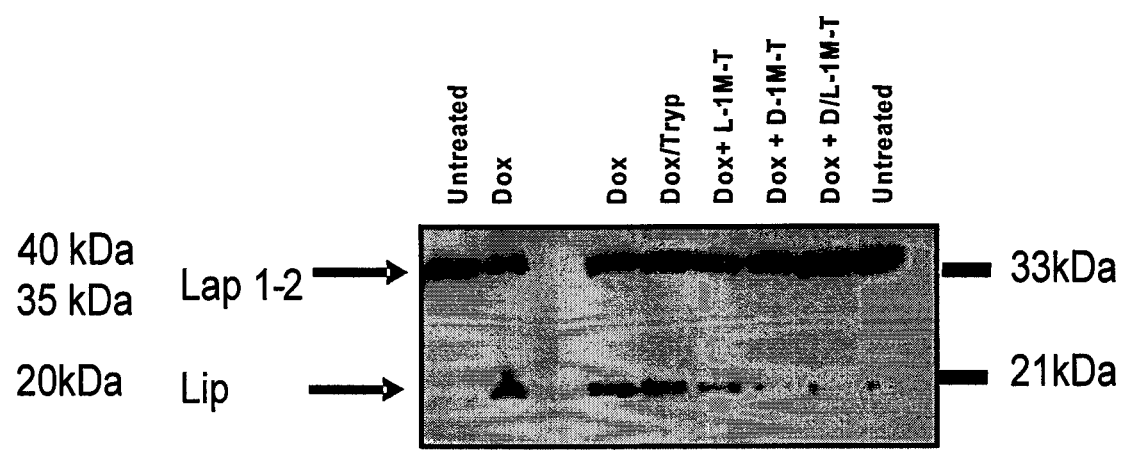
FIG. 9B is a Western blot demonstrating that IDO2, regardless of tryptophan levels, stimulates the expression of the LIP isoforms of NFIL-6. T-REx™ cells (control) and T-REx™ cells expressing IDO2 were either uninduced or induced with doxycycline in the presence or absence of added tryptophan. Cells were also optionally treated with the D, L and mixed DL racemic isomers of 1-methyl-tryptophan, (1M-D-T, 1M-L-T and 1M-LD-T, respectively).

FIG. 9B demonstrates that the same activation of LIP occurs following IDO2 activation, but it is not inhibited by excess tryptophan. These data show that IDO2 activates the same pathway leading to LIP activation but that this pathway is not dependent on tryptophan deprivation. Also this data shows that the IDO2 activation of LIP is inhibited by the D isoform and, to a lesser extent, the L isoform of 1 methyl tryptophan. The selectivity for the D isoform to inhibit IDO2's activation of LIP demonstrates that IDO2 and IDO1 activities can be distinguished pharmacologically.

Figure 9C:
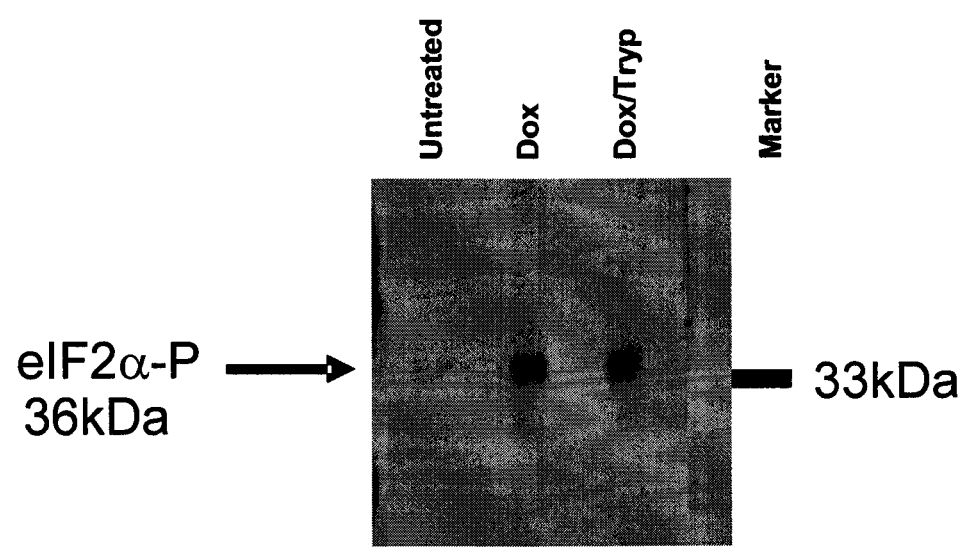
FIG. 9C is a Western blot demonstrating that IDO2 expression results in the phosphorylation of e1F2α. T-REx™ cells expressing IDO2 were either uninduced or induced with doxycycline in the presence or absence of added tryptophan.

FIG. 9C provides a Western blot demonstrating that, like IDO2's activation of LIP expression, IDO2 also activates the GCN2 kinase leading to e1f2-α phosphorylation (the protein target of GCN2). This activity is dependent of IDO2 expression which is not inhibited by excess tryptophan. These data suggest that IDO2 functions within this pathway but the activation of GCN2 kinase, phosphorylation of e1f2-alpha, and LIP expression is not dependent on tryptophan deprivation. Unlike IDO1, which activates GCN2 kinase pathway through the deprivation of tryptophan and can be relieved by exogenous tryptophan, the IDO2 mechanism of action is different and can not be relieved by exogenous tryptophan. Therefore, IDO2 functions more directly in activating the GCN2 pathway, perhaps by acting on the tryptophanyl-tRNA directly.

FIGS. 12A-12C provide schematics of murine and human IDO2 as well as primers which can be employed to amplify regions of IDO2.

Example 2

Figure 16C:
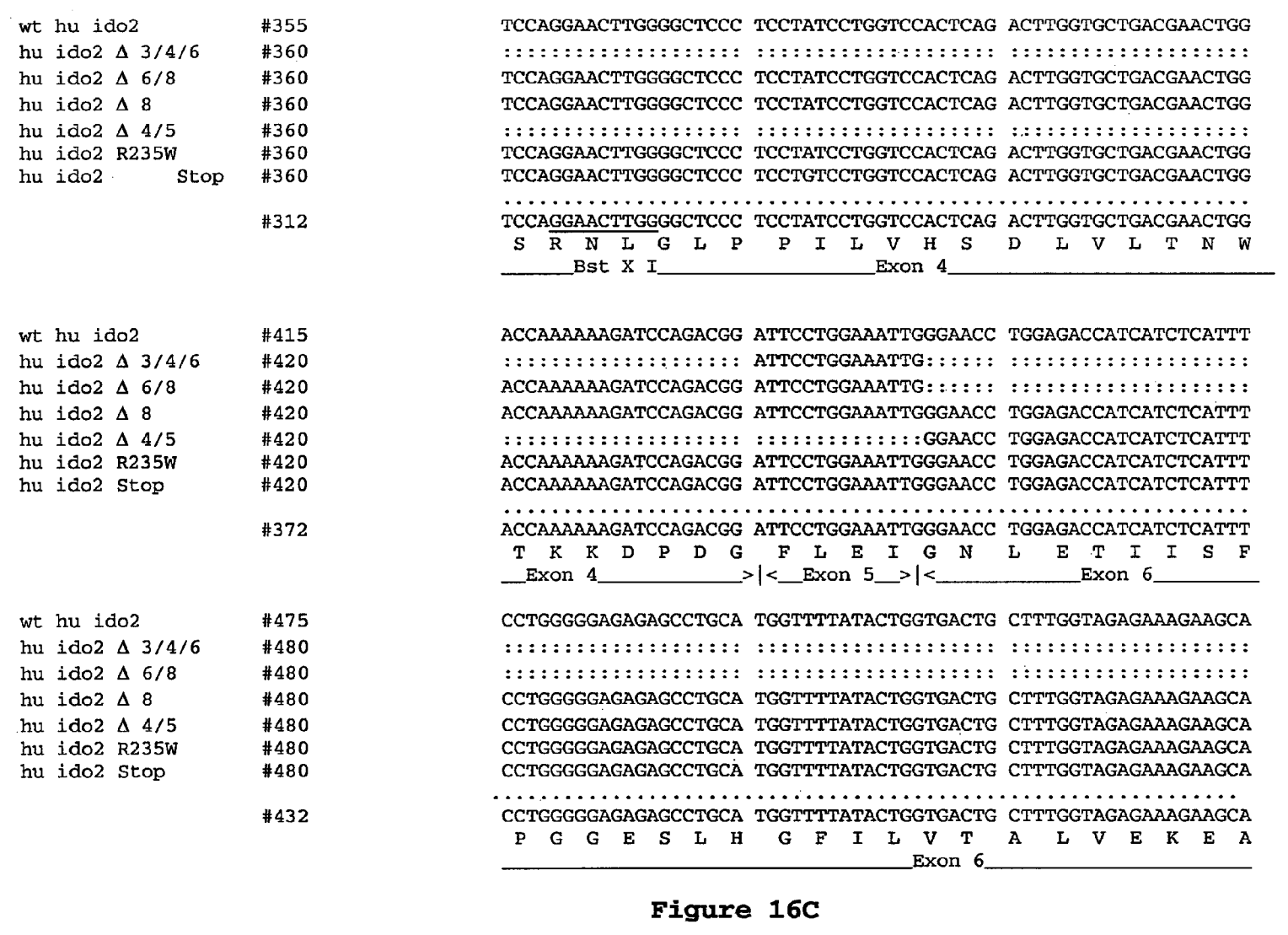
Figure 16D:
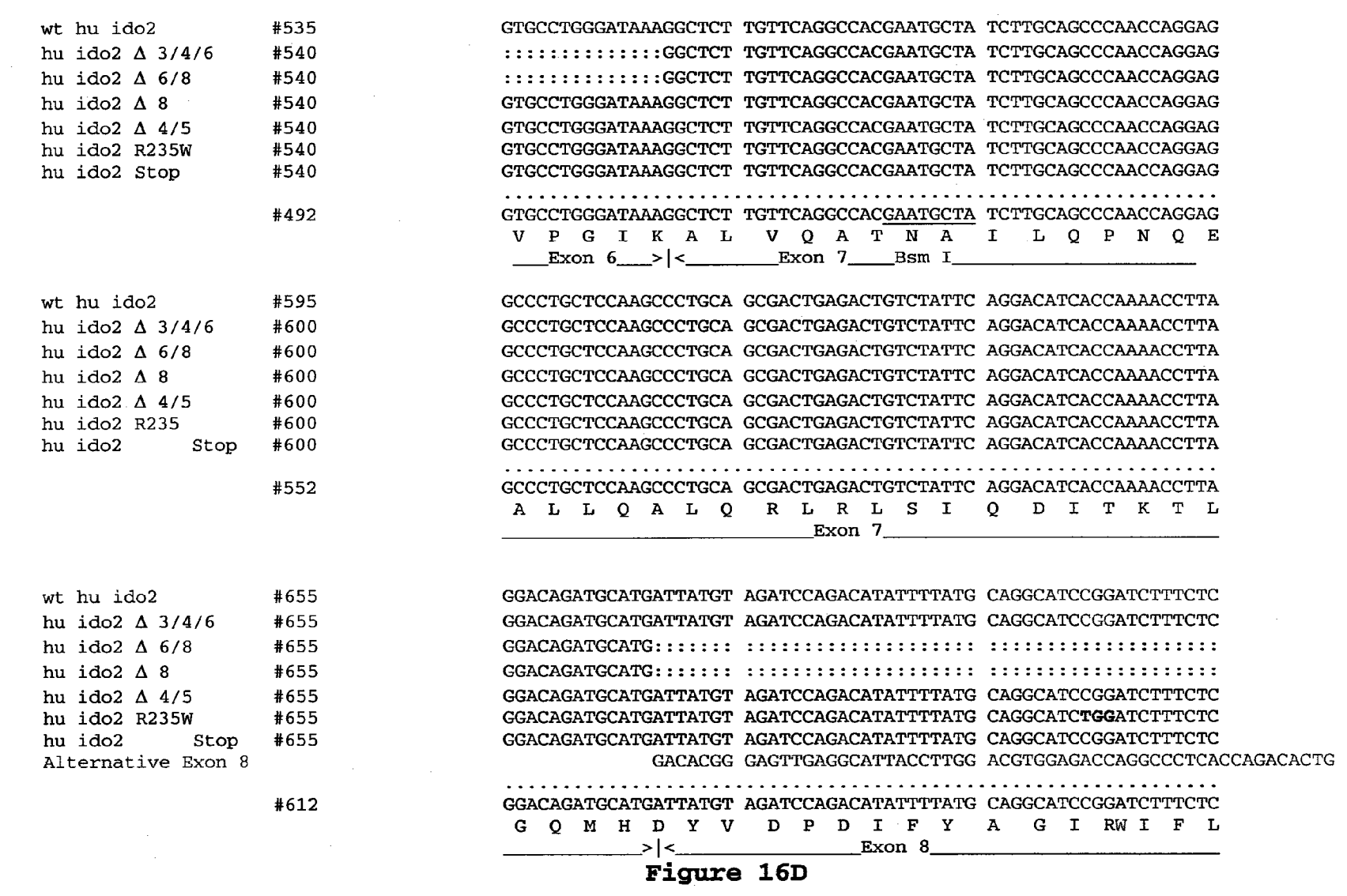
Figure 17:
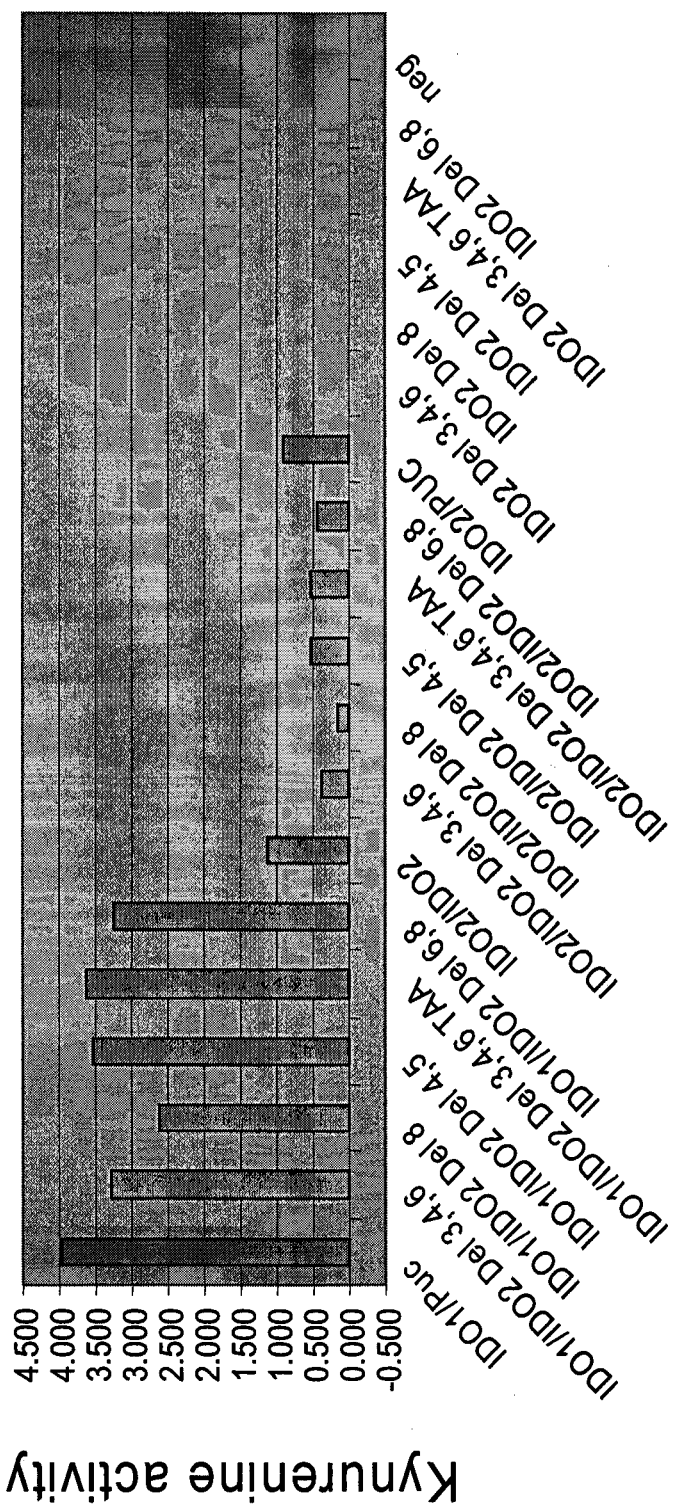
FIG. 17 is a graph of the kynurenine activity of various IDO2 splice variants or mutants alone or co-expressed with IDO2, IDO1, or empty vector (Puc).

Human IDO2 cDNAs were cloned from RNA isolated from normal human liver. Splice variants were identified which lead to alternative reading frames and/or early termination of the primary sequence of IDO2. These splice variants are IDO2 Δ3/4/6, IDO2 Δ8, IDO2 Δ6/8, and IDO2 Δ4/5. FIG. 16 provides the nucleotide sequences of these splice variants. Vectors comprising the splice variants were transiently transfected into 293 (T-Rex™) cells and a kynurenine detection assay was performed as described hereinabove to determine the presence of indole dioxygenase activity with the expressed IDO2 splice variants. As seen in FIG. 17, the tested splice variants did not possess detectable indole dioxygenase activity.

Two prominent single nucleotide polymorphisms (SNP) were also cloned. These two SNPs are not linked (i.e., they are not on the same allele) and are differentially represented in various populations as indicated by the SNP database. The R235W SNP encoded in exon 8 alters the arginine (R) present at amino acid position 235 to a tryptophan (W). The SNP at amino acid position 332 introduces a stop codon at Tyrosine 332 (Y332stop). Both SNPs render the IDO2 molecule inactive when assayed for the production of kynurenine following a transient transfection assay as described hereinabove. As such these SNPs may be important indicators/markers for the propensity or resistance to certain disease states.

Additionally, as seen in FIGS. 15A-15Y and 16, an alternative splice site exists in exon 8 of IDO2, leading to an alternate sequence for exon 8.

When the alternatively spliced variants are co-expressed with either wild-type IDO1 or IDO2 lower, the indole dioxygenase activity, as assessed by the kynurenine detection assay, is reduced compared to wild-type IDO1 or IDO2 alone, even though IDO1 or IDO2 protein levels are the same in each reaction (see FIG. 17). These data indicate that an RNA or peptide product of the truncated IDO2 and/or alternatively spliced IDO2 may function to inhibit IDO1 and IDO2 activity. Such interactions may be dependent on direct or indirect protein-protein interactions between the truncated product and the full length IDO1 and IDO2 peptides. Alternatively the spliced variants may inhibit co-factor activity and the normal activation of IDO1/2 enzyme via changes in the oxidative state of the Fe component of coordinated Heme group. Nevertheless the negative interaction of these splice variants suggests the utility of a compound or peptide whose interaction with the splice variants or full length IDO1 or IDO2 will block the negative and inhibitory interactions resulting in increased IDO1 or IDO2 activity. Applications for such a compound or peptide include diseases that have an autoimmune component.

Example 3

Figure 18:
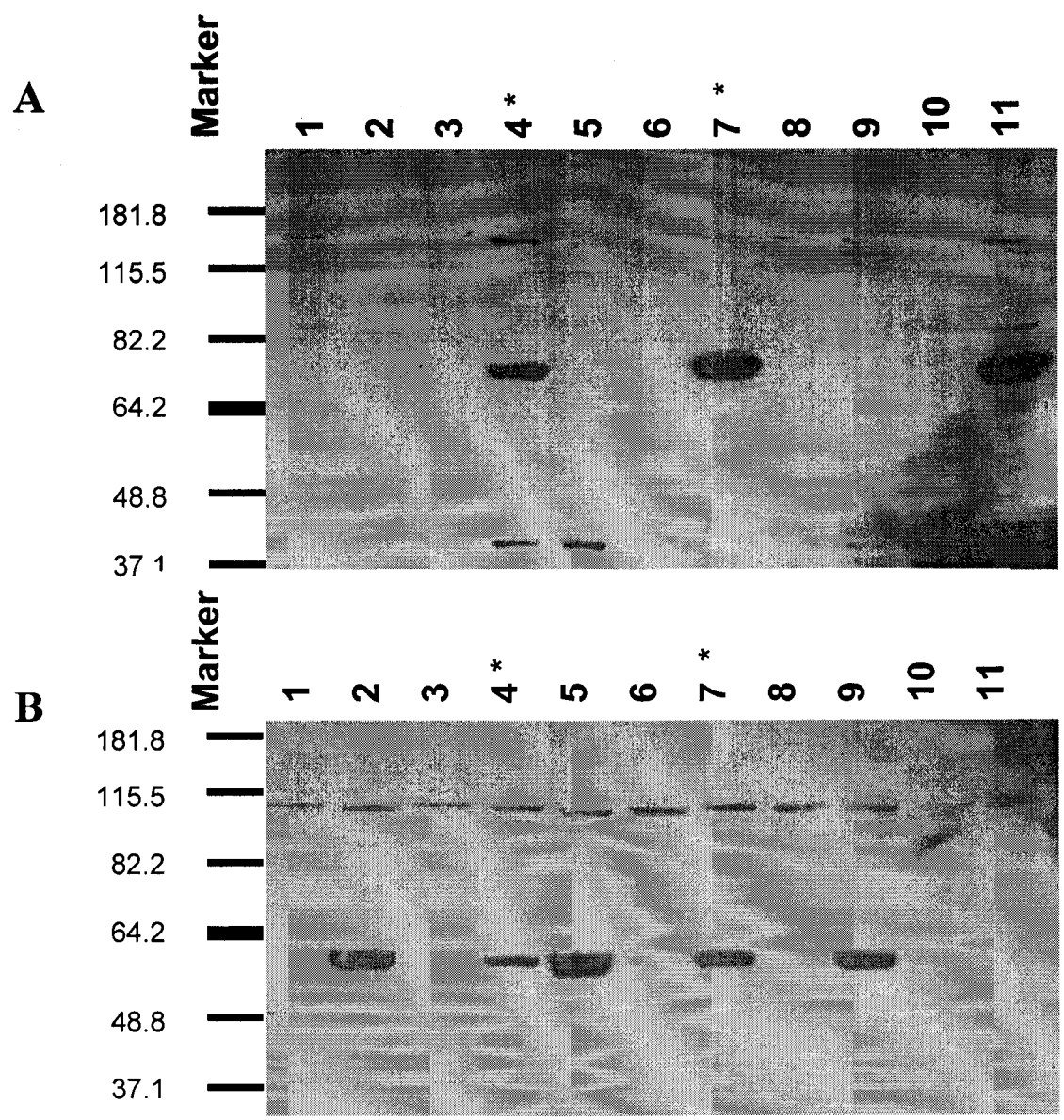
FIGS. 18A and 18B are images of Western blots of cellular lysates of 293 cells expressing the following: 1: no IDOs, 2: mouse IDO2 (WT), 3: human IDO2 (WT), 4: mouse IDO1/IDO2, 5: mouse IDO2, 6: mouse IDO2/1 chimera, 7: human IDO1/mouse IDO2, 8: human IDO2 (R-W), 9: mouse IDO2 (R—W), 10: hu8man IDO2 (Y-*), 11: human IDO1. The Western blot in FIG. 18A was probed with an anti-IDO1 polyclonal sera (1:200) and the Western blot in FIG. 18B was probed with an anti-muIDO2 monoclonal antibody (MAb 7.4.6; 1:100).

Monoclonal antibodies specific to mouse IDO2 were generated using standard techniques. FIG. 18 provides images of Western blots which demonstrate the species and IDO-isoform specificity of the generated monoclonal antibodies. Mouse or human IDO1 and/or IDO2 were expressed in 293 (T-REX) cells. Additionally, the R235W (R-W) and Y332stop (Y-*) isoforms of human and mouse IDO2 were also expressed in 293 (T-REX) cells. As seen in FIG. 18B, monoclonal antibodies derived from hybridoma clones (7.4.6, 7.4.9 and 8.8.6) are specific to mouse IDO2 protein and do not recognize the human or mouse IDO1 proteins (shown reacting with rabbit polyclonal sera directed to both human and mouse IDO1). FIG. 18A demonstrates the reactivity of an IDO1 polyclonal sera which recognizes both human and mouse IDO1.

Example 4

Figure 19:
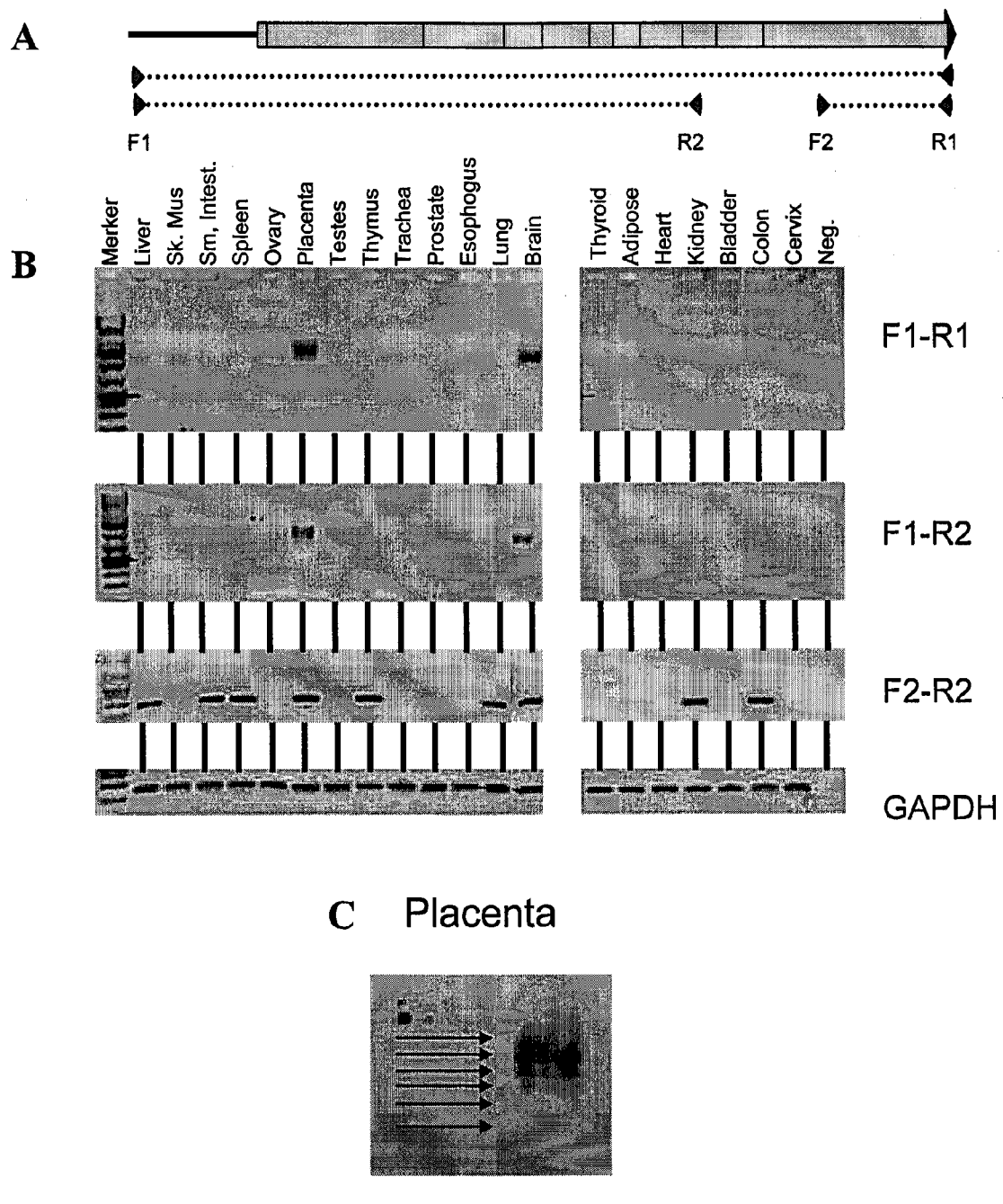
FIG. 19A is a schematic of human IDO2 mRNA and the location of the primers used for RT-PCR.
FIG. 19B provides images of the RT-PCR assays performed on total RNA from the indicated tissues. The primers used in the RT-PCR are indicated at the right of the panels and GAPDH is provided as a control.
FIG. 19C is an image of an agarose gel demonstrating the presence of various IDO2 isoforms in human placenta.

The tissue specific expression of human IDO2 was determined using T-PCR. A human tissue panel of total RNA (Ambion, Austin, Tex.) was analyzed by RT-PCR. The RT reaction utilized oligo-dt priming followed by the specific amplification using primers specific to different regions of the IDO2 mRNA (FIG. 19A). Primer F1 recognized a region in the 5' untranslated region of the mRNA. Transcripts containing this region of the gene (exon 1a) are detected only in the placenta and brain (FIG. 19B). In contrast, primers specific to the 3' end of the gene (primers spanning exons 9-10) demonstrated a broader pattern of expression. The presence of splice variants can be detected in both the placenta (FIG. 19C) and brain tissue. Without being bound by theory, this data suggests that there may be alternative promoters initiating at exon 1a and at exon 1, as exon 1 is more widely expressed than exon 1a. Primers F2-R2 were used because exons 9 and 10 are present in all splice variants detected so far.

Example 5

The present example describes the generation of an indoleamine 2,3-dioxygenase-2 (IDO-2) gene conditional knockout allele in mice using homologous recombination in mouse embryonic stem cells and subsequent blastocyst injection of the appropriate targeted ES cells.

The mouse IDO-2 gene is located on chromosome 8, only 6 kb downstream from the IDO gene. The fact that the two genes are so close together makes it less desirable to attempt to knock out IDO-2 function by eliminating the first exons. As described herein, IDO-2 is organized into ten exons. Exons 9 and 10 play a crucial role for the enzyme function. As such, a conditional allele that upon recombination will eliminate only these two exons was created.

RP23-339B16 BAC clone (which contains both IDO and IDO2 genes) was used for generating the homologous arms and the conditional KO region for the gene targeting vector, as well as the southern probes for screening targeted events. The recombination targeting vector (FIG. 21) will result in the Cre-dependent deletion of exons 9 and 10. Exons 9 and 10 were chosen because the analogous structural domain of IDO1 constitutes the major catalytic domain of the enzyme. Similarly in vitro mutagenesis studies on IDO2 demonstrate that this region is required for enzymatic activity.

Figure 21:
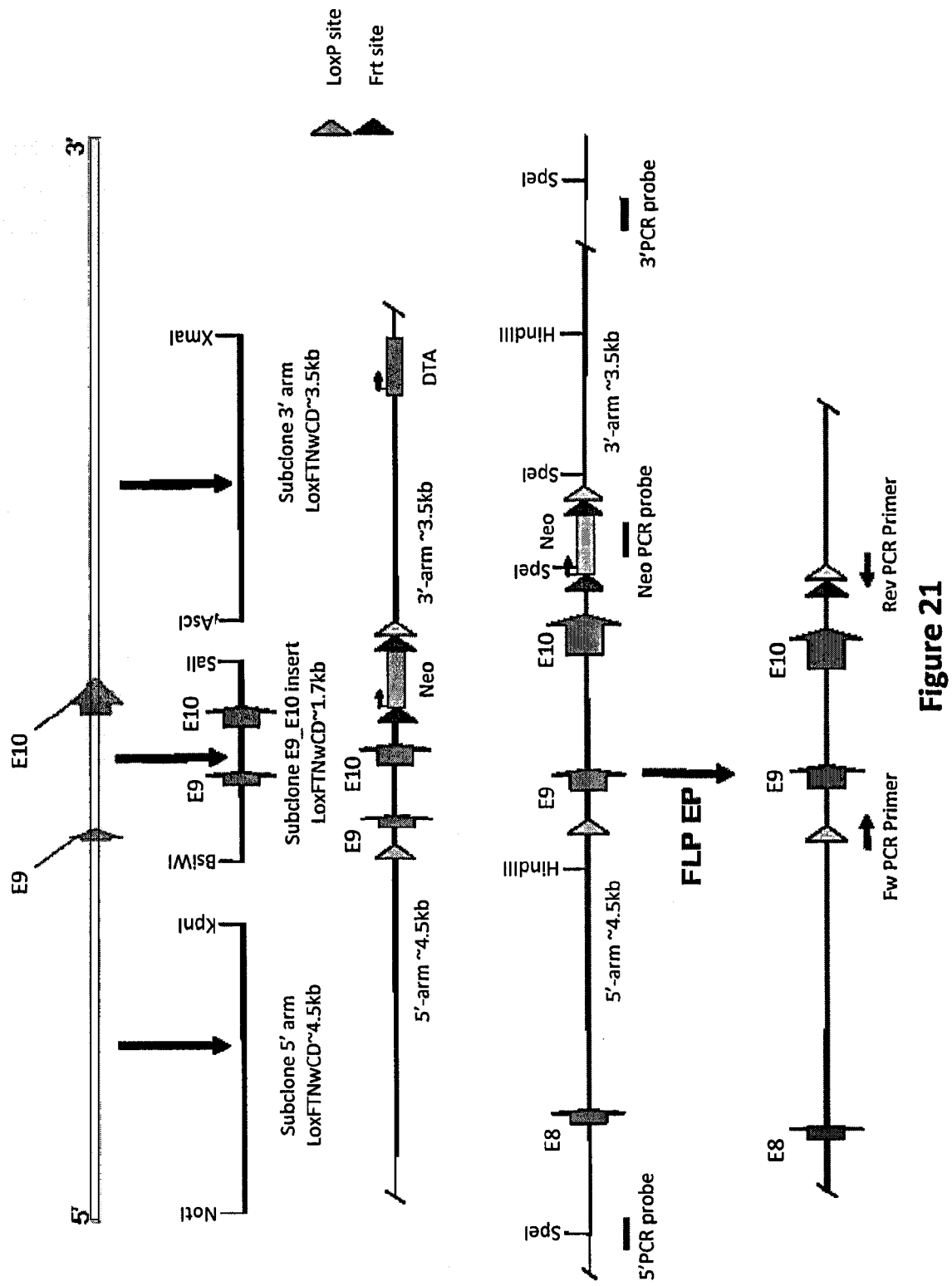
FIG. 21 is a schematic of a target vector strategy for the construction of a conditional IDO2 knockout mice strain. Removal of exons 9 and 10 in the IDO2 gene happens upon crossing with a transgenic Cre mouse expressing Cre recombinase under the control of tissue specific promoters.

As demonstrated in FIG. 21, the unconditional knock-out was generated using a positive (Neo) and negative (dipteria toxin A; DTA) selection approach, whereby the DNA construct possesses a DTA expression cassette distal from the homologous arms to negatively select for non-homologous recombination and a neomycin positive selection cassette flanked by the sites for the FLP recombinase. In addition, the targeting vector has two Lox-P sites for the Cre recombinase each flanking exons 9 and 10, which allows for the Cre-dependent excision of exons 9 and 10. Embryonic stem (ES) cells (C57/B16) were electroporated with the targeting construct and the surviving Neo$^R$ transfected clones were screened by Southern analysis to identify ES cells carrying targeted IDO2 alleles. Six of the ES cell clones containing the recombinant targeted conditional allele were electroporated with Flp recombinase-expressing plasmid to eliminate the neo cassette. Two positive FLP treated Neo$^{(-)}$ clones expanded for further analysis using long-range PCR and Southern analysis. Selected clones with normal karyotypes were either injected into blastocysts (to generate a conditional IDO2-knockout chimeric embryo) or electroporated with CRE recombinase to remove exons 9 and 10. Four CRE treated ES cell clones were'identified to possess the proper exon 9/10 deletion using PCR analysis, expanded, and injected into blastocysts (to generate an IDO2 knockout chimeric mouse embryo).

The 5' homologous arm (4.5 kb), 3' homologous arm (3.5 kb) and conditional KO region (1.7 kb) were generated by PCR. The fragments were cloned in the LoxFtNwCD or (for sequencing purposes) PCR 4.0 vectors and confirmed by restriction digestion and end-sequencing.

The final vector was obtained by standard molecular cloning. Aside from the homologous arms, the final vector also contains loxP sequences flanking the conditional KO region (0.25 kb), Frt sequences flanking the Neo expression cassette (for positive selection of the ES cells), and a DTA expression cassette (for negative expression of the ES cells). The final vector was confirmed by both restriction digestion and end sequencing analysis. NotI was used for linearizing the final vector prior to electroporation.

The 5' and 3' external probes were generated by PCR and were tested by genomic Southern analysis for screening of the ES cells. The probes were cloned in the pCR4.0 backbone and confirmed by sequencing. A screening strategy for mIDO-2 knockouts is provided in FIG. 22.

The offspring of the chimera pups for the conditional and unconditional IDO2 knockout animals were born, analyzed for germline transmission of the modified IDO2 alleles, and subsequently bred to homozygosity.

As indicated hereinabove, the homologous arms were generated by PCR. The 5'-arm was cloned into LoxFtNwCD in NotI/KpnI sites, upstream from loxP site. The template was BAC clone RP23-339B16 and the primers used were:

```
LDI_IDO2_5'F: Tm 57.8
                                       (SEQ ID NO: 148)
    actggcggccgcATGCCGAATCTATTACCATTACTGCC LDI_IDO2_5'R: Tm 60.4
                                       (SEQ ID NO: 149)
    actgggtaccACACCTTCATAGACCAGCCCACA
```

The E9/E10 CKO region was cloned in BsiWI/SalI sites, upstream from FRT site. The template was BAC clone RP23-339B16 and the primers used were:

```
LDI_IDO2_INSF: Tm 60.4
                                       (SEQ ID NO: 150)
    actgcgtacgcatatgTGTGGGGCTGGTCTATGAAGGTGT LDI_IDO2_INSR: Tm 52.8
                                       (SEQ ID NO: 151)
    actggtcgacGGGATATAGCACAAGAACAGCTAAG
```

The 3' arm was cloned in LoxFtNwCD in AscI/XmaI sites. BAC clone RP23-339B16 was used as the template and the primers used were:

```
LDI_IDO2_3'F: Tm 52.8
                                       (SEQ ID NO: 152)
    actgggcgcgccCTTAGCTGTTCTTGTGCTATATCCC LDI_IDO2_3'R: Tm 56.8
                                       (SEQ ID NO: 153)
    actgcccgggGGTGTCTGTGAGATTTTGAGAATAGTCC
```

The 5' and 3' arms and the CKO region were end sequenced. The sequence of the 5' end of the 5' arm was determined to be:

```
                                       (SEQ ID NO: 154)
ATGCCGAATCTATTACCATTACTGCCAAGTCCCATTGGGAGAAAAACTA

AAGTGTGCATTCGTGCATGTGTGCGTGTACGTGTGTGTCTAGAACTGAA

AATTTTATTTCCTTGCAAGTATCAGACTAGAGTTTTCCTGGCCTGCTAG

GTCCTCTGTTGCCTCTCCCCACCATGTCCCAATTTGACTCCTGACACA

GCACTGGCACTTGGCATTTTTCTAGAATTACACATTTTCCTGACTTTTC

TCTTGACTACCGCCAGAGGAAATTTCTCTTAAAGGGGCTCCTGTGGCTG

TGCTCAATCTAGTCGGATGAGTCAGGGAAATTCCCACATTAAAGCTAAA

CTGATCAGTGGCCTTAATCCCATCTGAAAAGTCCTCCTGCCCTGTCCTG

TAATAAATATATCATGGTGACCGGAACAGCTCATAGTATTAAGAGTCCT

AGGAATTCGGTTGGGAACCTTGGGGAGCTATTTTTAGAATCCTACCCTC

CAGTGTCTTTCAAAGGAATCATTTCTACTTCCTCTTGGCAGAGACTTGA

TAAGAACCAGAAGGGGACTTTGTTTGCATCGACATAAGTTCCGGGCAAT

GACACTTTTTATCTGGTATTTGGCATAAAGGCCATCCCTCCACTTCAAA

TGCTGAGACTGTTTACTGTGCCGCTAAGTGGCTGTACAAGATCCTAAAT

GTAGCTGTAGTTTCAACAAACATCTGGATTGTTGGGAGTTTCCAGTAGA

CTTCTCTTTAAAATGTCAGCCTCGCTATTCTGCATCTATCCCGAGTTTC

TCATTTGCTTCTTTAAAACACAGTTTTATTTAAGAGTGGATGTCCTGTG

GAAATGAGATGTATTCCCTCCAGTTCCCAGCC.
```

The sequence of the 3' end of 5' arm was determined to be:

```
                                       (SEQ ID NO: 155)
TGAGTGTATGCTCGTGTATGTATGTGAGCACTGCAGGTGTCTGCATGGT

GTGCCATGGTGCTCCACTGGGCTTCATGCTGTGCTCCCCTAGGCTTCAG

TCAAGTCAAGACTAGGTCAAGTCATGGAGGGTAAACAGAAGAGAGAGAG

AGCAGAAAATGAGGGACACAGGAAGGGTAGAGGGGGAAAGAGAGGGTTG

TGAAGCTCACGCGTGATCAGGAGCCCCAGGCTTTCTTCTTCCAGCCGCC

CATAGGCTCTGGTGCCCACAACATTGGTTACAACCCCGCTCTCCATCAT
```

-continued

CATGCTTGTCATCACTGCTGTGACAAACCGCTTAATAATGGTTCTCACG

GAACATTAAAAGCCAAGCCAAGTTTAACACCTCGAACATTTCCAAGTGT

TATGGGAATAACAGTTAAGTGTCTGGGTGTGCTTGTGTGTAATTGGGA

ATCTGTAGTGGTGGGGTTACCAGTGTCAGGCCACAGTGTTTGTGATGAG

CAGAGGGGTCGGGGTCTTTCTCAGATCCCTTATCTTGTCCTGTCAATGG

TGGTGATGTAATAGGTGCACGCCTGTGACAGAGCTGTTTAAAGCATTGT

AAGACCAATGAGTAAAGTTCCTACCCTTGCTTCTCCTTTAAGTGAGGCA

GAAAAAGGCTCCACCATGACGTGGTGTAAAGATGAAGTCAATCTAATAC

TTCCTTGGATACTCTAGCAAGCTTCATTCACACTTTTTATTTCTTCCTC

TTCCTCTTCCTCTTCCTCTTCCTCTTCCTCTTCCCCTCCTCCT

CTTCCTCCTCCTCTTCCTCCTCCTCTTCCTCCTCCTCCTCTTCCTCCTT

CTCCTCTTCCTCCTCCCCCTCCCCTTCCCCTGTGCTCCTCATTATTATT

ATTATTGCTCCTGTCTAGGTGGAAGGACAATCCAGCCATGCCTGTGGG

CTGGTCTATGAAGGTGT.

The sequence of the 5' end of CKO region (E9) was determined to be:

(SEQ ID NO: 156)
GGTACCAAAGGCCGCAATGGCCAAACCTGCAGGAAGTACCAGAGCTCCC

TAGGTTCTAGAACCGGTGACGTCAAGCTCGAATAACTTCGTATAATGTA

TGCTATACGAAGTTATCCTGCAGGTCGATCGAGACCGTACGCTATGTGT

GGGGCTGGTCTATGAAGGTGTTGCCACAGAGCCTCTGAAGTACTCTGGA

GGAAGTGCAGCCCAGAGCTCCGTGCTTCATGCCTTCGATGAGTTCCTGG

GCATTGAGCATTGCAAGGAAAGTGGTGAGCAGCAGTCTGATCTCACCTA

TGCTTTGATGGGACAGCGAGGTAGACTAGGGAGACATCTCTAGCAACTG

ATAAAGACGGGTGTAAATGAAAATGTCCTGAAGTTTATCCTTGCCTAAG

CCAGCAGGCAGCTGTGTGCATGTGCCCTCTCTTACACTGAGTTAGTCAG

TATTGGGGCATCGGATCTTATTAGGGTCTTCCAACAGTCCTGTGACCTG

GGTTGTTCACTGTCCTGTTGGCTGGGGTCTTTTATCCGCAGATTCCCCT

TTCTACAATGAGGTGATAATGTCACATTGAAAGGCCAGTCTGGAGCAGC

AAGTGATAGTGCTGAACTTCTCTGCTAAAGCCTTTCCCATGAAATGGCC

CAGCCTCCCACTGAATCTATGTGGACCAGGCGAGGGAGCCCATCGCTTT

GAAGCCTTTAAAAT.

The sequence of the CKO region (E10) was determined to be:

(SEQ ID NO: 157)
CAGAAATGAACATTTGAGCATTTGGCAGCTATAACAAAAGCCCGACAAG

GCTGAGGGAGAGCCCTATCAAGCATTTCTGGTACCTGAGTGTTTGGAAC

AGTGGGCAAACCCTCCCAAATGTCTGCCTCGAGCTAACGTATTTCTCCC

GGCTGTTTCTTTCAGTTGGCTTTCTACACAGAATGAGGGACTACATGCC

GCCTTCCCATAAGGCTTTCCTGGAAGATCTCCACGTAGCTCCTTCTCTG

AGAGACTACATACTGGCCTCTGGTCCTGGGGACTGCCTGATGGCCTATA

ACCAGTGTGTGGAGGCCCTGGGAGAGCTGCGCAGTTACCACATCAATGT

CGTGGCCAGATACATTATCTCCGCTGCCACCAGGGCCAGGAGCAGGGGG

CTAACTAATCCCTCACCCCATGCCTTGGAAGACAGGGGCACTGGGGGTA

CTGCCATGCTGAGCTTCTTGAAGAGTGTCAGGGAGAAGACCATGGAGGC

CCTCCTGTGTCCTGGTGCTTAGCAGTCATGTCCTGCACCCTAACACTTA

GATGTTCTCATCCTGCATCCCAGCGTTAGAGGTTCACATCCTGCATCCT

AGTGCTTAGCTGTTCTTGTGCTATATCCCGTCGACGAAGTTCCTATACT

TTCTAGAGAATAGGAACTTCGGATCCACGATTCGAGGGCCCCTGCAGGT

CAATTCTACCGGGTAGGGGAGGCGCTTTTCCCAAGGCAGTCTGGAGCAT

GCGCTTTANCAGCCCCGCTGGGCACTTGGCGCTACACAAGTGGCCTCTG

GCCTCGCACACATTCCACA.

The sequence of the 5' end of 3' arm was determined to be:

(SEQ ID NO: 158)
ATCCCAGCGCTTAGCAGTCATGTCCTGCATCCTAGTGCTTAGCATTTTA

TATCCAGCATCTTAGTGCTTAGAGATTCACATCCTGCATCCTAGAGCTT

AGCATTTTATATCCAGCATCCTTGTGCGTATCAGCTATGTTTTGTATCC

TGCTTAGCAGTTAACATCCTGCATCCTAGTACTTATCTGTTCTCATCCT

GCATCCTAGAGCTTAGCAGTCAGGTCCCGTGGGAGCAAGAACCAGGGTC

TGAGCTCTGTCTGAGCCCAAGCATGGCTTTACTGCTTTGTTAATTGTGG

CTCCCACCTCCACCCCACCCCAGCCAGTTTGCTTGCTAGAAGCCTTTCT

GCACTGCCTAATCCCCCTGCCTCACAGCAGAGAGCTGCAGCCATGACCT

CCTCATTCAGTATTAGGTGGACAAGTCGGAGATACCCAAACTCAATTTT

AAAAGAATCAAGTTGCTTTTGGGGCATGTTACTTCATCTTTTCTTACCC

TGGGCCTCTATGACCTCCTCATTCAGTATTAGGTGGACAAGTCGGAGAT

ACCCAAACTCAATTTTAAAAGAATCAAGTTGCTTTT.

The sequence of the 3' end of 3' arm was determined to be:

(SEQ ID NO: 159)
AGCTCTAAGAGAAGGAATACAGCTTGGGACAGAGTTTGTTTTGAAGTGG

GGTTCAGGTGCATTTCCTGGGTGTGTCCCTCATTTGGGGGTGTTAGGAG

GCAGACAATGCTAAGGGCATGGTTTGATATGGTAGACTGACCATCCTGG

GGTCCCTTCAGCTTGTGACACTCGCTGTACTGCTGGACTCTGCTGAGCC

CTTTGAAGCCAGGACTCCTCCTCTGCTGCAGGAGTGCAGTGTCCTTCTT

GCTGTATGAAGCTGGGACAATGCTCTTTGGCCTTCATACTGGACATCCC

ATTGAGAAGCTTGTCACTCTGTAGAGAATAGACATCGCCCCCTTGTGGT

TGTGAGGCTGCCCAGGACTTACTGCGGGGGGGGGGGGGCATGTTGTCC

AGCATAAGGAGAAGACCCCACTGCATGCTGCTGGGAAAAGGAAAGTA

ACGTTCAGAGTAGTTTCTACTGGCTGCCTGCGCTCTCACGCCTGTAAGA

ACAAACGTCCTAATGTCTGCATGTGGAGGAAGGAGCCAGGGGTGCTTAG

GGTGCTGTTGGTCCCACCAATGTACTACTCATCTGGAAGACCTTGTCTT

GGTTTTCTTGCCACTGGGACAAAGTGGGATTGGGTATCAGTCTCCCCAT

-continued

```
GTCGGGCAAATGTACTTGAACAAGCAGCATGGTGGACCAGACATGGGAC

TATTCTCAAAATCTCACAGACACCCCCGGGGGCATGTTACTTCATCTT

TTCTTACCCTGGGCCTCT.
```

The sequence of the 5' probe (SEQ ID NO: 160) is:

```
CTAGGGAGTCAGGAAGTCACACTGGTGAAGAGTGGGGGTGTGGGATGAC

CACACTGAGGAGTCACACTTGAGGAAGGGGGTGGCCACACTGAGGAGT

GTCTGAAAGCATTGAGACTGTACATCTCAGGTTATCAGGGCTTCAGAGA

AAACAGACAGGGAGAAGAGACAAGAACTGGATTCTGTGCGCAAAGGGGG

AAAAGCAAGCAGATGTGAAGGGTGTGCTGTTAGAGTTTATCTAAAGATG

TTTCTTTCAGAAATAAAGAGATATAAGCTTTAATTTGGATGAAATAAAT

GTGGTCTAATTTCCCAGAATGTAGAGGAACTCACTAATGTAGCAAGATT

GGCCTTTCAAAGCAGACCAAAGACATTGAGAATTAAGATAGCTATGATG

GCGTGCTTCCTTAGGTGGAAGTCCTATATGGAATCCCATACTCCCCAAA

TGTGACTGGTCG.
```

The sequence of the 3' probe (SEQ ID NO: 161) is:

```
AGGCAGGAGGGTCAGGAGTTCAAGGCCAGCCTAGTATACATGCAACAGT

GTCTCAAAAATCAAAACAGAGAGGAGGGCAGGAAAGGAGAAGGGAGCCA

GGGAGAGAAGGGAAGAGGAAGGGAGGGAGGGGGAAATGGAGGGAGGGGG

AGATGGAGGGAGGGGGAGATGGAGGGAGGGGGAGATGGAGGGAGGGGGA

GATGGAGGGAGGGGGAGATGGAGGGAGGGGGATGGGAAAGAGGGTTTAC

AGCCCTGGTTTATCTTGAACAGAATCCTTACTTTGTCCCTCAGAGTGAC

AGGACTGAAAAGATTGTCCCAGGATTTTGGCTGCAAAGCAAGGTCCACT

CAGAGACCACAGAGCTCG.
```

Example 6

Production of Recombinant IDO2 Using Baculovirus Expression Vectors

Figure 23A:
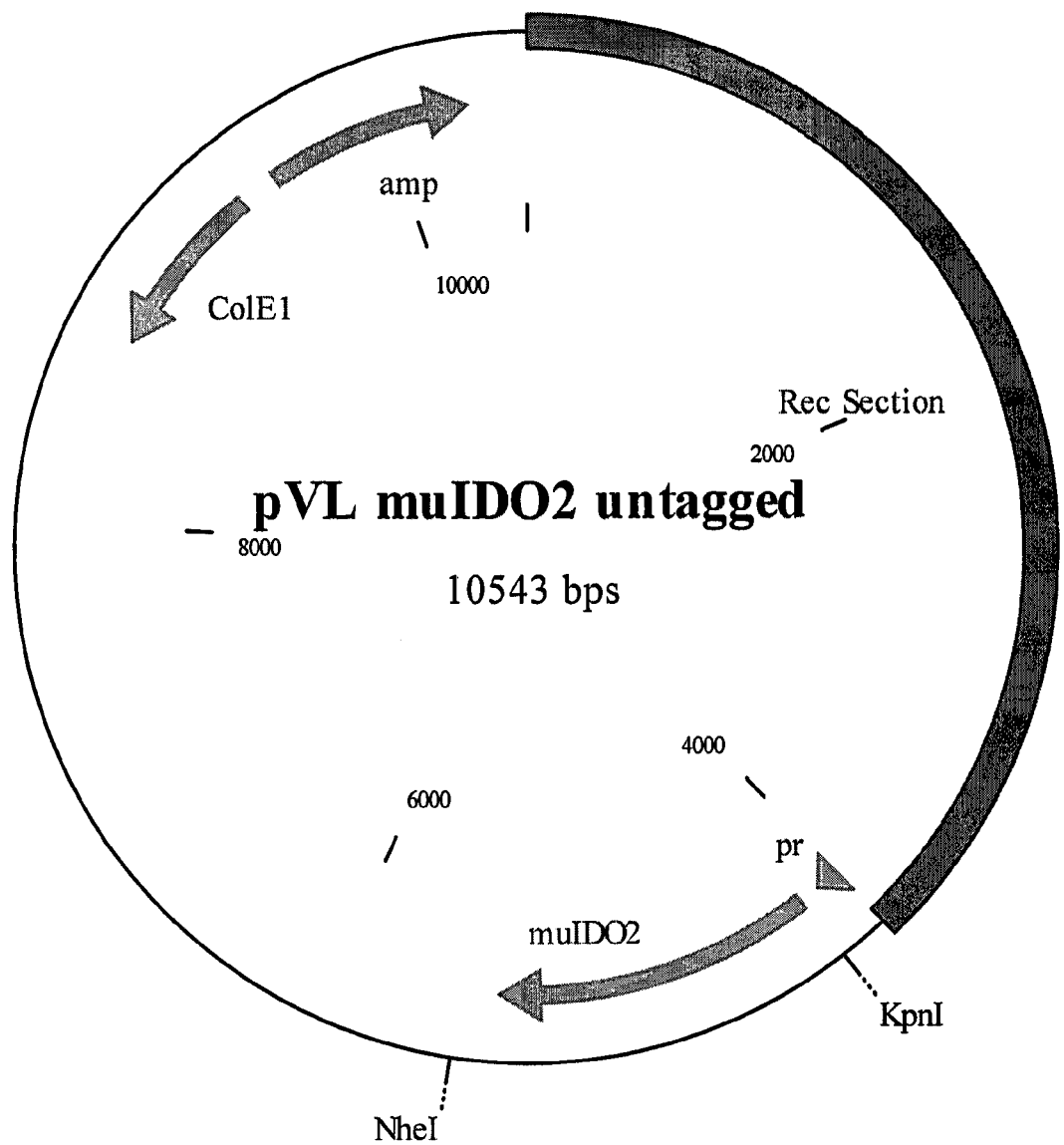
FIG. 23A is a schematic of vector pVLmuIDO2.
Figure 24A:
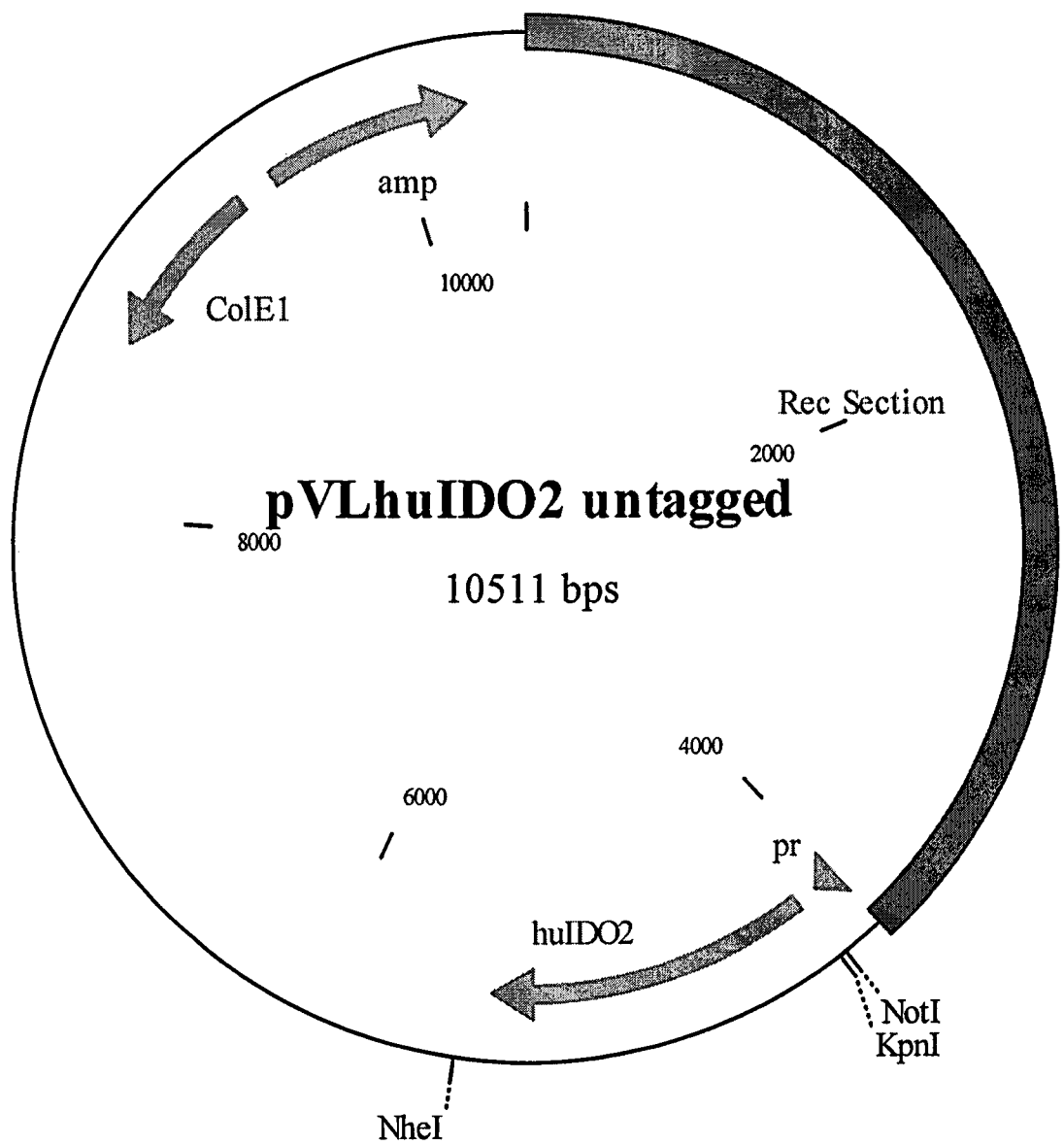
FIG. 24A is a schematic of vector pVLhuIDO2.

The recombinant transfer vectors (pVLmuIDO2, pVLhuIDO2; FIGS. 23 and 24, respectively) containing the complete coding regions of murine and human IDO2, respectively, were derived from eukaryotic expression vectors, pcDNAmuIDO2 and pcDNAhuIDO2. The KpnI/NheI insert fragments containing the complete ORF of pcDNAmuIDO2 and huIDO2 were cloned into KpnI/NheI digested pVL1392 recombination vector that was modified to contain KpnI, XbaI, NheI, SpeI multiple cloning sites at the original KpnI site (See FIGS. 23 and 24). The resulting vectors were analyzed by gel electrophoresis to verify the size and integrity of the inserted genes and inserted coding regions were also analyzed by standard diodeoxynucleotide automated sequencing (Macrogen, Inc., Rockville, Md.).

Approximately 2 µg of each purified recombination transfer vector, pVLmuIDO2 and pVLhuIDO2, was mixed with 0.5 µg of Baculogold linearized baculovirus DNA (Pharmingen, BD Biosciences, Franklin Lakes, N.J.) and added to 6 µL of Cell fectin (Invitrogen, Carlsbad, Calif.) in a total volume of 200 µL sf900II serum free medium (sf900II-SFM). The solution was incubated at room temperature for 30 minutes, supplemented with 800 µL of sf900II SFM (Gibco-BRL, Carlsbad, Calif.), mixed and added to 1×10$^6$ cells of the Spodoptera frugiperda cell line, Sf9, in a 6 well plate. Cells were incubated at 28° C. for 4 hours after which the media was replaced with 2 mL sf900II-SFM 5% FCS. Supernatants containing the recombinant baculovirus (recBV) were harvested after six days and stored at 4° C. indefinitely.

"High Five" cells (Invitrogen) were plated at 1×10$^5$ per well (24 well dish) in 0.5 mL "Express Five" medium (Invitrogen) and incubated at 28° C. for 24 hours. Media was replaced with 0.5 mL of media containing varying dilutions of recBVs containing the muIDO2 and huIDO2 ORFs. Typically 3, 10, 30 and 100 µL of a 1/100 dilution of the recBV viral stock were used. After 24 hours the cells were microscopically examined for signs of infection such as cell rounding, detachment and failure to divide. Optimal titers are established when 100% of the cells show signs of infection.

After 48 hours the media was removed and the cells collected and lysed in 400 µL of RIPA buffer, clarified by centrifugations and supplemented with Laemmli SDS PAGE running buffer. Briefly the lysates were heated to 80° C. for 10 minutes and 4 µL of material was subjected to SDS polyacrylamide gel electrophoresis (10% SDS-PAGE, Invitrogen) and either Coomassie blue stained or transferred to nitrocellulose membrane for Western analysis. For Western analysis, SDS-PAGE gel blots were typically blocked 1 hour at room temperature in PBS/0.1% Tween 20 and 3% nonfat dry milk, incubated with primary and secondary antibodies. Typically membranes are incubated for 1 hour at room temperature in blocking buffer, and then incubated with affinity purified rabbit anti-IDO2 antibody diluted at 1:5000 in blocking buffer. Membranes were washed at room temperature 3-5 times for 10 minutes each in washing buffer (PBS, 0.1% tween), after which the membrane was incubated with HRP-conjugated goat-anti-rabbit antibody (Santa Cruz) in blocking buffer for 1 hour at room temperature, followed by five 10 minutes washes in washing buffer. The membrane was prepared for exposure to X-ray film using a chemiluminescence method with SuperSignal® West Pico chemiluminescent substrate (Pierce cat. no. 34078, Rockford, Ill.). The highest dilution that gave the maximum amount of protein productions was used.

High five cells grown in Express Five-SFM media were plated at 2×10$^7$ cells per T175 flask in 30 mL of media. After four hours the media was removed and recBV was added at 5-10 infectious units per cell in 6 mL of media. The flask was rocked every 10-15 minutes to ensure infection of every cell over the period of 1 hour, after which an additional 15 mL of media was added. After 24 hours the media in each flask was supplemented with tryptophan (final 100 µM) and hemin (5 µM final). After 64 hours, the infected cells were dislodged by the addition of glass beads. The cell suspension was separated from the glass beads by pipetting and pelleted by centrifugation (3,000 rpm 5 minutes). The cell pellet was either frozen or processed immediately.

The cell pellet, containing approximately 1.8×10$^8$ cells, was resuspended in 40 mL 50 mM tris pH 8.8 and sonicated, 4×10 second pulses, on ice. The suspension was adjusted to 50 mM NaCl, 1% octylglucoside, vortexed, and clarified by centrifugation, 20 minutes at 13,000 rpm, at 4° C. The supernatant was passed over a DEAE-Sephacel column equilibrated in Tris pH 8.8, 50 mM NaCl, 1 mM EDTA (EQ buffer). The column was washed with 10 column volumes of equilibration buffer. The IDO2 proteins were eluted with 50 mM Tris pH 8.8, 0.5 M NaCl, 1 mM EDTA.

The eluted fractions were subjected to SDS-PAGE analysis followed by staining with Coomassie brilliant blue R-250. Peak IDO2 containing fractions were combined and dialyzed against EQ buffer. The dialysate was applied to a Mono Q column using the AKTAPurifier 100 fast protein liquid chromatography (FPLC) system. The column was equilibrated in EQ buffer and eluted using a linear gradient of EQ buffer with increasing NaCl 50 mM to 1 M. Elution profile was established by dual spectroscopic measurements at 280 nm and 403 nm and SDS PAGE followed by staining with Coomassie brilliant blue R-250 and/or Western analysis. The 404/280 absorbance ratio was approximately 1.8-2.0. Peak IDO2 eluates were contained in the 400-500 mM NaCl fractions. An additional peak containing IDO2 was also observed eluting at 250 nM NaCl which may contain mostly dimeric forms of the muIDO2 protein. Indeed, the early eluting peak contained IDO2 dimers as determined by a non-heat denatured sample analyzed by SDS-PAGE, whereby an 120 kDa band can be seen in samples not reduced or heated, while upon heating the larger bands resolves into a single major protein band at ~55 kDa. Both mIDO2 containing peaks were pooled and concentrated approximated 5 fold by centrifugal filtration (Amicon Ultra-4, Billerica, Mass.).

The concentrated material was applied to a gel filtration column, Superdex™ 200 (GE Healthcare, Piscataway, N.J.), equilibrated in EQ buffer. Fractions were collected and analyzed by SDS-PAGE/Coomassie staining and confirmed by Western analysis. IDO2 containing fractions were pooled and concentrated to approximately 2 μg/μL by centrifugal filtration (Amicon Ultra-4). The purified protein material exhibited 404-280 nM ratios of 1.5 to 1.8.

Figure 25A:
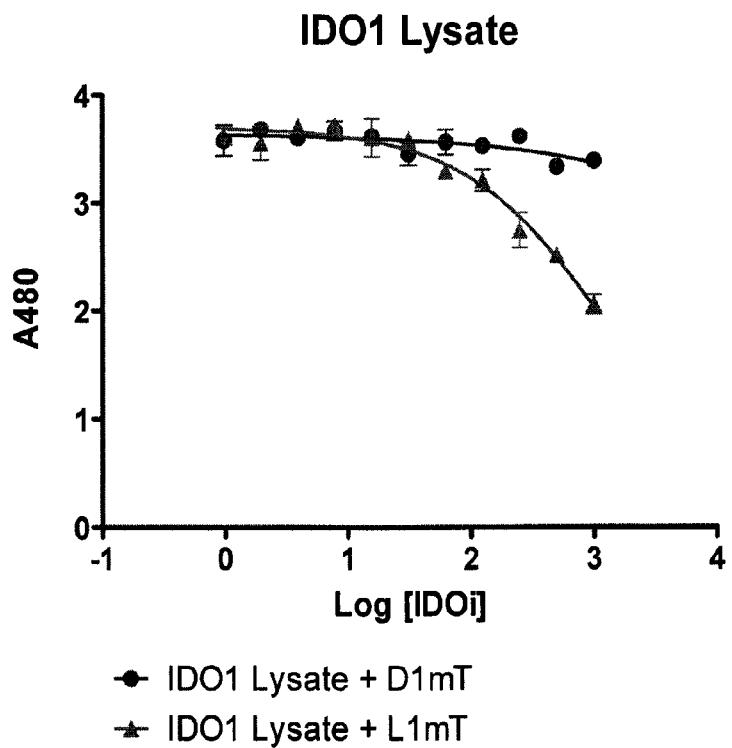
FIGS. 25A and 25B are graphs of the inhibition studies of varying amounts of D-1-methyl-tryptophan and L-1-methyl-tryptophan on IDO1 and IDO2 whole cell lysates, respectively.
Figure 25B:
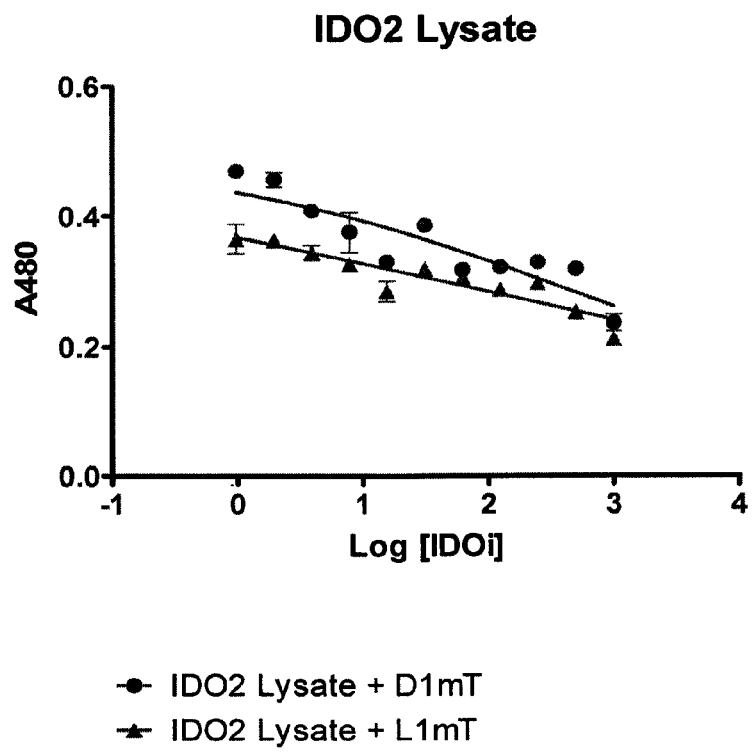

IDO2 activity was measured as the amount of kynurenine formed from L-tryptophan. The standard assay conditions consisted of a mixture containing 50 mM Pipes pH 6.5, between 50 and 600 nM of rmuIDO2 or rhuIDO2 (where 100 nM of rIDO2 is approximately 5.5 μg protein per mL reaction), 200 U catalase (0.2 mg/mL, sp act. ~1000 U/mg), 200 μM L-tryptophan, 10 μM methylene blue and 20 mM ascorbic acid. The mixture was incubated at various times ranging from 15 minutes to 4 hours at 37° C. before the reaction was stopped by adding trichloroacetic acid (TCA) to 3% final. The samples were then heated to 50-60° C. for 30 minutes to convert N-formyl-kynureneine to kynurenine, clarified by centrifugation, and supernatants (100 μL) were removed to a new dish, mixed with 100 μL Ehrlich's reagent (2% p-dimethylaminobenzaldehyde w/v in glacial acetic acid), and incubated 10-30 minutes at room temperature. Absorbance at 490 nm was determined on a plate reader and the data collected and analyzed using Excel software (Microsoft). Typically, samples were analyzed in triplicate and control values were typically averaged and subtracted from sample values. Enzyme activity was estimated based on the conversion of tryptophan to kynurenine using linear regression analysis based on an absorbance standard curve derived from assay measurements on known amounts of kynurenine. Inhibitions studies were performed whereby varying amounts (0-100 μM) of D or L stereoisomers of 1-methyl tryptophan (D-1MT or L-1MT) or MTH-trp and demonstrate that the purified recIDO2 proteins are inhibited by D-1MT (FIG. 25).

Example 7

Polyclonal rabbit anti-murine and anti-human IDO2 was prepared. Antisera were raised against a mixture of murine and human GST-IDO2 fusion protein. Antisera were screened for reactivity against the immunizing antigen by ELISA and western, and samples with high titer were purified by affinity chromatography. Specifically, antiserum was pre-absorbed to protein column containing GST. Since IDO2 and IDO1 possess conserved amino acid domains, the GST-unbound serum was passed over an IDO1-His-tagged peptide column. The unbound material was then affinity purified on an antigen specific peptide column containing human and mouse His-tagged IDO2. The resulting antibody was analyzed and determined to be IDO2 specific with no cross-reactivity with IDO1.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited in the foregoing specification in order to more fully describe the state of the art to which this invention pertains. The disclosure of each of these citations is incorporated by reference herein.

What is claimed is:

1. An isolated antibody immunologically specific for an indoleamine 2,3-dioxygenase-2 (IDO2) protein, wherein the amino acid sequence of said IDO2 is SEQ ID NO: 1,
wherein said antibody is immunologically specific for IDO2 to the exclusion of indoleamine 2,3-dioxygenase-1 (IDO1).

2. The antibody of claim 1, wherein said antibody is selected from the group consisting of a polyclonal antibody, a monoclonal antibody, chimeric antibody, single variable domain, bispecific antibody, Fab, Fab', F(ab')$_2$, F(v), scFv, scFv$_2$, and scFv-Fc.

3. The antibody of claim 2, wherein said antibody is a monoclonal antibody.

* * * * *

UNITED STATES PATENT AND TRADEMARK OFFICE
CERTIFICATE OF CORRECTION

| | | |
|---|---|---|
| PATENT NO. | : 8,436,151 B2 | |
| APPLICATION NO. | : 13/289597 | |
| DATED | : May 7, 2013 | |
| INVENTOR(S) | : George C. Prendergast et al. | |

It is certified that error appears in the above-identified patent and that said Letters Patent is hereby corrected as shown below:

In the specification,

At column 1, lines 14-17, please delete the paragraph:

"Pursuant to 35 U.S.C. §202(c), it is acknowledged that the U.S. Government has certain rights in the invention described herein, which was made in part with funds from the National Institutes of Health, Grant No. CA109542."

and insert therefor:

--This invention was made with government support under Grant No. CA109542 awarded by the National Institutes of Health. The government has certain rights in the invention.--

Signed and Sealed this
Seventeenth Day of November, 2015

Michelle K. Lee
*Director of the United States Patent and Trademark Office*

SEQUENCE LISTING

```
<160> NUMBER OF SEQ ID NOS: 163

<210> SEQ ID NO 1
<211> LENGTH: 420
<212> TYPE: PRT
<213> ORGANISM: Homo Sapiens

<400> SEQUENCE: 1

Met Leu His Phe His Tyr Tyr Asp Thr Ser Asn Lys Ile Met Glu Pro
  1               5                  10                  15

His Arg Pro Asn Val Lys Thr Ala Val Pro Leu Ser Leu Glu Ser Tyr
             20                  25                  30

His Ile Ser Glu Glu Tyr Gly Phe Leu Leu Pro Asp Ser Leu Lys Glu
         35                  40                  45

Leu Pro Asp His Tyr Arg Pro Trp Met Glu Ile Ala Asn Lys Leu Pro
     50                  55                  60

Gln Leu Ile Asp Ala His Gln Leu Gln Ala His Val Asp Lys Met Pro
```

```
                65                  70                  75                  80
Leu Leu Ser Cys Gln Phe Leu Lys Gly His Arg Glu Gln Arg Leu Ala
                85                  90                  95

His Leu Val Leu Ser Phe Leu Thr Met Gly Tyr Val Trp Gln Glu Gly
            100                 105                 110

Glu Ala Gln Pro Ala Glu Val Leu Pro Arg Asn Leu Ala Leu Pro Phe
        115                 120                 125

Val Glu Val Ser Arg Asn Leu Gly Leu Pro Pro Ile Leu Val His Ser
    130                 135                 140

Asp Leu Val Leu Thr Asn Trp Thr Lys Lys Asp Pro Asp Gly Asn Leu
145                 150                 155                 160

Glu Ile Gly Asn Leu Glu Thr Ile Ile Ser Phe Pro Gly Gly Glu Ser
                165                 170                 175

Leu His Gly Phe Ile Leu Val Thr Ala Leu Val Glu Lys Glu Ala Val
            180                 185                 190

Pro Gly Ile Lys Ala Leu Val Gln Ala Thr Asn Ala Ile Leu Gln Pro
        195                 200                 205

Asn Gln Glu Ala Leu Leu Gln Ala Leu Gln Arg Leu Arg Leu Ser Ile
    210                 215                 220

Gln Asp Ile Thr Lys Thr Leu Gly Gln Met His Asp Tyr Val Asp Pro
225                 230                 235                 240

Asp Ile Phe Tyr Ala Gly Ile Arg Ile Phe Leu Ser Gly Trp Lys Asp
                245                 250                 255

Asn Pro Ala Met Pro Ala Gly Leu Met Tyr Glu Gly Val Ser Gln Glu
            260                 265                 270

Pro Leu Lys Tyr Ser Gly Gly Ser Ala Gln Ser Thr Val Leu His
        275                 280                 285

Ala Phe Asp Glu Phe Leu Gly Ile Arg His Ser Lys Glu Ser Gly Asp
    290                 295                 300

Phe Leu Tyr Arg Met Arg Asp Tyr Met Pro Pro Ser His Lys Ala Phe
305                 310                 315                 320

Ile Glu Asp Ile His Ser Ala Pro Ser Leu Arg Asp Tyr Ile Leu Ser
                325                 330                 335

Ser Gly Gln Asp His Leu Leu Thr Ala Tyr Asn Gln Cys Val Gln Ala
            340                 345                 350

Leu Ala Glu Leu Arg Ser Tyr His Ile Thr Met Val Thr Lys Tyr Leu
        355                 360                 365

Ile Thr Ala Ala Lys Ala Lys His Gly Lys Pro Asn His Leu Pro
    370                 375                 380

Gly Pro Pro Gln Ala Leu Lys Asp Arg Gly Thr Gly Thr Ala Val
385                 390                 395                 400

Met Ser Phe Leu Lys Ser Val Arg Asp Lys Thr Leu Glu Ser Ile Leu
                405                 410                 415

His Pro Arg Gly
            420

<210> SEQ ID NO 2
<211> LENGTH: 405
<212> TYPE: PRT
<213> ORGANISM: Homo Sapiens

<400> SEQUENCE: 2

Met Glu Pro His Arg Pro Asn Val Lys Thr Ala Val Pro Leu Ser Leu
1               5                   10                  15

Glu Ser Tyr His Ile Ser Glu Glu Tyr Gly Phe Leu Leu Pro Asp Ser
```

```
                    20                  25                  30
Leu Lys Glu Leu Pro Asp His Tyr Arg Pro Trp Met Glu Ile Ala Asn
                35                  40                  45
Lys Leu Pro Gln Leu Ile Asp Ala His Gln Leu Gln Ala His Val Asp
 50                  55                  60
Lys Met Pro Leu Leu Ser Cys Gln Phe Leu Lys Gly His Arg Glu Gln
 65                  70                  75                  80
Arg Leu Ala His Leu Val Leu Ser Phe Leu Thr Met Gly Tyr Val Trp
                85                  90                  95
Gln Glu Gly Glu Ala Gln Pro Ala Glu Val Leu Pro Arg Asn Leu Ala
                100                 105                 110
Leu Pro Phe Val Glu Val Ser Arg Asn Leu Gly Leu Pro Pro Ile Leu
                115                 120                 125
Val His Ser Asp Leu Val Leu Thr Asn Trp Thr Lys Lys Asp Pro Asp
                130                 135                 140
Gly Phe Leu Glu Ile Gly Asn Leu Glu Thr Ile Ile Ser Phe Pro Gly
145                 150                 155                 160
Gly Glu Ser Leu His Gly Phe Ile Leu Val Thr Ala Leu Val Glu Lys
                165                 170                 175
Glu Ala Val Pro Gly Ile Lys Ala Leu Val Gln Ala Thr Asn Ala Ile
                180                 185                 190
Leu Gln Pro Asn Gln Glu Ala Leu Gln Ala Leu Gln Arg Leu Arg
                195                 200                 205
Leu Ser Ile Gln Asp Ile Thr Lys Thr Leu Gly Gln Met His Asp Tyr
                210                 215                 220
Val Asp Pro Asp Ile Phe Tyr Ala Gly Ile Arg Ile Phe Leu Ser Gly
225                 230                 235                 240
Trp Lys Asp Asn Pro Ala Met Pro Ala Gly Leu Met Tyr Glu Gly Val
                245                 250                 255
Ser Gln Glu Pro Leu Lys Tyr Ser Gly Gly Ser Ala Ala Gln Ser Thr
                260                 265                 270
Val Leu His Ala Phe Asp Glu Phe Leu Gly Ile Arg His Ser Lys Glu
                275                 280                 285
Ser Gly Asp Phe Leu Tyr Arg Met Arg Asp Tyr Met Pro Pro Ser His
                290                 295                 300
Lys Ala Phe Ile Glu Asp Ile His Ser Ala Pro Ser Leu Arg Asp Tyr
305                 310                 315                 320
Ile Leu Ser Ser Gly Gln Asp His Leu Leu Thr Ala Tyr Asn Gln Cys
                325                 330                 335
Val Gln Ala Leu Ala Glu Leu Arg Ser Tyr His Ile Thr Met Val Thr
                340                 345                 350
Lys Tyr Leu Ile Thr Ala Ala Ala Lys Ala Lys His Gly Lys Pro Asn
                355                 360                 365
His Leu Pro Gly Pro Gln Ala Leu Lys Asp Arg Gly Thr Gly Gly
                370                 375                 380
Thr Ala Val Met Ser Phe Leu Lys Ser Val Arg Asp Lys Thr Leu Glu
385                 390                 395                 400
Ser Ile Leu His Pro
                405

<210> SEQ ID NO 3
<211> LENGTH: 398
<212> TYPE: PRT
<213> ORGANISM: Mus musculus
```

<400> SEQUENCE: 3

Met Thr Leu Glu Val Pro Leu Ser Leu Gly Arg Tyr His Ile Ser Glu
1               5                   10                  15

Glu Tyr Gly Phe Leu Leu Pro Asn Pro Leu Glu Ala Leu Pro Asp His
            20                  25                  30

Tyr Lys Pro Trp Met Glu Ile Ala Leu Arg Leu Pro His Leu Ile Glu
        35                  40                  45

Asn Arg Gln Leu Arg Ala His Val Tyr Arg Met Pro Leu Leu Asp Cys
    50                  55                  60

Arg Phe Leu Lys Ser Tyr Arg Glu Gln Arg Leu Ala His Met Ala Leu
65                  70                  75                  80

Ala Ala Ile Thr Met Gly Phe Val Trp Gln Glu Gly Glu Gly Gln Pro
                85                  90                  95

Gln Lys Val Leu Pro Arg Ser Leu Ala Ile Pro Phe Val Glu Val Ser
            100                 105                 110

Arg Asn Leu Gly Leu Pro Pro Ile Leu Val His Ser Asp Leu Val Leu
        115                 120                 125

Thr Asn Trp Thr Lys Arg Asn Pro Glu Gly Pro Leu Glu Ile Ser Asn
130                 135                 140

Leu Glu Thr Ile Ile Ser Phe Pro Gly Gly Glu Ser Leu Arg Gly Phe
145                 150                 155                 160

Ile Leu Val Thr Val Leu Val Glu Lys Ala Ala Val Pro Gly Leu Lys
                165                 170                 175

Ala Leu Val Gln Gly Met Glu Ala Ile Arg Gln His Ser Gln Asp Thr
            180                 185                 190

Leu Leu Glu Ala Leu Gln Gln Leu Arg Leu Ser Ile Gln Asp Ile Thr
        195                 200                 205

Arg Ala Leu Ala Gln Met His Asp Tyr Val Asp Pro Asp Ile Phe Tyr
210                 215                 220

Ser Val Ile Arg Ile Phe Leu Ser Gly Trp Lys Asp Asn Pro Ala Met
225                 230                 235                 240

Pro Val Gly Leu Val Tyr Glu Gly Ala Ala Thr Glu Pro Leu Lys Tyr
                245                 250                 255

Ser Gly Gly Ser Ala Ala Gln Ser Ser Val Leu His Ala Phe Asp Glu
            260                 265                 270

Phe Leu Gly Ile Glu His Cys Lys Glu Ser Val Gly Phe Leu His Arg
        275                 280                 285

Met Arg Asp Tyr Met Pro Pro Ser His Lys Ala Phe Leu Glu Asp Leu
290                 295                 300

His Val Ala Pro Ser Leu Arg Asp Tyr Ile Leu Ala Ser Gly Pro Gly
305                 310                 315                 320

Asp Cys Leu Met Ala Tyr Asn Gln Cys Val Glu Ala Leu Gly Glu Leu
                325                 330                 335

Arg Ser Tyr His Ile Asn Val Val Ala Arg Tyr Ile Ile Ser Ala Ala
            340                 345                 350

Thr Arg Ala Arg Ser Arg Gly Leu Thr Asn Pro Ser Pro His Ala Leu
        355                 360                 365

Glu Asp Arg Gly Thr Gly Gly Thr Ala Met Leu Ser Phe Leu Lys Ser
370                 375                 380

Val Arg Glu Lys Thr Met Glu Ala Leu Leu Cys Pro Gly Ala
385                 390                 395

<210> SEQ ID NO 4
<211> LENGTH: 403

```
<212> TYPE: PRT
<213> ORGANISM: Mus musculus

<400> SEQUENCE: 4

Met Glu Pro Gln Ser Gln Ser Met Thr Leu Glu Val Pro Leu Ser Leu
 1               5                   10                  15

Gly Arg Tyr His Ile Ser Glu Glu Tyr Gly Phe Leu Leu Pro Asn Pro
             20                  25                  30

Leu Glu Ala Leu Pro Asp His Tyr Lys Pro Trp Met Glu Ile Ala Leu
         35                  40                  45

Arg Leu Pro His Leu Ile Glu Asn Arg Gln Leu Arg Ala His Val Tyr
     50                  55                  60

Arg Met Pro Leu Leu Asp Cys Arg Phe Leu Lys Ser Tyr Arg Glu Gln
 65                  70                  75                  80

Arg Leu Ala His Met Ala Leu Ala Ala Ile Thr Met Gly Phe Val Trp
             85                  90                  95

Gln Glu Gly Glu Gly Gln Pro Gln Lys Val Pro Arg Ser Leu Ala
            100                 105                 110

Ile Pro Phe Val Glu Val Ser Arg Asn Leu Gly Leu Pro Pro Ile Leu
        115                 120                 125

Val His Ser Asp Leu Val Leu Thr Asn Trp Thr Lys Arg Asn Pro Glu
    130                 135                 140

Gly Pro Leu Glu Ile Ser Asn Leu Glu Thr Ile Ile Ser Phe Pro Gly
145                 150                 155                 160

Gly Glu Ser Leu Arg Gly Phe Ile Leu Val Thr Val Leu Val Glu Lys
                165                 170                 175

Ala Ala Val Pro Gly Leu Lys Ala Leu Val Gln Gly Met Glu Ala Ile
            180                 185                 190

Arg Gln His Ser Gln Asp Thr Leu Leu Glu Ala Leu Gln Gln Leu Arg
        195                 200                 205

Leu Ser Ile Gln Asp Ile Thr Arg Ala Leu Ala Gln Met His Asp Tyr
    210                 215                 220

Val Asp Pro Asp Ile Phe Tyr Ser Val Ile Arg Ile Phe Leu Ser Gly
225                 230                 235                 240

Trp Lys Asp Asn Pro Ala Met Pro Val Gly Leu Val Tyr Glu Gly Ala
                245                 250                 255

Ala Thr Glu Pro Leu Lys Tyr Ser Gly Gly Ser Ala Ala Gln Ser Ser
            260                 265                 270

Val Leu His Ala Phe Asp Glu Phe Leu Gly Ile Glu Cys Lys Glu
        275                 280                 285

Ser Val Gly Phe Leu His Arg Met Arg Asp Tyr Met Pro Pro Ser His
    290                 295                 300

Lys Ala Phe Leu Glu Asp Leu His Val Ala Pro Ser Leu Arg Asp Tyr
305                 310                 315                 320

Ile Leu Ala Ser Gly Pro Gly Asp Cys Leu Met Ala Tyr Asn Gln Cys
                325                 330                 335

Val Glu Ala Leu Gly Glu Leu Arg Ser Tyr His Ile Asn Val Val Ala
            340                 345                 350

Arg Tyr Ile Ile Ser Ala Ala Thr Arg Ala Arg Ser Arg Gly Leu Thr
        355                 360                 365

Asn Pro Ser Pro His Ala Leu Glu Asp Arg Gly Thr Gly Gly Thr Ala
    370                 375                 380

Met Leu Ser Phe Leu Lys Ser Val Arg Glu Lys Thr Met Glu Ala Leu
385                 390                 395                 400
```

Leu Cys Pro

```
<210> SEQ ID NO 5
<211> LENGTH: 403
<212> TYPE: PRT
<213> ORGANISM: Homo Sapiens

<400> SEQUENCE: 5
```

| | | | | | | | | | | | | | | | |
|---|---|---|---|---|---|---|---|---|---|---|---|---|---|---|---|
| Met | Ala | His | Ala | Met | Glu | Asn | Ser | Trp | Thr | Ile | Ser | Lys | Glu | Tyr | His |
| 1 | | | | 5 | | | | | 10 | | | | | 15 | |
| Ile | Asp | Glu | Glu | Val | Gly | Phe | Ala | Leu | Pro | Asn | Pro | Gln | Glu | Asn | Leu |
| | | | 20 | | | | | 25 | | | | | 30 | | |
| Pro | Asp | Phe | Tyr | Asn | Asp | Trp | Met | Phe | Ile | Ala | Lys | His | Leu | Pro | Asp |
| | | | 35 | | | | | 40 | | | | | 45 | | |
| Leu | Ile | Glu | Ser | Gly | Gln | Leu | Arg | Glu | Arg | Val | Glu | Lys | Leu | Asn | Met |
| 50 | | | | | 55 | | | | | 60 | | | | | |
| Leu | Ser | Ile | Asp | His | Leu | Thr | Asp | His | Lys | Ser | Gln | Arg | Leu | Ala | Arg |
| 65 | | | | | 70 | | | | | 75 | | | | | 80 |
| Leu | Val | Leu | Gly | Cys | Ile | Thr | Met | Ala | Tyr | Val | Trp | Gly | Lys | Gly | His |
| | | | | 85 | | | | | 90 | | | | | 95 | |
| Gly | Asp | Val | Arg | Lys | Val | Leu | Pro | Arg | Asn | Ile | Ala | Val | Pro | Tyr | Cys |
| | | | 100 | | | | | 105 | | | | | 110 | | |
| Gln | Leu | Ser | Lys | Lys | Leu | Glu | Leu | Pro | Pro | Ile | Leu | Val | Tyr | Ala | Asp |
| | | | | 115 | | | | | 120 | | | | | 125 | |
| Cys | Val | Leu | Ala | Asn | Trp | Lys | Lys | Lys | Asp | Pro | Asn | Lys | Pro | Leu | Thr |
| 130 | | | | | 135 | | | | | 140 | | | | | |
| Tyr | Glu | Asn | Met | Asp | Val | Leu | Phe | Ser | Phe | Arg | Asp | Gly | Asp | Cys | Ser |
| 145 | | | | | 150 | | | | | 155 | | | | | 160 |
| Lys | Gly | Phe | Phe | Leu | Val | Ser | Leu | Leu | Val | Glu | Ile | Ala | Ala | Ala | Ser |
| | | | | 165 | | | | | 170 | | | | | 175 | |
| Ala | Ile | Lys | Val | Ile | Pro | Thr | Val | Phe | Lys | Ala | Met | Gln | Met | Gln | Glu |
| | | | 180 | | | | | 185 | | | | | 190 | | |
| Arg | Asp | Thr | Leu | Leu | Lys | Ala | Leu | Leu | Glu | Ile | Ala | Ser | Cys | Leu | Glu |
| | | | | 195 | | | | | 200 | | | | | 205 | |
| Lys | Ala | Leu | Gln | Val | Phe | His | Gln | Ile | His | Asp | His | Val | Asn | Pro | Lys |
| 210 | | | | | 215 | | | | | 220 | | | | | |
| Ala | Phe | Phe | Ser | Val | Leu | Arg | Ile | Tyr | Leu | Ser | Gly | Trp | Lys | Gly | Asn |
| 225 | | | | | 230 | | | | | 235 | | | | | 240 |
| Pro | Gln | Leu | Ser | Asp | Gly | Leu | Val | Tyr | Glu | Gly | Phe | Trp | Glu | Asp | Pro |
| | | | | 245 | | | | | 250 | | | | | 255 | |
| Lys | Glu | Phe | Ala | Gly | Gly | Ser | Ala | Gly | Gln | Ser | Ser | Val | Phe | Gln | Cys |
| | | | 260 | | | | | 265 | | | | | 270 | | |
| Phe | Asp | Val | Leu | Leu | Gly | Ile | Gln | Gln | Thr | Ala | Gly | Gly | Gly | His | Ala |
| | | | | 275 | | | | | 280 | | | | | 285 | |
| Ala | Gln | Phe | Leu | Gln | Asp | Met | Arg | Arg | Tyr | Met | Pro | Pro | Ala | His | Arg |
| 290 | | | | | 295 | | | | | 300 | | | | | |
| Asn | Phe | Leu | Cys | Ser | Leu | Glu | Ser | Asn | Pro | Ser | Val | Arg | Glu | Phe | Val |
| 305 | | | | | 310 | | | | | 315 | | | | | 320 |
| Leu | Ser | Lys | Gly | Asp | Ala | Gly | Leu | Arg | Glu | Ala | Tyr | Asp | Ala | Cys | Val |
| | | | | 325 | | | | | 330 | | | | | 335 | |
| Lys | Ala | Leu | Val | Ser | Leu | Arg | Ser | Tyr | His | Leu | Gln | Ile | Val | Thr | Lys |
| | | | 340 | | | | | 345 | | | | | 350 | | |
| Tyr | Ile | Leu | Ile | Pro | Ala | Ser | Gln | Gln | Pro | Lys | Glu | Asn | Lys | Thr | Ser |
| | | | | 355 | | | | | 360 | | | | | 365 | |
| Glu | Asp | Pro | Ser | Lys | Leu | Glu | Ala | Lys | Gly | Thr | Gly | Gly | Thr | Asp | Leu |

```
                    370                 375                 380
        Met Asn Phe Leu Lys Thr Val Arg Ser Thr Thr Glu Lys Ser Leu Leu
        385                 390                 395                 400

Lys Glu Gly

<210> SEQ ID NO 6
<211> LENGTH: 407
<212> TYPE: PRT
<213> ORGANISM: Mus musculus

<400> SEQUENCE: 6

Met Ala Leu Ser Lys Ile Ser Pro Thr Glu Gly Ser Arg Arg Ile Leu
 1               5                  10                  15

Glu Asp His His Ile Asp Glu Asp Val Gly Phe Ala Leu Pro His Pro
            20                  25                  30

Leu Val Glu Leu Pro Asp Ala Tyr Ser Pro Trp Val Leu Val Ala Arg
        35                  40                  45

Asn Leu Pro Val Leu Ile Glu Asn Gly Gln Leu Arg Glu Glu Val Glu
    50                  55                  60

Lys Leu Pro Thr Leu Ser Thr Asp Gly Leu Arg Gly His Arg Leu Gln
65                  70                  75                  80

Arg Leu Ala His Leu Ala Leu Gly Tyr Ile Thr Met Ala Tyr Val Trp
                85                  90                  95

Asn Arg Gly Asp Asp Asp Val Arg Lys Val Leu Pro Arg Asn Ile Ala
            100                 105                 110

Val Pro Tyr Cys Glu Leu Ser Glu Lys Leu Gly Leu Pro Pro Ile Leu
        115                 120                 125

Ser Tyr Ala Asp Cys Val Leu Ala Asn Trp Lys Lys Lys Asp Pro Asn
    130                 135                 140

Gly Pro Met Thr Tyr Glu Asn Met Asp Ile Leu Phe Ser Phe Pro Gly
145                 150                 155                 160

Gly Asp Cys Asp Lys Gly Phe Phe Leu Val Ser Leu Val Glu Ile
                165                 170                 175

Ala Ala Ser Pro Ala Ile Lys Ala Ile Pro Thr Val Ser Ser Ala Val
            180                 185                 190

Glu Arg Gln Asp Leu Lys Ala Leu Glu Lys Ala Leu His Asp Ile Ala
        195                 200                 205

Thr Ser Leu Glu Lys Ala Lys Glu Ile Phe Lys Arg Met Arg Asp Phe
    210                 215                 220

Val Asp Pro Asp Thr Phe His Val Leu Arg Ile Tyr Leu Ser Gly
225                 230                 235                 240

Trp Lys Cys Ser Ser Lys Leu Pro Glu Gly Leu Leu Tyr Glu Gly Val
                245                 250                 255

Trp Asp Thr Pro Lys Met Phe Ser Gly Gly Ser Ala Gly Gln Ser Ser
            260                 265                 270

Ile Phe Gln Ser Leu Asp Val Leu Leu Gly Ile Lys His Glu Ala Gly
        275                 280                 285

Lys Glu Ser Pro Ala Glu Phe Leu Gln Glu Met Arg Glu Tyr Met Pro
    290                 295                 300

Pro Ala His Arg Asn Phe Leu Phe Leu Glu Ser Ala Pro Pro Val
305                 310                 315                 320

Arg Glu Phe Val Ile Ser Arg His Asn Glu Asp Leu Thr Lys Ala Tyr
                325                 330                 335

Asn Glu Cys Val Asn Gly Leu Val Ser Val Arg Lys Phe His Leu Ala
            340                 345                 350
```

```
Ile Val Asp Thr Tyr Ile Met Lys Pro Ser Lys Lys Pro Thr Asp
        355                 360                 365

Gly Asp Lys Ser Glu Glu Pro Ser Asn Val Glu Ser Arg Gly Thr Gly
    370                 375                 380

Gly Thr Asn Pro Met Thr Phe Leu Arg Ser Val Lys Asp Thr Thr Glu
385                 390                 395                 400

Lys Ala Leu Leu Ser Trp Pro
                405

<210> SEQ ID NO 7
<211> LENGTH: 1224
<212> TYPE: DNA
<213> ORGANISM: Mus musculus

<400> SEQUENCE: 7
atggcactca gtaaaatatc tcctacagaa ggttctagaa ggatccttga agaccaccac      60
atagatgaag atgtgggctt tgctctacca catccactgg tggagctgcc cgacgcatac     120
agcccctggg tccttgtggc tagaaatctg cctgtgctga ttgagaacgg cagcttcga     180 gaagaagttg aaaagctgcc cacactgagc acggacggac tgagaggaca caggttacag    240
cgcctggcac acctggccct ggggtacatc accatggcgt atgtgtggaa ccgaggggat    300
gacgatgttc gaaaggtgct gccccgcaat attgctgttc cctactgcga gctctcagag    360
aagttgggcc tgcctcctat tctgtcttat gcagactgtg tcctggcaaa ctggaagaaa    420
aaggacccca tgggcccat gacatacgag aacatggaca ttctgttctc atttcctggt     480
ggggactgcg acaagggctt cttcctcgtc tctctattgg tggaaatcgc agcttctcct    540
gcaatcaaag caatccccac tgtatccagt gcagtagagc gtcaagacct gaaagcattg    600
gaaaaggcac tgcacgacat agctaccagt ctggagaaag ccaaggaaat ttttaagagg    660
atgcgtgact tgtgtgaccc agacacgttt tccacgttc tccgcatata tctgtctggc     720
tggaaatgca gctccaagct gccagaaggt ctgctgtatg agggggtctg gacacccca    780 aaaatgtttt caggggggcag tgcaggccag agcagcatct tccagagtct tgatgtcctt    840
ctgggaataa aacacgaggc tggcaaagaa tctcctgcag aattcctcca ggaaatgaga    900
gagtacatgc ctccagccca ccggaacttc ctttctcttct tagagtcagc ccccagtc    960 cgtgagtttg tcatttcaag acacaatgaa gacttgacga agcttataa cgagtgtgtg   1020 aatggtctgg tctctgtgag aaagttccac ctcgcaatag tagatactta cattatgaaa   1080
ccttcgaaga agaagcccac tgatggcgac aagtcggaag agccctcaaa tgtggaaagc   1140
agagggactg ggggtacgaa tcccatgact ttcctaagga gtgtgaaaga tacaaccgag   1200
aaagctcttc tgagttggcc ttag                                          1224

<210> SEQ ID NO 8
<211> LENGTH: 2279
<212> TYPE: DNA
<213> ORGANISM: Homo Sapiens

<400> SEQUENCE: 8
agtccagatg atagttaaga aagcagtaag aatacagaga gtccacaatg agatgaaaat      60
gcactgccag ttgaaacatc ctcctacact ggagctttat aaatatttta agacaaggaa     120
ttggattaga tttgacatta gaaatgtacc ataatacaga aggcaatgga cacctaaaga     180
acagaatgaa aaccttctta ggaaatgaag cttgacactt cacccaccag gccaccacaa    240
gaatgttgca tttcattat tatgatactt caaacaaaat aatggagccc cacagaccga    300
```

```
atgtgaagac agcagtgcca ttgtctttgg aaagctatca catatctgaa gagtatggct    360
ttcttcttcc agattctctg aaagaacttc cagatcatta taggccttgg atggaaattg    420
ccaacaaact tcctcaattg attgatgctc accagcttca agctcatgtg acaagatgc     480 ccctgctgag ctgccagttc ctgaagggtc accgggagca gcgcctggcc cacctggtcc    540
tgagcttcct caccatgggt tatgtctggc aggaaggaga ggcgcagcct gcagaggtcc    600
tgccaaggaa tcttgccctt ccatttgtcg aagtctccag gaacttgggg ctccctccta    660
tcctggtcca ctcagacttg gtgctgacga actggaccaa aaaagatcca gacgggaacc    720
tggagaccat catctcattt cctggggag agagcctgca tggttttata ctggtgactg     780 cttttggtaga gaaagaagca gtgcctggga taaaggctct tgttcaggcc acgaatgcta    840
tcttgcagcc caaccaggag gccctgctcc aagccctgca gcgactgaga ctgtctattc    900
aggacatcac caaaacctta ggacagatgc atgattatgt agatccagac atattttatg    960
caggcatccg gatctttctc tctggatgga agacaaccc agcaatgcct gcagggctga    1020
tgtatgaagg agtttcccaa gagcccctga atactccgg cgggagtgca gctcagagca    1080
cagtgcttca tgcctttgat gagttcttag cattcgtca tagcaaggaa agtggtgact    1140
ttctgtacag aatgagggat tacatgcctc cttcccataa ggccttcata gaagacatcc    1200
actcagcacc ttccctgagg gactacatcc tgtcatctgg acaggaccac ttgctgacag    1260
cttataacca gtgtgtgcag gccctggcag agctgcggag ctatcacatc accatggtca    1320 ccaaataccсt catcacagct gcagccaagg caaagcatgg gaagccaaac catctccag    1380 ggcctcctca ggctttaaaa gacaggggca caggtggaac cgcagttatg agctttctta    1440
agagtgtcag ggataagacc ttggagtcaa tccttcaccc acgtggttga gaggctgccc    1500 tctcccagc aatgcagagc ccccatggag ggcaggtggg cctggagaat gagggtcagg    1560
gttctgcctg ggatcatcca ggaaggatct cagccctatt catgtttctg ctctacagag    1620
cactatattc tccttgttga gagctgttgg cttcacaaag gagagttgat gtggccaagc    1680 cttttccctcc ctacctgatc actgcttaac ggcatgtata atggatactt cctcatgcag    1740 aaccccaga ggagtgactg tatgccattc tctttgccaa gtaatagaaa accaatctaa    1800
atgtcaaaaa tcagataaaa ttgcctgggg atacattact tgttgatttt cttaaaaaac    1860
aaattcactt aacaattcat taagttcata ctgagcactg cctccaagat taaaaccagg    1920
atttctgtgg tcccagacca gccctcttct ccctgaatgt gttgagttgg tgcaggagg    1980 ttggaaatgc tccagtggag atgggaagat agaggatgct gacaataagg acttggaagt    2040
cactagtgtg aaaatgagca gttaatgata tgggaacgga tgagactttc cacgtggtac    2100
ctagatttgc aaattctatt gtaatgcctt tatttttaga agaattattc tctcttctta    2160
ctctgaaaat ctgtatttgt aaaatgaatg aatggatcct atataagtaa ataagaaaac    2220
tgggaataag tagtaaatca atgtgtttag tgtgcaaata aatgtaaatg ctttattg      2279
```

<210> SEQ ID NO 9
<211> LENGTH: 1245
<212> TYPE: DNA
<213> ORGANISM: Homo Sapiens

<400> SEQUENCE: 9

```
atgttgcatt tcattatta tgatacttca aacaaaataa tggagcccca cagaccgaat     60
gtgaagacag cagtgccatt gtctttggaa agctatcaca tatctgaaga gtatggcttt    120
cttcttccag attctctgaa agaacttcca gatcattata ggccttggat ggaaattgcc    180
```

```
aacaaacttc ctcaattgat tgatgctcac cagcttcaag ctcatgtgga caagatgccc      240
ctgctgagct gccagttcct gaagggtcac cgggagcagc gcctggccca cctggtcctg      300
agcttcctca ccatgggtta tgtctggcag gaaggagagg cgcagcctgc agaggtcctg      360
ccaaggaatc ttgcccttcc atttgtcgaa gtctccagga acttggggct ccctcctatc      420 ctggtcccact cagacttggt gctgacgaac tggaccaaaa agatccaga cgggaacctg      480 gagaccatca tctcatttcc tgggggagag agcctgcatg gttttatact ggtgactgct      540
ttggtagaga agaagcagt gcctgggata aaggctcttg ttcaggccac gaatgctatc      600
ttgcagccca accaggaggc cctgctccaa gccctgcagc gactgagact gtctattcag      660
gacatcacca aaaccttagg acagatgcat gattatgtag atccagacat attttatgca      720
ggcatccgga tctttctctc tggatggaaa gacaacccag caatgcctgc agggctgatg      780
tatgaaggag tttcccaaga gcccctgaaa tactccggcg ggagtgcagc tcagagcaca      840
gtgcttcatg cctttgatga gttcttaggc attcgtcata gcaaggaaag tggtgacttt      900
ctgtacagaa tgagggatta catgcctcct tcccataagg ccttcataga agacatccac      960
tcagcacctt ccctgaggga ctacatcctg tcatctggac aggaccactt gctgacagct     1020
tataaccagt gtgtgcaggc cctggcagag ctgcggagct atcacatcac catggtcacc     1080
aaatacctca tcacagctgc agccaaggca aagcatggga agccaaacca tctcccaggg     1140
cctcctcagg cttttaaaga cagggggcaca ggtggaaccg cagttatgag ctttcttaag     1200
agtgtcaggg ataagacctt ggagtcaatc cttcacccac gtggt                     1245

<210> SEQ ID NO 10
<211> LENGTH: 2464
<212> TYPE: DNA
<213> ORGANISM: Mus musculus

<400> SEQUENCE: 10
cgcacaagta caaccacaca gaagacacag ctggaaagct ccctggcctg ggcattcctc       60
tggggcagag acctcacgcg aaaatatgga gcctcaaagt cagagcatga cgctggaggt      120
gccgttgtcc ttggggagat accacatttc tgaggaatat ggctttctcc ttccaaatcc      180
tctggaagca cttccagatc attacaagcc ttggatggaa attgccctca gacttcctca      240
cttaatcgag aaccgccagc tccgagctca cgtgtacagg atgcctctcc tggactgcag      300
attcctaaag agttaccgtg agcagcgcct ggcacacatg gcgctggccg ctatcaccat      360
gggattcgtc tggcaggagg gggaaggcca accccaaaag gtgctgccaa gatctcttgc      420
cattcctttt gttgaggtat ccaggaactt gggactcccg cctatcctgg tccactctga      480
cctggtgctg acaaactgga ccaaaaggaa cccagaagga ccgttggaaa tcagtaacct      540
ggaaaccatc atctcatttc cggggggaga gagcctgcgg ggcttcatcc tagtgacagt      600
cttggtggag aaggcagcag tgcccggcct taaggccctg gttcagggaa tggaggccat      660
tcggcaacac agtcaggaca ccctgctaga gccctgcag cagctgagac tctccatcca      720
ggatatcacc agagccttgg cccaaatgca tgattatgtg gacccagaca tattttactc      780
ggtcatccgg atcttcctct ctgggtggaa ggacaatcca gccatgcctg tggggctggt      840
ctatgaaggt gctgccacag agcctctgaa gtactctgga ggaagtgcag cccagagctc      900
cgtgcttcat gccttcgatg agttcctggg cattgagcat tgcaaggaaa gtgttggctt      960
tctacacaga atgagggact acatgccgcc ttcccataag gctttcctgg aagatctcca     1020
cgtagctcct tctctgagag actacatact ggcctctggt cctggggact gcctgatggc     1080
```

```
ctataaccag tgtgtggagg ccctgggaga gctgcgcagt taccacatca atgtcgtggc    1140
cagatacatt atctccgctg ccaccagggc caggagcagg gggctaacta atccctcacc    1200
ccatgccttg gaagacaggg gcactggggg tactgccatg ctgagcttct tgaagagtgt    1260
cagggagaag accatggagg ccctcctgtg tcctggtgct tagcagtcat gtcctgcacc    1320
ctaacactta gatgttctca tcctgcatcc cagcgttaga ggttcacatc ctgcatccta    1380
gtgcttagct gttcttgtgc tatatcccag cgcttagcag tcatgtcctg catcctagtg    1440
cttagcattt tatatccagc attttagtgc ttagagattc acatcctgca tcctagagct    1500
tagcatttta tatccagcat ccttgtgcgt atcagctatg ttttgtatcc tgcttagcag    1560
ttaacatcct gcatcctagt acttatctgt tctcatcctg catcctagag cttagcagtc    1620
aggtcccgtg ggagcaagaa ccagggtctg agctctgtct gagcccaagc atggctttac    1680
tgctttgtta attgtggctc ccacctccac cccacccag ccagtttgct tgctagaagc    1740 cttttctgcac tgcctaatcc ccctgcctca cagcagagag ctgcagccat gacctcctca    1800
ttcagtatta ggtggacaag tcggagatac ccaaactcaa ttttaaaaga atcaagttgc    1860
ttttggggca tgttacttca tctttttctta ccctgggcct cttcccttct tccctacctc    1920
cctcgtccct tagtctttca ccctctctc tttctcctt tgtcaccctc cccctcccct    1980
gcttactctc ttttcccttc cccctctcc tcatccctcc ttcctttctt ccttcccttt    2040
ttgtctgtga agcaccaggt ctgatgggcc tcaaactgtg atcttcctgt ctcacccttc    2100
aaaggttatg tgtatgtgac gtgtgtgtgt gtgtgtgtgt gtgtgtgtgt gtgtgtgttc    2160
gtttcttttg ttttttccta gtggagatga cacccaaaga tttgcacata ccaggcaatt    2220
gctccaccac ctgactacag tcccagctct ctgtattcct gaaggaaagt cttgatgagt    2280
tgcctaggct ggtattgagc tctttagccc aggcaggcct tagtctgagt agctgggatg    2340
tacagggatg agccactgag ccatgctgct gctgctaacg atgatgacga tgatgatgat    2400
gaagattatg ataactacag tcactgcaat aatgacggca agataatga aaaaaaaaa    2460 aaaa                                                                2464

<210> SEQ ID NO 11
<211> LENGTH: 1194
<212> TYPE: DNA
<213> ORGANISM: Mus musculus

<400> SEQUENCE: 11
atgacgctgg aggtgccgtt gtccttgggg agataccaca tttctgagga atatggcttt      60
ctccttccaa atcctctgga agcacttcca gatcattaca agccttggat ggaaattgcc     120
ctcagacttc ctcacttaat cgagaaccgc cagctccgag ctcacgtgta caggatgcct     180
ctcctggact gcagattcct aaagagttac cgtgagcagc gcctggcaca catggcgctg     240
gccgctatca ccatgggatt cgtctggcag gagggggaag ccaaccccca aaaggtgctg     300
ccaagatctc ttgccattcc ttttgttgag gtatccagga acttgggact cccgcctatc     360
ctggtccact ctgacctggt gctgacaaac tggaccaaaa ggaacccaga aggaccgttg     420
gaaatcagta acctgaaaac catcatctca tttccggggg gagagagcct gcggggcttc     480
atcctagtga cagtcttggt ggagaaggca gcagtgcccg gccttaaggc cctggttcag     540
ggaatggagg ccattcggca acacagtcag gacaccctgc tagaagccct gcagcagctg     600
agactctcca tccaggatat caccagagcc ttggcccaaa tgcatgatta tgtgacccca     660
gacatatttt actcggtcat ccggatcttc ctctctgggt ggaaggacaa tccagccatg     720
```

```
cctgtggggc tggtctatga aggtgctgcc acagagcctc tgaagtactc tggaggaagt      780
gcagcccaga gctccgtgct tcatgccttc gatgagttcc tgggcattga gcattgcaag      840
gaaagtgttg gctttctaca cagaatgagg gactacatgc cgccttccca taaggctttc     900
ctggaagatc tccacgtagc tccttctctg agagactaca tactggcctc tggtcctggg      960
gactgcctga tggcctataa ccagtgtgtg gaggccctgg agagctgcg cagttaccac     1020 atcaatgtcg tggccagata cattatctcc gctgccacca gggccaggag caggggcta    1080 actaatccct cacccatgc cttggaagac aggggcactg ggggtactgc catgctgagc     1140
ttcttgaaga gtgtcaggga aagaccatg gaggccctcc tgtgtcctgg tgct           1194
```

<210> SEQ ID NO 12
<211> LENGTH: 1227
<212> TYPE: DNA
<213> ORGANISM: Homo sapiens

<400> SEQUENCE: 12

```
atggagcccc acagaccgaa tgtgaagaca gcagtgccat tgtctttgga aagctatcac       60
atatctgaag agtatggctt tcttcttcca gattctctga aagaacttcc agatcattat      120
aggccttgga tggaaattgc caacaaactt cctcaattga ttgatgctca ccagcttcaa      180
gctcatgtgg acaagatgcc cctgctgagc tgccagttcc tgaagggtca ccgggagcag      240
cgcctggccc acctggtcct gagcttcctc accatgggtt atgtctggca ggaaggagag      300
gcgcagcctg cagaggtcct gccaaggaat cttgccctcc catttgtcga agtctccagg      360
aacttggggc tccctcctat cctggtccac tcagacttgg tgctgacgaa ctggaccaaa      420
aaagatccag acgggttcct ggaaattggg aacctggaga ccatcatctc atttcctggg      480
ggagagagcc tgcatggttt tatactggtg actgctttgg tagagaaaga agcagtgcct      540
gggataaagg ctcttgttca ggccacgaat gctatcttgc agcccaacca ggaggccctg      600
ctccaagccc tgcagcgact gagactgtct attcaggaca tcaccaaaac cttaggacag      660
atgcatgatt atgtagatcc agacatattt tatgcaggca tccggatctt tctctctggg      720
tggaaagaca acccagcaat gcctgcaggg ctgatgtatg aaggagtttc ccaagagccc      780
ctgaaatact ccggcgggag tgcagctcag agcacagtgc ttcatgcctt tgatgagttc      840
ttaggcattc gtcatagcaa ggaaagtggt gactttctgt acagaatgag ggattacatg      900
cctccttccc ataaggcctt catagaagac atccactcag caccttccct gagggactac      960
atcctgtcat ctggacagga ccacttgctg acagcttata ccagtgtgt gcaggccctg      1020 gcagagctgc ggagctatca catcaccatg gtcaccaaat acctcatcac agctgcagcc     1080
aaggcaaagc atgggaagcc aaaccatctc ccagggcctc ctcaggcttt aaaagacagg     1140
ggcacaggtg gaaccgcagt tatgagcttt cttaagagtg tcaggataa gaccttggag      1200 tcaatccttc acccacgtgg ttaggat                                         1227
```

<210> SEQ ID NO 13
<211> LENGTH: 1218
<212> TYPE: DNA
<213> ORGANISM: Mus musculus

<400> SEQUENCE: 13

```
atggagcctc aaagtcagag catgacgctg gaggtgccgt tgtccttggg gagataccac       60
atttctgagg aatatggctt tctccttcca atcctctgg aagcacttcc agatcattac       120
aagccttgga tggaaattgc cctcagactt cctcacttaa tcgagaaccg ccagctccga      180
```

```
gctcacgtgt acaggatgcc tctcctggac tgcagattcc taaagagtta ccgtgagcag    240
cgcctggcac acatggcgct ggccgctatc accatgggat tcgtctggca ggagggggaa    300
ggccaacccc aaaaggtgct gccaagatct cttgccattc cttttgttga ggtatccagg    360
aacttgggac tcccgcctat cctggtccac tctgacctgg tgctgacaaa ctggaccaaa    420
aggaacccag aaggaccgtt ggaaatcagt aacctggaaa ccatcatctc atttccgggg    480
ggagagagcc tgcggggctt catcctagtg acagtcttgg tggagaaggc agcagtgccc    540
ggccttaagg ccctggttca gggaatggag gccattcggc aacacagtca ggacaccctg    600
ctagaagccc tgcagcagct gagactctcc atccaggata tcaccagagc cttggcccaa    660
atgcatgatt atgtggaccc agacatattt tactcggtca tccggatctt cctctctggg    720
tggaaggaca atccagccat gcctgtgggg ctggtctatg aaggtgttgc cacagagcct    780
ctgaagtact ctggaggaag tgcagcccag agctccgtgc ttcatgcctt cgatgagttc    840
ctgggcattg agcattgcaa ggaaagtgtt ggctttctac acagaatgag ggactacatg    900
ccgccttccc ataaggcttt cctggaagat ctccacgtag ctccttctct gagagactac    960
atactggcct ctggtcctgg ggactgcctg atggcctata accagtgtgt ggaggccctg   1020
ggagagctgc gcagttacca catcaatgtc gtggccagat acattatctc cgctgccacc   1080
agggccagga gcaggggct aactaatccc tcaccccatg ccttggaaga caggggcact   1140
gggggtactg ccatgctgag cttcttgaag agtgtcaggg agaagaccat ggaggccctc   1200
ctgtgtcctg gtgcttag                                                 1218

<210> SEQ ID NO 14
<211> LENGTH: 52386
<212> TYPE: DNA
<213> ORGANISM: Mus musculus

<400> SEQUENCE: 14
tagttagaag gcagctcgtt tccagacaga tcatgccggg ccagcacagt tccacgagga     60 gcgattttt tggatggggg aagaaagtga agaagaggag aaagaggaaa aggggggtgaa    120 gggtcgcggt ctcagtcttt tatttgtgcc atgacataga tgccaggtaa tgaatgatga    180
atgatgcgca caggtgaagc ataggcctgc ctggagtgta tggtggttgc catggcaaca    240
gacccaagag ggtccttgtc gcttagggat gatgtcatag ctggattccg aggctggttg    300
taaagcagtt tctgatgcta acaatacata tatatgtaat gataacaaag aaaaagaggc    360
catgaatttg aaaggaagga aagaagttag gaaggaagga aggaaggaag gaaggaagga    420
aggaaggaag gaaggaagga aggaaggaag gaaggaaaga agatgggaat ttggagagat    480
gaaagggaag aatgatataa atacatttta atttcagcaa ataaatacat tttcaaagat    540
aaaaagccaa taagagaaa ccctgtctcg aaaaaacaac aacaaaccaa aaacaaacaa    600
acaaacaagc caataaaact gactcctagt ttagtcattt tgatacactg tcagaatccc    660
tcaggaacca aactcatgtt gagtatggat ctgcacagcc atagctgaga gttaagttcg    720
tgtctcccac tttgtccctg gatttaacag cccctttctc atactttatg aatgagaagg    780 gaagggggt gggggcttct cttggagtca gcattttaat tcctaatctt cattgttgac    840
ttactacttg gcttttcttc agaataaatt tgcggccatc ctggagttca acctcagggc    900
aaggttctcc cctaccgctg aagcaccgca caagtacaac cacacagaag acacagctgg    960
aaagctccct ggcctgggca ttcctctggg gcagagacct cacgcgaaaa tatggagcct   1020
caaagtcaga gcatgacgct ggaggtgccg ttgtccttgg ggagatacca catttctgag   1080
```

```
gaatatggct ttctccttcc aaatcctctg gtaaggattg gcttgtcctg gtcagcacat    1140
gtgtctggat tgttagtctt taccttatgt ggttattgga aggttcggta taagtcacca    1200
gctggaggaa gagtgggaat acagtcctgt gagtcccgga agagcagagg caactgctac    1260
tggggacagc acaaagccag tggtcccctc ccccagccc ccaaagtttc cttaaatcta     1320
tggtagttag cactgactaa tcagaagcaa aggtgctatc agagaggaga gactggatgg    1380
agacatgccc taaggacaat tagaaccta taactacagc aaagagtgga catgcacaca    1440
accacatggt gtgacacaga ataatggagt ggccccactg tatatccact ctgctttgga    1500
gacaggttcg ccatgcatcc cagacctaag cagccaaagg gcttagcctt ctgtgttgat    1560
gcaaaccagt ttatcttact tgctggtgac agcagagata atgggagacc tgcaatgttt    1620
ttagagccag taagaagatt agatgttatc gggaatttcc gatactcgtg aggaatgttg    1680
gaaaacaagc aggcctgact ttcagtccaa ctgcacagca gtctctagta tacctgctct    1740
tgttaagtgt agtctgggct tgggagacat atgccggcaa agtgctagtg gcaaagccca    1800
tgcttttggc atcttttaaa aactgaccgt acctaaggga gggtgaaggc cactgagtta    1860
aaagtccagg gacccgatgt tgcagtcgcg gtaactgctg atcagcacca actcacctag    1920
ttcctctctt acttgtgatt aaaaatatca gggtctcaaa cacctatcac agtgagactc    1980
ttgttgtttt gaaacagaga atattgtttt atgtagccca ggctggccac ttgcctccac    2040
ttccttactg ctgggaccat agctgaactc ccacagcaga tccttttgtg ttgaacggta    2100
ctggagggat ctaattgaag agaactaagt tctccacaga aagatgtcag ctacgacatc    2160
ggtcatagac atctgcaagc tgtccaggtt aggggttagt cattagaacc agggccagat    2220
ctcacagctt gaatcaagcc aggccttcct gctgctctct cacggacagt taggaagcag    2280
actgtactct gacatgatag cttgcagccg acggctcccg gctcctctgt gctccttgtc    2340
acgcaggccc tgctataaac taaagtgtct gacatgactt cctggtgcct cgtaaagtta    2400
ttaaaagtca gatttctcct ttgttctcgg aattggttcg agagccctca ggggatttgc    2460
tgagggtgtg tgtgtgtgtg tgtgtgtgtg tgtgtgtgtg tgtattctaa gagtgcttcc    2520
ctaaaagggt cctctgtact gtcaacggat cttcatagt ctctctctcc ctgtctccct     2580
gtctctctgt cttcctgtct ctctgtctct ctctgtttct gtctttctgt ctctgtctgt    2640
ctgtctgtct gtctatctct gtgtgtgtgt gtgtattttg aaggtaggag gatctgagcc    2700
tgaactacac acagctagat cctgtgactc tgtctcaaaa cagagacaca atcaaactct    2760
caactaatcg aaacaccaca aggcacactc cattctgggt gtgtggtctc agtccagcgt    2820
attcccatcc ttccaagttt acaggagagg aagggctgat ggcagataca cccttgtcat    2880
tactgggcat gtgtcctgag tttggaaaga gaacactgcc aagcagggga acgaatatca    2940
gggcaggcca tagctctggg gctttctggg ctgctttcct ctttgtaaat actgggacca    3000
ggcagacata cagataagac acaatagcaa catcaagttt ccccctatt tgttagaaag     3060 gttctatggt atggtgtgat ggatgggtac cccttaaaag aggtccctag tgctgttcac    3120
acagaaagga aatattccct gtcccaccca gctactcatt tatagcccag taatttcaat    3180
atgattcttt ctgtttcaat tttctttcat tcaagtgatg gttttcaatg tcttttttgt    3240
taaaggaaga ggaagaaacc ttgactagga tcaggtcctg gctgctccaa aggtcaagac    3300
agactcagtt cgacttcact ggacaaacag tcctgcaact ttacactggt tgggaaagaa    3360
cagtgggttt ggcccagtcc agtgccctag ggcatagcca agacctgttc ttcttgggcc    3420
aagggcaagt ggtaggtggc agaccttccc catctctttc agaaagtctc acttaagaaa    3480
```

```
acctagctgg ctagcaagtt caagggtata aattacccta tccagctgtt tctatcaatt    3540
caaagacttc caatttttag tgtctctatg aactttgct cctcgaatct gtaaaaatac     3600
cacaagaatt ctttgctaag acatctgtcc tctgtgtata tttggagga caagacatct    3660 ttttcagatg aagaatgtga ggaaatcagt ttgcaggaga ggaggcagtt aagaggaggc    3720
agcaagaggc tggcctgcag cagagctatg accccaagtg ccaggcccac tctgaaaatt    3780
gatttaacac ccttcctaaa cacaatgtga ctgctacttg agtcatttcc tctcacagca    3840
ctaagggcag ggcaggttag agcagtgggt cctgggctgt ggggtgagac ctttagggga    3900
gtttcaacaa acaatccaga tgccagagcc ccaccctgtt tattcagact ctagacccaa    3960
gagctgtacg ctgggaaggc cagatagga aacaagcca gagaatgcca gacagggagc      4020
acaagccagc aaagtcagcc gtgaaggtgc cacggccaat agagactcct aagtgcgaaa    4080
ataaataaac tgatgacatg cccactccat gcttaagggg aaagtagatc agagagggag    4140
agagagagag agagagagag gcacccagag gcagaggcct ctggacgatt ccgtagtaga    4200
tagagaaagc agactgaaga tggccaccag actggacatg gccaaggcta cctgggagga    4260
aaggaagaac aacagaagtc agagaataga gaaaacctag tgagagaagc aggaaggggt    4320 tggggggtg gatggagaga agttagcaat gacagcaggg ttctaagaag aaagagttgg     4380 ggagggagg tcctgtgagc tggagggagt ggagtgagtg gagggaaga gctgagaagg      4440 gacagatgct agcaggggct ttgagatgta cagcaggtac ttgtgatagg tgactggagg    4500
ccactggtga ccacatgtcc cttctgcaag aggtaaggga aaacattcct ttaggtagag    4560
ggaaaccagt gtcacaagtc cctgaggaaa gctggctttt tatctaaccc ccagaaatcc    4620
tcctgtagtc caggtgaagc tcatttctgg acatacagac tgccttttgg agtttgggga    4680
actggagttt cctttggacc tgacagtcag gagacgttgc acatgtaacg tagggtaga    4740 cacaagactg acaggaatgg caatgagaga ggacaacctc cagggaaaaa ccaacatgtc    4800
ccttctcatt cagaaattct aagcacttgg ttgaagcatt gggccacagc tggagagaag    4860
accggatagg aaattaattg ccacggacat ctgtattttt cagataagac aaaaaggaag    4920
aggtctaaca ttgtcctgaa atatgaggtt gccactgatg atctctggac acatcagact    4980
agtcagatag gggacttgaa acacaatgaa tccagagtct gtagtagaga caaagaggcc    5040
agattgcaaa atggttaatc ttgatcaagg ctggaaaatg tgtatggaaa taagagagac    5100
tgtaatatct taagaatggg gtttgtcctt gtgccagtat taagaacaa caacaaaaaa     5160 aaaaaaaaaa gaaaaagaaa aagaaagaaa gaaagaaaga gagaaagaaa gaaagagaaa    5220
aagaaaaatg gaggaaagtc atggggaaac aggtaatcag gcttgaatta aaaaaataaa    5280
aaaataaaat aaaaagttaa aggacttgac tagtcccagg tttctgcaca gatgaattaa    5340
aaaatgaaaa gaaagaaaa gaaagaaaa gaaagaaag ggaaaaaag aaaaaagaa         5400 aggaaaaaaa aaggaaagag aaaacaaaa gacaggaaaa gaagggagga aggaagaaga     5460
gaaagaaaga aagacagaca gaaagagaga gagaaaggaa ggaagaaagg aagagagaaa    5520
gaaagaaaga aagaaagaaa gaaagaaaga aagaaggaa ggaaggagga aggaaggaag     5580
gaaagaaaga aagaaaaga aagaaaaga aagaaaaga aagaaatga aagaaaaga        5640 aagaaaaga aagaaaaga aagaaaaga aagaaaaga aagagagga aggaagacag        5700 aggaaagggc ctggctgctt gtaggtactg tagcccggga gatcatagcc agaggcaagg    5760
acagctaggg aaatccagag tggtcatgac cgtgaaccac ttgaggagag ggaagagaaa    5820
agggcagccc agcccccagg ctagagaagt ttagggttgg ggcagggttt gtcagccagt    5880
```

```
gggtctttgt aactcccgag aacttgtagg cggctttgat atgctaagta ggcacctcag   5940
cctttcctct tgggtttgaa acccagaagg cctcagcaag tgggacaagc caagcccaac   6000
ttggaaagca gagttttaaa gggtgaaaca accaaccaaa aaggttcact ctcttctagc   6060
aagacgctta tgctgcaaag agacttaaga caatccggga gcaaggacag gacacacgct   6120
gaggatggga tgctaaatca gccctggaaa atacgtgtct aatacaggag gctctcgccc   6180
aagatctatt ggtttcctag cacagccgta aaatggctag ctattttaga acagtaacca   6240
gttctctgaa ctccatgcca gcctgtcccc aagtttccag ccctctgctt caaacacttc   6300
ttccaaccct tccaccctca atttcccaac agtcttctta aacaattcct tctccccatt   6360
ctcccaagac tagccactcc aaacggtaac aaccatatct tccataccaa ctgccttctc   6420
ttctccctct gctagcccaa tcccccctcc ttccctgact cagctggctc ttttatactc   6480
tatccagttc ctagtcatcc aagaagcaac caatgcttag ggtcataggg tcaagccttt   6540
gtaacagcta aaagttctta aagaggccag ttgactcgca actggagacc ctttattact   6600
tatttatttt tatgtctatg agtacactgt agctgtcttc agacacacac cagaaaaggg   6660
catcagatcc cattcagggg ttgtgagcca ccatgtggtt gctgggaatt gaactcagga   6720
cctatggaag agcaatcagg gctcttaacc ccgccgagct catctggaga ccctttaaag   6780
ggccaggagc ccaagataaa tcacattaca gttacatatg acccaaactc aggtgagcta   6840
gaccagtgaa gacttagact gatttctgga attaaggcac tgggcctgca gcacttccct   6900
ccaaagcctg cagtgcagaa tctgcccagg ccttttcccag gctccggtag cttcaacagc   6960
ttcctggcta ctagctcctg gcatcttttcc accccttcct tatatggcct tctgctgctc   7020
agtgtcttct cccctgatgc cttttcttct tcttttctta caaggatgct gctcattggt   7080
ttttaagacc caagctaatc ccagataatc tcatcagtaa agagccctct ccaaatagta   7140
tcacatactt agttcctaag gggacaactt atttgtgttc taagacttgg ggcaaagtat   7200
gagcagatgg tgcaatctta ggaatgctga ctgaaagaac tgtcttgtcc ctagattccc   7260
aaacctgatc tgtcaggaat gaatggggga aaaaagccca ggacaatgac aggcaagagt   7320
gtaaaatatc agtggtcgcc aagggggcttc gggacataaa ttcagtgagt gagtgcattc   7380
ttaccacgta tgaagaccat gccaaacaca gacataaata acgaaaatta aagattaaaa   7440
gtaaataaat tggccagatg tcatggcaaa tgcctgcatt cctagcaact agcagaagca   7500
ggaaggtatc aagttctagg cctgcctgta acactgaaca catatgagac cagcctgaga   7560
tatgtagaca aacaaaacaa aacaaaacga aagaccattg atcaatcaat aacataaacg   7620
ttcaggaaac acaggccaca caatcaggga ggctttgcct ttgtttaggg gctgggtttt   7680 ttttttatatt ttcctttcct tgttcttctt cttgtttgtt tgcttttttgt ttgtttgttt   7740 gcttgcttgc ttgcttttgt ttttcaaga cagggtttct ccgtgtaggc atctctggct   7800
atcctggaac tcattctgta gataaggctg tctttgaact cagagatctg cttgcctctg   7860
ccttcttaag gccgggacta aaggtgtgca cagtcactgc cacctacctg ctgtttcttt   7920
atcccctgca ttagtcaccc tcccacaccc gccagagctc tgggatagag actctgtgtt   7980
agggaatgga gcctacagct tccatcaggt gctatgtttt aattcacatt ttctattcct   8040
cttttctcat ttgtctgggg tgattctttt ggacaaaaaa aaatgttatc ttttataatt   8100
actaattagg atacaaacgt taaaatatat ctataatgta ctcttgtata tcattcataa   8160
tacctatttc gtattatact tccttatagt atatagcata ttttgataac aaggtcacga   8220
ggtcccaggc ctggaaccaa cttttttccta tgtaattggt tgaagttact gacaccgtag   8280
```

```
tagacttagc cctctggaaa cagcctttgg caatgaattt gactctgttt cagacaacca   8340
tcactttcct ggaaacggcc tctggcccat tcattacata tttcttgccc atctgtgaca   8400
cgctctgggt acaatcagca tgactcacta agagggtgtt cccgtttgct tctggtttct   8460
gtgagaaaac aaacaaaagc aactctggga ggcaagggtt tattcagatt ataagtccct   8520
gtcacagtca atcgctgagg gatgccaggt caagagctca agcagggccc tggatgcagg   8580
aagcagaaat cagagaaatg atgctctgtg gcttcctctc aattcacacc tcccgggacc   8640
acctgcctag ggatggcccc acccatagtg ggctggacct ccctccatca atcactaatc   8700
aagaaaacac cccacagatt tgtctacagg ccgatctggt agagacaatt tctcagtgaa   8760 ggctcccttct gacttaatgt caagttggca aaaactaaca ggcacagatg ggaaccagtc   8820
ataacagtgc tctgtacagt tctcccattg ctctttagaa tggtctcaca tggcctctca   8880
caatgctcac acagcttctc ctgggaattt aatgccccct tgcttcaact tctctttgctg   8940 tgccatgatg ctagcctttc ctatgtccaa tcccccaccc acatccactg aggttcttgt   9000
agactagaac cttccacatg agacagacta ccttaaccct tgtcttaggg gtaggctggc   9060
agggttacta tttctataaa acatactttc aattccattt taacgtttca tatgtattat   9120
atatatttat attatcaatg tagtgatgct aaatagacaa acagatgact aagtcttaa   9180 tgatgatcct ataagaattc ctaaaatata tctgtggtta ttaagctctt ttatagtggg   9240
acagccatta agtccttttc taattgtcaa aactgcaatg agaactctgc cagtctccca   9300
agtgtctcta gttaattgct attagatcgt aaccagactt tctcctactc agagcacatt   9360
ccaagcggtt gtaagacaat cagtcaaagt ttataaaaag ggacaattta tatatatcct   9420
gctaggacag aagataaaat attggctggt tttgtcgata ctaagcttca ctaataactt   9480
agttatggtt tgaacccttc agtgaacagg gtgatggatg ttgagcagga ttttttactcc   9540 tcatggatat gcatgtaaac tttctctgtt gtaaacttat atatcaattt atgatttgat   9600
ttttgtgtgt gaacttgtga tgaactttgt aacatgtgat cattctgaaa gatgtataag   9660
tactaaggac aaagagatga gaggcagata gagttgaatc ccccccccccc cccccaaga   9720 atcaatcatt tcccttccta gaattttttgc tcctgtagag aattttttcac tttccccact   9780 taggatcttt ctgcctttcc ccttagttag cttttcgtagg aaactttta caacttagta   9840 ataaatgcta taatcatttt tcgaagtgtc ccctttctt cctgtgactt ccgactagca   9900
ggccgaaagt tagagtggaa cagcttctgc tgagatagtg cgaaggctat ctactttatc   9960
ctttgctgtt tgaggaagat gtgctaagtg ccagagactg cagtttctgg cctccgagga   10020
acacagaagg caggtcagct acagtagcat cgagaagaac ccaacaagaa agaagagctc   10080
catgccaggg ctggcagcat tcctatgttt tatgtaatat ttactgctga gcaggggata   10140
atatctgaca tcatatgtta cttatacatt tttgttgatt aaaaactata ataatcatcc   10200
cttctcagca cccacagaaa accaaggcat gtggatctct gtgagcttgg ggccagcctg   10260
gttcacatgg tgagttccag gtcagctggt gttacataac atgaccttgt ctcaaaaata   10320
taataataat aacaataata atacaatatt atatatttta taataaataa taacaatcac   10380
tagtattaaa ataaaaataa aagaaaatat aaaatcatgc ttgttaaata ttgctttata   10440
ggacattatt tgactgtctt ttaacctggc aaataccccat cagcattctt tctcaaaact   10500
cagtaccact cgaggcctcc ttgacccact gtctcggtta ttcagcacta atgatctaag   10560
tgtatttttg gcacacagtt catattgtag acagcacttt gtaatttttt tcttttatgt   10620
ttactttttt tttttaactt ggataaataa gtataggcca ggacatttat ctgtaaaaag   10680
```

```
aaaggatgtg tattggaaag tttctatgag ctttgtgtca gaaggggttt ggcctggcca    10740
ctgaccacat gtgctaggga gggagagtta acctcccctc tccccatggg gagccttagc    10800
tgtttattct gttgctgtgg taagatgtcc tggtaagcaa cagaggcagg gagggagggg    10860
tttgtttggg ttcacagttc agcagaagcc acaggtggcc tgaccttaag gcatctggcc    10920
ttgtcgcacc cacacccaga gccacgggga tcttagctgc cgttctcatc gttccatagt    10980
ctagggtcta ggcccatgta atgatgccac ccacagccat cctaactaga caaacaacca    11040
ctcagagctg tgcccagagg ctcacctctc agtcattcca gaccccgtta acagacggc     11100 cagtactaac tgttacactt tctgtatttc agtgtgggaa gaacaaaaga gaagcctcat    11160
ggcacaaaca cccaccgatt aagacaagca tcagcatgaa gactagaaac aatattaaac    11220
aatattaaaa gtgactttgg gaagagggga aattttttaag tatgatttaa gaccagaaaa   11280
cgagtgagat gtggtttgtt tcattattcc attaggaaca gctatttaaa atacacataa    11340
aggacaccat acctgggata tatactgggt tttagtctgg actaaggat gacacttggt     11400 ttttaaacaa aggaaaaatt gagtgactaa agcttatgaa aattgaactt gcagaaatct    11460
aaaaatttaa atctagaata gtaacaaatt gatatcatca attcgggagt tacatagatc    11520
acctaacaaa ccacattggg acctcctaag tgttatcatt ttagacaaga gggtaagaat    11580
cggggtactc tttcgtctac tttagagagt tcatgctttt ttgaatgccc tgttagcaat    11640
gttgatccag aagactacat catcttcttc tttatgaatt gggaagccag caacaaagca    11700
actgagtagc aaaggcttat tcttggctaa gaataggaga catgagaaac aaactcacaa    11760
gttcactccg cgatctgttg tggttatagg cataggatca aggagttgag tgggaaggag    11820
aggctagtaa tcaggggaca tattgttact gggagacatg ttcaagtatt tcctaagact    11880
aggtggagat ttcccaggaa atccatcaat atatcttttt caactatttt aaaaacttca    11940
ctcatttatt ttagtatgtg tgtgaaaaag agacagagat atatagagag agaaagggg     12000 agggagggag aaggagacgg ggaaagaaag acagggagat agagagacag agaaaaaaga    12060
cagagggagg aatgggtaga gggaaaggga gagagagaag agggtcagag agagggggg     12120 agagagagaa agaaaagggg gggaggggaa aagggagaga gaaatagaga cagagaggga    12180
gggagggaaa gaagaaggaa aggggagggg ggaggggggag agagagaaag acacacacac    12240
acacacacac acacacacac acacacacac acacacgggg gtgggggag agagaatgct    12300 gatgtcatag tgtgccactg gagatcagtg gacaactgtc tcaggaacta gttctctcct    12360
gccaccttgt gggatgcagg atgaccttag atcctacctg ctggctagcc tacctttccc    12420
atcttttatg gatctttctt gtcagaaacg aatgactgtg atgttactga ggttggttgg    12480
catggagcat gcaatgtagg tgttatattg tgaaggtaga ggtgtttagc agtcactccg    12540
gcacttatct gagacccaaa taattctggc caacctacct gaagagcaac ctctggccta    12600
tactatcttg ttataaaagg aaatcagatt aaagccagga agacattctc taggctaact    12660
aggaagactt ctctctcctg ccctctacac tgaaacattc ctctttaaaa aaattatgtg    12720
tctttggaat tattattatt agtattagta gtagtatttt ggttgctatt gttgcacatg    12780
ttaagcaatg agctaacatt tcccatcatg cctaccatca tataaatgtt aggtttgagt    12840
tcggggctaa gcagaccaca tttccatgtc atcttacagg tacttgcagg cccaccatag    12900
aacagttgta gaactctgac aaacttccag agctccgctg aacttcagaa atactgaat     12960 cccagaggtc ccacaagtct ctatcctcct ctctgcagaa ccctcagagc tgattctggg    13020
cttcctggtg ctacacggaa atataaaaca acccgtctga atgtatcaga caaattccct    13080
```

```
agataaccag acggtagaga gcaatggcta agtcacatcc cccagggatg ggggaacctc   13140
actaattaat taaatggtaa atgtggtagg tacatgtacg aactgacatc aaagaagatg   13200
catgctgtct aaccagaaac ttgcctggtg ctactgtctc tagtatgata aatttaaatc   13260
tgacagttag gagtaaccaa tataattctg tactttcttc agtctctaga gcagagactc   13320
tcaacctgtg gtttgagacc cccttttggag cttgcatatc agagattttg catagccaat   13380
atttacacta ttatttgtaa cttgtaacaa ctttacagtt atgaagtagc aacaaaataa   13440
ctttatggtt gcggggggggg ggggggtcacc acaacatgag gaactgtatt aaagagttgc   13500
acacggtatt aggaagggtg agaccccgtg ctatagagga aaggctggaa agtcaaatgg   13560
tttttacatg agttgtagtg ctgcctaaga ggagtgttta gcaatcttct gggtaagact   13620
caaagagacc cagaagccta gcaatacccg tggtagaggt gtcacctcct actcaaatgg   13680
gttgtaaaac accttttcaaa ctgctctcct ctcttctgga ttactggcaa gccttggtcc   13740
ctgtctgtgg ttgtcagact caggctgtgt caatcactta gcggatggat aactggctac   13800
agagctccac cagaaggtca gcttccgtat gtctggggtg aggaccagga gcctgtgggt   13860
tgaatcgttc ccaagggata aaagtactgt ggacgctgag tgcactcgga tgctttgtgg   13920
ttgcgtttgt ctgttgagct tacagcagtc catgcatgag acattggaaa caaagagctg   13980
cagccttcct ctgggatcta aggggaaaga atagactgca gcctagagtc ttggttctca   14040
gaaatgaact gtttaaggtt tctcacgtaa gctaggaagg cagagcccag ctaggtttca   14100
tttaattatg atgggattcc ttatttaggt accaaagaag gaaaaggctc ctctggtgat   14160
ggttagtgac agcttctttt ctgggtccca gccaatcaag ggggcatctg agttctacag   14220
actttaagtg cgtgatttt ctatttcaaa gtaaacacga gatattctag cccagcattt   14280
gagtcactat gttcaaatat attctaaaat gcccagatca caccagcgag attaagtaag   14340
ttggcagttc acagatacat caacatgaat ctatctttct ttctttcttt ctttctttct   14400
ttctttcttt ctttctttct ttctttcttt cattcattat ctatttatct gcctacctat   14460
catctatcta cctacctagc tatctagcta tgtctatctt ccagtccgta aatctatctc   14520
tgtgcatcta tctatctatc tatctatcta tctatctatc tatctatcta tctatctatc   14580
tatctatctt tcattatcta tttatctgtc tacctatcat ctatctacct acctagctat   14640
ctagctatgt ctatcttcca gtctgtaaat ctatctctgt gcatctatct atctatctat   14700
ctatctatct ctatcatta tcaaccatct ttctatccat catccatctc tctctctctc   14760
atatctctct catatatata catatgcata tgtatacgag atccttttctc ctgaggaagg   14820 agtcaagatt cacagtccta ggcaagtgct gtactcctgg gcaatagggc agcctttgct   14880
tttattctta gtctttctct tgatgccaac caaatgcgta tcagcttcaa ttctgctctc   14940
ttcagctgtg tacctgcagc tgtttcctgg agaaaatgac accatcaacc atttctctcc   15000
aggacaaagg ctgggtgggc tgggaggggt gcgggtggag tgagtgcagg acaggagacc   15060
aaaggctgaa ccagatgacg gtcttgccca gaacgcctcc acccgtccag aactacagcc   15120
gctgctcccc atgcagtttg actctgaaag tataacaacg taaaaacaga attctaggcc   15180
tttaggccca ggcttgagaa tgtggccttt gtaaaggtat gctaatcata aaagagatag   15240
cgacattcct ctacccaccc gcttcctggg ttcaaagagt gctcattcaa agaaagtcac   15300
cctgaggatt accagaacct gcaatgcaaa tgtgctattg ttagaggctc ttagaagctg   15360
tcttgagagt taacacttac caggtattcc ttgtgactct gtaactttta cacttccttg   15420
tgactcttaa ctggtatctt tggtatcttc caacaatgcc ctccccactt ccttgagttt   15480
```

```
cggtttcttc ctttaaatac ccccttaccc agctactcgg ggtgccacgg tcctctaccc    15540
ctgcgtggtg tatgaccatg ggcccgagag cgcttttgaa taaaaatcct cttgcaattt    15600
gcagcaagac ccgtttcttg tgggtgattt tggggtgtcg cctctcctga gtcagaacgt    15660
gggggagccc tcacattgtg ggtctttcaa ctcgaggctt ccagttcgtc ctgagttact    15720
ttagagtcaa agaaagaaaa gggaagatta aatgaagttc aaaacctcca cagcgtatgg    15780
caagatgttg gaaatactag ggatgcaagt caaccaggag ttttagccca gaatcacagg    15840
agatctagat gttcatgacc ccgaccccca cccctaaac ccaacttcca ccccacccc      15900 cgccacccca acagcaacaa gaagtgacac gtgggtctcc tgttgatctc tgcctctcca    15960
gagctggact ttcaagtgtc ctggcttatt actgtccctc tgtgttgtca catttgctca    16020
gggtcagctc tcctctcctc ttcccggttc ttagcataac gcttattcct ctctgtagtc    16080
tcacagcctg atctttaccc ccagtgagct gagaaactgg atccatggga agctaagccc    16140
ctcacttctg catctgccag gatgcatctc cttctccgct cctcttcttc ctcatgcctt    16200
gctgcctctg tgtcccccgc cccctcttc ttcccagtgt tcctcttcca gcagcagacc    16260
atgaactcca tactgctctt atccctagaa gacctctgta aaagcaggtt cccttcatt    16320 gatgtctctc ctaaaagtc catcacatcg ccccacactt ccccagcaca ggaccatttg    16380
gacttagctt ccaagatcct gttctcagtt tcaatagcaa aggtgtagag aaactggcat    16440
gaacctcttt gtgttgcttt gtctctaagg gatggccttc ttttaactct tgccttggac    16500
tgggctcagt gggccctcct caatccgtgc gaatcagagg acagatgggc gccgtagagt    16560
cggcgagtga caaacagaaa cggcggcgag tgtgtagaat ctgagtgtat ttttacaaag    16620
tgaacaccag tcttatatag tacagaaaat aaagggatag gatgtcacag caggcaaagt    16680
acattgaagt tacctgacac aaaacaaagt aatgacttca aaaggacttt caggaaccag    16740
gtaatagtta cagtaaagat aaaacagctc tgcttagggt cagctaagga caggtaagga    16800
tttcacaccc tactcacaat ttgtgctact cctttgaacc ttgtgaaagc tagcaccagg    16860
gagttctgct ctagcagacc ttctcatgaa taatgcaata ccacaaaccc cctatttcct    16920
aggacttgat aaattctttc atgagtataa cttggctgtt cttttaagta tctgtgggga    16980
agctccattt gtcagaagaa ttcaccaact tgcttctaat atgcaatgta gcctgctata    17040
cctggctgta caagattcct gtctcagtgg gattctctaa ctctttcatg gtaaacccac    17100
ctattagcta ggccatggtg tattcccttg tttgggttag acttggctac tgtcctaagt    17160
cctaagtaat caccctgcag accagccctg agctattcta gctctgttct ttgtaatgcc    17220
taattagttt caccatttct actagaagta aatttgaatg ttactgaata ggtaacattc    17280
tcactgaatt tctactgaat tccaagctcg tcggcttcaa gaattttcta ggacgttgga    17340
acactggtgg aggcttacct atgttaaaat tcaaccttta aaggcactta taataaaaca    17400
atactaaaag agagcatgtg catccatata ccagactaac acggggatag ggtatgagta    17460
tacaggttat gagaatgcca aggttctagg aggttgagtt tccttgaaac tctttgcctc    17520
catgagtgct tccaggcctc tcggcctgtc aagcagactt cactggagtg ggtatagcaa    17580
actctgtatc gatgcccttg atcttctgat tattgccttt cataaaatta tcttacattt    17640
tgactgccat atggtctttc tctatggctc attgaacccc gagagtgttc ttttatctgt    17700
tgccagtgga gtcagttcct gtgcctacct tgtaaatatc cccagtgtgc taatctaggc    17760
tttccttggt gtttcggttt gcataacctt aagaagcact ggccacactc tgtgctttct    17820
cttttagtga cttctgagtc acacttcttg gcacatcatt tgaatttcta cagaagtgga    17880
```

```
agctgaattg attgagaact agcttttgc ctactctgat ctctacttgc atttcctgta    17940
tgtgctctga cccattgcat ggctgctctg ttcataaaca cggtcatggt tttcacccca    18000
tttcttcata actcagaggc cctatgggct ccatccatgt tttgtgtaca attttttatt    18060
tttttatttt attttatttt ggttttttcga gacagggttt ctctgtgtag tcctggctgt    18120
cctggaactc actctgtaga ccaggctggc ctccaactca gaaatctgcc tgcctctgcc    18180
tcccaagtgc tgggattaaa ggcgcgcttg accaccgccc tgcttcctgt acattttctg    18240
aaaggccaaa tcaccttctt ttgcaacgca tacagctttc cgctgagatc gcccaggtct    18300
gttgcttgtt ttcagaagct gacacagaca atgggagtgg aggagtttca gtacaagtcg    18360
attcatagag atagatgcag cctaactggg cagcccaagc cttcaattgc agctatgctg    18420
gaggctgaag caggggacc tcaaggtcaa cggcagcctg agaaactcac agagactgtc    18480
tcaaaataaa aaatatatat ataaaataaa actatacact tgactcttat ctacaatgta    18540
gtacgtggga ggaggctgag gtcgaagact gtgagtttga tcagcctggg ctacatagca    18600
aacatctgcc tcaaaagact ggaaatacaa actaaaagt gaagaaaaga gaagccacgt    18660
tcagacttca aaaccaggct ccattgtcat gtttctggga ctattcccta tccattccca    18720
gagtagactg acagaattag ccccccacccc ttctcgagcg tctcaagccc acacctgagc    18780
atagagcatg tgatttacat ggggatccat ttttcctcca cttctccct cccgtgttat    18840
atgatcggag cctaaggtct gtaaccttgt cagctgcgtg tccgtgtggc tagtctagcc    18900
taaggccagg cttgccggaa gttctcttgg cacacctggg ttgacttgac ttctcctgaa    18960
gagcattcca aagctgctct ctgtaaaatt ctcagctgtt tctatttgaa atgcaggaag    19020
cacttccaga tcattacaag ccttggatgg aaattgccct cagacttcct cacttaatcg    19080
agaaccgcca gctccgagct cacgtgtaca gggtacgtcg atttgttctt tgcttcatgc    19140
tcctcctctc cccacccgtt ccgtctccat atccctttcc ttctcagctc tctgggagtg    19200
aaacggttga cctggcagtg ggaaccgact gtcaccactg aggctttcag caaacctgtc    19260
ttccttagtg cgcacaaaca gcacctgaga tgtgtcaagt cctcatcgtg tttgtgcaaa    19320
agacgatgat agatgagact tgaaaataaa ttctggggaa acgaggaaga cacacattgg    19380
agattggtgg gagccgcttg gcctgcttct gtaaaagcct gcctgtcagg cagagtcaag    19440
ccaggggctg aatgttctgt taatctcgga ggaaggaaca cggaggaata gaggcctctg    19500
gatgagtaca gatatcagat atacatcagc cgctgtctct gctggcttgt gactttgctt    19560
cccgtgatac tacagagtat ataaagcctt agagaattaa actcaaggct gctgcagcac    19620
tgactggata gccttcccgg tttttaagct ttgtttctga gtcttctttt ccatctctcc    19680
tacaatcctc actcacccct cagaagacct gttcaacttt gtactggcag gaccggcagg    19740
ggagatgctc agtggacttg tcccaagtca cgtggtcact gctctgcttc ctctgggcag    19800
gtaccttgac cttagtgtgt tacatactag tcagatcaaa tgtctttctg attttttaaac    19860
tcagagtcag tcttggctat gtagaagaag tgaaatccat agacaccaca ttagaatctg    19920
catgcaccta agtatatgac gcacgtctgt gacagagcga gcaatttccc tccaaaagga    19980
ataagaaaaa tatgaccccc acagaagaca ttcttccatt caggaatttt atagtaagtg    20040
tgaaacggag agttggcctc agaatcttgc ttccttcttt gagaaatgga tgaagttctc    20100
atttaatggt tgtgagcatc aatggctttt gtaaggaccc tcccctcct catcttcatc    20160
tgtcacaaga acaccacaag atgtcagatg ttcaagcaag gcgctccacc ctccaggacc    20220
ttctttgctg atgcttaatg tccaattatg agttgatttt taaaaatatt cattgaatga    20280
```

```
tccttatagc atattcagaa atcaggacag gcagctggcc ttggtaatac tctagataac   20340 ccccctctg aaccccccac tgaggctgaa gaccatgtaa gaaagtgcaa ctaaaggagt    20400
taattgttgc acaaaactca cacaaagcct cacaaaggta gtttgtacac gctgttgaca   20460 cattcacta acaaaaacat cgaggggaaa aaagatggga aacagtagaa gataataatt    20520
aatggtgacc tatggcctac acacacacac acacacacac acacacacac acacacacac   20580
acacacacat gcacacatca ccacacacgt gtgtatgcat atgctcacac atgtacaaac   20640
atatatcacc acatatgtga cacacacata cacactcata tcaccacaca catgtgtaca   20700
cacatgcaca cacacacatc accacacaca tatgcataca taggaacata tagtacacac   20760
atatcaccac atagatggca cacacacact cacataccat cacatatatg catgcatata   20820
gacatgcaca cacatgcccc cccacacaaa cacacatata tgtacaaaac ctatagtgaa   20880
cacactaccc tgagtcaagc tatgagtttt aagaacatac atactgtccc ccaaaactcg   20940
tcacaaggtg ttttgtcctc aaagggaaag ctcctctcta tctaactgat gtctagaacc   21000
cacaaatatg ttagttgtgt accagagggg acggcgggtg gttagttagt agagggtctc   21060
ccacaaaccc atgtgtctgt cttcatccac catcttttac actgatgaat gagttactag   21120
ccagtaactc atgcagtgag gcaaagcagt tatgatggtt ctgggtgaca agcaagtgaa   21180
gagtattggt gaggatacta agcacgcgca tgcactttgc tacaactagt ctgtcatgtg   21240
aactgccatc tcacagaaac attcatacaa aaaaagtgc agatgaatat gcaaagctgt    21300
ttgctgtagc cactttcata gcaacggtaa atacaatgta acagaaatac aatgtaacag   21360
aagacaggag agcagaagga gaagcccatg aatctccatt cacaaatata tctgttacat   21420
aaatgaaaag ggacagatat taagtggtca cgtaggcacc tgcctgtatc cttccgccac   21480
gctacacatc tttgctctgt agtttactga gcattaggaa gttcgcgaca gtatctatat   21540
gcagaattat tgaacctcta cttcaacaac atgtgcatgt gagcttaata tttatagatg   21600
atagaggtag aaatagacat atttactatc tgacagagtc ctaacatgta gcccaggatg   21660
gctttgaatt agacatcttc ctatctccgc ctccagagtg ctggtatcag tcttcataaa   21720
gacttctata tgaaaacaaa tgtcctgttt tctatgtatt cgccttcgtg tcaaactata   21780
cttttcaaga agttcaagaa gtgatgtcca caagaacctg atgtgtgtca gaaacactca   21840
gctccccagt gaagttggca ggagggctcg cctggttcag agaagccttg cgtgctccct   21900
gagttctgag aggagagtat cgaggttaat tctcccaggt taaatacgca atcaaataat   21960
gtcagggaga tgacgggtgt gtgtcgtcct cccagaccat ctgtgactgt ttgagtaagc   22020
aaaaggattg actaaaaagc tatcatttcc ttttcagtcc ctacagtcac ttttgaatca   22080
caggtatgtt taggaggtga ggccaacaat cctgaaatgt gcagggactc tccagaaagc   22140
agtcatcatc ccctggacct cgttcctta caccgaggcg tcctggcttg taggtggcct    22200
tcttcaacaa ctgaggggtg acaaggacaa agcctgagaa gacacagcct agattgtgaa   22260
gactttgaaa gatttttata ctgactgcat gctaaaatat ctttatacg ttgactcaac    22320 aaagtacatt atcagaacta attttacttc ttgtttgcct taaaaaaaaa aaagtggctg   22380
ctgaaagtat acgagatcct ttctcctgag gaaggagtca agattcacag tcctaggcaa   22440
gtgctgtact cctgggcaat agggcagcct ttgctttat tcttagtctt tctcttgatg    22500
ccaaccaaat gcgtatcagc ttcaattctg ctctcttcag ctgtgtacct gcagctgttt   22560
cctggagaaa atgacaccat caaccatttc tctccaggac aaaggctggg tgggctggga   22620
ggggtgcggg tggagtgagt gcaggacagg agaccaaagg ctgaaccaga tgacggtctt   22680
```

```
gcccagaacg cctccacccg tccagaacta cagccgctgc tccccatgca gtttgactct   22740
gaaagtataa caacgtaaaa acagaattct aggcctttag gcccaggctt gagaatgtgg   22800
cctttgtaaa ggtatgctaa tcataaaaga gatagcgaca ttcctctacc cacccgcttc   22860
ctgggttcaa agagtgctca ttcaaagaaa gtcaccctga ggattaccag aacctgcaat   22920
gcaaatgtgc tattgttaga ggctcttaga agctgtcttg agagttaaca cttaccaggt   22980
attccttgtg actcttgtaa ctttacactt ccttgtgact cttaactggt atctttggta   23040
tcttccaaca atgccctccc cacttccttg agtttcggtt tcttcctttt aatacccact   23100
tacccagcta ctcggggtgc cacggtcctc taccectgcg tggtgtatga ccatgggccc   23160
gagagcgctt ttgaataaaa atcctcttgc aatttgcagc aagacccgtt tcttgtgggt   23220
gattttgggg tgtcgcctct cctgagtcag aacgtggggg agccctcaca ttgtgggtct   23280
ttcaactcga ggcttccagt tcgtcctgag ttactttaga gtcaaagaaa gaaaagggaa   23340
gattaaatga agttcaaaac ctccacagcg tatggcaaga tgttggaaat actagggatg   23400
caagtcaacc aggagtttta gcccagaatc acaggagatc tagatgttca tgaccccgac   23460 cccacccc taaacccaac ttccacccc acccccgcca cccaacagc aacaagaagt   23520 gacacgtggg tctcctgttg atctctgcct ctccagagct ggactttcaa gtgtcctggc   23580
ttattactgt ccctctgtgt tgtcacattt gctcagggtc agctctcctc tcctcttccc   23640
ggttcttagc ataacgctta ttcctctctg tagtctcaca gcctgatctt taccccagt    23700 gagctgagaa actggatcca tgggaagcta agccctcac ttctgcatct gccaggatgc    23760
atctccttct ccgctcctct tcttcctcat gccttgctgc ctctgtgtcc cccgccccc    23820 tcttcttccc agtgttcctc ttccagcagc agaccatgaa ctccatactg ctcttatccc   23880
tagaagacct ctgtaaaagc aggttccctt tcattgatgt ctctcctaaa aagtccatca   23940
catcgcccca cacttcccca gcacaggacc atttggactt agcttccaag atcctgttct   24000
cagtttcaat agcaaaggtg tagagaaact ggcatgaacc tctttgtgtt gcttttgtctc  24060 taagggatgg ccttcttta actcttgcct tggactgggc tcagtgggcc ctcctcaatc   24120
cgtgcgaatc agaggacaga tgggcgccgt agagtcggcg agtgacaaac agaaacggcg   24180
gcgagtgtgt agaatctgag tgtattttta caaagtgaac accagtctta tatagtacag   24240
aaaataaagg gataggatgt cacagcaggc aaagtacatt gaagttaccl gacacaaaac   24300 aaagtaatga cttcaaaagg actttcagga accaggtaat agttacagta aagataaaac   24360
agctctgctt agggtcagct aaggacaggt aaggatttca caccctactc acaatttgtg   24420
ctactccttt gaaccttgtg aaagctagca ccagggagtt ctgctctagc agaccttctc   24480
atgaataatg caataccaca aacccccat ttcctaggac ttgataaatt ctttcatgag   24540
tataacttgg ctgttcttt aagtatctgt ggggaagctc catttgtcag aagaattcac   24600
caacttgctt ctaatatgca atgtagcctg ctatacctgg ctgtacaaga ttcctgtctc   24660
agtgggattc tctaactctt tcatggtaaa cccaccatt agctaggcca tggtgtattc   24720
ccttgtttgg gttagacttg gctactgtcc taagtcctaa gtaatcaccc tgcagaccag   24780
ccctgagcta ttctagctct gttctttgta atgcctaatt agtttcacca tttctactag   24840
aagtaaattt gaatgttact gaataggtaa cattctcact gaatttctac tgaattccaa   24900
gctcgtcggc ttcaagaatt ttctaggacg ttggaacact ggtggaggct tacctatgtt   24960
aaaattcaac ctttaaaggc acttataata aacaatact aaaagagagc atgtgcatcc   25020
atataccaga ctaacacggg gatagggtat gagtatacag gttatgagaa tgccaaggtt   25080
```

```
ctaggaggtt gagtttcctt gaaactcttt gcctccatga gtgcttccag gcctctcggc   25140
ctgtcaagca gacttcactg gagtgggtat agcaaactct gtatcgatgc ccttgatctt   25200
ctgattattg cctttcataa aattatctta cattttgact gccatatggt ctttctctat   25260
ggctcattga accccgagag tgttctttt atctgtgcca gtggagtcag ttcctgtgcc    25320
taccttgtaa atatccccag tgtgctaatc taggctttcc ttggtgtttc ggtttgcata   25380
accttaagaa gcactggcca cactctgtgc tttctctttt agtgacttct gagtcacact   25440
tcttggcaca tcatttgaat ttctacagaa gtggaagctg aattgattga gaactagctt   25500
tttgcctact ctgatctcta cttgcatttc ctgtatgtgc tctgacccat tgcatggctg   25560
ctctgttcat aaaacacggtc atggttttca ccccatttct tcataactca gaggccctat   25620
gggctccatc catgttttgt gtacaatttt ttattttttt attttatttt attttggttt   25680
ttcgagacag ggtttctctg tgtagtcctg gctgtcctgg aactcactct gtagaccagg   25740
ctggcctcca actcagaaat ctgcctgcct ctgcctccca agtgctggga ttaaaggcgc   25800
gcttgaccac cgccctgctt cctgtacatt ttctgaaagg ccaaatcacc ttcttttgca   25860
acgcatacag ctttccgctg agatcgccca ggtctgttgc ttgttttcag aagctgacac   25920
agacaatggg agtggaggag tttcagtaca agtcgattca tagagataga tgcagcctaa   25980
ctgggcagcc caagccttca attgcagcta tgctggaggc tgaagcaggg ggacctcaag   26040
gtcaacggca gcctgagaaa ctcacagaga ctgtctcaaa ataaaaaata tatatataaa   26100
ataaaactat acacttgact cttatctaca atgtagtacg tgggaggagg ctgaggtcga   26160
agactgtgag tttgatcagc ctgggctaca tagcaaacat ctgcctcaaa agactggaaa   26220
tacaaaacta aaagtgaaga aaagagaagc cacgttcaga cttcaaaacc aggctccatt   26280
gtcatgtttc tgggactatt ccctatccat tcccagagta gactgacaga attagccccc   26340
accccttctc gagcgtctca agcccacacc tgagcataga gcatgtgatt tacatgggga   26400 tccattttc ctccacttct cccctcccgt gttatatgat cggagcctaa ggtctgtaac   26460
cttgtcagct gcgtgtccgt gtggctagtc tagcctaagg ccaggcttgc cggaagttct   26520
cttggcacac ctgggttgac ttgacttctc ctgaagagca ttccaaagct gctctctgta   26580
aaattctcag ctgtttctat ttgaaatgca ggaagcactt ccagatcatt acaagccttg   26640
gatggaaatt gccctcagac ttcctcactt aatcgagaac cgccagctcc gagctcacgt   26700
gtacagggta cgtcgatttg ttcttgctt catgctcctc ctctccccac ccgttccgtc   26760
tccatatccc tttccttctc agctctctgg gagtgaaacg gttgacctgg cagtgggaac   26820
cgactgtcac cactgaggct ttcagcaaac ctgtcttcct tagtgcgcac aaacagcacc   26880
tgagatgtgt caagtcctca tcgtgtttgt gcaaagacg atgatagatg agacttgaaa   26940
ataaattctg gggaaacgag gaagacacac attggagatt ggtgggagcc gcttggcctg   27000
cttctgtaaa agcctgcctg tcaggcagag tcaagccagg ggctgaatgt tctgttaatc   27060
tcggaggaag gaacacggag gaatagaggc ctctggatga gtacagatat cagatataca   27120
tcagccgctg tctctgctgg cttgtgactt tgcttcccgt gatactacag agtatataaa   27180
gccttagaga attaaactca aggctgctgc agcactgact ggatagcctt cccggttttt   27240
aagctttgtt tctgagtctt cttttccatc tctcctacaa tcctcactca cccctcagaa   27300
gacctgttca actttgtact ggcaggaccg gcagggagat tgctcagtgg acttgtccca   27360
agtcacgtgg tcactgctct gcttcctctg ggcaggtacc ttgaccttag tgtgttacat   27420
actagtcaga tcaaatgtct ttctgatttt taaactcaga gtcagtcttg gctatgtaga   27480
```

```
agaagtgaaa tccatagaca ccacattaga atctgcatgc acctaagtat atgacgcacg    27540
tctgtgacag agcgagcaat ttccctccaa aaggaataag aaaaatatga cccccacaga    27600
agacattctt ccattcagga attttatagt aagtgtgaaa cggagagttg gcctcagaat    27660
cttgcttcct tctttgagaa atggatgaag ttctcattta atggttgtga gcatcaatgg    27720
cttttgtaag gaccctcccc ctcctcatct tcatctgtca caagcacacc acaagatgtc    27780
agatgttcaa gcaaggcgct ccaccctcca ggaccttctt tgctgatgct taatgtccaa    27840
ttatgagttg attttttaaaa atattcattg aatgatcctt atagcatatt cagaaatcag    27900
gacaggcagc tggccttggt aatactctag ataacccccc ctctgaaccc cccactgagg    27960
ctgaagacca tgtaagaaag tgcaactaaa ggagttaatt gttgcacaaa actcacacaa    28020
agcctcacaa aggtagtttg tacacgctgt tgacacatta cactaacaaa aacatcgagg    28080
ggaaaaaaga tgggaaacag tagaagataa taattaatgg tgacctatgg cctacacaca    28140
cacacacaca cacacacaca cacacacaca cacacacaca cacatgcaca catcaccaca    28200
cacgtgtgta tgcatatgct cacacatgta caaacatata tcaccacata tgtgacacac    28260
acatacacac tcatatcacc acacacatgt gtacacacat gcacacacac acatcaccac    28320
acacatatgc atacatagga acatatagta cacacatatc accacataga tggcacacac    28380
acactcacat accatcacat atatgcatgc atatagacat gcacacacat gccccccac    28440 acaaacacac atatatgtac aaaacctata gtgaacacac taccctgagt caagctatga    28500
gttttaagaa catacatact gtcccccaaa actcgtcaca aggtgtttg tcctcaaagg    28560 gaaagctcct ctctatctaa ctgatgtcta gaacccacaa atatgttagt tgtgtaccag    28620
aggggacggc gggtggttag ttagtagagg gtctcccaca aacccatgtg tctgtcttca    28680
tccaccatct tttacactga tgaatgagtt actagccagt aactcatgca gtgaggcaaa    28740
gcagttatga tggttctggg tgacaagcaa gtgaagagta ttggtgagga tactaagcac    28800
gcgcatgcac tttgctacaa ctagtctgtc atgtgaactg ccatctcaca gaaacattca    28860
tacaaaaaaa agtgcagatg aatatgcaaa gctgtttgct gtagccactt tcatagcaac    28920
ggtaaataca atgtaacaga atacaatgt aacagaagac aggagagcag aaggagaagc    28980
ccatgaatct ccattcacaa atatatctgt tacataaatg aaaagggaca gatattaagt    29040
ggtcacgtag gcacctgcct gtatccttcc gccacgctac acatctttgc tctgtagttt    29100
actgagcatt aggaagttcg cgacagtatc tatatgcaga attattgaac ctctacttca    29160
acaacatgtg catgtgagct taatatttat agatgataga ggtagaaata gacatattta    29220
ctatctgaca gagtcctaac atgtagccca ggatggcttt gaattagaca tcttcctatc    29280
tccgcctcca gagtgctggt atcagtcttc ataaagactt ctatatgaaa acaaatgtcc    29340
tgttttctat gtattcgcct tcgtgtcaaa ctatactttt caagaagttc aagaagtgat    29400
gtccacaaga acctgatgtg tgtcagaaac actcagctcc ccagtgaagt tggcaggagg    29460
gctcgcctgg ttcagagaag ccttgcgtgc tccctgagtt ctgagaggag agtatcgagg    29520
ttaattctcc caggttaaat acgcaatcaa ataatgtcag ggagatgacg ggtgtgtgtc    29580
gtcctcccag accatctgtg actgtttgag taagcaaaag gattgactaa aaagctatca    29640
tttccttttc agtccctaca gtcacttttg aatcacaggt atgtttagga ggtgaggcca    29700
acaatcctga aatgtgcagg gactctccag aaagcagtca tcatcccctg gacctcgttc    29760 cttacaccg aggcgtcctg gcttgtaggt ggccttcttc aacaactgag gggtgacaag    29820
gacaaagcct gagaagacac agcctagatt gtgaagactt tgaaagattt ttatactgac    29880
```

```
tgcatgctaa aatatctttt atacgttgac tcaacaaagt acattatcag aactaatttt     29940
acttcttgtt tgccttaaaa aaaaaaaagt ggctgctgaa aattttcaaa gaaaacccgt     30000
gactcattgc atgattctcg tgatcggggc tgtggtcaat ccgcacgcag aactgcttca     30060
atccttcttg attctgtgac ctccgagacg aaaattcctc tttggttccc gcagggggtgt    30120 ttagcctcaa atttcaagtc atcctcttcc ccctagcggc cggaggagga agggctctgc     30180 atacccccagc ccgcccctag gaagccaatg tccccagcgt tttacaagtg gcgcatgccc    30240
tctgaggcaa gcctgcgagc caaagggagt gaagtggtgg cgagagctga agagatgagc     30300
aatgagccgg tggcagccag gcaggacagg gaagctggcg tggtcggatt gtgtactgat     30360
gctgttttcc agggtggccc tttccgtgtc accaggagct gtggtttcca atggggatga     30420
agtggggaca gagctgggtg gaaagcccccg ccacctcatc tggctgggct gtggttgttt    30480
gagcatcaga gcaagcttta tatccagccg atccatggtt tttgtggggg actttacatc    30540
cctaacctca ctgggtctcg ctgcgttcaa aattttaata cagttacagg gttcgagaag    30600
ctgagggctt ccaggtatta catatctatt aatgctgctg tgcgggcttg gagggaagaa    30660
cttatctcgc cctcaatgct tactctgtga tcctcaaagc aatagatgga gaccagtgta    30720
tggcacaaac tgggcacatc ctaggccatg gaccccagga cctggcacct cctctactgc    30780
attcctctaa gagctggttt aagtgggtgt gcatgaagct aatagctgca atagctgtgg    30840
gaccctcaag tcacgggtcc tggtcctggt cctccaccgt tgttttttgt ttttttggttt   30900 ttgttttttgt ttttttgtttt ttgttttttt tttttggctt tgttttgttt tgttttgttt   30960
tgttttgttt tgttttgttt tttcagctgc taatccttt aatctcttga ctagatgcct     31020
ctcctggact gcagattcct aaagagttac cgtgagcagc gcctggcaca catggcgctg    31080
gccgctatca ccatgggatt cgtctggcag gaggggggaag gccaaccccca aaaggtgagg  31140 agcaaggaga aatcaggctc tgctgaggtc cctgcacctg gaattacgac accagctcca    31200
ggttccgttg cctagttttcc aaaaatcagc ggaaggcaag aaaagagggt tagattttt    31260 ttttccattt tcttttcttt tcttttttct tttttttttt ctttttgctac ggagctgatt   31320 ttcttttaga ctaatgtcca ctttcaaaga ctccagccat tccaataata tgtgaggagc    31380
ttccttaggc cccaaggact cagaaaaacac cctgcagaat tttatacttc taaatacatt    31440
ggttattatg actttcataa ttaccccatt gtacagacat ctggggatct gtcccaagct    31500
caaggccttt gtcccagagc agcctgggga cagttgggaa agccagtttc tgagtccact    31560
gaagtagcca tccttctcca gtacaacttg gacacttcct tatttcctta ttctgcccag    31620
ctgattgctg ctttagttta ttaaccctttt gtctaactcc ctccaataac tttcagtttt   31680
cagtctgtcc ctcagagcac aaacccttttc ttctctaccc ctggaggaaa ctaatatttc    31740
ttttgagtca tggtcttaca aagcagcccc aaaccagtct agaacctgct ctcttgtcca    31800
agttgttctc caacctgtga tcttcttgcc ccggccttcc aaatgctggc attgcagtca    31860
ctccaggcac gtgacaccct gtgcagttat gctcccagtc agtgttggga tggaatccag    31920
gacctgtgtg tgccgagtga atactttatc actcaacagg acctccgttt tctcttcctt    31980 tccctaagt ttctctttcc cagaaatcaa ggtgttgaca tcattccaga atgcgtgaga    32040
agcccgaggt gtgcttcaag ggctcatctt acccacagag aaacacttga gaccaagaag    32100
caaggacagc acagagctcc tgttccttca gactctaaca cgataccata ttgtatctca    32160
tctaaaggac tcgagtgtct agggtctgct gttggaaagt ttaaacccca ggccagtgtg    32220
acagaacctc ctgatgagtt ctgctgcata ggccccctaa accaatctcc tgaattatga    32280
```

```
gttagagagg aggaagcaat gtccagcccc caaggccatc ccaggctcat caccccctcat   32340 tttggaagtc ttccctgacc ttcccagtgg aagtgtctga ctcacatctt cccattctcc   32400
ccagccctga cttctgtgga tgcttggcag agctctacgc cctgtaagct gtaactgttc   32460
tctacctaaa gcacacctct tccctaactc ggaggaagaa agaatggcag acacagatct   32520
ttagactctt cagtcctggg ctggggagac gactcagtgg gtaaattggg agcaagcagg   32580
ccgagacact gaagctaaga ttcccacaac cagtgagaaa actggcacag gcagcaggga   32640
gcaagagaga ccctgtctca aacatggtgg aaggtgtcaa ctggagtcca cacattcccc   32700
ttggcatgaa tgtgcctaca tttacgtctg tctgtctgtc tgtctgtctg tctctctgtg   32760
tctctctcac acacacacac aaacagacag agagagacag agacagggag aaatttctat   32820
tttagaagga aaatgattgg ggggaggggga acataaaaat gttcttttgt tgttgttgtt   32880
tgtttgtttg tttgtttgtt tttacacctc taccagtttg gcctttccat ggccgggacc   32940
tcatggacct gagcatctgc tctggactgt ggacagatag agatctgtac tcaagggaca   33000
ccccaaacgt tagtgggtga aagggtaggg ctatggacag gggctttgca acctgaaggg   33060
tccttggggc gtgagcgaga agcttgtgtt tcagtggagt cctgaacggg tgttaggagg   33120
ttgatgtcat accccaggtc ggaaccctag caaatcatgt taagagtcag aagagacaaa   33180
ggacggtcaa gggggggggg gtctgtcatt gagtgactac ctgacgttat ggggcttgac   33240
tcatgaggtg acacaaacat cagttctgca agctgaaatt ctctgtcctc tttatccttt   33300
ctggggtgcg ctctctatct ctctgtctct gtctctgtct gtctgtctgt ctgtctgtct   33360
gtctgtcttt ctcctatccc cccctctctc acacacacat atacacacct ctgtttttt   33420 ttatctatgt acatctttac ttctattttg catcatgtgc atctagcctt gtatctatat   33480
atagatcata tatattattt ataatctatc atccatctag aaagcacttt accttgatag   33540
ttcttagtct ttgatttaca ttaaacattt tggtgaaata attctctttc tccttttctc   33600
ctccttctcc tcctccttct ttctcctcct cttccttctc ctcctttttc tcctgtctcc   33660
tcttcttcct cctcttcctc ctcctcctct ttctcctgtc tcctcttctt cctcctcttc   33720
ctggtacagt ttccagaggt tctgtttatc atgtgcacag tgtattccat ctctgggttt   33780
tgcatctctt gaaatgtgtt ctcataacca gcattctcac cgggtctctc ccatgaagca   33840
tgtgtagggt ataggtgtgg aacattcaga gaattcgtgc ttggtctcca ggtcgcttat   33900
cacaggcaac cgtgatgatt ttctctgcca gtagaatata ctaattgtct ggattcctgt   33960
cctaaaggtg ctgccaagat ctcttgccat tccttttgtt gaggtatcca ggaacttggg   34020
actcccgcct atcctggtcc actctgacct ggtgctgaca aactggacca aaaggaaccc   34080
agaagggtaa ggagggaaag gattccttca gttagcagca gattgagaaa agactcagga   34140
cttgaactgt cttcgcagaa aagactcagg gtcttagggc tgttttatag tgagctgtgt   34200
gctcccattc atttaattta gggttccaat aaaagggaat gcacacattt aaacctgaga   34260
catttcttct tcctgggctc tcaggcacac tggcttgctg cttccagtgc ccatctggat   34320
ctcttaatca gactgtcagc ctccagctgt aataatgaca ctgggctgtt ttttctcagc   34380
atgttctgtg ttccattcaa gtcaggttag gatggggtgt ctggaggtga tctctatggt   34440
tctgaataaa tgatttcacg tgggtggaat tctgattcac accatctatt ctgtctagtt   34500
tacaccattc cacacttgtc ccgggcacaa aagcatctgt ttattgactt ttcaacaaac   34560
aaccaatcca tggaaacttc attttcacag ttgaatctgt ctcaggcggt cgacgcaagg   34620
cagcatttac ttttgttata aattaaaaca gcaaacaaga agtccaggct ggacataaag   34680
```

```
ggacctttct tggcatgctg gttgtaggta gccatgcagt gctgaaagag atggttgaga   34740
tctgctgtgg acccttcaa gagacccttc cttttaagaa ctggggaggg ctcctcttat   34800
ctacagtctg ctgagcctta gaacttcatg ctttctggga tgatgatgtc atatgacgat   34860
gatgtcatat gataatgtta catgatgtca tacgatgttg atgttgtatg gtgatgctat   34920
atgatgaatg gtatcatgat ggcatcatat gttgatgata agcttgtttg tgactgggga   34980
ctgaatgaac cttcacctgt gaggcaggag ctccacccct gttttctatc cccagccctc   35040
tcttcagcgt ttatttagat acagtttctc tcacaatgcc aaagctgacc tgaaattcac   35100
actgtagcat aagcagtccc tgacttggtg atccttagac ctcctcagcc ccttgactat   35160
ctgccactaa cagcatgcac aaccaggcct gacttggtct ttgaccaatt atacagcaac   35220
gaaaaactga tctgcattga aagctactaa atctaactta gaattggagt aggtgagatg   35280
ataaatatgt gcgcctggac tattgtgaag ctgggtttgt gattcaaggg aaattgggag   35340
atgaagtctt aagggaggtg acagggttga aaacaacccc aggaaatgaa tgtcccatca   35400
agtgaggtac agcacccaga gatgcaaatg caagcctgga gctcccccac cgtatttctt   35460
ctgagccatc atcttcctga gtcttttaag atgtctaccc agggcttatt aagtgctttg   35520
aagaaatgaa agaaatagaa gcaacacccc cccccacctc caccccacc acccaaacag    35580 ttcagtattg agacaaagta gctcttaaca caagtcaaag aacaacataa acagtatctt   35640
cagaactcca gggggaacag cagggaaagc atggtgcctg accagacgct gatgtaaggc   35700
cactcctaac aggtgggtag gattagagta actgaagtgg ggtctgcacc gagaggcagc   35760
tagagagagg caagcaagaa tgtgtacata cacagacaca cgacacgggc tgtcaagtga   35820
gatctggttt ctgctgtcac ccagtggctc actgtccatc ctaggtgggt cctgatccgt   35880
acatgtgcca gggcattgca gatgagtgtg ggagcctggg tacccgggac ctcaagaatt   35940
atatctggtt actaactaag ttgttttctt ttttttttc tttttctctt tgttatcacc   36000
aataactatt atgcgaccag accgttggaa atcaggtaag atgtgccttt agaaccaccc   36060
actgttacct ttaaaggctt gtgataaagc aagagggtgg catggtcagc tgtatggatg   36120
gaatagcatc agctgtctat gaactcctga aaattcgaag tgcattaaaa agtcaatagt   36180
ccaagcagta gctctgatgg aggttagctt ctaggggtgc agggattaat ttttcttaac   36240 cacatttcc tgtatgtcca tgatttaaaa aaaaagtgta gtgtaagaaa agaaaccgtg    36300
gctctgtgaa aactggcaga gatttcttat ttctgaagaa catcagcaaa aggccagaaa   36360
caggcaggtc acagtgacag aagggtccct ttgtaatccc ttcttacctg atgggctgga   36420
gcccttgtga gtaggtgtgg tctatagtca taggctccac cttccccggg gagcagagct   36480
agcagaggag ccagagtcac atcctgcgct ctctctctct ctctctctca cacacacaca   36540
cacacacaca cacacacaca cacacacaca caccctcctc agctctgtgg agcatacagg   36600
tggatggcaa atattcccca ggctaacacc tctgctggac cgaggagatg tgtgactcac   36660
ctccgctttg ctgttttgag gtttgaggct gggcttgct tatgtttgag atgctgggga   36720
caacgcagat gtgtgcagat actcatctgg gttctgtatc aggtcagatt tggctctgat   36780
gggaagacag gacagcagca ggttgattag aaatgacctc cctcctcctc ctcctcctct   36840
tcttcttctt cttcttcttc ttcttcttct tcttcttctt cttcttcttc ttcttcttct   36900
tcttcttctt cttcttcttc ttcttcttct tcttcttctt cttcttcttc ttccacacat   36960
tatattctat ccacagtttc tcctccccta ctcctcccag tcctcctctc acttctcctt   37020
tccctagatc tactcctact tttccaaaaa aaaaaaaaaa aaaagcaag cctcctggag    37080
```

```
ctatcctcca aacctgccct gacatagtta caaacagcag cccctcattt caaggcttga   37140
tgaggcaacc cactaggagg acaaggatcc aaagagcagg caagagtcag agacactctt   37200
ccactcccac tattcggagt tccacaggaa cacgaaacta cacacaacca caacatatga   37260
gcagacggcg taggtcacgc cgatgcaggt tctgtgattg tcacttcagt ctctgtgagc   37320
ccccatgagg tcggcttgtt tttgattccg tgggctgtgt tctcctggcg ttctcaaccc   37380
ctctgactac tgtagtctgt cctgcccctc ttctgtagcg ttcctggagc tccacctact   37440
gtttggatgt ggtaatgaca ggcttccggc cgcggttctg tggcagcaat tcatccttgg   37500
gttagaactc tagtcaggca cgcaggcaca cacccataat ggtcatagtt ctcaggtcat   37560
aggaatttgg ctctaactga tctgattttc ttcttttctt ggtctcttcc tccagtaacc   37620
tggaaaccat catctcattt ccggggggag agagcctgcg gggcttcatc ctagtgacag   37680
tcttggtgga gaaggcagca gtgcccggcc ttaaggtatc ttcttactca cccggccctc   37740
tccctatggt ggttttcccc acgtggacag acagaggcct cctcctccta gggttgacga   37800
tgaagagaca tatctgagtt ctagcctgtg gtgtcagtgc ccttttagcc tggagtgaac   37860
cgacttctcc gtctacaccc aggtaccaca cgctgagtgc aacagacacc cactgcgcta   37920
gctgttccac ttcatggacc tgcagaagct agagactcag aggtcaaaaa gaaaaagact   37980
gttttatgga aaggcagata aaggcatatc catgcatatc tgtagggatg ccagagtaga   38040
aacgactgtg atatgggaaa cccagaagga atgagaaagc acttgtgttg aggctcttga   38100
tgtcacaatt tacgctccag agatattcca gtagtgtggg ctactccgtg gcgatctgca   38160
tcccgcgggg gttttaataa aaaaagttac ttcgtagcac ctcaactgag aacgtggatc   38220
ttattcctag gccctggttc agggaatgga ggccattcgg caacacagtc aggacaccct   38280
gctagaagcc ctgcagcagc tgagactctc catccaggat atcaccagag ccttggccca   38340
aatgcatggt aagatactgg agcagcgtct ccagtggcct ggacttgggc aggtcctacg   38400
tggatgatgg tggtccatct ctccacaaga tggcgctagt gttctatatt tagcgtaaag   38460
cgtcccagtc agagaattgt ttttttttt tttttttccag tcggcagaaa tattttttt   38520 agaatcgttc tttatagttt cgtgtggttg gggtagcttc ccttctccag ggtccagata   38580
cgactttggc atgctgatct cttaacgaag cctgggagat tggatgggcc acaaggggga   38640
atgttggtta tacaggttag gcttgctggc gggcagggct gtcccgtggg ggcgtctgta   38700
aggccctcaa gagtcatttg cttttcctct ctgaccatgt tacaaatcca gaaagaccct   38760
catgatccgc tgaaggaggt ccaaggaccc ggagagctcc ccaattagac tccttccaag   38820
ccatctgatc ctgagacaaa tttctctatg tgatgacttt ttttcaaggt tttagaacta   38880
gctgtattca cacacgtggc gaaggagaag gacacgtgtc cacactttttc aaagatggca   38940 acagtatcct ccacaccatc ccatgaagcc cttagtgtgg gcacgccctc ctcgcgtctc   39000
cggatggagg atatgtccta gcctctgaaa tacttgcagt caaaataggg cactagtgag   39060
gacagtttag tccagtgttc agtgagtttt catccccagt gctgagacgc catgggaagg   39120
gcagtgttcc tggcacacaa gcaggctgac aacagcctat cagacaagga cacacagcta   39180
aggggctaag ggctgtccga tgatccttac tcagtgtggc actgaggagc ggaaacaggt   39240
cgccaccacc ttgcctctat gcaggcacct tgccagcagt acagagtcag caaggggagg   39300
cgcttgccat actataacag ttaccataaa agagagatca tgtttaaaaa caaaatcaaa   39360
cgctggaagg cataggcagg gggtcgtgcg tgtccttggc acggagtctg gtctgcatgg   39420
gctgcttttg tgtgtgattc ggagagcgtg gctgggtgga ttccctccac tcccaaaccc   39480
```

```
ccaactagat tttaccaata accaatcact gtgtttagag cccagcttca gcaagcatcc   39540
tgggtttccc tcaggacatc cttccttcct tcccaggcat gtagggtcca taaaaatgcc   39600
ttttgtggac atcggaggcc cactgcgctg caagccaagt ccccaggcct ttgcccagcc   39660
taacatagtt gtacaaataa ggtttgttta atgccatttg caagcaaaaa ttctccactg   39720
aaatatggtc ccaggactgt tcgttagctc ttacgtaaga aatgattcag gaagaacagg   39780
ttggaaatat aatcccccat actttcttct gaagttttca tcttttatac ttaagttctt   39840
aactcatcta ttatcatctg catgtgctat gagatagcaa atgaattcaa tctccctcct   39900
gcaggtaacg tccacatggt ctctccttag atttggttaa aggagcaggt tttctgcagt   39960
ggcctctgct ctttcccttt gggtgtgtct ctctgctctg ggtgcccttag gtctcttctt   40020 cctttttctct ggaaagttcc ctccctggtt ttcttcttca ggggcctggc tgtctctcgg   40080
gagccttagc aggaaccaca aaaagaaaca cagaaaccaa accctcaaat ggggacttag   40140
ttcaagctgc attaagtatg gattctgata ttatacgtgc aatttctatc acggaaggaa   40200
aacaggccaa gggactagaa gcagcataaa atattagtct gcatttcctg atgacttctt   40260
ctaactcatt tgtcacggtt gctgggtggt ctttatctgt cacatgctgt cttgacacaa   40320
ggacccctct ctggtataca ccttcattgg ctacccagtt tccctgtgtg agaattcagc   40380
atctgcattt tcatgcgcag ggttccttga gtttcttcca aaggaaggca gatgcctaaa   40440
ttctgtttta tcaacagtta tttgcattct tgtgtgtggc aaacatatct ttttatttag   40500
ttacttctgc gctgtttgtt tctacccttat agaatgaagc aggtatttaa acgttaactt   40560
ggaatccagc cctttggtaa actacattct tattgattac agcagtaatt tacagggtta   40620
gctgggtttc tatgcagaga tcttgttgct gagacgtatg cttaggttca tcattaatta   40680 tcttttttctt aaaaataatt ttccctcaca taatatatcc ttccccttttt ctcccctcag   40740 tttctgccca ccttccctcc cacccagatc caccaccttc tgtgttacac tggaaaacca   40800
acaggcttct aagggtaat aataaaataa agtaagagaa aacaaaaact atcatgttaa    40860
gttggacaag acaaacaaac agatggaaag gagcctggga aaaggcacat gcacacacac   40920
acacacacac acacacacac acacacacac caagagacaa aaagtcagct gtaagtgcac   40980
atgcatccac acactcagga taccacaaaa cactaaacca gaaatcatag catatataca   41040
aaggacctgt agggtaaaaa aaaaaaaaa aaaaaaaaa aaaagtgtgt gtgtgtgtgt     41100
gtgtgtgtgt gtgtgtgtgt gatagagaga gagagagaga gatggggggga gggagaggga   41160 gagggagagg gggagggagg agaaggagag ggagaggaag agagggagga gagggagaga   41220
gagggagaga gggagagggg gaggaggag aggaagagag ggagagaggg agagggagga   41280
gagagaggga gagagggaga ggggagggga ggagaaggag agagagaggg aggagaggag   41340 ggaggggggag gggaggggga gggagggggg aggggagggg gaggggaggg ggaggagaaa   41400
cagacagaga gagacagaca cagagatatg agacagagag acagatcctg tctagagcgc   41460
tggcgagttt tatgtgaact cagcacatat agatcatcta agaggagagc tcctcagtgc   41520
agaagaggcc ctcatagggc agggctgtgc tcaagcctgt ggggcatttt tcaattagt    41580 gattgatggg gaggacccag cccatcgtga gtggagccac ccctgggctg gtggtccagg   41640
tttctataag agagcaggct gagcaaccta tgaggatcaa gccagtaagc agcgtccctc   41700
cacggtctct gcatcagctc ctgcctccag gtgccatccc tgttggcgtt cctgtcctga   41760
gttcccttga ttaggaagca cggtgtggaa gcatacgatg gataaatgct ttgttcctca   41820
agttgcttgg gtcaggttgg ttttttcacag tgatagcaac cgtaaccaag acaacatgtg   41880
```

```
aagtaaaata aaagataaaa ataagataca ctcttgaaaa tggaggggt aggagtccct   41940 gttgtgacat tatgagagac tgaacctcca aagacgccat tttgtttgac ttctgctgca   42000
gtctagtact ggacatgcag cctgccctaa gaggtggga ccaggagggg aagcagtgat   42060
cgggatgtaa aatgaatgaa tgaatgagtg aatgaatgaa tgaatgaatg aggaaaagag   42120
tattttgttt tcccagtgag acttccttag agaaaactaa attttttgttt tcaagtagct   42180 gtcacttgga ggcagcatct gggtgagggg tgagtgctgt gtccacttct cctctcagct   42240
gtgaccctgt gtggtgcaga ccagtgaagg ccctgtgcat gctgtgactt cgttgacctt   42300
ggtgattgaa aaggccttgt tttcttggtg tccttcaccc ccccccctcc gcccaactct   42360
taatttctgt tttctctacc atatggttct ctgagcactg aggggtgggg gttgatggaa   42420
acatcaaaga ccatttataa ctgagtgttc cgaggtctct cactctctgc acactgtctg   42480
gctgtgggtc tctgcgtttg tttcctatct gctgcaggag aagcctgtc cgatggtgac   42540 ggagcaaggc gctgatctct gagaacagca gaacatcatc aagagtcatt gtgttgcgtt   42600
ttgttttttg tttttgtttt tgttttttgtt ttaaagtcaa tattatttag tttcccccct   42660
aggtccctgg gctatctagt ttcagcatgt tggtcaccca atcaatttcg ggcatgaatt   42720
ccattgtgtg gagtgggact taagtcaaat cagacgtagc ttagatgctt ctataaactt   42780
tgtacaactg cactagcata tcttgcaaac aggataccat tgtagaacaa agggtctgta   42840
actggctata cacacacaca cacacacaca cacacacaca cacacacaca catatatatt   42900
atattatata ttatatatta attatatatt tatgaatcac ttttgaaata tctaccgaat   42960
atattttata ttttcatgta aattctattg tatctatcaa catgatcact tggctttacc   43020
tttaattcat taagttgtgt aaaatagtaa tgcatacaca tcccacttcc tatgcaaagg   43080
gctggatact gtacttaaca atctggagaa gaagcaaaca tcaaagtcta ggggaggtcc   43140
cagaaaacag gctagctcag gggacacagt cgcactggtg aagaccaccc tggggagtca   43200 cacccctagaa gggagagtgt aaccatacta aggaatcaca cttgaggaga ggtgagacta   43260
ccctggggag tcacacctga gaagagaggg tgtgaccacc ctagggagtc aggaagtcac   43320
actggtgaag agtgggggtg tgggatgacc acactgagga gtcacacttg aggaagggg   43380 gtggccacac tgaggagtgt ctgaaagcat tgagactgta catctcaggt tatcagggct   43440
tcagagaaaa cagacaggga gaagagacaa gaactggatt ctgtgcgcaa agggggaaaa   43500
gcaagcagat gtgaagggtg tgctgttaga gtttatctaa agatgtttct ttcagaaata   43560
aagagatata agctttaatt tggatgaaat aaatgtggtc taatttccca gaatgtagag   43620
gaactcacta atgtagcaag attggccttt caaagcagac caaagacatt gagaattaag   43680
atagctatga tggcgtgctt ccttaggtgg aagtcctata tggaatccca tactccccaa   43740
atgtgactgg tcggtgcagc ttgggctaa cagctctgtt gacctgtggt gacccctgga   43800
aagccctgtg ggatagagga actcctggat gtcagtcatt tgctctgcct ctcttgtgaa   43860
agcagtggtc tctgtttttc ttccttctct cggcttttca tattctcttg catatcctgt   43920
ttatttgaaa tgtttcttaa aggatgctca tagtctctca ctggtggtgg tgaagtacaa   43980
aaccctgctg cacagcaaac agaggggcc agcatacgga acggattaac agccctatga   44040
gagcccacac gctcttcaag agaacattcc atctgtattt gctgctgcca ttctgggatc   44100
tgcatacatc agataggagt gggaagccct gggaaaacag cagggtccaa ggcacatgtg   44160
gccaattgct ttttgcccat ggtaaagttc acatttgatt gctttccaga ttatgtggac   44220
ccagacatat tttactcggt catccggatc ttcctctctg ggtaagtaca gcttaattgg   44280
```

```
tttcctgctt gagacctgta gagttcccca gatttgtgcg aggatagaca gacagaagct   44340
tcctaaagta agaagtatag caagtgactc aagctggcaa agtcaccacc tgggtccact   44400
ctaggaggct ggaccccaaa atgatcagaa ggaaaaaggt tccaacaaag ctgggaactt   44460
aaatccaaaa ggggcaaaag gggctgtctt cagccaccag agggagacca tggaccctct   44520
gagaacccca acgtgatgac agggggcaaaa attaaagatg ggagagagag tgggcaggga   44580
gaatgtgggg aggagatgga agggagggta gaggagagaa aggctggaaa atgatagcta   44640
cttctttgtc ccttgacctt tgaggacata gcattcaggg gacccatcag gagacaagag   44700
tccaggctgt cacctgacag aaccatcaat gccttgatct tagactccct ctccttcgga   44760
gttgtgagaa atacagtatg attgatcata ttcagcttga agtattttgc tatggtggta   44820
gcaggtaccc ttgatttgtc tcacggctat acacttctct gtctgtctgc ctacctcgca   44880 tgcccctgc tccatcaagc acatgtcttc acccagttat ttctaccttg acaagcttta   44940
accaggttgc catccaattc accaaccaac agagccgatt cactttttgaa cgtttgtgtc   45000 ttgttgactt ggaggtgccg gtgatgttat cagaagcatc caagctgtgc ctggagacag   45060
caagagacag accagatgcc gaatctatta ccattactgc caagtcccat gggagaaaa   45120 actaaagtgt gcattcgtgc atgtgtgcgt gtacgtgtgt gtctagaact gaaaatttta   45180
tttccttgca agtatcagac tagagttttc ctggcctgct aggtcctctg ttgcctctcc   45240
ccaccatgtc cccaatttga ctcctgacac agcactggca cttggcattt ttctagaatt   45300
acacattttc ctgactttc tcttgactac cgccagagga aatttctctt aaaggggctc   45360
ctgtggctgt gctcaatcta gtcggatgag tcagggaaat tcccacatta aagctaaact   45420
gatcagtggc cttaatccca tctgaaaagt cctcctgccc tgtcctgtaa taaatatatc   45480
atggtgaccg gaacagctca tagtattaag agtcctagga attcggttgg gaaccttggg   45540
gagctatttt tagaatccta ccctccagtg tctttcaaag gaatcatttc tacttcctct   45600
tggcagagac ttgataagaa ccagaagggg actttgtttg catcgacata agttccgggc   45660
aatgacactt tttatctggt atttggcata aaggccatcc ctccacttca aatgctgaga   45720
ctgtttactg tgccgctaag tggctgtaca agatcctaaa tgtagctgta gtttcaacaa   45780
acatctggat tgttgggagt ttccagtaga cttctcttta aaatgtcagc ctcgctattc   45840
tgcatctatc ccgagtttct catttgcttc tttaaaacac agttttattt aagagtggat   45900
gtcctgtgga aatgagatgt attccctcca gttcccagcc tgccacaggt ctcagagagg   45960
ccaggaacgg ggggcccagg ttgctctgca gggaaacatc gcctcatttt gttgtctgcc   46020
ttaacttcct ctttccttgg gattgctaga aatacaccag gagcaggtct aaaaataacc   46080
ttaccgtaga ggccagaatt taaaatggcc ccatcccttt acaaatggca gctcagccct   46140
acgtggagaa agaggcagtt gtgtctccca gtgctgctgg ggatggggtg taaaaacaga   46200
cccaagttca tcatctgacc tcagagctgg tgttttctgc atcaccttca gcatggctgg   46260
ctttggcgaa ggcactccag cgagtgctga aaggacattg cctgatgacg tccttggcat   46320
ttgtcatatc tgatagatcc cttaagcact ggttgtgccg tactgactga aaagctcttt   46380
tctccttcct tccttccttc cttccttcct tccttcttc cttccttcct tccaataaat   46440
ccatagtgag ggcctaccac atcctagaca ccactgtatg tgctgaaaac agcagtaaag   46500
aaaagcagtc acgtggtcct tgtggagcct gtgacttcag gatggggaga aggtattgac   46560
aaagcaaacc gaatcaaagc aaacatccaa cagtatgtgt tacaactaga ggctgcatga   46620
agcaatgccg ggtaggatgc gggctgctag ggagggacca ctgggtgtgg tggctcaggt   46680
```

```
atcttgttta ctgatatcta gaaataccac atccccagtg atatgggaac agatgtcaca   46740
ggcaatggag tgctctcaga agaagattcc tgttgtaaga ggagggaaca gttcctgtga   46800
caggaggagg gagcagacat gaagaataga cttagatgta tgtgagaagg aggatgcctg   46860
ccattgtgga ggactctcag tgtgggcagt gctgccttcc tttctgagtg gcacagtcct   46920
gtttggggct gcaggttgtc agtacccctc ctgagtgggg tagggtggca gagaacaaga   46980
ttacaaagaa agcatcagag gtggacccaa ggggaagatg ccgagatgga gatgaatgtc   47040
aaccatcttg aagatgaggg gagaggtgga gagtatacag cctgtgggtc ctgacgcctg   47100
tcacagagaa acagaaacat gtgcgtgccc ttggccgctc tggacacaga ttgcagccca   47160
tgtgctggtg tggaccaggt ccattatcca caccgtcgtc atgtctgcaa catcacttgc   47220
tcataaaata ccattctaca gtttctctag ccccgaactc ttatatttgt ttttgggttg   47280
ttcacaggcc tctttggatt ccattcaaat cctcgaacag gtgcaagaag cagattcccc   47340
tacagactag gggaactgag ggtcagaaag gctgtgcact gtagctgaga gatgagagtg   47400
gcagcaggca ttcttagcct ccagggttgc tagaacaata aatagctggt gcttaccgaa   47460
tgtctaatgt gctccagaca cctggcaaat agtatttgag tcggatctta caatgaccca   47520
taagctaagt atgaatgtca atgccaaaca tagctcttat ctcaaaggaa taagagttag   47580
tttattcttt ggccaaatat taatgcccag aaacacagat tccagttgtc ccaaattaac   47640
atgttccact ggggaaatga aggagttttc atagctcaag ggcaaagcaa gttaccaatc   47700
aaggggtttt ttgagaacac tggtgggggc cccaggcagg caagttacag caaacaagaa   47760
ctctgtacat agtcacatgc agacgggtag tggaagcctg ttgtctacta ggtcaataca   47820
ttccaaacca tcaaagatac tgggtcaggc aggacggagt taaagatagc ccattgtcgt   47880
ttgactctgg atcttcaaac tttccaactc tccacgatca atcagttttg tagaatcttt   47940
aacataggca tggcttcccc ctccctcctc ccacacaccc cagcgccacc tggaacttca   48000
gtttatacta acactactca gacaagggag ccaaggctct gagaggtccc atgtgctaac   48060
ccagggctag caaccaatgc acagtagagc ttagattctg tatctgccca gaatagagac   48120
cttgtcccac agtttgtgtg acgctccctt ctacctgtgt atccttcctt cttcttttctt   48180 atgctgtatc tcttttctga acatgacttc ctcagttggt taccattgaa attcactaat   48240
cggttgactt taaacagcca ccaaatctgg caacctggcc acttgctgtg ttggcagcct   48300
cagagcagag tctggggaaa ggtctaggat gcaggtgggg ggagctagcc tgaacacaag   48360
gcttggattg acagggagca gaaacagcca tgtaaacctg ctacttgccc tgtcaaccag   48420
gggctggttt gcttgctggc aaaagaggtc aatgtgcttc ttggcgaagg tagacatcta   48480
tgggataaag aaaagtagac tgcaacttag agatgcatgt gtgtgtgtgt gtgtgtgtgt   48540
gtgtgtgtgt gtgtgttcct ggaatgctgg gggtctggga acttagctca agtctttgat   48600
tctttaggaa agaaggtaaa aattgcctgg tcctatctac tgtcaagtgg tcggggtgag   48660
agagtgagtg tatgctcgtg tatgtatgtg agcactgcag gtgtctgcat ggtgtgccat   48720
ggtgctccac tgggcttcat gctgtgctcc cctaggcttc agtcaagtca agactaggtc   48780
aagtcatgga gggtaaacag aagagagaga gagcagaaaa tgagggacac aggaagggta   48840 gaggggggaaa gagagggttg tgaagctcac gcgtgatcag gagccccagg cttcttcttctt   48900 ccagccgccc ataggctctg gtgcccacaa cattggttac aaccccgctc tccatcatca   48960
tgcttgtcat cactgctgtg acaaaccgct taataatggt tctcacgaaa cattaaaagc   49020
caagccaagt ttaacaccctc gaacatttcc aagtgttatg gggaataaca gttaagtgtc   49080
```

-continued

```
tgggtgtgct tgtgtgtaat tgggaatctg tagtggtggg gttaccagtg tcaggccaca    49140
gtgtttgtga tgagcagagg ggtcggggtc tttctcagat cccttatctt gtcctgtcaa    49200
tggtggtgat gtaataggtg cacgcctgtg acagagctgt ttaaagcatt gtaagaccaa    49260
tgagtaaagt tcctaccctt gcttctcctt taagtgaggc agaaaaaggc tccaccatga    49320
cgtggtgtaa agatgaagtc aatctaatac ttccttggat actctagcaa gcttcattca    49380
cactttttat ttcttcctct tcctcttcct cttcctcttc ctcttcctct tcctcttccc    49440
ctcctcctct tcctcctcct cttcctcctc ctcttcctcc tcctcctctt cctccttctc    49500
ctcttcctcc tcccctccc cttccctgt gctcctcatt attattatta ttgctcctgt    49560
ctaggtggaa ggacaatcca gccatgcctg tggggctggt ctatgaaggt gttgccacag    49620
agcctctgaa gtactctgga ggaagtgcag cccagagctc cgtgcttcat gccttcgatg    49680
agttcctggg cattgagcat tgcaaggaaa gtggtgagca gcagtctgat ctcacctatg    49740
ctttgatggg acagcgaggt agactaggga gacatctcta gcaactgata aagacgggtg    49800
taaatgaaaa tgtcctgaag tttatccttg cctaagccag caggcagctg tgtgcatgtg    49860
ccctctctta cactgagtta gtcagtattg gggcatcgga tcttattagg gtcttccaac    49920
agtcctgtga cctgggttgt tcactgtcct gttggctggg gtcttttatc cgcagattcc    49980
cctttctaca atgaggtgat aatgtcacat tgaaaggcca gtctggagca gcaagtgata    50040
gtgctgaact tctctgctaa agcctttccc atgaaatggc ccagcctccc actgaatcta    50100
tgtggaccag gcgagggagc ccatcgcttt gaagccttta aaatagttgt tattgatttt    50160
tctggcagca tagagctatc ctttaatgac taccaaaaaa aaaaatattg ctaccaaact    50220
ttaatttgga tcagaaccaa aaagaattaa aactctctgg cacgaacctg ttctctggaa    50280
cagtcagggt tgtttctggg tttcagcatt tgattttagt cactgactct caacaaccaa    50340
ccaaccaaac aaacaaacaa acaaccaaac aaccaaacaa caacaacaaa acctaaccca    50400
aacaacaaca gttaaaggtg taatggtttt caagaaaaca ctgagttttc agtgtttcgg    50460
cttctctggg ttttttactaa aatacctgct taccaatgtc gtctctacgt gcacagtaac    50520
ttccatttcc tgcccccctg cccgccccc atttataagt atctagcaaa cagaattcac    50580
cagagtgttc tgtgtttgtg tgtgtgcgtg tagactcgtc tcttagtcct cagcagggaa    50640
taccacatca gtcatacaca cggagcagta gatttctgtc caactttatt atctgagaga    50700
tgtttgcttc ttttttctccc ctgtgtctcc tgtcaacaac cagaaatgaa catttgagca    50760
tttggcagct ataacaaaag cccgacaagg ctgagggaga gccctatcaa gcatttctgg    50820
tacctgagtg tttggaacag tgggcaaacc ctcccaaatg tctgcctcga gctaacgtat    50880
ttctcccggc tgtttctttc agttggcttt ctacacagaa tgagggacta catgccgcct    50940
tcccataagg ctttcctgga agatctccac gtagctcctt ctctgagaga ctacatactg    51000
gcctctggtc ctggggactg cctgatggcc tataaccagt gtgtggaggc cctgggagag    51060
ctgcgcagtt accacatcaa tgtcgtggcc agatacatta tctccgctgc caccagggcc    51120
aggagcaggg ggctaactaa tccctcaccc catgccttgg aagacagggg cactgggggt    51180
actgccatgc tgagcttctt gaagagtgtc agggagaaga ccatggaggc cctcctgtgt    51240
cctggtgctt agcagtcatg tcctgcaccc taacacttag atgttctcat cctgcatccc    51300
agcgttagag gttcacatcc tgcatcctag tgcttagctg ttcttgtgct atatcccagc    51360
gcttagcagt catgtcctgc atcctagtgc ttagcatttt atatccagca tcttagtgct    51420
tagagattca catcctgcat cctagagctt agcatttat atccagcatc cttgtgcgta    51480
```

-continued

| | |
|---|---|
| tcagctatgt tttgtatcct gcttagcagt taacatcctg catcctagta ccttatctgtt | 51540 |
| ctcatcctgc atcctagagc ttagcagtca ggtcccgtgg gagcaagaac cagggtctga | 51600 |
| gctctgtctg agcccaagca tggctttact gctttgttaa ttgtggctcc cacctccacc | 51660 |
| ccaccccagc cagtttgctt gctagaagcc tttctgcact gcctaatccc cctgcctcac | 51720 |
| agcagagagc tgcagccatg acctcctcat tcagtattag gtggacaagt cggagatacc | 51780 |
| caaactcaat tttaaaagaa tcaagttgct tttgggcat gttacttcat cttttcttac | 51840 |
| cctgggcctc ttcccttctt ccctacctcc ctcgtccctt agtctttcac ccctctctct | 51900 |
| ttctcctttt gtcaccctcc ccctcccctg cttactctct tttcccttcc ccctctcct | 51960 |
| catccctcct tccttctc cttccttttt tgtctgtgaa gcaccaggtc tgatgggcct | 52020 |
| caaactgtga tcttcctgtc tcaccctca aaggttatgt gtatgtgacg tgtgtgtgtg | 52080 |
| tgtgtgtgtg tgtgtgtgtg tgtgtgtgtt cgtttctttt gttttccct agtggagatg | 52140 |
| acacccaaag atttgcacat accaggcaat tgctccacca cctgactaca gtcccagctc | 52200 |
| tctgtattcc tgaaggaaag tcttgatgag ttgcctaggc tggtattgag ctctttagcc | 52260 |
| caggcaggcc ttagtctgag tagctgggat gtacagggat gagccactga gccatgctgc | 52320 |
| tgctgctaac gatgatgacg atgatgatga tgaagattat gataactaca gtcactgcaa | 52380 |
| taatga | 52386 |

<210> SEQ ID NO 15
<211> LENGTH: 61540
<212> TYPE: DNA
<213> ORGANISM: Homo sapiens

<400> SEQUENCE: 15

| | |
|---|---|
| ccaaaagttg tttggtagga gagggttgag gctgggagag gtggctcatg cctgtaatcc | 60 |
| cagcactttg ggaggccaag gtgggtggat ctcctgaggt caggagttcc agaccagcct | 120 |
| ggtcaacatg gtgaaacccc atctctacta aaaatacaaa aaattggcgt ggtggtgggt | 180 |
| gcctacaatc ccaattactt gggagactga ggcaggataa tcgctcgaac ctgggaggca | 240 |
| gaggttgcag tgagcagaga tcgcgccact gcactcaagc ctaaccaaca ggggcaaaac | 300 |
| tctaggacta gagctaaggt atcaaaaaaa aaaaaaaaa aaaaaagaag tagagtgttt | 360 |
| aattaaataa tttgttcttg ctgtaaaatg taaagtagat attcctcttc aaagactttc | 420 |
| ctccccgtct aattaggaat aaatagtaac ttctcttaga agcaaaattt attcaaagac | 480 |
| ctgtgctaac attcttaaat atctgctagc cacaataagg aaatcaatgt actttatgtt | 540 |
| cttagctccc acaatttagc ctaaatattt tccctggcat gtttatactg gtctaagcaa | 600 |
| gcattaggtc atagcctgtt cctcttcctt atttaaaagt gttttttacct ttctcagcgt | 660 |
| tccacaagtt acttcctcct tcctttgttc tcctctacct gtgcctcttt taaaaagttc | 720 |
| taagttgcta gccaattggg acaaatacag aatgtaaggt cccattccag ccaacggaaa | 780 |
| ctggacacag cagtagggtg gatgtgtcag gttataaatg accctgtctc ctttgtttgg | 840 |
| tgtactctag tggcaaaact gctggcaagt gtaccttttc tgcaggaagt aaaaatggcc | 900 |
| ttactaaata aattaaattt atgttcaagt gctattcttt ttttttttttt tttcgagatg | 960 |
| gaatttcact tttgttgccc agcctggagt gcaatggcgc gatctcggct cactgcaacc | 1020 |
| tccacctccc aggttcaagc aattctcctg cctcagcctc ccgagtagct gggattacag | 1080 |
| gcatgcgcca ccacgctcgg ctaatttgt attttttagta gagatggggt ttctccatga | 1140 |
| tgaggctggt ctcaaactcc tgacctcagg tgatccgcct gccttggcct tccaaagtgc | 1200 |

```
cttggccttc caaagtggcg tgagccactg cgcccagcct cgagtgctat ttctttacgg    1260
cacggaagaa caaacatttc aaacaatgct attaccaagt ttgttagtat ttattatctc    1320
atttgctaaa cctaaaaaat atatatcctt ctttaacgtg atcgaatatt tcaaaaagtt    1380
attgtgttgt ttcttaaaat aaatcaatca taatcctaga ctatgttact caaactacat    1440
acaacacctt ctgagcttct ggcaggccct tcctcccctc cctgctcacc acagatcact    1500
ggaataattg tctgcatgta acttctaatt ttgaagtggt tgtggtttat caaacctgga    1560
acatggcact tccaagtaca tgagctaagg tcacagtaag actcaagccc cttcaacaga    1620
atacctggaa tttctctgtt aaagattttc tcctttacct gactacatgt ttgtaatgca    1680
gatccctcca ggagcgctta cttataaact gtcctggatc actaacgcga cattttgatg    1740
taaattagtt tatcttgacg tgctaatggt agaaaaaaag agaacatgag gaaacttggg    1800
tgctttcagg gctggtagga aggattaaat ctttgcggca atttctgaga aggggaagga    1860
aaccttgcta acaattttga tagtttactc catttggctg gagtaactct gatccatttg    1920
tcaaattcac gatggagcag gtacctgtta gggtacaggt ttgataaacc acaaccacag    1980
gtctatttca tttctccttt tccaaagtgg aacaaatttg tctctggggt taaaactgct    2040
tttctcatat tggtgtgtaa gagaaaatga gggaatttct ttgagtttgt ttggtttgtc    2100
tgtttgttta agcagcattt tttaaataat ttactcagcc ctgtctcaga gaaagtccat    2160
gatgatctgg aattcaacct cagggaaaag ttctctcctg tgcctgagac actgcgcaac    2220
taactggaac cgaaggatgg aacctgggtg tttaatttat taggaacaat tgattcttca    2280
gtgacacttt ccatgcagat acttcaaaca aaataatgga gccccacaga ccgaatgtga    2340
agacagcagt gccattgtct ttggaaagct atcacatatc tgaagagtat ggctttcttc    2400
ttccagattc tctggtaagg atagagcctt ggtaaggata ggtcagaata tgtttcttga    2460
gatgttggtt ggtttgtttt ttaaaaatgt atgtgattat taagagacca atataaaatat    2520 caagttgttt acctgagaaa gatgctacaa agagcataga ttatcattac tatcaaaaga    2580
gaagtgacag ataccacaga gaacaggtca aatggaacat tttttgtttc agtttctttt    2640
gactagattg tcaggccaga gaaattataa gcaaacctgt agttatcaag aaaaagcatg    2700
aacttaaata taaataaaga acaaatacag agcctcagca cctggaacat ggcacttcca    2760
agtacatgag ctaaggtcac agtaagactc aagccccttc aacagagtac ctggaatttc    2820
tctgttaaag attttctcct ttgcatgact acatgtttgt aatgcagatc cccccaggag    2880
cgcttactta taaactgtcc tggatcacta tcgcgacatt ttgatgtaaa ttagtttatc    2940
ttgacttgct aatggtagaa aaaagagaa catgaggaaa cttgggtgct ttcagggctg    3000
gtaggaagga ttaaatcttt gtggcaattt ctgagaaggg gaaggaaacc ttgctaacaa    3060
acaatacctc tttcttaatt ctacttaggg ctcaaattgt aatgcaaatc tttttcatca    3120
tttagcccct ataaacactg ttttttctcat ctggtgtggt ccaaggccta gaacattaaa    3180
actatcaaag cttttacaga ccatcaggtg tcatcccccct ctttctacat ctgagctagc    3240
tgaaatccag aggaaatgac ttgctgaaag tcatgagtgg caaaagcaga actagttctg    3300
cttataactc ttgactttta gttattatta ttattaatta ttattattac atcctaaatg    3360
agggccaagg ccactcagtt aaaaatcgtg gggtccaggc caggtgcagt ggctcacgcc    3420
tataatccca gcacttttgg gaggccaagg caggtggatc acttgaggtt caggagttca    3480
agaccaggtt gatcaacatg gtgaaacccc gtctctacta aaaatacaaa aattggccag    3540
gcgtggtggc acatgcctgt agttccagct attggggagg ctgaggcagg agaatccttg    3600
```

```
aacccaggag ggggaggttg caatgagtgg agatcatgct gttgggaatg aagtttttgg   3660
tgtcacagaa aaagaatgaa catgggaaca aatgatctct cagcaaaagg acctttactt   3720
tctgcagaaa gggtgctact caatagctgt ccagccacga gagcacacca aacaaaggag   3780
acagagttat ttataacctg acgcatctac cctactgctg tgtccagctt ccattggctg   3840
gaataggacc tcacatttta cactttaccc aatcggctat tagtttaaaa cttttttaat   3900
tggataaggg aacagaacaa agaaagaaaa gcaagttgcc cagggatagt taaggaaaca   3960
tctccatata aggaatggca tgcactatgg gctgggctt ttctagttct gtacagacat    4020
gccggagcaa gctacgacag ctgatttgga cagccactaa tagtggctag caatcttata   4080
gtaagaaatt gtgacttttt ataatctttg aagaactttc ccatttctga cagtgccact   4140
gcactccagc ctgggcaaca gagcgaaac tcgtctcaaa acaaaacaaa acaaaacaaa    4200
acaaaacaaa acagctctct actcttggaa gcagcagagt ttttatcttc atttatatca   4260
ctccggtaac actcagaagt agacaagcct cagggtaggg attcagtaaa agcccactga   4320
attccacact attctttaat catagttaaa tggcaaatta ggctggaggg tggggtgga    4380 acctctccaa aattactgca atgactgcaa catcggaccc caagattttt ttttttttt    4440 ctgagataga atctctttct atcgcccagg ctggagtgca gtggcactgt gagaaatggg   4500 aatgaccgg actgtttcct ctgacactgc cactaggttg accaagtgtc cctatttgtt    4560
aggtactgga tggacgcctg acatgcaaga ctctcagtgc taaatcagga aagtgctggg   4620
acaattcgga tgagtcggtc acgctaagtt gcacttaata gctcttgtga ctttgactga   4680
attacaaaca tccctgacc ctcaattttc acatttactg gatggagatc tggtgccacc    4740
tccactagat tgctatggag aatgaatgtg aaagcatttt cataaatcca gtgtaaggac   4800
cagaagccag tcttctgacc ttgagccagt gcttgttaaa aactccactc tatacatcta   4860
acccaattca ggaatatcct gcctagttcc aaaggaagaa aagaccaaat tgctcttatt   4920
gggattaaat gcgtacactg agctgaggaa aaacagtatt acaaatgagc taaacatgac   4980
gtagatccac agttgtagaa ttcccctctt tgttctttcc tctttcataa ctacggaaac   5040
agatgagaaa catttacggc atcaggttct tgtgatgctc cctgcctgat atgctatggt   5100
tttgttaatg gaatgtccat tcctgagctt atgcagaaaa aagtcccttg ggaaagtggt   5160
tttactgtgt tatgttcatt ttccccatag ttctcaaaat gtacttcctt gtttcagttt   5220
taattttctt tcattggtgt gaccattttc aactgctccc tttctgggaa gaggtagcag   5280
acggacattt tcatcaaaat ctgccccagg ttgcttcaca gataaggagg gacccagcca   5340
ctaaaatcac caggcagagt gttgcaagag tagatagaga atcacaattg gctgccctgc   5400 tcaagggac accagatctt actttcgttt agttgaaagg caagcgtcag agtcgggagg    5460
ctgtaccttc atgtccagtg gcctcacaga agttccttca gtatctcttt tagatgaaac   5520
tcttttagaa gttccttcag tatctctttt ggtttctcac tatagatagt tacttgaaca   5580
tgtctgaaga aaacgtggtc aagacagtga ataaaaaaaa ttctggtttt gggaagcagt   5640
ctgacttagt ttcaaatatt ctatcccact gtttctgtca atgttcaaac ctttccaagc   5700
tccaacattt attgtggaaa atgtgtgcct caccaactca tgcaaataaa tgtttcatgt   5760
gccctacgtg tgtagagggg gcatggatgt gtgtttttgg agggagggct aattttctt    5820 tagacatgga gaatacgagg aaattagctt ggcatcaaga aggttacagc aggagacaag   5880
agtgaagaga actgagagag cccggaaatg aggctctgga gttcagattt ttttttttt    5940 gagatggcgt cttgtacccc aggttggagt gcaatggcaa aatctcagct cactgcaacc   6000
```

```
tccgcctccc gggttcaagc gattctcctg cctcagcctc ctgagtagct gggattacag    6060
gcatgagcca ccatgcctgg ctaattctgt agttttagta cagatggggt ttctccatgt    6120
tggtcaggct ggtctcaaac tcccaacctc aggtgatcca ccctccttgg cctcccaaag    6180
ttcaaggatt acagccatga accactgcgc ctggcctaat ttttgtattt ttagtagaga    6240
cagggtttca ccatgttggt caggctggtc ttgaactcct gacctcgtga tctgcccacc    6300
tcagcctcat gaagtgctgg gattacaggc atgagccaca gggccaggcc tggagttcag    6360
atttaacaca tcctgtaaat gacatgatgc atctgatatt tgaagagttt tcctcaaaga    6420
atgttacatg caaggtggtt tagagttgtt gtttccggct atatagcaaa agtacttggg    6480
gagttttaaa aaatactgat gccgaagctc cacctagaat agttcattca gaatctctag    6540
cataattgac ctcagtactt gaaatatgat tattataaat gttagtcaac tgcttttta    6600 ggctctatga ctgatagaaa tctttcactt ttatatcatc tccagttaat gagtcccata    6660
aattgaaatc tagtgtttaa attttactt catatttatt tttactgatt gttttattat    6720 tattatttt gagacagagt ccgctttgtc gcccaggcta gagtgcagtg acgccatctc    6780
ggctccctgc aacctccgcc tcctgggttc aaacgattct cctgcctcag cctcctgagt    6840
agctgggatt acaggagccc accaccaacc acccagct aatttttgta tttttagtag    6900
acggggtttc gccatgttgg ccaggctggt ctcgaacccc tgacctcaag tgatccaccc    6960
gcctcggccc tctgtctcaa aacaaaaaca aaaacaataa caaaacttttt ctcttctacc    7020 cgagatgttt aagtttaaat cacacctttt gtacaaaaat tccctgtctt gtccttaaaa    7080
ataatttgta atcactagct agttttgaga tcgattgcca tctaaccgaa tgccatttgt    7140
tctctctctc tagtttcaac ttaataaccc tttctgcatt ttctattctt tcaaaattt    7200 tccggccatt ttattgtttc tatttagtga aaatttattc actggtttct atgcctaagg    7260
gcatttagga agttgcttag gatacagacg tgataaaaag accagtgtaa aaactctcca    7320
ctcctagaca ttatattcta gtcctcatct cctgtcattt aagtcctcag tgattctatg    7380
cacttttgct tttggtttgg gcagatgctc tgagtttaat gtttctctga gatgaggacc    7440
ccctattcaa ctcacaaatc ccataaggag gcctctgtgc ctttgctggt gccccagaca    7500
gggtgctgat gcttacttat cttcaagatt gtgaagtcag atttaatagt atagtcgttt    7560
gccagagctg ctgtaacagt agccacaaac agttgggctt aaaataccac aaacaggagg    7620
gcttaaatca cagaagttga ttttctcaca gttcttgagg caggaagtcc aagatcaagg    7680
tgtcgtggag ttggtttctt ctgatgtctt gctccttggc ttgtagatgg cctccttatt    7740
attgtgtcct cacatggtct tttctccact atgcacaaat tccctatgtc tctctctctt    7800
tttttttttt tttttttttt ttgagacaga gttgcactct gtcacccagg ctggagtgca    7860
gtggtgcaat ctcggctcac tgcaaccttt gcctcccggg ttcaagcaat tctcctgcct    7920
cagtctcctg aatagctggt attacaggtg cgcaccacaa agcccagcta atttttgta    7980 tttttagtag agatagggtt tcgctatttt ggtcaggttg gttttgaact cctggcctca    8040
agtgatccgc gcacctcggc ctctcaaagt gctaggatta caggcataag ctactgtgcc    8100
cagtctcccc ctgtctcttt gtgtccaaat ttcctcttct ttagggacac caatcagatt    8160
aaattggacc cacctaaag gcctcatttc aatgtacctc cttcaagggc ctatctccaa    8220
atacagttat attttaggt actagggcta gggcttcagc ataggaattt gggggagaca    8280
caatttagca catagcagaa aatataaggc caggaaaaaa tattctggca tgctagatgg    8340
actcattaac aaatattaac caatataaac caattaacaa atatttcttt aatatttgcc    8400
```

```
tttttttttt ttttttttg aaacagagtt tcactcttgt tgcctaggct ggagtgcagt   8460
ggcacgttct tggctcactg aaacctctgc ctcctgggtt caagtgattc tcctgcctca   8520
tcctcccaag tagctgggat tacaggtgcg ggccatcaca cccggcttat tttttgtatt   8580
tttagtagag atggggtttc actatgttgg ccaggctggt ctcgaacttc tgacctcagg   8640
tgatccacct gccttggcat ctgaaaatgc tggggttaca ggttgcctgg tgattttaa    8700
gaggaatgac tgagctctca tgccaggtgg ggggagggga cagagaaagt tgaatactct   8760
gacgatagcc atgatccata gctctgaagc ttagactcga atctacccat cccgcaagga   8820
agaaaacaaa gaaataaaaa agaagaaaag aaatctccca atgtcaggtc ccaccctctt   8880
tagaagtaat ttcagcaaaa ctttgttgct attttggcat gtcctctact gtagtagctt   8940
gtcaaaatac tgtccccaaa cgttttctat atttctagat tttactgttt aatgtataat   9000
aataatgttc taacattaaa acgtaaccat agcaatgctc cgactcactt gatctttaaa   9060
tatattgttg aactcaattt tgtgacatct tcagaattgt cttttgtat tcataaatag    9120
caacagtgga tagttgcctt ggttagtgtt attatttcaa ggattaatct ttaggttacg   9180
ttttcttcat aagatgcatt agatgacttt ttttttttt ttttgagac agagtcttgc     9240
tctgttgctc agactggagt gcagtggtgc agtctcagct cactgcaatc tccacctcct   9300
ggctcaagag agtctctcga ctcagcctcc tgagtagctg ggattacagg cacgcaccac   9360
catgcctggc taattttgt atccttttta gtaaagacgg gatttcccca tgttggccag    9420
gctgatctcc aactcctgac ctcaagtgat ccatctggct tggcctccca aagtgctggg   9480
attacaggca tgagccacca cacgcagcca attagatgcc ttctcatgct tttctgtgtt   9540
gtgaaacaga tcatctatcc gttgatatag catagctctt cagactacag acattttagg   9600
ctataagttt tgaattacat tttctattcc ctttatgctt cttgttctag ttaggtttt    9660
tatttctaaa taaaaatatg aattttgca atttcccaaa tgcgaactca actgaaattt    9720
tcaagtgtat tagcaaaatt tattcatagc agcctcttac atttcattaa gaattgattt   9780
tttcttattc cctgttgaag tttgtttata aaatatagta atagtaataa ctatatagaa   9840
agtgttcact ttgtagtagg ccctatgtta actttaacta cactttttaa atctaagcct   9900
catagtagtc ttggatggat gcggtggctc acgcctgtaa ccccagcact tgggaggct    9960
gaggcgggtg gatcacgatg tcaggagttc aagaccagcc tggccaacat ggtgacactg   10020
tctctactaa aaagacaaaa atcagccgga cgtggtggta tacacctgta gtcccagcta   10080
tttgggatgc tgagtcagga gaattgcttg aacccaggtg gtggaggttg cagtgaaccg   10140
agatcacaca agtgcactct agcctggatg acagagtgag actccatctc aaaaaaaaaa   10200
aaaaaaaaa aaagagatca ataaataaaa taaataaata atcctcacaa tagtcttcac    10260
catttgcaaa tgatccattt gacaataaat gaattcagca ctatcatgga aatatatttc   10320
caagctgacc agttttctcc atttccaccc cacttcaatc caccttcatg tagccctagg   10380
actattgtct cctccccttg tttccttatt tccattcctg ttcagctgta acacattctg   10440
ttcatagcag tcaagtgatg cttacaaatg gaaatcaggc tagaggtggt agttcacacc   10500
tataattcca gcattttggg aggctgaggc aggaggatca catgaggcca ggagtttgag   10560
accagcctgg gcaacatagc gagacccat ctctacaaaa ataaaaaga attagctgtg     10620
catgatccta tgtgcctgtg ttccagctac ttgggaggct gaggtgggaa gattgcttga   10680
cccagggagt ttgaggctgc aataagctat atttgtacca ctacactcca gtgtgggtga   10740
cagagtgaga tcctgtctct aaaaaacgta aaatgaaaat aaaaccttga tagtttgctc   10800
```

```
tttaaaactc ttcctacagg gcccctgtga tgctcacctg tctctagaag ggcatgtaat   10860
agctctttct ccttcacttt actttgatgc aatgtcagaa cagcttcttt ccatcaaaac   10920
ttaaaccttt gatttcattt aaaatcatct gcttcaaatt ctaatctttc tgatagttta   10980
ggttctaatt tttctgatgt taatattgtc acccaagttt cctgttcata tttacctggt   11040
ttattttatt tttattttta tttatgtatt tgagatggag tctagctctg tcacccaggc   11100
tggagtgcag tggtgcgatc tcagctcact gcaaccttcg cctcctgggt tcacgccatt   11160
ctcctgcctc agcctcccga gtagctggga ttacagggac cgccaccat gcccggctca    11220
tttttttgtat ttctactaga gacgtggttt caccgtgtta gccaggatgg tcttgatctc   11280
ctgacctcgt gatctgcccg catcggcctc ctagagtgct gggattacag gcgtgagcca   11340
ccgcgcccag actttatttt atttttttgag acgaagtctt gctctcttcc ccaggctgga   11400
gtgcagtggc ttgatctcag ctcactgcaa cctctgcctc ccaggttcag gcgattctcc   11460
cgcctctgcc tcccaggttc aggcgattct cccgcctcag cctcccgaac agctggggtt   11520
acagatgcct gctaccacac ccagctaatt ttttctttt tttggagaca gtctcactct    11580
gtcgcccagg ctggagtgca ctggcgtgat ctcagctcac tgcaacctcc gcctcctggg   11640
ttcaagcgat tctcctgcat caacctccta gtagctggg attacagacg tctgccacca    11700
catcaaacta atttttgtat ttttagtagc tgagattata ggctcgtgtc accacgcctg   11760
gctaattttt gtattttag tagagacggg gtttcaccat gatggccagg ctcgtcttga    11820
acctctgacc tcaagtgatc tgcccatctc agcctcccaa agtgctggga ttacaggtgt   11880
gagccactgg gcctggcacc tggtttattt ttgtgcatgc ttttatttt aattttccta    11940
tgctactttc ttagccaaaa tttatactta atctaatcaa gcattaatct aacaaagagt   12000
ttagtgttca tataaaatac agttttacaa atctgttttt ctttaaatta taaatttgtt   12060
aagaaaatta tccaaagaat gatccagaaa caaagaatg gctgtgtgtc ttttcaatat    12120
catcctggag cattgtctca accatctcac tttacggtga ctaaaacatc tagaggtttt   12180
cccttttgttt tctgtacttc ttagtattga ttaatactgt tgtgctactt cagtctgaag   12240
ttccatgtta atctgtagat ttttttttttt tttttgaga cagtgtctcg ctctgtcgcc   12300
caggctggag tgcagtggtg cgattggctc actgcaagct ctgcctccca ggttcaggcc   12360
attctcctgc cttagcctcc cgagtagctg ggactacagg tgcccgccac cacgctgggc   12420
taatttttc tatttttttt tttaggagag acggggtttc accgtgttag ccaggatggt   12480
cttgatctcc tgacttcgtg atctgcctac cttggcctcc caaagtgctg ggattacagg   12540
cgtgagccac tgtgcccggc tgttaatttg tagattttta tacagaaaag cagcaaaata   12600
tttctgttga gtagaaaata taactccaat gcttatgact gtattcctta taggacacta   12660
actcattatg tgtctaacct agcaatttta tgtcaacact attttctcaa acctctataa   12720
actttggctg gcacagtgg tcacacctg taatcttagc actttgagag gctgaggcag     12780
gtggatcacc ttaggtcagg agttcaagac aaggctggcc aacatggcaa aaccccatct   12840
ctactaaaga tacaaaaaat tagccaggca tggtgacatg cccctgtaat cccagctact   12900
caggaggctg aggcaggaga atctcttgaa ctcaggaggt ggagccaaga tcatgccact   12960
gcattccagc ctgagcaata gggtgaaact gtgcctcaaa atgaataaat aaaataaata   13020
aataagtcag agattgtgaa taggatgttg gatatacccca agttatgaat taattaggag   13080
cttgaaccca ggaggcagag gttgcagtga gctgagatcg caccactgca ctttagcctg   13140
agcgatagag tgaaactgtg tctcaatcaa tcaatcaatc agagattgtg agtaggatgt   13200
```

```
tggatgtacc caagttatga attaattagg agcttgaacc caggtttgtc tcagatcctc   13260
agggactgaa gacttccaag tgaattatgg gtaatgtata ggtctatact actccaaatt   13320
tacagttttc agacttccct gggttctcat ggaccttcca tgtcatttct atgtttaggt   13380
tgaggtccct ggtcttttct cctctgtaat taatttcaca cccaccccta tctcaactca   13440
cacaacttga tcttcactcc catctgctaa gaaattgagt ccataaaaag tgaactcctt   13500
taaactctag atcttctact gctgcaagga cagacattcc attctggctc tctctctcct   13560
cctttgcttc ttccagtcct tgctccttc tgcattctgt tactctcctc tctcctttgt    13620
cttcaatctc tccctcttgc aatagccaac tataaactgc tcaagcttct cattcttaaa   13680
agatctctct gaaatgcaaa ttccctactg ccttatggct ctccttcaaa agtaatctac   13740
attttctcta ttttctaatt cctcaacaca ctaacgtttg aaccctgctt ctatgaccct   13800
gacctaaatt tctattaaat gtacatagat aaactaatat atatttgtga cttcctaata   13860
ttgttttgtt ttttaaagag gtcaatctta ctttaactct gtaatgatgc ggttgacctt   13920
ctgatgattc tctacttctg tgaaatcctc tactgtcttg acttttaat taatttattt     13980 ttttttgaga cggagtctcg ctctgttgcc caggatggag tgcagtggca caatctcggc   14040
tcactgcaag ctccacctcc cgggttcatg ccattctcct gcctcagcct cccgagtagc   14100
tgggactaca ggtgcccgcc aacacgccca gctaattttt ttgtattttt agtagagacg   14160
gggtttcacc gtgttagcca ggatggtctt gatctcctga cctcgtgatc tgcctgcatt   14220
ggcctcccaa agagttggga ttataggcgt gagccaccgc acctggccct actgtcttga   14280
cttttatagg gtcattctat tcaagctcat tgagcgtctg tcactatgtt tttgatctgt   14340
attgctggaa tcagttcctc tatctgcctt gtgaatattc tccattgtgc taatctaggc   14400 ttctccttc attttcata ttccctcaca tggctttata cactcttgtg gttttaacca     14460
caatataggg ttttttactgt agttatgctt tcaaattgta tacttctttt ttttttttt     14520 ttttgaaatg gagtgttact ctgttactcc agtctggagt gcagtggtac gatcttggct   14580
cactgcaact ttcgcctccc aggttcaagc gattctccta catcagcctc ccgagtagct   14640
gggattacag gcatgtgcca acacgcctgc ctaatttttt attttttagta gagacaggat    14700 ttcaccatgt tggtcaagcc cgtcacaaac tcctgacctt aggtgatccg ccctcctcgg   14760 cctcccaag tgctgaaatt acaggtatga gccatcgtgc ccagcccaa ttgtatgttt      14820 ctaatatgac ttttctcctg aactttaaac tgtgtatcca acttctcagc acagtcatat   14880
cttttgattc cacaggtaat ttaatgtcaa tatatttaaa aatgaattta ccacctttat    14940
ccccactctt tgactttcac ctgcattct gtttcaattc ttgtttccat ccattcattt     15000
gctcacctaa ttcataaaca tggaaatcat cctcaattcc tcttcttctt agcccaaaaa   15060
ttcaattgtg caggttatgc actgagaaaa agagcctcag gttagggga taaatcagag     15120 attggtgaac tttttctgaa gggccaaata ctaactgctt taagcttgct taccatatgg   15180
tttatgttgc aactaccaac tctcctgctg taatgtaaaa gcaaccatag atagcatgta    15240
aacaaatgag acaggctggg tgccaatgaa aattcacgaa aattaatgta gtttactgtc   15300
ccttgggtga gagttggggg tcactgaaat tcggactatg tcttacttgg ctaaaccaca   15360
ggcctagagt gggccataaa tggagctatt gggctagtga ttttcttgcc ttaagccccc   15420
agccccaaat ttaataatca catcatttta atttcatttt ccaagtgtat ctttaatata    15480
tggcttctcc tttccaaatt cactgtcatt acctaagttt agtccttgaa caatatttta   15540
aaggcttcct tatctgactt tatatcttaa agtcctacaa atttatcttc ctaaaattca   15600
```

```
aatcaaacca tgtcaccaac ttacagaaag ggaaaattca tatattctac acacagcaca   15660
tttcatgtaa ctttctaggc tcatctttca tcatccttt gatgcaggat tttctgctcc    15720
tcagctcagc gaaatccagg atcttgtctc atgaccagga agaattaggc aggtggacat   15780
agtgaagggt gaggatgacg gaatttatta agcaaaaggg gagttctctg caaagagagg   15840
ggtttcacca gcagtctccc acctcacaat ggagcaccag gactttcaca cacaaactga   15900
aaaggctagg ctcctcccca gcataaggca tgaattcctg gtggttccac cagttttcct   15960
actatgcatg tgggtgtgcc caagcaaacc ataggtagta tcagaaaagg caacatttga   16020
ttggttaaaa ggcattattc acccaagcaa accataggta gtatcagaaa aggcaacatt   16080
tgattggtta aaaggcatta ttcagaaaga atcaatcggg aaagggtgag ccaataggggg  16140 aagttctccc tctgggtcac gggtttcatc tgggaccagg agtctggcct ttcagccttt   16200
agactgtttt aggcttgaag gtgggtttca cagggaccct tccctatctg cctaggcatc   16260
tgtctgcctc ctgcctctat cactttctct tgagttttat attttagcaa cactgagtca   16320
tctttgtccc aggaagcacc tacatctgtt tatctgctgt cccctctacc tttactacct   16380
tcccttcttc acatttatac ccagaaaagt cacttcccct ccaaaaattg ggatcaactg   16440
tcatattttt atgaatattt cactttaatt cctcacaaca gctgacagaa ttaactactt   16500
cctcttcttt gcaagttatt tggctcacac agatatcagt aattaaacat attttactgc   16560
attggcatat atctgactaa tgtgttttc tcccgtacta ggcaatatgc tccttagtca    16620
tctgtgtatc tgaggtgagc acagggccta actagcatat ggtgcattct caatgttcgt   16680
tcaactgcat tgacttgaat tccctgaag actgaaatgt gaaaatagct actctcggaa    16740 gccccttcc agagaggtct aaaatattta catgtttcta ttttaaatgc agaaagaact    16800
tccagatcat tataggcctt ggatggaaat tgccaacaaa cttcctcaat tgattgatgc   16860
tcaccagctt caagctcatg tggacaaggt attcttctct tcacccctc atcacattct    16920 gttttcatca tcataccact tttctttctt agccttgtgg aagtgtgtca attgtcctgg   16980
gaaactgttc attaccattg aacttatcag caaagctata tcttccttcc tgaaaaacag   17040
aatgacccct tcgtaatctg atacatgtgt tttcctaagg ttttcagagc cagcacaaaa   17100
caatgcctga cacatgccaa taactcacca aatgttgtt taaagaagaa tctgggtggg    17160
aatgataaac taactaatgg acaaggtatc gcctaagaag gtcagcttgg aaattctcag   17220
gttcctcatt ccatgtacgt actcaaggct ctgttgttac tgaggggtc taacttgatt    17280 ttgtcctagg tgttatagaa tagttaaatg gagggaattt ctgaattata aaattggcca   17340
tgggttctac aaaacatcca ataagcctgt aaattccaca aaagtgttga ttaggctgat   17400
acaaaggtaa ttgcagtttt tgccattact tttaatgaca aaaaccacaa acactttgt    17460 accaacctaa tagctatgta accctgaaaa agttactcaa ctctgtaatc ccatttcctt   17520
atttataaaa tgagagaaac tctggtctca cagtattgtt atgggaagta aatcactttc   17580
aaagtggccc ttttgtagtt cttgtcctat aatagcattc agtatacatt cattacttct   17640
ctgtagtctc ttctccatct gtcctaatct atcagtttgg agtaccacat aattgcggaa   17700
gtccatgaaa agttttccgc tctccaaaat ttcccttgc tgatggataa tatttaatgt    17760
ctagaattac aaattctttt taaaatactc attgaatgtt gctttgtgc aaagcactag    17820 aaccttgtaa aagatgagta agggactggc ttcaatgtct gtgaagatag caaactaaac   17880
agagtaattt ctttgcctga tagataaaat gttgtgttga catgaccaaa gaaatccaaa   17940
aataagaaaa aaactatctg taaacacaga aaaatagaga aaagttccaa tgatggaata   18000
```

```
aaaatttaaa ggattttttt gaacgtatta agcaaatcat gtataaaatc cagaaataag   18060
tttacaggac ccatgtcaag gatttaacca aagcagaggg agatccccat gagtcccctt   18120
ttcccatctc agaatagcag agaagagaag caagggaagc ctggaacagt tggcaagagg   18180
gcaggttaga attcagtttg tgaattatga ggtcgtctgc cgtaggcatt taccaggctt   18240
tatttgattt aactgccata aaggaagaga aggacttgtt aaattggggc tcctcttagc   18300
acagcattga aaccagtccc tattccttct tggccttttg gctaaaattg agtgtgaaat   18360
ctatcaccta acatttgtac tgggtttagg ctgggtgtgg tggctcacgc ctgtaatcct   18420
agcactttgg gaggccaagg ctggcggatt gcctgagctc aggagttcga gaccagcctg   18480
agaaacatgg tgaaaccatg tctctactaa aaatagaaaa aattagcagg gtatggtggc   18540
acatgcctgt agtcccagct atttgggagg ctggggcaga agaatcactt gaacccagga   18600
gacagaggtt gcagttagct gagatcacac cactgaactc tagcctgggc cacagagtga   18660
gactctgtct caaaaaacaa aacaaaacaa acaaacaaat atatatatat taaaatacaa   18720 attttactg ggtttaatag tgtcttccta gaagtcatgt tcatgcataa tctgtgaaag   18780
tggtcttatt tggaaatagg gtgtgtacag ttgtattcga gttaagctga ggtgatactg   18840
gattaaattg tatatgatga gtgtccttat aagaagagga aaattaaac acaggaacat   18900 agactcaagg gaaaacatca cgtgaagatg gaggtagaat tggaatgatg cattgacaag   18960
ccaagatgtg ccaaggattg ctggcagtca ccaggagtta ggagacaggc atggaacaga   19020
atggaacaaa ttctccctca gaggctccag aagaaatcaa ccctattgat accttaattt   19080
gggacttcta tcttccataa ctgtggcaga gtacatttct gctatttaa gtcatgatgt   19140 ttgtggtcat tagttatggc agcgcataaa actaacacaa cactcttggt ctctatcgct   19200 tcttttttt ttttttttt ttgagacaga gtctcactct gtctcccagg ctggaatgca   19260
gtggtgcaat cttggctcac tgcaacctcc agctcccagg ttcaagcaat tctcctgcct   19320
cagcctcctg agtagctggg actacaggca cccgccacca tgcccatgta atttttgtat   19380
ttgtagtaga cacggggttt caccatattg gccaggctgg tctcgaactc ctaaccttgt   19440
gatccaccag cctcagcctc ccaaagccct gggattacag gcctgagcca ccatgcacgg   19500
cctctatccc tactcttaat tgcctggaaa atacctaaca aatgaaggcc agttttttaga   19560 ctttaccacc aaaggctgaa attgaaacag gaattgtttg tgagaagcaa acacaatagt   19620
ttcgagagac tgaatcagtt agcaatttcc tgtgagaggc aaatgtaata gtttctagaa   19680
ccacagatgg agctataaca aaaacatgtg ttctctggat cctttacttg ctacagacaa   19740
cacaataagt gaatttacag ctttgatctt acagtgcacc taagccaacc accttgtctt   19800
agaatgtctc aacatacctc tctgtatctt gaaacaaat atattaattg ccttagaccc   19860
attcactcac atttcctagg aagacatgat cagagggagc tatgcaagaa gaaatccagc   19920
agaactctgg aaatacaata agaaaatcca tattagacac taatcttaat aaaactaacc   19980
ttcgttcatg aatttgaata gacaaaatta ccaaataata tggaaaaaat gggcaactca   20040
aaaagaagag ggtagcccac ttggcattca ggaccaatgg cctccaataa ataagatgat   20100
attagtgctt taaatatttt atttagtgta tccagtatat tgccttccta aattaagtga   20160
aagctgatat ataaaaagaa ctattagaaa taaaaaacca cacacatccc agaactcctc   20220
aatataaacc taacaaattc agtaaaacat tgattgcaaa aaatatatat agtgacttag   20280
ggacttcctt gataaatttc ataaagcata agaaaaatc aaagagtgca aaccatcaga   20340
aaaatacaaa tatataaaaa agagaaatac aggtgatcca aattccttt aatggaatcc   20400
```

```
cataagcaga tgggtggagg aaaagtaaaa cttccaacat ataagcacaa aattttaga   20460 ccttaagaaa tatttgagtt ttttatatca gaaagacagt gttggggtga gggttggggg   20520
gcacatgtaa atactcagat aaaattgtga attttctagg gtaaagaaat ctgcatattc   20580
atagaaaaca aaaatgaaaa atagtttatt tacagagtaa atacatacga ctgtttacct   20640
gtaatgctaa atattaaaag acagtttctt ttcttttttt tgagacagag tttcactctt   20700
gtcgcccagg ctggagtgca gtggtgctat atcgactcac tgcaacctct gcctctgggt   20760
tcaagcaatt gtcctgcctc agcttcccga gtagctggga ttacaggcac ccgccaccac   20820
acccagctca tttttgtatt tttattagag acggggtttc accatgttgg ccaggctggt   20880
ctcaaactcc tgacctcagg tgatccaccc gccttggcct cccaaagtgc tgggattaca   20940
ggcgtgagcc accgtgctgg cctaaaagac aatttcatac ctatttgtat ggctaatttt   21000
ttaaaaatct ggccatatca aaatactgaa gaggacgtat agcaatagag actttcattc   21060
attgctggtt gaaatgcaaa atggtacagc cagtttgaaa actagcttgg cagattctta   21120
taaaatgaaa catagattta ccatgcaact cagcaatggc attcctaagc atttatccaa   21180
gtaaatggaa aatgtatgtt cccagaaaaa aaatccatat atgaatgttt ataacagctt   21240
tattcataat caccaaaaaa aaaaaaaaat ctggaagaaa acaggatatc cttcaaccgg   21300
ggaatgaata aaccaaatta taataattgt aaattgtggg atggatagtg gaatagtatt   21360
cagcgataca aatgattgag caattaattt gtgcaatgac agggatgaac cttaaataca   21420
tttacctaaa tgaaagatgt caggcctata ttgtatgatt cttttcaaat gacttttag   21480 aaagggcaaa actagaagga ttaaatatag ctttatggtt actagagaca ggtaaggagt   21540
gggtagttga ctgcaaaggt aatatatagg ggaatgttta gcatgatgaa actgttttat   21600
atggcactca ggtgatggat atatggctct aggcactgaa aaacccatgg aattgtatgt   21660
cacaaagaat ggactttcat gtatgcaaat tttaaaaaat aaaccagaaa attgggagaa   21720
tactaggatg gaatgcagac tgtgataaat aaaactaact ggactctcag caaactaaca   21780
caggaacaga acaccaaaca ccgcatgttc ttacttataa gtgggagttg aacaatgaga   21840
acacaaggac acagagaggg gaacatcaca caccgggggcc tgttgtgggg tggggggcta   21900
ggggagggag agcattagga caaataccta aagcatgagg ggcttaaaac ctagatgatg   21960
ggttgacagg cgcagcaaac caccatggca catgtataca tatgtaacaa accagcacat   22020
tctgcacatg tatcccagaa cttaaagcaa attttttaaaa aagtaaaaaa aaaaaaaaca   22080
aacaacaaca cctaactgga ctacaaatgc actatataac ttcgatgaag agagtgggga   22140
gtagggaaag gaacggactt aaattactcc agaaaatagt gttgtgttgt gactagaatc   22200
tataaggctt acggtaaatg aaactttaca ggatcactat actctaattg gtaaatcagt   22260
ttttcatggg gtgcgggtga acagttgtga aactgcttta catgtagtca tacctttgca   22320
ttttgcagat atttcaattt ttacaaattg aagattcgta gcaaccttgc atcaagcaag   22380
tctgtcaacc ccattttcc aatagtgtgt acgcatttgg tgtctgtgtg tcatattttg   22440
ataattataa caatagttaa aacttttct ttactattac atctgttaca gtgatctgtg   22500
atcagtgatc tttaatgtta ctatcataat cgttttgaag gtgccataaa ctgtgcccct   22560
ataagtcctg aaacttaatt gataaatgta tgtgttctga ctgctccact gaccagccat   22620
tgccccatct ctctcccct cctcaggcct cctgatttcc tgagacataa taatattgaa   22680
attaggccaa ttaataatcc tacaatggcc tctaagtgtt caagtgaaag gagttgcatg   22740
tctctcactt taaaaatcta aaactagagg ctggtcatgg tggctcaggc ctctaatccc   22800
```

```
agcactttgg gaagccaagg cggggagatc acctgagttc aggacttcga gaccagcctg   22860
gccaacatgg cgaaactctg tcttgactaa aaatgcaaaa attagccagg catggtggtg   22920
cacacctgta atcctagcta ctcaggagac tgaggcagaa caatcgtttg aaccctggaa   22980
atggaggttg cagtgagcct agattgtgcg attgcactcc agccagggca acaagagtaa   23040
aactccttct caaaaaaaaa aaaaaaaata tctaaagcta gaaatgatta agcttggtga   23100
gaaagtcatg tcaaaaccag ataggcttaa agctgggcct cttttgccaa acagccaagc   23160
tgggagtgca aaggaaaagc ttttgaagaa aattaaaagt gctactccag tgaacatacg   23220
aatgataaga aagcaaaaga gccttattgc tggtatagag aagtttgag tattttggat    23280 agaagatcaa accagccaca acttccctta aaccaaagcc taattcaaag aaaggcccta   23340
attctcttca attctacaaa gtctgagagg gctgaagaag ctgtagtaaa aaagttttaa   23400
accagcagaa tctggttcat gaagtatgag gctagaagcc atctccacaa cataaaagtg   23460
caaggtgaag cagcaagtgc tgatggagaa gctgcagcta attatccaga agatccagct   23520
aaaatcatca atgaaggtgg ctacatttat tttttatttt tgttatttat taatttattt   23580
attttgagac aaagtcttgc tctgtccccc aggctggagt gtggtggcat gatgttggct   23640
cactgcaacc tccacctcct aggttcaagc aattctcctg cctcagcctt cccagtacct   23700
gggattacag gcatctgcca caacgcctga ctaattttg tatctttggt agagacgggg    23760
tttcaccaca ttggccaggc tggtcttgaa ctcctgacct caggtgatcc acccgccttg   23820
gcctcccaaa gagctggatt acaggcatga gccaccacgc ctggccagtg gctacattta   23880
aaaataggtg ttcaatgcag acaaaaccat cttttattgg aagaagattc caaccaggac   23940
tttttttttt ttttttttt tgagacagag tctcactctg tcgccaggct ggagtgcagt    24000
gatgcgatct cagctcactg caatctctgc ctcccgggtt caagtgtttc cctgcctca    24060 gcctcctgag tagctgggac tacaggcacg tgccaccatg cccagctaat ttttgcagtt   24120
ttagtagaga cgggttttca ccatgttggc caagatggtc tctatctctg acctcgtgat   24180 ccaccccccct tggcctccca aagtgctggg attacaggtg tgagccactg cgccggccc    24240 aggactttca tagttagaaa aaagtcaatg cctagcttga aaggacaggc tgactctctt   24300
gttaggggct agtgcagctg gtgactttaa gttgaagcca gtgctcattt accattcctg   24360
aaatcttagg gcccttacca gctatgctaa atctactctg cctgtgctct gtaaacggac   24420
aataaggcct ggatgatggc atatctattt acagcatgct ttactgaata ctttaagctc   24480
actgttgcga cctactgctc agaaaaaaat attcctttca aaatattact gcttattaac   24540
aatgcctctg gtcacccaag agctctactg gagatataca ggaaataaat gttgttttca   24600
tgtctgctaa cacatttgtt ctgcaaccta tggatcaagg ggtcattttg gctttcaagt   24660
cttattattt aagaactata ctttgtaagg ctattcctga cacagataat gatccctctg   24720
aagaatctgg gcaaagtcaa atggaaacct ggaaaggatt cactattcta gatactatta   24780
aaagcattca tgattcatgg aggacgtcaa aataaaaaca ttaataggag tttgcaagaa   24840
gtcaaccctc atggatgact ttgaggggtt caagacttga gcagaggaag tcactggaga   24900
tgtcgcagaa atagtatgag aactaaaatt agaagtggaa tctgatttta aactgagtt    24960 gctgcaatct tacgattgaa cttttctttt cttttttttt tgagatgccc ctgctgagct   25020
gccagttcct gaagggtcac cgggagcagc gcctggccca cctggtcctg agcttcctca   25080
ccatgggtta tgtctggcag gaaggagagg cgcagcctgc agaggtgagg gccagagagc   25140
agcttctcct gttacccggc aggttacctg cgcctggagt aacgtgctcc ctgcttggtg   25200
```

```
ctaccctgtt ttcctggaaa atgggtactt tcttcttctc gatgggcatc agtttaagca   25260
acgatgaagg gctcatttat tatttattat tattatttt ttattttatt ttgagccagt    25320
ctcactctgt cactcaggct ggagggcagt ggggtgatct tggctcactg caacctcccc   25380
ttccaggttc aagcaattct cctgcctcag cctttcttgt agctgagact acaggcaccc   25440
accaccacac ctggctaatt tttgtatttt tagtagagat gggtttcacc atgttgccca   25500
ggctggtctc gaactcttga cctcaggtaa tctgcctgcc tgggcttccc acagtgctgg   25560
gattataggc gtgagccact gcgttcagcc tgaagggcca tttaaatgaa ggattttttt   25620 atttaatt ttctgactaa gagctaattt gttttttaaa ctggtagcta tttcttcctt     25680
ttataagctt ttgaatgttt gtttgtttgt ttttggcact ctcttccaag aatgtttgaa   25740
gacctgcatt tgaaggcaga ttgccttttt gctttaaaac agggttgcac catgttgccc   25800
aggctggagt gcagtggtgc aatcatagct cactgcagcc tcaactcctc ccaggctcaa   25860
gcaaccctcc cacctcagcc tcctgagaag ctggggctac cagcatgtac cgccacaccc   25920
agctaatgtt aaaattttt tgtagagatg agggtcttgc tgttttgccc aggctgatct    25980
taaactcctg gcctcaagtg atcctcctgc ctttgcctcc tgtgctggga ttacaggcgt   26040
gagccaccat gccgggcctg aagacagact ctgagaattc ataaaaacct cacagcattt   26100
tgtactctta tgtatataaa ttatctaggt tgctcttcat aatcctgtaa agtaacaaga   26160
gccataccgg cccattttac aactgaaaag cacagacact tatttcctta atcaaggtca   26220
gacagcaaat tagtggaaaa gccaaggcca gaacccaggt cttctgattt tactagtgca   26280
gccttctttc cccaggggac acattgacat ttacaacact catctttatt tttttttaa    26340 tactgctttc tatccagcca attattagtc tgtcttttaa taattcatcc aaatctcttc   26400
tgaatcattg cataactttg tacagtttcc acccacagtg tcttttactt ttattttgg    26460 aagtaactgt tttaaaagt tactgttatt tttaaaagtg tgccttcccc agaaatcagg    26520
gagttaccca tgtcctagaa ctccacggtg aagagaacag cctgtgccca tcgtgtttgc   26580
ctgattgatc ctacctcttg tctctcgggg aaacacagga gactcaggga agaggaaaag   26640
tgtagagtca ttgcagcctt gttatttgtc aatgcatctc ttttctttt cttttctttt    26700 ttttgataca gagtttcact cttgtcgccc aggctagagt gcagtggcgt gatctcggct   26760
cactgcaacc tcggcttcct gggtccaagg gattctcctg actcagtctc ctgagtagct   26820
gggattacag gcacctgccg ccacggccag ctaattttt ttgtattttt agtagagacg    26880
ggtttcacca cgttggccag gctgatctcg aactcctgac ctcaggtgat ccacccacct   26940
gagcctccca aagtgctgtg attacaggca tgggcccag cacccggcca gtgcattgca    27000 ttttttttt tttttcgag acggagtctc actctgtcac ccaggctgga gtgcagtggc    27060
acgatcttgg ctcactgcaa gctccgcctc ccaggttcac gccagtctcc tatctcagcc   27120
tcccaagtaa ctgggactac aggcgcccac cacaacgcct ggctaatttt tatatttta    27180 gtaaagacgg cgtttcacca tgttagccag gatggtctcg atctcttgac ctcgtgatct   27240
gcccgccttc gcctcccaaa gtgctgggat tacaggcgtg agccaccgtg cccggcgtgc   27300
atttttaaaa gtgtgtctga tgctgaaaag tttgaagtct aggcacgtcc cagtgggtcc   27360
tctttatacc atcccctctg caaaccatta tcctaaattg gggtttgggg gagagaagag   27420
tgacagtgga aagaagtctc caccttcccag ctgtgccctg gtagttccag gggacccgga   27480
ggctccccac acccaccacc ccgcctcaga tcacctttca ctttcttgt ttctcctccc    27540 ttgacttttc agctcagaaa gtacctggct ctccaatgcc ttctgaggaa agtttacccg   27600
```

```
aggttcacat tgcaagactc attaaagctc tttagtgttt tccacccgag aaaaaattca    27660
agggaaaaat gaagacaaaa gcagggcatt cttaatggat attttatctt aaggagaaat    27720
gaaaatggag atggaagagg gggcacaagg atggggtttg aatctagact cgttcagcct    27780
ttacctccga tagagaacct catacagctt ttctggactt ctggctgata aagagccgtg    27840
gagggttcct tggataaaaa aggttgaagg gggtctgtcc tgtggtggct tacttgaagg    27900
tattactggg tttgacttat ggagtaagag acggagtcag tttccccaca ggctgaggca    27960
gtctgtcctc atgcttttct agggcactgt ggtctcccag gctcatacct aggtgcacac    28020
acaggtttct gcatctagct ttgtatctct atgagtcggt caatcaataa atctatctat    28080
catctgtcta ctgatctatc atctatctat ctagctagct atcatctctc tatcatctat    28140
ctatgtatct atcatctctc tctatatatg tgtgtatata tatatatata tgtatatata    28200
tatttctatc cttccatcta cttacctatc tatcaaaatt ttttccgtt gataatattc     28260 tcgggcccca gtttatgttt aattgttttg gtaatgcctt tctttgcaca gtcagtttac    28320
agaggttatt ttatattcta tatgtatgtg tggtccagcg ttgtaatttt cacatatatt    28380
gcaccgtgta ctcataagca gtatttccac tgggtcatta acagaaagat atgtgtgcgg    28440
catatgaatg tgcatcactc aggtaattca agcttggttc ccagatcatt tctgtaccac    28500
aggattgccg aaataaaaga caaccatggt tatttcctct gctgcaagct ttctagaata    28560
tgctatttgt ctggatttat atctgaaagg tcctgccaag gaatcttgcc cttccatttg    28620
tcgaagtctc caggaacttg gggctccctc ctatcctggt ccactcagac ttggtgctga    28680
cgaactggac caaaaaagat ccagacgggt aaggaaggaa gagaatgctt tgaatttcca    28740
taactttccc ccaggaaaca cccaggcttt tttttataat tagggaagtt catatttatg    28800
gtctgccgta tggttccaaa gaaggggtga gcttgaccaa aaattcaaat atcacaggcc    28860
ccagaagttt cctcttaatc cattctgaac acattggctc agaccatttt gtcttgtttg    28920
tttccacatg acgtgtgaat ttctcaacct gaccttcaag ctcctgcaaa atcagctttt    28980
atttgttctt tctcttcaaa ctgtttattc cctaagatgc cctccattca tatcaggtta    29040
aaaccagttg gctttgataa gtaatcatta tataatgatc agaagagaat gattatggat    29100
gaattcagag cagatgctcc aggtgggttg gattgagaat ttgattaata attccatcta    29160
ttccaccaaa gtcacatcat tcctttgaca gttgggctgg gaatagggc atttgtctac     29220 agaaggaata gcatgagatt ttaacaaaca agaaattcaa caaacagaat tagacagatg    29280
atctgagatg ttaaattttc ctttcacctt aattttttgca gccaaattta tttcagctct   29340
agatgaaaga gacagcactt tcttttgtgg ctgactacaa cagctgaaga ttcactgagg    29400
tttgatatga ggaagaactt cctcagccat gggattgcca gaggcgatga tgggaatcta    29460
cttaaagggg ttacatattt agtagacagc ctagatttta agactaattt atgtgccccg    29520
gccgggcccg gtggctcacc cctgtaatcc cggcactttg ggaggctgag gcaggtggat    29580
catctgaggt caggagttga agaccagcct ggccaacatg gtgaaacccc gtctctacta    29640
aaaatacaaa aaaattagcc gggcatggtg gcacatacct gtaatgccag ctgctcggga    29700
ggctgaggca ggagaattgc ttgaacgaag gaagtagagg ttgcagtgag cgaaatcatg    29760
ccattgcact ccagcctagg tgacaaactc tgtctcaaaa gaaaaaaaaa ttatgtgccc    29820
cattggaaga agtgagattc ggccatctca tctctctcgg gagctctgag ccctggagtt    29880
ttatgttttc tgcaattatg aattgtgatc cttgattaat tatgctttaa taataaaatg    29940
ggtgactact gaaagctgct gaatctgggt aagaatttgg atgaaaaaaa taatatatgt    30000
```

```
gcgtaattta ttctgttcaa ggtactgaat attgaataag ctggatttat tactcaaaga    30060
gaaagacaga ataagagaag gttgaaggga aaaatgactg tactagaatg gtagtcaaaa    30120
atgcaacaac aggcaggtgc agcggctcat gcctataatc ccagcacatt gggaggccca    30180
ggtgggcagg tcacctgaga tcaggagttt gagaccagcg tggccaacat ggccaaaccc    30240
cctctctact aaaaatacaa aaattagcca ggtgtggcag tgggtgcctg caatcccagc    30300
tactcaggag gctgaggcag gagaatcact tgaacctggg aggcagaggt tgcagtaagc    30360
tgagactgca ccactgcact ccagcctggg tgacagagtg agatcctatc tcaaaaacaa    30420
acaaaacaaa acaaaacaat aacaaaaaag ctattaatag cttcctaggg agtaagagtg    30480
aagggctagt ttaattccag agatgcggac acagtcctgg gtctcaccaa ttattctgct    30540
tggtaattac cttttgaagc cttttaatat gcctaacaca gagctaagtg ctatgaagaa    30600
atgaaagaaa tagaagcaaa gtactcccca tgtggttaaa taacaagaca ctacatgaca    30660
aatgtcaaag agtgactcaa acaatatgtc ctttagaatt tcagagaaat gacatcaatg    30720
caggctttac aagtcagtaa aaatcttggt gatgaggcag aacttgatgt aaggcaaatc    30780
ctaaaagttg agtaggaatc aactagctag aataaaatgt ggggttgtgg taaatacaaa    30840
aatgtaagat gagtgaaata acttatttat ttatttattt attttcagag acggagtctc    30900
cctctgtctc ccaggctgga gtgcagtggc atgatctcgg ctcactgcaa cctctgcctc    30960
ctgggtttga gcaattctcc tgcctcagcc tcctgagtag ctgggattgc aggcacctac    31020
caccacaccc gactaatttt tgtatttttta gagagatggg gttttaccac gttggccagt    31080
ctggtatcga atcctcgacc tcataatcca cctgcctcag ccttccaaag tgctaggatt    31140
acaggcatga gccactgtgc ccagcctaat aatatattaa gatggccaca ggccaaatat    31200
tctggggctg gaatgtgagt ggaaatgtcg ctcacccttt atcacatagc accccatagt    31260
ccagccacaa cttgcagaat tcaaagtaag tgtggatgtg tgtgtgcctg cagtgccttg    31320
cacacaagtg tgcatgcctg tggacatgtg accctagaag ttattaatat atctggttta    31380
caaactgaat tgttcttta tttttttttct ctcttggtgg tcatcaataa ctgaaattgg    31440
gctagattcc tggaaattgg gtaagttctc agaaatcatt tacgcacttt agaatccagg    31500
ccaaatttaa aatcttacaa taaaacaaag aacaaagcat gctaaattat atgtataata    31560
taatatcaac catataaaat gcataaaaaa tatactagaa ggaaatgtgc ctaaaattca    31620
cagtctaaaa tttaacagtg attgcctctt ccttgtatag ataagggatt ttttttttact    31680 gtattttcca gtctgtacat aataaaacaa gtaatgtgca atgcaaacaa acaaaatga    31740 aactttatca aatttcagta actccttgaa gtttaatttt tttttgaga ctgagtctta    31800 gtctgttgcc caggttggag tgcagtggtg tgatctcggc tcactgcaac ctctgcctct    31860
gggttcaagg gattctcctg cctcagcctc ccgagtacct gagattacag gcacccacca    31920
ccacacctgg ctaattttg tatttttagt tgagacagcg tttcactata ttggccaggc    31980
aggtcttgaa ctcctgacct caggtgatcc acccgccttg gcctcccaaa gtgctgggat    32040
tgcaggcgtg agccactgca cccagttgaa gtttaatagt gtgaaaaaaa tatttctcat    32100
ctcactatat cttctatggg aggccagatt gcagattgtc tacagaaaaa tcccttcaaa    32160
agaccttgtt attacataga ctggagctca tggggcaggt ctggtccaca catccttagg    32220
ctccgcttct cctggaaaac aaaaatagcc tctgatccag tgttgcctct cccatcacca    32280
aacctcagct tctatcgcca aactcatcaa ataagagtgt ccagtagaaa aactgggcag    32340
atgggggcac agaaggtgaa gacatcattt cccaagctaa tgttgctgct ggaacaatgt    32400
```

```
aagtcttgac tttgtcttgg tttggtttgg tttgacattg gtttgttttt catctttgtc    32460
tcatgcttaa aatgtgaagg gcaaatatga tccttagagt taaggtttta ggttttgtag    32520
atgttttact ccatttaaat gacagcagat catttagaaa tgattcctct gtaacagcct    32580
tccagatccc attcgattgt acagcattga gatagataga tagatagata gatagataga    32640
tagatagata gatagacgga atttggccct gtgttccccac ccatatctca tgtcaaattg    32700
taacccccac atgtcaggag agggatccag tgggaggtga caggatcatg gggttggatt    32760
tccccaatgc tattctcatg atagtgagtt ctcacaatat ctcattatta ttattattat    32820
tattattatt gcaacagagt ctcactctat ctcccaggct ggagtgcagt ggtgtcatct    32880
cggctctctg caacctcttg cctcagtctc ttgcgtagct gggattacag gcatgccccg    32940
ccatgcccag ctaattttg tatttttagt agagacggag tttcaccatg ttggccaggc    33000
tgatctcgaa ctcctgacct caggtaatct gcctacctcg ctctcccaaa gtgctggaat    33060
tacaggcgtg agccactgtg cctggccagt tctcacaaga tctgatggtt taaaagtgtg    33120
gcacttcccc cacctcctgc cgccatgtaa gatgcttgct taccttcca ccatgattga    33180 aaagtttcat gaggcctcct agccatgctt cctggtaagc ctaaggatct ctgagtcaat    33240
tacacctcgt ttctttataa attacccagt ctcaggtatt tctttatagc agtgtaagaa    33300
tgaactaata cacacataaa cagattagag gcagcactgg cctgagttgt gaaactcttc    33360
ccagcctggt cctgcgatta gctggctata tgaccttgga caagctgctt tgcttctctg    33420
ggccatggtt tcatacctgc aaaaaaaaga gcatggactt ggctgttgcc tgggtctctc    33480
tagccctgtg gagaatcagc tacatctctt actaggaact tctcattcag ccagttattc    33540
cactgcggag atggtccagg accattaggg ccatgctaga cattgggagg ctgcctgtca    33600
ggtgaacatg aaattgaact tatctgttct cttcctccc tgaatgttgc tgaaggtaga    33660
tgcccatcct cagggctgtc ttacggagag gagaaagttg tgcagtgatt ccaccctgca    33720
gttatctaac tcggcaggga actctgggca gtgagtactc acggtacagt ctccacacct    33780
ctaatcatgt gctcctctcc ttcccaagga acctggagac catcatctca tttcctgggg    33840
gagagagcct gcatggtttt atactggtga ctgctttggt agagaaagaa gcagtgcctg    33900
ggataaaggt atcttctcac ttgatagcac ctttttctttt taaatgagct tgagctttac    33960
ttcccactca gtgcctttcc tgcagtggat ttctcaacac aaatgaacat agaccttgtc    34020
ctgcttagtt caagtctgag agaagagatc taagctctag gccaccatat ttgctccctt    34080
ttctcaattc ctataaaact cggaatggac cttttgtcca ttcaacaaac aggcattggt    34140
ttgggcaatg ggaaattgga tcgaacaaga cagacatttt cccagccctg acagaagctt    34200
atgatggata cagtggatga agatggatta acgtggatta caggtgtgag ccactgcacc    34260
gggcctcaaa ctggaaattc ttcaggagtc agacaggtat caggaaggct ggatagaaga    34320
caaaagacag tgatgcagct tgtgatcaac tacagcgtta atgccttgcc taaaaatatt    34380
tcagttagat ttctgccttc gctctgtcgc tcaggccaga gtgcaatggc gtggttttag    34440
ctcactgcaa tctccacctc ccaggttcaa gcaattctcc tccctcagcc tcctaagtag    34500
tgcacgccac cacgcctggc taattttttgt attttttagta gagacagggt ttcaccatgt    34560
tggtcaggct ggcctcgaac tcctgacctc gtgatctgct tgcctcagcc tcccaaagtg    34620
ctgggattac aggtgtgagc caccctgccc agccaacact acctcccttg ataagcatat    34680
gttgagcacc tactggtcct caatagggtg acccatttct gctatattat agcgctttct    34740
ttctctctca gtagttaaac tccatggtta ctttagttct catccatgtg tttagtccat    34800
```

```
tagaagatac agagtcaaat atcggccttc caagtgtagt tcagatgaag tagagactca   34860
aggaagacaa ggaagtcttc ccagcagagg ggattctaga gctgggggct ctgtagaatc   34920
tgtctgtgta ttagtccatt ttcacactgt tataaacata ctacctgaga ctgggtaatt   34980
tataaaggaa agaagtttaa ttgactcata gttctgcatg gatggggagg cctcaggaaa   35040
cttacagcca tggaggaaag tgaaggggaa gcaagaacct cttcacgagg cagcaggaga   35100
gagagcaaag gggggagctg ccaaacactt ttatacaatc agattttgtg aaaactctcc   35160
ctcgtatcat gagaacagta tgggagagcc caccccata attcaatcac ctcccaccag    35220
gtccctccat cagcctgtgg ggattaccat ccaagatgag atttgggtgg ggacacagat   35280
ttcaacacag atttaaatct gactttatat gagagcttcg gagcaaggat gccccagttg   35340
gagatgcagt agaactgatc ataacgtgac aaatccgaga gaagaagagt aaaataatag   35400
tactcaggcc cttgggaggt gcaagaagta acagccagat gaaattccag aaacacttac   35460
ctaggggtct gtctgggagg tccccaggga gcttctggct gtcaggccaa ccccacagtg   35520
gatctagctt aggacgttcc caggaagctc tgacaaactg tccggtcctc ccctgggttc   35580
caacagtatg aggcttactc tgcctgcatg gactttaagg gagtgctaat aagttgtgta   35640
catgcatctc atccctaggc tcttgttcag gccacgaatg ctatcttgca gcccaaccag   35700
gaggccctgc tccaagccct gcagcgactg agactgtcta ttcaggacat caccaaaacc   35760
ttaggacaga tgcatggtaa gatgcttccg aagctcctga aggatccccc aggggtcctg   35820
ggctctgctt aggggaagag ggcctgggga ccaggcatgt cctgaagggg gtgataatac   35880
attcatccac cagatgacgc tggtggacta tctttgtttt aggttaaaca catattatct   35940
tggagagcta ttgtcacagc tttgtattct ccctctcctt tatattctcc cgtgattaag   36000
atggtttccc ttctgcagtg gccagatatt tcttaggcat gttgaggtct tgcctgaagc   36060
ttgagaggag gggatgggat gcacagtaat gttggtcgcg cgtgccccat cctgcagtgt   36120
taggtactgc agagcaggtt gtctacactc tgtaatgccc cttttattct aaccccctgt   36180
gttggttcct gagatgtctg accttggttt taagccttgt ctaatggatg gcctgtattc   36240
cctttctgta gctagggcag gctgatttgt caaaggtagg aaagttgtca gaatcaaaat   36300
ggagtcactt gtgttgaata aaaattttta aaccttgaca aatagagctg gggaaggcta   36360
caaagagaga gctcccgtgt ataaatgcct gataacaaaa tcttttccaa aggactgaaa   36420
aaatcaccac cttgcacaaa ggccatcaca accttacata cacaaaaaaa tacttacaca   36480
acgacatctg cccagcaact gccttttccaa cattggcctt gtgccaccct ttttattgat   36540
gctcatagcc aaggttaatg atctcaaaac agttacataa ttgtcctcat ttttcctttta   36600 aaaacctttg tcttccttta tctttctgaa tacccacatg gttattatg gcacatgtat    36660 tcccattgca atgccctatt ccagaataaa tatcagtttc cattagggag cctctccctg   36720
ttaatctgct taacacaggc atggtcagtt acggggccca accttcctgg accggttaca   36780
tcttattctg gttactgcat tcagtttcca acatctggga ggctcttcaa attcttctct   36840
cagaggaatc tgaagaatgt atgtgtttag gaggatgtga gagaggggtg tggtttctta   36900
acaagagaat atcagagtct aagtatcatt ttccctgaat cttgcttccc tgcaggaaag   36960
aaagattctg ggaaaagaga gtgttacaa gaagcaggac tggagggagg gagaaagacg    37020
ctaggtactg ccaagcttta ttatcttgta ttaaaaaagt aaatataatt tgtcatccca   37080
gcctctcagc actagtagaa atctatctga agtcacagga ttaggtatta tccacttcct   37140
ggttttatag tttatatttg tattttctct atttccttga atttaattt taaagccctc    37200
```

```
atgatcacat cagtaggtct tctgccaaac agctcccta agttgtatgg tggctttgcc   37260
aagctgaaat gagatgagat gtgttttagc tttgccaaga aagcctgagt ccatcactta   37320
ggatagcaag gctattaggg agatagtgca ggtgtcttca gatcacatgg atgagcaaaa   37380
ggaagcaatt ttggaagatt atgagaaacc ttccaacagg tcccagtgta catagcagta   37440
agatggtgca tgcagtgtct aactgtcaca ggctttccta gggctcactt tcagactcac   37500 ttctttttt ttttttttt ttttgtgaga tggagtctca ctctgtcact caggctggag    37560
tgcagtggca cgatcttggc tcactgcaag ctctgcctcc cgggttcaag cgattctctt   37620
gcctcagtct ccctagtagc tgggattata ggcatgcacc accatgccca gctaatttt    37680 gtatttag tagagatggg gtttcgccat gttggccagg ctggtctcga actcctgacc    37740
tcaggtgatc tgcctacctt ggcctcccaa agtgctggga ttacagccgt gagccactgc   37800
gcccagctca gactcacttt ttaggcccag gccaacctgc tgtgttctcc tgctcagctt   37860
ctgcaggagg tctcatcgtc taaggaggtc ccagggctac cgcccttgtt ttctcaaaag   37920
gcacattttc ccacacagac ataatttcgt ttcagtgttt tactcctagt cacattcatc   37980
tatatggaca aatagctgaa tggattggac tgtgttttct aaagatggcc ccatgccatc   38040
ctgcgcgctc ctccacagcg tggcctgggc attcctttcg accaggggtg gactctgtgc   38100
ccctacttgt gatgtacgtg ttgccaatag aatgtagtat aggggatagc acagacttct   38160
gaggcaagac tagaagaggt gatgcaggtt taaccttgtg tcctgagcca ctaggtaaaa   38220
agtccaccta ccctgagatc actctgctgt gcaaacgaca caggcaaacc acatcaaaga   38280
gccatgtggg ttctccagtt ggcttctgcc caggagtgaa ggtgccctca gatggttcta   38340
ggctcccatc ccaacttatg tcctgtcttg aagtcttccc aactgaggca ccagccactg   38400
tggagcagag tcaagccatt gccatcttgt tctgcccaga ttccccatca acagaatata   38460 gtggttttt cacacctcta tgtttggagt ggtttctatg cagcaatagt aaccacaaga    38520
aataaagtta taaaaatagt aacaaacact agaaactgca agatttaagg aatcacctga   38580
atgctccagt cattgtctct ggtttgtaat gataaacttt cttctgcgtg ataaatagag   38640
cttggctgga ctttttccct ctgcttccat tccccaaaat ggagcgtacc aaacaattgc   38700
ttctttcaga gcccagcttt agcaagagtc atgagctcta atcccttcat ccataaatac   38760
ttcctttcca ggcacgtaga gcccttcaca ctcagggctg agtagaaaat gcctgttgca   38820
gactgcagtg gcgttttgga gagccaccct cctggtacct gagtcactag tcctttgccc   38880
agcttttctc agttttgtaa agcgctcact tctgagtgga agacagaacc agcccggtct   38940
attttcataa tctgccccca taaggcagaa gtccacacgg tactgaaaac ataaccatat   39000
ctatgtcagt ctgccactgc ctgccgcctg tcaaccgtgc gtgtctgcat ccagtccttc   39060
tttggagctg cttccagcg actcagccag atctgagctt tctgactcat tggaaggtta    39120
aactattttc agactttcaa gtgttgagat tattaagaca tgtgttttt tttttcttct    39180 tttttggca tgcttactga tcgcccctgt tctctaggaa gtaatgttct tcttggaaaa    39240
ggtgaaggat atttttctcc ccaaaaagcc atggaaatgt ttgcctttat ttacttccaa   39300
attaacagaa tttccagctt ttgcttgacc catcggcgca ttggcagcgt taagaatttt   39360 ttctttagc agtaatgagg agtcgaaggg tttcttccta accatttagt gtatgcattt    39420
aaatcaggtt tcttttgag taaattgggg ctaagctgta gtgtgaactt ctgctactgt    39480 tccttctca ttagttcact tgatttcatg gaaggaattt tccatctcag cctgtgaact    39540
tattttgtct aaactcaatt ggaaagtaat taacactgag attcttcttt aataaattct   39600
```

```
atatgataat aaaatcatac aaacatctct ttatttttct ttttgaccta gaaaagatgt   39660
tcacaggcca gacctggtgg ctgaagcctg taatcccagc acactgagag gaagaggcgg   39720
gtggatcaca tgaggtcagt ccagggcag ggtagccaac gtggtgaaac cccatctcta    39780
gtaaaaacac aaaaattagc tgggcatggt ggcacatgcc tgcaatccca gctactcagg   39840
aggctgaggc aggagaatca cttgaacctg ggagatggaa gttgcagtga gcctagatcc   39900
tgccactgca ctccagcctg ggcgacagag tgagactctg tccccaaaaa aataaataaa   39960
taaaagatgt tcacaatata ttgttaagtg aaaaaagcag gctacataac ttgcataata   40020
tgagtgcatt ttaataaaaa tatacatatt tagcaaaata aaaggacaaa tggtatttat   40080
taaaatattt acgttgatta tttcaacaca gaggatgata gttgattttg cttaatttct   40140
tccctccttc ttttcaattt gaattttcta taatgaagat tgtttctttt tctttctttc   40200
tttttttttt ttgagatgga gtttcgctct tgttgcccag gctggggtgc gatggcgcca   40260
tctcggttca ccacaacctc tgcgtcccag gtttaagtga ttcttctgcc tcagcctccc   40320
tagtagctgg gattataggc gtgtgccacc acacccggct gattttgtat ttttagtaga   40380
gacgggcttt ctccatgttg gtcaggctgg tctcgaactc ctgaccttag gtgatctgcc   40440
cacctcagcc tcccaaagtg ctgggattac aggcatgagc caccgcgcct ggactgatta   40500 tttttaaat agggttagaa agtgaggaag ttactaaact ccgattagcc caaatatgcc   40560
ccagtgggtc cttctggcag agtaaatgtc tcggttcagc ctgaatctgg gaaattgttc   40620
ctacggttca gcctgaatct gggaaattgt tcctacctta taaactggag tatccttcag   40680
aaatgacatt tactcaaact tccttttagg cagactgcat aatagcaatt tttaatatta   40740
accatttaaa aaaaaccttc agattaatta acaccaaaag aataattggg aaaatacaac   40800
tcctcacttt aaaaaagaaa caaccaaagt aaatactaaa aaactatatg atgttatatt   40860
atctaagctt agtttactgc aaagatcaag agcacactac tagttgacgg cctctattca   40920
cactgttcat agccctcgct cgcttctcca gccattcact cactcatgca aaaggtctgt   40980
acacacaatg atgcctgatg gtataatagg aaccttaaca tttcaattaa aaggcaaaat   41040
gaggacactt accatcagcc tataaaatta ttcttattat tcttcttctt cttctcctcc   41100
tcctcctcct cttcttcctt cttcttcttc ttcttcttct ccttctcctt ctccttctcc   41160
ttctccttct ccttctcctt ctccttctcc ttcttcttct tcctcttctt cttcttcttc   41220
ttcttctttt tttttgaga tggagtcttg ctctgttgcc caggctggag tgcagtggtg    41280
tgatctcggc tcactgcaac ctctgcctcc caggttcaag ctattctcct gcctcagcct   41340
cccaagtaac tgggattaca ggtgcatgcc accacgcccg gataattttt tgtattttta   41400
ctagggatgg ggtttcacca tgttggccag gctagtctct aactcctgac ctcaagtgat   41460
ccacctgcct cggcctccca agtgctgggt gtgggcggc aagccaccca ggtgccaagg    41520
caagagacag agggcacgag ctgttccagt ataatgagga aaatatatag aataagaata   41580
gttatactag aaatagatta tagatatgat tacatatgaa tatcattctt cattagtttg   41640
tagcactact ctttattcca gtattataat aatctttgtt ctacaattat aacctaggaa   41700
aaaccaggcc atacagagat aggagctaaa gggacagggt gagaagtgac cagaagagtg   41760
tgagccttct gttatgcccg gacagggcca ctagagggct ccttggtcta gcggtaacgc   41820
ccgcgtctgg gaagatgcct gtcacctaac ggaccgtggt ctagcggtag cgtcagtgcc   41880
tagaaaaggc actcttttta aatatacttt ttatttttgt ttaatcttcc ctgatttcct   41940
atagatctga gatatgtcat gcttattttc attgctatct aaaaatctca ataaacttta   42000
```

```
tacctaagag taaaaaaaaa aaaaagaaa agaaaaggcg ctcgttactt agccgaccgg    42060
gaaagggagt ctcccttcc ccggggagt tagagaagac tctgctccac cacctcttgt    42120
ggagggcctg acatgagtca ggcctgcctg cagtcatctg gaggcctaac cgtctccctg    42180
tgatgctgtg cttcagcggt cacgctccta gtcctgaaca cctggctccg ccttttagat    42240
agcagtagca gaattagtga aagtactaaa agtctttgaa atgcagaagt aatggcgtaa    42300
gctgtcacgt ctctctctcc gcctcagctg ccaaacagag aagggtcccc tgtccagtgg    42360
acacgtgact tgggtgacct tacctgtcat tggagacgac tcatactcct taccctgccc    42420
cttgccttgt atctaataaa taacagctca atctggcatt tggggccact actggtctcc    42480
gcatcttggt ggtagtggtc ccccgggccc agccgtcttt tattctatct ctttgtcttg    42540
tgtctttatt tctaccatct cttgtctccg cacacgagga gaaaaaccca cagaccctgt    42600
agggctggcc cctacagctg ggaattacag gcatgagcca ccgcatccag ccagcctaaa    42660
attcttctga aggataataa tatagtactt gaagacacgg tttgaaaaaa atcatactaa    42720
atgaaagggc accattttac aagcactaga actacattaa acttaaatga attccaacac    42780
tcttaataat gtaactcaaa aacaagtcta gtgttaacaa aagctccaat aactaaaact    42840
acattaacag gcacaatgaa cattgtaaac gccgctaatt ggcaccaagt ttaatagggc    42900
agacaatatt ttcttctgca ttcacactta ctcagttaca ctgttgaaaa atgctgctgc    42960
tcaagctatg aatgctttac aaaagaaatc attttaataa atacagtaaa tgctaaaact    43020
ctagctaaac tattatgcaa gatatacaac caagacaaat acaaattcat aatacaagca    43080
acttgcattc aaaatgaact ctaccactat attttattaa aagggcagac tttatgaatt    43140
aacccagctg cttcctgaat tacaaaagtg gcatgactca atatgaaaat aagaaactgt    43200
ctacaaattt ctgacagtaa taaattgtaa tatacaatac atgcaggagt cttacggaag    43260
aataaactct cctaggaaac aaaaatattt tatacttta aaatccaaag taaaaaaaaa    43320
agaaatcatt gccagatgcg gtggctcatg cctgtaatcc aagcactttg ggaggccaag    43380
gcaggatcgc ttgagcccag gagtttgaga ccagcctggg caacatagca aaaccccatc    43440
tctacaaaaa aatacaaaaa ttagatggta atggtggtga gcgcctgtgg ttccagctac    43500
ccaggaggct gaggtgggag gatgcacctc aaggctgcaa tgagccaagg tcacaccatt    43560
gtactgaagc ctggggacag agtgagaccc tgtctcaata agtaaataaa taaatatctt    43620
ttatgaaaaa gattctctag tcagaattaa caccctcaact agccaaacat caggaagtta    43680
cattacagct acttaataca caaagggaca cattttcacc agtcgttgtc ttctgatatt    43740
tctattccag aaacacacac tctcacttcc ctacactccc catcccatca tttcttcaga    43800
gcatggaaac agaatttgtt gaacaccaga atctcttgc tatggtggta cataagtcat    43860
aacatttgtt gctgcccagc agcaggtatg aagccggctg gtgactggct agcaaatgcc    43920
tattctgtaa gctcctcact tagcccatct gtagctctga cttctccacc aattcccttc    43980
tctcctttca cagcctttct gagtttctga gggataattt cagaggttcc atataactgt    44040
caaagcctat ggtagacatg gcaaagtgaa atcctctcc actggccatt tctgtttctc    44100 ttggggcat ctttcacttg cctcaggtgt tataaagctg atgaacacac gtacacgttg    44160
tttaacactt tcttgggcat ttcccatttg agatatgca tgtttcatta tcctagtgac    44220
atgtgcaatc agaaaatgta tattttgttc tctgcaactt tcttttgaaa aatgtatatt    44280
tgaacaaaat atacattttt tgtatcttca tgaccattca tgctgtcctc actgtcatca    44340
tgaggctcta tataacataa tgactcctcc agggcagtct tcggaaattc ccagtgcaga    44400
```

```
agcacgtgtc atacagcagt ccccattcat ctccagtgca gctctggctg gctcccatgt   44460
ctgatcagct gtttggttgg acagaaaatg actgcaaggg aatcagttcc agtgtgagct   44520
ctgtttgcag aactcagact cccctccctc ccatgttaat gcttttttc ttcttctttt    44580 tttttttttt ttttttttga cagagtctca ttctgtcacc caggctggag tgcaatgcta   44640
tgatctcggc tcactacaac ctgtgcctcc ccggttcaag caattctcgt gcctcaactt   44700
cccgagtagc tgagattaca ggtgcacacc accacacccc actaattttt ttgtattttt   44760
agtagagacg gggttttgcc atgttgccaa ggctggtgtc aaactcctga gctcaggaaa   44820
tccaccttcc tcagcctccc aaagtgctag gattacaggc gtgagccacc atgcccagcc   44880
ccatgttaat gcttctaaag tttgccctca cttctttaga aattccttca gtacatcctt   44940
taagacttcc tctagtgagt gtctgctggt ggtaaactct cccctctaaa agttgcttta   45000
tttctcctca attcctgaag gatattttg ctagcagcta tattctttta gatgttgaac    45060
atatcggtac aaaagcttct ggtttccatg gttgctattg agatgttagc tgtcggttta   45120
tctttctccc ctgactatgt gtacctgttt ctctgtatct gtctacttt tgggttgctc    45180 aatttattgg ccttgggctt cattctgctg ctgctttttt tttttttttt tttttgagat   45240
ggagtcttcc tctgttgccc aggctggagt gcagtggtgc aatcttggct caatgcaacc   45300
tctgcctctc ggttcaagcg attctcctgc ctcagcctac cgagtagctg ggattacagg   45360
cacctgccaa cacgccaggc taattttttgt attttttagta gaaataggat ttcactatgt   45420
tggccaggct ggtctcaaac tcttgacttc aggtgatcca cccacctcag tctcccaaag   45480
tgctaagatt acaggcctga gccaccacgc ctggccacaa ttttaaact ttttattttt    45540 acaggcacct gccaacatgc acaactaatt tttgtatttt tagtagaaac aggatttcac   45600
tgtgttggcc aggctggtct caaactcttg acctcaggtc atccaccacc ttggtctccc   45660
aaagtgctag gattacaggc gggagccacc atgcctggcc aaaattgtta aacttttat    45720 tttcttcctc aagaggatga gaagaaaggt caattgtaag ctttagaagt cttgcccaat   45780
agccaatctg agaatattct ccgtaaacat tcaccagagg cagccagtga ccatgggata   45840
cttttggtga gaggaattga ttgctggggt caggaatggg aggaaagcat acttctcatt   45900
agataccttg ttgaacttcg taaattgtgt gccaaatgca tgtcttacct agacttcata   45960
aattaatttc tttaaaaata atcaaagaca atttttttaaa gacttattta atttaaggtg   46020
attataaaac atccagtata ctttcactat taaaaaagta agtattcctg tctgggcttg   46080
gtggatcaca cctgtaatcc cagcactctg ggaggctgag gtggtcggat catgaggtca   46140
agagattgag accatcctgg ccaatatgat gaaaccatgt ctctcctaaa aatacaaaaa   46200
ctagctgggc gtagtggcgt gcctgtagtc ctagttactc aggaagctga ggcaggagaa   46260
tcgcttgaac ccaggaggcg gaggttgcag tgaactgaga tcgtgccact gcactccagt   46320
gtggcaacag agtgagactc catcttcaaa aaaaaaaaaa agtattccta aacagcatat   46380
tatcatgata tattattttg ttttgtaggg ttttgaacct tgtctaaaaa gaattaaaat   46440
gtataaattt cttcctgcaa tttccctatt tcactaaggg tcattcacat tggtcatata   46500
gacatagcac attttcacca ctatatagca gcattttgta caaatagact acaatttact   46560
tattctgcac ttatttctgt ttgtttgttt tgctatgaaa agcaatgtca ttacatatat   46620
tcatgcccat agctacaagt ttacatattt caggttttct gtagggtgga caccagggag   46680
ttgaattgtt caacaggact ttacattcat ctttagtttt attggccaac accaaattgt   46740
tcttcacaat gtttgaacta agttgaaatt ccacctcccc atcacattta gttttgtcaa   46800
```

```
cttcatttct tcattcatta attcattcat tcagtctttt gtttatttgt ttattgccag   46860
tctgataggc gtatagtggt gcttcatcat ggttttactt tgcatttctc tgattttctt   46920
tttaaatttt taaaaaatta tttttatgta gaaacaaggt ctcgctacat ggcccaggct   46980
ggtcttgaac tcctggcttc aaatgatcct cccacattgg cctttcaaag taccgagatt   47040
gattataggc gtgtgccact gtggccagct gatttccctg atttctgatg agttaacaat   47100
ctcttctttc tctctctctc tctctgtgta tacaggtact caccattcgt gcctatttc    47160 tgtaaaatat gtggctttcc tcatttttt tttttttttt tttttttgag gcagagtctc    47220
gctctgttgc aggctagagt gcagtggtgc gatcttggct caccacaacc tccacttcct   47280
gggttcgagc aattctcctg cctcagcctt cagagtagct gggactacag gcgtgcacca   47340
ccatgcccag ctaattttg tattttagt agagattggg tttcactatg ttggccagac    47400
tggtctcaaa ctcctgactt tgtgatctgc ccacctcagc ctcccaaagt gctgggatta   47460
caggagtgag ccactgcgcc cagccatctt tcctcatttt tatactaatt aggcttttat   47520
cttacttgtt tttttaatg tttttgtac actctgaagg ctgattttg ttaattgtat     47580 gtgttgcatt tttatggtt tgtcttatgc cttttgaaag taaagttct taatttaaat    47640 atagccaacc tgtaaatcat ttgtgaaagt ctgtggttta agaggtcttg aataagaaat   47700
tatcccatca tcataagtca taaatacttt ttgttgttg ttgagacaga atctcatttt    47760
gttgtccagg ctggagtgca gtgggttgat ctcagctcac tgcaacctct gcctcctggg   47820
ttcagcaatt ctcctgcctc agcctcccaa gtagctgtga taataagcat gtgccaccac   47880
accagtctaa ttttgtatt tttagtggag acaggatttc atcatgttgg ccaggctggt    47940
ctcaaactcc tgacttcaag tgatccacct gtctcagcct cccaaagtgc tgggattata   48000
ggtgtgaacc accatgcctg gcccataaat acatttttat gtattttctt ctaaagttgt   48060
tttgtctttc acttttagt ttttaattca catataatta ctacttgcta cttataatta    48120
tctgtaagta gtatgagatg agaaataaat tctatttccc tcctatggat aagcacaaac   48180
ctgcagtatt agcacagtct tatgtcagat tttctaaaat gaatgggtgt gttttctagg   48240
ctctctgttc tgtttcatta tctgtctttt cctgcaacga tatcatctgc cttaaaaact   48300
ctagccttgt ggtattcctc attttcaagc agagcaaacc ccgtcacctt gcttttctcc   48360
tccagcatcg cttgtgctat cctggactaa gaccttcata tagactgtta gaatcatcta   48420
gccaagttcc attttaaaaa tctatgttgg agctgggcgc ggtggctcac gcctgtaatc   48480
ccagcacttt gggaggctga ggagggcaga tcacttgagg tcaggagttg gagaccagcc   48540
tgatgaaacc ccgtctctac taaaaataca aaaattagct ggacgttggg cacttgaatt   48600
ctagctactc aggaggctga ggcaggagaa tcgcttgaac ctggcaggcg ggggtgcag    48660 tgagccgcga tcatgccact gtactccagc ctgggtgaca gagtgaggct ccatctccaa   48720
aaataaataa ataaataaaa taaaatatct atgttggaaa ttttgtacaa attttattaa   48780
atgtctacat taatttggag aaaaatgact tgattttgat tatctattca atatttctgt   48840
attatgaata aggcaaaaag agaggcagag aatagcataa aataataact aaaattcctg   48900
ggtaaaccac ctcaaatcat ttcttcatat ggctcaatat tcttttgtga catggcctga   48960
aatatatcca gacagagaac tcttctcttc aatacatttc ttcttttagg tattcatatt   49020
gagttttcct gtccatgaac atggtataag agagtatatc ccttcgggag gccaaggtgg   49080
gtggatcacc tgaggtcagg agtttgagac gagcctggcc aacatggtaa agtcccatct   49140
ctactaaaaa cccaagaatt atccaggtgt ggtgacacat gcctgtagtc ccagctactc   49200
```

```
aggatgctga agcaggagaa ttgcttgaac caaggaggcg gaggttgcaa tgagccaagg    49260
tcatgccatt gcactccagc ctgggtgaag agcgagactc catctcaaaa aaaaaaaaaa    49320
aaaaaaaaag aaaacgagaa tatatccttt catttactag tttttcttca atttctttca    49380
agataaaggg cttacctatc ttctgcttta ttcatagtta cttgatattt ttgtttctaa    49440
taaatatggt gtctgtctat ttacctgcct cttacctgtt catttccagt ttcaaaaatg    49500
atgttgatat ttgaatatta accttaaatc tagcaccttg gtaaacacta ttattcattc    49560
taataattat cagtagatta tatgtgtttt ttatttataa atcatattgt ttgagtagca    49620
tgctttgctt cttcatttat aaaatttaca acttttattt ctttttaata attttttttct   49680 tattctcctg gctaggactt ctaacacagt attgagtgga agtgctgatc cttgtttagt    49740
ttcacatttg aaaaagatt gctttacta tttcactgtt aagtataata tgcaccatag     49800
gctttctgtg gattcctttt atccatttaa gaacatctct tattcctaat tagctgaagt    49860
tttctgcatg tttgttttca tcatgagtgg attttttttac atctattgaa atcattttac   49920
atagaagata tttcacacct attgaaatgg tcatttcact tttccttctt taatatgtta    49980 agtgggcaa aatattaaag tatcacctgt cattctgctt cagcaaaaag tagtagtgtc     50040
ttagcagtat tggtgaaaag acagcatcaa ataaaaaga tgtagaagta ggacccagta     50100
aaaatctagc gcatggggca ttgtcacatg taagcagaca gaatgtgaca ccaccaagga    50160
gcatctgaag ggctggaggc tgaaggaaga catgagtcac ccaggctcat ggacacttca    50220
gagaaattag ggagcaggaa gaagaaatag gatcaaagac tacgtatgtt ggttggaaaa    50280
ggaagctgat ggtatggaga tgttattatt taggtctcac ataaagatg tagataaata    50340 ggtagatagg tagatagatg atagatagag agatagatag ataaatacat agatagatag    50400
atgataaata gatgttgtta tttaggcctc acataaagat gtagacagat tagacagaca    50460
gatgatagat agatagatag atagatagat agatagatag atagacgata gatagataga    50520
tagataatct cagaaacaga gacacagtga tctcagtaag ataggcatat gccaggtgac    50580
agaattcaga ggggtcccac tacgtgaaaa caatagaaca accttcgaaa agaaatttag    50640
tacaaataag agggcaggct tccttacata caagttagta aactggaaga atcagttatc    50700
ctcaaacatt ggaatagatc aaaaatagtt gtttatatta atgaaggtag ctaaacatga    50760
agctaagtga acctgtctct gacctagtgt ggcaatccct gggcaaggga cacttgctcc    50820
gctcttgtat ccttcactga atattcagac tttcagttaa gcatcggtga atttagtttt    50880
catctcttgt gaaaaccttg agagaggtaa ttctctctgc ttttcttctt ttcccttcct    50940
tcattttctc aaacattgcc tgtttaaaat acgaaatttt aaaagatggc cttgttctct    51000 ttttgttgt tattattaag tacagagaaa ggaagaacca caaatagcaa agggcaacat    51060
atggaatagt ttagaagttc cgggagcacc catgagggca actgcagaag agaacattct    51120
atcccccgtt gctgcagctt tcattccagg tctccatgca tatcagatag ggaaggaact    51180
ccgggacagc agcagggccc atgcacatgt aaccaattgc tttctttgcc tgtagtaaag    51240
ttcacatttt gattgcttct ccagattatg tagatccaga catattttat gcaggcatcc    51300
ggatctttct ctctgggtaa gtatagttca gttgttttcc tgtgtgaagt ctctgtagca    51360
ttgactgaat gtataagggg acgaagagac agaagcttcc tagcgtaaga aacataccaa    51420
gtgactcttg ctagggatcc actctcaggt aaaagaagtg ggataccatc tgcacaacaa    51480
ataacactga gggctaagta tttcagttaa gagtgtttgt tcctaggcag ttcagatcca    51540
tttatattca cttttcttag aatcctagct caatgacaga agaagaaaaa cacagtatgt    51600
```

```
cactcacaca gttctatcac ttacatctac ttttcttct tgttattaag gcatgtagaa    51660
ggctggggag tgtagtatag agttggatag catcgaagct ttcttctaaa gttcctggaa    51720
gagctacact gtggtttgaa cgaatgtgtc cctccaaaat tcatatgtta aaacctaatt    51780
gtgatggtga ggtattcgaa ggtgggttct ctgggaggtg attatgtctc ctctgagagg    51840
agaagacaat cccctgagtg gaactaatgc ccttataaag gggctggagg gagttcactt    51900 ggccttttt gctccttttt tcttccattc cttgtcccctt ccactatgtg aggacacggg    51960
agttgaggca ttaccttgga cgtggagacc aggccctcac cagacactga acttgccagc    52020
accttgatct tggacttccc agcctccaga actgtgagaa atacatttct gttatgggta    52080
gtccccaact caatacagtt tgacttacca ttttttgact ttatgttggt gcaaaagcat    52140
acatattcag tagaaactac tttgagtacc catacaacca ttctgttttt cacatttggt    52200
acagtattta ataaattcca taacatattc aacatgttga cataaataag ctttgcgtta    52260
ggtgattttg cccaactgtg ggctaatgta agtgttctga gcacatttaa gggcagctag    52320
gctaagctaa ggtgtttggt aggtcagatg tattaaatgc attttttgtc ttatgatatt    52380
ttcaacttac attgggttta tcaggatgta acccactgtg aattaaggaa tatctgtatt    52440
tacaaattac ccagtctaat gtattttgtt gtagcaacag gaacaaacta aaacactacc    52500 ccaaccatt ttttcatat tttctgagta ctcttctttt gtcacatggc ttgaaatttc    52560
ttcacataga gaactctact attatttat tttattttat tttattttat tttttgagac    52620
agagtcttgc tcttttcacc caggctggag tgcagtggtg ccatcttggc tcacggcaac    52680
ctctgcctcc tggattcaaa ctactctcct gcctcagcct cccgagtagc tgcgattaca    52740
ggtggctgcc accaagcctg gctaattctt gtatttttag tagagacgga gtattgccat    52800
gttagtcagg ctggtctcga actcctgacc tcaggtgatc tgcccacctt ggcctcccaa    52860
aatgttggga ttacaggctt gagccaccac gtctggctga taactctact tttagatact    52920 ctcttttgctt aaacaaatta gccattcctt ccttgacatg ttttaatcag attgccttcc    52980
tattaacttc ggaaattaag agtttctgct atgtttttgt ttaatttta aacagtgaaa    53040 aatgaaaggt ggaggcaatg gctggatgag gtgaatatgt caaatagata tcatctagtg    53100
ggccatctta ttaactagga gacacctgaa gtgctatcaa tagaaataat ctgaagctgt    53160
gtctggatac agcaagagac atgcaaatgc taaaaatcta ctatattaca ttggtgcaag    53220
gacagagtag caaacatac taagtatttt ctccagattg ggtgtgtttg acgtgtgaag    53280
cacttcaaac agagtccagc ctgggaggga gtggggatgg aatcctcctt gtagagggta    53340
cagagtggaa gcaagaaggt ttccaagatt gagagtaatg ggtgtatggt ttatggggga    53400
aagggaaaac aaaagaagg gtgcagaaat ggagctggga gtgtgtttta gtatttaggc    53460
tttctctgta tacctttgat aggattagaa aaagaaaaat ggaccatttt taaaaatttc    53520
atgctaccac atagcaggct tatactatag atgcagaaac agactgggat ttaggaagca    53580
ccccaattct ggaaaatccc ttttgcttc acattgctct ctaaatctgt atgttttccc    53640
ttgttacgta acaatttacc acaaatttag cagcttaaaa caatatgcat tcattgtttc    53700
acaattctgt aagtcggaat cataggcaag ctcaactgac ttttccattt agggtcgcaa    53760
aaggccgaag tcaatttatc tattgggctg ggctcttaac tgaagatctg gggaagaatt    53820
cccttcaaaa ctcatttagg ttgttgtcag aattcagtgt tttgtggttc tagaactgag    53880 atctgttttcc ttgttggctg tcagacagga gctgctctca gcttcttgag gcatccagta    53940
ttccttatca tgtgtttttt ttttccatc tcagcactgg cacttttttt tttttttttt    54000
```

```
ttgagacaga gtcttgcttt gtcacccagg ctggggtgca gtggcacgat ctcggctcac   54060
cacaacctcc atctcccggg ttcaagtgat tctcctgcct cagcctcccg agtagctggg   54120
attacaggca cccgccacca gcccggctga tttttgtatt tttcatagag atgtggtctc   54180
accatgttgg ccaggctggt cttgaactcc tgacctcaag tgatcctccc acttcagcct   54240
cccaaagtgc tgagattaca ggcatgagcc atcatgccca gccagcactg acaattctaa   54300
tccttctagc actttgattc cttctcacct ctccttctgc ctctagccag agaaaactct   54360
ctgattttaa aggtcttatg tgattagatt cagcttacct aggtaattca ggataactcc   54420
ctatgtcaag gtcaactgat taataacctt aattacacct gcaaagtccc ctttgccata   54480
atatatcata ctgacagaca tgctatagca taatactaat agttctaaga attatgataa   54540
gaatcttgga aaaccatttt tagaattata cctaccacag tatccttcaa gggataaatt   54600
gattctactt cttctctatg tcagaagcat ctgatgagga tgaactatat attctgaaat   54660
ccccatgatt agatgtgtac tagaaggtga ttttactttc attaaaataa attcggagtc   54720
attgacacat tttatctttg atttacataa atgcctccgc tctgtttctt accctcaaaa   54780
tatttcccat gtagctaagt ggccagtacc gaatcctaca tgcattaata agtgtagatg   54840
gacaaaaata tctggattac tgagaattcc cattagcatt gtctagaaaa atgtaaattt   54900
gcttttttgt tcttgattta tcctattttt gatttattat ttatatttat ttatttattt   54960
atttattttt agatggaggt ctcgctttgt cgcccaggct ggagcgcaat ggcgcaatct   55020
tggctcactg caacctctgc ctcccaggtt caagctttcc tcctgcctca gcctcccaag   55080
tagctgggac tacaggcacc tgccacagtg cccggctaat ttttgtattt tcagtagaga   55140
cagggttttg ccctgtgggc caggctgttc ttgaactcct gacctcaggt gatctgccca   55200
ccttggtccc ccaaagtgct gggattacag gcatgagcca ccacacctgg ccttttttgct   55260 tacttttaa aaacattttt atttaggaga atggagatat ttcatatgta gatgacacat   55320
attcattccc tttagttccc acacacattc aatttcttga ggaagttagc ctttgcaaaa   55380
aaaaaaaaat gatctcattt ttttttcccc actaaaactt ctcatttttct tggggttgct   55440 agaaagttgc tacaagaaag gctaaaaata attgtgccta cagatatttg aaaggaaaat   55500
agttcctctt ttttcacagt agcagcttgg acctgagaat gtatgggagc ataattggg   55560 ctgctcaaag aaacacaatt tcccttcctc agactagaat taccaaccta gagaacatga   55620 gttttttaaag tagatgtgct tcttttatct ttttggactt gtatgctggt gttttctctg   55680
tcaccttcac tgtggaaatc ctcttgaggg tgaggcactg aaagcagatt gattaatgtc   55740
tcttggccat ttgagacatt ggatggctct tttaagttgg ccacgttctt tcaagaacta   55800
tgcttgggct acatattctg gatatataat acatacttgt aggatgttat ttttaaatca   55860
ttcatttatc acatatttag tgagtgccta ccccatgtca gttctaggtg ctggaaatag   55920
agcagtaaaa ccaaccctca acttggcccc tctggagctt acatttcaat gcggtgggtg   55980
gggggatgga caattaatac acaagtaaat ctaataaaag cgtcatacaa tatacattac   56040
aatggtaagc acaatgaaga aatggaaagc tggatagaga gtattagaga ctgtcgaatg   56100
tagtggccaa attttcctgt ttattgtggt ccaagagtgc cacagccctc tatgacattt   56160
gagcagacac ctggaggaag tgagggagtg agccgccaag aaggaatggc aagtgcaata   56220
accctgaggt gggagcgtgt tggtcgtggt ggaagagctg caggaagcca gcagggccgc   56280
aacactcagg ggagaataag aaagagtgag gtgacagtag agaccggatc atgtagagct   56340
ttgtcagctt cttttctgag tgagatggac aacacggaca cgtttgaaa agaataacaa   56400
```

```
tgtgatctgc cttcagttgc aaatcatctc tgtattgact gagtaggaaa taaactccaa   56460
gaataaagac ggaaacaggg aaaatattta agaagcgatc attacaatcc agggtggtgg   56520
cttgtactag ggtacaaggg ctaaaggtgt tgagaaatgg tcagattctg gatatatact   56580
gaaatcaaag ttgatggaaa gatatgagtc aaagataatt tgcaggtttt ggggtcctgg   56640
ttcactgaaa gaacagagac atcatttact ccaatgagga agactatagg aggaacaggt   56700
ttagcaaaga agaaaggaaa tcaggagatc agtttgggga cacggtcata tcaagtaggc   56760
agttggatgt atgggtctgg aatataggggg agtggtctag ctatcagtgt aaatagcttt   56820
ttacatttgt aaatagtcag gatataggct tttcttttc tttttgtgag acacagtctt   56880
gctctttcgc ccaaactgga gtgcaatggc acaatctcag ctcactgcaa cctctgcctc   56940
tgggttcaag cgatactcct gcctcagcct cccgagtagc tgggactaca ggtgtgcacc   57000
accataccag gctaattttt gtgttttaa tggaaatggg gtttcaccat gttgaccagg   57060
ctggtgtcaa actcctgacc tcaatcgatc tcccgcctg ggcctccaa agtgctggga   57120 ttacaggcat gagccacccc atccagctgg gatatagttg ttttctaaat ctatgaggct   57180
agagaagacc atttgggaat tgagagcagt gagcagtcca cggactgacc cttttgagagt   57240 gcaacattta gcagtactca agatgggaag gagctagtga aaaagcccca aatgactaca   57300
taagaccatc aaccagatta caagaaaga cccgaacatg tgtgcccata tatcacccaa   57360
cagcagttat gtcttttcatg tttcttcccc ataaaatgtt gttcatcaac tttattagac   57420
tagggtctta acattggaca aatcacaaaa cctctctgga gcctatttta tttttcaaca   57480
gctgtaggaa gcaaatacaa attggaaatc taaggctcag aaagatttgt acaaagttac   57540
acagtaatga aaggggagcc gggattccca ctcactctaa agaatatgat aaaatggcta   57600
gtattcactg aatgcttaac atgttccagg ccctgggcag gtattatttt aattagttct   57660
cacaataatc caataaggga gatactaatt tactcagatg agaaagctga ggctcagaga   57720
ggttaatgaa ctaagccaag gctcactgtt aataaatagc aaaggtaaaa ttaaattcca   57780
tatctgcttg agatagaggc cttgctccta atagctgcag cctgtcaggg cctggcagca   57840
gtaacctctc ctttcctctt cccaccattc ccctgcactg ctttctgtac cgcatctctt   57900
ttcagagtga tgttgcccca attgcggagg ccactgtgct gtttatccag tgaaagctgt   57960
agcacagcca acccaaagcg tccccagtga aaacaacctg gctccttaca gcacttccag   58020
cctcagagca gtatttgaaa aatatcatga acagcaaaca cagcagtctg tctgtggctt   58080
ttatatgtgt atatggtgtg tgtgtatgtc ccttctcttg agcaaaataa cttttagaat   58140
tatagaaaaa aaatgtgcaa catcaatgtg gatctgctgt ttaaactcat aacagagaaa   58200
gtagcttgtt tctggctata ggaggaaaag acgatattcc ttagtaaaaa tggaaatcca   58260 catatgggggt tcttgtaaaa atgaagatag aaaattgcaa gtttggggat caagttctgg   58320
ttctatcatc ctttaacagt atgaccctgg aaccttaatt gctttgagtc tttgttactt   58380
tatctatgaa atgaagtatt taaaaaaact ccaaaaatct gtcctgatgt acacacaaga   58440
ggtcaaatga gaaaatgaat gtgaagatgc tttataaact atacagcatg gtaggtgcaa   58500
atgtgacatg aacttgtttt ggacacatta taaagtcacc cccacaaact gtgattgttc   58560
aagactatgc aaagtcagac acaggaaaat aagtaaaaca gatggaggca taagaggggg   58620
gaactcagag aaaacagtga agaacaggaa tcaggaagac aaaggagagg aaaggtgggg   58680
aggagaggag aaggaaaggg ggaagggaat ggaggagagg agaacagctg cttcacagag   58740
catggccggc agcccagtcc cagccttct gcatgtccct gacttcagcc tctggcgagg   58800
```

```
cacaggctta ctctgtgctt cctgctgtta ctcttcttat ccatccttat tatcaatacc   58860
tgtggtcaac aaagtatttg ataaaggcat cctcaaagtc aggtaacatc tgtacgttat   58920
agattacaaa gttgagtaat atccagaatt ggtagtttaa cgtgatgact tcttaacaat   58980
tatcactgtt tcagggaagg gcaaaggtgt gtgtgtgtgt gtgttcatct gtgtgtatct   59040
gtgtatgtaa ttgtgggtgt ttgtgtatat ttgtgaggct cttttacttgg cggagttaaa   59100 aagtatctgc tcatcaaggt tgagattagc aaaggaagtg aagattttc cagagcccct    59160 aaaatgtgcc ttttgaccaa cactgaggac atctttataa ctgagtatgt gcaataaata   59220
tgtcttggga cctgtgccac aaattcctct ctaaatagcc tttacctctc tggaataacc   59280
ctttagatga ggaagaaaag ggctgtgatt ttatagcttg ttatgaagct ggagtgaaga   59340
tgatgcttca gtacttaccc tacaaagata cccccaatcc ctcaccctaa aattaccatt   59400
gaaatcatgt tccctttctc attcactctc agtttccatg tcagaaaata taccattacc   59460
tccctgcacc cctttcatct ctctcacttt tctcttgctt agatggaaag acaacccagc   59520
aatgcctgca gggctgatgt atgaaggagt ttcccaagag cccctgaaat actccggcgg   59580
gagtgcagct cagagcacag tgcttcatgc ctttgatgag ttcttaggca ttcgtcatag   59640
caaggaaagt ggtaagtcag acattttgtt ttcccttgag agtagaggga ggaagaggag   59700
aggtgttttt tttttttcca attgataaaa ccaaatataa attaaaatgt catgaagttt   59760
atacttctct aagtcagcca agaaactgca tgactgccaa tgttttgtg tcaagccaat    59820 taatattgga atatcagatg tcagcttgat cttgggtttt acttccaaat cttaaaatgt   59880
tgctctgttt ccaactgttc actatcactt tggtttggat cttagacac tagcttcctt    59940 tttctgaaat gggggagaga tgtggagttt gaaggctatg agtctgggcc agctggaaac   60000
aggtctggga tcttccaaga aagtccttcc ccacaaaatg gtgcaacttc tagccaaatc   60060
tatttatacc agcagaggga tctatcaccc tggaagcttg aaattgttca ttttcttacc   60120
tgccaggatc aagttaagtt tttaacagtt gcaaaaagac acttcatact atggagtttt   60180
caagttggat tagaagaaaa agaatcacca gaacttagtg tcgtagattc aagtcacttc   60240
tctaaaactg tcataatttt tcacggattt tggcatttgg tgacattaat ggttgattta   60300
cttaccatgc ataatattaa acccataacg aatttcctat aaatatctat tgatttgatt   60360
tttaaatcac ttggcttcaa gaggctatta ctaaaacagt gactcattct ttatctttt    60420 tgccttcacg ggctttatat aacttttctc ttttcttgtg ctccctccaa aacaaagcac   60480
tgagaaaaca aaattcacca gagtattcag ctagtcagtt caagggtttg tgttctacat   60540
ttgaagatat tccttatagc agctaccaac gggatacttt gtttacattt gttgtgtagt   60600
aaatatttat atattggcaa acaaatctag ttccaactct gtcatctgag atgttcttac   60660
tttgtttcct cttctccatc tcctgtcaac tgttagaaat atacatttga gtacgtgaag   60720
tctgcaaaca aaagggccaa ggtagatttg agttagaaca ccagcaacag tttctggtgc   60780
attcttgtct gaaaaagcag agaagattgg gcaccgtggg tcatgcctgt aatcccaaaa   60840
ttttggaagt ctgaggcagg tggatcgctt gagcccagga gttcaagaca agcctgggca   60900
acatagcaag aacccgtctc tactaaaagg aatacaaaaa aatattagct gggtgtggtg   60960
gcgcacacct gtagtttcag ctactcagaa gactgaggtg ggaggatcac ttgaactcag   61020
gggcagaggt ggcagtaagc tgagatcaca ccactgcact ccagcctggg caacagagca   61080
agatctcatc tagagaaaaa aaaaataaaa agaagaaga agcagacgag ctctgctata   61140
tttccatgtg gagctatgac gttatgctgt attgtttctt tcaggtgact ttctgtacag   61200
```

```
aatgagggat tacatgcctc cttcccataa ggccttcata gaagacatcc actcagcacc    61260
ttccctgagg gactacatcc tgtcatctgg acaggaccac ttgctgacag cttataacca    61320
gtgtgtgcag gccctggcag agctgcggag ctatcacatc accatggtca ccaaatacct    61380
catcacagct gcagccaagg caaagcatgg gaagccaaac catctcccag ggcctcctca    61440
ggctttaaaa gacagggggca caggtggaac cgcagttatg agctttctta agagtgtcag    61500
ggataagacc ttggagtcaa tccttcaccc acgtggttag                         61540
```

```
<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
tccggtacca tggagcctca aagtcag                                             27

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
atccggtacc atggcactca gtaaaata                                            28

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
tgtcctggtg ctaagggtca agacaattct                                          30

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
tgagttggcc taagggtcaa gacaattct                                           29

<210> SEQ ID NO 20
<211> LENGTH: 1266
<212> TYPE: DNA
<213> ORGANISM: Homo sapiens

<400> SEQUENCE: 20
atgttgcatt tcattatta tgatacttca aacaaaataa tggagcccca cagaccgaat     60
gtgaagacag cagtgccatt gtctttggaa agctatcaca tatctgaaga gtatggcttt    120
cttcttccag attctctgaa agaacttcca gatcattata ggccttggat ggaaattgcc    180
aacaaacttc ctcaattgat tgatgctcac cagcttcaag ctcatgtgga caagatgccc    240
ctgctgagct gccagttcct gaagggtcac cgggagcagc gcctgcccca cctggtcctg    300
agcttcctca ccatgggtta tgtctggcag gaaggagagg cgcagcctgc agaggtcctg    360
```

```
ccaaggaatc ttgcccttcc atttgtcgaa gtctccagga acttgggget ccctcctate    420 ctggtccact cagacttggt gctgacgaac tggaccaaaa aagatccaga cgggttcctg    480
gaaattggga acctggagac catcatctca tttcctgggg gagagagcct gcatggtttt    540
atactggtga ctgctttggt agagaaagaa gcagtgcctg ggataaaggc tcttgttcag    600
gccacgaatg ctatcttgca gcccaaccag gaggccctgc tccaagccct gcagcgactg    660
agactgtcta ttcaggacat caccaaaacc ttaggacaga tgcatgatta tgtagatcca    720
gacatatttt atgcaggcat ccggatcttt ctctctgggt ggaaagacaa cccagcaatg    780
cctgcagggc tgatgtatga aggagtttcc caagagcccc tgaaatactc cggcgggagt    840
gcagctcaga gcacagtgct tcatgccttt gatgagttct taggcattcg tcatagcaag    900
gaaagtggtg actttctgta cagaatgagg gattacatgc ctccttccca taaggccttc    960
atagaagaca tccactcagc accttccctg agggactaca tcctgtcatc tggacaggac    1020
cacttgctga cagcttataa ccagtgtgtg caggccctgg cagagctgcg gagctatcac    1080
atcaccatgg tcaccaaata cctcatcaca gctgcagcca aggcaaagca tgggaagcca    1140
aaccatctcc cagggcctcc tcaggcttta aaagacaggg gcacaggtgg aaccgcagtt    1200
atgagctttc ttaagagtgt cagggataag accttggagt caatccttca cccacgtggt    1260
taggat                                                              1266

<210> SEQ ID NO 21
<211> LENGTH: 73660
<212> TYPE: DNA
<213> ORGANISM: Homo sapiens

<400> SEQUENCE: 21
ccctggcctt ggaagatgcc ctagagacgc tgaggtggtt gtacttttgc cataggagtg     60
gcagccagag aactgagccc aatgaatgca aaggctggtg cctggaaata ttgtgacttt    120
gccacagaaa gaagatggag aatttttaaag ttggaaatct gcctggtaag ggatcatttg    180
ctggtgtctg caaagttgag tccatacaca ctggtttgga aatttcagtc cagatgatag    240
ttaagaaagc agtaagaata cagagagtcc acaatgagat gaaaatgcac tgccagttga    300 acatcctcc tacactggag ctttataaat attttaaaga caaggattgg attagatttg    360
acattagaaa tgtaccataa tacagaaggc aatggacacc taaagaacag aatgaaaacc    420
ttcttaggaa atgaagcttg acacttcacc caccaggcca ccacaagaat gttgcatttt    480
cattattatg gtaagtacac tggtaacttc ttttctaacc tcgtatgcat aatgtaaaca    540
tcaagactga caatttgggg ctagcaactc aattggaaaa tcactgttct ctattgtaaa    600
attcctaatt atgtttccct agaaattgca aagtgcacat gtacttgcat ttaatgtttg    660
gtccatgggc tgaatgcttt gtgcattact tttctggttg ttgttgttgt tgttgttgtt    720
gttgttgttg ttgttgtttt gagacagagt ctcactctgt tgccaggctg gagtgcagtg    780
gcatgatctc ggctcactgc aacctctgcc tcccaggttc aagcaattct tctgccacag    840
ccttccaagt aactgggatt acaggcgctc accaccacac cctgctaatt tttgtacttt    900
tagtagagac ggggttttcac catgttggcc aggctggcct caaactcctg acctcaagtg    960
atccacctgc tttgacctcc caaaatgctg ggattacagg catgagccac cttgcccagc   1020
ctgtgcatta cttttgagga cacatttgac aatggcacag tcaagaacac cacataaagt   1080
agtattggca gattatgaaa tagcaattgt tttggaagac agcaaaacct gaagtatttt   1140
cagacatgta cattatgaag tattataccct tctttaacta tgtgcaagtt aaaatcagtc   1200
```

```
ataactgaaa atcaaaaggg caataatgaa catacttcat ccagaagagg tatccacaaa   1260
acttctgaaa gaggtcttag tatatccagg gatggagata ttattacaat gtattatcca   1320
aatgatggaa gttttctctt gctgatagaa tgcatccacc tactaacatc agtaagtaca   1380
ggtttaacaa tttaccagaa atgtactgga ggaaatatga atatgcttcc agatttattc   1440
tacctaaagg atctggctct attttacaag gtcatctatt ttacaaggta ctgtagatgc   1500
attttgatga aaaaaattac cctgctattg attttgaggt ctggtattat gatagagcaa   1560
aaactatcca aaagagattt aattcaagtc attgcaaaat cttggaaaat gtgtgagaaa   1620
tcttacacat ggaaggagg aagtaaagat ggtagcttaa acatgtgttc cactgtgaac   1680
aattctctgc aaacccaccc ccaaaagtca aggaggctga caggctgaag aaagaggctg   1740
tcaaatctag tttctcagaa aaagaaaaat taatagggac ttaagaacag aagccatata   1800
tctgccctga gatgagctgg tggatcctca cactgttacc cccagaccca gggcttatat   1860
accacaggga aagacaattg cagtaatttg cttaacggca ggatttacgg caagtacatg   1920
ctcttaagag tagattaagt agtaaccta gaggcattcc tagaactgga gttaatcaga   1980
agtcaacaca gtggattagc atccaagatg gagttgcttt agcctccaca aagagaaaat   2040
gaagataaat ttggtccatg ctaattaggg ggtgttccat ttgtttgaaa ctgaaatcta   2100
taatttccaa agaagaaaat aaacgtggaa gtcgtccttc cttttttggta tgcatagaca   2160 atctggcagt gttaggcccc taaggcctta tcacctcctc cttctgtggg tcaaacttta   2220
cagtgagagg aaagacatct tttaaaagaa gaataatcat gactagttta atcatgacta   2280
gttcatcttc cctgcaatag atacccatat ttaacatacc tattgtacaa gaatatgat    2340 tgcacagcta caactttggg acaaactcct tttctgccgc tttcaatgat cgtcttccaa   2400
aatcagaaca gcttttgaat tttattttgt gaaaaatgtc gtttgagtga cacagtaaac   2460
tctgtggagc tctgtggata cagttgaatg atggctccca gttatcatg caggtgggat     2520 tatattccaa cagttatgtt tcacagaaag gcaaataac caggtacgga aaaaatgaaa    2580
aatttgcagc ttcatcaaa cagaaattgc agtgtctttc atctctttaa agttttctaa   2640
tcaaaattct agttttcatc aattaaaact ttatttaggt agatacattt aataagtaac   2700 ttttttgttgg cttaaaggga atgaacttta tgtaatgtaa ctgtctattt caggaagctt    2760
ttctatgaga atttaaaact acaccaaaat atcttctttt tttttttttt gagacaaggt   2820
gtcacattgt ctctcaggct ggagtgcagt ggtgtgatcc tagctcactg tagccttgaa   2880
ttcctgggct caactgatcc tgctacctca acccccacg tagctaggac tacaggcctg    2940
caccaccaca tctggctaat tttttatatt tttgtagaga atggtctgg ctacgttgcc     3000 caggctggtc ccaaactcct ggcctcaggt gatcctcctg cgtcaacctc ccaaagtgtt   3060
gggattacag gtgtgagcaa acctgccatc tcaaaacatg tgtattttaa tgagacaaca   3120
aagatcaagg gaactttagt ccttacaatg taatgatcaa aaaagtgaaa tagataatca   3180
acataacatt gcttgtagac catgcaaaca atcttattgc atttgtatat ttgtaatgaa   3240
ctgttttata ataacaaaat gtaaaatgtg tattttattt gtccttttat tgttttccta   3300
cttcttagac atgttaagaa ctatggaaaa agatatggga gtttgtgaaa atttaaataa   3360
ttcatattta tattacaaga aacagatatt agaatatgtt tgttttatat ttcttttgta   3420
gcagaatttt ctagccaggc attgtggctt acacctgtaa ttccagcact ttgggaggct   3480
gaggtgggac aatcacttaa gcccaagagt ttgaaatcag tgagggcaac atagtgagac   3540
tctatctcta caaaaaattc tctatctata tctatataaa ggaattttgt gaggaaaact   3600
```

```
atatattttg tatataaatg aatttatca ggaaatatat ctgtaaatga attttataaa    3660
atatagcatc actttatcct tgatttattt catttaataa ttattttaaa gtaatatact    3720
aataaactca ttttaaaaac tgctatgacc ataaaactat tagagataac ataagagaaa    3780
atctaggtga ccttgggttt ggagataact ttttatatat aacaccaaag gcgcaatcaa    3840
tgaaaaaaaa tgacaagctc tatatcacat atcaatatta aaatgtgatc tgtgaaaggc    3900
atcgtcaaga gaacaaaaag acaagccaca gactgggaga aaatatttgc aaaagacata    3960
tgtgataaaa gacaattatc aaaatataca aataattctt aaaactcaaa aataagaaaa    4020
tgaacaactc agttaaataa tgggcaaaag atctcaacag aaaccccatc aaagaagaaa    4080
cacagtggca agcatatgaa aatatgatct acatcatatg ccattaggaa attgcaaatt    4140
aaaacaatga gataccacta catttctaca ttggtgaaaa ttccaagtac tgacagcact    4200
ctcagtgctg gtgaggatat ggtgcagtag aaatccacac tcatgccggg cacagtggct    4260
catgcctgta atcccagcac tttgggaggc tgaggcgggt ggatcaccag gtcaggagtt    4320
tgagatcagc ctgaccaaca tggtgaaacc ccggctctac taaaaataca aaaattagcc    4380
cggtgtggtg gcgggcgcct gctactcggg agtctgaggc aggagaatcg cttgaaccca    4440
ggaggtggag gttgcagtga gccgagatgg cgccactgca ctctagcctg ggcgacagag    4500
caagactcca tctcaaaaaa aaaaaaaaaa aaaagaggcc aggagtggtg gctcacacct    4560
gtaatcccag cactttggga gactgaggta ggcggatcac ttgaggtcag gagttggaga    4620
ccagccttgc aacatgacaa aaaccctgtc tctactaaaa ccacaaaaat tagccaggag    4680
tattggcaca tgcctgtagt cccagttact cgggaggctg agacaggaga atttcttgaa    4740
cccgggaggc ggaggctgca gtgagccgat atcgcaccac tgtactccag cctgaacgac    4800
agggcgagac tctgtctcaa aaaaaaaaaa aaaaaaaaa aaaggaaag aagaaagaa    4860
agaaaaaaga aaattccgtg attgcagtct ttacgtattt atttgttatt aagtacagta    4920
aaataaagaa ggatagatgt catggaaaat gtcacgaaaa taaagagtt aaaaaaaaaa    4980
aaaagtaggc tgcaatgcca gatgcctgaa aagttaatca acgaaaggac ttaaatgtcc    5040
ccattgaatt taggaacaaa gaagtaatta atgaactggg caaaaacact caatgtacca    5100
gcgttatcga tttagaaact gaaactaagt atatctgatg ttgcttttag gaaacaagta    5160
aatgaggtcc taaaaagtta aactgtgacc atatttctt tccttttct aatttctcct    5220
tgggccattt ccaaaaagcc ctaatacccc gactgataga aatggatacc ttgctgtgca    5280
ctggtactac tgtgattcat ggaaagctga tcatgcaacc caagacgcca aaattcccag    5340
ccttactgtt acgaaagaaa gtttctaagc acaattgtct ctagccaact tcctcttagt    5400
aagaaagagg ccaggcaggg cttcatgcag ggtacagccc tgagtttctt actgcgtggt    5460
aagtttctgg ggctgggagt aaagcagcgt gaccgaaagc agtacaaagt tctaccggac    5520
acgcagatcc cggtcctaca aatatgaggt ccataatgag actgagatat cattcatcca    5580
acaaatattt attgaatacc aaacattggg cttacggcta aaggaaaata caaagttgtg    5640
ttggatatgg gttctgtttt caaggagctt ataatctaat aggaaagatg aggttactac    5700
attagtagca atcagaccag atagaactgg aagtgtgatg taaatgaggt acagattgat    5760
tgtagaattt tgcagaaaga aaacaattct gaagaaatgt tcatggaagt attagcagtt    5820
gagatgtatc ttaaaagata agtggggttc ctgttggaaa cattcaaaac tctctcttct    5880
agctatttta aaatacgcaa tatattatta actatggtca ccttactgtg ctatagaaca    5940
ctagaactta ttcctactat ctaactataa ttttgtaccc actaaccaac ctctccctgt    6000
```

-continued

```
ccctcctccc cctattcatc ccaccctctg gtaaccactg ttctactctc tgcttcccaa    6060
aacaaagaaa tgatcactgt ttcggtgatg gagatgtcaa ttaccctgat ttgatcatta    6120
cacattgcat acatgtatag aaatatcaca tgcaactctt aagtatatac cattcttatg    6180
taccaaatac aaataaaatt gaaaaaaaaa aaaactttg gctgggcgcg gtaggtcatg    6240
ccagcacttt gggaggctga ggcaggcgga tcacctgagg tcaggagttc cagaccagcc    6300
tggccaacat ggtgaaaccc aatctcttct aaaaaataca aaaattagct ggtgtggtg    6360 gcagggcgcc gtaatcccag ctactcagga ggctgaggca ggagaaatgc ttgaacctgg    6420
aaggcagagg ctacagtgag ccgagatcat gccactgcac ttcagcctgg gtgacaaagc    6480
aagactccat ctcaaaaaaa aaaaaaaaa agcctcctga gtaactggga ctacaggcat    6540
gcgacaatac tcccggctct cttttaaaa atgagaagta aagtagtgg tgactgtcaa    6600 gaaagtattt tggaaaaata ctatgaataa ccagaccaaa gaaaccaaat accagttgtt    6660
tcaggagcag taaatcattt ttgagggctt gagcaaaggt cttgctagaa aggtgcttag    6720
gggtcagatt ttggacataa tgccaggcca agaaaatttg cactttattt cattaacaat    6780
gaggagctct tgaaagtttt attggcagga cctaagatag ttacagaccc acaagtaaca    6840
tgggtctaga ccttgggaac aagaaaagtc aagatcgagt atgcagactt gggaaccgag    6900
tataactaat ggttaagatt aaataaaaat acataagaac actgagatag agaaatggct    6960
cattaatgct gcaaatgtct gcatgtttag ggatgaaata gaaaagaag tcagaaaaat    7020 acagttcaaa caataggaaa gaaaaccaga aatgcatgat tctaagaaat gaatgggtgg    7080
acatggtggc tcacatctgt aatcccagca ctttgggagg ccgaggcaga aggatagcta    7140
cagcccagga gttcaagacc acccagagca acacagcaaa accccatctc tacaaaaaac    7200
aaaaataaaa attagccaag catggtggta cacacctgta gtcccagcta ctcactcaac    7260
aggctgaggc agaaggatca cttgagccca ggaggtgaag gatacagtaa gctatgattg    7320
caccattgca ctccagcctg gctgagagaa tgagagcttg tttccaaaaa taaaaaataa    7380
gaaagaattt ttagaatgag aggaaaacaa catgaaacat gagaaaaata acattccctg    7440
ttatatggta ggtgcttcgc ttatagtttc tcattaattc atcatgtaat gtctctggga    7500
taaacattat ggatttcctg cagaaacaga agctcagaat tttatgccag gtgttgaaag    7560
gccatgtagc taatagatga tagaacacag actcacactc tggtagtcct gagttaacag    7620
tagaaaagtc ctgggctggg cgtggtggtt cacgcctgta atcccagcat tttgggaggt    7680
tgaggcaggc agatcaccag aggtcaggag tttgagacca gcctggccaa catgactaaa    7740
gcctgtctct accaaaacca caattaccca gcgtggtggc gggcacttat agtaccaact    7800
actcaggagg ctgaggcaga agaattgctt gaacctggga ggtagaggtt tcagtgaggc    7860
aagatcaagc cacggcactc cagcctgggt gacagaatga gactctgtat aacaaacaaa    7920
caaacaaaat cagtaagaaa gtcccagact aagaggcatc aaatcaggat tctactccaa    7980
ctctgatgcc agcttccagg aatacacttg ataagttgtt tcattcccat aaatcttggg    8040
tgattcgtgt ttaatgagag cattgaactg aatcatttat tctatgactc agttctaata    8100
tttcacaatt ctatggttgt ataatattac aggaaattct tgagaaggtg cagagggaat    8160
ggatgaaaaa aaccacatga ctaacataaa aaataatggg gccatctttt catttgagat    8220
tgaaggaaag aacagagga caattaaaca tgcagagtct gagaacttgc atttaggagg    8280
cataagatgc tgaactgcaa aattggttag atattgggct gaagagaatt gagaattttt    8340
taataataaa aactcttggc agggcgcagt ggctcacgcc tgtaatccca gcagtttggg    8400
```

```
aggctgaggt gggtggatca cttgaggtca ggagtttgag accagcgtga ctaacgtggg   8460
gaaacccgt ctttaagaaa aatgcaaaaa atattagctg ggtgtggtgg tacaagcctg   8520
taatcccagc tacttgagag gcttaggcag gaggatcacg tgagcccagg aggtggaggt   8580
tgcagtaagc cgagattgtg ccactgtact ccagtctgga tgacagaggg acactatctc   8640
aaaaaacaaa caaacactct taagaaatta ggtgtagaaa gaatgttcct caataccata   8700
aaggccatat gtaagaaacc tatagctggc cgggcgcggt ggctcaagcc tgtaatccca   8760
gcactctagg aggccgaggc gggcagatcg cgaggtcagg agatcgagac catcctggct   8820
aacacagtga aaccccgtct ctactaaaaa tacaaaaaat tagccgggcg aggtggctgg   8880
tgcctgtagt cccagctact cgggaggctg aggcaggaga atggcgtgaa ccccgggggg   8940
cggagcctgc agtgagctga gatcgcgcca ctgcactcca gcctgggcga cagcgagact   9000
ccatctcaaa aaaaaaaaa aaaaaaaaa ggaaacctat agctaacatc atactgaatg   9060
gtgaacagtt gaatgctttc gtctaagaac tggaacaaga caagcacgcc aactctcacc   9120
actcttactc aacatagtac tttaagtcct agccagagca atcaaacagg ggaagtggat   9180
aattgagaat ggctcgagag gtgctgtggc tcagtcctgt tgtcctggca cagaaggagc   9240
tgaggccagg cgttcaagaa tggctcctag atgtctcata aggaaccata aatcaaacaa   9300
cttcaaaac tgaaacctgc gtgagaacgg ttgcattagt taatctggga gcttcctgct   9360
ttttttagc tttcatattt atcttagaga aagggaggaa ggagagatgt gtatggatac   9420
ataagcattc aaatacattt gtgtataatc ttatgaccag aattcaggtc caatgaacaa   9480
aaaggtaggg tcttcggaat ttccccagtg agatctatga cctgaatatt attacgcaag   9540
gatccacttt gggattacag gcgtgaacca ctacacccag cccaggactt tcctgctgtt   9600
aactcaggac taccacaatg tgagtctctg ttctgtaatg cccaaccttg tttttactaa   9660
ccccgctttt agactccccg ttttccttta atcacctagc cttgtttcca cctgaattga   9720
ctctccctta gctaagagag ccagacagac tccatcttgg ctctttcact ggcagcccct   9780
tcctcaagga cttagcttgt gcaagctgac tcccagcaca tccaggaatg caattaactg   9840
gtaagatact gtggcaagct atatccgcaa ttcacaggaa ttcgtctgat tgataacgcc   9900
caaagccccg agtctatcac cttgtaatag tcttaaagcc cctgcacctg gaactgttta   9960
ctttcctgta accatttatc cttttaactt tttgcctaat ttatttctgt aaaattgttt  10020
taactggacc cccctcccct ttctaaacca aagtataaaa gaaaatctag tcccttcttt  10080
ggggctgaga gaattttgag cgatagccgt ctctcggtcg ctggctaata aaggattctt  10140
aatttgtctg aaagtgtggc gttttttccaa ctcgttcagg tacaacagtt ctagcatcta  10200
ttagctatgt ggcctttcaa cacctggcat aaaattctga acaatggctt ggaaattaag  10260
ataccttagc tctagtcctt gctctgctaa taattaatag agtgaaactg acagggtta  10320
ttcacatgtg tgtgcctcag tttactgtta actgaagaat gacaaagttc ataaatttga  10380
aaaggagagg tttcttatat ggggttgcaa cctgcagggt ggccatgcta cagtctggga  10440
agcattgcct ctggctggaa gccagaaaca ggcactttca gggtcagaag aataagacag  10500
agatttatgc tgaatggggt gaccaaatat acatattcaa taggctatag gaggagttat  10560
gaatatttat gaaggagaa atgtgtacat gtgcaatttg gcttcatgcc ccttcatggg  10620
acctacattc aaaaaatggc agccttagca tgatctgagg gaggatcttt cagccctctg  10680
aggtcaaaag tgaaggagag gacaggaaac cctcactgtg tgttctccgt aggggccaga  10740
accactgcat gttttggtgaa cctggctggt tgttatgttg aaactgcaaa agggagggat  10800
```

```
aacagtcagg tgcttgtttg ataccagggg tagaggagac tttcaaaagg gctggtttct   10860
gtttagccct tagggaagaa tgtctaaaga gaattaccta caagggtata acgaggagtg   10920
tctgacattc catctagtaa tgaactagaa ctcagttttc aagttaactc tgggaccctc   10980
ttagccaaga agaggtccat tcagttggtt gaagagctta ggatttcatt tatatctctc   11040
atcactaatc tgcaaaagct ggtagtgaaa ccgcctttgc aaaattatga ctgagacagc   11100
gaaagagatc taacttaatc gattccgtct tgcttctaac ctccaagctg tccttattca   11160
ttcccgggca taggctgaac taactccggg agaagcttag tttatagttt ttagtttaaa   11220
acaaagatag taacagccct ttcccaaagc agacctcctt cttgccttgg aactagactg   11280
cctttagtgg gactaacatt agccacaaga ttagaaactg tggcttagga gtcatacagc   11340
tggaggctac aagattctga ctctccctaa actgctccta agatcagtcc ttgagatatt   11400
ttgcagaccc tgtacttgat ggatcaggtg gcaccaccca gattgataaa gtggctcatc   11460
tgatcttgtg gcccccaccc aggaactgac tcagcacaag aagagagctt tgactctcta   11520
tgatttcatc tctgacccgt cagcactcct ggctcgctgg cctccctcag gccaccaagt   11580
tgtccttaaa aactctgctc ccactgggcg gtggctcatg cctgtaatcc cagcactttg   11640
ggaggccaag gcaggcggat cacaaggtca ggagattgag accatctggc taacatggta   11700
aaccctgtct ctactaaaag tacaaaaaat tagctgggca tggtggcacg cacctgtagt   11760
cccagctact cgggaggctg aggcaggaga atcacttgaa cctgggaggc agaggttaca   11820
gtgagccgag atcatgccac tgcactccag cctgggcaac agagtgagag acttcatctc   11880
aaaaaaataa atagataaat aaccctcgct ccctgaatga atgctcccgg agactgattt   11940
gaatcataat aaaactccag tctcccgcac agcctgctct tcatgaatta ctctttctct   12000
attgcaaatc ccctgtcttg ataaattggc tctgtctaga cagtgggcaa ggtgacctca   12060
ctgggcagtt acagtagtac ccacttcata agtgaaatca cttatcttag tggtagggtc   12120
ccaaaagttg tttggtagga gagggttgag gctgggagag gtggctcatg cctgtaatcc   12180
cagcactttg ggaggccaag gtgggtggat ctcctgaggt caggagttcc agaccagcct   12240
ggtcaacatg gtgaaacccc atctctacta aaaatacaaa aaattggcgt ggtggtgggt   12300
gcctacaatc ccaattactt gggagactga ggcaggataa tcgctcgaac ctgggaggca   12360
gaggttgcag tgagcagaga tcgcgccact gcactcaagc ctaaccaaca ggggcaaaac   12420
tctaggacta gagctaaggt atcaaaaaaa aaaaaaaaa aaaaagaag tagagtgttt   12480 aattaaataa tttgttcttg ctgtaaaatg taaagtagat attcctcttc aaagactttc   12540
ctccccgtct aattaggaat aaatagtaac ttctcttaga agcaaaattt attcaaagac   12600
ctgtgctaac attcttaaat atctgctagc cacaataagg aaatcaatgt actttatgtt   12660
cttagctccc acaatttagc ctaaatattt tccctggcat gtttatactg gtctaagcaa   12720
gcattaggtc atagcctgtt cctcttcctt atttaaaagt gttttacct ttctcagcgt   12780 tccacaagtt acttcctcct tcctttgttc tcctctacct gtgcctcttt taaaagttc    12840 taagttgcta gccaattggg acaaatacag aatgtaaggt cccattccag ccaacggaaa   12900
ctggacacag cagtagggtg gatgtgtcag gttataaatg accctgtctc ctttgtttgg   12960
tgtactctag tggcaaaact gctggcaagt gtaccttttc tgcaggaagt aaaaatggcc   13020
ttactaaata aattaaattt atgttcaagt gctatttctt ttttttttt tttcgagatg    13080 gaatttcact tttgttgccc agcctggagt gcaatgcgc gatctcggct cactgcaacc    13140
tccacctccc aggttcaagc aattctcctg cctcagcctc ccgagtagct gggattacag   13200
```

-continued

```
gcatgcgcca ccacgctcgg ctaattttgt attttagta gagatggggt ttctccatga   13260
tgaggctggt ctcaaactcc tgacctcagg tgatccgcct gccttggcct tccaaagtgc   13320
cttggccttc caaagtggcg tgagccactg cgcccagcct cgagtgctat ttctttacgg   13380
cacggaagaa caaacatttc aaacaatgct attaccaagt ttgttagtat ttattatctc   13440
atttgctaaa cctaaaaaat atatatcctt ctttaacgtg atcgaatatt tcaaaaagtt   13500
attgtgttgt ttcttaaaat aaatcaatca taatcctaga ctatgttact caaactacat   13560
acaacacctt ctgagcttct ggcaggccct tcctccccct cctgctcacc acagatcact   13620
ggaataattg tctgcatgta acttctaatt ttgaagtggt tgtggtttat caaacctgga   13680
acatggcact tccaagtaca tgagctaagg tcacagtaag actcaagccc cttcaacaga   13740
atacctggaa tttctctgtt aaagattttc tcctttacct gactacatgt ttgtaatgca   13800
gatccctcca ggagcgctta cttataaact gtcctggatc actaacgcga catttgatg    13860 taaattagtt tatcttgacg tgctaatggt agaaaaaaag agaacatgag gaaacttggg   13920
tgctttcagg gctggtagga aggattaaat ctttgcggca atttctgaga aggggaagga   13980
aaccttgcta acaattttga tagtttactc catttggctg gagtaactct gatccatttg   14040
tcaaattcac gatggagcag gtacctgtta gggtacaggt ttgataaacc acaaccacag   14100
gtctatttca tttctccttt tccaaagtgg aacaaatttg tctctggggt taaaactgct   14160
tttctcatat tggtgtgtaa gagaaaatga gggaatttct ttgagtttgt ttggtttgtc   14220
tgtttgttta agcagcattt tttaaataat ttactcagcc ctgtctcaga gaaagtccat   14280
gatgatctgg aattcaacct cagggaaaag ttctctcctg tgcctgagac actgcgcaac   14340
taactgaaac cgaaggatgg aacctgggtg tttaatttat taggaacaat tgattcttca   14400
gtgacacttt ccatgcagat acttcaaaca aaataatgga gccccacaga ccgaatgtga   14460
agacagcagt gccattgtct ttggaaagct atcacatatc tgaagagtat ggctttcttc   14520
ttccagattc tctggtaagg atagagcctt ggtaaggata ggtcagaata tgtttcttga   14580
gatgttggtt ggtttgtttt ttaaaaatgt atgtgattat taagagacca atataaaatat   14640 caagttgttt acctgagaaa gatgctacaa agagcataga ttatcattac tatcaaaaga   14700
gaagtgacag ataccacaga gaacaggtca aatggaacat ttttgtttc agtttctttt    14760 gactagattg tcaggccaga gaattataa gcaaacctgt agttatcaag aaaaagcatg     14820
aacttaaata taaataaaga acaaatacag agcctcagca cctggaacat ggcacttcca    14880
agtacatgag ctaaggtcac agtaagactc aagccccttc aacagagtac ctggaatttc   14940
tctgttaaag attttctcct ttgcatgact acatgtttgt aatgcagatc ccccaggag     15000 cgcttactta taaactgtcc tggatcacta tcgcgacatt tgatgtaaa ttagtttatc     15060 ttgacttgct aatggtagaa aaaagagaa catgaggaaa cttgggtgct tcagggctg     15120 gtaggaagga ttaaatcttt gtggcaattt ctgagaaggg gaaggaaacc ttgctaacaa   15180
acaatacctc tttcttaatt ctacttaggg ctcaaattgt aatgcaaatc ttttcatca    15240 tttagcccct ataaacactg tttttctcat ctggtgtggt ccaaggccta gaacattaaa   15300
actatcaaag cttttacaga ccatcaggtg tcatccccct ctttctacat ctgagctagc   15360
tgaaatccag aggaaatgac ttgctgaaag tcatgagtgg caaaagcaga actagttctg   15420
cttataactc ttgactttta gttattatta ttattaatta ttattattac atcctaaatg   15480
agggccaagg ccactcagtt aaaaatcgtg gggtccaggc caggtgcagt ggctcacgcc   15540
tataatccca gcacttttgg gaggccaagg caggtggatc acttgaggtt caggagttca   15600
```

```
agaccaggtt gatcaacatg gtgaaacccc gtctctacta aaaatacaaa aattggccag   15660
gcgtggtggc acatgcctgt agttccagct attggggagg ctgaggcagg agaatccttg   15720
aacccaggag gggaggttg caatgagtgg agatcatgct gttgggaatg aagttttgg    15780 tgtcacagaa aaagaatgaa catgggaaca aatgatctct cagcaaaagg acctttactt   15840
tctgcagaaa gggtgctact caatagctgt ccagccacga gagcacacca aacaaaggag   15900
acagagttat ttataacctg acgcatctac cctactgctg tgtccagctt ccattggctg   15960
gaataggacc tcacatttta cactttaccc aatcggctat tagtttaaaa ctttttttaat   16020 tggataaggg aacagaacaa agaaagaaaa gcaagttgcc cagggatagt taaggaaaca   16080
tctccatata aggaatggca tgcactatgg gctgggcctt ttctagttct gtacagacat   16140
gccggagcaa gctacgacag ctgatttgga cagccactaa tagtggctag caatcttata   16200
gtaagaaatt gtgactttt ataatctttg aagaactttc ccatttctga cagtgccact   16260
gcactccagc ctgggcaaca agagcgaaac tcgtctcaaa acaaaacaaa acaaaacaaa   16320
acaaaacaaa acagctctct actcttggaa gcagcagagt ttttatcttc atttatatca   16380
ctccggtaac actcagaagt agacaagcct cagggtaggt attcagtaaa agcccactga   16440
attccacact attctttaat catagttaaa tggcaaatta ggctggaggg tggggtgga    16500 acctctccaa aattactgca atgactgcaa catcggaccc caagatttt tttttttttt    16560 ctgagataga atctctttct atcgcccagg ctggagtgca gtggcactgt gagaaatggg   16620 aatgaccgg actgtttcct ctgacactgc cactaggttg accaagtgtc cctatttgtt    16680
aggtactgga tggacgcctg acatgcaaga ctctcagtgc taaatcagga aagtgctggg   16740
acaattcgga tgagtcggtc acgctaagtt gcacttaata gctcttgtga ctttgactga   16800
attacaaaca tccctgacc ctcaatttc acatttactg gatggagatc tggtgccacc    16860
tccactagat tgctatggag aatgaatgtg aaagcatttt cataaatcca gtgtaaggac   16920
cagaagccag tcttctgacc ttgagccagt gcttgttaaa aactccactc tatacatcta   16980
acccaattca ggaatatcct gcctagttcc aaaggaagaa aagaccaaat tgctcttatt   17040
gggattaaat gcgtacactg agctgaggaa aaacagtatt acaaatgagc taaacatgac   17100
gtagatccac agttgtagaa ttcccctctt tgttctttcc tctttcataa ctacggaaac   17160
agatgagaaa catttacggc atcaggttct tgtgatgctc cctgcctgat atgctatggt   17220
tttgttaatg gaatgtccat tcctgagctt atgcagaaaa aagtcccttg ggaaagtggt   17280
tttactgtgt tatgttcatt ttccccatag ttctcaaaat gtacttcctt gtttcagttt   17340
taattttctt tcattggtgt gaccatttc aactgctccc tttctgggaa gaggtagcag    17400
acggacattt tcatcaaaat ctgccccagg ttgcttcaca gataaggagg gacccagcca   17460
ctaaaatcac caggcagagt gttgcaagag tagatagaga atcacaattg gctgccctgc   17520
tcaaggggac accagatctt actttcgttt agttgaaagg caagcgtcag agtcgggagg   17580
ctgtaccttc atgtccagtg gcctcacaga agttccttca gtatctcttt tagatgaaac   17640
tcttttagaa gttccttcag tatctctttt ggtttctcac tatagatagt tacttgaaca   17700
tgtctgaaga aaacgtggtc aagacagtga ataaaaaaaa ttctggtttt gggaagcagt   17760
ctgacttagt ttcaaatatt ctatcccact gtttctgtca atgttcaaac ctttccaagc   17820
tccaacattt attgtggaaa atgtgtgcct caccaactca tgcaaataaa tgtttcatgt   17880
gccctacgtg tgtagagggg gcatggatgt gtgttttgg agggagggct aattttctt     17940 tagacatgga gaatacgagg aaattagctt ggcatcaaga aggttacagc aggagacaag   18000
```

```
agtgaagaga actgagagag cccggaaatg aggctctgga gttcagattt tttttttttt   18060
gagatggcgt cttgtacccc aggttggagt gcaatggcaa aatctcagct cactgcaacc   18120
tccgcctccc gggttcaagc gattctcctg cctcagcctc ctgagtagct gggattacag   18180
gcatgagcca ccatgcctgg ctaattctgt agttttagta cagatggggt ttctccatgt   18240
tggtcaggct ggtctcaaac tcccaacctc aggtgatcca cctccttgg cctcccaaag    18300 ttcaaggatt acagccatga accactgcgc ctggcctaat ttttgtattt ttagtagaga   18360
cagggtttca ccatgttggt caggctggtc ttgaactcct gacctcgtga tctgcccacc   18420
tcagcctcat gaagtgctgg gattacaggc atgagccaca gggccaggcc tggagttcag   18480
atttaacaca tcctgtaaat gacatgatgc atctgatatt tgaagagttt tcctcaaaga   18540
atgttacatg caaggtggtt tagagttgtt gtttccggct atatagcaaa agtacttggg   18600
gagttttaaa aaatactgat gccgaagctc cacctagaat agttcattca gaatctctag   18660
cataattgac ctcagtactt gaaatatgat tattataaat gttagtcaac tgcttttta    18720 ggctctatga ctgatagaaa tctttcactt ttatatcatc tccagttaat gagtcccata   18780
aattgaaatc tagtgtttaa atttttactt catatttatt tttactgatt gttttattat   18840 tattatttt gagacagagt ccgctttgtc gcccaggcta gagtgcagtg acgccatctc    18900
ggctccctgc aacctccgcc tcctgggttc aaacgattct cctgcctcag cctcctgagt   18960
agctgggatt acaggagccc accaccaacc acccagct aatttttgta tttttagtag    19020
acggggtttc gccatgttgg ccaggctggt ctcgaacccc tgacctcaag tgatccaccc   19080
gcctcggccc tctgtctcaa acaaaaaca aaaacaataa caaaacttttt ctcttctacc   19140 cgagatgttt aagtttaaat cacaccattt gtacaaaaat tccctgtctt gtccttaaaa   19200
ataatttgta atcactagct agttttgaga tcgattgcca tctaaccgaa tgccatttgt   19260
tctctctctc tagtttcaac ttaataaccc tttctgcatt ttctattctt tcaaaattt    19320 tccggccatt ttattgtttc tatttagtga aaatttattc actggtttct atgcctaagg   19380
gcatttagga agttgcttag gatacagacg tgataaaaag accagtgtaa aaactctcca   19440
ctcctagaca ttatattcta gtcctcatct cctgtcattt aagtcctcag tgattctatg   19500
cacttttgct tttggtttgg gcagatgctc tgagtttaat gtttctctga gatgaggacc   19560
ccctattcaa ctcacaaatc ccataaggag gcctctgtgc ctttgctggt gccccagaca   19620
gggtgctgat gcttacttat cttcaagatt gtgaagtcag atttaatagt atagtcgttt   19680
gccagagctg ctgtaacagt agccacaaac agttgggctt aaaataccac aaacaggagg   19740
gcttaaatca cagaagttga ttttctcaca gttcttgagg caggaagtcc aagatcaagg   19800
tgtcgtggag ttggtttctt ctgatgtctt gctccttggc ttgtagatgg cctccttatt   19860
attgtgtcct cacatggtct tttctccact atgcacaaat tccctatgtc tctctctctt   19920
tttttttttt ttttttttt ttgagacaga gttgcactct gtcacccagg ctggagtgca   19980
gtggtgcaat ctcggctcac tgcaaccttt gcctcccggg ttcaagcaat tctcctgcct   20040
cagtctcctg aatagctggt attacaggtg cgcaccacaa agcccagcta attttttgta   20100
tttttagtag agatagggtt tcgctatttt ggtcaggttg gttttgaact cctggcctca   20160
agtgatccgc gcacctcggc ctctcaaagt gctaggatta caggcataag ctactgtgcc   20220
cagtctcccc ctgtctcttt gtgtccaaat ttcctcttct ttagggacac caatcagatt   20280
aaattggacc caccctaaag gcctcatttc aatgtacctc cttcaagggc ctatctccaa   20340
atacagttat attttaggt actagggcta gggcttcagc ataggaattt gggggagaca    20400
```

```
caatttagca catagcagaa aatataaggc caggaaaaaa tattctggca tgctagatgg    20460
actcattaac aaatattaac caatataaac caattaacaa atatttcttt aatatttgcc    20520
tttttttttt ttttttttg aaacagagtt tcactcttgt tgcctaggct ggagtgcagt    20580
ggcacgttct tggctcactg aaacctctgc ctcctgggtt caagtgattc tcctgcctca    20640
tcctcccaag tagctgggat tacaggtgcg ggccatcaca cccggcttat ttttgtatt    20700
tttagtagag atggggtttc actatgttgg ccaggctggt ctcgaacttc tgacctcagg    20760
tgatccacct gccttggcat ctgaaaatgc tggggttaca ggttgcctgg tgatttttaa    20820
gaggaatgac tgagctctca tgccaggtgg ggggagggga cagagaaagt tgaatactct    20880
gacgatagcc atgatccata gctctgaagc ttagactcga atctacccat cccgcaagga    20940
agaaaacaaa gaaataaaaa agaagaaaag aaatctccca atgtcaggtc ccaccctctt    21000
tagaagtaat ttcagcaaaa cttgttgct attttggcat gtcctctact gtagtagctt    21060
gtcaaaatac tgtccccaaa cgttttctat atttctagat tttactgttt aatgtataat    21120
aataatgttc taacattaaa acgtaaccat agcaatgctc cgactcactt gatctttaaa    21180
tatattgttg aactcaattt tgtgacatct tcagaattgt cttttgtat tcataaatag    21240
caacagtgga tagttgcctt ggttagtgtt attatttcaa ggattaatct ttaggttacg    21300
ttttcttcat aagatgcatt agatgacttt tttttttt ttttgagac agagtcttgc    21360
tctgttgctc agactggagt gcagtggtgc agtctcagct cactgcaatc tccacctcct    21420
ggctcaagag agtctctcga ctcagcctcc tgagtagctg ggattacagg cacgcaccac    21480
catgcctggc taattttgt atccttttta gtaaagacgg gatttcccca tgttggccag    21540
gctgatctcc aactcctgac ctcaagtgat ccatctggct tggcctccca aagtgctggg    21600
attacaggca tgagccacca cacgcagcca attagatgcc ttctcatgct tttctgtgtt    21660
gtgaaacaga tcatctatcc gttgatatag catagctctt cagactacag acattttagg    21720
ctataagttt tgaattacat tttctattcc ctttatgctt cttgttctag ttaggttttt    21780
tatttctaaa taaaaatatg aattttgca atttcccaaa tgcgaactca actgaaattt    21840
tcaagtgtat tagcaaaatt tattcatagc agcctcttac atttcattaa gaattgattt    21900
tttcttattc cctgttgaag tttgtttata aaatatagta atagtaataa ctatatagaa    21960
agtgttcact ttgtagtagg ccctatgtta actttaacta cactttttaa atctaagcct    22020
catagtagtc ttggatggat gcggtggctc acgcctgtaa ccccagcact tgggaggct    22080
gaggcgggtg gatcacgatg tcaggagttc aagaccagcc tggccaacat ggtgacactg    22140
tctctactaa aaagacaaaa atcagccgga cgtggtggta tacacctgta gtcccagcta    22200
tttgggatgc tgagtcagga gaattgcttg aacccaggtg gtggaggttg cagtgaaccg    22260
agatcacaca agtgcactct agcctggatg acagagtgag actccatctc aaaaaaaaaa    22320
aaaaaaaaaa aaagagatca ataaataaaa taaataaata atcctcacaa tagtcttcac    22380
catttgcaaa tgatccatt gacaataaat gaattcagca ctatcatgga aatatatttc    22440
caagctgacc agttttctcc atttccaccc cacttcaatc caccttcatg tagccctagg    22500
actattgtct cctcccctg tttccttatt tccattcctg ttcagctgta acacattctg    22560
ttcatagcag tcaagtgatg cttacaaatg gaaatcaggc tagaggtggt agttcacacc    22620
tataattcca gcattttggg aggctgaggc aggaggatca catgaggcca ggagtttgag    22680
accagcctgg gcaacatagc gagacccat ctctacaaaa ataaaaaga attagctgtg    22740
catgatccta tgtgcctgtg ttccagctac ttgggaggct gaggtgggaa gattgcttga    22800
```

```
cccagggagt tgaggctgc aataagctat atttgtacca ctacactcca gtgtgggtga   22860
cagagtgaga tcctgtctct aaaaaacgta aaatgaaaat aaaaccttga tagtttgctc   22920
tttaaaactc ttcctacagg gcccctgtga tgctcacctg tctctagaag ggcatgtaat   22980
agctctttct ccttcacttt actttgatgc aatgtcagaa cagcttcttt ccatcaaaac   23040
ttaaaccttt gatttcattt aaaatcatct gcttcaaatt ctaatctttc tgatagttta   23100
ggttctaatt tttctgatgt taatattgtc acccaagttt cctgttcata tttacctggt   23160
ttattttatt tttattttta tttatgtatt tgagatggag tctagctctg tcacccaggc   23220
tggagtgcag tggtgcgatc tcagctcact gcaaccttcg cctcctgggt tcacgccatt   23280
ctcctgcctc agcctcccga gtagctggga ttacagggac ccgccaccat gcccggctca   23340
ttttttgtat ttctactaga gacgtggttt caccgtgtta gccaggatgg tcttgatctc   23400
ctgacctcgt gatctgcccg catcggcctc ctagagtgct gggattacag gcgtgagcca   23460
ccgcgcccag actttatttt atttttttgag acgaagtctt gctctcttcc ccaggctgga   23520
gtgcagtggc ttgatctcag ctcactgcaa cctctgcctc ccaggttcag gcgattctcc   23580
cgcctctgcc tcccaggttc aggcgattct cccgcctcag cctcccgaac agctggggtt   23640
acagatgcct gctaccacac ccagctaatt tttttctttt tttggagaca gtctcactct   23700
gtcgcccagg ctggagtgca ctggcgtgat ctcagctcac tgcaacctcc gcctcctggg   23760
ttcaagcgat tctcctgcat caacctccta gtagctggga attacagacg tctgccacca   23820
catcaaacta attttttgtat ttttagtagc tgagattata ggctcgtgtc accacgcctg   23880
gctaattttt gtatttttag tagagacggg gtttcaccat gatggccagg ctcgtcttga   23940
acctctgacc tcaagtgatc tgcccatctc agcctcccaa agtgctggga ttacaggtgt   24000
gagccactgg gcctggcacc tggtttattt ttgtgcatgc ttttatttttt aattttccta   24060
tgctactttc ttagccaaaa tttatactta atctaatcaa gcattaatct aacaaagagt   24120
ttagtgttca tataaaatac agttttacaa atctgttttt ctttaaatta taaatttgtt   24180
aagaaaatta tccaaagaat gatccagaaa caaagaatg gctgtgtgtc ttttcaatat   24240
catcctggag cattgtctca accatctcac tttacggtga ctaaaacatc tagaggtttt   24300
cccttttgttt tctgtacttc ttagtattga ttaatactgt tgtgctactt cagtctgaag   24360
ttccatgtta atctgtagat tttttttttt ttttttgaga cagtgtctcg ctctgtcgcc   24420
caggctggag tgcagtggtg cgattggctc actgcaagct ctgcctccca ggttcaggcc   24480
attctcctgc cttagcctcc cgagtagctg ggactacagg tgcccgccac cacgctgggc   24540
taatttttc tattttttt tttaggagag acggggtttc accgtgttag ccaggatggt   24600
cttgatctcc tgacttcgtg atctgcctac cttggcctcc caaagtgctg ggattacagg   24660
cgtgagccac tgtgcccggc tgttaatttg tagatttta tacagaaaag cagcaaaata   24720
tttctgttga gtagaaaata taactccaat gcttatgact gtattcctta taggacacta   24780
actcattatg tgtctaacct agcaatttta tgtcaacact attttctcaa acctctataa   24840
actttggctg ggcacagtgg gtcacacctg taatcttagc actttgagag gctgaggcag   24900
gtggatcacc ttaggtcagg agttcaagac aaggctggcc aacatggcaa accccatct   24960
ctactaaaga tacaaaaaat tagccaggca tggtgacatg cccctgtaat cccagctact   25020
caggaggctg aggcaggaga atctcttgaa ctcaggaggt ggagccaaga tcatgccact   25080
gcattccagc ctgagcaata gggtgaaact gtgcctcaaa atgaataaat aaaataaata   25140
aataagtcag agattgtgaa taggatgttg gatatacca agttatgaat taattaggag   25200
```

```
cttgaaccca ggaggcagag gttgcagtga gctgagatcg caccactgca ctttagcctg   25260
agcgatagag tgaaactgtg tctcaatcaa tcaatcaatc agagattgtg agtaggatgt   25320
tggatgtacc caagttatga attaattagg agcttgaacc caggtttgtc tcagatcctc   25380
agggactgaa gacttccaag tgaattatgg gtaatgtata ggtctatact actccaaatt   25440
tacagttttc agacttccct gggttctcat ggaccttcca tgtcatttct atgtttaggt   25500
tgaggtccct ggtcttttct cctctgtaat taatttcaca cccaccccta tctcaactca   25560
cacaacttga tcttcactcc catctgctaa gaaattgagt ccataaaaag tgaactcctt   25620
taaactctag atcttctact gctgcaagga cagacattcc attctggctc tctctctcct   25680
cctttgcttc ttccagtcct ttgctccttc tgcattctgt tactctcctc tctcctttgt   25740
cttcaatctc tccctcttgc aatagccaac tataaactgc tcaagcttct cattcttaaa   25800
agatctctct gaaatgcaaa ttccctactg ccttatggct ctccttcaaa agtaatctac   25860
attttctcta ttttctaatt cctcaacaca ctaacgtttg aaccctgctt ctatgaccct   25920
gacctaaatt tctattaaat gtacatagat aaactaatat atatttgtga cttcctaata   25980
ttgttttgtt tttaaagag gtcaatctta ctttaactct gtaatgatgc ggttgacctt    26040
ctgatgattc tctacttctg tgaaatcctc tactgtcttg acttttaat taatttattt     26100 ttttttgaga cggagtctcg ctctgttgcc caggatggag tgcagtggca caatctcggc    26160
tcactgcaag ctccacctcc cgggttcatg ccattctcct gcctcagcct cccgagtagc    26220
tgggactaca ggtgcccgcc aacacgccca gctaattttt ttgtattttt agtagagacg   26280
gggtttcacc gtgttagcca ggatggtctt gatctcctga cctcgtgatc tgcctgcatt    26340
ggcctcccaa agagttggga ttataggcgt gagccaccgc acctggccct actgtcttga   26400
cttttatagg gtcattctat tcaagctcat tgagcgtctg tcactatgtt tttgatctgt     26460
attgctggaa tcagttcctc tatctgcctt gtgaatattc tccattgtgc taatctaggc     26520
ttctcctttc attttcata ttccctcaca tggctttata cactcttgtg gttttaacca    26580
caatataggg tttttactgt agttatgctt tcaaattgta tacttctttt tttttttttt      26640
ttttgaaatg gagtgttact ctgttactcc agtctggagt gcagtggtac gatcttggct    26700
cactgcaact ttcgcctccc aggttcaagc gattctccta catcagcctc ccgagtagct    26760
gggattacag gcatgtgcca acacgcctgc ctaatttttt attttagta gagacaggat    26820 ttcaccatgt tggtcaagcc cgtcacaaac tcctgacctt aggtgatccg ccctcctcgg    26880 cctcccaag tgctgaaatt acaggtatga gccatcgtgc ccagccccaa ttgtatgttt     26940
ctaatatgac ttttctcctg aactttaaac tgtgtatcca acttctcagc acagtcatat    27000
cttttgattc cacaggtaat ttaatgtcaa tatatttaaa aatgaattta ccacctttat    27060
ccccactctt tgactttcac ctgcatttct gtttcaattc ttgttccat ccattcattt      27120 gctcacctaa ttcataaaca tggaaatcat cctcaattcc tcttcttctt agcccaaaaa    27180
ttcaattgtg caggttatgc actgagaaaa agagcctcag gttagggga taaatcagag    27240 attggtgaac tttttctgaa gggccaaata ctaactgctt taagcttgct taccatatgg    27300
tttatgttgc aactaccaac tctccctgctg taatgtaaaa gcaaccatag atagcatgta    27360
aacaaatgag acaggctggg tgccaatgaa aattcacgaa aattaatgta gtttactgtc     27420
ccttgggtga gagttggggg tcactgaaat tcggactatg tcttacttgg ctaaaccaca    27480
ggcctagagt gggccataaa tggagctatt gggctagtga ttttcttgcc ttaagccccc    27540
agccccaaat ttaataatca catcattta atttcatttt ccaagtgtat ctttaatata      27600
```

```
tggcttctcc tttccaaatt cactgtcatt acctaagttt agtccttgaa caatatttta    27660
aaggcttcct tatctgactt tatatcttaa agtcctacaa atttatcttc ctaaaattca    27720
aatcaaacca tgtcaccaac ttacagaaag ggaaaattca tatattctac acacagcaca    27780
tttcatgtaa ctttctaggc tcatctttca tcatccttt gatgcaggat tttctgctcc    27840
tcagctcagc gaaatccagg atcttgtctc atgaccagga agaattaggc aggtggacat    27900
agtgaagggt gaggatgacg gaatttatta agcaaaaggg gagttctctg caaagagagg    27960
ggtttcacca gcagtctccc acctcacaat ggagcaccag gactttcaca cacaaactga    28020
aaaggctagg ctcctcccca gcataaggca tgaattcctg gtggttccac cagttttcct    28080
actatgcatg tgggtgtgcc caagcaaacc ataggtagta tcagaaaagg caacatttga    28140
ttggttaaaa ggcattattc acccaagcaa accataggta gtatcagaaa aggcaacatt    28200
tgattggtta aaaggcatta ttcagaaaga atcaatcggg aaagggtgag ccaatagggg    28260
aagttctccc tctgggtcac gggtttcatc tgggaccagg agtctggcct ttcagccttt    28320
agactgtttt aggcttgaag gtgggtttca cagggaccct tccctatctg cctaggcatc    28380
tgtctgcctc ctgcctctat cactttctct tgagttttat attttagcaa cactgagtca    28440
tctttgtccc aggaagcacc tacatctgtt tatctgctgt ccctctacc tttactacct    28500 tcccttcttc acatttatac ccagaaaagt cacttcccct ccaaaaattg ggatcaactg    28560
tcatattttt atgaatattt cactttaatt cctcacaaca gctgacagaa ttaactactt    28620
cctcttcttt gcaagttatt tggctcacac agatatcagt aattaaacat attttactgc    28680
attggcatat atctgactaa tgtgttttc tcccgtacta ggcaatatgc tccttagtca    28740
tctgtgtatc tgaggtgagc acagggccta actagcatat ggtgcattct caatgttcgt    28800
tcaactgcat tgacttgaat tcccctgaag actgaaatgt gaaaatagct actctcggaa    28860 gccccttttcc agagaggtct aaaatattta catgtttcta ttttaaatgc agaaagaact    28920
tccagatcat tataggcctt ggatggaaat tgccaacaaa cttcctcaat tgattgatgc    28980
tcaccagctt caagctcatg tggacaaggt attcttctct tcaccccctc atcacattct    29040
gttttcatca tcataccact tttctttctt agccttgtgg aagtgtgtca attgtcctgg    29100
gaaactgttc attaccattg aacttatcag caaagctata tcttccttcc tgaaaaacag    29160
aatgacccct tcgtaatctg atacatgtgt tttcctaagg ttttcagagc cagcacaaaa    29220
caatgcctga cacatgccaa taactcacca aatgtttgtt taagaagaa tctgggtggg    29280 aatgataaac taactaatgg acaaggtatc gcctaagaag gtcagcttgg aaattctcag    29340
gttcctcatt ccatgtacgt actcaaggct ctgttgttac tgagggggtc taacttgatt    29400
ttgtcctagg tgttatagaa tagttaaatg gagggaattt ctgaattata aaattggcca    29460
tgggttctac aaaacatcca ataagcctgt aaattccaca aaagtgttga ttaggctgat    29520
acaaaggtaa ttgcagtttt tgccattact tttaatgaca aaaaccacaa acactttttgt    29580 accaacctaa tagctatgta accctgaaaa agttactcaa ctctgtaatc ccatttcctt    29640
atttataaaa tgagagaaac tctggtctca cagtattgtt atgggaagta aatcactttc    29700
aaagtggccc ttttgtagtt cttgtcctat aatagcattc agtatacatt cattacttct    29760
ctgtagtctc ttctccatct gtcctaatct atcagtttgg agtaccacat aattgcggaa    29820
gtccatgaaa agttttccgc tctccaaaat ttcccttttgc tgatggataa tatttaatgt    29880
ctagaattac aaattctttt taaaatactc attgaatgtt tgctttgtgc aaagcactag    29940
aaccttgtaa aagatgagta agggactggc ttcaatgtct gtgaagatag caaactaaac    30000
```

```
agagtaattt ctttgcctga tagataaaat gttgtgttga catgaccaaa gaaatccaaa    30060
aataagaaaa aaactatctg taaacacaga aaaatagaga aaagttccaa tgatggaata    30120
aaaatttaaa ggattttttt gaacgtatta agcaaatcat gtataaaatc cagaaataag    30180
tttacaggac ccatgtcaag gatttaacca aagcagaggg agatccccat gagtcccctt    30240
ttcccatctc agaatagcag agaagagaag caagggaagc ctggaacagt tggcaagagg    30300
gcaggttaga attcagtttg tgaattatga ggtcgtctgc cgtaggcatt taccaggctt    30360
tatttgattt aactgccata aaggaagaga aggacttgtt aaattggggc tcctcttagc    30420
acagcattga aaccagtccc tattccttct tggcctttttg gctaaaattg agtgtgaaat    30480
ctatcaccta acatttgtac tgggtttagg ctgggtgtgg tggctcacgc ctgtaatcct    30540
agcactttgg gaggccaagg ctggcggatt gcctgagctc aggagttcga gaccagcctg    30600
agaaacatgg tgaaaccatg tctctactaa aaatagaaaa aattagcagg gtatggtggc    30660
acatgcctgt agtcccagct atttgggagg ctggggcaga agaatcactt gaacccagga    30720
gacagaggtt gcagttagct gagatcacac cactgaactc tagcctgggc cacagagtga    30780
gactctgtct caaaaacaa aacaaaacaa acaaacaaat atatatatat taaaatacaa    30840
atttttactg ggtttaatag tgtcttccta gaagtcatgt tcatgcataa tctgtgaaag    30900
tggtcttatt tggaaatagg gtgtgtacag ttgtattcga gttaagctga ggtgatactg    30960
gattaaattg tatatgatga gtgtccttat aagaagagga aaaattaaac acaggaacat    31020
agactcaagg gaaacatca cgtgaagatg gaggtagaat tggaatgatg cattgacaag    31080
ccaagatgtg ccaaggattg ctggcagtca ccaggagtta ggagacaggc atggaacaga    31140
atggaacaaa ttctccctca gaggctccag aagaaatcaa ccctattgat accttaattt    31200
gggacttcta tcttccataa ctgtggcaga gtacatttct gctattttaa gtcatgatgt    31260
ttgtggtcat tagttatggc agcgcataaa actaacacaa cactcttggt ctctatcgct    31320 tcttttttttt tttttttttt ttgagacaga gtctcactct gtctcccagg ctggaatgca    31380
gtggtgcaat cttggctcac tgcaacctcc agctcccagg ttcaagcaat tctcctgcct    31440
cagcctcctg agtagctggg actacaggca cccgccacca tgcccatgta attttttgtat    31500 ttgtagtaga cacggggttt caccatattg gccaggctgg tctcgaactc ctaaccttgt    31560
gatccaccag cctcagcctc ccaaagccct gggattacag gcctgagcca ccatgcacgg    31620
cctctatccc tactcttaat tgcctggaaa ataccctaaca aatgaaggcc agttttttaga    31680 ctttaccacc aaaggctgaa attgaaacag gaattgtttg tgagaagcaa acacaatagt    31740
ttcgagagac tgaatcagtt agcaatttcc tgtgagaggc aaatgtaata gtttctagaa    31800
ccacagatgg agctataaca aaaacatgtg ttctctggat cctttacttg ctacagacaa    31860
cacaataagt gaatttacag ctttgatctt acagtgcacc taagccaacc accttgtctt    31920
agaatgtctc aacatatccta tctgtatctt gaaacaaaat atattaattg ccttagaccc    31980
attcactcac atttcctagg aagacatgat cagagggagc tatgcaagaa gaaatccagc    32040
agaactctgg aaatacaata agaaaatcca tattagacac taatcttaat aaaactaacc    32100
ttcgttcatg aatttgaata gacaaaatta ccaaataata tggaaaaaat gggcaactca    32160 aaagaagag ggtagcccac ttggcattca ggaccaatgg cctccaataa ataagatgat    32220
attagtgctt taaatatttt atttagtgta tccagtatat tgccttccta aattaagtga    32280
aagctgatat ataaaagaa ctattagaaa taaaaaacca cacacatccc agaactcctc    32340
aatataaacc taacaaattc agtaaaacat tgattgcaaa aaatatatat agtgacttag    32400
```

```
ggacttcctt gataaatttc ataaagcata aagaaaaatc aaagagtgca aaccatcaga   32460
aaaatacaaa tatataaaaa agagaaatac aggtgatcca aattcctttt aatggaatcc   32520
cataagcaga tgggtggagg aaaagtaaaa cttccaacat ataagcacaa aatttttaga   32580
ccttaagaaa tatttgagtt ttttatatca gaaagacagt gttggggtga gggttggggg   32640
gcacatgtaa atactcagat aaaattgtga atttttctagg gtaaagaaat ctgcatattc   32700
atagaaaaca aaaatgaaaa atagtttatt tacagagtaa atacatacga ctgtttacct   32760
gtaatgctaa atattaaaag acagtttctt ttcttttttt tgagacagag tttcactctt   32820
gtcgcccagg ctggagtgca gtggtgctat atcgactcac tgcaacctct gcctctgggt   32880
tcaagcaatt gtcctgcctc agcttcccga gtagctggga ttacaggcac ccgccaccac   32940
acccagctca ttttttgtatt tttattagag acggggtttc accatgttgg ccaggctggt   33000
ctcaaactcc tgacctcagg tgatccaccc gccttggcct cccaaagtgc tgggattaca   33060
ggcgtgagcc accgtgctgg cctaaaagac aatttcatac ctatttgtat ggctaatttt   33120
ttaaaaatct ggccatatca aaatactgaa gaggacgtat agcaatagag actttcattc   33180
attgctggtt gaaatgcaaa atggtacagc cagtttgaaa actagcttgg cagattctta   33240
taaaatgaaa catagatttta ccatgcaact cagcaatggc attcctaagc atttatccaa   33300
gtaaatggaa aatgtatgtt cccagaaaaa aaatccatat atgaatgttt ataacagctt   33360
tattcataat caccaaaaaa aaaaaaaaat ctggaagaaa acaggatatc cttcaaccgg   33420
ggaatgaata aaccaaatta taataattgt aaattgtggg atggatagtg gaatagtatt   33480
cagcgataca aatgattgag caattaattt gtgcaatgac agggatgaac cttaaataca   33540
tttacctaaa tgaaagatgt caggcctata ttgtatgatt cttttcaaat gacttttag    33600 aaagggcaaa actagaagga ttaaatatag ctttatggtt actagagaca ggtaaggagt   33660
gggtagttga ctgcaaaggt aatatatagg ggaatgttta gcatgatgaa actgttttat   33720
atggcactca ggtgatggat atatggctct aggcactgaa aaacccatgg aattgtatgt   33780
cacaaagaat ggactttcat gtatgcaaat tttaaaaaat aaaccagaaa attgggagaa   33840
tactaggatg gaatgcagac tgtgataaat aaaactaact ggactctcag caaactaaca   33900
caggaacaga acaccaaaca ccgcatgttc ttacttataa gtgggagttg acaatgaga    33960 acacaaggac acagagaggg gaacatcaca caccgggcc tgttgtgggg tgggggggcta   34020 ggggagggag agcattagga caaataccta aagcatgagg ggcttaaaac ctagatgatg   34080
ggttgacagg cgcagcaaac caccatggca catgtataca tatgtaacaa accagcacat   34140
tctgcacatg tatcccagaa cttaaagcaa atttttaaaa aagtaaaaaa aaaaaaaca   34200 aacaacaaca cctaactgga ctacaaatgc actatataac ttcgatgaag agagtgggga   34260
gtagggaaag gaacggactt aaattactcc agaaaatagt gttgtgttgt gactagaatc   34320
tataaggctt acggtaaatg aaactttaca ggatcactat actctaattg gtaaatcagt   34380
ttttcatggg gtgcgggtga acagttgtga aactgcttta catgtagtca tacctttgca   34440
ttttgcagat atttcaattt ttacaaattg aagattcgta gcaaccttgc atcaagcaag   34500
tctgtcaacc ccattttcc aatagtgtgt acgcatttgg tgtctgtgtg tcatatttg    34560 ataattataa caatagttaa aacttttct ttactattac atctgttaca gtgatctgtg   34620
atcagtgatc tttaatgtta ctatcataat cgttttgaag gtgccataaa ctgtgcccct   34680
ataagtcctg aaacttaatt gataaatgta tgtgttctga ctgctccact gaccagccat   34740
tgccccatct ctctccccct cctcaggcct cctgatttcc tgagacataa taatattgaa   34800
```

```
attaggccaa ttaataatcc tacaatggcc tctaagtgtt caagtgaaag gagttgcatg    34860
tctctcactt taaaaatcta aaactagagg ctggtcatgg tggctcaggc ctctaatccc    34920
agcactttgg gaagccaagg cggggagatc acctgagttc aggacttcga gaccagcctg    34980
gccaacatgg cgaaactctg tcttgactaa aaatgcaaaa attagccagg catggtggtg    35040
cacacctgta atcctagcta ctcaggagac tgaggcagaa caatcgtttg aaccctggaa    35100
atggaggttg cagtgagcct agattgtgcg attgcactcc agccagggca acaagagtaa    35160
aactccttct caaaaaaaaa aaaaaaaata tctaaagcta gaaatgatta agcttggtga    35220
gaaagtcatg tcaaaaccag ataggcttaa agctgggcct cttttgccaa acagccaagc    35280
tgggagtgca aaggaaaagc ttttgaagaa aattaaaagt gctactccag tgaacatacg    35340
aatgataaga aagcaaaaga gccttattgc tggtatagag gaagtttgag tattttggat    35400
agaagatcaa accagccaca acttccctta aaccaaagcc taattcaaag aaaggcccta    35460
attctcttca attctacaaa gtctgagagg gctgaagaag ctgtagtaaa aaagttttaa    35520
accagcagaa tctggttcat gaagtatgag gctagaagcc atctccacaa cataaaagtg    35580
caaggtgaag cagcaagtgc tgatggagaa gctgcagcta attatccaga agatccagct    35640
aaaatcatca atgaaggtgg ctacattttat tttttatttt tgttatttat taatttattt    35700
attttgagac aaagtcttgc tctgtccccc aggctggagt gtggtggcat gatgttggct    35760
cactgcaacc tccacctcct aggttcaagc aattctcctg cctcagcctt cccagtacct    35820
gggattacag gcatctgcca caacgcctga ctaattttttg tatctttggt agagacgggg    35880
tttcaccaca ttggccaggc tggtcttgaa ctcctgacct caggtgatcc acccgccttg    35940
gcctcccaaa gagctggatt acaggcatga gccaccacgc ctggccagtg gctacattta    36000
aaaataggtg ttcaatgcag acaaaaccat cttttattgg aagaagattc caaccaggac    36060
tttttttttt tttttttttt tgagacagag tctcactctg tcgccaggct ggagtgcagt    36120
gatgcgatct cagctcactg caatctctgc ctcccgggtt caagtgtttc ccctgcctca    36180
gcctcctgag tagctgggac tacaggcacg tgccaccatg cccagctaat ttttgcagtt    36240
ttagtagaga cggggtttca ccatgttggc caagatggtc tctatctctg acctcgtgat    36300 ccaccccccct tggcctccca aagtgctggg attacaggtg tgagccactg cgccggccc     36360 aggactttca tagttagaaa aaagtcaatg cctagcttga aaggacaggc tgactctctt    36420
gttaggggct agtgcagctg gtgactttaa gttgaagcca gtgctcattt accattcctg    36480
aaatcttagg gcccttacca gctatgctaa atctactctg cctgtgctct gtaaacggac    36540
aataaggcct ggatgatggc atatctattt acagcatgct ttactgaata ctttaagctc    36600
actgttgcga cctactgctc agaaaaaaat attcctttca aaatattact gcttattaac    36660
aatgcctctg gtcacccaag agctctactg gagatataca ggaaataaat gttgttttca    36720
tgtctgctaa cacatttgtt ctgcaaccta tggatcaagg ggtcattttg gctttcaagt    36780
cttattattt aagaactata ctttgtaagg ctattcctga cacagataat gatccctctg    36840
aagaatctgg gcaaagtcaa atggaaacct ggaaaggatt cactattcta gatactatta    36900
aaagcattca tgattcatgg aggacgtcaa aataaaaaca ttaataggag tttgcaagaa    36960
gtcaaccctc atggatgact ttgaggggtt caagacttga gcagaggaag tcactggaga    37020
tgtcgcagaa atagtatgag aactaaaatt agaagtggaa tctgatttta aactgagtt     37080 gctgcaatct tacgattgaa cttttctttt cttttttttt tgagatgccc ctgctgagct    37140
gccagttcct gaagggtcac cgggagcagc gcctggccca cctggtcctg agcttcctca    37200
```

```
ccatgggtta tgtctggcag gaaggagagg cgcagcctgc agaggtgagg gccagagagc   37260
agcttctcct gttacccggc aggttacctg cgcctggagt aacgtgctcc ctgcttggtg   37320
ctaccctgtt ttcctggaaa atgggtactt tcttcttctc gatgggcatc agtttaagca   37380
acgatgaagg gctcatttat tatttattat tattattttt ttattttatt ttgagccagt   37440
ctcactctgt cactcaggct ggagggcagt ggggtgatct tggctcactg caacctcccc   37500
ttccaggttc aagcaattct cctgcctcag cctttcttgt agctgagact acaggcaccc   37560
accaccacac ctggctaatt tttgtatttt tagtagagat gggtttcacc atgttgccca   37620
ggctggtctc gaactcttga cctcaggtaa tctgcctgcc tgggcttccc acagtgctgg   37680
gattataggc gtgagccact gcgttcagcc tgaagggcca tttaaatgaa ggattttttt   37740
attttaattt ttctgactaa gagctaattt gttttttaaa ctggtagcta tttcttcctt   37800
ttataagctt ttgaatgttt gtttgtttgt ttttggcact ctcttccaag aatgtttgaa   37860
gacctgcatt tgaaggcaga ttgccttttt gctttaaaac agggttgcac catgttgccc   37920
aggctggagt gcagtggtgc aatcatagct cactgcagcc tcaactcctc ccaggctcaa   37980
gcaaccctcc cacctcagcc tcctgagaag ctggggctac cagcatgtac cgccacaccc   38040
agctaatgtt aaaaattttt tgtagagatg agggtcttgc tgttttgccc aggctgatct   38100
taaactcctg gcctcaagtg atcctcctgc ctttgcctcc tgtgctggga ttacaggcgt   38160
gagccaccat gccgggcctg aagacagact ctgagaattc ataaaaacct cacagcattt   38220
tgtactctta tgtatataaa ttatctaggt tgctcttcat aatcctgtaa agtaacaaga   38280
gccataccgg cccatttac aactgaaaag cacagacact tatttcctta atcaaggtca   38340
gacagcaaat tagtggaaaa gccaaggcca gaacccaggt cttctgattt tactagtgca   38400
gccttctttc cccaggggac acattgacat ttacaacact catctttatt tttttttaa   38460 tactgctttc tatccagcca attattagtc tgtcttttaa taattcatcc aaatctcttc   38520
tgaatcattg cataactttg tacagtttcc acccacagtg tcttttactt ttattttttgg   38580 aagtaactgt ttttaaaagt tactgttatt tttaaaagtg tgccttcccc agaaaatcagg   38640 gagttaccca tgtcctagaa ctccacggtg aagagaacag cctgtgccca tcgtgtttgc   38700
ctgattgatc ctacctcttg tctctcgggg aaacacagga gactcaggga agaggaaaag   38760
tgtagagtca ttgcagcctt gttatttgtc aatgcatctc ttttcttttt cttttcttt   38820 ttttgataca gagtttcact cttgtcgccc aggctagagt gcagtggcgt gatctcggct   38880
cactgcaacc tcggcttcct gggtccaagg gattctcctg actcagtctc ctgagtagct   38940
gggattacag gcacctgccg ccacggccag ctaattttttt ttgtattttt agtagagacg   39000
ggtttcacca cgttggccag gctgatctcg aactcctgac ctcaggtgat ccacccacct   39060
gagcctccca aagtgctgtg attacaggca tgggcccag cacccggcca gtgcattgca   39120 ttttttttt tttttttcgag acggagtctc actctgtcac ccaggctgga gtgcagtggc   39180
acgatcttgg ctcactgcaa gctccgcctc ccaggttcac gccagtctcc tatctcagcc   39240
tcccaagtaa ctgggactac aggcgcccac cacaacgcct ggctaatttt tatattttta   39300
gtaaagacgg cgtttcacca tgttagccag gatggtctcg atctcttgac ctcgtgatct   39360
gcccgccttc gcctcccaaa gtgctgggat tacaggcgtg agccaccgtg cccggcgtgc   39420
attttttaaa gtgtgtctga tgctgaaaag tttgaagtct aggcacgtcc cagtgggtcc   39480
tctttatacc atccctctg caaaccatta tcctaaattg gggtttgggg gagagaagag   39540
tgacagtgga aagaagtctc cacctcccag ctgtgccctg gtagttccag gggacccgga   39600
```

```
ggctccccac acccaccacc ccgcctcaga tcacctttca cttctttgt ttctcctccc   39660 ttgactttc agctcagaaa gtacctggct ctccaatgcc ttctgaggaa agtttacccg   39720
aggttcacat tgcaagactc attaaagctc tttagtgttt tccacccgag aaaaaattca   39780
agggaaaaat gaagacaaaa gcagggcatt cttaatggat attttatctt aaggagaaat   39840
gaaaatggag atggaagagg gggcacaagg atggggtttg aatctagact cgttcagcct   39900
ttacctccga tagagaacct catacagctt ttctggactt ctggctgata aagagccgtg   39960
gagggttcct tggataaaaa aggttgaagg gggtctgtcc tgtggtggct tacttgaagg   40020
tattactggg tttgacttat ggagtaagag acggagtcag tttccccaca ggctgaggca   40080
gtctgtcctc atgctttct agggcactgt ggtctcccag gctcatacct aggtgcacac   40140
acaggtttct gcatctagct ttgtatctct atgagtcggt caatcaataa atctatctat   40200
catctgtcta ctgatctatc atctatctat ctagctagct atcatctctc tatcatctat   40260
ctatgtatct atcatctctc tctatatatg tgtgtatata tatatatata tgtatatata   40320
tatttctatc cttccatcta cttacctatc tatcaaaatt ttttccgtt gataatattc   40380 tcgggcccca gtttatgttt aattgttttg gtaatgccctt tctttgcaca gtcagtttac   40440
agaggttatt ttatattcta tatgtatgtg tggtccagcg ttgtaatttt cacatatatt   40500
gcaccgtgta ctcataagca gtatttccac tgggtcatta acagaaagat atgtgtgcgg   40560
catatgaatg tgcatcactc aggtaattca agcttggttc ccagatcatt tctgtaccac   40620
aggattgccg aaataaaaga caaccatggt tatttcctct gctgcaagct ttctagaata   40680
tgctatttgt ctggatttat atctgaaagg tcctgccaag gaatcttgcc cttccatttg   40740
tcgaagtctc caggaacttg gggctccctc ctatcctggt ccactcagac ttggtgctga   40800
cgaactggac caaaaaagat ccagacgggt aaggaaggaa gagaatgctt tgaatttcca   40860
taactttccc ccaggaaaca cccaggcttt tttttataat tagggaagtt catatttatg   40920
gtctgccgta tggttccaaa gaagggtga gcttgaccaa aaattcaaat atcacaggcc   40980
ccagaagttt cctcttaatc cattctgaac acattggctc agaccatttt gtcttgtttg   41040
tttccacatg acgtgtgaat ttctcaacct gaccttcaag ctcctgcaaa atcagctttt   41100
atttgttctt tctcttcaaa ctgtttattc cctaagatgc cctccattca tatcaggtta   41160
aaaccagttg gctttgataa gtaatcatta tataatgatc agaagagaat gattatggat   41220
gaattcagag cagatgctcc aggtgggttg gattgagaat ttgattaata attccatcta   41280
ttccaccaaa gtcacatcat tcctttgaca gttgggctgg aatagggc atttgtctac   41340 agaaggaata gcatgagatt ttaacaaaca agaaattcaa caaacagaat tagacagatg   41400
atctgagatg ttaaattttc ctttcacctt aattttgca gccaaattta tttcagctct   41460
agatgaaaga gacagcactt tcttttgtgg ctgactacaa cagctgaaga ttcactgagg   41520
tttgatatga ggaagaactt cctcagccat gggattgcca gaggcgatga tgggaatcta   41580 cttaaaggg ttacatattt agtagacagc ctagatttta agactaattt atgtgccccg   41640
gccgggcccg gtggctcacc cctgtaatcc cggcactttg ggaggctgag gcaggtggat   41700
catctgaggt caggagttga agaccagcct ggccaacatg gtgaaacccc gtctctacta   41760
aaaatacaaa aaaattagcc gggcatggtg gcacatacct gtaatgccag ctgctcggga   41820
ggctgaggca ggagaattgc ttgaacgaag gaagtagagg ttgcagtgag cgaaatcatg   41880
ccattgcact ccagcctagg tgacaaactc tgtctcaaaa gaaaaaaaaa ttatgtgccc   41940
cattggaaga agtgagattc ggccatctca tctctctcgg gagctctgag ccctggagtt   42000
```

```
ttatgttttc tgcaattatg aattgtgatc cttgattaat tatgctttaa taataaaatg   42060
ggtgactact gaaagctgct gaatctgggt aagaatttgg atgaaaaaaa taatatatgt   42120
gcgtaattta ttctgttcaa ggtactgaat attgaataag ctggatttat tactcaaaga   42180
gaaagacaga ataagagaag gttgaaggga aaaatgactg tactagaatg gtagtcaaaa   42240
atgcaacaac aggcaggtgc agcggctcat gcctataatc ccagcacatt gggaggccca   42300
ggtgggcagg tcacctgaga tcaggagttt gagaccagcg tggccaacat ggccaaaccc   42360
cctctctact aaaaatacaa aaattagcca ggtgtggcag tgggtgcctg caatcccagc   42420
tactcaggag gctgaggcag gagaatcact tgaacctggg aggcagaggt tgcagtaagc   42480
tgagactgca ccactgcact ccagcctggg tgacagagtg agatcctatc tcaaaaacaa   42540
acaaaacaaa acaaaacaat aacaaaaaag ctattaatag cttcctaggg agtaagagtg   42600
aagggctagt ttaattccag agatgcggac acagtcctgg gtctcaccaa ttattctgct   42660
tggtaattac cttttgaagc cttttaatat gcctaacaca gagctaagtg ctatgaagaa   42720
atgaaagaaa tagaagcaaa gtactcccca tgtggttaaa taacaagaca ctacatgaca   42780
aatgtcaaag agtgactcaa acaatatgtc ctttagaatt tcagagaaat gacatcaatg   42840
caggctttac aagtcagtaa aaatcttggt gatgaggcag aacttgatgt aaggcaaatc   42900
ctaaaagttg agtaggaatc aactagctag aataaaatgt ggggttgtgg taaatacaaa   42960
aatgtaagat gagtgaaata acttatttat ttatttattt attttcagag acggagtctc   43020
cctctgtctc ccaggctgga gtgcagtggc atgatctcgg ctcactgcaa cctctgcctc   43080
ctgggtttga gcaattctcc tgcctcagcc tcctgagtag ctgggattgc aggcacctac   43140
caccacaccc gactaatttt tgtattttta gagagatggg gttttaccac gttggccagt   43200
ctggtatcga atcctcgacc tcataatcca cctgcctcag ccttccaaag tgctaggatt   43260
acaggcatga gccactgtgc ccagcctaat aatatattaa gatggccaca ggccaaatat   43320
tctggggctg gaatgtgagt ggaaatgtcg ctcacccttt atcacatagc accccatagt   43380
ccagccacaa cttgcagaat tcaaagtaag tgtggatgtg tgtgtgcctg cagtgccttg   43440
cacacaagtg tgcatgcctg tggacatgtg acccctagaag ttattaatat atctggttta   43500
caaactgaat tgttcttttta ttttttttct ctcttggtgg tcatcaataa ctgaaattgg   43560
gctagattcc tggaaattgg gtaagttctc agaaatcatt tacgcacttt agaatccagg   43620
ccaaatttaa aatcttacaa taaaacaaag aacaaagcat gctaaattat atgtataata   43680
taatatcaac catataaaat gcataaaaaa tatactagaa ggaaatgtgc ctaaaattca   43740
cagtctaaaa tttaacagtg attgcctctt ccttgtatag ataagggatt ttttttttact   43800 gtattttcca gtctgtacat aataaaacaa gtaatgtgca atgcaaacaa acaaaatga   43860 aactttatca aatttcagta actccttgaa gtttaatttt tttttgaga ctgagtctta   43920 gtctgttgcc caggttggag tgcagtggtg tgatctcggc tcactgcaac ctctgcctct   43980
gggttcaagg gattctcctg cctcagcctc ccgagtacct gagattacag gcacccacca   44040
ccacacctgg ctaattttg tatttttagt tgagacagcg tttcactata ttggccaggc   44100
aggtcttgaa ctcctgacct caggtgatcc acccgccttg gcctcccaaa gtgctgggat   44160
tgcaggcgtg agccactgca cccagttgaa gtttaatagt gtgaaaaaaa tatttctcat   44220
ctcactatat cttctatggg aggccagatt gcagattgtc tacagaaaaa tcccttcaaa   44280
agaccttgtt attacataga ctggagctca tggggcaggt ctggtccaca catccttagg   44340
ctccgcttct cctggaaaac aaaaatagcc tctgatccag tgttgcctct cccatcacca   44400
```

```
aacctcagct tctatcgcca aactcatcaa ataagagtgt ccagtagaaa aactgggcag   44460 atggggggcac agaaggtgaa gacatcattt cccaagctaa tgttgctgct ggaacaatgt   44520
aagtcttgac tttgtcttgg tttggtttgg tttgacattg gtttgttttt catctttgtc   44580
tcatgcttaa aatgtgaagg gcaaatatga tccttagagt taaggtttta ggttttgtag   44640 atgtttact ccatttaaat gacagcagat catttagaaa tgattcctct gtaacagcct   44700
tccagatccc attcgattgt acagcattga gatagataga tagatagata gatagataga   44760
tagatagata gatagacgga atttggccct gtgttcccac ccatatctca tgtcaaattg   44820 taaccccac atgtcaggag agggatccag tgggaggtga caggatcatg gggttggatt   44880
tccccaatgc tattctcatg atagtgagtt ctcacaatat ctcattatta ttattattat   44940
tattattatt gcaacagagt ctcactctat ctcccaggct ggagtgcagt ggtgtcatct   45000
cggctctctg caacctcttg cctcagtctc ttgcgtagct gggattacag gcatgccccg   45060
ccatgcccag ctaatttttg tattttagt agagacggag tttcaccatg ttggccaggc   45120
tgatctcgaa ctcctgacct caggtaatct gcctacctcg ctctcccaaa gtgctggaat   45180
tacaggcgtg agccactgtg cctggccagt tctcacaaga tctgatggtt taaaagtgtg   45240
gcacttcccc cacctcctgc cgccatgtaa gatgcttgct tacccttcca ccatgattga   45300
aaagtttcat gaggcctcct agccatgctt cctggtaagc ctaaggatct ctgagtcaat   45360
tacacctcgt ttctttataa attacccagt ctcaggtatt tctttatagc agtgtaagaa   45420
tgaactaata cacacataaa cagattagag gcagcactgg cctgagttgt gaaactcttc   45480
ccagcctggt cctgcgatta gctggctata tgaccttgga caagctgctt tgcttctctg   45540
ggccatggtt tcatacctgc aaaaaaaaga gcatggactt ggctgttgcc tgggtctctc   45600
tagccctgtg gagaatcagc tacatctctt actaggaact tctcattcag ccagttattc   45660
cactgcggag atggtccagg accattaggg ccatgctaga cattgggagg ctgcctgtca   45720
ggtgaacatg aaattgaact tatctgttct cttcctccc tgaatgttgc tgaaggtaga   45780
tgcccatcct cagggctgtc ttacggagag gagaaagttg tgcagtgatt ccaccctgca   45840
gttatctaac tcggcaggga actctgggca gtgagtactc acggtacagt ctccacacct   45900
ctaatcatgt gctcctctcc ttcccaagga acctggagac catcatctca tttcctgggg   45960
gagagagcct gcatggtttt atactggtga ctgctttggt agagaaagaa gcagtgcctg   46020
ggataaaggt atcttctcac ttgatagcac cttttctttt taaatgagct tgagctttac   46080
ttcccactca gtgcctttcc tgcagtggat ttctcaacac aaatgaacat agaccttgtc   46140
ctgcttagtt caagtctgag agaagagatc taagctctag gccaccatat ttgctccctt   46200
ttctcaattc ctataaaact cggaatggac cttttgtcca ttcaacaaac aggcattggt   46260
ttgggcaatg ggaaattgga tcgaacaaga cagacatttt cccagccctg acagaagctt   46320
atgatggata cagtggatga agatggatta acgtggatta caggtgtgag ccactgcacc   46380
gggcctcaaa ctggaaattc ttcaggagtc agacaggtat caggaaggct ggatagaaga   46440
caaaagacag tgatgcagct tgtgatcaac tacagcgtta atgccttgcc taaaaatatt   46500
tcagttagat ttctgccttc gctctgtcgc tcaggccaga gtgcaatggc gtggttttag   46560
ctcactgcaa tctccacctc ccaggttcaa gcaattctcc ccctcagcc tcctaagtag   46620 tgcacgccac cacgcctggc taattttttgt attttttagta gagacagggt ttcaccatgt   46680
tggtcaggct ggcctcgaac tcctgacctc gtgatctgct tgcctcagcc tcccaaagtg   46740
ctgggattac aggtgtgagc caccctgccc agccaacact acctcccttg ataagcatat   46800
```

```
gttgagcacc tactggtcct caatagggtg acccatttct gctatattat agcgctttct   46860
ttctctctca gtagttaaac tccatggtta ctttagttct catccatgtg tttagtccat   46920
tagaagatac agagtcaaat atcggccttc caagtgtagt tcagatgaag tagagactca   46980
aggaagacaa ggaagtcttc ccagcagagg ggattctaga gctgggggct ctgtagaatc   47040
tgtctgtgta ttagtccatt ttcacactgt tataaacata ctacctgaga ctgggtaatt   47100
tataaaggaa agaagtttaa ttgactcata gttctgcatg gatggggagg cctcaggaaa   47160
cttacagcca tggaggaaag tgaaggggaa gcaagaacct cttcacgagg cagcaggaga   47220
gagagcaaag gggggagctg ccaaacactt ttatacaatc agattttgtg aaaactctcc   47280
ctcgtatcat gagaacagta tgggagagcc caccccccata attcaatcac ctccccaccag  47340 gtccctccat cagcctgtgg ggattaccat ccaagatgag atttgggtgg ggacacagat   47400
ttcaacacag atttaaatct gactttatat gagagcttcg gagcaaggat gcccagttg   47460 gagatgcagt agaactgatc ataacgtgac aaatccgaga gaagaagagt aaaataatag   47520
tactcaggcc cttgggaggt gcaagaagta acagccagat gaaattccag aaacacttac   47580
ctaggggtct gtctgggagg tccccaggga gcttctggct gtcaggccaa ccccacagtg   47640
gatctagctt aggacgttcc caggaagctc tgacaaactg tccggtcctc ccctgggttc   47700
caacagtatg aggcttactc tgcctgcatg gactttaagg gagtgctaat aagttgtgta   47760
catgcatctc atccctaggc tcttgttcag gccacgaatg ctatcttgca gcccaaccag   47820
gaggccctgc tccaagccct gcagcgactg agactgtcta ttcaggacat caccaaaacc   47880
ttaggacaga tgcatggtaa gatgcttccg aagctcctga aggatccccc aggggtcctg   47940
ggctctgctt aggggaagag ggcctgggga ccaggcatgt cctgaagggg gtgataatac   48000
attcatccac cagatgacgc tggtggacta tctttgtttt aggttaaaca catattatct   48060
tggagagcta ttgtcacagc tttgtattct ccctctcctt tatattctcc cgtgattaag   48120
atggtttccc ttctgcagtg gccagatatt tcttaggcat gttgaggtct tgcctgaagc   48180
ttgagaggag gggatgggat gcacagtaat gttggtcgcg cgtgccccat cctgcagtgt   48240
taggtactgc agagcaggtt gtctacactc tgtaatgccc cttttattct aaccccctgt   48300
gttggttcct gagatgtctg accttggttt taagccttgt ctaatggatg gcctgtattc   48360
cctttctgta gctagggcag gctgatttgt caaaggtagg aaagttgtca gaatcaaaat   48420
ggagtcactt tgtgttgaata aaaattttta aaccttgaca aatagagctg gggaaggcta   48480
caaagagaga gctcccgtgt ataaatgcct gataacaaaa tcttttccaa aggactgaaa   48540
aaatcaccac cttgcacaaa ggccatcaca accttacata cacaaaaaaa tacttacaca   48600
acgacatctg cccagcaact gcctttccaa cattggcctt gtgccaccct ttttattgat   48660
gctcatagcc aaggttaatg atctcaaaac agttacataa ttgtcctcat ttttccttta   48720
aaaacctttg tcttccttta tctttctgaa tacccacatg gtttattatg gcacatgtat   48780
tcccattgca atgccctatt ccagaataaa tatcagtttc cattagggag cctctccctg   48840
ttaatctgct taacacaggc atggtcagtt acggggccca accttcctgg accgttaca   48900 tcttattctg gttactgcat tcagtttcca acatctggga ggctcttcaa attcttctct   48960
cagaggaatc tgaagaatgt atgtgtttag gaggatgtga gagaggggtg tggtttctta   49020
acaagagaat atcagagtct aagtatcatt ttccctgaat cttgcttccc tgcaggaaag   49080
aaagattctg ggaaaagaga gtgttacaa gaagcaggac tggagggagg gagaaagacg   49140
ctaggtactg ccaagcttta ttatcttgta ttaaaaaagt aaatataatt tgtcatccca   49200
```

```
gcctctcagc actagtagaa atctatctga agtcacagga ttaggtatta tccacttcct   49260
ggttttatag tttatatttg tattttctct atttccttga attttaattt taaagccctc   49320
atgatcacat cagtaggtct tctgccaaac agctcccttta agttgtatgg tggcttttgcc  49380 aagctgaaat gagatgagat gtgttttagc tttgccaaga aagcctgagt ccatcactta   49440
ggatagcaag gctattaggg agatagtgca ggtgtcttca gatcacatgg atgagcaaaa   49500
ggaagcaatt ttggaagatt atgagaaacc ttccaacagg tcccagtgta catagcagta   49560
agatggtgca tgcagtgtct aactgtcaca ggctttccta gggctcactt tcagactcac   49620
ttcttttttt tttttttttt ttttgtgaga tggagtctca ctctgtcact caggctggag   49680
tgcagtggca cgatcttggc tcactgcaag ctctgcctcc cgggttcaag cgattctctt   49740
gcctcagtct ccctagtagc tgggattata ggcatgcacc accatgccca gctaattttt   49800 gtattttttag tagagatggg gtttcgccat gttggccagg ctggtctcga actcctgacc   49860
tcaggtgatc tgcctacctt ggcctcccaa agtgctggga ttacagccgt gagccactgc   49920
gcccagctca gactcacttt ttaggcccag gccaacctgc tgtgttctcc tgctcagctt   49980
ctgcaggagg tctcatcgtc taaggaggtc ccagggctac cgcccttgtt ttctcaaaag   50040
gcacattttc ccacacagac ataatttcgt ttcagtgttt tactcctagt cacattcatc   50100
tatatggaca aatagctgaa tggattggac tgtgttttct aaagatggcc ccatgccatc   50160
ctgcgcgctc ctccacagcg tggcctgggc attccttttcg accaggggtg gactctgtgc  50220
ccctacttgt gatgtacgtg ttgccaatag aatgtagtat aggggatagc acagacttct   50280
gaggcaagac tagaagaggt gatgcaggtt taaccttgtg tcctgagcca ctaggtaaaa   50340
agtccaccta ccctgagatc actctgctgt gcaaacgaca caggcaaacc acatcaaaga   50400
gccatgtggg ttctccagtt ggcttctgcc caggagtgaa ggtgccctca gatggttcta   50460
ggctcccatc ccaacttatg tcctgtcttg aagtcttccc aactgaggca ccagccactg   50520
tggagcagag tcaagccatt gccatcttgt tctgcccaga ttccccatca acagaatata   50580
gtggtttttt cacacctcta tgtttggagt ggttttctatg cagcaatagt aaccacaaga   50640
aataaagtta taaaaatagt aacaaacact agaaactgca agatttaagg aatcacctga   50700
atgctccagt cattgtctct ggtttgtaat gataaacttt cttctgcgtg ataaatagag   50760
cttggctgga cttttttccct ctgcttccat tccccaaaat ggagcgtacc aaacaattgc   50820
ttctttcaga gcccagcttt agcaagagtc atgagctcta atcccttcat ccataaaatac  50880 ttcctttcca ggcacgtaga gcccttcaca ctcagggctg agtagaaaat gcctgttgca   50940
gactgcagtg gcgttttgga gagccaccct cctggtacct gagtcactag tcctttgccc   51000
agcttttctc agttttgtaa agcgctcact tctgagtgga agacagaacc agcccggtct   51060
attttcataa tctgccccca taaggcagaa gtccacacgg tactggaaac ataaccatat   51120
ctatgtcagt ctgccactgc ctgccgcctg tcaaccgtgc gtgtctgcat ccagtccttc   51180
tttggagctg cttttcagcg actcagccag atctgagctt tctgactcat tggaaggtta   51240
aactattttc agactttcaa gtgttgagat tattaagaca tgtgtttttt tttttcttct   51300
ttttttggca tgcttactga tcgcccctgt tctctaggaa gtaatgttct tcttggaaaa   51360
ggtgaaggat attttttctcc ccaaaaagcc atggaaatgt ttgcctttat ttacttccaa   51420
attaacagaa tttccagctt ttgcttgacc catcggcgca ttggcagcgt taagaatttt   51480
ttcttttagc agtaatgagg agtcgaaggg tttcttccta accatttagt gtatgcattt   51540
aaatcaggtt tctttttgag taaattgggg ctaagctgta gtgtgaactt ctgctactgt   51600
```

```
tcctttctca ttagttcact tgatttcatg gaaggaattt tccatctcag cctgtgaact    51660
tattttgtct aaactcaatt ggaaagtaat taacactgag attcttcttt aataaattct    51720
atatgataat aaaatcatac aaacatctct ttattttct ttttgaccta gaaaagatgt     51780
tcacaggcca gacctggtgg ctgaagcctg taatcccagc acactgagag gaagaggcgg    51840
gtggatcaca tgaggtcagt ccagggcag ggtagccaac gtggtgaaac cccatctcta     51900
gtaaaaacac aaaaattagc tgggcatggt ggcacatgcc tgcaatccca gctactcagg    51960
aggctgaggc aggagaatca cttgaacctg ggagatggaa gttgcagtga gcctagatcc    52020
tgccactgca ctccagcctg ggcgacagag tgagactctg tccccaaaaa aataaataaa    52080
taaaagatgt tcacaatata ttgttaagtg aaaaaagcag gctacataac ttgcataata    52140
tgagtgcatt ttaataaaaa tatacatatt tagcaaaata aaaggacaaa tggtatttat    52200
taaaatattt acgttgatta tttcaacaca gaggatgata gttgattttg cttaatttct    52260
tccctccttc ttttcaattt gaattttcta taatgaagat tgtttctttt tctttctttc    52320 ttttttttt ttgagatgga gtttcgctct tgttgcccag gctggggtgc gatggcgcca    52380
tctcggttca ccacaacctc tgcgtcccag gtttaagtga ttcttctgcc tcagcctccc    52440
tagtagctgg gattataggc gtgtgccacc acaccggct gattttgtat ttttagtaga     52500
gacgggcttt ctccatgttg gtcaggctgg tctcgaactc ctgaccttag gtgatctgcc    52560
cacctcagcc tcccaaagtg ctgggattac aggcatgagc caccgcgcct ggactgatta    52620 tttttaaat agggttagaa agtgaggaag ttactaaact ccgattagcc caaatatgcc     52680
ccagtgggtc cttctggcag agtaaatgtc tcggttcagc ctgaatctgg gaaattgttc    52740
ctacggttca gcctgaatct gggaaattgt tcctacctta taaactggag tatccttcag    52800
aaatgacatt tactcaaact tccttttagg cagactgcat aatagcaatt tttaatatta    52860
accatttaaa aaaaaccttc agattaatta acaccaaaag aataattggg aaaatacaac    52920
tcctcacttt aaaaaagaaa caaccaaagt aaatactaaa aaactatatg atgttatatt    52980
atctaagctt agtttactgc aaagatcaag agcacactac tagttgacgg cctctattca    53040
cactgttcat agccctcgct cgcttctcca gccattcact cactcatgca aaaggtctgt    53100
acacacaatg atgcctgatg gtataatagg aaccttaaca tttcaattaa aaggcaaaat    53160
gaggacactt accatcagcc tataaaatta ttcttattat tcttcttctt cttctcctcc    53220
tcctcctcct cttcttcctt cttcttcttc ttcttcttct ccttctcctt ctccttctcc    53280
ttctccttct ccttctcctt ctccttctcc ttcttcttct tcctcttctt cttcttcttc    53340
ttcttctttt ttttttgaga tggagtcttg ctctgttgcc caggctggag tgcagtggtg    53400
tgatctcggc tcactgcaac ctctgcctcc caggttcaag ctattctcct gcctcagcct    53460
cccaagtaac tgggattaca ggtgcatgcc accacgcccg gataattttt tgtattttta    53520
ctagggatgg ggtttcacca tgttggccag gctagtctct aactcctgac ctcaagtgat    53580
ccacctgcct cggcctccca aagtgctggg tgtgggcggc aagccaccca ggtgccaagg    53640
caagagacag agggcacgag ctgttccagt ataatgagga aaatatatag aataagaata    53700
gttatactag aaatagatta tagatatgat tacatatgaa tatcattctt cattagtttg    53760
tagcactact ctttattcca gtattataat aatctttgtt ctacaattat aacctaggaa    53820
aaaccaggcc atacagagat aggagctaaa gggacagggt gagaagtgac cagaagagtg    53880
tgagccttct gttatgcccg acagggcca ctagagggct ccttggtcta gcggtaacgc     53940
ccgcgtctgg gaagatgcct gtcacctaac ggaccgtggt ctagcggtag cgtcagtgcc    54000
```

```
tagaaaaggc actctttta aatatacttt ttattttgt ttaatcttcc ctgatttcct    54060
atagatctga gatatgtcat gcttattttc attgctatct aaaaatctca ataaacttta    54120
tacctaagag taaaaaaaaa aaaaagaaa agaaaaggcg ctcgttactt agccgaccgg    54180
gaaagggagt ctcccttcc ccgggggagt tagagaagac tctgctccac cacctcttgt    54240
ggagggcctg acatgagtca ggcctgcctg cagtcatctg gaggcctaac cgtctccctg    54300
tgatgctgtg cttcagcggt cacgctccta gtcctgaaca cctggctccg ccttttagat    54360
agcagtagca gaattagtga aagtactaaa agtctttgaa atgcagaagt aatggcgtaa    54420
gctgtcacgt ctctctctcc gcctcagctg ccaaacagag aagggtcccc tgtccagtgg    54480
acacgtgact tgggtgacct tacctgtcat tggagacgac tcatactcct taccctgccc    54540
cttgccttgt atctaataaa taacagctca atctggcatt tggggccact actggtctcc    54600
gcatcttggt ggtagtggtc ccccgggccc agccgtcttt tattctatct ctttgtcttg    54660
tgtctttatt tctaccatct cttgtctccg cacacgagga gaaaaaccca cagaccctgt    54720
agggctggcc cctacagctg ggaattacag gcatgagcca ccgcatccag ccagcctaaa    54780
attcttctga aggataataa tatagtactt gaagacacgg tttgaaaaaa atcatactaa    54840
atgaaagggc accattttac aagcactaga actacattaa acttaaatga attccaacac    54900
tcttaataat gtaactcaaa aacaagtcta gtgttaacaa aagctccaat aactaaaact    54960
acattaacag gcacaatgaa cattgtaaac gccgctaatt ggcaccaagt ttaatagggc    55020
agacaatatt ttcttctgca ttcacactta ctcagttaca ctgttgaaaa atgctgctgc    55080
tcaagctatg aatgctttac aaaagaaatc attttaataa atacagtaaa tgctaaaact    55140
ctagctaaac tattatgcaa gatatacaac caagacaaat acaaattcat aatacaagca    55200
acttgcattc aaaatgaact ctaccactat attttattaa aagggcagac tttatgaatt    55260
aacccagctg cttcctgaat tacaaaagtg gcatgactca atatgaaaat aagaaactgt    55320
ctacaaattt ctgacagtaa taaattgtaa tatacaatac atgcaggagt cttacggaag    55380
aataaactct cctaggaaac aaaaatattt tatactttta aaatccaaag taaaaaaaaa    55440
agaaatcatt gccagatgcg gtggctcatg cctgtaatcc aagcactttg ggaggccaag    55500
gcaggatcgc ttgagcccag gagtttgaga ccagcctggg caacatagca aaccccatc     55560
tctacaaaaa aatacaaaaa ttagatggta atggtggtga gcgcctgtgg ttccagctac    55620
ccaggaggct gaggtgggag gatgcacctc aaggctgcaa tgagccaagg tcacaccatt    55680
gtactgaagc ctggggacag agtgagaccc tgtctcaata agtaaataaa taatatctt    55740
ttatgaaaaa gattctctag tcagaattaa caccctcaact agccaaacat caggaagtta    55800
cattacagct acttaataca caaagggaca cattttcacc agtcgttgtc ttctgatatt    55860
tctattccag aaaacacacac tctcacttcc ctacactccc catcccatca tttcttcaga    55920
gcatggaaac agaatttgtt gaacaccaga aatctcttgc tatggtggta cataagtcat    55980
aacatttgtt gctgcccagc agcaggtatg aagccggctg gtgactggct agcaaatgcc    56040
tattctgtaa gctcctcact tagcccatct gtagctctga cttctccacc aattcccttc    56100
tctccttca cagcctttct gagtttctga gggataattt cagaggttcc atataactgt    56160
caaagcctat ggtagacatg gcaaagtgaa atcctctcc actggccatt tctgtttctc    56220
ttgggggcat ctttcacttg cctcaggtgt tataaagctg atgaacacac gtacacgttg    56280
tttaacactt tcttgggcat ttcccatttg agatatggca tgtttcatta tcctagtgac    56340
atgtgcaatc agaaaatgta tattttgttc tctgcaactt tcttttgaaa aatgtatatt    56400
```

```
tgaacaaaat atacattttt tgtatcttca tgaccattca tgctgtcctc actgtcatca   56460
tgaggctcta tataacataa tgactcctcc agggcagtct tcggaaattc ccagtgcaga   56520
agcacgtgtc atacagcagt ccccattcat ctccagtgca gctctggctg gctcccatgt   56580
ctgatcagct gtttggttgg acagaaaatg actgcaaggg aatcagttcc agtgtgagct   56640
ctgtttgcag aactcagact cccctccctc ccatgttaat gctttttttc ttcttctttt   56700
tttttttttt tttttttttga cagagtctca ttctgtcacc caggctggag tgcaatgcta   56760
tgatctcggc tcactacaac ctgtgcctcc ccggttcaag caattctcgt gcctcaactt   56820
cccgagtagc tgagattaca ggtgcacacc accacacccc actaattttt ttgtattttt   56880
agtagagacg gggttttgcc atgttgccaa ggctggtgtc aaactcctga gctcaggaaa   56940
tccaccttcc tcagcctccc aaagtgctag gattacaggc gtgagccacc atgcccagcc   57000
ccatgttaat gcttctaaag tttgccctca cttctttaga aattccttca gtacatcctt   57060
taagacttcc tctagtgagt gtctgctggt ggtaaactct cccctctaaa agttgcttta   57120
tttctcctca attcctgaag gatatttttg ctagcagcta tattctttta gatgttgaac   57180
atatcggtac aaaagcttct ggtttccatg gttgctattg agatgttagc tgtcggttta   57240
tctttctccc ctgactatgt gtacctgttt ctctgtatct gtctacttttt tgggttgctc   57300 aatttattgg ccttgggctt cattctgctg ctgcttttttt ttttttttttt tttttgagat   57360 ggagtcttcc tctgttgccc aggctggagt gcagtggtgc aatcttggct caatgcaacc   57420
tctgcctctc ggttcaagcg attctcctgc ctcagcctac cgagtagctg ggattacagg   57480
cacctgccaa cacgccaggc taattttttgt attttttagta gaaataggat ttcactatgt   57540
tggccaggct ggtctcaaac tcttgacttc aggtgatcca cccacctcag tctcccaaag   57600
tgctaagatt acaggcctga gccaccacgc ctggccacaa ttttttaaact ttttattttt   57660 acaggcacct gccaacatgc acaactaatt tttgtatttt tagtagaaac aggatttcac   57720
tgtgttggcc aggctggtct caaactcttg acctcaggtc atccaccacc ttggtctccc   57780
aaagtgctag gattacaggc gggagccacc atgcctggcc aaaattgtta aacttttttat   57840 tttcttcctc aagaggatga gaagaaaggt caattgtaag cttttagaagt cttgcccaat   57900 agccaatctg agaatattct ccgtaaacat tcaccagagg cagccagtga ccatgggata   57960
cttttggtga gaggaattga ttgctggggt caggaatggg aggaaagcat acttctcatt   58020
agataccttg ttgaacttcg taaattgtgt gccaaatgca tgtcttacct agacttcata   58080
aattaatttc tttaaaaata atcaaagaca attttttaaa gacttattta atttaaggtg   58140
attataaaac atccagtata cttttcactat taaaaaagta agtattcctg tctgggcttg   58200
gtggatcaca cctgtaatcc cagcactctg ggaggctgag gtggtcggat catgaggtca   58260
agagattgag accatcctgg ccaatatgat gaaaccatgt ctctcctaaa aatacaaaaa   58320
ctagctgggc gtagtggcgt gcctgtagtc ctagttactc aggaagctga ggcaggagaa   58380
tcgcttgaac ccaggaggcg gaggttgcag tgaactgaga tcgtgccact gcactccagt   58440
gtggcaacag agtgagactc catcttcaaa aaaaaaaaaa agtattccta aacagcatat   58500
tatcatgata tattattttg ttttgtaggg ttttgaacct tgtctaaaaa gaattaaaat   58560
gtataaattt cttcctgcaa tttccctatt tcactaaggg tcattcacat tggtcatata   58620
gacatagcac attttcacca ctatatagca gcatttttgta caaatagact acaatttact   58680
tattctgcac ttatttctgt ttgtttgttt tgctatgaaa agcaatgtca ttacatatat   58740
tcatgcccat agctacaagt ttacatattt caggttttct gtagggtgga caccagggag   58800
```

```
ttgaattgtt caacaggact ttacattcat ctttagtttt attggccaac accaaattgt   58860
tcttcacaat gtttgaacta agttgaaatt ccacctcccc atcacattta gttttgtcaa   58920
cttcatttct tcattcatta attcattcat tcagtctttt gtttatttgt ttattgccag   58980
tctgataggc gtatagtggt gcttcatcat ggttttactt tgcatttctc tgattttctt   59040
tttaaatttt taaaaaatta ttttttatgta gaaacaaggt ctcgctacat ggcccaggct   59100
ggtcttgaac tcctggcttc aaatgatcct cccacattgg cctttcaaag taccgagatt   59160
gattataggc gtgtgccact gtggccagct gatttccctg atttctgatg agttaacaat   59220
ctcttctttc tctctctctc tctctgtgta tacaggtact caccattcgt gcctatttcc   59280
tgtaaaatat gtggctttcc tcatttttttt tttttttttt tttttttgag gcagagtctc   59340
gctctgttgc aggctagagt gcagtggtgc gatcttggct caccacaacc tccacttcct   59400
gggttcgagc aattctcctg cctcagcctt cagagtagct gggactacag gcgtgcacca   59460
ccatgcccag ctaattttgt attttttagt agagattggg tttcactatg ttggccagac   59520
tggtctcaaa ctcctgactt tgtgatctgc ccacctcagc ctcccaaagt gctggnatta   59580
caggagtgag ccactgcgcc cagccatctt tcctcatttt tatactaatt aggcttttat   59640
cttacttgtt ttttttaatg ttttttgtac actctgaagg ctgattttg ttaattgtat   59700
gtgttgcatt tttatggtt tgtccttatgc cttttgaaag taaagttct taatttaaat   59760
atagccaacc tgtaaatcat ttgtgaaagt ctgtggttta agaggtcttg aataagaaat   59820
tatcccatca tcataagtca taaatacttt tttgttgttg ttgagacaga atctcatttt   59880
gttgtccagg ctggagtgca gtgggttgat ctcagctcac tgcaacctct gcctcctggg   59940
ttcagcaatt ctcctgcctc agcctcccaa gtagctgtga taataagcat gtgccaccac   60000
accagtctaa tttttgtatt tttagtggag acaggatttc atcatgttgg ccaggctggt   60060
ctcaaactcc tgacttcaag tgatccacct gtctcagcct cccaaagtgc tgggattata   60120
ggtgtgaacc accatgcctg gcccataaat acattttat gtattttctt ctaaagttgt   60180
tttgtctttc acttttagt ttttaattca catataatta ctacttgcta cttataatta   60240
tctgtaagta gtatgagatg agaaataaat tctatttccc tcctatggat aagcacaaac   60300
ctgcagtatt agcacagtct tatgtcagat tttctaaaat gaatgggtgt gttttctagg   60360
ctctctgttc tgtttcatta tctgtctttt cctgcaacga tatcatctgc cttaaaaact   60420
ctagccttgt ggtattcctc attttcaagc agagcaaacc ccgtcacctt gcttttctcc   60480
tccagcatcg cttgtgctat cctggactaa gaccttcata tagactgtta gaatcatcta   60540
gccaagttcc attttaaaaa tctatgttgg agctgggcgc ggtggctcac gcctgtaatc   60600
ccagcacttt gggaggctga ggagggcaga tcacttgagg tcaggagttg gagaccagcc   60660
tgatgaaacc ccgtctctac taaaaataca aaaattagct ggacgttggg cacttgaatt   60720
ctagctactc aggaggctga ggcaggagaa tcgcttgaac ctggcaggcg ggggtgcag   60780
tgagccgcga tcatgccact gtactccagc ctgggtgaca gagtgaggct ccatctccaa   60840
aaataaataa ataaataaaa taaatatct atgttgaaa ttttgtacaa attttattaa   60900
atgtctacat taatttggag aaaaatgact tgatttgat tatctattca atatttctgt   60960
attatgaata aggcaaaaag agaggcagag aatagcataa aataataact aaaattcctg   61020
ggtaaaccac ctcaaatcat ttcttcatat ggctcaatat tcttttgtga catggcctga   61080
aatatatcca gacagagaac tcttctcttc aatacatttc ttctttaggt attcatatt   61140
gagttttcct gtccatgaac atggtataag agagtatatc ccttcgggag gccaaggtgg   61200
```

-continued

```
gtggatcacc tgaggtcagg agtttgagac gagcctggcc aacatggtaa agtcccatct   61260
ctactaaaaa cccaagaatt atccaggtgt ggtgacacat gcctgtagtc ccagctactc   61320
aggatgctga agcaggagaa ttgcttgaac caaggaggcg gaggttgcaa tgagccaagg   61380
tcatgccatt gcactccagc ctgggtgaag agcgagactc catctcaaaa aaaaaaaaaa   61440 aaaaaaaag aaaacgagaa tatatccttt catttactag ttttcttca atttctttca    61500 agataaaggg cttacctatc ttctgcttta ttcatagtta cttgatattt ttgtttctaa   61560
taaatatggt gtctgtctat ttacctgcct cttacctgtt catttccagt ttcaaaaatg   61620
atgttgatat ttgaatatta accttaaatc tagcaccttg gtaaacacta ttattcattc   61680
taataattat cagtagatta tatgtgtttt ttatttataa atcatattgt ttgagtagca   61740
tgctttgctt cttcatttat aaaatttaca acttttattt cttttttaata atttttttct  61800 tattctcctg gctaggactt ctaacacagt attgagtgga agtgctgatc cttgtttagt   61860
ttcacatttg aaaaaagatt gcttttacta tttcactgtt aagtataata tgcaccatag   61920
gctttctgtg gattcctttt atccatttaa gaacatctct tattcctaat tagctgaagt   61980
tttctgcatg tttgttttca tcatgagtgg attttttttac atctattgaa atcattttac   62040
atagaagata tttcacacct attgaaatgg tcatttcact ttttccttctt taatatgtta   62100 agtgggcaa atattaaag tatcacctgt cattctgctt cagcaaaaag tagtagtgtc    62160
ttagcagtat tggtgaaaag acagcatcaa ataaaaaga tgtagaagta ggacccagta   62220
aaaatctagc gcatggggca ttgtcacatg taagcagaca gaatgtgaca ccaccaagga   62280
gcatctgaag ggctggaggc tgaaggaaga catgagtcac ccaggctcat ggacacttca   62340
gagaaattag ggagcaggaa gaagaaatag gatcaaagac tacgtatgtt ggttggaaaa   62400
ggaagctgat ggtatggaga tgttattatt taggtctcac ataaagatg tagataaata   62460 ggtagatagg tagatagatg atagatagag agatagatag ataaatacat agatagatag   62520 atgataaaata gatgttgtta tttaggcctc acataaagat gtagacagat tagacagaca   62580
gatgatagat agatagatag atagatagat agatagatag atagacgata gatagataga   62640
tagataatct cagaaacaga gacacagtga tctcagtaag ataggcatat gccaggtgac   62700
agaattcaga ggggtcccac tacgtgaaaa caatagaaca accttcgaaa agaaatttag   62760
tacaaataag agggcaggct tccttacata caagttagta aactggaaga atcagttatc   62820
ctcaaacatt ggaatagatc aaaaatagtt gtttatatta atgaaggtag ctaaacatga   62880
agctaagtga acctgtctct gacctagtgt ggcaatccct gggcaaggga cacttgctcc   62940
gctcttgtat ccttcactga atattcagac tttcagttaa gcatcggtga atttagtttt   63000
catctcttgt gaaaaccttg agagaggtaa ttctctctgc ttttcttctt ttcccttcct   63060
tcattttctc aaacattgcc tgtttaaaat acgaaatttt aaaagatggc cttgttctct   63120
tttttgttgt tattattaag tacagagaaa ggaagaacca caaatagcaa agggcaacat   63180
atggaatagt ttagaagttc cgggagcacc catgagggca actgcagaag agaacattct   63240 atccccgtt gctgcagctt tcattccagg tctccatgca tatcagatag ggaaggaact    63300
ccgggacagc agcagggccc atgcacatgt aaccaattgc tttctttgcc tgtagtaaag   63360
ttcacatttt gattgcttct ccagattatg tagatccaga catatttat gcaggcatcc    63420 ggatctttct ctctgggtaa gtatagttca gttgttttcc tgtgtgaagt ctctgtagca   63480
ttgactgaat gtataagggg acgaagagac agaagcttcc tagcgtaaga aacataccaa   63540
gtgactcttg ctagggatcc actctcaggt aaaagaagtg ggataccatc tgcacaacaa   63600
```

| | |
|---|---|
| ataacactga gggctaagta tttcagttaa gagtgtttgt tcctaggcag ttcagatcca | 63660 |
| tttatattca cttttcttag aatcctagct caatgacaga agaagaaaaa cacagtatgt | 63720 |
| cactcacaca gttctatcac ttacatctac ttttcttct tgttattaag gcatgtagaa | 63780 |
| ggctggggag tgtagtatag agttggatag catcgaagct ttcttctaaa gttcctggaa | 63840 |
| gagctacact gtggtttgaa cgaatgtgtc cctccaaaat tcatatgtta aaacctaatt | 63900 |
| gtgatggtga ggtattcgaa ggtgggttct ctggaggtg attatgtctc ctctgagagg | 63960 |
| agaagacaat cccctgagtg gaactaatgc ccttataaag gggctggagg gagttcactt | 64020 |
| ggcccttttt gctccttttt tcttccattc cttgtccctt ccactatgtg aggacacggg | 64080 |
| agttgaggca ttaccttgga cgtggagacc aggccctcac cagacactga acttgccagc | 64140 |
| accttgatct tggacttccc agcctccaga actgtgagaa atacatttct gttatgggta | 64200 |
| gtccccaact caatacagtt tgacttacca ttttttgact ttatgttggt gcaaaagcat | 64260 |
| acatattcag tagaaactac tttgagtacc catacaacca ttctgttttt cacatttggt | 64320 |
| acagtattta ataaattcca taacatattc aacatgttga cataaataag ctttgcgtta | 64380 |
| ggtgattttg cccaactgtg ggctaatgta agtgttctga gcacatttaa gggcagctag | 64440 |
| gctaagctaa ggtgtttggt aggtcagatg tattaaatgc atttttttgtc ttatgatatt | 64500 |
| ttcaacttac attgggttta tcaggatgta acccactgtg aattaaggaa tatctgtatt | 64560 |
| tacaaattac ccagtctaat gtattttgtt gtagcaacag gaacaaacta aaacactacc | 64620 |
| ccaaaccatt tttttcatat tttctgagta ctcttcttt gtcacatggc ttgaaatttc | 64680 |
| ttcacataga gaactctact attatttat tttatttat tttatttat tttttgagac | 64740 |
| agagtcttgc tcttttcacc caggctggag tgcagtggtg ccatcttggc tcacggcaac | 64800 |
| ctctgcctcc tggattcaaa ctactctcct gcctcagcct cccgagtagc tgcgattaca | 64860 |
| ggtggctgcc accaagcctg gctaattctt gtattttag tagagacgga gtattgccat | 64920 |
| gttagtcagg ctggtctcga actcctgacc tcaggtgatc tgcccacctt ggcctcccaa | 64980 |
| aatgttggga ttacaggctt gagccaccac gtctggctga taactctact tttagatact | 65040 |
| ctctttgctt aaacaaatta gccattcctt ccttgacatg ttttaatcag attgccttcc | 65100 |
| tattaacttc ggaaattaag agtttctgct atgttttgt ttaattttta aacagtgaaa | 65160 |
| aatgaaaggt ggaggcaatg gctggatgag gtgaatatgt caaatagata tcatctagtg | 65220 |
| ggccatctta ttaactagga gacacctgaa gtgctatcaa tagaaataat ctgaagctgt | 65280 |
| gtctggatac agcaagagac atgcaaatgc taaaaatcta ctatattaca ttggtgcaag | 65340 |
| gacagagtag caaacacatac taagtatttt ctccagattg ggtgtgtttg acgtgtgaag | 65400 |
| cacttcaaac agagtccagc ctgggaggga gtggggatgg aatcctcctt gtagagggta | 65460 |
| cagagtggaa gcaagaaggt ttccaagatt gagagtaatg ggtgtatggt ttatggggaa | 65520 |
| aagggaaaac aaaaagaagg gtgcagaaat ggagctggga gtgtgtttta gtatttaggc | 65580 |
| tttctctgta tacctttgat aggattagaa aaagaaaaat ggaccatttt taaaaatttc | 65640 |
| atgctaccac atagcaggct tatactatag atgcagaaac agactgggat ttaggaagca | 65700 |
| ccccaattct ggaaaatccc ttttgcttc acattgctct ctaaatctgt atgttttccc | 65760 |
| ttgttacgta acaatttacc acaaatttag cagcttaaaa caatatgcat tcattgtttc | 65820 |
| acaattctgt aagtcggaat cataggcaag ctcaactgac ttttccattt agggtcgcaa | 65880 |
| aaggccgaag tcaatttatc tattgggctg ggctcttaac tgaagatctg gggaagaatt | 65940 |
| cccttcaaaa ctcatttagg ttgttgtcag aattcagtgt tttgtggttc tagaactgag | 66000 |

```
atctgtttcc ttgttggctg tcagacagga gctgctctca gcttcttgag gcatccagta    66060
ttccttatca tgtgttttt ttttccatc tcagcactgg cacttttttt tttttttttt    66120
ttgagacaga gtcttgcttt gtcacccagg ctggggtgca gtggcacgat ctcggctcac    66180
cacaacctcc atctcccggg ttcaagtgat tctcctgcct cagcctcccg agtagctggg    66240
attacaggca cccgccacca gcccggctga ttttgtatt tttcatagag atgtggtctc    66300
accatgttgg ccaggctggt cttgaactcc tgacctcaag tgatcctccc acttcagcct    66360
cccaaagtgc tgagattaca ggcatgagcc atcatgccca gccagcactg acaattctaa    66420
tccttctagc actttgattc cttctcacct ctccttctgc ctctagccag agaaaactct    66480
ctgattttaa aggtcttatg tgattagatt cagcttacct aggtaattca ggataactcc    66540
ctatgtcaag gtcaactgat taataaccct aattacacct gcaaagtccc ctttgccata    66600
atatatcata ctgacagaca tgctatagca taatactaat agttctaaga attatgataa    66660
gaatcttgga aaccatttt tagaattata cctaccacag tatccttcaa gggataaatt    66720
gattctactt cttctctatg tcagaagcat ctgatgagga tgaactatat attctgaaat    66780
ccccatgatt agatgtgtac tagaaggtga ttttacttc attaaaataa attcggagtc    66840
attgacacat tttatctttg atttacataa atgcctccgc tctgtttctt accctcaaaa    66900
tatttcccat gtagctaagt ggccagtacc gaatcctaca tgcattaata agtgtagatg    66960
gacaaaaata tctggattac tgagaattcc cattagcatt gtctagaaaa atgtaaattt    67020
gcttttgt tcttgattta tcctatttt gatttattat ttatattat ttatttattt    67080
atttattttt agatggaggt ctcgctttgt cgcccaggct ggagcgcaat ggcgcaatct    67140
tggctcactg caacctctgc ctcccaggtt caagctttcc tcctgcctca gcctcccaag    67200
tagctgggac tacaggcacc tgccacagtg cccggctaat ttttgtattt tcagtagaga    67260
cagggttttg ccctgtgggc caggctgttc ttgaactcct gacctcaggt gatctgccca    67320
ccttggtccc ccaaagtgct gggattacag gcatgagcca ccacacctgg ccttttgct    67380
tacttttaa aaacattttt atttaggaga atggagatat ttcatatgta gatgacacat    67440
attcattccc tttagttccc acacacattc aatttcttga ggaagttagc ctttgcaaaa    67500
aaaaaaaat gatctcattt ttttttcccc actaaaactt ctcatttct tggggttgct    67560
agaaagttgc tacaagaaag gctaaaaata attgtgccta cagatatttg aaaggaaaat    67620
agttcctctt ttttcacagt agcagcttgg acctgagaat gtatgggagc ataattggg    67680
ctgctcaaag aaacacaatt tcccttcctc agactagaat taccaaccta gagaacatga    67740
gttttttaaag tagatgtgct tctttatct ttttggactt gtatgctggt gttttctctg    67800
tcaccttcac tgtggaaatc ctcttgaggg tgaggcactg aaagcagatt gattaatgtc    67860
tcttggccat ttgagacatt ggatggctct tttaagttgg ccacgttctt tcaagaacta    67920
tgcttgggct acatattctg gatatataat acatacttgt aggatgttat ttttaaatca    67980
ttcatttatc acatatttag tgagtgccta ccccatgtca gttctaggtg ctggaaatag    68040
agcagtaaaa ccaaccctca acttggcccc tctggagctt acatttcaat gcggtgggtg    68100
gggggatgga caattaatac acaagtaaat ctaataaaag cgtcatacaa tatacattac    68160
aatggtaagc acaatgaaga aatggaaagc tggatagaga gtattagaga ctgtcgaatg    68220
tagtggccaa attttcctgt ttattgtggt ccaagagtgc cacagccctc tatgacattt    68280
gagcagacac ctggaggaag tgagggagtg agccgccaag aaggaatggc aagtgcaata    68340
accctgaggt gggagcgtgt tggtcgtggt ggaagagctg caggaagcca gcagggccgc    68400
```

```
aacactcagg ggagaataag aaagagtgag gtgacagtag agaccggatc atgtagagct   68460
ttgtcagctt cttttctgag tgagatggac aacacggaca cgttttgaaa agaataacaa   68520
tgtgatctgc cttcagttgc aaatcatctc tgtattgact gagtaggaaa taaactccaa   68580
gaataaagac ggaaacaggg aaaatattta agaagcgatc attacaatcc agggtggtgg   68640
cttgtactag ggtacaaggg ctaaaggtgt tgagaaatgg tcagattctg gatatatact   68700
gaaatcaaag ttgatggaaa gatatgagtc aaagataatt tgcaggtttt ggggtcctgg   68760
ttcactgaaa gaacagagac atcatttact ccaatgagga agactatagg aggaacaggt   68820
ttagcaaaga agaaaggaaa tcaggagatc agtttgggga cacggtcata tcaagtaggc   68880
agttggatgt atgggtctgg aatataggg agtggtctag ctatcagtgt aaatagcttt   68940
ttacatttgt aaatagtcag gatataggct tttcttttc ttttgtgag acacagtctt   69000 gctctttcgc ccaaactgga gtgcaatggc acaatctcag ctcactgcaa cctctgcctc   69060
tgggttcaag cgatactcct gcctcagcct cccgagtagc tgggactaca ggtgtgcacc   69120
accataccag gctaattttt gtgttttaa tggaaatggg gtttcaccat gttgaccagg   69180
ctggtgtcaa actcctgacc tcaatcgatc tccccgcctg gcctcccaa agtgctggga   69240 ttacaggcat gagccacccc atccagctgg gatatagttg ttttctaaat ctatgaggct   69300
agagaagacc atttgggaat tgagagcagt gagcagtcca cggactgacc ctttgagagt   69360
gcaacattta gcagtactca agatgggaag gagctagtga aaaagcccca aatgactaca   69420
taagaccatc aaccagatta caaagaaaga cccgaacatg tgtgcccata tatcacccaa   69480
cagcagttat gtcttttcatg tttcttcccc ataaaatgtt gttcatcaac tttattagac   69540
tagggtctta acattggaca aatcacaaaa cctctctgga gcctatttta tttttcaaca   69600
gctgtaggaa gcaaatacaa attggaaatc taaggctcag aaagatttgt acaaagttac   69660
acagtaatga aaggggagcc gggattccca ctcactctaa agaatatgat aaaatggcta   69720
gtattcactg aatgcttaac atgttccagg ccctgggcag gtattatttt aattagttct   69780
cacaataatc caataaggga gatactaatt tactcagatg agaaagctga ggctcagaga   69840
ggttaatgaa ctaagccaag gctcactgtt aataaatagc aaaggtaaaa ttaaattcca   69900
tatctgcttg agatagaggc cttgctccta atagctgcag cctgtcaggg cctggcagca   69960
gtaacctctc ctttcctctt cccaccattc ccctgcactg ctttctgtac cgcatctctt   70020
ttcagagtga tgttgcccca attgcggagg ccactgtgct gtttatccag tgaaagctgt   70080
agcacagcca acccaaagcg tccccagtga aaacaacctg gctccttaca gcacttccag   70140
cctcagagca gtatttgaaa aatatcatga acagcaaaca cagcagtctg tctgtggctt   70200
ttatatgtgt atatggtgtg tgtgtatgtc ccttctcttg agcaaaataa cttttagaat   70260
tatagaaaaa aaatgtgcaa catcaatgtg gatctgctgt ttaaactcat aacagagaaa   70320
gtagcttgtt tctggctata ggaggaaaag acgatattcc ttagtaaaaa tggaaatcca   70380 catatgggt tcttgtaaaa atgaagatag aaaattgcaa gtttggggat caagttctgg   70440
ttctatcatc ctttaacagt atgaccctgg aaccttaatt gctttgagtc tttgttactt   70500
tatctatgaa atgaagtatt taaaaaaact ccaaaaatct gtcctgatgt acacacaaga   70560
ggtcaaatga gaaaatgaat gtgaagatgc tttataaact atacagcatg gtaggtcaa   70620 atgtgacatg aacttgtttt ggacacatta taaagtcacc cccacaaact gtgattgttc   70680
aagactatgc aaagtcagac acaggaaaat aagtaaaaca gatggaggca taagaggggg   70740
gaactcagag aaaacagtga agaacaggaa tcaggaagac aaaggagagg aaaggtgggg   70800
```

```
aggagaggag aaggaaaggg ggaagggaat ggaggagagg agaacagctg cttcacagag   70860
catggccggc agcccagtcc cagcctttct gcatgtccct gacttcagcc tctggcgagg   70920
cacaggctta ctctgtgctt cctgctgtta ctcttcttat ccatccttat tatcaatacc   70980
tgtggtcaac aaagtatttg ataaaggcat cctcaaagtc aggtaacatc tgtacgttat   71040
agattacaaa gttgagtaat atccagaatt ggtagtttaa cgtgatgact tcttaacaat   71100
tatcactgtt tcagggaagg gcaaaggtgt gtgtgtgtgt gtgttcatct gtgtgtatct   71160
gtgtatgtaa ttgtgggtgt ttgtgtatat ttgtgaggct ctttacttgg cggagttaaa   71220
aagtatctgc tcatcaaggt tgagattagc aaaggaagtg aagattttc cagagcccct    71280 aaaatgtgcc ttttgaccaa cactgaggac atctttataa ctgagtatgt gcaataaata   71340
tgtcttggga cctgtgccac aaattcctct ctaaatagcc tttacctctc tggaataacc   71400
ctttagatga ggaagaaaag ggctgtgatt ttatagcttg ttatgaagct ggagtgaaga   71460
tgatgcttca gtacttaccc tacaaagata cccccaatcc ctcaccctaa aattaccatt   71520
gaaatcatgt tccctttctc attcactctc agtttccatg tcagaaaata taccattacc   71580
tccctgcacc cctttcatct ctctcacttt tctcttgctt agatggaaag acaacccagc   71640
aatgcctgca gggctgatgt atgaaggagt ttcccaagag cccctgaaat actccggcgg   71700
gagtgcagct cagagcacag tgcttcatgc ctttgatgag ttcttaggca ttcgtcatag   71760
caaggaaagt ggtaagtcag acattttgtt ttcccttgag agtagaggga ggaagaggag   71820
aggtgttttt ttttttttcca attgataaaa ccaaatataa attaaaatgt catgaagttt   71880
atacttctct aagtcagcca agaaactgca tgactgccaa tgttttgtg tcaagccaat     71940 taatattgga atatcagatg tcagcttgat cttgggtttt acttccaaat cttaaaatgt   72000
tgctctgttt ccaactgttc actatcactt tggtttggat cttagacac tagcttcctt     72060 tttctgaaat gggggagaga tgtggagttt gaaggctatg agtctgggcc agctggaaac   72120
aggtctggga tcttccaaga aagtccttcc ccacaaaatg gtgcaacttc tagccaaatc   72180
tatttatacc agcagaggga tctatcaccc tggaagcttg aaattgttca ttttcttacc   72240
tgccaggatc aagttaagtt tttaacagtt gcaaaaagac acttcatact atggagtttt   72300
caagttggat tagaagaaaa agaatcacca gaacttagtg tcgtagattc aagtcacttc   72360
tctaaaactg tcataatttt tcacggattt tggcatttgg tgacattaat ggttgattta   72420
cttaccatgc ataatattaa acccataacg aatttcctat aaatatctat tgatttgatt   72480
tttaaatcac ttggcttcaa gaggctatta ctaaaacagt gactcattct ttatcttttt   72540
tgccttcacg ggctttatat aactttctcc ttttcttgtg ctccctccaa aacaaagcac   72600
tgagaaaaca aaattcacca gagtattcag ctagtcagtt caagggtttg tgttctacat   72660
ttgaagatat tccttatagc agctaccaac gggatacttt gtttacattt gttgtgtagt   72720
aaatatttat atattggcaa acaaatctag ttccaactct gtcatctgag atgttcttac   72780
tttgtttcct cttctccatc tcctgtcaac tgttagaaat atacatttga gtacgtgaag   72840
tctgcaaaca aagggccaa ggtagatttg agttagaaca ccagcaacag tttctggtgc     72900
attcttgtct gaaaagcag agaagattgg gcaccgtggg tcatgcctgt aatcccaaaa    72960
ttttggaagt ctgaggcagg tggatcgctt gagcccagga gttcaagaca agcctgggca   73020
acatagcaag aacccgtctc tactaaaagg aatacaaaaa aatattagct gggtgtggtg   73080
gcgcacacct gtagtttcag ctactcagaa gactgaggtg ggaggatcac ttgaactcag   73140
gggcagaggt ggcagtaagc tgagatcaca ccactgcact ccagcctggg caacagagca   73200
```

| | |
|---|---|
| agatctcatc tagagaaaaa aaaaataaaa aagaagaaga agcagacgag ctctgctata | 73260 |
| tttccatgtg gagctatgac gttatgctgt attgtttctt tcaggtgact ttctgtacag | 73320 |
| aatgagggat tacatgcctc cttcccataa ggccttcata gaagcatcc actcagcacc | 73380 |
| ttccctgagg gactacatcc tgtcatctgg acaggaccac ttgctgacag cttataacca | 73440 |
| gtgtgtgcag gccctggcag agctgcggag ctatcacatc accatggtca ccaaatacct | 73500 |
| catcacagct gcagccaagg caaagcatgg gaagccaaac catctcccag ggcctcctca | 73560 |
| ggctttaaaa gacaggggca caggtggaac cgcagttatg agctttctta agagtgtcag | 73620 |
| ggataagacc ttggagtcaa tccttcaccc acgtggttag | 73660 |

<210> SEQ ID NO 22
<211> LENGTH: 890
<212> TYPE: DNA
<213> ORGANISM: Homo sapiens

<400> SEQUENCE: 22

| | |
|---|---|
| ggcttatgga gccccacaga ccgaatgtga agacagcagt gccattgtct ttggaaagct | 60 |
| atcacatatc tgaagagtat ggcttttcttc ttccagattc tctgaaagaa cttccagatc | 120 |
| attataggcc ttggatggaa attgccaaca aacttcctca attgattgat gctcaccagc | 180 |
| ttcaagctca tgtggacaag attcctggaa attgggctct tgttcaggcc acgaatgcta | 240 |
| tcttgcagcc caaccaggag gccctgctcc aagccctgca gcgactgaga ctgtctattc | 300 |
| aggacatcac caaaaccta ggacagatgc atgattatgt agatccagac atattttatg | 360 |
| caggcatccg gatctttctc tctggatgga agacaaccc agcaatgcct gcagggctga | 420 |
| tgtatgaagg agtttcccaa gagccctga aatactccgg cggagtgca gctcagagca | 480 |
| cagtgcttca tgcctttgat gagttcttag gcattcgtca tagcaaggaa agtggtgact | 540 |
| ttctgtacag aatgagggat tacatgcctc cttcccataa ggccttcata gaagacatcc | 600 |
| actcagcacc ttccctgagg gactacatcc tgtcctctgg acaggaccac ttgctgacag | 660 |
| cttataacca gtgtgtgcag gccctggcag agctgcggag ctatcacatc accatggtca | 720 |
| ccaaatacct catcacagct gcagccaagg caaagcatgg gaagccaaac catctcccag | 780 |
| ggcctcctca ggctttaaaa gacaggggca caggtggaac cgcagttatg agctttctta | 840 |
| agagtgtcag ggataagacc ttggagtcaa tccttcaccc acgtggttag | 890 |

<210> SEQ ID NO 23
<211> LENGTH: 1177
<212> TYPE: DNA
<213> ORGANISM: Homo sapiens

<400> SEQUENCE: 23

| | |
|---|---|
| ggcttatgga gccccacaga ccgaatgtga agacagcagt gccattgtct ttggaaagct | 60 |
| atcacatatc tgaagagtat ggcttttcttc ttccagattc tctgaaagaa cttccagatc | 120 |
| attataggcc ttggatggaa attgccaaca aacttcctca attgattgat gctcaccagc | 180 |
| ttcaagctca tgtggacaag atgccctgc tgagctgcca gttcctgaag gtcaccggg | 240 |
| agcagcgcct ggcccacctg gtcctgagct tcctcaccat gggttatgtc tggcaggaag | 300 |
| gagaggcgca gcctgcagag gtcctgccaa ggaatcttgc ccttccattt gtcgaagtct | 360 |
| ccaggaactt ggggctcccct cctatcctgg tccactcaga cttggtgctg acgaactgga | 420 |
| ccaaaaaaga tccagacgga ttcctggaaa ttgggaacct ggagaccatc atctcatttc | 480 |
| ctggggggaga gagcctgcat ggttttatac tggtgactgc tttggtagag aaagaagcag | 540 |

| | |
|---|---|
| tgcctgggat aaaggctctt gttcaggcca cgaatgctat cttgcagccc aaccaggagg | 600 |
| ccctgctcca agccctgcag cgactgagac tgtctattca ggacatcacc aaaaccttag | 660 |
| gacagatgca tgatggaaag acaacccagc aatgcctgca gggctgatgt atgaaggagt | 720 |
| ttcccaagag cccctgaaat actccggcgg gagtgcagct cagagcacag tgcttcatgc | 780 |
| cttttgatgag ttcttaggca ttcgtcatag caaggaaagt ggtgactttc tgtacagaat | 840 |
| gagggattac atgcctcctt cccataaggc cttcatagaa gacatccact cagcaccttc | 900 |
| cctgagggac tacatcctgt cctctggaca ggaccacttg ctgacagctt ataaccagtg | 960 |
| tgtgcaggcc ctggcagagc tgcggagcta tcacatcacc atggtcacca aatacctcat | 1020 |
| cacagctgca gccaaggcaa agcatgggaa gccaaaccat ctcccagggc ctcctcaggc | 1080 |
| tttaaaagac aggggcacag gtggaaccgc agttatgagc tttcttaaga gtgtcaggga | 1140 |
| taagaccttg gagtcaatcc ttcacccacg tggttag | 1177 |

<210> SEQ ID NO 24
<211> LENGTH: 1077
<212> TYPE: DNA
<213> ORGANISM: Homo sapiens

<400> SEQUENCE: 24

| | |
|---|---|
| ggcttatgga gccccacaga ccgaatgtga agacagcagt gccattgtct ttggaaagct | 60 |
| atcacatatc tgaagagtat ggctttcttc ttccagattc tctgaaagaa cttccagatc | 120 |
| attataggcc ttggatggaa attgccaaca aacttcctca attgattgat gctcaccagc | 180 |
| ttcaagctca tgtggacaag atgcccctgc tgagctgcca gttcctgaag ggtcaccggg | 240 |
| agcagcgcct ggcccacctg gtcctgagct tcctcaccat gggttatgtc tggcaggaag | 300 |
| gagaggcgca gcctgcagag gtcctgccaa ggaatcttgc ccttccattt gtcgaagtct | 360 |
| ccaggaactt ggggctccct cctatcctgg tccactcaga cttggtgctg acgaactgga | 420 |
| ccaaaaaaga tccagacgga ttcctggaaa ttgggctctt gttcaggcca cgaatgctat | 480 |
| cttgcagccc aaccaggagg ccctgctcca agccctgcag cgactgagac tgtctattca | 540 |
| ggacatcacc aaaaccttag acagatgca tgatggaaag acaacccagc aatgcctgca | 600 |
| gggctgatgt atgaaggagt ttcccaagag cccctgaaat actccggcgg gagtgcagct | 660 |
| cagagcacag tgcttcatgc cttttgatgag ttcttaggca ttcgtcatag caaggaaagt | 720 |
| ggtgactttc tgtacagaat gagggattac atgcctcctt cccataaggc cttcatagaa | 780 |
| gacatccact cagcaccttc cctgagggac tacatcctgt cctctggaca ggaccacttg | 840 |
| ctgacagctt ataaccagtg tgtgcaggcc ctggcagagc tgcggagcta tcacatcacc | 900 |
| atggtcacca aatacctcat cacagctgca gccaaggcaa agcatgggaa gccaaaccat | 960 |
| ctcccagggc ctcctcaggc tttaaaagac aggggcacag gtggaaccgc agttatgagc | 1020 |
| tttcttaaga gtgtcaggga taagaccttg gagtcaatcc ttcacccacg tggttag | 1077 |

<210> SEQ ID NO 25
<211> LENGTH: 1096
<212> TYPE: DNA
<213> ORGANISM: Homo sapiens

<400> SEQUENCE: 25

| | |
|---|---|
| ggcttatgga gccccacaga ccgaatgtga agacagcagt gccattgtct ttggaaagct | 60 |
| atcacatatc tgaagagtat ggctttcttc ttccagattc tctgaaagaa cttccagatc | 120 |
| attataggcc ttggatggaa attgccaaca aacttcctca attgattgat gctcaccagc | 180 |

```
ttcaagctca tgtggacaag atgcccctgc tgagctgcca gttcctgaag ggtcaccggg    240
agcagcgcct ggcccacctg gtcctgagct tcctcaccat gggttatgtc tggcaggaag    300
gagaggcgca gcctgcagag ggaacctgga gaccatcatc tcatttcctg ggggagagag    360
cctgcatggt tttatactgg tgactgcttt ggtagagaaa gaagcagtgc ctgggataaa    420
ggctcttgtt caggccacga atgctatctt gcagcccaac caggaggccc tgctccaagc    480
cctgcagcga ctgagactgt ctattcagga catcaccaaa accttaggac agatgcatga    540
ttatgtagat ccagacatat tttatgcagg catccggatc tttctctctg gatgaaaga    600 caacccagca atgcctgcag ggctgatgta tgaaggagtt tcccaagagc ccctgaaata    660
ctccggcggg agtgcagctc agagcacagt gcttcatgcc tttgatgagt tcttaggcat    720
tcgtcatagc aaggaaagtg gtgactttct gtacagaatg agggattaca tgcctccttc    780
ccataaggcc ttcatagaag acatccactc agcaccttcc ctgagggact acatcctgtc    840
ctctggacag gaccacttgc tgacagctta taaccagtgt gtgcaggccc tggcagagct    900
gcggagctat cacatcacca tggtcaccaa atacctcatc acagctgcag ccaaggcaaa    960
gcatgggaag ccaaaccatc tcccagggcc tcctcaggct taaaagaca ggggcacagg   1020 tggaaccgca gttatgagct ttcttaagag tgtcagggat aagaccttgg agtcaatcct   1080
tcacccacgt ggttag                                                   1096

<210> SEQ ID NO 26
<211> LENGTH: 1229
<212> TYPE: DNA
<213> ORGANISM: Homo sapiens

<400> SEQUENCE: 26
ggcttatgga gccccacaga ccgaatgtga agacagcagt gccattgtct ttggaaagct     60
atcacatatc tgaagagtat ggcttttctt ttccagattc tctgaaagaa cttccagatc    120
attataggcc ttggatggaa attgccaaca aacttcctca attgattgat gctcaccagc    180
ttcaagctca tgtggacaag atgcccctgc tgagctgcca gttcctgaag ggtcaccggg    240
agcagcgcct ggcccacctg gtcctgagct tcctcaccat gggttatgtc tggcaggaag    300
gagaggcgca gcctgcagag gtcctgccaa ggaatcttgc ccttccattt gtcgaagtct    360
ccaggaactt ggggctccct cctatcctgg tccactcaga cttggtgctg acgaactgga    420
ccaaaaaaga tccagacgga ttcctggaaa ttgggaacct ggagaccatc atctcatttc    480
ctgggggaga gagcctgcat ggttttatac tggtgactgc tttggtagag aaagaagcag    540
tgcctgggat aaaggctctt gttcaggcca cgaatgctat cttgcagccc aaccaggagg    600
ccctgctcca agccctgcag cgactgagac tgtctattca ggacatcacc aaaaccttag    660
gacagatgca tgattatgta gatccagaca tattttatgc aggcatctgg atctttctct    720
ctggatggaa agacaaccca gcaatgcctg cagggctgat gtatgaagga gtttcccaag    780
agcccctgaa atactccggc gggagtgcag ctcagagcac agtgcttcat gcctttgatg    840
agttcttagg cattcgtcat agcaaggaaa gtggtgactt tctgtacaga atgagggatt    900
acatgcctcc tttcccataag gccttcatag aagacatcca ctcagcacct tccctgaggg    960
actacatcct gtcctctgga caggaccact tgctgacagc ttataaccag tgtgtgcagg   1020
ccctggcaga gctgcggagc tatcacatca ccatggtcac caaatacctc atcacagctg   1080
cagccaaggc aaagcatggg aagccaaacc atctcccagg gcctcctcag gctttaaaag   1140
acaggggcac aggtggaacc gcagttatga gctttcttaa gagtgtcagg gataagacct   1200
```
tggagtcaat ccttcaccca cgtggttag                                        1229

<210> SEQ ID NO 27
<211> LENGTH: 1225
<212> TYPE: DNA
<213> ORGANISM: Homo sapiens

<400> SEQUENCE: 27
tatggagccc cacagaccga atgtgaagac agcagtgcca ttgtctttgg aaagctatca       60
catatctgaa gagtatggct ttcttcttcc agattctctg aaagaacttc cagatcatta      120
taggccttgg atggaaattg ccaacaaact tcctcaattg attgatgctc accagcttca      180
agctcatgtg acaagatgc ccctgctgag ctgccagttc ctgaagggtc accgggagca       240
gcgcctggcc cacctggtcc tgagcttcct caccatgggg tatgtctggc aggaaggaga      300
ggcgcagcct gcagaggtcc tgccaaggaa tcttgcccctt ccatttgtcg aagtctccag     360
gaacttgggg ctccctcctg tcctggtcca ctcagacttg gtgctgacga actggaccaa      420
aaaagatcca gacggattcc tggaaattgg gaacctggag accatcatct catttcctgg      480
gggagagagc ctgcatggtt ttatactggt gactgctttg gtagagaaag aagcagtgcc      540
tgggataaag gctcttgttc aggccacgaa tgctatcttg cagcccaacc aggaggccct      600
gctccaagcc ctgcagcgac tgagactgtc tattcaggac atcaccaaaa ccttaggaca      660
gatgcatgat tatgtagatc cagacatatt ttatgcaggc atccggatct ttctctctgg      720
atggaaagac aacccagcaa tgcctgcagg gctgatgtat gaaggagttt cccaagagcc      780
cctgaaatac tccggcggga gtgcagctca gagcacagtg cttcatgcct ttgatgagtt      840
cttaggcatt cgtcatagca aggaaagtgg tgactttctg tacagaatga gggattacat      900
gcctccttcc cataaggcct tcatagaaga catccactca gcaccttccc tgagggacta      960
catcctgtcc tctggacagg accacttgct gacagcttat aaccagtgtg tgcaggccct     1020
ggcagagctg cggagctaac acatcaccat ggtcaccaaa tacctcatca gctgcagc       1080
caaggcaaag catgggaagc caaaccatct cccaggcct cctcaggctt taaaagacag      1140
gggcacaggt ggaaccgcag ttatgagctt tcttaagagt gtcagggata agaccttgga     1200
gtcaatcctt cacccacgtg gttag                                          1225

<210> SEQ ID NO 28
<211> LENGTH: 407
<212> TYPE: PRT
<213> ORGANISM: Homo sapiens

<400> SEQUENCE: 28

Met Glu Pro His Arg Pro Asn Val Lys Thr Ala Val Pro Leu Ser Leu
 1               5                  10                  15

Glu Ser Tyr His Ile Ser Glu Glu Tyr Gly Phe Leu Leu Pro Asp Ser
            20                  25                  30

Leu Lys Glu Leu Pro Asp His Tyr Arg Pro Trp Met Glu Ile Ala Asn
        35                  40                  45

Lys Leu Pro Gln Leu Ile Asp Ala His Gln Leu Gln Ala His Val Asp
    50                  55                  60

Lys Met Pro Leu Leu Ser Cys Gln Phe Leu Lys Gly His Arg Glu Gln
65                  70                  75                  80

Arg Leu Ala His Leu Val Leu Ser Phe Leu Thr Met Gly Tyr Val Trp
                85                  90                  95

Gln Glu Gly Glu Ala Gln Pro Ala Glu Val Leu Pro Arg Asn Leu Ala

```
              100                 105                 110
Leu Pro Phe Val Glu Val Ser Arg Asn Leu Gly Leu Pro Ile Leu
            115                 120                 125

Val His Ser Asp Leu Val Leu Thr Asn Trp Thr Lys Lys Asp Pro Asp
130                 135                 140

Gly Phe Leu Glu Ile Gly Asn Leu Glu Thr Ile Ile Ser Phe Pro Gly
145                 150                 155                 160

Gly Glu Ser Leu His Gly Phe Ile Leu Val Thr Ala Leu Val Glu Lys
                165                 170                 175

Glu Ala Val Pro Gly Ile Lys Ala Leu Val Gln Ala Thr Asn Ala Ile
                180                 185                 190

Leu Gln Pro Asn Gln Glu Ala Leu Leu Gln Ala Leu Gln Arg Leu Arg
                195                 200                 205

Leu Ser Ile Gln Asp Ile Thr Lys Thr Leu Gly Gln Met His Asp Tyr
                210                 215                 220

Val Asp Pro Asp Ile Phe Tyr Ala Gly Ile Arg Ile Phe Leu Ser Gly
225                 230                 235                 240

Trp Lys Asp Asn Pro Ala Met Pro Ala Gly Leu Met Tyr Glu Gly Val
                245                 250                 255

Ser Gln Glu Pro Leu Lys Tyr Ser Gly Ser Ala Ala Gln Ser Thr
                260                 265                 270

Val Leu His Ala Phe Asp Glu Leu Gly Ile Arg His Ser Lys Glu
                275                 280                 285

Ser Gly Asp Phe Leu Tyr Arg Met Arg Asp Tyr Met Pro Pro Ser His
                290                 295                 300

Lys Ala Phe Ile Glu Asp Ile His Ser Ala Pro Ser Leu Arg Asp Tyr
305                 310                 315                 320

Ile Leu Ser Ser Gly Gln Asp His Leu Leu Thr Ala Tyr Asn Gln Cys
                325                 330                 335

Val Gln Ala Leu Ala Glu Leu Arg Ser Tyr His Ile Thr Met Val Thr
                340                 345                 350

Lys Tyr Leu Ile Thr Ala Ala Lys Ala Lys His Gly Lys Pro Asn
                355                 360                 365

His Leu Pro Gly Pro Pro Gln Ala Leu Lys Asp Arg Gly Thr Gly Gly
                370                 375                 380

Thr Ala Val Met Ser Phe Leu Lys Ser Val Arg Asp Lys Thr Leu Glu
385                 390                 395                 400

Ser Ile Leu His Pro Arg Gly
                405

<210> SEQ ID NO 29
<211> LENGTH: 101
<212> TYPE: DNA
<213> ORGANISM: Homo sapiens

<400> SEQUENCE: 29
gacacgggag ttgaggcatt accttggacg tggagaccag gccctcacca gacactgaac      60
ttgccagcac cttgatcttg gacttcccag cctccagaac t                         101

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
```
actctgacct ggtgctgaca aact                                    24

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
tgcaggatgt gaacctctaa cgct                                    24

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
tggagcctca aagtcagagc atga                                    24

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
agtttgtcag caccaggtca gagt                                    24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
tgcctgatgg cctataacca gtgt                                    24

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
tgcaggatgt gaacctctaa cgct                                    24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
aaccacacag aagacacagc tgga                                    24

<210> SEQ ID NO 37
<211> LENGTH: 24
<212> TYPE: DNA
<213> ORGANISM: Artificial Sequence

```
<220> FEATURE:
<223> OTHER INFORMATION: Primer

<400> SEQUENCE: 37
tgagggcaat tccatccaa ggct                                            24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
accgcacaag tacaaccaca caga                                           24

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
agccttatgg gaaggcggca tg                                             22

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
actgatttcc aacggtcctt c                                              21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
tcggagctgg cggttctcga t                                              21

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
aaggtgctgc caagatctc                                                 19

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
cttcatgcct tcgatgag                                                  18
```

```
<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
agagaaagaa gcagtgcctg ggat                                          24

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
taagctgtca gcaagtggtc ctgt                                          24

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
tgagacactg cgcaactaac tgga                                          24

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
atcccaggca ctgcttcttt ctct                                          24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
acaggaccac ttgctgacag ctta                                          24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
acgtgggtga aggattgact ccaa                                          24

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
```
tgttggcaat ttcatccaa ggc                                        23

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
aaccacgtgg gtgaaggatt gact                                      24

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ttcagtgaca ctttccatgc ag                                        22

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
atggagcccc acagaccgaa tg                                        22

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
gaagggcaag attccttggc ag                                        22

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
attgatgctc accagcttca ag                                        22

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
cttcatacat cagccctgca gg                                        22

<210> SEQ ID NO 57
<211> LENGTH: 22
<212> TYPE: DNA
<213> ORGANISM: Artificial Sequence

```
<220> FEATURE:
<223> OTHER INFORMATION: Primer

<400> SEQUENCE: 57
gtagagaaag aagcagtgcc tg                                              22

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
ggcatccgga tctttctctc tg                                              22

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
ctaaccacgt gggtgaagga ttg                                             23

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
ggtactgcca tgctgagc                                                   18

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
aagctgcccg ttctcaatca g                                               21

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
ctcgtatgtc atgggcccat tg                                              22

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
gaagttccgg tgggctggag gc                                              22
```

```
<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
ggtgctgccc cgcaataatg c                                          21

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
ccagagtctt gatgtccttc                                            20

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
cctcaaatgt ggaaagcaga g                                          21

<210> SEQ ID NO 67
<211> LENGTH: 28
<212> TYPE: DNA
<213> ORGANISM: Artificial Sequence
<220> FEATURE:
<223> OTHER INFORMATION: Primer

<400> SEQUENCE: 67
atccggtacc atggagcctc aaagtcag                                   28

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gttgagctct ccaggaactt ggga                                       24

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
agtgttgaat tcctacagga aatgagg                                    27

<210> SEQ ID NO 70
<211> LENGTH: 27
<212> TYPE: DNA
<213> ORGANISM: Artificial Sequence
<220> FEATURE:
<223> OTHER INFORMATION: Primer

<400> SEQUENCE: 70
```
ctgaaagctt ataaccagtg tgtggag        27

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
catcctgtac acgtgagctc g        21

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
tggagagctc aacaaaagga atgg        24

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
ctgtaggaat tcaacacttt ccttgcaatg        30

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
tataagcttt caggcagtcc ccag        24

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
gaagacacag ctggaaagct c        21

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ccatgctgac ctccaggctc        20

<210> SEQ ID NO 77
<211> LENGTH: 28
<212> TYPE: DNA
<213> ORGANISM: Artificial Sequence

```
<220> FEATURE:
<223> OTHER INFORMATION: Primer

<400> SEQUENCE: 77
atccggtacc atggcactca gtaaaata                                        28

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
gaagtgtaca agctgcccac actg                                            24

<210> SEQ ID NO 79
<211> LENGTH: 22
<212> TYPE: DNA
<213> ORGANISM: Artificial Sequence
<220> FEATURE:
<223> OTHER INFORMATION: Primer

<400> SEQUENCE: 79
gaggatgcat gactttgtgg ac                                              22

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
agcttgtaca cttcttctcg aag                                             23

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
gtcatgcatc ctcttaaaaa taac                                            24

<210> SEQ ID NO 82
<211> LENGTH: 33
<212> TYPE: DNA
<213> ORGANISM: Artificial Sequence
<220> FEATURE:
<223> OTHER INFORMATION: Primer

<400> SEQUENCE: 82
gtcgcgctag caaactcaat ggtgatggtg atg                                  33

<210> SEQ ID NO 83
<211> LENGTH: 23
<212> TYPE: DNA
<213> ORGANISM: Artificial Sequence
<220> FEATURE:
<223> OTHER INFORMATION: Target sequence

<400> SEQUENCE: 83
aatgtgaaga cagcagtgcc att                                             23
```

```
<210> SEQ ID NO 84
<211> LENGTH: 23
<212> TYPE: DNA
<213> ORGANISM: Artificial Sequence
<220> FEATURE:
<223> OTHER INFORMATION: Target sequence

<400> SEQUENCE: 84
aagacagcag tgccattgtc ttt                                              23

<210> SEQ ID NO 85
<211> LENGTH: 23
<212> TYPE: DNA
<213> ORGANISM: Artificial Sequence
<220> FEATURE:
<223> OTHER INFORMATION: Target sequence

<400> SEQUENCE: 85
aattgattga tgctcaccag ctt                                              23

<210> SEQ ID NO 86
<211> LENGTH: 23
<212> TYPE: DNA
<213> ORGANISM: Artificial Sequence
<220> FEATURE:
<223> OTHER INFORMATION: Target sequence

<400> SEQUENCE: 86
aacctggaga ccatcatctc att                                              23

<210> SEQ ID NO 87
<211> LENGTH: 23
<212> TYPE: DNA
<213> ORGANISM: Artificial Sequence
<220> FEATURE:
<223> OTHER INFORMATION: Target sequence

<400> SEQUENCE: 87
aaccttagga cagatgcatg att                                              23

<210> SEQ ID NO 88
<211> LENGTH: 23
<212> TYPE: DNA
<213> ORGANISM: Artificial Sequence
<220> FEATURE:
<223> OTHER INFORMATION: Target sequence

<400> SEQUENCE: 88
aaggagtttc ccaagagccc ctt                                              23

<210> SEQ ID NO 89
<211> LENGTH: 23
<212> TYPE: DNA
<213> ORGANISM: Artificial Sequence
<220> FEATURE:
<223> OTHER INFORMATION: Target sequence

<400> SEQUENCE: 89
aatgagggat tacatgcctc ctt                                              23

<210> SEQ ID NO 90
<211> LENGTH: 23
<212> TYPE: DNA
<213> ORGANISM: Artificial Sequence
<220> FEATURE:
<223> OTHER INFORMATION: Target sequence

<400> SEQUENCE: 90
```
aagagtgtca gggataagac ctt                                          23

<210> SEQ ID NO 91
<211> LENGTH: 21
<212> TYPE: RNA
<213> ORGANISM: Artificial Sequence
<220> FEATURE:
<223> OTHER INFORMATION: siRNA

<400> SEQUENCE: 91
ugugaagaca gcagugccau u                                            21

<210> SEQ ID NO 92
<211> LENGTH: 21
<212> TYPE: RNA
<213> ORGANISM: Artificial Sequence
<220> FEATURE:
<223> OTHER INFORMATION: siRNA

<400> SEQUENCE: 92
gacagcagug ccauugucuu u                                            21

<210> SEQ ID NO 93
<211> LENGTH: 21
<212> TYPE: RNA
<213> ORGANISM: Artificial Sequence
<220> FEATURE:
<223> OTHER INFORMATION: siRNA

<400> SEQUENCE: 93
uugauugaug cucaccagcu u                                            21

<210> SEQ ID NO 94
<211> LENGTH: 21
<212> TYPE: RNA
<213> ORGANISM: Artificial Sequence
<220> FEATURE:
<223> OTHER INFORMATION: siRNA

<400> SEQUENCE: 94
ccuggagacc aucaucucau u                                            21

<210> SEQ ID NO 95
<211> LENGTH: 21
<212> TYPE: RNA
<213> ORGANISM: Artificial Sequence
<220> FEATURE:
<223> OTHER INFORMATION: siRNA

<400> SEQUENCE: 95
ccuuaggaca gaugcaugau u                                            21

<210> SEQ ID NO 96
<211> LENGTH: 21
<212> TYPE: RNA
<213> ORGANISM: Artificial Sequence
<220> FEATURE:
<223> OTHER INFORMATION: siRNA

<400> SEQUENCE: 96
ggaguuuccc aagagccccu u                                            21

<210> SEQ ID NO 97
<211> LENGTH: 21
<212> TYPE: RNA
<213> ORGANISM: Artificial Sequence

```
<220> FEATURE:
<223> OTHER INFORMATION: siRNA

<400> SEQUENCE: 97
ugagggauua caugccuccu u                                        21

<210> SEQ ID NO 98
<211> LENGTH: 21
<212> TYPE: RNA
<213> ORGANISM: Artificial Sequence
<220> FEATURE:
<223> OTHER INFORMATION: siRNA

<400> SEQUENCE: 98
gagugucagg gauaagaccu u                                        21

<210> SEQ ID NO 99
<211> LENGTH: 25
<212> TYPE: DNA
<213> ORGANISM: Artificial Sequence
<220> FEATURE:
<223> OTHER INFORMATION: siRNA

<400> SEQUENCE: 99
caaacuuccu caauugauug augct                                    25

<210> SEQ ID NO 100
<211> LENGTH: 25
<212> TYPE: DNA
<213> ORGANISM: Artificial Sequence
<220> FEATURE:
<223> OTHER INFORMATION: siRNA

<400> SEQUENCE: 100
gugccauugu cuuuggaaag cuatc                                    25

<210> SEQ ID NO 101
<211> LENGTH: 25
<212> TYPE: DNA
<213> ORGANISM: Artificial Sequence
<220> FEATURE:
<223> OTHER INFORMATION: siRNA

<400> SEQUENCE: 101
gugccauugu cuuuggaaag cuatc                                    25

<210> SEQ ID NO 102
<211> LENGTH: 25
<212> TYPE: RNA
<213> ORGANISM: Artificial Sequence
<220> FEATURE:
<223> OTHER INFORMATION: siRNA

<400> SEQUENCE: 102
caaggaaagu ggugacuuuc uguac                                    25

<210> SEQ ID NO 103
<211> LENGTH: 25
<212> TYPE: DNA
<213> ORGANISM: Artificial Sequence
<220> FEATURE:
<223> OTHER INFORMATION: siRNA

<400> SEQUENCE: 103
gcagcucaga gcacagugcu ucatg                                    25
```

```
<210> SEQ ID NO 104
<211> LENGTH: 25
<212> TYPE: RNA
<213> ORGANISM: Artificial Sequence
<220> FEATURE:
<223> OTHER INFORMATION: siRNA

<400> SEQUENCE: 104
gcaugggaag ccaaaccauc uccca                                          25

<210> SEQ ID NO 105
<211> LENGTH: 25
<212> TYPE: DNA
<213> ORGANISM: Artificial Sequence
<220> FEATURE:
<223> OTHER INFORMATION: siRNA

<400> SEQUENCE: 105
agagaaagaa gcagugccug ggata                                          25

<210> SEQ ID NO 106
<211> LENGTH: 25
<212> TYPE: DNA
<213> ORGANISM: Artificial Sequence
<220> FEATURE:
<223> OTHER INFORMATION: siRNA

<400> SEQUENCE: 106
ccuuaggaca gaugcaugau uaugt                                          25

<210> SEQ ID NO 107
<211> LENGTH: 21
<212> TYPE: RNA
<213> ORGANISM: Artificial Sequence
<220> FEATURE:
<223> OTHER INFORMATION: siRNA

<400> SEQUENCE: 107
aggcacugcu gucuucacau u                                              21

<210> SEQ ID NO 108
<211> LENGTH: 21
<212> TYPE: RNA
<213> ORGANISM: Artificial Sequence
<220> FEATURE:
<223> OTHER INFORMATION: siRNA

<400> SEQUENCE: 108
agacaauggc acugcugucu u                                              21

<210> SEQ ID NO 109
<211> LENGTH: 21
<212> TYPE: RNA
<213> ORGANISM: Artificial Sequence
<220> FEATURE:
<223> OTHER INFORMATION: siRNA

<400> SEQUENCE: 109
gcuggugagc aucaaucaau u                                              21

<210> SEQ ID NO 110
<211> LENGTH: 21
<212> TYPE: RNA
<213> ORGANISM: Artificial Sequence
<220> FEATURE:
<223> OTHER INFORMATION: siRNA

<400> SEQUENCE: 110
```

-continued ugacaugaug gucuccaggu u                                              21

<210> SEQ ID NO 111
<211> LENGTH: 21
<212> TYPE: RNA
<213> ORGANISM: Artificial Sequence
<220> FEATURE:
<223> OTHER INFORMATION: siRNA

<400> SEQUENCE: 111
ucaugcaucu guccgaaggu u                                              21

<210> SEQ ID NO 112
<211> LENGTH: 21
<212> TYPE: RNA
<213> ORGANISM: Artificial Sequence
<220> FEATURE:
<223> OTHER INFORMATION: siRNA

<400> SEQUENCE: 112
ggggcucuug ggaaacuccu u                                              21

<210> SEQ ID NO 113
<211> LENGTH: 21
<212> TYPE: RNA
<213> ORGANISM: Artificial Sequence
<220> FEATURE:
<223> OTHER INFORMATION: siRNA

<400> SEQUENCE: 113
ggaggcaugu aaucccucau u                                              21

<210> SEQ ID NO 114
<211> LENGTH: 21
<212> TYPE: RNA
<213> ORGANISM: Artificial Sequence
<220> FEATURE:
<223> OTHER INFORMATION: siRNA

<400> SEQUENCE: 114
ggucuuaucc cugacacucu u                                              21

<210> SEQ ID NO 115
<211> LENGTH: 27
<212> TYPE: RNA
<213> ORGANISM: Artificial Sequence
<220> FEATURE:
<223> OTHER INFORMATION: siRNA

<400> SEQUENCE: 115
agcaucaauc aauugaggaa guuuguu                                        27

<210> SEQ ID NO 116
<211> LENGTH: 27
<212> TYPE: RNA
<213> ORGANISM: Artificial Sequence
<220> FEATURE:
<223> OTHER INFORMATION: siRNA

<400> SEQUENCE: 116
gauagcuuuc caaagacaau ggcacug                                        27

<210> SEQ ID NO 117
<211> LENGTH: 27
<212> TYPE: RNA
<213> ORGANISM: Artificial Sequence

```
<220> FEATURE:
<223> OTHER INFORMATION: siRNA

<400> SEQUENCE: 117
cuccaagguc uuaucccuga cacucuu                                              27

<210> SEQ ID NO 118
<211> LENGTH: 27
<212> TYPE: RNA
<213> ORGANISM: Artificial Sequence
<220> FEATURE:
<223> OTHER INFORMATION: siRNA

<400> SEQUENCE: 118
guacagaaag ucaccacuuu ccuugcu                                              27

<210> SEQ ID NO 119
<211> LENGTH: 27
<212> TYPE: RNA
<213> ORGANISM: Artificial Sequence
<220> FEATURE:
<223> OTHER INFORMATION: siRNA

<400> SEQUENCE: 119
caugaagcac ugugcucuga gcugcac                                              27

<210> SEQ ID NO 120
<211> LENGTH: 27
<212> TYPE: RNA
<213> ORGANISM: Artificial Sequence
<220> FEATURE:
<223> OTHER INFORMATION: siRNA

<400> SEQUENCE: 120
ugggagaugg uuuggcuucc caugcuu                                              27

<210> SEQ ID NO 121
<211> LENGTH: 27
<212> TYPE: RNA
<213> ORGANISM: Artificial Sequence
<220> FEATURE:
<223> OTHER INFORMATION: siRNA

<400> SEQUENCE: 121
uaucccaggc acugcuucuu ucucuac                                              27

<210> SEQ ID NO 122
<211> LENGTH: 27
<212> TYPE: RNA
<213> ORGANISM: Artificial Sequence
<220> FEATURE:
<223> OTHER INFORMATION: siRNA

<400> SEQUENCE: 122
uaucccaggc acugcuucuu ucucuac                                              27

<210> SEQ ID NO 123
<211> LENGTH: 27
<212> TYPE: RNA
<213> ORGANISM: Artificial Sequence
<220> FEATURE:
<223> OTHER INFORMATION: siRNA

<400> SEQUENCE: 123
acauaaucau gcaucugucc uaagguu                                              27
```

```
<210> SEQ ID NO 124
<211> LENGTH: 21
<212> TYPE: RNA
<213> ORGANISM: Artificial Sequence
<220> FEATURE:
<223> OTHER INFORMATION: siRNA

<400> SEQUENCE: 124
aaggaaccca gaaggaccgu u                                              21

<210> SEQ ID NO 125
<211> LENGTH: 21
<212> TYPE: RNA
<213> ORGANISM: Artificial Sequence
<220> FEATURE:
<223> OTHER INFORMATION: siRNA

<400> SEQUENCE: 125
ccuggaaacc aucaucucau u                                              21

<210> SEQ ID NO 126
<211> LENGTH: 21
<212> TYPE: RNA
<213> ORGANISM: Artificial Sequence
<220> FEATURE:
<223> OTHER INFORMATION: siRNA

<400> SEQUENCE: 126
ugagggacua caugccgccu u                                              21

<210> SEQ ID NO 127
<211> LENGTH: 21
<212> TYPE: RNA
<213> ORGANISM: Artificial Sequence
<220> FEATURE:
<223> OTHER INFORMATION: siRNA

<400> SEQUENCE: 127
aaggugcugc caagaucucu u                                              21

<210> SEQ ID NO 128
<211> LENGTH: 25
<212> TYPE: DNA
<213> ORGANISM: Artificial Sequence
<220> FEATURE:
<223> OTHER INFORMATION: siRNA

<400> SEQUENCE: 128
ccagaaggac cguuggaaau cagta                                          25

<210> SEQ ID NO 129
<211> LENGTH: 25
<212> TYPE: RNA
<213> ORGANISM: Artificial Sequence
<220> FEATURE:
<223> OTHER INFORMATION: siRNA

<400> SEQUENCE: 129
gaaguacucu ggaggaagug cagcc                                          25

<210> SEQ ID NO 130
<211> LENGTH: 25
<212> TYPE: RNA
<213> ORGANISM: Artificial Sequence
<220> FEATURE:
<223> OTHER INFORMATION: siRNA

<400> SEQUENCE: 130
```

-continued caaggaaagu guuggcuuuc uacac                                                  25

<210> SEQ ID NO 131
<211> LENGTH: 25
<212> TYPE: RNA
<213> ORGANISM: Artificial Sequence
<220> FEATURE:
<223> OTHER INFORMATION: siRNA

<400> SEQUENCE: 131
ccaugggauu cgucuggcag gaggg                                                  25

<210> SEQ ID NO 132
<211> LENGTH: 25
<212> TYPE: RNA
<213> ORGANISM: Artificial Sequence
<220> FEATURE:
<223> OTHER INFORMATION: siRNA

<400> SEQUENCE: 132
guacugccau gcugagcuuc uugaa                                                  25

<210> SEQ ID NO 133
<211> LENGTH: 25
<212> TYPE: DNA
<213> ORGANISM: Artificial Sequence
<220> FEATURE:
<223> OTHER INFORMATION: siRNA

<400> SEQUENCE: 133
cuaugaaggu gcugccacag agcct                                                  25

<210> SEQ ID NO 134
<211> LENGTH: 25
<212> TYPE: RNA
<213> ORGANISM: Artificial Sequence
<220> FEATURE:
<223> OTHER INFORMATION: siRNA

<400> SEQUENCE: 134
gugucaggga gaagaccaug gaggc                                                  25

<210> SEQ ID NO 135
<211> LENGTH: 25
<212> TYPE: RNA
<213> ORGANISM: Artificial Sequence
<220> FEATURE:
<223> OTHER INFORMATION: siRNA

<400> SEQUENCE: 135
gucagagcau gacgcuggag gugcc                                                  25

<210> SEQ ID NO 136
<211> LENGTH: 21
<212> TYPE: RNA
<213> ORGANISM: Artificial Sequence
<220> FEATURE:
<223> OTHER INFORMATION: siRNA

<400> SEQUENCE: 136
cgguccuucu ggguuccuuu u                                                      21

<210> SEQ ID NO 137
<211> LENGTH: 21
<212> TYPE: RNA
<213> ORGANISM: Artificial Sequence

```
<220> FEATURE:
<223> OTHER INFORMATION: siRNA

<400> SEQUENCE: 137
ugugaugaug guuuccaggu u                                              21

<210> SEQ ID NO 138
<211> LENGTH: 21
<212> TYPE: RNA
<213> ORGANISM: Artificial Sequence
<220> FEATURE:
<223> OTHER INFORMATION: siRNA

<400> SEQUENCE: 138
ggcggcaugu aguccucau u                                               21

<210> SEQ ID NO 139
<211> LENGTH: 21
<212> TYPE: RNA
<213> ORGANISM: Artificial Sequence
<220> FEATURE:
<223> OTHER INFORMATION: siRNA

<400> SEQUENCE: 139
gagaucuugg cagcaccuuu u                                              21

<210> SEQ ID NO 140
<211> LENGTH: 27
<212> TYPE: RNA
<213> ORGANISM: Artificial Sequence
<220> FEATURE:
<223> OTHER INFORMATION: siRNA

<400> SEQUENCE: 140
uacugauuuc caacgguccu ucgggu                                         27

<210> SEQ ID NO 141
<211> LENGTH: 27
<212> TYPE: RNA
<213> ORGANISM: Artificial Sequence
<220> FEATURE:
<223> OTHER INFORMATION: siRNA

<400> SEQUENCE: 141
ggcugcacuu ccuccagagu acuucag                                        27

<210> SEQ ID NO 142
<211> LENGTH: 27
<212> TYPE: RNA
<213> ORGANISM: Artificial Sequence
<220> FEATURE:
<223> OTHER INFORMATION: siRNA

<400> SEQUENCE: 142
guguagaaag ccaacacuuu ccuugca                                        27

<210> SEQ ID NO 143
<211> LENGTH: 27
<212> TYPE: RNA
<213> ORGANISM: Artificial Sequence
<220> FEATURE:
<223> OTHER INFORMATION: siRNA

<400> SEQUENCE: 143
cccuccugcc agacgaaucc cauggug                                        27
```

```
<210> SEQ ID NO 144
<211> LENGTH: 27
<212> TYPE: RNA
<213> ORGANISM: Artificial Sequence
<220> FEATURE:
<223> OTHER INFORMATION: siRNA

<400> SEQUENCE: 144
uucaagaagc ucagcauggc aguaccc                                        27

<210> SEQ ID NO 145
<211> LENGTH: 27
<212> TYPE: RNA
<213> ORGANISM: Artificial Sequence
<220> FEATURE:
<223> OTHER INFORMATION: siRNA

<400> SEQUENCE: 145
aggcucugug gcagcaccuu cauagac                                        27

<210> SEQ ID NO 146
<211> LENGTH: 27
<212> TYPE: RNA
<213> ORGANISM: Artificial Sequence
<220> FEATURE:
<223> OTHER INFORMATION: siRNA

<400> SEQUENCE: 146
gccuccaugg ucuucucccu gacacuc                                        27

<210> SEQ ID NO 147
<211> LENGTH: 27
<212> TYPE: RNA
<213> ORGANISM: Artificial Sequence
<220> FEATURE:
<223> OTHER INFORMATION: siRNA

<400> SEQUENCE: 147
ggcaccucca gcgucaugcu cugacuu                                        27

<210> SEQ ID NO 148
<211> LENGTH: 38
<212> TYPE: DNA
<213> ORGANISM: Artificial Sequence
<220> FEATURE:
<223> OTHER INFORMATION: Primer

<400> SEQUENCE: 148
actggcggcc gcatgccgaa tctattacca ttactgcc                            38

<210> SEQ ID NO 149
<211> LENGTH: 34
<212> TYPE: DNA
<213> ORGANISM: Artificial Sequence
<220> FEATURE:
<223> OTHER INFORMATION: Primer

<400> SEQUENCE: 149
actgggtacc acaccttcat agaccagccc caca                                34

<210> SEQ ID NO 150
<211> LENGTH: 40
<212> TYPE: DNA
<213> ORGANISM: Artificial Sequence
<220> FEATURE:
<223> OTHER INFORMATION: Primer

<400> SEQUENCE: 150
```

```
actgcgtacg catatgtgtg gggctggtct atgaaggtgt                    40
```

<210> SEQ ID NO 151
<211> LENGTH: 35
<212> TYPE: DNA
<213> ORGANISM: Artificial Sequence
<220> FEATURE:
<223> OTHER INFORMATION: Primer

<400> SEQUENCE: 151

```
actggtcgac gggatatagc acaagaacag ctaag                        35
```

<210> SEQ ID NO 152
<211> LENGTH: 37
<212> TYPE: DNA
<213> ORGANISM: Artificial Sequence
<220> FEATURE:
<223> OTHER INFORMATION: Primer

<400> SEQUENCE: 152

```
actgggcgcg cccttagctg ttcttgtgct atatccc                      37
```

<210> SEQ ID NO 153
<211> LENGTH: 38
<212> TYPE: DNA
<213> ORGANISM: Artificial Sequence
<220> FEATURE:
<223> OTHER INFORMATION: Primer

<400> SEQUENCE: 153

```
actgcccggg ggtgtctgtg agattttgag aatagtcc                     38
```

<210> SEQ ID NO 154
<211> LENGTH: 865
<212> TYPE: DNA
<213> ORGANISM: Artificial Sequence
<220> FEATURE:
<223> OTHER INFORMATION: Synthetic Sequence

<400> SEQUENCE: 154

```
atgccgaatc tattaccatt actgccaagt cccattggga gaaaaactaa agtgtgcatt    60
cgtgcatgtg tgcgtgtacg tgtgtgtcta gaactgaaaa ttttatttcc ttgcaagtat   120
cagactagag ttttcctggc ctgctaggtc ctctgttgcc tctccccacc atgtcccaa    180
tttgactcct gacacagcac tggcacttgg cattttttcta gaattacaca ttttcctgac   240
ttttctcttg actaccgcca gaggaaattt ctcttaaagg ggctcctgtg gctgtgctca   300
atctagtcgg atgagtcagg gaaattccca cattaaagct aaactgatca gtggccttaa   360
tcccatctga aaagtcctcc tgccctgtcc tgtaataaat atatcatggt gaccggaaca   420
gctcatagta ttaagagtcc taggaattcg gttgggaacc ttggggagct attttttagaa  480
tcctaccctc cagtgtcttt caaaggaatc atttctactt cctcttggca gagacttgat   540
aagaaccaga aggggacttt gtttgcatcg acataagttc cggcaatgaa cactttttat   600
ctggtatttg gcataaaggc catccctcca cttcaaatgc tgagactgtt tactgtgccg   660
ctaagtggct gtacaagatc ctaaatgtag ctgtagtttc aacaaacatc tggattgttg   720
ggagtttcca gtagacttct cttttaaatg tcagcctcgc tattctgcat ctatcccgag   780
tttctcattt gcttctttaa aacacagttt tatttaagag tggatgtcct gtggaaatga   840
gatgtattcc ctccagttcc cagcc                                        865
```

<210> SEQ ID NO 155
<211> LENGTH: 948
<212> TYPE: DNA
<213> ORGANISM: Artificial Sequence
<220> FEATURE:
<223> OTHER INFORMATION: Synthetic Sequence

<400> SEQUENCE: 155

```
tgagtgtatg ctcgtgtatg tatgtgagca ctgcaggtgt ctgcatggtg tgccatggtg      60
ctccactggg cttcatgctg tgctcccta ggcttcagtc aagtcaagac taggtcaagt     120
catggagggt aaacagaaga gagagagagc agaaaatgag ggacacagga agggtagagg     180
gggaaagaga gggttgtgaa gctcacgcgt gatcaggagc cccaggcttt cttcttccag     240
ccgcccatag gctctggtgc ccacaacatt ggttacaacc ccgctctcca tcatcatgct     300
tgtcatcact gctgtgacaa accgcttaat aatggttctc acggaacatt aaaagccaag     360
ccaagtttaa cacctcgaac atttccaagt gttatgggga ataacagtta agtgtctggg     420
tgtgcttgtg tgtaattggg aatctgtagt ggtggggtta ccagtgtcag gccacagtgt     480
ttgtgatgag cagaggggtc ggggtctttc tcagatccct tatcttgtcc tgtcaatggt     540
ggtgatgtaa taggtgcacg cctgtgacag agctgtttaa agcattgtaa gaccaatgag     600
taaagttcct acccttgctt ctcctttaag tgaggcagaa aaaggctcca ccatgacgtg     660
gtgtaaagat gaagtcaatc taatacttcc ttggatactc tagcaagctt cattcacact     720
ttttatttct tcctcttcct cttcctcttc ctcttcctct tcctcttcct cttcccctcc     780
tcctcttcct cctcctcttc ctcctcctct tcctcctcct cctcttcctc cttctcctct     840
tcctcctccc cctcccttc ccctgtgctc ctcattatta ttattattgc tcctgtctag     900
gtggaaggac aatccagcca tgcctgtggg gctggtctat gaaggtgt                  948
```

<210> SEQ ID NO 156
<211> LENGTH: 700
<212> TYPE: DNA
<213> ORGANISM: Artificial Sequence
<220> FEATURE:
<223> OTHER INFORMATION: Synthetic Sequence

<400> SEQUENCE: 156

```
ggtaccaaag gccgcaatgg ccaaacctgc aggaagtacc agagctccct aggttctaga      60
accggtgacg tcaagctcga ataacttcgt ataatgtatg ctatacgaag ttatcctgca     120
ggtcgatcga gaccgtacgc tatgtgtggg gctggtctat gaaggtgttg ccacagagcc     180
tctgaagtac tctggaggaa gtgcagccca gagctccgtg cttcatgcct tcgatgagtt     240
cctgggcatt gagcattgca aggaaagtgg tgagcagcag tctgatctca cctatgcttt     300
gatgggacag cgaggtagac tagggagaca tctctagcaa ctgataaaga cgggtgtaaa     360
tgaaaatgtc ctgaagttta tccttgccta agccagcagg cagctgtgtg catgtgccct     420
ctcttacact gagttagtca gtattggggc atcggatctt attagggtct tccaacagtc     480
ctgtgacctg ggttgttcac tgtcctgttg gctggggtct tttatccgca gattcccctt     540
tctacaatga ggtgataatg tcacattgaa aggccagtct ggagcagcaa gtgatagtgc     600
tgaacttctc tgctaaagcc tttcccatga aatggcccag cctcccactg aatctatgtg     660
gaccaggcga gggagcccat cgctttgaag cctttaaaat                           700
```

<210> SEQ ID NO 157
<211> LENGTH: 803
<212> TYPE: DNA
<213> ORGANISM: Artificial Sequence

```
<220> FEATURE:
<223> OTHER INFORMATION: Synthetic Sequence
<220> FEATURE:
<221> NAME/KEY: misc_feature
<222> LOCATION: (744)...(744)
<223> OTHER INFORMATION: n = a, c, t, g

<400> SEQUENCE: 157
cagaaatgaa catttgagca tttggcagct ataacaaaag cccgacaagg ctgagggaga      60
gccctatcaa gcatttctgg tacctgagtg tttggaacag tgggcaaacc ctcccaaatg     120
tctgcctcga gctaacgtat ttctcccggc tgtttctttc agttggcttt ctacacagaa     180
tgagggacta catgccgcct tcccataagg ctttcctgga agatctccac gtagctcctt     240
ctctgagaga ctacatactg gcctctggtc ctggggactg cctgatggcc tataaccagt     300
gtgtggaggc cctgggagag ctgcgcagtt accacatcaa tgtcgtggcc agatacatta     360
tctccgctgc caccagggcc aggagcaggg ggctaactaa tccctcaccc catgccttgg     420
aagacagggg cactgggggt actgccatgc tgagcttctt gaagagtgtc agggagaaga     480
ccatggaggc cctcctgtgt cctggtgctt agcagtcatg tcctgcaccc taacacttag     540
atgttctcat cctgcatccc agcgttagag gttcacatcc tgcatcctag tgcttagctg     600
ttcttgtgct atatcccgtc gacgaagttc ctatactttc tagagaatag gaacttcgga     660
tccacgattc gagggcccct gcaggtcaat tctaccgggt aggggaggcg cttttcccaa     720
ggcagtctgg agcatgcgct ttancagccc cgctgggcac ttgcgctac acaagtggcc      780 tctggcctcg cacacattcc aca                                            803

<210> SEQ ID NO 158
<211> LENGTH: 575
<212> TYPE: DNA
<213> ORGANISM: Artificial Sequence
<220> FEATURE:
<223> OTHER INFORMATION: Synthetic Sequence

<400> SEQUENCE: 158
atcccagcgc ttagcagtca gtcctgcat cctagtgctt agcattttat atccagcatc       60
ttagtgctta gagattcaca tcctgcatcc tagagcttag cattttatat ccagcatcct     120
tgtgcgtatc agctatgttt tgtatcctgc ttagcagtta acatcctgca tcctagtact     180
tatctgttct catcctgcat cctagagctt agcagtcagg tcccgtggga gcaagaacca     240
gggtctgagc tctgtctgag cccaagcatg gctttactgc tttgttaatt gtggctccca     300
cctccacccc accccagcca gtttgcttgc tagaagcctt tctgcactgc ctaatccccc     360
tgcctcacag cagagagctg cagccatgac ctcctcattc agtattaggt ggacaagtcg     420 gagatacccca aactcaattt taaaagaatc aagttgcttt tggggcatgt tacttcatct    480
tttcttaccc tgggcctcta tgacctcctc attcagtatt aggtggacaa gtcggagata    540
cccaaactca attttaaaag aatcaagttg ctttt                               575

<210> SEQ ID NO 159
<211> LENGTH: 753
<212> TYPE: DNA
<213> ORGANISM: Artificial Sequence
<220> FEATURE:
<223> OTHER INFORMATION: Synthetic Sequence

<400> SEQUENCE: 159
agctctaaga gaaggaatac agcttgggac agagtttgtt ttgaagtggg gttcaggtgc       60
atttcctggg tgtgtccctc atttgggggt gttaggaggc agacaatgct aagggcatgg     120
```

```
tttgatatgg tagactgacc atcctggggt cccttcagct tgtgacactc gctgtactgc      180
tggactctgc tgagcccttt gaagccagga ctcctcctct gctgcaggag tgcagtgtcc      240
ttcttgctgt atgaagctgg gacaatgctc tttggccttc atactggaca tcccattgag      300
aagcttgtca ctctgtagag aatagacatc gccccttgt ggttgtgagg ctgcccagga      360
cttactgcgg ggggggggg ggcatgttgt ccagcataag gagagaagac cccactgcat      420
gctgctggga aaggaaagt aacgttcaga gtagtttcta ctggctgcct gcgctctcac      480
gcctgtaaga acaaacgtcc taatgtctgc atgtggagga aggagccagg ggtgcttagg      540
gtgctgttgg tcccaccaat gtactactca tctggaagac cttgtcttgg ttttcttgcc      600
actgggacaa agtgggattg ggtatcagtc tccccatgtc gggcaaatgt acttgaacaa      660
gcagcatggt ggaccagaca tgggactatt ctcaaaatct cacagacacc cccgggggc      720 atgttacttc atcttttctt accctgggcc tct                                  753
```

<210> SEQ ID NO 160
<211> LENGTH: 453
<212> TYPE: DNA
<213> ORGANISM: Artificial Sequence
<220> FEATURE:
<223> OTHER INFORMATION: Synthetic Sequence

<400> SEQUENCE: 160

```
ctagggagtc aggaagtcac actggtgaag agtgggggtg tgggatgacc acactgagga      60
gtcacacttg aggaagggg gtggccacac tgaggagtgt ctgaaagcat tgagactgta      120
catctcaggt tatcagggct tcagagaaaa cagacaggga gaagagacaa gaactggatt      180
ctgtgcgcaa agggggaaaa gcaagcagat gtgaaggtg tgctgttaga gtttatctaa      240
agatgtttct ttcagaaata aagagatata agctttaatt tggatgaaat aaatgtggtc      300
taatttccca gaatgtagag gaactcacta atgtagcaag attggccttt caaagcagac      360
caaagacatt gagaattaag atagctatga tggcgtgctt ccttaggtgg aagtcctata      420
tggaatccca tactccccaa atgtgactgg tcg                                  453
```

<210> SEQ ID NO 161
<211> LENGTH: 361
<212> TYPE: DNA
<213> ORGANISM: Artificial Sequence
<220> FEATURE:
<223> OTHER INFORMATION: Synthetic Sequence

<400> SEQUENCE: 161

```
aggcaggagg gtcaggagtt caaggccagc ctagtataca tgcaacagtg tctcaaaaat      60
caaaacagag aggagggcag gaaaggagaa gggagccagg gagagaaggg aagaggaagg      120
gagggagggg gaaatggagg gaggggagga tggagggagg gggagatgga gggaggggga      180
gatggaggga ggggagatg gagggagggg gagatggagg gaggggatg ggaaagaggg      240 tttacagccc tggtttatct tgaacagaat ccttactttg tccctcagag tgacaggact      300
gaaaagattg tcccaggatt ttggctgcaa agcaaggtcc actcagagac cacagagctc      360
g                                                                      361
```

<210> SEQ ID NO 162
<211> LENGTH: 10543
<212> TYPE: DNA
<213> ORGANISM: Artificial Sequence
<220> FEATURE:
<223> OTHER INFORMATION: Synthetic Sequence

<400> SEQUENCE: 162

```
aagctttact cgtaaagcga gttgaaggat catatttagt tgcgtttatg agataagatt    60
gaaagcacgt gtaaaatgtt tcccgcgcgt tggcacaact atttacaatg cggccaagtt   120
ataaaagatt ctaatctgat atgttttaaa acacctttgc ggcccgagtt gtttgcgtac   180
gtgactagcg aagaagatgt gtggaccgca gaacagatag taaaacaaaa ccctagtatt   240
ggagcaataa tcgatttaac caacacgtct aaatattatg atggtgtgca ttttttgcgg   300
gcgggcctgt tatacaaaaa aattcaagta cctggccaga cttttgccgcc tgaaagcata   360
gttcaagaat ttattgacac ggtaaaagaa tttacagaaa agtgtcccgg catgttggtg   420
ggcgtgcact gcacacacgg tattaatcgc accggttaca tggtgtgcag atatttaatg   480
cacaccctgg gtattgcgcc gcaggaagcc atagatagat tcgaaaaagc cagaggtcac   540
aaaattgaaa gacaaaatta cgttcaagat ttattaattt aattaatatt atttgcattc   600
tttaacaaat actttatcct atttttcaaa tgttgcgctt cttccagcga accaaaacta   660
tgcttcgctt gctccgttta gcttgtagcc gatcagtggc gttgttccaa tcgacggtag   720
gattaggccg gatattctcc accacaatgt tggcaacgtt gatgttacgt ttatgctttt   780
ggttttccac gtacgtcttt tggccggtaa tagccgtaaa cgtagtgccg tcgcgcgtca   840
cgcacaacac cggatgtttg cgcttgtccg cggggtattg aaccgcgcga tccgacaaat   900
ccaccacttt ggcaactaaa tcggtgacct gcgcgtcttt tttctgcatt atttcgtctt   960
tcttttgcat ggtttcctgg aagccggtgt acatgcggtt tagatcagtc atgacgcgcg  1020
tgacctgcaa atctttggcc tcgatctgct tgtccttgat ggcaacgatg cgttcaataa  1080
actcttgttt tttaacaagt tcctcggttt tttgcgccac caccgcttgc agcgcgtttg  1140
tgtgctcggt gaatgtcgca atcagcttag tcaccaactg tttgctctcc tcctcccgtt  1200
gtttgatcgc gggatcgtac ttgccggtgc agagcacttg aggaattact tcttctaaaa  1260
gccattcttg taattctatg gcgtaaggca atttggactt cataatcagc tgaatcacgc  1320
cggatttagt aatgagcact gtatgcggct gcaaatacag cgggtcgccc cttttcacga  1380
cgctgttaga ggtagggccc ccattttgga tggtctgctc aaataacgat ttgtatttat  1440
tgtctacatg aacacgtata gctttatcac aaactgtata ttttaaactg ttagcgacgt  1500
ccttggccac gaaccggacc tgttggtcgc gctctagcac gtaccgcagg ttgaacgtat  1560
cttctccaaa tttaaattct ccaattttaa cgcgagccat tttgatacac gtgtgtcgat  1620
tttgcaacaa ctattgtttt ttaacgcaaa ctaaacttat tgtggtaagc aataattaaa  1680
tatgggggaa catgcgccgc tacaacactc gtcgttatga acgcagacgg cgccggtctc  1740
ggcgcaagcg gctaaaacgt gttgcgcgtt caacgcggca aacatcgcaa aagccaatag  1800
tacagttttg atttgcatat taacggcgat ttttaaatt atcttattta ataaatagtt  1860
atgacgccta caactccccg cccgcgttga ctcgctgcac ctcgagcagt tcgttgacgc  1920
cttcctccgt gtggccgaac acgtcgagcg ggtggtcgat gaccagcggc gtgccgcacg  1980
cgacgcacaa gtatctgtac accgaatgat cgtcgggcga aggcacgtcg gcctccaagt  2040
ggcaatattg gcaaattcga aaatatatac agttgggttg tttgcgcata tctatcgtgg  2100
cgttgggcat gtacgtccga acgttgattt gcatgcaagc cgaaattaaa tcattgcgat  2160
tagtgcgatt aaaacgttgt acatcctcgc ttttaatcat gccgtcgatt aaatcgcgca  2220
atcgagtcaa gtgatcaaag tgtggaataa tgttttcttt gtattcccga gtcaagcgca  2280
gcgcgtattt taacaaacta gccatcttgt aagttagttt catttaatgc aactttatcc  2340
```

```
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gttttttacga agcgatgaca   2520 tgaccccccgt agtgacaacg atcacgccca aaagaactgc cgactacaaa attaccgagt   2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta     3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatcttta    3180 atcaaatccc aagatgtgta taaaccacca aactgccaaa aaatgaaaac tgtcgacaag   3240
ctctgtccgt ttgctggcaa ctgcaagggt ctcaatccta tttgtaatta ttgaataata    3300
aaacaattat aaatgctaaa tttgttttt attaacgata caaaccaaac gcaacaagaa     3360
catttgtagt attatctata attgaaaacg cgtagttata atcgctgagg taatatttaa    3420
aatcattttc aaatgattca cagttaattt gcgacaatat aatttatttt tcacataaac    3480
tagacgcctt gtcgtcttct tcttcgtatt ccttctcttt ttcattttttc tcctcataaa   3540 aattaacata gttattatcg tatccatata tgtatctatc gtatagagta aattttttgt    3600
tgtcataaat atatatgtct tttttaatgg ggtgtatagt accgctgcgc atagtttttc    3660
tgtaatttac aacagtgcta ttttctggta gttcttcgga gtgtgttgct ttaattatta   3720
aatttatata atcaatgaat ttgggatcgt cggttttgta caatatgttg ccggcatagt    3780
acgcagcttc ttctagttca attacaccat tttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atcagatctg   4140
cagcggccgc tccagaattc tagaaggtac catggagcct caaagtcaga gcatgacgct   4200
ggaggtgccg ttgtccttgg ggagatacca catttctgag gaatatggct ttctccttcc   4260
aaatcctctg gaagcacttc cagatcatta caagccttgg atggaaattg ccctcagact   4320
tcctcactta atcgagaacc gccagctccg agctcacgtg tacaggatgc ctctcctgga   4380
ctgcagattc ctaaagagtt accgtgagca gcgcctggca cacatggcgc tggccgctat   4440
caccatggga ttcgtctggc aggagggga aggccaaccc caaaaggtgc tgccaagatc    4500
tcttgccatt cctttttgttg aggtatccag gaacttggga ctcccgccta tcctggtcca  4560
ctctgacctg gtgctgacaa actggaccaa aaggaaccca aaggaccgt tggaaatcag    4620 taacctggaa accatcatct catttccggg gggagagagc ctgcggggct tcatcctagt    4680
gacagtcttg gtggagaagg cagcagtgcc cggccttaag gccctggttc agggaatgga   4740
```

```
ggccattcgg caacacagtc aggacaccct gctagaagcc ctgcagcagc tgagactctc    4800
catccaggat atcaccagag ccttggccca aatgcatgat tatgtggacc cagacatatt    4860
ttactcggtc atccggatct tcctctctgg gtggaaggac aatccagcca tgcctgtggg    4920
gctggtctat gaaggtgctg ccacagagcc tctgaagtac tctggaggaa gtgcagccca    4980
gagctccgtg cttcatgcct tcgatgagtt cctgggcatt gagcattgca aggaaagtgt    5040 tggcttteta cacagaatga gggactacat gccgccttcc cataaggctt tcctggaaga    5100
tctccacgta gctccttctc tgagagacta catactggcc tctggtcctg ggactgcct    5160 gatggcctat aaccagtgtg tggaggccct gggagagctg cgcagttacc acatcaatgt    5220
cgtggccaga tacattatct ccgctgccac cagggccagg agcagggggc taactaatcc    5280
ctcaccccat gccttggaag acaggggcac tgggggtact gccatgctga gcttcttgaa    5340
gagtgtcagg gagaagacca tggaggccct cctgtgtcct ggtgcttagg gtcaagacaa    5400
ttctgcagat atccagcaca gtggcggccg ctcgagtcta gagggcccgc ggttcgaagg    5460
taagcctatc cctaaccctc tcctcggtct cgattctacg cgtaccggtc atcatcacca    5520
tcaccattga gtttgctagc cactagtacc gactctgctg aagaggagga aattctcctt    5580
gaagtttccc tggtgttcaa agtaaaggag tttgcaccag acgcacctct gttcactggt    5640
ccggcgtatt aaaacacgat acattgttat tagtacattt attaagcgct agattctgtg    5700
cgttgttgat ttacagacaa ttgttgtacg tattttaata attcattaaa tttataatct    5760
ttagggtggt atgttagagc gaaaatcaaa tgattttcag cgtctttata tctgaattta    5820
aatattaaat cctcaataga tttgtaaaat aggtttcgat tagtttcaaa caagggttgt    5880
ttttccgaac cgatggctgg actatctaat ggattttcgc tcaacgccac aaaacttgcc    5940
aaatcttgta gcagcaatct agctttgtcg atattcgttt gtgttttgtt ttgtaataaa    6000
ggttcgacgt cgttcaaaat attatgcgct tttgtatttc tttcatcact gtcgttagtg    6060
tacaattgac tcgacgtaaa cacgttaaat aaagcttgga catatttaac atcgggcgtg    6120
ttagctttat taggccgatt atcgtcgtcg tcccaaccct cgtcgttaga agttgcttcc    6180
gaagacgatt ttgccatagc cacacgacgc ctattaattg tgtcggctaa cacgtccgcg    6240
atcaaatttg tagttgagct ttttggaatt atttctgatt gcgggcgttt ttgggcgggt    6300
ttcaatctaa ctgtgcccga ttttaattca gacaacacgt tagaaagcga tggtgcaggc    6360
ggtggtaaca tttcagacgg caaatctact aatggcggcg gtggtggagc tgatgataaa    6420
tctaccatcg gtggaggcgc aggcggggct ggcggcggag cggaggcgg aggtggtggc    6480 ggtgatgcag acggcggttt aggctcaaat gtctctttag caacacagt cggcacctca    6540 actattgtac tggtttcggg cgccgttttt ggtttgaccg gtctgagacg agtgcgattt    6600
ttttcgtttc taatagcttc caacaattgt tgtctgtcgt ctaaaggtgc agcgggttga    6660
ggttccgtcg gcattggtgg agcgggcggc aattcagaca tcgatggtgg tggtggtggt    6720
ggaggcgctg gaatgttagg cacgggagaa ggtggtggcg gcggtgccgc cggtataatt    6780
tgttctggtt tagtttgttc gcgcacgatt gtgggcaccg gcgcaggcgc cgctggctgc    6840
acaacggaag gtcgtctgct tcgaggcagc gcttggggtg gtggcaattc aatattataa    6900
ttggaataca aatcgtaaaa atctgctata agcattgtaa tttcgctatc gtttaccgtg    6960
ccgatattta caaccgctc aatgtaagca attgtattgt aaagagattg tctcaagctc    7020
gccgcacgcc gataacaagc cttttcattt ttactacagc attgtagtgg cgagacactt    7080
cgctgtcgtc gacgtacatg tatgctttgt tgtcaaaaac gtcgttggca agctttaaaa    7140
```

```
tatttaaaag aacatctctg ttcagcacca ctgtgttgtc gtaaatgttg tttttgataa    7200
tttgcgcttc cgcagtatcg acacgttcaa aaaattgatg cgcatcaatt ttgttgttcc    7260
tattattgaa taaataagat tgtacagatt catatctacg attcgtcatg gccaccacaa    7320
atgctacgct gcaaacgctg gtacaatttt acgaaaactg caaaaacgtc aaaactcggt    7380
ataaaataat caacgggcgc tttggcaaaa tatctatttt atcgcacaag cccactagca    7440
aattgtattt gcagaaaaca atttcggcgc acaattttaa cgctgacgaa ataaaagttc    7500
accagttaat gagcgaccac ccaaatttta taaaaatcta ttttaatcac ggttccatca    7560
acaaccaagt gatcgtgatg gactacattg actgtcccga tttatttgaa acactacaaa    7620
ttaaaggcga gctttcgtac caacttgtta gcaatattat tagacagctg tgtgaagcgc    7680
tcaacgattt gcacaagcac aatttcatac acaacgacat aaaactcgaa aatgtcttat    7740
atttcgaagc acttgatcgc gtgtatgttt gcgattacgg attgtgcaaa cacgaaaact    7800
cacttagcgt gcacgacggc acgttggagt attttagtcc ggaaaaaatt cgacacacaa    7860
ctatgcacgt ttcgtttgac tggtacgcgg cgtgttaaca tacaagttgc taacgtaatc    7920
atggtcatag ctgttttcctg tgtgaaattg ttatccgctc acaattccac acaacatacg    7980
agccggaagc ataaagtgta aagcctgggg tgcctaatga gtgagctaac tcacattaat    8040
tgcgttgcgc tcactgcccg ctttccagtc gggaaacctg tcgtgccagc tgcattaatg    8100
aatcggccaa cgcgcgggga gaggcggttt gcgtattggg cgctcttccg cttcctcgct    8160
cactgactcg ctgcgctcgg tcgttcggct gcggcgagcg gtatcagctc actcaaaggc    8220
ggtaatacgg ttatccacag aatcagggga taacgcagga agaacatgt gagcaaaagg    8280 ccagcaaaag gccaggaacc gtaaaaaggc cgcgttgctg gcgtttttcc ataggctccg    8340
cccccctgac gagcatcaca aaaatcgacg ctcaagtcag aggtggcgaa acccgacagg    8400
actataaaga taccaggcgt ttccccctgg aagctccctc gtgcgctctc ctgttccgac    8460
cctgccgctt accggatacc tgtccgcctt tctcccttcg ggaagcgtgg cgctttctca    8520
tagctcacgc tgtaggtatc tcagttcggt gtaggtcgtt cgctccaagc tgggctgtgt    8580
gcacgaaccc cccgttcagc ccgaccgctg cgccttatcc ggtaactatc gtcttgagtc    8640
caacccggta agacacgact tatcgccact ggcagcagcc actggtaaca ggattagcag    8700
agcgaggtat gtaggcggtg ctacagagtt cttgaagtgg tggcctaact acggctacac    8760
tagaaggaca gtatttggta tctgcgctct gctgaagcca gttaccttcg gaaaaagagt    8820
tggtagctct tgatccggca aacaaaccac cgctggtagc ggtggttttt ttgtttgcaa    8880
gcagcagatt acgcgcagaa aaaaaggatc tcaagaagat cctttgatct ttttctacggg    8940 gtctgacgct cagtggaacg aaaactcacg ttaagggatt ttggtcatga gattatcaaa    9000
aaggatcttc acctagatcc ttttaaatta aaaatgaagt tttaaatcaa tctaaagtat    9060
atatgagtaa acttggtctg acagttacca atgcttaatc agtgaggcac ctatctcagc    9120
gatctgtcta tttcgttcat ccatagttgc ctgactcccc gtcgtgtaga taactacgat    9180
acgggagggc ttaccatctg gccccagtgc tgcaatgata ccgcgagacc cacgctcacc    9240
ggctccagat ttatcagcaa taaaccagcc agccggaagg gccgagcgca gaagtggtcc    9300
tgcaacttta tccgcctcca tccagtctat taattgttgc cgggaagcta gagtaagtag    9360
ttcgccagtt aatagtttgc gcaacgttgt tgccattgct acaggcatcg tggtgtcacg    9420
ctcgtcgttt ggtatggctt cattcagctc cggttcccaa cgatcaaggc gagttacatg    9480
atcccccatg ttgtgcaaaa aagcggttag ctccttcggt cctccgatcg ttgtcagaag    9540
```

```
taagttggcc gcagtgttat cactcatggt tatggcagca ctgcataatt ctcttactgt    9600
catgccatcc gtaagatgct tttctgtgac tggtgagtac tcaaccaagt cattctgaga    9660
atagtgtatg cggcgaccga gttgctcttg cccggcgtca atcgggata ataccgcgcc    9720 acatagcaga actttaaaag tgctcatcat tggaaaacgt tcttcggggc gaaaactctc    9780
aaggatctta ccgctgttga gatccagttc gatgtaaccc actcgtgcac ccaactgatc    9840
ttcagcatct tttactttca ccagcgtttc tgggtgagca aaaacaggaa ggcaaaatgc    9900
cgcaaaaaag gaataaggg cgacacggaa atgttgaata ctcatactct tcctttttca    9960
atattattga agcatttatc agggttattg tctcatgagc ggatacatat ttgaatgtat   10020
ttagaaaaat aaacaaatag gggttccgcg cacatttccc cgaaaagtgc cacctgacgt   10080
ctaagaaacc attattatca tgacattaac ctataaaaat aggcgtatca cgaggccctt   10140
tcgtctcgcg cgtttcggtg atgacggtga aacctctga cacatgcagc tcccggagac   10200
ggtcacagct tgtctgtaag cggatgccgg gagcagacaa gcccgtcagg gcgcgtcagc   10260
gggtgttggc gggtgtcggg gctggcttaa ctatgcggca tcagagcaga ttgtactgag   10320
agtgcaccat atgcggtgtg aaataccgca cagatgcgta aggagaaaat accgcatcag   10380
gcgccattcg ccattcaggc tgcgcaactg ttgggaaggg cgatcggtgc gggcctcttc   10440
gctattacgc cagctggcga aagggggatg tgctgcaagg cgattaagtt gggtaacgcc   10500
agggttttcc cagtcacgac gttgtaaaac gacggccagt gcc                     10543

<210> SEQ ID NO 163
<211> LENGTH: 10511
<212> TYPE: DNA
<213> ORGANISM: Artificial Sequence
<220> FEATURE:
<223> OTHER INFORMATION: Synthetic Sequence

<400> SEQUENCE: 163
aagctttact cgtaaagcga gttgaaggat catatttagt tgcgtttatg agataagatt      60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca tttttttgcgg    300 gcgggcctgt tatacaaaaa aattcaagta cctggccaga cttttgccgcc tgaaagcata    360 gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840 cgcacaaacac cggatgtttg cgcttgtccg cggggtattg aaccgcgcga tccgacaaat    900
ccaccacttt ggcaactaaa tcggtgacct gcgcgtcttt ttctgcattt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
```

```
actcttgttt tttaacaagt tcctcggttt tttgcgccac caccgcttgc agcgcgtttg    1140
tgtgctcggt gaatgtcgca atcagcttag tcaccaactg tttgctctcc tcctcccgtt    1200
gtttgatcgc gggatcgtac ttgccggtgc agagcacttg aggaattact tcttctaaaa    1260
gccattcttg taattctatg gcgtaaggca atttggactt cataatcagc tgaatcacgc    1320
cggatttagt aatgagcact gtatgcggct gcaaatacag cgggtcgccc cttttcacga    1380
cgctgttaga ggtagggccc ccattttgga tggtctgctc aaataacgat ttgtatttat    1440
tgtctacatg aacacgtata gctttatcac aaactgtata ttttaaactg ttagcgacgt    1500
ccttggccac gaaccggacc tgttggtcgc gctctagcac gtaccgcagg ttgaacgtat    1560
cttctccaaa tttaaattct ccaatttaaa cgcgagccat tttgatacac gtgtgtcgat    1620
tttgcaacaa ctattgtttt ttaacgcaaa ctaaacttat tgtggtaagc aataattaaa    1680
tatgggggaa catgcgccgc tacaacactc gtcgttatga acgcagacgg cgccggtctc    1740
ggcgcaagcg gctaaaacgt gttgcgcgtt caacgcggca acatcgcaa aagccaatag     1800 tacagttttg atttgcatat taacggcgat tttttaaatt atcttattta ataaatagtt    1860
atgacgccta caactccccg cccgcgttga ctcgctgcac ctcgagcagt tcgttgacgc    1920
cttcctccgt gtggccgaac acgtcgagcg ggtggtcgat gaccagcggc gtgccgcacg    1980
cgacgcacaa gtatctgtac accgaatgat cgtcgggcga aggcacgtcg gcctccaagt    2040
ggcaatattg gcaaattcga aaatatatac agttgggttg tttgcgcata tctatcgtgg    2100
cgttgggcat gtacgtccga acgttgattt gcatgcaagc cgaaattaaa tcattgcgat    2160
tagtgcgatt aaaacgttgt acatcctcgc ttttaatcat gccgtcgatt aaatcgcgca    2220
atcgagtcaa gtgatcaaag tgtggaataa tgttttcttt gtattcccga gtcaagcgca    2280
gcgcgtattt taacaaacta gccatcttgt aagttagttt catttaatgc aactttatcc    2340
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gttttttacga agcgatgaca   2520 tgaccccccgt agtgacaacg atcacgccca aaagaactgc cgactacaaa attaccgagt    2580
atgtcggtga cgttaaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aaatgaaaac tgtcgacaag    3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aatttatttt tcacataaac    3480
```

```
tagacgcctt gtcgtcttct tcttcgtatt ccttctcttt ttcattttc tcctcataaa    3540
aattaacata gttattatcg tatccatata tgtatctatc gtatagagta aatttttgt    3600
tgtcataaat atatatgtct tttttaatgg ggtgtatagt accgctgcgc atagttttc    3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tccctttct atactattgt    3900
ctgcgagcag ttgtttgttg ttaaaaataa cagccattgt aatgagacgc acaaactaat   3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atcagatctg   4140
cagcggccgc tccagaattc tagaaggtac ccatggagcc ccacgaccg aatgtgaaga    4200
cagcagtgcc attgtctttg gaaagctatc acatatctga agagtatggc tttcttcttc   4260
cagattctct gaaagaactt ccagatcatt ataggccttg gatggaaatt gccaacaaac   4320
ttcctcaatt gattgatgct caccagcttc aagctcatgt ggacaagatg cccctgctga   4380
gctgccagtt cctgaagggt caccgggagc agcgcctggc ccacctggtc ctgagcttcc   4440
tcaccatggg ttatgtctgg caggaaggag aggcgcagcc tgcagaggtc ctgccaagga   4500
atcttgccct tccatttgtc gaagtctcca ggaactgggg gctccctcct atcctggtcc   4560
actcagactt ggtgctgacg aactggacca aaaaagatcc agacgggttc ctggaaattg   4620
ggaacctgga gaccatcatc tcatttcctg ggggagagag cctgcatggt tttatactgg   4680
tgactgcttt ggtagagaaa gaagcagtgc ctgggataaa ggctcttgtt caggccacga   4740
atgctatctt gcagcccaac caggaggccc tgctccaagc cctgcagcga ctgagactgt   4800
ctattcagga catcaccaaa accttaggac agatgcatga ttatgtagat ccagacatat   4860
tttatgcagg catccggatc tttctctctg ggtggaaaga caacccagca atgcctgcag   4920
ggctgatgta tgaaggagtt cccaagagc ccctgaaata ctccggcggg agtgcagctc    4980
agagcacagt gcttcatgcc tttgatgagt tcttaggcat tcgtcatagc aaggaaagtg   5040
gtgactttct gtacagaatg agggattaca tgcctccttc ccataaggcc ttcatagaag   5100
acatccactc agcaccttcc ctgagggact acatcctgtc atctggacag gaccacttgc   5160
tgacagctta taaccagtgt gtgcaggccc tggcagagct gcggagctat cacatcacca   5220
tggtcaccaa atacctcatc acagctgcag ccaaggcaaa gcatgggaag ccaaaccatc   5280
tcccagggcc tcctcaggct ttaaaagaca ggggcacagg tggaaccgca gttatgagct   5340
ttcttaagag tgtcagggat aagaccttgg agtcaatcct tcacccacgt ggttaacgct   5400
cgagtctaga gggcccgcgg ttcgaaggta agcctatccc taaccctctc ctcggtctcg   5460
attctacgcg taccggtcat catcaccatc accattgagt ttgctagcca ctagtaccga   5520
ctctgctgaa gaggaggaaa ttctccttga agtttccctg gtgttcaaag taaaggagtt   5580
tgcaccagac gcacctctgt tcactggtcc ggcgtattaa aacacgatac attgttatta   5640
gtacatttat taagcgctag attctgtgcg ttgttgattt acagacaatt gttgtacgta   5700
ttttaataat tcattaaatt tataatcttt agggtggtat gttagagcga aaatcaaatg   5760
attttcagcg tctttatatc tgaatttaaa tattaaatcc tcaatagatt tgtaaaatag   5820
gtttcgatta gtttcaaaca agggttgttt ttccgaaccg atggctggac tatctaatgg   5880
```

```
attttcgctc aacgccacaa aacttgccaa atcttgtagc agcaatctag ctttgtcgat    5940
attcgtttgt gttttgtttt gtaataaagg ttcgacgtcg ttcaaaatat tatgcgcttt    6000
tgtatttctt tcatcactgt cgttagtgta caattgactc gacgtaaaca cgttaaataa    6060
agcttggaca tatttaacat cgggcgtgtt agctttatta ggccgattat cgtcgtcgtc    6120
ccaaccctcg tcgttagaag ttgcttccga agacgatttt gccatagcca cacgacgcct    6180
attaattgtg tcggctaaca cgtccgcgat caaatttgta gttgagcttt ttggaattat    6240
ttctgattgc gggcgttttt gggcgggttt caatctaact gtgcccgatt ttaattcaga    6300
caacacgtta gaaagcgatg gtgcaggcgg tggtaacatt tcagacggca aatctactaa    6360
tggcggcggt ggtggagctg atgataaatc taccatcggt ggaggcgcag gcggggctgg    6420
cggcggaggc ggaggcggag gtggtggcgg tgatgcagac ggcggtttag gctcaaatgt    6480
ctctttaggc aacacagtcg gcacctcaac tattgtactg gtttcgggcg ccgttttttgg   6540 tttgaccggt ctgagacgag tgcgattttt ttcgtttcta atagcttcca acaattgttg    6600
tctgtcgtct aaaggtgcag cgggttgagg ttccgtcggc attggtggag cgggcggcaa    6660
ttcagacatc gatggtggtg gtggtggtgg aggcgctgga atgttaggca cgggagaagg    6720
tggtggcggc ggtgccgccg gtataatttg ttctggttta gtttgttcgc gcacgattgt    6780
gggcaccggc gcaggcgccg ctggctgcac aacggaaggt cgtctgcttc gaggcagcgc    6840
ttggggtggt ggcaattcaa tattataatt ggaatacaaa tcgtaaaaat ctgctataag    6900
cattgtaatt tcgctatcgt ttaccgtgcc gatatttaac aaccgctcaa tgtaagcaat    6960
tgtattgtaa agagattgtc tcaagctcgc cgcacgccga taacaagcct tttcattttt    7020
actacagcat tgtagtggcg agacacttcg ctgtcgtcga cgtacatgta tgctttgttg    7080
tcaaaaacgt cgttggcaag ctttaaaata tttaaaagaa catctctgtt cagcaccact    7140
gtgttgtcgt aaatgttgtt tttgataatt tgcgcttccg cagtatcgac acgttcaaaa    7200
aattgatgcg catcaatttt gttgttccta ttattgaata aataagattg tacagattca    7260
tatctacgat tcgtcatggc caccacaaat gctacgctgc aaacgctggt acaattttac    7320
gaaaactgca aaaacgtcaa aactcggtat aaaataatca acgggcgctt tggcaaaata    7380
tctattttat cgcacaagcc cactagcaaa ttgtatttgc agaaaacaat ttcggcgcac    7440
aattttaacg ctgacgaaat aaaagttcac cagttaatga gcgaccaccc aaattttata    7500
aaaatctatt ttaatcacgg ttccatcaac aaccaagtga tcgtgatgga ctacattgac    7560
tgtcccgatt tatttgaaac actacaaatt aaaggcgagc tttcgtacca acttgttagc    7620
aatattatta gacagctgtg tgaagcgctc aacgatttgc acaagcacaa tttcatacac    7680
aacgacataa aactcgaaaa tgtcttatat ttcgaagcac ttgatcgcgt gtatgtttgc    7740
gattacggat tgtgcaaaca cgaaaactca cttagcgtgc acgacggcac gttggagtat    7800
tttagtccgg aaaaaattcg acacacaact atgcacgttt cgtttgactg gtacgcggcg    7860
tgttaacata caagttgcta acgtaatcat ggtcatagct gtttcctgtg tgaaattgtt    7920
atccgctcac aattccacac aacatacgag ccggaagcat aaagtgtaaa gcctggggtg    7980
cctaatgagt gagctaactc acattaattg cgttgcgctc actgcccgct ttccagtcgg    8040
gaaacctgtc gtgccagctg cattaatgaa tcggccaacg cgcggggaga ggcggtttgc    8100
gtattgggcg ctcttccgct tcctcgctca ctgactcgct gcgctcggtc gttcggctgc    8160
ggcgagcggt atcagctcac tcaaaggcgg taatacggtt atccacagaa tcaggggata    8220
acgcaggaaa gaacatgtga gcaaaaggcc agcaaaaggc caggaaccgt aaaaaggccg    8280
```

-continued

```
cgttgctggc gttttccat aggctccgcc ccctgacga gcatcacaaa aatcgacgct    8340
caagtcagag gtggcgaaac ccgacaggac tataaagata ccaggcgttt ccccctggaa    8400
gctccctcgt gcgctctcct gttccgaccc tgccgcttac cggatacctg tccgcctttc    8460
tcccttcggg aagcgtggcg ctttctcata gctcacgctg taggtatctc agttcggtgt    8520
aggtcgttcg ctccaagctg gctgtgtgc acgaaccccc cgttcagccc gaccgctgcg    8580
ccttatccgg taactatcgt cttgagtcca acccggtaag acacgactta tcgccactgg    8640
cagcagccac tggtaacagg attagcagag cgaggtatgt aggcggtgct acagagttct    8700
tgaagtggtg gcctaactac ggctacacta aaggacagt atttggtatc tgcgctctgc    8760
tgaagccagt taccttcgga aaagagttg gtagctcttg atccggcaaa caaaccaccg    8820
ctggtagcgg tggtttttt gtttgcaagc agcagattac gcgcagaaaa aaaggatctc    8880
aagaagatcc tttgatcttt tctacggggt ctgacgctca gtggaacgaa aactcacgtt    8940
aagggatttt ggtcatgaga ttatcaaaaa ggatcttcac ctagatcctt ttaaattaaa    9000
aatgaagttt taaatcaatc taaagtatat atgagtaaac ttggtctgac agttaccaat    9060
gcttaatcag tgaggcacct atctcagcga tctgtctatt tcgttcatcc atagttgcct    9120
gactccccgt cgtgtagata actacgatac gggagggctt accatctggc cccagtgctg    9180
caatgatacc gcgagaccca cgctcaccgg ctccagattt atcagcaata aaccagccag    9240
ccggaagggc cgagcgcaga agtggtcctg caactttatc cgcctccatc cagtctatta    9300
attgttgccg ggaagctaga gtaagtagtt cgccagttaa tagtttgcgc aacgttgttg    9360
ccattgctac aggcatcgtg gtgtcacgct cgtcgtttgg tatggcttca ttcagctccg    9420
gttcccaacg atcaaggcga gttacatgat cccccatgtt gtgcaaaaaa gcggttagct    9480
ccttcggtcc tccgatcgtt gtcagaagta agttggccgc agtgttatca ctcatggtta    9540
tggcagcact gcataattct cttactgtca tgccatccgt aagatgcttt tctgtgactg    9600
gtgagtactc aaccaagtca ttctgagaat agtgtatgcg gcgaccgagt tgctcttgcc    9660
cggcgtcaat acgggataat accgcgccac atagcagaac tttaaaagtg ctcatcattg    9720
gaaaacgttc ttcggggcga aaactctcaa ggatcttacc gctgttgaga tccagttcga    9780
tgtaacccac tcgtgcaccc aactgatctt cagcatcttt tactttcacc agcgtttctg    9840
ggtgagcaaa aacaggaagg caaaatgccg caaaaaaggg aataagggcg acacggaaat    9900
gttgaatact catactcttc cttttcaat attattgaag catttatcag ggttattgtc    9960
tcatgagcgg atacatattt gaatgtattt agaaaaataa acaaataggg gttccgcgca   10020
catttccccg aaaagtgcca cctgacgtct aagaaaccat tattatcatg acattaacct   10080
ataaaaatag gcgtatcacg aggccctttc gtctcgcgcg tttcggtgat gacggtgaaa   10140
acctctgaca catgcagctc ccggagacgt cacagcttg tctgtaagcg gatgccggga   10200
gcagacaagc ccgtcagggc gcgtcagcgg gtgttggcgg gtgtcggggc tggcttaact   10260
atgcggcatc agagcagatt gtactgagag tgcaccatat gcggtgtgaa ataccgcaca   10320
gatgcgtaag gagaaaatac cgcatcaggc gccattcgcc attcaggctg cgcaactgtt   10380
gggaagggcg atcggtgcgg gcctcttcgc tattacgcca gctggcgaaa gggggatgtg   10440
ctgcaaggcg attaagttgg gtaacgccag ggttttccca gtcacgacgt tgtaaaacga   10500
cggccagtgc c                                                        10511
```